US011384128B2

(12) United States Patent
Mahr et al.

(10) Patent No.: US 11,384,128 B2
(45) Date of Patent: Jul. 12, 2022

(54) PEPTIDES AND COMBINATION OF PEPTIDES FOR USE IN IMMUNOTHERAPY AGAINST OVARIAN CANCER AND OTHER CANCERS

(71) Applicant: Immatics Biotechnologies GmbH, Tuebingen (DE)

(72) Inventors: Andrea Mahr, Tuebingen (DE); Toni Weinschenk, Tuebingen (DE); Helen Hoerzer, Tuebingen (DE); Oliver Schoor, Tuebingen (DE); Jens Fritsche, Tuebingen (DE); Harpreet Singh, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 17/520,097

(22) Filed: Nov. 5, 2021

(65) Prior Publication Data

US 2022/0119470 A1 Apr. 21, 2022

Related U.S. Application Data

(63) Continuation of application No. 16/713,157, filed on Dec. 13, 2019, which is a continuation of application (Continued)

(30) Foreign Application Priority Data

Jul. 1, 2015 (GB) ..................... 1511546

(51) Int. Cl.
| A61K 39/00 | (2006.01) |
| C07K 14/47 | (2006.01) |
| C07K 14/74 | (2006.01) |
| C12N 15/115 | (2010.01) |
| C07K 7/08 | (2006.01) |
| C07K 7/06 | (2006.01) |
| C07K 16/28 | (2006.01) |
| C12N 5/0783 | (2010.01) |
| A61K 35/17 | (2015.01) |

(Continued)

(52) U.S. Cl.
CPC .......... *C07K 14/4748* (2013.01); *A61K 35/17* (2013.01); *A61K 39/0011* (2013.01); *C07K 7/06* (2013.01); *C07K 7/08* (2013.01); *C07K 14/4705* (2013.01); *C07K 14/4738* (2013.01); *C07K 14/705* (2013.01); *C07K 14/70539* (2013.01); *C07K 14/82* (2013.01); *C07K 16/18* (2013.01); *C07K 16/28* (2013.01); *C07K 16/2833* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3069* (2013.01); *C07K 16/32* (2013.01); *C12N 5/0636* (2013.01); *C12N 15/115* (2013.01); *C12P 21/02* (2013.01); *C12Q 1/6881* (2013.01); *C12Q 1/6886* (2013.01); *G01N 33/56977* (2013.01); *G01N 33/57449* (2013.01); *G01N 33/57492* (2013.01); *A61K 38/00* (2013.01); *A61K 39/00* (2013.01); *A61K 2035/124* (2013.01); *A61K 2039/5158* (2013.01); *C07K 2317/24* (2013.01); *C07K 2317/31* (2013.01); *C07K 2317/34* (2013.01); *C07K 2319/00* (2013.01); *C07K 2319/40* (2013.01); *C12N 2310/16* (2013.01); *C12N 2320/30* (2013.01); *C12N 2501/50* (2013.01); *C12N 2501/998* (2013.01); *C12Q 2600/158* (2013.01); *G01N 2333/70539* (2013.01)

(58) Field of Classification Search
CPC ...... C07K 14/4748; C07K 7/08; C07K 16/30; A61K 39/0011; A61K 38/00; C12N 5/0636
See application file for complete search history.

(56) References Cited

U.S. PATENT DOCUMENTS

| 6,858,710 B2 | 2/2005 | Bangur et al. |
| 9,023,803 B2 | 5/2015 | Singh et al. |
| (Continued) | | |

FOREIGN PATENT DOCUMENTS

| EP | 1760089 A1 | 3/2007 |
| WO | 01/47944 A2 | 7/2001 |
| (Continued) | | |

OTHER PUBLICATIONS

Great Britain Search Report dated Apr. 18, 2016 in counterpart Great Britain Application No. GB1511546.2.

(Continued)

*Primary Examiner* — Sheela J. Huff
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 38 Drawing Sheets

Specification includes a Sequence Listing.

Related U.S. Application Data

No. 16/281,790, filed on Feb. 21, 2019, now Pat. No. 10,533,041, which is a continuation of application No. 16/101,081, filed on Aug. 10, 2018, now Pat. No. 10,239,925, which is a continuation of application No. 15/980,328, filed on May 15, 2018, now Pat. No. 10,174,089, which is a continuation of application No. 15/198,471, filed on Jun. 30, 2016, now Pat. No. 10,000,539.

(60) Provisional application No. 62/187,507, filed on Jul. 1, 2015.

(51) Int. Cl.

| | |
|---|---|
| *C07K 16/30* | (2006.01) |
| *C12P 21/02* | (2006.01) |
| *C12Q 1/6881* | (2018.01) |
| *G01N 33/569* | (2006.01) |
| *C07K 14/82* | (2006.01) |
| *C07K 16/32* | (2006.01) |
| *C12Q 1/6886* | (2018.01) |
| *G01N 33/574* | (2006.01) |
| *C07K 14/705* | (2006.01) |
| *C07K 16/18* | (2006.01) |
| *A61K 38/00* | (2006.01) |
| *A61K 35/12* | (2015.01) |

(56) References Cited

U.S. PATENT DOCUMENTS

| | | |
|---|---|---|
| 9,056,069 B2 | 6/2015 | Singh et al. |
| 2009/0274714 A1 | 11/2009 | Singh et al. |
| 2013/0096016 A1 | 4/2013 | Weinschenk et al. |

FOREIGN PATENT DOCUMENTS

| | | |
|---|---|---|
| WO | 2003/104429 A2 | 12/2003 |
| WO | 2006/029176 A2 | 3/2006 |
| WO | 2007/028573 A1 | 3/2007 |
| WO | 2011/151403 A | 4/2008 |
| WO | 2013/040142 A2 | 3/2013 |
| WO | 2014/011465 A2 | 1/2014 |

OTHER PUBLICATIONS

Steffen, W. et al., "Multipeptide immune response to cancer vaccine IMA901 after single-dose cyclophosphamide associates with longer patient survival" Nature Medicine, (2012) vol. 18: 1254-1265.
Sebastian Ochsenreither, "Cyclin-A1 represents a new immunogenic targetable antigen expressed in acute myeloid leukemia stem cells with characteristics of a cancer-testis antigen," Blood, vol. 119, No. 23, Apr. 23, 2012 (Apr. 23, 2012), pp. 5492-5501.
C. Hassan et al., "The Huamn Leukocyte Antigen-presented Ligandome of B Lymphocytes," Molecular & Cellular Proteomics, vol. 12, No. 7, Jul. 1, 2013 (Jul. 1, 2013), pp. 1829-1843.
International Search Report for PCT/EP2016/065166, dated Feb. 28, 2017.

Peptide: VLVSDGVHSV (A*02)
Seq ID No: 6

Figure 1D

Peptide: FLDTLKDLI (A*02)
Seq ID No: 58

Peptide detected on 6 cell lines (1 lymphocytic, 1 kidney, 1 pancreatic, 2 PBMCs, K562-A2), 4 normal tissues (2 bone marrows, 2 spleens), 49 cancer tissues (1 breast cancer, 3 colon cancers, 2 esophageal cancers, 1 gallbaldder cancer, 2 leukemias, 3 liver cancers, 21 lung cancers, 7 ovarian cancers, 23 rectum cancers, 1 skin cancer, 4 stomach cancers, 1 testis cancer, 1 urinary bladder cancer) (from left to right)

Peptide: VLVSDGVHSV (A*02)
Seq ID No: 6

Peptide: LLLDITPEI (A*02)
Seq ID No: 143

Peptide: RLWEEGEELEL (A*02)
Seq ID No: 150

Peptide: SLNDEVPEV (A*02)
Seq ID No: 157

Peptide: ALLPLSPYL (A*02)
Seq ID No: 427

Peptide: KLAEGLDIQL (A*02)
Seq ID No: 449

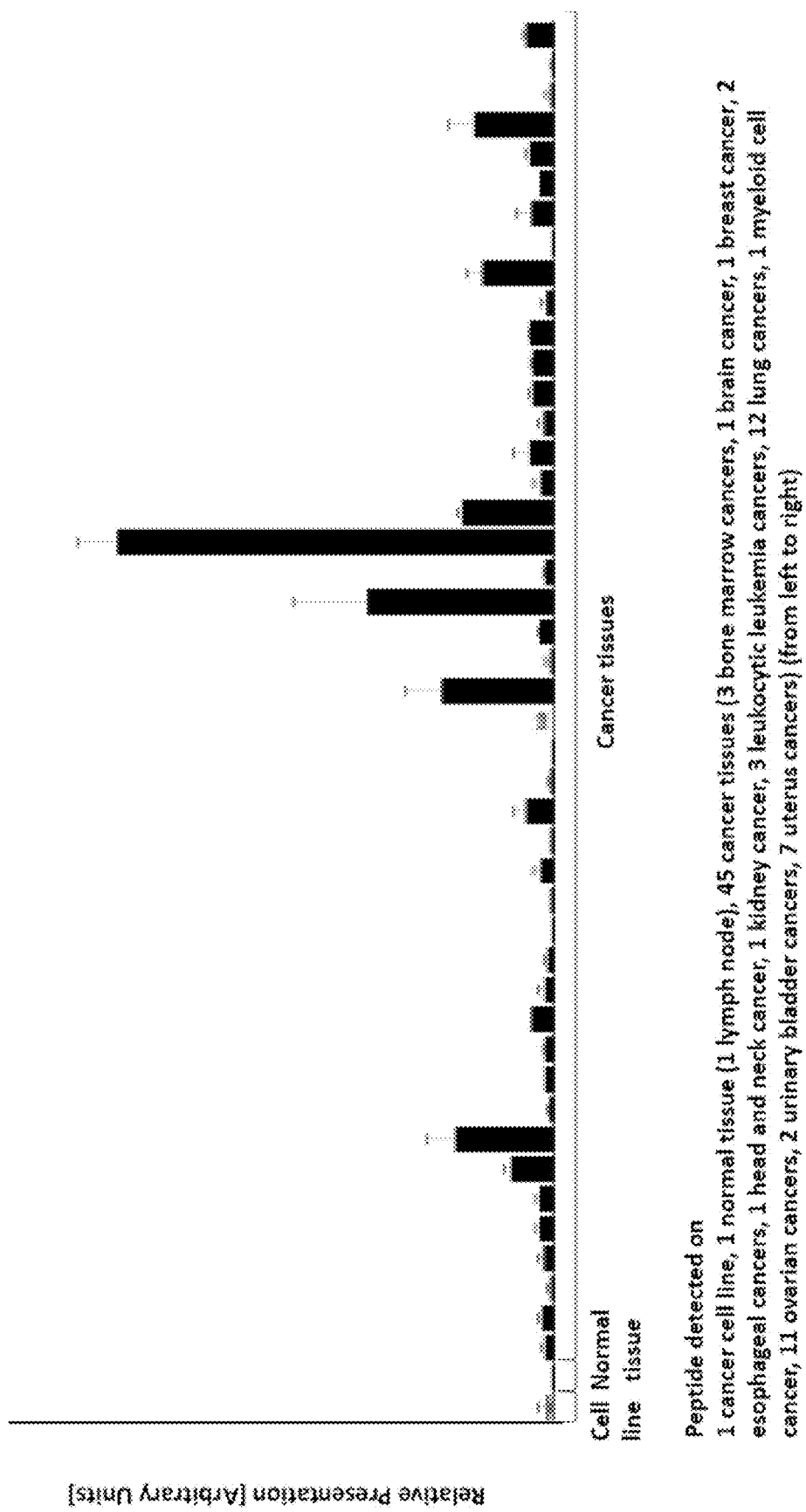

Peptide: KIFEMLEGV (A*02)
Seq ID No: 11

Peptide: KLDDLTQDLTV (A*02)
Seq ID No: 32

Peptide detected on
1 cell line, 1 normal tissue (1 liver), 29 cancer tissues (2 bile duct cancers, 1 esophageal cancer, 2 head and neck cancers, 4 liver cancers, 4 lung cancers, 3 lymph node cancers, 8 ovarian cancers, 1 prostate cancer, 1 rectum cancer, 2 urinary bladder cancers, 1 uterus cancer) (from left to right)

Peptide: FLLEDDIHVS (A*02)
Seq ID No: 38

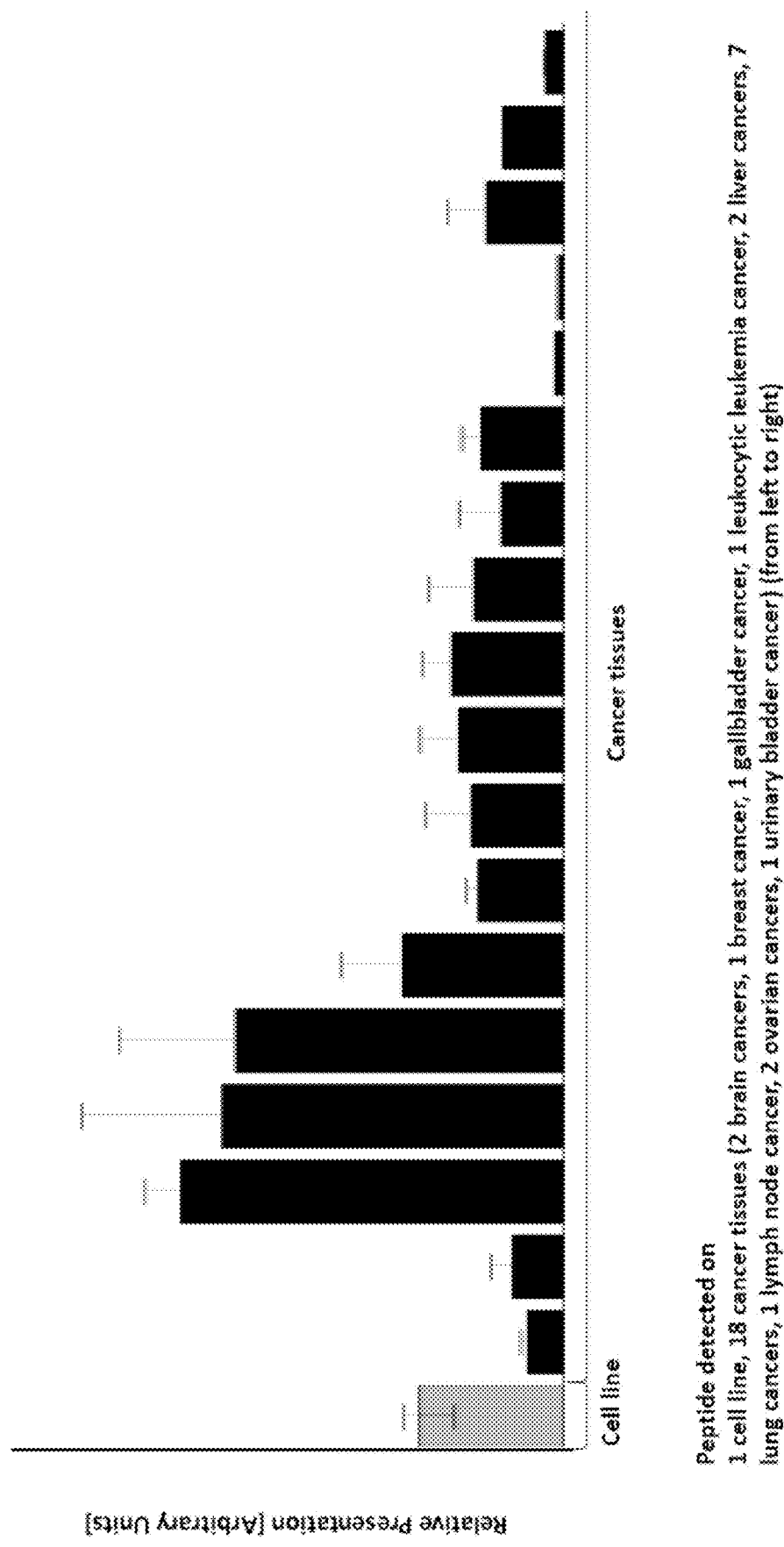

Peptide: TLAELQPPVQL (A*02)
Seq ID No: 57

Peptide: ILVEADGAWVV (A*02)
SEQ ID NO: 77

Peptide detected on
4 cell lines, 19 cancer tissues (1 brain cancer, 2 breast cancers, 1 colon cancer, 1 leukocytic leukemia cancer, 4 lung cancers, 3 lymph node cancers, 3 ovarian cancers, 1 prostate cancer, 1 skin cancer, 1 urinary bladder cancer, 1 uterus cancer) (from left to right)

Peptide: ALNPEIVSV (A*02)
SEQ ID NO: 148

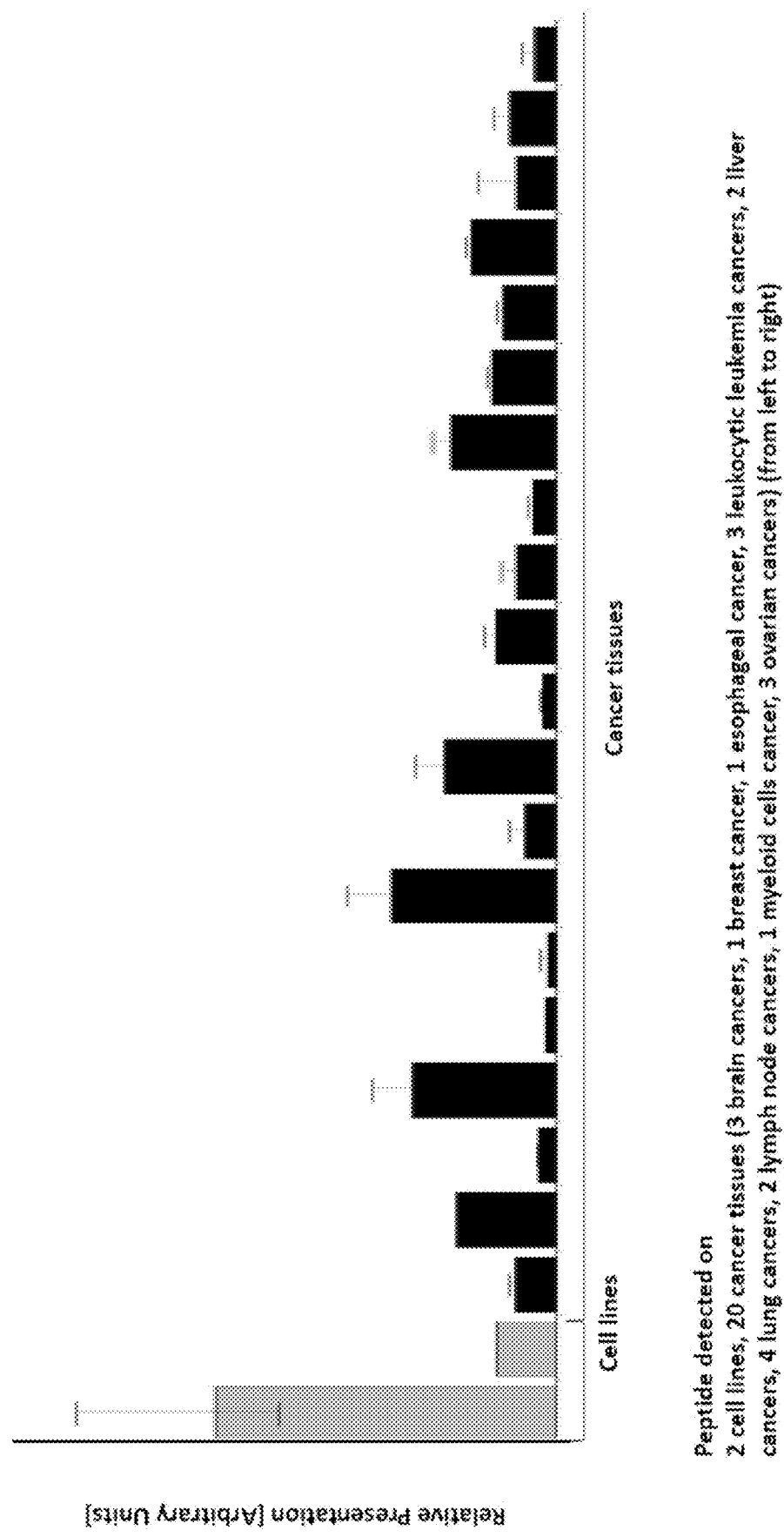

Peptide: YLMDINGKMWL (A*02)
SEQ ID NO: 184

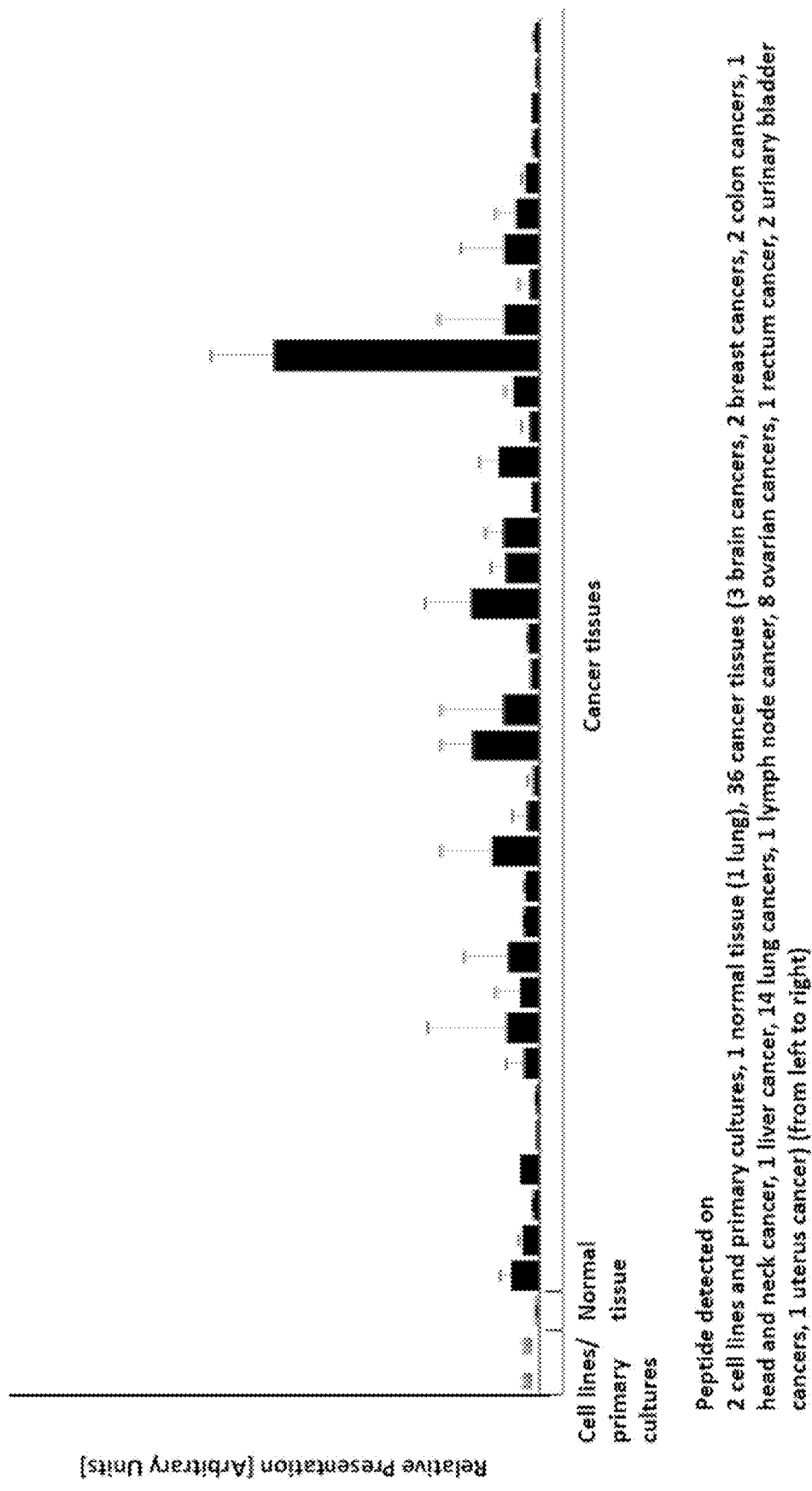

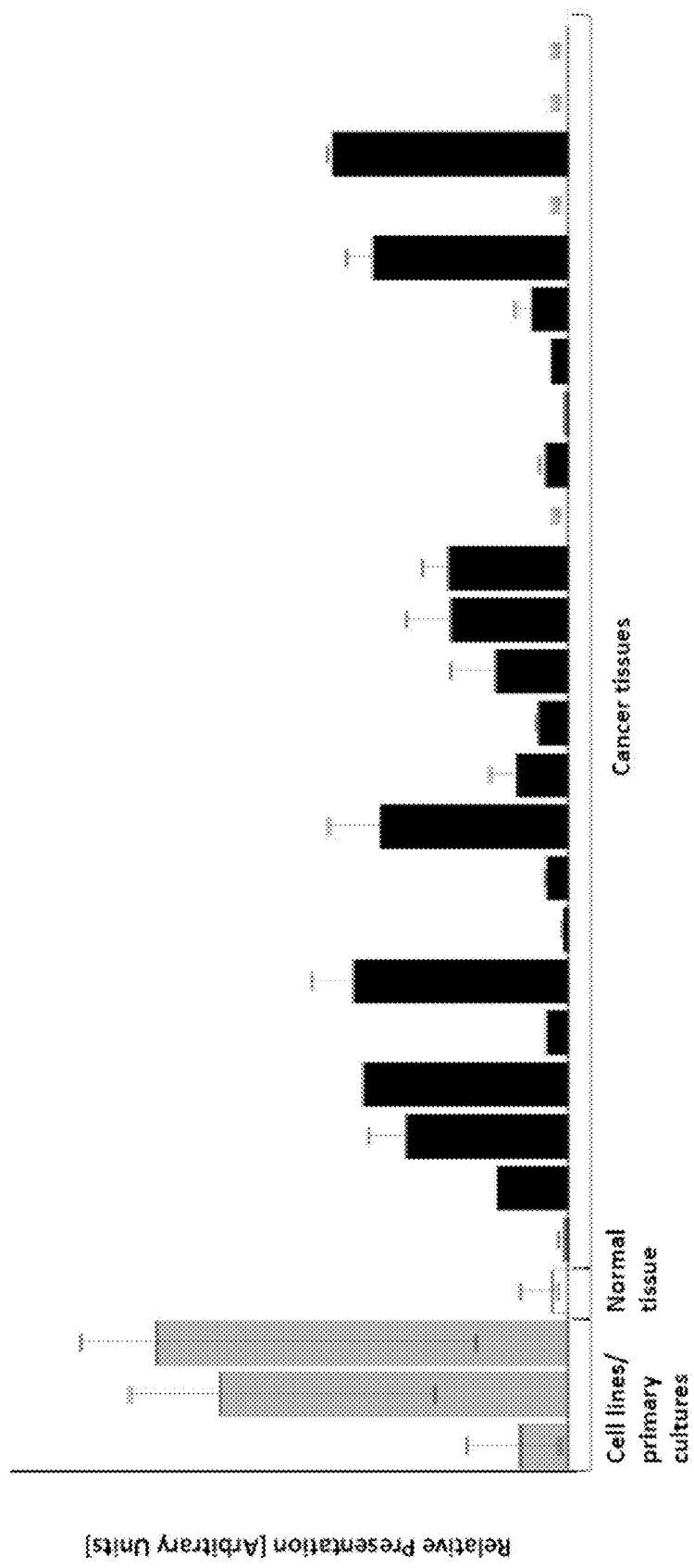

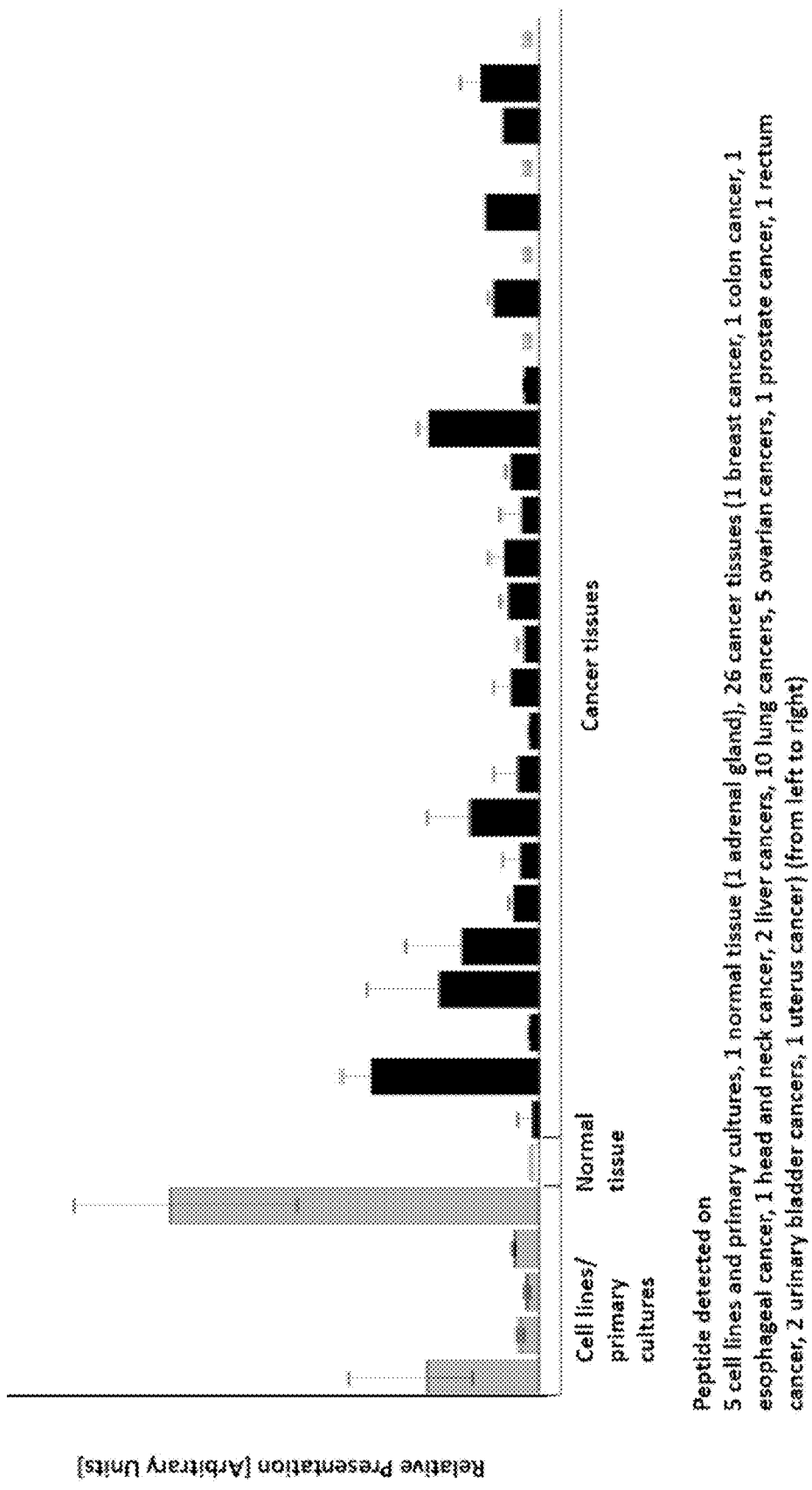

Peptide: SLVESHLSDQLTL (A*02)
SEQ ID NO: 463

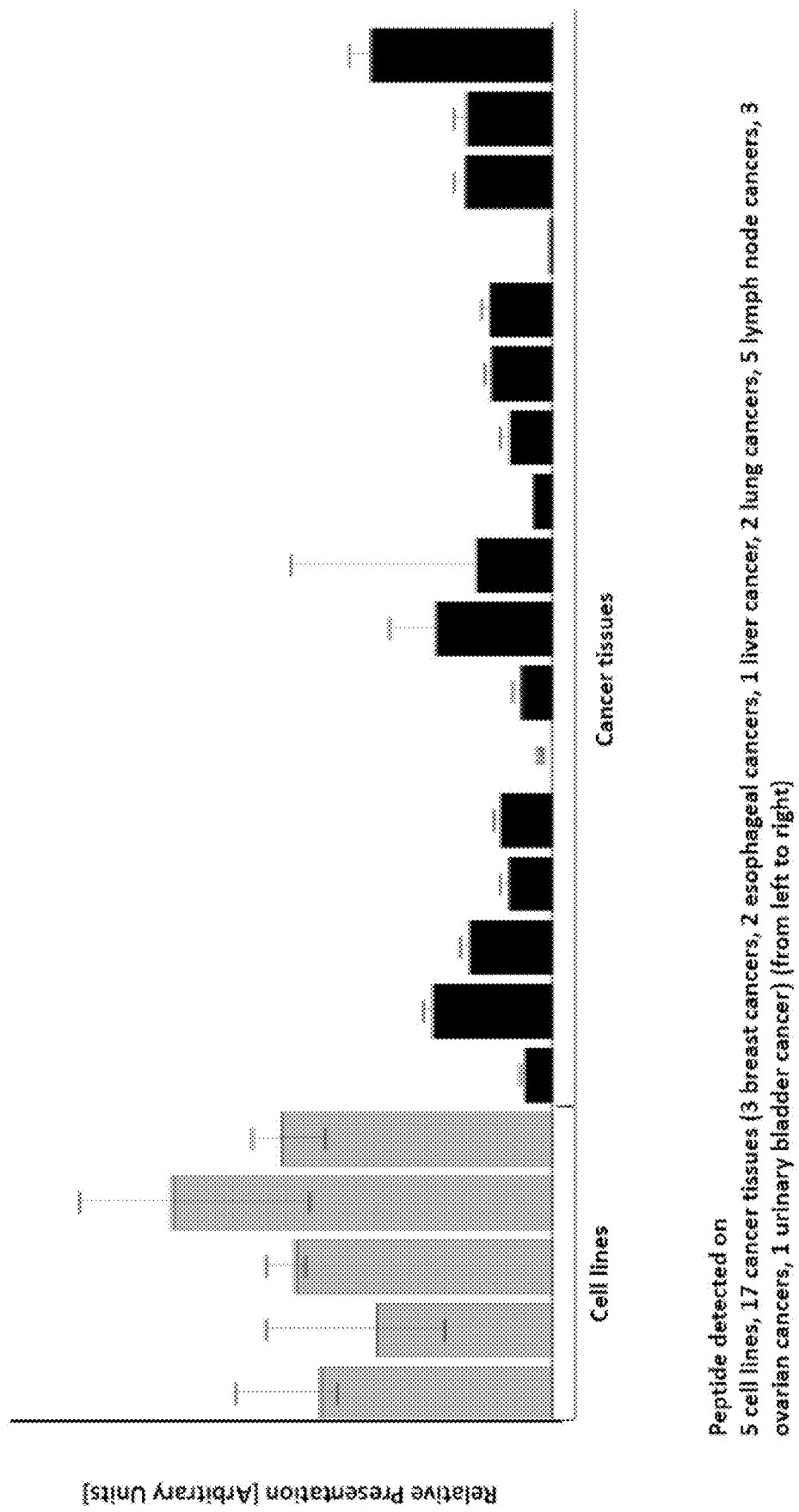

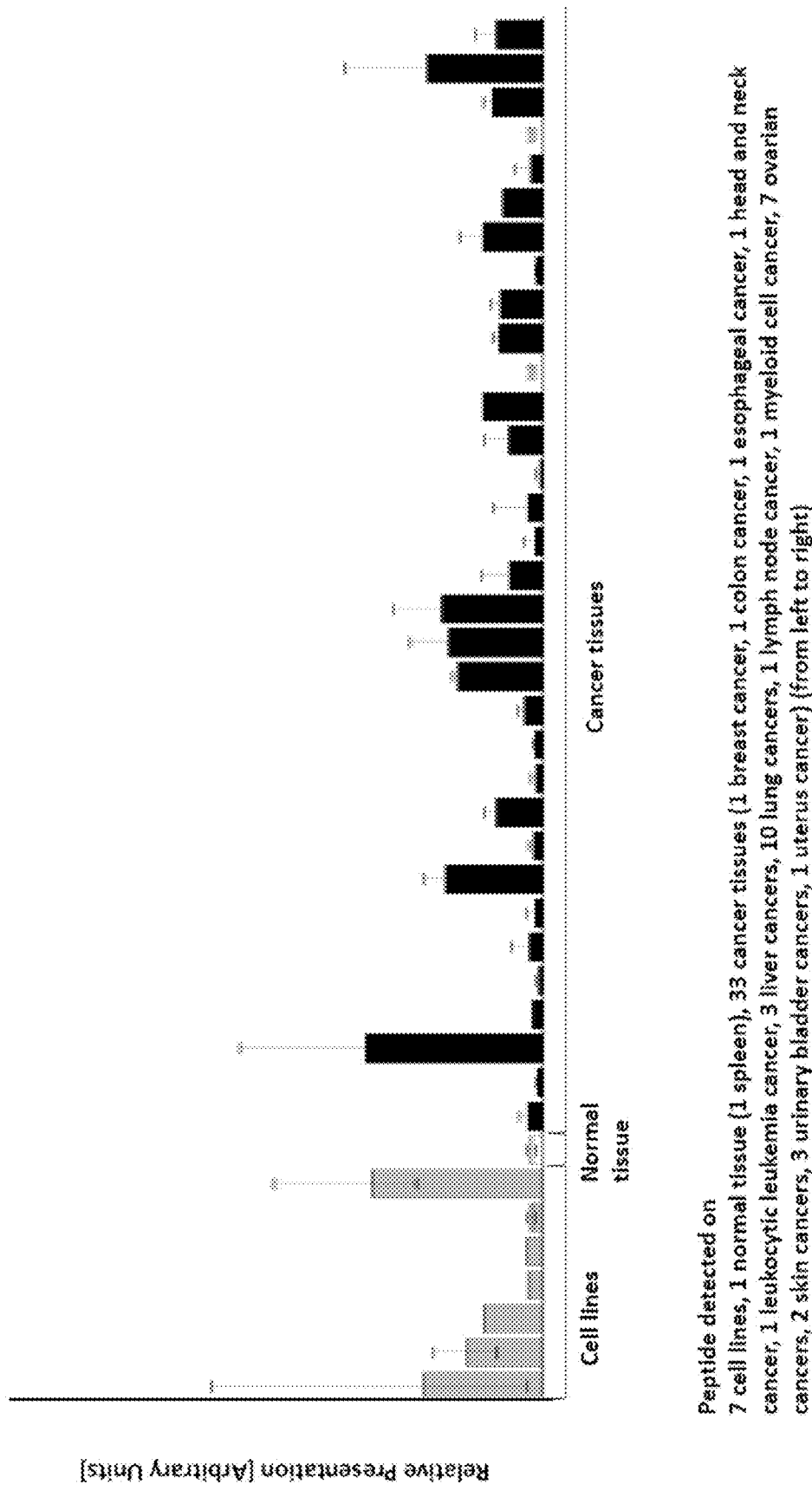

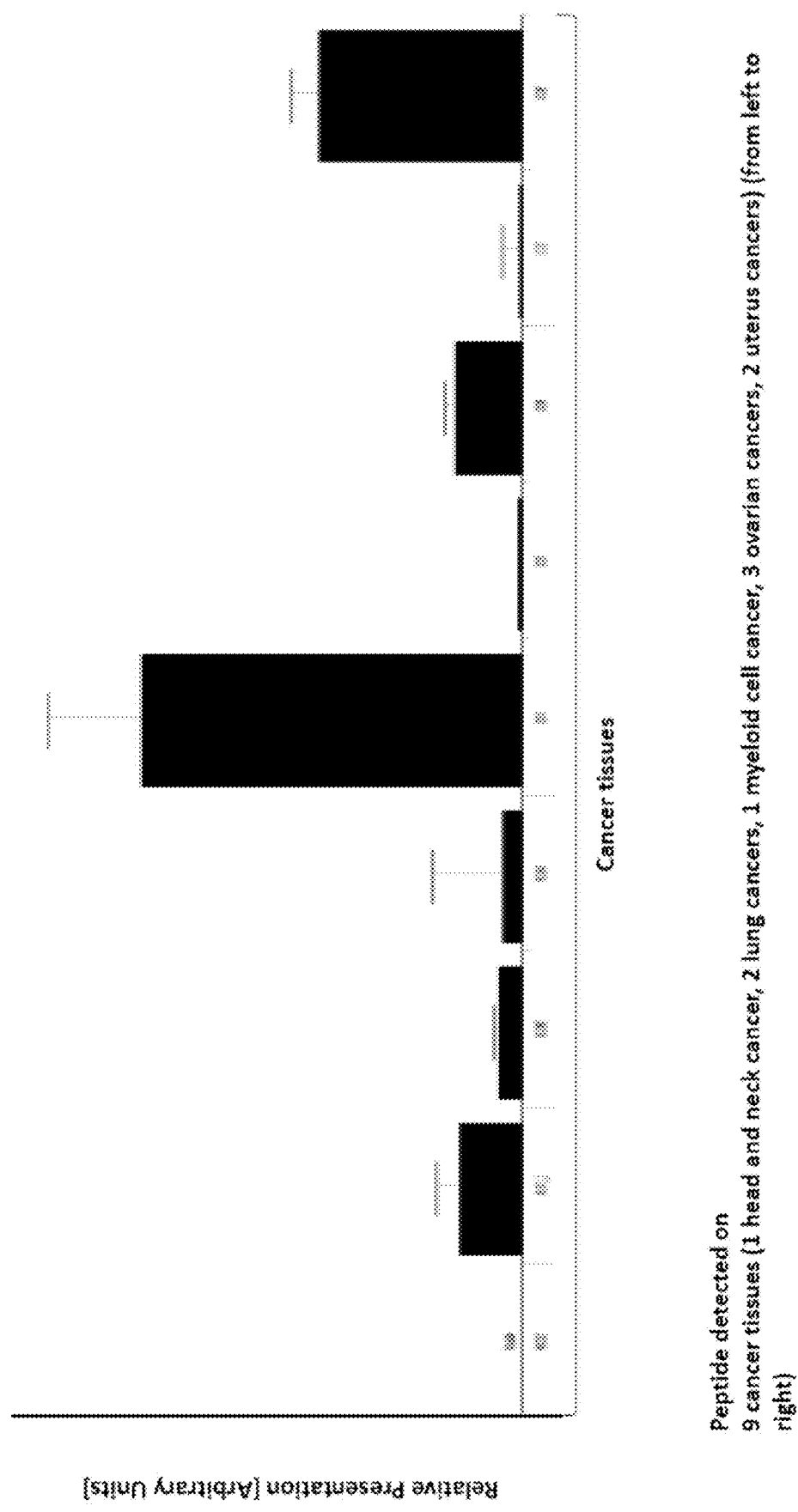

Peptide: ALWDIETGQQTTT (A*02)
SEQ ID NO: 560

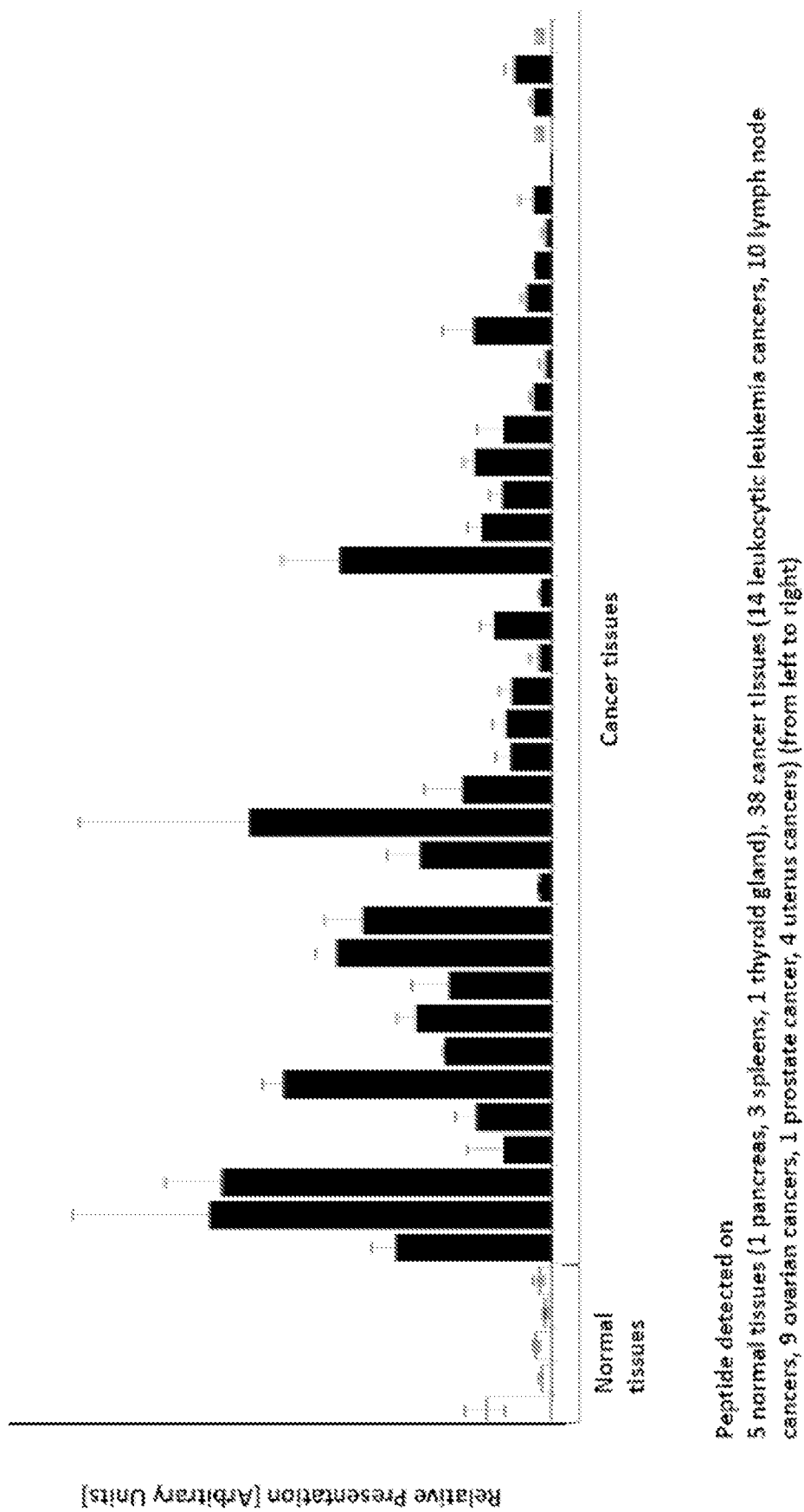

Peptide: KLLNKIYEA (A*02)
SEQ ID NO: 620

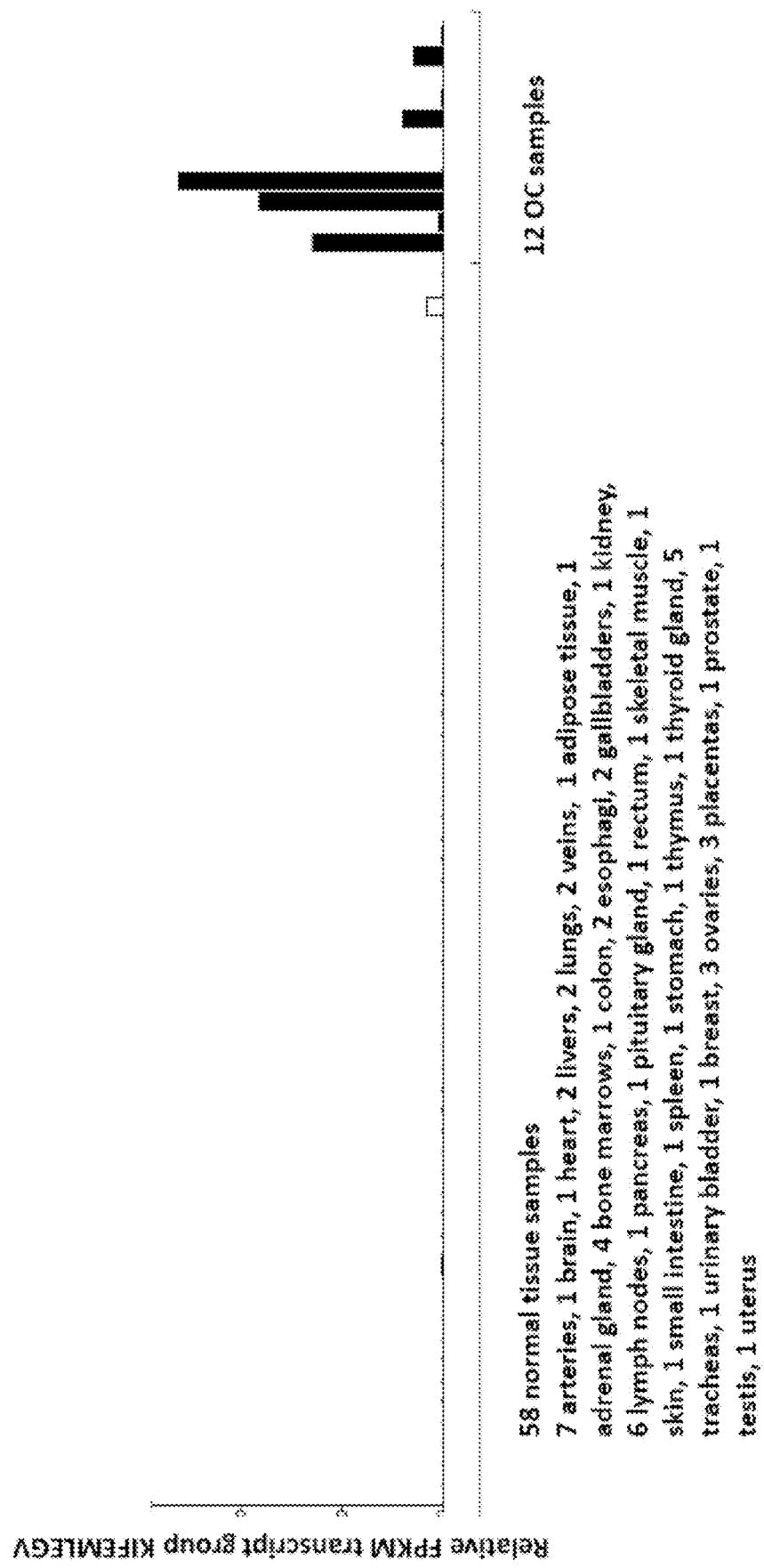

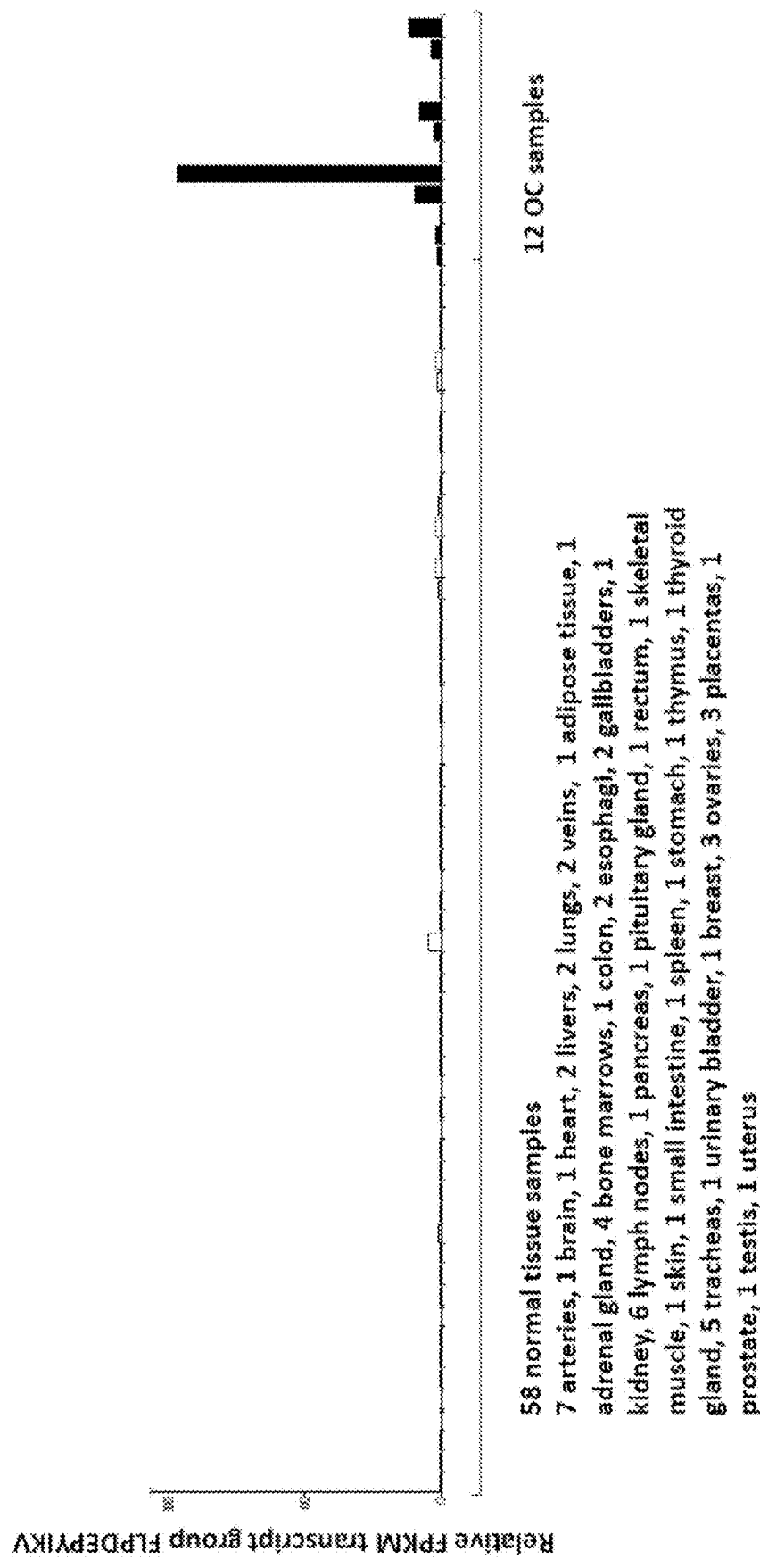

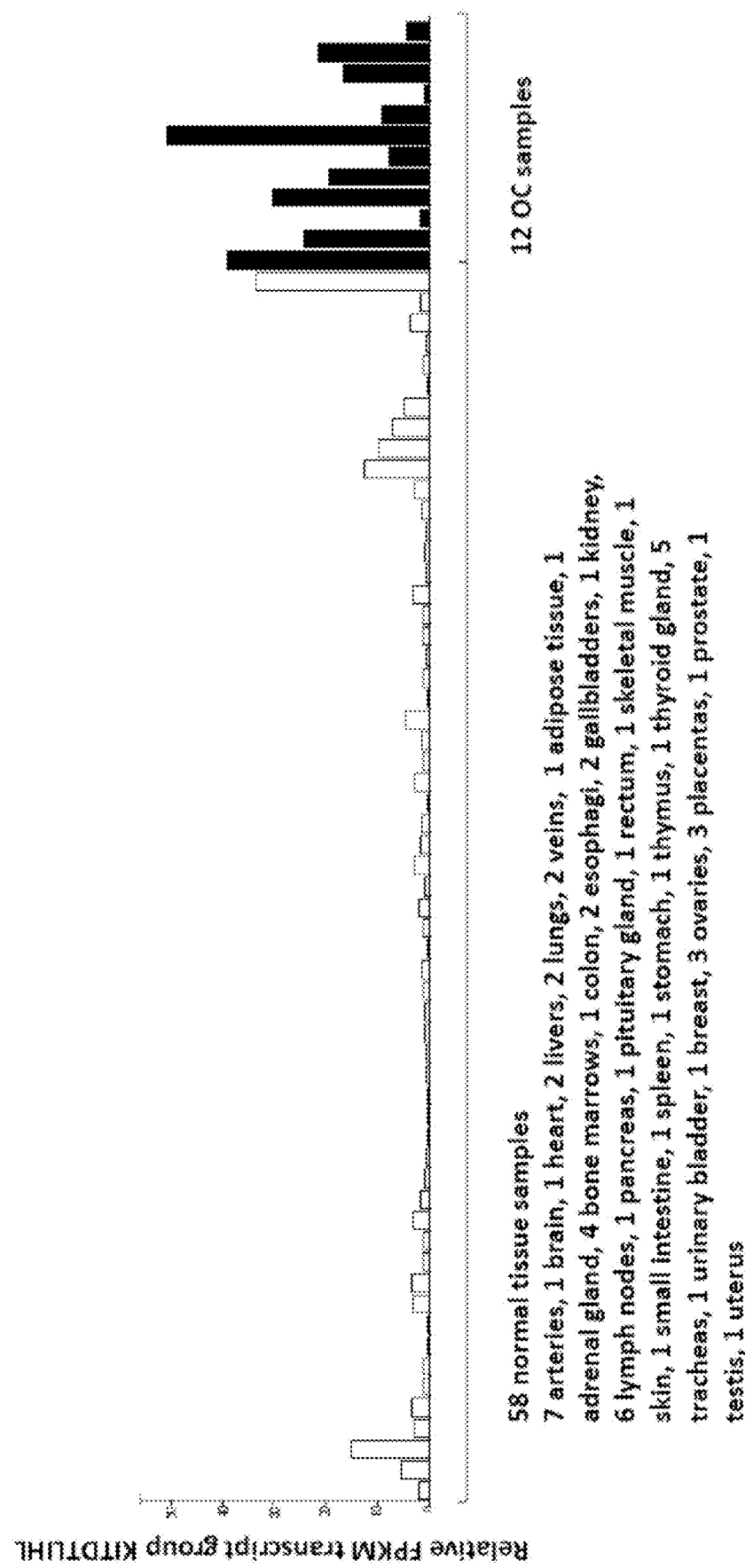

Gene: IDO1
Peptide: YHIDEEVGF
Seq ID No: 116

SEQUENCE LISTING

<160> NUMBER OF SEQ ID NOS: 665

<210> SEQ ID NO 1
<211> LENGTH: 11

-continued

```
<212> TYPE: PRT
<213> ORGANISM: Homo sapiens

<400> SEQUENCE: 1

Ser Leu Met Glu Pro Pro Ala Val Leu Leu
1               5                   10

<210> SEQ ID NO 2
<211> LENGTH: 9
<212> TYPE: PRT
<213> ORGANISM: Homo sapiens

<400> SEQUENCE: 2

Ser Leu Leu Glu Ala Asp Pro Phe Leu
1               5

<210> SEQ ID NO 3
<211> LENGTH: 9
<212> TYPE: PRT
<213> ORGANISM: Homo sapiens

<400> SEQUENCE: 3

Ser Leu Ala Ser Lys Leu Thr Thr Leu
1               5

<210> SEQ ID NO 4
<211> LENGTH: 9
<212> TYPE: PRT
<213> ORGANISM: Homo sapiens

<400> SEQUENCE: 4

Gly Ile Met Glu His Ile Thr Lys Ile
1               5

<210> SEQ ID NO 5
<211> LENGTH: 9
<212> TYPE: PRT
<213> ORGANISM: Homo sapiens

<400> SEQUENCE: 5

His Leu Thr Glu Val Tyr Pro Glu Leu
1               5

<210> SEQ ID NO 6
<211> LENGTH: 10
<212> TYPE: PRT
<213> ORGANISM: Homo sapiens

<400> SEQUENCE: 6

Val Leu Val Ser Asp Gly Val His Ser Val
1               5                   10

<210> SEQ ID NO 7
<211> LENGTH: 9
<212> TYPE: PRT
<213> ORGANISM: Homo sapiens

<400> SEQUENCE: 7

Ser Leu Val Gly Leu Leu Leu Tyr Leu
1               5

<210> SEQ ID NO 8
<211> LENGTH: 11
<212> TYPE: PRT
<213> ORGANISM: Homo sapiens
```

<400> SEQUENCE: 8

Phe Thr Leu Gly Asn Val Val Gly Met Tyr Leu
1               5                   10

<210> SEQ ID NO 9
<211> LENGTH: 9
<212> TYPE: PRT
<213> ORGANISM: Homo sapiens

<400> SEQUENCE: 9

Gly Ala Ala Lys Asp Leu Pro Gly Val
1               5

<210> SEQ ID NO 10
<211> LENGTH: 10
<212> TYPE: PRT
<213> ORGANISM: Homo sapiens

<400> SEQUENCE: 10

Phe Leu Ala Thr Phe Pro Leu Ala Ala Val
1               5                   10

<210> SEQ ID NO 11
<211> LENGTH: 9
<212> TYPE: PRT
<213> ORGANISM: Homo sapiens

<400> SEQUENCE: 11

Lys Ile Phe Glu Met Leu Glu Gly Val
1               5

<210> SEQ ID NO 12
<211> LENGTH: 9
<212> TYPE: PRT
<213> ORGANISM: Homo sapiens

<400> SEQUENCE: 12

Ser Leu Trp Pro Asp Pro Met Glu Val
1               5

<210> SEQ ID NO 13
<211> LENGTH: 9
<212> TYPE: PRT
<213> ORGANISM: Homo sapiens

<400> SEQUENCE: 13

Tyr Leu Met Asp Glu Ser Leu Asn Leu
1               5

<210> SEQ ID NO 14
<211> LENGTH: 12
<212> TYPE: PRT
<213> ORGANISM: Homo sapiens

<400> SEQUENCE: 14

Ala Ala Tyr Gly Gly Leu Asn Glu Lys Ser Phe Val
1               5                   10

<210> SEQ ID NO 15
<211> LENGTH: 9
<212> TYPE: PRT
<213> ORGANISM: Homo sapiens

<400> SEQUENCE: 15

Val Leu Thr Phe Lys Ile Phe Leu
1               5

<210> SEQ ID NO 16
<211> LENGTH: 9
<212> TYPE: PRT
<213> ORGANISM: Homo sapiens

<400> SEQUENCE: 16

Val Leu Phe Gln Gly Gln Ala Ser Leu
1               5

<210> SEQ ID NO 17
<211> LENGTH: 11
<212> TYPE: PRT
<213> ORGANISM: Homo sapiens

<400> SEQUENCE: 17

Gly Leu Leu Pro Gly Asp Arg Leu Val Ser Val
1               5                   10

<210> SEQ ID NO 18
<211> LENGTH: 9
<212> TYPE: PRT
<213> ORGANISM: Homo sapiens

<400> SEQUENCE: 18

Tyr Leu Val Ala Lys Leu Val Glu Val
1               5

<210> SEQ ID NO 19
<211> LENGTH: 11
<212> TYPE: PRT
<213> ORGANISM: Homo sapiens

<400> SEQUENCE: 19

Phe Met Val Asp Asn Glu Ala Ile Tyr Asp Ile
1               5                   10

<210> SEQ ID NO 20
<211> LENGTH: 9
<212> TYPE: PRT
<213> ORGANISM: Homo sapiens

<400> SEQUENCE: 20

Arg Met Ile Glu Tyr Phe Ile Asp Val
1               5

<210> SEQ ID NO 21
<211> LENGTH: 9
<212> TYPE: PRT
<213> ORGANISM: Homo sapiens

<400> SEQUENCE: 21

Val Leu Asp Glu Leu Asp Met Glu Leu
1               5

<210> SEQ ID NO 22
<211> LENGTH: 11
<212> TYPE: PRT
<213> ORGANISM: Homo sapiens

<400> SEQUENCE: 22

Ile Met Glu Glu Asn Pro Gly Ile Phe Ala Val

```
1               5              10
```

<210> SEQ ID NO 23
<211> LENGTH: 10
<212> TYPE: PRT
<213> ORGANISM: Homo sapiens

<400> SEQUENCE: 23

```
Val Leu Leu Asp Asp Ile Phe Ala Gln Leu
1               5              10
```

<210> SEQ ID NO 24
<211> LENGTH: 9
<212> TYPE: PRT
<213> ORGANISM: Homo sapiens

<400> SEQUENCE: 24

```
Ser Leu Ser Asp Gly Leu Glu Glu Val
1               5
```

<210> SEQ ID NO 25
<211> LENGTH: 10
<212> TYPE: PRT
<213> ORGANISM: Homo sapiens

<400> SEQUENCE: 25

```
Phe Leu Pro Asp Glu Pro Tyr Ile Lys Val
1               5              10
```

<210> SEQ ID NO 26
<211> LENGTH: 9
<212> TYPE: PRT
<213> ORGANISM: Homo sapiens

<400> SEQUENCE: 26

```
Ala Leu Leu Glu Leu Ala Glu Glu Leu
1               5
```

<210> SEQ ID NO 27
<211> LENGTH: 9
<212> TYPE: PRT
<213> ORGANISM: Homo sapiens

<400> SEQUENCE: 27

```
Ile Leu Ala Asp Ile Val Ile Ser Ala
1               5
```

<210> SEQ ID NO 28
<211> LENGTH: 11
<212> TYPE: PRT
<213> ORGANISM: Homo sapiens

<400> SEQUENCE: 28

```
Gln Leu Leu Asp Glu Thr Ser Ala Ile Thr Leu
1               5              10
```

<210> SEQ ID NO 29
<211> LENGTH: 13
<212> TYPE: PRT
<213> ORGANISM: Homo sapiens

<400> SEQUENCE: 29

```
Lys Met Leu Gly Ile Pro Ile Ser Asn Ile Leu Met Val
1               5              10
```

<210> SEQ ID NO 30
<211> LENGTH: 9
<212> TYPE: PRT
<213> ORGANISM: Homo sapiens

<400> SEQUENCE: 30

Leu Ile Leu Asp Trp Val Pro Tyr Ile
1               5

<210> SEQ ID NO 31
<211> LENGTH: 10
<212> TYPE: PRT
<213> ORGANISM: Homo sapiens

<400> SEQUENCE: 31

Tyr Leu Ala Pro Glu Leu Phe Val Asn Val
1               5                   10

<210> SEQ ID NO 32
<211> LENGTH: 11
<212> TYPE: PRT
<213> ORGANISM: Homo sapiens

<400> SEQUENCE: 32

Lys Leu Asp Asp Leu Thr Gln Asp Leu Thr Val
1               5                   10

<210> SEQ ID NO 33
<211> LENGTH: 9
<212> TYPE: PRT
<213> ORGANISM: Homo sapiens

<400> SEQUENCE: 33

Val Leu Leu Ser Leu Leu Glu Lys Val
1               5

<210> SEQ ID NO 34
<211> LENGTH: 11
<212> TYPE: PRT
<213> ORGANISM: Homo sapiens

<400> SEQUENCE: 34

Ile Leu Val Glu Ala Asp Ser Leu Trp Val Val
1               5                   10

<210> SEQ ID NO 35
<211> LENGTH: 9
<212> TYPE: PRT
<213> ORGANISM: Homo sapiens

<400> SEQUENCE: 35

Lys Ile Asn Asp Thr Ile Tyr Glu Val
1               5

<210> SEQ ID NO 36
<211> LENGTH: 10
<212> TYPE: PRT
<213> ORGANISM: Homo sapiens

<400> SEQUENCE: 36

Tyr Val Leu Glu Asp Leu Glu Val Thr Val
1               5                   10

<210> SEQ ID NO 37

```
<211> LENGTH: 11
<212> TYPE: PRT
<213> ORGANISM: Homo sapiens

<400> SEQUENCE: 37

Leu Leu Trp Asp Val Val Thr Gly Gln Ser Val
1               5                   10

<210> SEQ ID NO 38
<211> LENGTH: 10
<212> TYPE: PRT
<213> ORGANISM: Homo sapiens

<400> SEQUENCE: 38

Phe Leu Leu Glu Asp Asp Ile His Val Ser
1               5                   10

<210> SEQ ID NO 39
<211> LENGTH: 9
<212> TYPE: PRT
<213> ORGANISM: Homo sapiens

<400> SEQUENCE: 39

Ser Val Ala Pro Asn Leu Pro Ala Val
1               5

<210> SEQ ID NO 40
<211> LENGTH: 9
<212> TYPE: PRT
<213> ORGANISM: Homo sapiens

<400> SEQUENCE: 40

Thr Leu Leu Val Lys Val Phe Ser Val
1               5

<210> SEQ ID NO 41
<211> LENGTH: 9
<212> TYPE: PRT
<213> ORGANISM: Homo sapiens

<400> SEQUENCE: 41

Ser Leu Met Pro His Ile Pro Gly Leu
1               5

<210> SEQ ID NO 42
<211> LENGTH: 9
<212> TYPE: PRT
<213> ORGANISM: Homo sapiens

<400> SEQUENCE: 42

Val Leu Leu Gln Lys Ile Val Ser Ala
1               5

<210> SEQ ID NO 43
<211> LENGTH: 9
<212> TYPE: PRT
<213> ORGANISM: Homo sapiens

<400> SEQUENCE: 43

Val Leu Ser Ser Leu Glu Ile Asn Ile
1               5

<210> SEQ ID NO 44
<211> LENGTH: 11
<212> TYPE: PRT
```

```
<213> ORGANISM: Homo sapiens

<400> SEQUENCE: 44

Ile Leu Asp Pro Ile Ser Ser Gly Phe Leu Leu
1               5                   10

<210> SEQ ID NO 45
<211> LENGTH: 9
<212> TYPE: PRT
<213> ORGANISM: Homo sapiens

<400> SEQUENCE: 45

Ser Leu Trp Gln Asp Ile Pro Asp Val
1               5

<210> SEQ ID NO 46
<211> LENGTH: 9
<212> TYPE: PRT
<213> ORGANISM: Homo sapiens

<400> SEQUENCE: 46

Ile Leu Thr Glu Glu Asn Ile His Leu
1               5

<210> SEQ ID NO 47
<211> LENGTH: 10
<212> TYPE: PRT
<213> ORGANISM: Homo sapiens

<400> SEQUENCE: 47

Ile Leu Leu Ser Val Pro Leu Leu Val Val
1               5                   10

<210> SEQ ID NO 48
<211> LENGTH: 10
<212> TYPE: PRT
<213> ORGANISM: Homo sapiens

<400> SEQUENCE: 48

Ala Leu Ala Glu Leu Tyr Glu Asp Glu Val
1               5                   10

<210> SEQ ID NO 49
<211> LENGTH: 9
<212> TYPE: PRT
<213> ORGANISM: Homo sapiens

<400> SEQUENCE: 49

Tyr Leu Pro Ala Val Phe Glu Glu Val
1               5

<210> SEQ ID NO 50
<211> LENGTH: 9
<212> TYPE: PRT
<213> ORGANISM: Homo sapiens

<400> SEQUENCE: 50

Ser Leu Ser Glu Leu Glu Ala Leu Met
1               5

<210> SEQ ID NO 51
<211> LENGTH: 9
<212> TYPE: PRT
<213> ORGANISM: Homo sapiens
```

```
<400> SEQUENCE: 51

Leu Leu Pro Asp Leu Glu Phe Tyr Val
1               5

<210> SEQ ID NO 52
<211> LENGTH: 11
<212> TYPE: PRT
<213> ORGANISM: Homo sapiens

<400> SEQUENCE: 52

Phe Leu Leu Ala His Gly Leu Gly Phe Leu Leu
1               5                   10

<210> SEQ ID NO 53
<211> LENGTH: 11
<212> TYPE: PRT
<213> ORGANISM: Homo sapiens

<400> SEQUENCE: 53

Lys Met Ile Glu Thr Asp Ile Leu Gln Lys Val
1               5                   10

<210> SEQ ID NO 54
<211> LENGTH: 12
<212> TYPE: PRT
<213> ORGANISM: Homo sapiens

<400> SEQUENCE: 54

Ser Leu Leu Glu Gln Gly Lys Glu Pro Trp Met Val
1               5                   10

<210> SEQ ID NO 55
<211> LENGTH: 10
<212> TYPE: PRT
<213> ORGANISM: Homo sapiens

<400> SEQUENCE: 55

Ser Leu Leu Asp Leu Glu Thr Leu Ser Leu
1               5                   10

<210> SEQ ID NO 56
<211> LENGTH: 10
<212> TYPE: PRT
<213> ORGANISM: Homo sapiens

<400> SEQUENCE: 56

Lys Leu Tyr Glu Gly Ile Pro Val Leu Leu
1               5                   10

<210> SEQ ID NO 57
<211> LENGTH: 11
<212> TYPE: PRT
<213> ORGANISM: Homo sapiens

<400> SEQUENCE: 57

Thr Leu Ala Glu Leu Gln Pro Pro Val Gln Leu
1               5                   10

<210> SEQ ID NO 58
<211> LENGTH: 9
<212> TYPE: PRT
<213> ORGANISM: Homo sapiens

<400> SEQUENCE: 58
```

Phe Leu Asp Thr Leu Lys Asp Leu Ile
1               5

<210> SEQ ID NO 59
<211> LENGTH: 9
<212> TYPE: PRT
<213> ORGANISM: Homo sapiens

<400> SEQUENCE: 59

Ile Met Glu Asp Ile Ile Leu Thr Leu
1               5

<210> SEQ ID NO 60
<211> LENGTH: 10
<212> TYPE: PRT
<213> ORGANISM: Homo sapiens

<400> SEQUENCE: 60

Ser Leu Thr Ile Asp Gly Ile Tyr Tyr Val
1               5                   10

<210> SEQ ID NO 61
<211> LENGTH: 9
<212> TYPE: PRT
<213> ORGANISM: Homo sapiens

<400> SEQUENCE: 61

Phe Leu Gln Gly Tyr Gln Leu His Leu
1               5

<210> SEQ ID NO 62
<211> LENGTH: 12
<212> TYPE: PRT
<213> ORGANISM: Homo sapiens

<400> SEQUENCE: 62

Val Leu Leu Asp Val Ser Ala Gly Gln Leu Leu Met
1               5                   10

<210> SEQ ID NO 63
<211> LENGTH: 11
<212> TYPE: PRT
<213> ORGANISM: Homo sapiens

<400> SEQUENCE: 63

Tyr Leu Leu Pro Ser Gly Gly Ser Val Thr Leu
1               5                   10

<210> SEQ ID NO 64
<211> LENGTH: 10
<212> TYPE: PRT
<213> ORGANISM: Homo sapiens

<400> SEQUENCE: 64

Tyr Ala Ala Pro Gly Gly Leu Ile Gly Val
1               5                   10

<210> SEQ ID NO 65
<211> LENGTH: 10
<212> TYPE: PRT
<213> ORGANISM: Homo sapiens

<400> SEQUENCE: 65

Leu Lys Val Asn Gln Gly Leu Glu Ser Leu
1               5                   10

<210> SEQ ID NO 66
<211> LENGTH: 11
<212> TYPE: PRT
<213> ORGANISM: Homo sapiens

<400> SEQUENCE: 66

Phe Leu Asp Glu Asn Ile Gly Gly Val Ala Val
1               5                   10

<210> SEQ ID NO 67
<211> LENGTH: 10
<212> TYPE: PRT
<213> ORGANISM: Homo sapiens

<400> SEQUENCE: 67

Thr Leu Leu Ala Glu Ala Leu Val Thr Val
1               5                   10

<210> SEQ ID NO 68
<211> LENGTH: 11
<212> TYPE: PRT
<213> ORGANISM: Homo sapiens

<400> SEQUENCE: 68

Ser Leu Met Glu Leu Pro Arg Gly Leu Phe Leu
1               5                   10

<210> SEQ ID NO 69
<211> LENGTH: 13
<212> TYPE: PRT
<213> ORGANISM: Homo sapiens

<400> SEQUENCE: 69

Phe Gln Leu Asp Pro Ser Ser Gly Val Leu Val Thr Val
1               5                   10

<210> SEQ ID NO 70
<211> LENGTH: 9
<212> TYPE: PRT
<213> ORGANISM: Homo sapiens

<400> SEQUENCE: 70

Gly Leu Leu Asp Tyr Pro Val Gly Val
1               5

<210> SEQ ID NO 71
<211> LENGTH: 9
<212> TYPE: PRT
<213> ORGANISM: Homo sapiens

<400> SEQUENCE: 71

Gly Ile Leu Ala Arg Ile Ala Ser Val
1               5

<210> SEQ ID NO 72
<211> LENGTH: 10
<212> TYPE: PRT
<213> ORGANISM: Homo sapiens

<400> SEQUENCE: 72

Ser Leu Leu Glu Leu Asp Gly Ile Asn Leu
1               5                   10

```
<210> SEQ ID NO 73
<211> LENGTH: 9
<212> TYPE: PRT
<213> ORGANISM: Homo sapiens

<400> SEQUENCE: 73

Asn Ile Phe Asp Leu Gln Ile Tyr Val
1               5

<210> SEQ ID NO 74
<211> LENGTH: 12
<212> TYPE: PRT
<213> ORGANISM: Homo sapiens

<400> SEQUENCE: 74

Ala Leu Leu Asp Pro Glu Val Leu Ser Ile Phe Val
1               5                   10

<210> SEQ ID NO 75
<211> LENGTH: 9
<212> TYPE: PRT
<213> ORGANISM: Homo sapiens

<400> SEQUENCE: 75

Gly Leu Leu Glu Val Met Val Asn Leu
1               5

<210> SEQ ID NO 76
<211> LENGTH: 9
<212> TYPE: PRT
<213> ORGANISM: Homo sapiens

<400> SEQUENCE: 76

Ile Leu Ile Asp Ser Ile Tyr Lys Val
1               5

<210> SEQ ID NO 77
<211> LENGTH: 11
<212> TYPE: PRT
<213> ORGANISM: Homo sapiens

<400> SEQUENCE: 77

Ile Leu Val Glu Ala Asp Gly Ala Trp Val Val
1               5                   10

<210> SEQ ID NO 78
<211> LENGTH: 13
<212> TYPE: PRT
<213> ORGANISM: Homo sapiens

<400> SEQUENCE: 78

Ser Leu Phe Ser Ser Leu Glu Pro Gln Ile Gln Pro Val
1               5                   10

<210> SEQ ID NO 79
<211> LENGTH: 11
<212> TYPE: PRT
<213> ORGANISM: Homo sapiens

<400> SEQUENCE: 79

Ser Leu Phe Ile Gly Glu Lys Ala Val Leu Leu
1               5                   10

<210> SEQ ID NO 80
<211> LENGTH: 10
```

```
<212> TYPE: PRT
<213> ORGANISM: Homo sapiens

<400> SEQUENCE: 80

Phe Leu Tyr Asp Asn Leu Val Glu Ser Leu
1               5                   10

<210> SEQ ID NO 81
<211> LENGTH: 9
<212> TYPE: PRT
<213> ORGANISM: Homo sapiens

<400> SEQUENCE: 81

Phe Leu Phe Ser Gln Leu Gln Tyr Leu
1               5

<210> SEQ ID NO 82
<211> LENGTH: 9
<212> TYPE: PRT
<213> ORGANISM: Homo sapiens

<400> SEQUENCE: 82

Phe Leu Ser Ser Val Thr Tyr Asn Leu
1               5

<210> SEQ ID NO 83
<211> LENGTH: 9
<212> TYPE: PRT
<213> ORGANISM: Homo sapiens

<400> SEQUENCE: 83

Ile Leu Ala Pro Thr Val Met Met Ile
1               5

<210> SEQ ID NO 84
<211> LENGTH: 10
<212> TYPE: PRT
<213> ORGANISM: Homo sapiens

<400> SEQUENCE: 84

Val Thr Phe Gly Glu Lys Leu Leu Gly Val
1               5                   10

<210> SEQ ID NO 85
<211> LENGTH: 9
<212> TYPE: PRT
<213> ORGANISM: Homo sapiens

<400> SEQUENCE: 85

Lys Met Ser Glu Leu Arg Val Thr Leu
1               5

<210> SEQ ID NO 86
<211> LENGTH: 9
<212> TYPE: PRT
<213> ORGANISM: Homo sapiens

<400> SEQUENCE: 86

Asn Leu Ile Gly Lys Ile Glu Asn Val
1               5

<210> SEQ ID NO 87
<211> LENGTH: 14
<212> TYPE: PRT
<213> ORGANISM: Homo sapiens
```

<400> SEQUENCE: 87

Ala Leu Pro Glu Ala Pro Ala Pro Leu Leu Pro His Ile Thr
1               5                   10

<210> SEQ ID NO 88
<211> LENGTH: 10
<212> TYPE: PRT
<213> ORGANISM: Homo sapiens

<400> SEQUENCE: 88

Phe Leu Leu Val Gly Asp Leu Met Ala Val
1               5                   10

<210> SEQ ID NO 89
<211> LENGTH: 10
<212> TYPE: PRT
<213> ORGANISM: Homo sapiens

<400> SEQUENCE: 89

Tyr Ile Leu Pro Thr Glu Thr Ile Tyr Val
1               5                   10

<210> SEQ ID NO 90
<211> LENGTH: 9
<212> TYPE: PRT
<213> ORGANISM: Homo sapiens

<400> SEQUENCE: 90

Thr Leu Leu Gln Ile Ile Glu Thr Val
1               5

<210> SEQ ID NO 91
<211> LENGTH: 11
<212> TYPE: PRT
<213> ORGANISM: Homo sapiens

<400> SEQUENCE: 91

Ile Met Gln Asp Phe Pro Ala Glu Ile Phe Leu
1               5                   10

<210> SEQ ID NO 92
<211> LENGTH: 11
<212> TYPE: PRT
<213> ORGANISM: Homo sapiens

<400> SEQUENCE: 92

Tyr Leu Ile Pro Phe Thr Gly Ile Val Gly Leu
1               5                   10

<210> SEQ ID NO 93
<211> LENGTH: 9
<212> TYPE: PRT
<213> ORGANISM: Homo sapiens

<400> SEQUENCE: 93

Leu Leu Gln Ala Ile Lys Leu Tyr Leu
1               5

<210> SEQ ID NO 94
<211> LENGTH: 10
<212> TYPE: PRT
<213> ORGANISM: Homo sapiens

<400> SEQUENCE: 94

Tyr Leu Ile Asp Ile Lys Thr Ile Ala Ile
1               5                   10

<210> SEQ ID NO 95
<211> LENGTH: 9
<212> TYPE: PRT
<213> ORGANISM: Homo sapiens

<400> SEQUENCE: 95

Ser Val Ile Pro Gln Ile Gln Lys Val
1               5

<210> SEQ ID NO 96
<211> LENGTH: 10
<212> TYPE: PRT
<213> ORGANISM: Homo sapiens

<400> SEQUENCE: 96

Tyr Ile Phe Thr Asp Asn Pro Ala Ala Val
1               5                   10

<210> SEQ ID NO 97
<211> LENGTH: 9
<212> TYPE: PRT
<213> ORGANISM: Homo sapiens

<400> SEQUENCE: 97

Ser Leu Ile Asn Gly Ser Phe Leu Val
1               5

<210> SEQ ID NO 98
<211> LENGTH: 10
<212> TYPE: PRT
<213> ORGANISM: Homo sapiens

<400> SEQUENCE: 98

Leu Ile Ile Asp Gln Ala Asp Ile Tyr Leu
1               5                   10

<210> SEQ ID NO 99
<211> LENGTH: 10
<212> TYPE: PRT
<213> ORGANISM: Homo sapiens

<400> SEQUENCE: 99

Ala Leu Val Ser Lys Gly Leu Ala Thr Val
1               5                   10

<210> SEQ ID NO 100
<211> LENGTH: 9
<212> TYPE: PRT
<213> ORGANISM: Homo sapiens

<400> SEQUENCE: 100

Tyr Leu Leu Ser Thr Asn Ala Gln Leu
1               5

<210> SEQ ID NO 101
<211> LENGTH: 11
<212> TYPE: PRT
<213> ORGANISM: Homo sapiens

<400> SEQUENCE: 101

Ile Leu Val Gly Gly Gly Ala Leu Ala Thr Val

```
1               5                   10

<210> SEQ ID NO 102
<211> LENGTH: 10
<212> TYPE: PRT
<213> ORGANISM: Homo sapiens

<400> SEQUENCE: 102

Tyr Leu Phe Glu Ser Glu Gly Leu Val Leu
1               5                   10

<210> SEQ ID NO 103
<211> LENGTH: 9
<212> TYPE: PRT
<213> ORGANISM: Homo sapiens

<400> SEQUENCE: 103

Thr Leu Ala Glu Glu Val Val Ala Leu
1               5

<210> SEQ ID NO 104
<211> LENGTH: 9
<212> TYPE: PRT
<213> ORGANISM: Homo sapiens

<400> SEQUENCE: 104

Ser Thr Met Glu Gln Asn Phe Leu Leu
1               5

<210> SEQ ID NO 105
<211> LENGTH: 9
<212> TYPE: PRT
<213> ORGANISM: Homo sapiens

<400> SEQUENCE: 105

Leu Leu Leu Glu His Ser Phe Glu Ile
1               5

<210> SEQ ID NO 106
<211> LENGTH: 11
<212> TYPE: PRT
<213> ORGANISM: Homo sapiens

<400> SEQUENCE: 106

Leu Leu Tyr Asp Ala Val His Ile Val Ser Val
1               5                   10

<210> SEQ ID NO 107
<211> LENGTH: 11
<212> TYPE: PRT
<213> ORGANISM: Homo sapiens

<400> SEQUENCE: 107

Phe Leu Gln Pro Val Asp Asp Thr Gln His Leu
1               5                   10

<210> SEQ ID NO 108
<211> LENGTH: 11
<212> TYPE: PRT
<213> ORGANISM: Homo sapiens

<400> SEQUENCE: 108

Ala Leu Phe Pro Gly Val Ala Leu Leu Leu Ala
1               5                   10
```

```
<210> SEQ ID NO 109
<211> LENGTH: 9
<212> TYPE: PRT
<213> ORGANISM: Homo sapiens

<400> SEQUENCE: 109

Ile Ile Leu Ser Ile Leu Glu Gln Ala
1               5

<210> SEQ ID NO 110
<211> LENGTH: 9
<212> TYPE: PRT
<213> ORGANISM: Homo sapiens

<400> SEQUENCE: 110

Phe Leu Ser Gln Val Asp Phe Glu Leu
1               5

<210> SEQ ID NO 111
<211> LENGTH: 10
<212> TYPE: PRT
<213> ORGANISM: Homo sapiens

<400> SEQUENCE: 111

Tyr Val Trp Gly Phe Tyr Pro Ala Glu Val
1               5                   10

<210> SEQ ID NO 112
<211> LENGTH: 9
<212> TYPE: PRT
<213> ORGANISM: Homo sapiens

<400> SEQUENCE: 112

Phe Leu Ile Thr Ser Asn Asn Gln Leu
1               5

<210> SEQ ID NO 113
<211> LENGTH: 10
<212> TYPE: PRT
<213> ORGANISM: Homo sapiens

<400> SEQUENCE: 113

Gly Leu Leu Pro Thr Pro Leu Phe Gly Val
1               5                   10

<210> SEQ ID NO 114
<211> LENGTH: 11
<212> TYPE: PRT
<213> ORGANISM: Homo sapiens

<400> SEQUENCE: 114

Ser Leu Val Gly Glu Pro Ile Leu Gln Asn Val
1               5                   10

<210> SEQ ID NO 115
<211> LENGTH: 11
<212> TYPE: PRT
<213> ORGANISM: Homo sapiens

<400> SEQUENCE: 115

Ala Ile Ala Gly Ala Gly Ile Leu Tyr Gly Val
1               5                   10

<210> SEQ ID NO 116
```

```
<211> LENGTH: 9
<212> TYPE: PRT
<213> ORGANISM: Homo sapiens

<400> SEQUENCE: 116

Tyr His Ile Asp Glu Glu Val Gly Phe
1               5

<210> SEQ ID NO 117
<211> LENGTH: 11
<212> TYPE: PRT
<213> ORGANISM: Homo sapiens

<400> SEQUENCE: 117

Ile Leu Pro Asp Gly Glu Asp Phe Leu Ala Val
1               5                   10

<210> SEQ ID NO 118
<211> LENGTH: 9
<212> TYPE: PRT
<213> ORGANISM: Homo sapiens

<400> SEQUENCE: 118

Lys Leu Ile Asp Asn Asn Ile Asn Val
1               5

<210> SEQ ID NO 119
<211> LENGTH: 10
<212> TYPE: PRT
<213> ORGANISM: Homo sapiens

<400> SEQUENCE: 119

Phe Leu Tyr Ile Gly Asp Ile Val Ser Leu
1               5                   10

<210> SEQ ID NO 120
<211> LENGTH: 10
<212> TYPE: PRT
<213> ORGANISM: Homo sapiens

<400> SEQUENCE: 120

Ala Leu Leu Gly Ile Pro Leu Thr Leu Val
1               5                   10

<210> SEQ ID NO 121
<211> LENGTH: 11
<212> TYPE: PRT
<213> ORGANISM: Homo sapiens

<400> SEQUENCE: 121

Gly Val Val Asp Pro Arg Ala Ile Ser Val Leu
1               5                   10

<210> SEQ ID NO 122
<211> LENGTH: 10
<212> TYPE: PRT
<213> ORGANISM: Homo sapiens

<400> SEQUENCE: 122

Phe Leu Leu Ala Glu Asp Asp Ile Tyr Leu
1               5                   10

<210> SEQ ID NO 123
<211> LENGTH: 11
<212> TYPE: PRT
```

<213> ORGANISM: Homo sapiens

<400> SEQUENCE: 123

Asn Leu Trp Asp Leu Thr Asp Ala Ser Val Val
1               5                   10

<210> SEQ ID NO 124
<211> LENGTH: 10
<212> TYPE: PRT
<213> ORGANISM: Homo sapiens

<400> SEQUENCE: 124

Ala Leu Tyr Glu Thr Glu Leu Ala Asp Ala
1               5                   10

<210> SEQ ID NO 125
<211> LENGTH: 9
<212> TYPE: PRT
<213> ORGANISM: Homo sapiens

<400> SEQUENCE: 125

Val Gln Ile His Gln Val Ala Gln Val
1               5

<210> SEQ ID NO 126
<211> LENGTH: 9
<212> TYPE: PRT
<213> ORGANISM: Homo sapiens

<400> SEQUENCE: 126

Val Leu Ala Tyr Phe Leu Pro Glu Ala
1               5

<210> SEQ ID NO 127
<211> LENGTH: 9
<212> TYPE: PRT
<213> ORGANISM: Homo sapiens

<400> SEQUENCE: 127

Lys Ile Gly Asp Glu Pro Pro Lys Val
1               5

<210> SEQ ID NO 128
<211> LENGTH: 10
<212> TYPE: PRT
<213> ORGANISM: Homo sapiens

<400> SEQUENCE: 128

Tyr Leu Phe Asp Asp Pro Leu Ser Ala Val
1               5                   10

<210> SEQ ID NO 129
<211> LENGTH: 11
<212> TYPE: PRT
<213> ORGANISM: Homo sapiens

<400> SEQUENCE: 129

Gly Leu Leu Asp Gly Gly Val Asp Ile Leu Leu
1               5                   10

<210> SEQ ID NO 130
<211> LENGTH: 11
<212> TYPE: PRT
<213> ORGANISM: Homo sapiens

```
<400> SEQUENCE: 130

Phe Leu Trp Asn Gly Glu Asp Ser Ala Leu Leu
1               5                   10

<210> SEQ ID NO 131
<211> LENGTH: 11
<212> TYPE: PRT
<213> ORGANISM: Homo sapiens

<400> SEQUENCE: 131

Phe Val Pro Pro Val Thr Val Phe Pro Ser Leu
1               5                   10

<210> SEQ ID NO 132
<211> LENGTH: 11
<212> TYPE: PRT
<213> ORGANISM: Homo sapiens

<400> SEQUENCE: 132

Leu Leu Val Glu Gln Pro Pro Leu Ala Gly Val
1               5                   10

<210> SEQ ID NO 133
<211> LENGTH: 9
<212> TYPE: PRT
<213> ORGANISM: Homo sapiens

<400> SEQUENCE: 133

Lys Val Leu Ser Asn Ile His Thr Val
1               5

<210> SEQ ID NO 134
<211> LENGTH: 9
<212> TYPE: PRT
<213> ORGANISM: Homo sapiens

<400> SEQUENCE: 134

Tyr Leu Gln Glu Leu Ile Phe Ser Val
1               5

<210> SEQ ID NO 135
<211> LENGTH: 9
<212> TYPE: PRT
<213> ORGANISM: Homo sapiens

<400> SEQUENCE: 135

Ala Leu Ser Glu Val Asp Phe Gln Leu
1               5

<210> SEQ ID NO 136
<211> LENGTH: 11
<212> TYPE: PRT
<213> ORGANISM: Homo sapiens

<400> SEQUENCE: 136

Tyr Leu Ala Asp Pro Ser Asn Leu Phe Val Val
1               5                   10

<210> SEQ ID NO 137
<211> LENGTH: 9
<212> TYPE: PRT
<213> ORGANISM: Homo sapiens

<400> SEQUENCE: 137
```

```
Thr Leu Val Leu Thr Leu Pro Thr Val
1               5
```

<210> SEQ ID NO 138
<211> LENGTH: 10
<212> TYPE: PRT
<213> ORGANISM: Homo sapiens

<400> SEQUENCE: 138

```
Tyr Gln Tyr Pro Arg Ala Ile Leu Ser Val
1               5                   10
```

<210> SEQ ID NO 139
<211> LENGTH: 12
<212> TYPE: PRT
<213> ORGANISM: Homo sapiens

<400> SEQUENCE: 139

```
Ser Val Met Glu Val Asn Ser Gly Ile Tyr Arg Val
1               5                   10
```

<210> SEQ ID NO 140
<211> LENGTH: 9
<212> TYPE: PRT
<213> ORGANISM: Homo sapiens

<400> SEQUENCE: 140

```
Tyr Met Asp Ala Pro Lys Ala Ala Leu
1               5
```

<210> SEQ ID NO 141
<211> LENGTH: 9
<212> TYPE: PRT
<213> ORGANISM: Homo sapiens

<400> SEQUENCE: 141

```
Tyr Leu Asp Phe Ser Asn Asn Arg Leu
1               5
```

<210> SEQ ID NO 142
<211> LENGTH: 9
<212> TYPE: PRT
<213> ORGANISM: Homo sapiens

<400> SEQUENCE: 142

```
Phe Leu Phe Ala Thr Pro Val Phe Ile
1               5
```

<210> SEQ ID NO 143
<211> LENGTH: 9
<212> TYPE: PRT
<213> ORGANISM: Homo sapiens

<400> SEQUENCE: 143

```
Leu Leu Leu Asp Ile Thr Pro Glu Ile
1               5
```

<210> SEQ ID NO 144
<211> LENGTH: 11
<212> TYPE: PRT
<213> ORGANISM: Homo sapiens

<400> SEQUENCE: 144

```
Tyr Ile Met Glu Pro Ser Ile Phe Asn Thr Leu
1               5                   10
```

```
<210> SEQ ID NO 145
<211> LENGTH: 11
<212> TYPE: PRT
<213> ORGANISM: Homo sapiens

<400> SEQUENCE: 145

Phe Leu Ala Thr Ser Gly Thr Leu Ala Gly Ile
1               5                   10

<210> SEQ ID NO 146
<211> LENGTH: 12
<212> TYPE: PRT
<213> ORGANISM: Homo sapiens

<400> SEQUENCE: 146

Ser Leu Ala Thr Ala Gly Asp Gly Leu Ile Glu Leu
1               5                   10

<210> SEQ ID NO 147
<211> LENGTH: 9
<212> TYPE: PRT
<213> ORGANISM: Homo sapiens

<400> SEQUENCE: 147

Ser Leu Leu Glu Ala Val Ser Phe Leu
1               5

<210> SEQ ID NO 148
<211> LENGTH: 9
<212> TYPE: PRT
<213> ORGANISM: Homo sapiens

<400> SEQUENCE: 148

Ala Leu Asn Pro Glu Ile Val Ser Val
1               5

<210> SEQ ID NO 149
<211> LENGTH: 9
<212> TYPE: PRT
<213> ORGANISM: Homo sapiens

<400> SEQUENCE: 149

Asn Leu Leu Glu Leu Phe Val Gln Leu
1               5

<210> SEQ ID NO 150
<211> LENGTH: 11
<212> TYPE: PRT
<213> ORGANISM: Homo sapiens

<400> SEQUENCE: 150

Arg Leu Trp Glu Glu Gly Glu Glu Leu Glu Leu
1               5                   10

<210> SEQ ID NO 151
<211> LENGTH: 9
<212> TYPE: PRT
<213> ORGANISM: Homo sapiens

<400> SEQUENCE: 151

Lys Ile Leu Gln Gln Leu Val Thr Leu
1               5
```

<210> SEQ ID NO 152
<211> LENGTH: 9
<212> TYPE: PRT
<213> ORGANISM: Homo sapiens

<400> SEQUENCE: 152

Ile Leu Phe Glu Asp Ile Phe Asp Val
1               5

<210> SEQ ID NO 153
<211> LENGTH: 9
<212> TYPE: PRT
<213> ORGANISM: Homo sapiens

<400> SEQUENCE: 153

Phe Leu Ile Ala Asn Val Leu Tyr Leu
1               5

<210> SEQ ID NO 154
<211> LENGTH: 9
<212> TYPE: PRT
<213> ORGANISM: Homo sapiens

<400> SEQUENCE: 154

Ala Leu Asp Asp Gly Thr Pro Ala Leu
1               5

<210> SEQ ID NO 155
<211> LENGTH: 10
<212> TYPE: PRT
<213> ORGANISM: Homo sapiens

<400> SEQUENCE: 155

Arg Val Ala Asn Leu His Phe Pro Ser Val
1               5                   10

<210> SEQ ID NO 156
<211> LENGTH: 11
<212> TYPE: PRT
<213> ORGANISM: Homo sapiens

<400> SEQUENCE: 156

Ala Ile Ser Gln Gly Ile Thr Leu Pro Ser Leu
1               5                   10

<210> SEQ ID NO 157
<211> LENGTH: 9
<212> TYPE: PRT
<213> ORGANISM: Homo sapiens

<400> SEQUENCE: 157

Ser Leu Asn Asp Glu Val Pro Glu Val
1               5

<210> SEQ ID NO 158
<211> LENGTH: 11
<212> TYPE: PRT
<213> ORGANISM: Homo sapiens

<400> SEQUENCE: 158

Lys Leu Phe Asp Val Asp Glu Asp Gly Tyr Ile
1               5                   10

<210> SEQ ID NO 159
<211> LENGTH: 10

```
<212> TYPE: PRT
<213> ORGANISM: Homo sapiens

<400> SEQUENCE: 159

Gly Leu Val Gly Asn Pro Leu Pro Ser Val
1               5                   10

<210> SEQ ID NO 160
<211> LENGTH: 10
<212> TYPE: PRT
<213> ORGANISM: Homo sapiens

<400> SEQUENCE: 160

Phe Leu Phe Asp Glu Glu Ile Glu Gln Ile
1               5                   10

<210> SEQ ID NO 161
<211> LENGTH: 9
<212> TYPE: PRT
<213> ORGANISM: Homo sapiens

<400> SEQUENCE: 161

Ala Leu Leu Glu Gly Val Asn Thr Val
1               5

<210> SEQ ID NO 162
<211> LENGTH: 9
<212> TYPE: PRT
<213> ORGANISM: Homo sapiens

<400> SEQUENCE: 162

Tyr Gln Gln Ala Gln Val Pro Ser Val
1               5

<210> SEQ ID NO 163
<211> LENGTH: 11
<212> TYPE: PRT
<213> ORGANISM: Homo sapiens

<400> SEQUENCE: 163

Ala Leu Asp Glu Met Gly Asp Leu Leu Gln Leu
1               5                   10

<210> SEQ ID NO 164
<211> LENGTH: 11
<212> TYPE: PRT
<213> ORGANISM: Homo sapiens

<400> SEQUENCE: 164

Ala Leu Leu Pro Gln Pro Lys Asn Leu Thr Val
1               5                   10

<210> SEQ ID NO 165
<211> LENGTH: 9
<212> TYPE: PRT
<213> ORGANISM: Homo sapiens

<400> SEQUENCE: 165

Ser Leu Leu Asp Glu Ile Arg Ala Val
1               5

<210> SEQ ID NO 166
<211> LENGTH: 9
<212> TYPE: PRT
<213> ORGANISM: Homo sapiens
```

<400> SEQUENCE: 166

Tyr Leu Asn His Leu Glu Pro Pro Val
1               5

<210> SEQ ID NO 167
<211> LENGTH: 11
<212> TYPE: PRT
<213> ORGANISM: Homo sapiens

<400> SEQUENCE: 167

Lys Val Leu Glu Val Thr Glu Glu Phe Gly Val
1               5                   10

<210> SEQ ID NO 168
<211> LENGTH: 9
<212> TYPE: PRT
<213> ORGANISM: Homo sapiens

<400> SEQUENCE: 168

Lys Ile Leu Asp Ala Asp Ile Gln Leu
1               5

<210> SEQ ID NO 169
<211> LENGTH: 9
<212> TYPE: PRT
<213> ORGANISM: Homo sapiens

<400> SEQUENCE: 169

Asn Leu Pro Glu Tyr Leu Pro Phe Val
1               5

<210> SEQ ID NO 170
<211> LENGTH: 9
<212> TYPE: PRT
<213> ORGANISM: Homo sapiens

<400> SEQUENCE: 170

Arg Leu Gln Glu Thr Leu Ser Ala Ala
1               5

<210> SEQ ID NO 171
<211> LENGTH: 9
<212> TYPE: PRT
<213> ORGANISM: Homo sapiens

<400> SEQUENCE: 171

Leu Leu Leu Pro Leu Gln Ile Leu Leu
1               5

<210> SEQ ID NO 172
<211> LENGTH: 10
<212> TYPE: PRT
<213> ORGANISM: Homo sapiens

<400> SEQUENCE: 172

Val Leu Tyr Ser Tyr Thr Ile Ile Thr Val
1               5                   10

<210> SEQ ID NO 173
<211> LENGTH: 11
<212> TYPE: PRT
<213> ORGANISM: Homo sapiens

<400> SEQUENCE: 173

Leu Leu Asp Ser Ala Ser Ala Gly Leu Tyr Leu
1               5                   10

<210> SEQ ID NO 174
<211> LENGTH: 9
<212> TYPE: PRT
<213> ORGANISM: Homo sapiens

<400> SEQUENCE: 174

Ala Leu Ala Gln Tyr Leu Ile Thr Ala
1               5

<210> SEQ ID NO 175
<211> LENGTH: 9
<212> TYPE: PRT
<213> ORGANISM: Homo sapiens

<400> SEQUENCE: 175

Tyr Leu Phe Glu Asn Ile Ser Gln Leu
1               5

<210> SEQ ID NO 176
<211> LENGTH: 12
<212> TYPE: PRT
<213> ORGANISM: Homo sapiens

<400> SEQUENCE: 176

Tyr Leu Met Glu Gly Ser Tyr Asn Lys Val Phe Leu
1               5                   10

<210> SEQ ID NO 177
<211> LENGTH: 11
<212> TYPE: PRT
<213> ORGANISM: Homo sapiens

<400> SEQUENCE: 177

Tyr Leu Leu Pro Glu Glu Tyr Thr Ser Thr Leu
1               5                   10

<210> SEQ ID NO 178
<211> LENGTH: 9
<212> TYPE: PRT
<213> ORGANISM: Homo sapiens

<400> SEQUENCE: 178

Ala Leu Thr Glu Ile Ala Phe Val Val
1               5

<210> SEQ ID NO 179
<211> LENGTH: 9
<212> TYPE: PRT
<213> ORGANISM: Homo sapiens

<400> SEQUENCE: 179

Lys Val Leu Asn Glu Leu Tyr Thr Val
1               5

<210> SEQ ID NO 180
<211> LENGTH: 12
<212> TYPE: PRT
<213> ORGANISM: Homo sapiens

<400> SEQUENCE: 180

Phe Gln Ile Asp Pro His Ser Gly Leu Val Thr Val

```
1               5                  10

<210> SEQ ID NO 181
<211> LENGTH: 10
<212> TYPE: PRT
<213> ORGANISM: Homo sapiens

<400> SEQUENCE: 181

Leu Leu Trp Ala Gly Thr Ala Phe Gln Val
1               5                  10

<210> SEQ ID NO 182
<211> LENGTH: 10
<212> TYPE: PRT
<213> ORGANISM: Homo sapiens

<400> SEQUENCE: 182

Met Leu Leu Glu Ala Pro Gly Ile Phe Leu
1               5                  10

<210> SEQ ID NO 183
<211> LENGTH: 9
<212> TYPE: PRT
<213> ORGANISM: Homo sapiens

<400> SEQUENCE: 183

Phe Gly Leu Asp Leu Val Thr Glu Leu
1               5

<210> SEQ ID NO 184
<211> LENGTH: 11
<212> TYPE: PRT
<213> ORGANISM: Homo sapiens

<400> SEQUENCE: 184

Tyr Leu Met Asp Ile Asn Gly Lys Met Trp Leu
1               5                  10

<210> SEQ ID NO 185
<211> LENGTH: 10
<212> TYPE: PRT
<213> ORGANISM: Homo sapiens

<400> SEQUENCE: 185

Phe Leu Ile Asp Asp Lys Gly Tyr Thr Leu
1               5                  10

<210> SEQ ID NO 186
<211> LENGTH: 9
<212> TYPE: PRT
<213> ORGANISM: Homo sapiens

<400> SEQUENCE: 186

Thr Leu Phe Phe Gln Gln Asn Ala Leu
1               5

<210> SEQ ID NO 187
<211> LENGTH: 11
<212> TYPE: PRT
<213> ORGANISM: Homo sapiens

<400> SEQUENCE: 187

Arg Gln Ile Ser Ile Arg Gly Ile Val Gly Val
1               5                  10
```

<210> SEQ ID NO 188
<211> LENGTH: 10
<212> TYPE: PRT
<213> ORGANISM: Homo sapiens

<400> SEQUENCE: 188

Gly Leu Phe Pro Val Thr Pro Glu Ala Val
1               5                   10

<210> SEQ ID NO 189
<211> LENGTH: 9
<212> TYPE: PRT
<213> ORGANISM: Homo sapiens

<400> SEQUENCE: 189

Ala Leu Gln Arg Lys Leu Pro Tyr Val
1               5

<210> SEQ ID NO 190
<211> LENGTH: 9
<212> TYPE: PRT
<213> ORGANISM: Homo sapiens

<400> SEQUENCE: 190

Phe Leu Ser Ser Leu Thr Glu Thr Ile
1               5

<210> SEQ ID NO 191
<211> LENGTH: 11
<212> TYPE: PRT
<213> ORGANISM: Homo sapiens

<400> SEQUENCE: 191

Leu Leu Gln Glu Gly Gln Ala Leu Glu Tyr Val
1               5                   10

<210> SEQ ID NO 192
<211> LENGTH: 10
<212> TYPE: PRT
<213> ORGANISM: Homo sapiens

<400> SEQUENCE: 192

Lys Met Leu Asp Gly Ala Ser Phe Thr Leu
1               5                   10

<210> SEQ ID NO 193
<211> LENGTH: 11
<212> TYPE: PRT
<213> ORGANISM: Homo sapiens

<400> SEQUENCE: 193

Gln Leu Leu Asp Ala Asp Gly Phe Leu Asn Val
1               5                   10

<210> SEQ ID NO 194
<211> LENGTH: 9
<212> TYPE: PRT
<213> ORGANISM: Homo sapiens

<400> SEQUENCE: 194

Ala Leu Pro Leu Phe Val Ile Thr Val
1               5

<210> SEQ ID NO 195

```
<211> LENGTH: 10
<212> TYPE: PRT
<213> ORGANISM: Homo sapiens

<400> SEQUENCE: 195

Gly Leu Phe Ala Asp Leu Leu Pro Arg Leu
1               5                   10

<210> SEQ ID NO 196
<211> LENGTH: 9
<212> TYPE: PRT
<213> ORGANISM: Homo sapiens

<400> SEQUENCE: 196

Tyr Leu Tyr Ser Val Glu Ile Lys Leu
1               5

<210> SEQ ID NO 197
<211> LENGTH: 9
<212> TYPE: PRT
<213> ORGANISM: Homo sapiens

<400> SEQUENCE: 197

Ala Leu Gly Pro Glu Gly Gly Arg Val
1               5

<210> SEQ ID NO 198
<211> LENGTH: 9
<212> TYPE: PRT
<213> ORGANISM: Homo sapiens

<400> SEQUENCE: 198

Lys Thr Ile Asn Lys Val Pro Thr Val
1               5

<210> SEQ ID NO 199
<211> LENGTH: 10
<212> TYPE: PRT
<213> ORGANISM: Homo sapiens

<400> SEQUENCE: 199

Ala Leu Gln Asp Val Pro Leu Ser Ser Val
1               5                   10

<210> SEQ ID NO 200
<211> LENGTH: 9
<212> TYPE: PRT
<213> ORGANISM: Homo sapiens

<400> SEQUENCE: 200

Leu Leu Phe Gly Ser Val Gln Glu Val
1               5

<210> SEQ ID NO 201
<211> LENGTH: 9
<212> TYPE: PRT
<213> ORGANISM: Homo sapiens

<400> SEQUENCE: 201

Arg Leu Val Asp Tyr Leu Glu Gly Ile
1               5

<210> SEQ ID NO 202
<211> LENGTH: 12
<212> TYPE: PRT
```

<213> ORGANISM: Homo sapiens

<400> SEQUENCE: 202

Ala Leu Leu Asp Gln Gln Gly Ser Arg Trp Thr Leu
1               5                   10

<210> SEQ ID NO 203
<211> LENGTH: 11
<212> TYPE: PRT
<213> ORGANISM: Homo sapiens

<400> SEQUENCE: 203

Val Leu Leu Glu Asp Ala His Ser His Thr Leu
1               5                   10

<210> SEQ ID NO 204
<211> LENGTH: 9
<212> TYPE: PRT
<213> ORGANISM: Homo sapiens

<400> SEQUENCE: 204

Lys Ile Ala Glu Asn Val Glu Glu Val
1               5

<210> SEQ ID NO 205
<211> LENGTH: 11
<212> TYPE: PRT
<213> ORGANISM: Homo sapiens

<400> SEQUENCE: 205

Ser Leu Tyr Pro Gly Thr Glu Thr Met Gly Leu
1               5                   10

<210> SEQ ID NO 206
<211> LENGTH: 13
<212> TYPE: PRT
<213> ORGANISM: Homo sapiens

<400> SEQUENCE: 206

Val Leu Gln Glu Gly Lys Leu Gln Lys Leu Ala Gln Leu
1               5                   10

<210> SEQ ID NO 207
<211> LENGTH: 9
<212> TYPE: PRT
<213> ORGANISM: Homo sapiens

<400> SEQUENCE: 207

Gly Leu Thr Ser Thr Asn Ala Glu Val
1               5

<210> SEQ ID NO 208
<211> LENGTH: 9
<212> TYPE: PRT
<213> ORGANISM: Homo sapiens

<400> SEQUENCE: 208

Lys Ile Ser Pro Val Thr Phe Ser Val
1               5

<210> SEQ ID NO 209
<211> LENGTH: 9
<212> TYPE: PRT
<213> ORGANISM: Homo sapiens

<400> SEQUENCE: 209

Lys Leu Ile Glu Ser Lys His Glu Val
1               5

<210> SEQ ID NO 210
<211> LENGTH: 9
<212> TYPE: PRT
<213> ORGANISM: Homo sapiens

<400> SEQUENCE: 210

Leu Leu Leu Asn Ala Val Leu Thr Val
1               5

<210> SEQ ID NO 211
<211> LENGTH: 9
<212> TYPE: PRT
<213> ORGANISM: Homo sapiens

<400> SEQUENCE: 211

Leu Leu Trp Pro Gly Ala Ala Leu Leu
1               5

<210> SEQ ID NO 212
<211> LENGTH: 10
<212> TYPE: PRT
<213> ORGANISM: Homo sapiens

<400> SEQUENCE: 212

Ala Leu Trp Asp Gln Asp Asn Leu Ser Val
1               5                   10

<210> SEQ ID NO 213
<211> LENGTH: 11
<212> TYPE: PRT
<213> ORGANISM: Homo sapiens

<400> SEQUENCE: 213

Val Thr Ala Ala Tyr Met Asp Thr Val Ser Leu
1               5                   10

<210> SEQ ID NO 214
<211> LENGTH: 10
<212> TYPE: PRT
<213> ORGANISM: Homo sapiens

<400> SEQUENCE: 214

Phe Leu Leu Asp Leu Asp Pro Leu Leu Leu
1               5                   10

<210> SEQ ID NO 215
<211> LENGTH: 9
<212> TYPE: PRT
<213> ORGANISM: Homo sapiens

<400> SEQUENCE: 215

Gln Leu Ile Asn His Leu His Ala Val
1               5

<210> SEQ ID NO 216
<211> LENGTH: 9
<212> TYPE: PRT
<213> ORGANISM: Homo sapiens

<400> SEQUENCE: 216

```
Asn Leu Trp Glu Asp Pro Tyr Tyr Leu
1               5

<210> SEQ ID NO 217
<211> LENGTH: 9
<212> TYPE: PRT
<213> ORGANISM: Homo sapiens

<400> SEQUENCE: 217

Ala Leu Ile His Pro Val Ser Thr Val
1               5

<210> SEQ ID NO 218
<211> LENGTH: 9
<212> TYPE: PRT
<213> ORGANISM: Homo sapiens

<400> SEQUENCE: 218

Ser Ala Leu Glu Glu Leu Val Asn Val
1               5

<210> SEQ ID NO 219
<211> LENGTH: 9
<212> TYPE: PRT
<213> ORGANISM: Homo sapiens

<400> SEQUENCE: 219

Lys Leu Ser Asp Ile Gly Ile Thr Val
1               5

<210> SEQ ID NO 220
<211> LENGTH: 9
<212> TYPE: PRT
<213> ORGANISM: Homo sapiens

<400> SEQUENCE: 220

Leu Leu Gln Lys Phe Val Pro Glu Ile
1               5

<210> SEQ ID NO 221
<211> LENGTH: 9
<212> TYPE: PRT
<213> ORGANISM: Homo sapiens

<400> SEQUENCE: 221

Ala Leu Tyr Glu Glu Gly Leu Leu Leu
1               5

<210> SEQ ID NO 222
<211> LENGTH: 9
<212> TYPE: PRT
<213> ORGANISM: Homo sapiens

<400> SEQUENCE: 222

Asn Leu Ile Glu Asn Val Gln Arg Leu
1               5

<210> SEQ ID NO 223
<211> LENGTH: 10
<212> TYPE: PRT
<213> ORGANISM: Homo sapiens

<400> SEQUENCE: 223

Ala Leu Leu Glu Asn Ile Ala Leu Tyr Leu
1               5                   10
```

<210> SEQ ID NO 224
<211> LENGTH: 9
<212> TYPE: PRT
<213> ORGANISM: Homo sapiens

<400> SEQUENCE: 224

Thr Leu Ile Asp Ala Gln Trp Val Leu
1               5

<210> SEQ ID NO 225
<211> LENGTH: 9
<212> TYPE: PRT
<213> ORGANISM: Homo sapiens

<400> SEQUENCE: 225

Ser Leu Leu Lys Val Leu Pro Ala Leu
1               5

<210> SEQ ID NO 226
<211> LENGTH: 9
<212> TYPE: PRT
<213> ORGANISM: Homo sapiens

<400> SEQUENCE: 226

Met Leu Tyr Val Val Pro Ile Tyr Leu
1               5

<210> SEQ ID NO 227
<211> LENGTH: 9
<212> TYPE: PRT
<213> ORGANISM: Homo sapiens

<400> SEQUENCE: 227

Ala Leu Met Asn Thr Leu Leu Tyr Leu
1               5

<210> SEQ ID NO 228
<211> LENGTH: 9
<212> TYPE: PRT
<213> ORGANISM: Homo sapiens

<400> SEQUENCE: 228

Ala Met Gln Glu Tyr Ile Ala Val Val
1               5

<210> SEQ ID NO 229
<211> LENGTH: 9
<212> TYPE: PRT
<213> ORGANISM: Homo sapiens

<400> SEQUENCE: 229

Arg Leu Pro Gly Pro Leu Gly Thr Val
1               5

<210> SEQ ID NO 230
<211> LENGTH: 9
<212> TYPE: PRT
<213> ORGANISM: Homo sapiens

<400> SEQUENCE: 230

Ile Leu Val Asp Trp Leu Val Glu Val
1               5

```
<210> SEQ ID NO 231
<211> LENGTH: 11
<212> TYPE: PRT
<213> ORGANISM: Homo sapiens

<400> SEQUENCE: 231

Phe Leu Ser Pro Gln Gln Pro Pro Leu Leu Leu
1               5                   10

<210> SEQ ID NO 232
<211> LENGTH: 12
<212> TYPE: PRT
<213> ORGANISM: Homo sapiens

<400> SEQUENCE: 232

Ala Leu Leu Glu Ala Gln Asp Val Glu Leu Tyr Leu
1               5                   10

<210> SEQ ID NO 233
<211> LENGTH: 9
<212> TYPE: PRT
<213> ORGANISM: Homo sapiens

<400> SEQUENCE: 233

Val Leu Ser Glu Thr Leu Tyr Glu Leu
1               5

<210> SEQ ID NO 234
<211> LENGTH: 11
<212> TYPE: PRT
<213> ORGANISM: Homo sapiens

<400> SEQUENCE: 234

Ala Leu Met Glu Asp Thr Gly Arg Gln Met Leu
1               5                   10

<210> SEQ ID NO 235
<211> LENGTH: 10
<212> TYPE: PRT
<213> ORGANISM: Homo sapiens

<400> SEQUENCE: 235

Tyr Leu Asn Asp Leu His Glu Val Leu Leu
1               5                   10

<210> SEQ ID NO 236
<211> LENGTH: 9
<212> TYPE: PRT
<213> ORGANISM: Homo sapiens

<400> SEQUENCE: 236

Gly Leu Leu Glu Ala Lys Val Ser Leu
1               5

<210> SEQ ID NO 237
<211> LENGTH: 11
<212> TYPE: PRT
<213> ORGANISM: Homo sapiens

<400> SEQUENCE: 237

Ala Leu Leu Glu Ala Ser Gly Thr Leu Leu Leu
1               5                   10

<210> SEQ ID NO 238
<211> LENGTH: 9
```

```
<212> TYPE: PRT
<213> ORGANISM: Homo sapiens

<400> SEQUENCE: 238

Tyr Leu Ile Ser Phe Gln Thr His Ile
1               5

<210> SEQ ID NO 239
<211> LENGTH: 10
<212> TYPE: PRT
<213> ORGANISM: Homo sapiens

<400> SEQUENCE: 239

Ala Ala Phe Ala Gly Lys Leu Leu Ser Val
1               5                   10

<210> SEQ ID NO 240
<211> LENGTH: 9
<212> TYPE: PRT
<213> ORGANISM: Homo sapiens

<400> SEQUENCE: 240

Ile Leu Leu Glu Gln Ala Phe Tyr Leu
1               5

<210> SEQ ID NO 241
<211> LENGTH: 11
<212> TYPE: PRT
<213> ORGANISM: Homo sapiens

<400> SEQUENCE: 241

Ser Leu Val Glu Val Asn Pro Ala Tyr Ser Val
1               5                   10

<210> SEQ ID NO 242
<211> LENGTH: 9
<212> TYPE: PRT
<213> ORGANISM: Homo sapiens

<400> SEQUENCE: 242

Ala Ile Ala Tyr Ile Leu Gln Gly Val
1               5

<210> SEQ ID NO 243
<211> LENGTH: 9
<212> TYPE: PRT
<213> ORGANISM: Homo sapiens

<400> SEQUENCE: 243

Leu Leu Leu Asn Glu Leu Pro Ser Val
1               5

<210> SEQ ID NO 244
<211> LENGTH: 10
<212> TYPE: PRT
<213> ORGANISM: Homo sapiens

<400> SEQUENCE: 244

Ser Leu Phe Gly Gly Thr Glu Ile Thr Ile
1               5                   10

<210> SEQ ID NO 245
<211> LENGTH: 9
<212> TYPE: PRT
<213> ORGANISM: Homo sapiens
```

<400> SEQUENCE: 245

Ser Met Ile Asp Asp Leu Leu Gly Val
1               5

<210> SEQ ID NO 246
<211> LENGTH: 9
<212> TYPE: PRT
<213> ORGANISM: Homo sapiens

<400> SEQUENCE: 246

Leu Leu Trp Glu Val Val Ser Gln Leu
1               5

<210> SEQ ID NO 247
<211> LENGTH: 11
<212> TYPE: PRT
<213> ORGANISM: Homo sapiens

<400> SEQUENCE: 247

Val Leu Leu Pro Asn Asp Leu Leu Glu Lys Val
1               5                   10

<210> SEQ ID NO 248
<211> LENGTH: 10
<212> TYPE: PRT
<213> ORGANISM: Homo sapiens

<400> SEQUENCE: 248

Phe Leu Phe Pro Asn Gln Tyr Val Asp Val
1               5                   10

<210> SEQ ID NO 249
<211> LENGTH: 9
<212> TYPE: PRT
<213> ORGANISM: Homo sapiens

<400> SEQUENCE: 249

Leu Leu Asp Gly Phe Leu Val Asn Val
1               5

<210> SEQ ID NO 250
<211> LENGTH: 11
<212> TYPE: PRT
<213> ORGANISM: Homo sapiens

<400> SEQUENCE: 250

Ala Leu Ser Glu Glu Gly Leu Leu Val Tyr Leu
1               5                   10

<210> SEQ ID NO 251
<211> LENGTH: 10
<212> TYPE: PRT
<213> ORGANISM: Homo sapiens

<400> SEQUENCE: 251

Ala Leu Tyr Thr Gly Phe Ser Ile Leu Val
1               5                   10

<210> SEQ ID NO 252
<211> LENGTH: 9
<212> TYPE: PRT
<213> ORGANISM: Homo sapiens

<400> SEQUENCE: 252

```
Leu Leu Ile Gly Thr Asp Val Ser Leu
1               5

<210> SEQ ID NO 253
<211> LENGTH: 9
<212> TYPE: PRT
<213> ORGANISM: Homo sapiens

<400> SEQUENCE: 253

Gly Leu Asp Ala Ala Thr Ala Thr Val
1               5

<210> SEQ ID NO 254
<211> LENGTH: 9
<212> TYPE: PRT
<213> ORGANISM: Homo sapiens

<400> SEQUENCE: 254

Thr Leu Leu Ala Phe Ile Met Glu Leu
1               5

<210> SEQ ID NO 255
<211> LENGTH: 9
<212> TYPE: PRT
<213> ORGANISM: Homo sapiens

<400> SEQUENCE: 255

Val Leu Ala Ser Tyr Asn Leu Thr Val
1               5

<210> SEQ ID NO 256
<211> LENGTH: 11
<212> TYPE: PRT
<213> ORGANISM: Homo sapiens

<400> SEQUENCE: 256

Phe Leu Pro Pro Glu His Thr Ile Val Tyr Ile
1               5                   10

<210> SEQ ID NO 257
<211> LENGTH: 9
<212> TYPE: PRT
<213> ORGANISM: Homo sapiens

<400> SEQUENCE: 257

Ser Ile Phe Ser Ala Phe Leu Ser Val
1               5

<210> SEQ ID NO 258
<211> LENGTH: 9
<212> TYPE: PRT
<213> ORGANISM: Homo sapiens

<400> SEQUENCE: 258

Glu Leu Ala Glu Arg Val Pro Ala Ile
1               5

<210> SEQ ID NO 259
<211> LENGTH: 9
<212> TYPE: PRT
<213> ORGANISM: Homo sapiens

<400> SEQUENCE: 259

Thr Leu Met Arg Gln Leu Gln Gln Val
```

```
<210> SEQ ID NO 260
<211> LENGTH: 13
<212> TYPE: PRT
<213> ORGANISM: Homo sapiens

<400> SEQUENCE: 260

Thr Leu Leu Glu Gly Pro Asp Pro Ala Glu Leu Leu Leu
1               5                   10

<210> SEQ ID NO 261
<211> LENGTH: 9
<212> TYPE: PRT
<213> ORGANISM: Homo sapiens

<400> SEQUENCE: 261

Tyr Val Leu Glu Phe Leu Glu Glu Ile
1               5

<210> SEQ ID NO 262
<211> LENGTH: 9
<212> TYPE: PRT
<213> ORGANISM: Homo sapiens

<400> SEQUENCE: 262

Leu Leu Trp Gly Asp Leu Ile Trp Leu
1               5

<210> SEQ ID NO 263
<211> LENGTH: 10
<212> TYPE: PRT
<213> ORGANISM: Homo sapiens

<400> SEQUENCE: 263

Leu Leu Val Ser Asn Leu Asp Phe Gly Val
1               5                   10

<210> SEQ ID NO 264
<211> LENGTH: 9
<212> TYPE: PRT
<213> ORGANISM: Homo sapiens

<400> SEQUENCE: 264

Ser Leu Gln Glu Gln Leu His Ser Val
1               5

<210> SEQ ID NO 265
<211> LENGTH: 9
<212> TYPE: PRT
<213> ORGANISM: Homo sapiens

<400> SEQUENCE: 265

Leu Leu Phe Gly Gly Thr Lys Thr Val
1               5

<210> SEQ ID NO 266
<211> LENGTH: 9
<212> TYPE: PRT
<213> ORGANISM: Homo sapiens

<400> SEQUENCE: 266

Lys Ile Thr Asp Thr Leu Ile His Leu
1               5
```

```
<210> SEQ ID NO 267
<211> LENGTH: 9
<212> TYPE: PRT
<213> ORGANISM: Homo sapiens

<400> SEQUENCE: 267

Ala Leu Gln Asp Phe Leu Leu Ser Val
1               5

<210> SEQ ID NO 268
<211> LENGTH: 9
<212> TYPE: PRT
<213> ORGANISM: Homo sapiens

<400> SEQUENCE: 268

Ile Ala Gly Pro Gly Leu Pro Asp Leu
1               5

<210> SEQ ID NO 269
<211> LENGTH: 11
<212> TYPE: PRT
<213> ORGANISM: Homo sapiens

<400> SEQUENCE: 269

Arg Val Leu Glu Val Gly Ala Leu Gln Ala Val
1               5                   10

<210> SEQ ID NO 270
<211> LENGTH: 11
<212> TYPE: PRT
<213> ORGANISM: Homo sapiens

<400> SEQUENCE: 270

Leu Leu Leu Asp Glu Glu Gly Thr Phe Ser Leu
1               5                   10

<210> SEQ ID NO 271
<211> LENGTH: 10
<212> TYPE: PRT
<213> ORGANISM: Homo sapiens

<400> SEQUENCE: 271

Leu Val Tyr Pro Leu Glu Leu Tyr Pro Ala
1               5                   10

<210> SEQ ID NO 272
<211> LENGTH: 9
<212> TYPE: PRT
<213> ORGANISM: Homo sapiens

<400> SEQUENCE: 272

Ala Leu Gly Asn Thr Val Pro Ala Val
1               5

<210> SEQ ID NO 273
<211> LENGTH: 9
<212> TYPE: PRT
<213> ORGANISM: Homo sapiens

<400> SEQUENCE: 273

Asn Leu Phe Gln Ser Val Arg Glu Val
1               5

<210> SEQ ID NO 274
```

```
<211> LENGTH: 9
<212> TYPE: PRT
<213> ORGANISM: Homo sapiens

<400> SEQUENCE: 274

Ser Leu Leu Phe Ser Leu Phe Glu Ala
1               5

<210> SEQ ID NO 275
<211> LENGTH: 9
<212> TYPE: PRT
<213> ORGANISM: Homo sapiens

<400> SEQUENCE: 275

Tyr Leu Val Tyr Ile Leu Asn Glu Leu
1               5

<210> SEQ ID NO 276
<211> LENGTH: 10
<212> TYPE: PRT
<213> ORGANISM: Homo sapiens

<400> SEQUENCE: 276

Ala Leu Phe Thr Phe Ser Pro Leu Thr Val
1               5                  10

<210> SEQ ID NO 277
<211> LENGTH: 11
<212> TYPE: PRT
<213> ORGANISM: Homo sapiens

<400> SEQUENCE: 277

Leu Leu Pro Pro Leu Glu Ser Leu Ala Thr Val
1               5                  10

<210> SEQ ID NO 278
<211> LENGTH: 9
<212> TYPE: PRT
<213> ORGANISM: Homo sapiens

<400> SEQUENCE: 278

Gln Leu Leu Asp Val Val Leu Thr Ile
1               5

<210> SEQ ID NO 279
<211> LENGTH: 10
<212> TYPE: PRT
<213> ORGANISM: Homo sapiens

<400> SEQUENCE: 279

Ala Leu Trp Gly Gly Thr Gln Pro Leu Leu
1               5                  10

<210> SEQ ID NO 280
<211> LENGTH: 11
<212> TYPE: PRT
<213> ORGANISM: Homo sapiens

<400> SEQUENCE: 280

Val Leu Pro Asp Pro Glu Val Leu Glu Ala Val
1               5                  10

<210> SEQ ID NO 281
<211> LENGTH: 9
<212> TYPE: PRT
```

<213> ORGANISM: Homo sapiens

<400> SEQUENCE: 281

Ile Leu Arg Glu Ser Thr Glu Glu Leu
1               5

<210> SEQ ID NO 282
<211> LENGTH: 9
<212> TYPE: PRT
<213> ORGANISM: Homo sapiens

<400> SEQUENCE: 282

Leu Leu Ala Asp Val Val Pro Thr Thr
1               5

<210> SEQ ID NO 283
<211> LENGTH: 13
<212> TYPE: PRT
<213> ORGANISM: Homo sapiens

<400> SEQUENCE: 283

Ala Leu Tyr Ile Gly Asp Gly Tyr Val Ile His Leu Ala
1               5                   10

<210> SEQ ID NO 284
<211> LENGTH: 9
<212> TYPE: PRT
<213> ORGANISM: Homo sapiens

<400> SEQUENCE: 284

Ile Leu Leu Ser Gln Thr Thr Gly Val
1               5

<210> SEQ ID NO 285
<211> LENGTH: 9
<212> TYPE: PRT
<213> ORGANISM: Homo sapiens

<400> SEQUENCE: 285

Gln Leu Leu His Val Gly Val Thr Val
1               5

<210> SEQ ID NO 286
<211> LENGTH: 9
<212> TYPE: PRT
<213> ORGANISM: Homo sapiens

<400> SEQUENCE: 286

Tyr Leu Phe Pro Gly Ile Pro Glu Leu
1               5

<210> SEQ ID NO 287
<211> LENGTH: 9
<212> TYPE: PRT
<213> ORGANISM: Homo sapiens

<400> SEQUENCE: 287

Phe Leu Asn Glu Phe Phe Leu Asn Val
1               5

<210> SEQ ID NO 288
<211> LENGTH: 9
<212> TYPE: PRT
<213> ORGANISM: Homo sapiens

<400> SEQUENCE: 288

Asn Leu Ile Asn Glu Ile Asn Gly Val
1               5

<210> SEQ ID NO 289
<211> LENGTH: 10
<212> TYPE: PRT
<213> ORGANISM: Homo sapiens

<400> SEQUENCE: 289

Val Leu Leu Glu Ile Glu Asp Leu Gln Val
1               5                   10

<210> SEQ ID NO 290
<211> LENGTH: 12
<212> TYPE: PRT
<213> ORGANISM: Homo sapiens

<400> SEQUENCE: 290

Gly Leu Leu Asp Leu Asn Asn Ala Ile Leu Gln Leu
1               5                   10

<210> SEQ ID NO 291
<211> LENGTH: 11
<212> TYPE: PRT
<213> ORGANISM: Homo sapiens

<400> SEQUENCE: 291

Gly Leu Asp Ser Asn Leu Lys Tyr Ile Leu Val
1               5                   10

<210> SEQ ID NO 292
<211> LENGTH: 9
<212> TYPE: PRT
<213> ORGANISM: Homo sapiens

<400> SEQUENCE: 292

Leu Leu Trp Glu Ala Gly Ser Glu Ala
1               5

<210> SEQ ID NO 293
<211> LENGTH: 10
<212> TYPE: PRT
<213> ORGANISM: Homo sapiens

<400> SEQUENCE: 293

Gly Leu Gly Glu Leu Gln Glu Leu Tyr Leu
1               5                   10

<210> SEQ ID NO 294
<211> LENGTH: 9
<212> TYPE: PRT
<213> ORGANISM: Homo sapiens

<400> SEQUENCE: 294

Ile Leu Asp Pro Phe Gln Tyr Gln Leu
1               5

<210> SEQ ID NO 295
<211> LENGTH: 9
<212> TYPE: PRT
<213> ORGANISM: Homo sapiens

<400> SEQUENCE: 295

-continued

Val Leu Asp Arg Glu Ser Pro Asn Val
1               5

<210> SEQ ID NO 296
<211> LENGTH: 9
<212> TYPE: PRT
<213> ORGANISM: Homo sapiens

<400> SEQUENCE: 296

Phe Met Glu Gly Ala Ile Ile Tyr Val
1               5

<210> SEQ ID NO 297
<211> LENGTH: 10
<212> TYPE: PRT
<213> ORGANISM: Homo sapiens

<400> SEQUENCE: 297

Val Leu Ala Asp Ile Glu Leu Ala Gln Ala
1               5                   10

<210> SEQ ID NO 298
<211> LENGTH: 9
<212> TYPE: PRT
<213> ORGANISM: Homo sapiens

<400> SEQUENCE: 298

Val Met Ile Thr Lys Leu Val Glu Val
1               5

<210> SEQ ID NO 299
<211> LENGTH: 9
<212> TYPE: PRT
<213> ORGANISM: Homo sapiens

<400> SEQUENCE: 299

Tyr Leu Leu Glu Thr Ser Gly Asn Leu
1               5

<210> SEQ ID NO 300
<211> LENGTH: 9
<212> TYPE: PRT
<213> ORGANISM: Homo sapiens

<400> SEQUENCE: 300

Ala Leu Leu Gly Gln Thr Phe Ser Leu
1               5

<210> SEQ ID NO 301
<211> LENGTH: 10
<212> TYPE: PRT
<213> ORGANISM: Homo sapiens

<400> SEQUENCE: 301

Phe Leu Val Glu Asp Leu Val Asp Ser Leu
1               5                   10

<210> SEQ ID NO 302
<211> LENGTH: 11
<212> TYPE: PRT
<213> ORGANISM: Homo sapiens

<400> SEQUENCE: 302

Ala Leu Leu Gln Glu Gly Glu Val Tyr Ser Ala
1               5                   10

```
<210> SEQ ID NO 303
<211> LENGTH: 9
<212> TYPE: PRT
<213> ORGANISM: Homo sapiens

<400> SEQUENCE: 303

Ala Ile Leu Pro Gln Leu Phe Met Val
1               5

<210> SEQ ID NO 304
<211> LENGTH: 9
<212> TYPE: PRT
<213> ORGANISM: Homo sapiens

<400> SEQUENCE: 304

Met Thr Leu Gly Gln Ile Tyr Tyr Leu
1               5

<210> SEQ ID NO 305
<211> LENGTH: 10
<212> TYPE: PRT
<213> ORGANISM: Homo sapiens

<400> SEQUENCE: 305

Ser Ile Ala Asn Phe Ser Glu Phe Tyr Val
1               5                   10

<210> SEQ ID NO 306
<211> LENGTH: 9
<212> TYPE: PRT
<213> ORGANISM: Homo sapiens

<400> SEQUENCE: 306

Ala Leu Val Asn Val Gln Ile Pro Leu
1               5

<210> SEQ ID NO 307
<211> LENGTH: 9
<212> TYPE: PRT
<213> ORGANISM: Homo sapiens

<400> SEQUENCE: 307

Ala Leu Pro Val Ser Leu Pro Gln Ile
1               5

<210> SEQ ID NO 308
<211> LENGTH: 10
<212> TYPE: PRT
<213> ORGANISM: Homo sapiens

<400> SEQUENCE: 308

Ser Gln Tyr Ser Gly Gln Leu His Glu Val
1               5                   10

<210> SEQ ID NO 309
<211> LENGTH: 10
<212> TYPE: PRT
<213> ORGANISM: Homo sapiens

<400> SEQUENCE: 309

Gly Leu Phe Asp Gly Val Pro Thr Thr Ala
1               5                   10
```

```
<210> SEQ ID NO 310
<211> LENGTH: 10
<212> TYPE: PRT
<213> ORGANISM: Homo sapiens

<400> SEQUENCE: 310

Phe Leu Val Asp Thr Pro Leu Ala Arg Ala
1               5                   10

<210> SEQ ID NO 311
<211> LENGTH: 9
<212> TYPE: PRT
<213> ORGANISM: Homo sapiens

<400> SEQUENCE: 311

Arg Leu Tyr Thr Gly Met His Thr Val
1               5

<210> SEQ ID NO 312
<211> LENGTH: 9
<212> TYPE: PRT
<213> ORGANISM: Homo sapiens

<400> SEQUENCE: 312

Ile Ile Ser Asp Leu Thr Ile Ala Leu
1               5

<210> SEQ ID NO 313
<211> LENGTH: 10
<212> TYPE: PRT
<213> ORGANISM: Homo sapiens

<400> SEQUENCE: 313

Val Leu Phe Asp Asp Glu Leu Leu Met Val
1               5                   10

<210> SEQ ID NO 314
<211> LENGTH: 10
<212> TYPE: PRT
<213> ORGANISM: Homo sapiens

<400> SEQUENCE: 314

Ala Leu Ile Ala Glu Gly Ile Ala Leu Val
1               5                   10

<210> SEQ ID NO 315
<211> LENGTH: 9
<212> TYPE: PRT
<213> ORGANISM: Homo sapiens

<400> SEQUENCE: 315

Tyr Leu Gln Asp Val Val Glu Gln Ala
1               5

<210> SEQ ID NO 316
<211> LENGTH: 9
<212> TYPE: PRT
<213> ORGANISM: Homo sapiens

<400> SEQUENCE: 316

Ile Leu Leu Glu Arg Leu Trp Tyr Val
1               5

<210> SEQ ID NO 317
<211> LENGTH: 9
```

```
<212> TYPE: PRT
<213> ORGANISM: Homo sapiens

<400> SEQUENCE: 317

Ser Leu Ala Ala Leu Val Val His Val
1               5

<210> SEQ ID NO 318
<211> LENGTH: 10
<212> TYPE: PRT
<213> ORGANISM: Homo sapiens

<400> SEQUENCE: 318

Gly Leu Ile Asn Thr Gly Val Leu Ser Val
1               5                   10

<210> SEQ ID NO 319
<211> LENGTH: 9
<212> TYPE: PRT
<213> ORGANISM: Homo sapiens

<400> SEQUENCE: 319

Ser Leu Glu Pro Gln Ile Gln Pro Val
1               5

<210> SEQ ID NO 320
<211> LENGTH: 10
<212> TYPE: PRT
<213> ORGANISM: Homo sapiens

<400> SEQUENCE: 320

Lys Met Phe Glu Phe Val Glu Pro Leu Leu
1               5                   10

<210> SEQ ID NO 321
<211> LENGTH: 13
<212> TYPE: PRT
<213> ORGANISM: Homo sapiens

<400> SEQUENCE: 321

Gly Leu Phe Glu Asp Val Thr Gln Pro Gly Ile Leu Leu
1               5                   10

<210> SEQ ID NO 322
<211> LENGTH: 9
<212> TYPE: PRT
<213> ORGANISM: Homo sapiens

<400> SEQUENCE: 322

Thr Leu Met Thr Ser Leu Pro Ala Leu
1               5

<210> SEQ ID NO 323
<211> LENGTH: 11
<212> TYPE: PRT
<213> ORGANISM: Homo sapiens

<400> SEQUENCE: 323

Ile Gln Ile Gly Glu Glu Thr Val Ile Thr Val
1               5                   10

<210> SEQ ID NO 324
<211> LENGTH: 10
<212> TYPE: PRT
<213> ORGANISM: Homo sapiens
```

<400> SEQUENCE: 324

Phe Leu Tyr Asp Glu Ile Glu Ala Glu Val
1               5                   10

<210> SEQ ID NO 325
<211> LENGTH: 13
<212> TYPE: PRT
<213> ORGANISM: Homo sapiens

<400> SEQUENCE: 325

Phe Ile Met Pro Ala Thr Val Ala Asp Ala Thr Ala Val
1               5                   10

<210> SEQ ID NO 326
<211> LENGTH: 9
<212> TYPE: PRT
<213> ORGANISM: Homo sapiens

<400> SEQUENCE: 326

Phe Leu Pro Glu Ala Leu Asp Phe Val
1               5

<210> SEQ ID NO 327
<211> LENGTH: 12
<212> TYPE: PRT
<213> ORGANISM: Homo sapiens

<400> SEQUENCE: 327

Gly Leu Ala Pro Phe Thr Glu Gly Ile Ser Phe Val
1               5                   10

<210> SEQ ID NO 328
<211> LENGTH: 9
<212> TYPE: PRT
<213> ORGANISM: Homo sapiens

<400> SEQUENCE: 328

Ala Leu Asn Asp Gln Val Phe Glu Ile
1               5

<210> SEQ ID NO 329
<211> LENGTH: 10
<212> TYPE: PRT
<213> ORGANISM: Homo sapiens

<400> SEQUENCE: 329

Phe Leu Val Thr Leu Asn Asn Val Glu Val
1               5                   10

<210> SEQ ID NO 330
<211> LENGTH: 9
<212> TYPE: PRT
<213> ORGANISM: Homo sapiens

<400> SEQUENCE: 330

Gln Leu Ala Leu Lys Val Glu Gly Val
1               5

<210> SEQ ID NO 331
<211> LENGTH: 9
<212> TYPE: PRT
<213> ORGANISM: Homo sapiens

<400> SEQUENCE: 331

Lys Val Asp Thr Val Trp Val Asn Val
1               5

<210> SEQ ID NO 332
<211> LENGTH: 9
<212> TYPE: PRT
<213> ORGANISM: Homo sapiens

<400> SEQUENCE: 332

Tyr Leu Ile Ser Glu Leu Glu Ala Ala
1               5

<210> SEQ ID NO 333
<211> LENGTH: 9
<212> TYPE: PRT
<213> ORGANISM: Homo sapiens

<400> SEQUENCE: 333

Phe Leu Pro Asp Ala Asn Ser Ser Val
1               5

<210> SEQ ID NO 334
<211> LENGTH: 9
<212> TYPE: PRT
<213> ORGANISM: Homo sapiens

<400> SEQUENCE: 334

Thr Leu Thr Lys Val Leu Val Ala Leu
1               5

<210> SEQ ID NO 335
<211> LENGTH: 9
<212> TYPE: PRT
<213> ORGANISM: Homo sapiens

<400> SEQUENCE: 335

Tyr Ser Leu Ser Ser Val Val Thr Val
1               5

<210> SEQ ID NO 336
<211> LENGTH: 9
<212> TYPE: PRT
<213> ORGANISM: Homo sapiens

<400> SEQUENCE: 336

Ile Leu Leu Thr Ala Ile Val Gln Val
1               5

<210> SEQ ID NO 337
<211> LENGTH: 12
<212> TYPE: PRT
<213> ORGANISM: Homo sapiens

<400> SEQUENCE: 337

His Leu Leu Ser Glu Leu Glu Ala Ala Pro Tyr Leu
1               5                   10

<210> SEQ ID NO 338
<211> LENGTH: 10
<212> TYPE: PRT
<213> ORGANISM: Homo sapiens

<400> SEQUENCE: 338

Ser Val Leu Glu Asp Pro Val His Ala Val

```
1               5                  10
```

<210> SEQ ID NO 339
<211> LENGTH: 13
<212> TYPE: PRT
<213> ORGANISM: Homo sapiens

<400> SEQUENCE: 339

```
Gly Leu Trp Glu Ile Glu Asn Asn Pro Thr Val Lys Ala
1               5                  10
```

<210> SEQ ID NO 340
<211> LENGTH: 9
<212> TYPE: PRT
<213> ORGANISM: Homo sapiens

<400> SEQUENCE: 340

```
Ala Leu Leu Ser Met Thr Phe Pro Leu
1               5
```

<210> SEQ ID NO 341
<211> LENGTH: 12
<212> TYPE: PRT
<213> ORGANISM: Homo sapiens

<400> SEQUENCE: 341

```
Ser Gln Ile Ala Leu Asn Glu Lys Leu Val Asn Leu
1               5                  10
```

<210> SEQ ID NO 342
<211> LENGTH: 9
<212> TYPE: PRT
<213> ORGANISM: Homo sapiens

<400> SEQUENCE: 342

```
His Ile Tyr Asp Lys Val Met Thr Val
1               5
```

<210> SEQ ID NO 343
<211> LENGTH: 11
<212> TYPE: PRT
<213> ORGANISM: Homo sapiens

<400> SEQUENCE: 343

```
Ser Leu Leu Glu Val Asn Glu Glu Ser Thr Val
1               5                  10
```

<210> SEQ ID NO 344
<211> LENGTH: 11
<212> TYPE: PRT
<213> ORGANISM: Homo sapiens

<400> SEQUENCE: 344

```
Tyr Leu Gln Asp Gln His Leu Leu Leu Thr Val
1               5                  10
```

<210> SEQ ID NO 345
<211> LENGTH: 9
<212> TYPE: PRT
<213> ORGANISM: Homo sapiens

<400> SEQUENCE: 345

```
Val Ile Trp Lys Ala Leu Ile His Leu
1               5
```

<210> SEQ ID NO 346
<211> LENGTH: 9
<212> TYPE: PRT
<213> ORGANISM: Homo sapiens

<400> SEQUENCE: 346

Leu Leu Asp Ser Lys Val Pro Ser Val
1               5

<210> SEQ ID NO 347
<211> LENGTH: 12
<212> TYPE: PRT
<213> ORGANISM: Homo sapiens

<400> SEQUENCE: 347

Ser Leu Phe Lys His Asp Pro Ala Ala Trp Glu Ala
1               5                   10

<210> SEQ ID NO 348
<211> LENGTH: 9
<212> TYPE: PRT
<213> ORGANISM: Homo sapiens

<400> SEQUENCE: 348

Ile Leu Leu Asp Val Lys Thr Arg Leu
1               5

<210> SEQ ID NO 349
<211> LENGTH: 9
<212> TYPE: PRT
<213> ORGANISM: Homo sapiens

<400> SEQUENCE: 349

Ser Leu Thr Glu Tyr Leu Gln Asn Val
1               5

<210> SEQ ID NO 350
<211> LENGTH: 12
<212> TYPE: PRT
<213> ORGANISM: Homo sapiens

<400> SEQUENCE: 350

Ala Leu Leu Asp Val Thr His Ser Glu Leu Thr Val
1               5                   10

<210> SEQ ID NO 351
<211> LENGTH: 9
<212> TYPE: PRT
<213> ORGANISM: Homo sapiens

<400> SEQUENCE: 351

Ser Leu Ile Pro Asn Leu Arg Asn Val
1               5

<210> SEQ ID NO 352
<211> LENGTH: 10
<212> TYPE: PRT
<213> ORGANISM: Homo sapiens

<400> SEQUENCE: 352

Ser Leu Leu Glu Leu Leu His Ile Tyr Val
1               5                   10

<210> SEQ ID NO 353

-continued

```
<211> LENGTH: 9
<212> TYPE: PRT
<213> ORGANISM: Homo sapiens

<400> SEQUENCE: 353

Tyr Leu Phe Glu Met Asp Ser Ser Leu
1               5

<210> SEQ ID NO 354
<211> LENGTH: 9
<212> TYPE: PRT
<213> ORGANISM: Homo sapiens

<400> SEQUENCE: 354

Leu Ile Leu Glu Gly Val Asp Thr Val
1               5

<210> SEQ ID NO 355
<211> LENGTH: 11
<212> TYPE: PRT
<213> ORGANISM: Homo sapiens

<400> SEQUENCE: 355

Ser Ile Gln Gln Ser Ile Glu Arg Leu Leu Val
1               5                   10

<210> SEQ ID NO 356
<211> LENGTH: 9
<212> TYPE: PRT
<213> ORGANISM: Homo sapiens

<400> SEQUENCE: 356

Lys Leu Leu Gly Lys Leu Pro Glu Leu
1               5

<210> SEQ ID NO 357
<211> LENGTH: 9
<212> TYPE: PRT
<213> ORGANISM: Homo sapiens

<400> SEQUENCE: 357

Ser Met His Asp Leu Val Leu Gln Val
1               5

<210> SEQ ID NO 358
<211> LENGTH: 9
<212> TYPE: PRT
<213> ORGANISM: Homo sapiens

<400> SEQUENCE: 358

Ala Leu Asp Glu Tyr Thr Ser Glu Leu
1               5

<210> SEQ ID NO 359
<211> LENGTH: 9
<212> TYPE: PRT
<213> ORGANISM: Homo sapiens

<400> SEQUENCE: 359

Tyr Leu Leu Pro Glu Ser Val Asp Leu
1               5

<210> SEQ ID NO 360
<211> LENGTH: 11
<212> TYPE: PRT
```

```
<213> ORGANISM: Homo sapiens

<400> SEQUENCE: 360

Ala Leu Asp Ser Gly Ala Ser Leu Leu His Leu
1               5                   10

<210> SEQ ID NO 361
<211> LENGTH: 10
<212> TYPE: PRT
<213> ORGANISM: Homo sapiens

<400> SEQUENCE: 361

Ala Leu Tyr Glu Leu Glu Gly Thr Thr Val
1               5                   10

<210> SEQ ID NO 362
<211> LENGTH: 9
<212> TYPE: PRT
<213> ORGANISM: Homo sapiens

<400> SEQUENCE: 362

Thr Leu Tyr Gly Leu Ser Val Leu Leu
1               5

<210> SEQ ID NO 363
<211> LENGTH: 11
<212> TYPE: PRT
<213> ORGANISM: Homo sapiens

<400> SEQUENCE: 363

Lys Val Leu Asp Val Ser Asp Leu Glu Ser Val
1               5                   10

<210> SEQ ID NO 364
<211> LENGTH: 9
<212> TYPE: PRT
<213> ORGANISM: Homo sapiens

<400> SEQUENCE: 364

Leu Leu Gln Asn Glu Gln Phe Glu Leu
1               5

<210> SEQ ID NO 365
<211> LENGTH: 12
<212> TYPE: PRT
<213> ORGANISM: Homo sapiens

<400> SEQUENCE: 365

Tyr Val Ile Asp Gln Gly Glu Thr Asp Val Tyr Val
1               5                   10

<210> SEQ ID NO 366
<211> LENGTH: 12
<212> TYPE: PRT
<213> ORGANISM: Homo sapiens

<400> SEQUENCE: 366

Arg Leu Leu Asp Met Gly Glu Thr Asp Leu Met Leu
1               5                   10

<210> SEQ ID NO 367
<211> LENGTH: 9
<212> TYPE: PRT
<213> ORGANISM: Homo sapiens
```

```
<400> SEQUENCE: 367

Ser Leu Gln Asn His Asn His Gln Leu
1               5

<210> SEQ ID NO 368
<211> LENGTH: 10
<212> TYPE: PRT
<213> ORGANISM: Homo sapiens

<400> SEQUENCE: 368

Ile Leu Leu Glu Glu Val Ser Pro Glu Leu
1               5                   10

<210> SEQ ID NO 369
<211> LENGTH: 10
<212> TYPE: PRT
<213> ORGANISM: Homo sapiens

<400> SEQUENCE: 369

Gly Leu Phe Pro Glu His Leu Ile Asp Val
1               5                   10

<210> SEQ ID NO 370
<211> LENGTH: 9
<212> TYPE: PRT
<213> ORGANISM: Homo sapiens

<400> SEQUENCE: 370

Ser Leu Leu Gln Asp Leu Val Ser Val
1               5

<210> SEQ ID NO 371
<211> LENGTH: 9
<212> TYPE: PRT
<213> ORGANISM: Homo sapiens

<400> SEQUENCE: 371

Phe Leu Gln Ala His Leu His Thr Ala
1               5

<210> SEQ ID NO 372
<211> LENGTH: 9
<212> TYPE: PRT
<213> ORGANISM: Homo sapiens

<400> SEQUENCE: 372

Thr Met Leu Leu Asn Ile Pro Leu Val
1               5

<210> SEQ ID NO 373
<211> LENGTH: 11
<212> TYPE: PRT
<213> ORGANISM: Homo sapiens

<400> SEQUENCE: 373

Ser Leu Leu Glu Asp Lys Gly Leu Ala Glu Val
1               5                   10

<210> SEQ ID NO 374
<211> LENGTH: 10
<212> TYPE: PRT
<213> ORGANISM: Homo sapiens

<400> SEQUENCE: 374
```

Phe Leu Leu Gln Gln His Leu Ile Ser Ala
1               5                   10

<210> SEQ ID NO 375
<211> LENGTH: 9
<212> TYPE: PRT
<213> ORGANISM: Homo sapiens

<400> SEQUENCE: 375

Ser Leu Thr Glu Thr Ile Glu Gly Val
1               5

<210> SEQ ID NO 376
<211> LENGTH: 11
<212> TYPE: PRT
<213> ORGANISM: Homo sapiens

<400> SEQUENCE: 376

Ala Met Phe Glu Ser Ser Gln Asn Val Leu Leu
1               5                   10

<210> SEQ ID NO 377
<211> LENGTH: 9
<212> TYPE: PRT
<213> ORGANISM: Homo sapiens

<400> SEQUENCE: 377

Phe Leu Leu Asp Ser Ser Ala Ser Val
1               5

<210> SEQ ID NO 378
<211> LENGTH: 9
<212> TYPE: PRT
<213> ORGANISM: Homo sapiens

<400> SEQUENCE: 378

Ala Leu Gly Tyr Phe Val Pro Tyr Val
1               5

<210> SEQ ID NO 379
<211> LENGTH: 9
<212> TYPE: PRT
<213> ORGANISM: Homo sapiens

<400> SEQUENCE: 379

Ile Met Glu Gly Thr Leu Thr Arg Val
1               5

<210> SEQ ID NO 380
<211> LENGTH: 10
<212> TYPE: PRT
<213> ORGANISM: Homo sapiens

<400> SEQUENCE: 380

Thr Leu Ile Glu Asp Glu Ile Ala Thr Ile
1               5                   10

<210> SEQ ID NO 381
<211> LENGTH: 9
<212> TYPE: PRT
<213> ORGANISM: Homo sapiens

<400> SEQUENCE: 381

Phe Ile Asp Glu Ala Tyr Val Glu Val
1               5

<210> SEQ ID NO 382
<211> LENGTH: 9
<212> TYPE: PRT
<213> ORGANISM: Homo sapiens

<400> SEQUENCE: 382

Ala Leu Gln Asn Tyr Ile Lys Glu Ala
1               5

<210> SEQ ID NO 383
<211> LENGTH: 11
<212> TYPE: PRT
<213> ORGANISM: Homo sapiens

<400> SEQUENCE: 383

Ala Leu Leu Glu Leu Glu Asn Ser Val Thr Leu
1               5                   10

<210> SEQ ID NO 384
<211> LENGTH: 10
<212> TYPE: PRT
<213> ORGANISM: Homo sapiens

<400> SEQUENCE: 384

Ile Leu Phe Ala Asn Pro Asn Ile Phe Val
1               5                   10

<210> SEQ ID NO 385
<211> LENGTH: 10
<212> TYPE: PRT
<213> ORGANISM: Homo sapiens

<400> SEQUENCE: 385

Ser Leu Leu Glu Gln Gly Leu Val Glu Ala
1               5                   10

<210> SEQ ID NO 386
<211> LENGTH: 9
<212> TYPE: PRT
<213> ORGANISM: Homo sapiens

<400> SEQUENCE: 386

Ile Leu Phe Arg Tyr Pro Leu Thr Ile
1               5

<210> SEQ ID NO 387
<211> LENGTH: 9
<212> TYPE: PRT
<213> ORGANISM: Homo sapiens

<400> SEQUENCE: 387

Ala Leu Phe Gln Ala Thr Ala Glu Val
1               5

<210> SEQ ID NO 388
<211> LENGTH: 10
<212> TYPE: PRT
<213> ORGANISM: Homo sapiens

<400> SEQUENCE: 388

Ser Leu Thr Ile Asp Gly Ile Arg Tyr Val
1               5                   10

```
<210> SEQ ID NO 389
<211> LENGTH: 9
<212> TYPE: PRT
<213> ORGANISM: Homo sapiens

<400> SEQUENCE: 389

Leu Leu Ala Asp Val Thr His Leu Leu
1               5

<210> SEQ ID NO 390
<211> LENGTH: 9
<212> TYPE: PRT
<213> ORGANISM: Homo sapiens

<400> SEQUENCE: 390

Ala Leu Phe Met Lys Gln Ile Tyr Leu
1               5

<210> SEQ ID NO 391
<211> LENGTH: 10
<212> TYPE: PRT
<213> ORGANISM: Homo sapiens

<400> SEQUENCE: 391

Tyr Val Tyr Pro Gln Arg Leu Asn Phe Val
1               5                   10

<210> SEQ ID NO 392
<211> LENGTH: 10
<212> TYPE: PRT
<213> ORGANISM: Homo sapiens

<400> SEQUENCE: 392

Ala Leu Leu His Pro Gln Gly Phe Glu Val
1               5                   10

<210> SEQ ID NO 393
<211> LENGTH: 13
<212> TYPE: PRT
<213> ORGANISM: Homo sapiens

<400> SEQUENCE: 393

Gly Leu Leu Asp Thr Gln Thr Ser Gln Val Leu Thr Ala
1               5                   10

<210> SEQ ID NO 394
<211> LENGTH: 11
<212> TYPE: PRT
<213> ORGANISM: Homo sapiens

<400> SEQUENCE: 394

Leu Leu Ala Val Ile Gly Gly Leu Val Tyr Leu
1               5                   10

<210> SEQ ID NO 395
<211> LENGTH: 10
<212> TYPE: PRT
<213> ORGANISM: Homo sapiens

<400> SEQUENCE: 395

Ala Leu Ala Leu Gly Gly Ile Ala Val Val
1               5                   10

<210> SEQ ID NO 396
<211> LENGTH: 9
```

```
<212> TYPE: PRT
<213> ORGANISM: Homo sapiens

<400> SEQUENCE: 396

Ala Leu Leu Pro Asp Leu Pro Ala Leu
1               5

<210> SEQ ID NO 397
<211> LENGTH: 10
<212> TYPE: PRT
<213> ORGANISM: Homo sapiens

<400> SEQUENCE: 397

Tyr Leu Phe Gly Glu Arg Leu Leu Glu Cys
1               5                   10

<210> SEQ ID NO 398
<211> LENGTH: 12
<212> TYPE: PRT
<213> ORGANISM: Homo sapiens

<400> SEQUENCE: 398

Lys Leu Leu Glu Glu Asp Gly Thr Ile Ile Thr Leu
1               5                   10

<210> SEQ ID NO 399
<211> LENGTH: 9
<212> TYPE: PRT
<213> ORGANISM: Homo sapiens

<400> SEQUENCE: 399

Tyr Leu Phe Glu Pro Leu Tyr His Val
1               5

<210> SEQ ID NO 400
<211> LENGTH: 11
<212> TYPE: PRT
<213> ORGANISM: Homo sapiens

<400> SEQUENCE: 400

Ser Leu Leu Thr Glu Gln Asp Leu Trp Thr Val
1               5                   10

<210> SEQ ID NO 401
<211> LENGTH: 11
<212> TYPE: PRT
<213> ORGANISM: Homo sapiens

<400> SEQUENCE: 401

Ile Leu Leu Asp Asp Thr Gly Leu Ala Tyr Ile
1               5                   10

<210> SEQ ID NO 402
<211> LENGTH: 10
<212> TYPE: PRT
<213> ORGANISM: Homo sapiens

<400> SEQUENCE: 402

Val Leu Phe Ser Gly Ala Leu Leu Gly Leu
1               5                   10

<210> SEQ ID NO 403
<211> LENGTH: 9
<212> TYPE: PRT
<213> ORGANISM: Homo sapiens
```

<400> SEQUENCE: 403

Lys Leu Tyr Asp Arg Ile Leu Arg Val
1               5

<210> SEQ ID NO 404
<211> LENGTH: 11
<212> TYPE: PRT
<213> ORGANISM: Homo sapiens

<400> SEQUENCE: 404

Ala Ile Asp Ile Ser Gly Arg Asp Pro Ala Val
1               5                   10

<210> SEQ ID NO 405
<211> LENGTH: 9
<212> TYPE: PRT
<213> ORGANISM: Homo sapiens

<400> SEQUENCE: 405

Ala Leu Tyr Asp Val Phe Leu Glu Val
1               5

<210> SEQ ID NO 406
<211> LENGTH: 10
<212> TYPE: PRT
<213> ORGANISM: Homo sapiens

<400> SEQUENCE: 406

Ser Val Gln Gly Glu Asp Leu Tyr Leu Val
1               5                   10

<210> SEQ ID NO 407
<211> LENGTH: 9
<212> TYPE: PRT
<213> ORGANISM: Homo sapiens

<400> SEQUENCE: 407

Tyr Leu Met Asp Leu Ile Asn Phe Leu
1               5

<210> SEQ ID NO 408
<211> LENGTH: 9
<212> TYPE: PRT
<213> ORGANISM: Homo sapiens

<400> SEQUENCE: 408

Val Leu Asp Asp Ser Ile Tyr Leu Val
1               5

<210> SEQ ID NO 409
<211> LENGTH: 9
<212> TYPE: PRT
<213> ORGANISM: Homo sapiens

<400> SEQUENCE: 409

Leu Leu Asp Ala Met Asn Tyr His Leu
1               5

<210> SEQ ID NO 410
<211> LENGTH: 9
<212> TYPE: PRT
<213> ORGANISM: Homo sapiens

<400> SEQUENCE: 410

-continued

Val Leu Ser Asp Val Ile Pro Ser Ile
1               5

<210> SEQ ID NO 411
<211> LENGTH: 9
<212> TYPE: PRT
<213> ORGANISM: Homo sapiens

<400> SEQUENCE: 411

Leu Leu Ala His Leu Ser Pro Glu Leu
1               5

<210> SEQ ID NO 412
<211> LENGTH: 11
<212> TYPE: PRT
<213> ORGANISM: Homo sapiens

<400> SEQUENCE: 412

Tyr Leu Asp Asp Leu Asn Glu Gly Val Tyr Ile
1               5                   10

<210> SEQ ID NO 413
<211> LENGTH: 9
<212> TYPE: PRT
<213> ORGANISM: Homo sapiens

<400> SEQUENCE: 413

Thr Leu Leu Glu Lys Val Glu Gly Cys
1               5

<210> SEQ ID NO 414
<211> LENGTH: 9
<212> TYPE: PRT
<213> ORGANISM: Homo sapiens

<400> SEQUENCE: 414

Tyr Val Asp Asp Ile Phe Leu Arg Val
1               5

<210> SEQ ID NO 415
<211> LENGTH: 9
<212> TYPE: PRT
<213> ORGANISM: Homo sapiens

<400> SEQUENCE: 415

Leu Leu Asp Lys Val Tyr Ser Ser Val
1               5

<210> SEQ ID NO 416
<211> LENGTH: 11
<212> TYPE: PRT
<213> ORGANISM: Homo sapiens

<400> SEQUENCE: 416

Val Leu Ser Asp Ile Ile Gln Asn Leu Ser Val
1               5                   10

<210> SEQ ID NO 417
<211> LENGTH: 9
<212> TYPE: PRT
<213> ORGANISM: Homo sapiens

<400> SEQUENCE: 417

Asn Leu Gln Asp Thr Glu Tyr Asn Leu

```
<210> SEQ ID NO 418
<211> LENGTH: 10
<212> TYPE: PRT
<213> ORGANISM: Homo sapiens

<400> SEQUENCE: 418

Ala Leu Ala Glu Leu Glu Asn Ile Glu Val
1               5                   10

<210> SEQ ID NO 419
<211> LENGTH: 10
<212> TYPE: PRT
<213> ORGANISM: Homo sapiens

<400> SEQUENCE: 419

Gly Gln Tyr Glu Gly Lys Val Ser Ser Val
1               5                   10

<210> SEQ ID NO 420
<211> LENGTH: 9
<212> TYPE: PRT
<213> ORGANISM: Homo sapiens

<400> SEQUENCE: 420

Phe Met Tyr Asp Thr Pro Gln Glu Val
1               5

<210> SEQ ID NO 421
<211> LENGTH: 9
<212> TYPE: PRT
<213> ORGANISM: Homo sapiens

<400> SEQUENCE: 421

Arg Leu Pro Glu Thr Leu Pro Ser Leu
1               5

<210> SEQ ID NO 422
<211> LENGTH: 9
<212> TYPE: PRT
<213> ORGANISM: Homo sapiens

<400> SEQUENCE: 422

Phe Leu Pro Lys Leu Leu Leu Leu Ala
1               5

<210> SEQ ID NO 423
<211> LENGTH: 9
<212> TYPE: PRT
<213> ORGANISM: Homo sapiens

<400> SEQUENCE: 423

Gly Leu Asp Gly Pro Pro Pro Thr Val
1               5

<210> SEQ ID NO 424
<211> LENGTH: 9
<212> TYPE: PRT
<213> ORGANISM: Homo sapiens

<400> SEQUENCE: 424

Thr Leu Leu Asp Ala Leu Tyr Glu Ile
1               5
```

<210> SEQ ID NO 425
<211> LENGTH: 9
<212> TYPE: PRT
<213> ORGANISM: Homo sapiens

<400> SEQUENCE: 425

Phe Leu Tyr Glu Lys Ser Ser Gln Val
1               5

<210> SEQ ID NO 426
<211> LENGTH: 9
<212> TYPE: PRT
<213> ORGANISM: Homo sapiens

<400> SEQUENCE: 426

Arg Leu Ala Asp Lys Ser Val Leu Val
1               5

<210> SEQ ID NO 427
<211> LENGTH: 9
<212> TYPE: PRT
<213> ORGANISM: Homo sapiens

<400> SEQUENCE: 427

Ala Leu Leu Pro Leu Ser Pro Tyr Leu
1               5

<210> SEQ ID NO 428
<211> LENGTH: 11
<212> TYPE: PRT
<213> ORGANISM: Homo sapiens

<400> SEQUENCE: 428

Lys Leu Gly His Thr Asp Ile Leu Val Gly Val
1               5                   10

<210> SEQ ID NO 429
<211> LENGTH: 9
<212> TYPE: PRT
<213> ORGANISM: Homo sapiens

<400> SEQUENCE: 429

Gly Leu Val Asn Asp Leu Ala Arg Val
1               5

<210> SEQ ID NO 430
<211> LENGTH: 11
<212> TYPE: PRT
<213> ORGANISM: Homo sapiens

<400> SEQUENCE: 430

His Leu Tyr Ser Ser Ile Glu His Leu Thr Thr
1               5                   10

<210> SEQ ID NO 431
<211> LENGTH: 9
<212> TYPE: PRT
<213> ORGANISM: Homo sapiens

<400> SEQUENCE: 431

Ser Leu Val Asn Val Val Pro Lys Leu
1               5

<210> SEQ ID NO 432

```
<211> LENGTH: 9
<212> TYPE: PRT
<213> ORGANISM: Homo sapiens

<400> SEQUENCE: 432

Thr Leu Ile Glu Glu Ser Ala Lys Val
1               5

<210> SEQ ID NO 433
<211> LENGTH: 9
<212> TYPE: PRT
<213> ORGANISM: Homo sapiens

<400> SEQUENCE: 433

Ala Met Leu Asn Glu Pro Trp Ala Val
1               5

<210> SEQ ID NO 434
<211> LENGTH: 10
<212> TYPE: PRT
<213> ORGANISM: Homo sapiens

<400> SEQUENCE: 434

Lys Val Ser Asn Ser Gly Ile Thr Arg Val
1               5                   10

<210> SEQ ID NO 435
<211> LENGTH: 9
<212> TYPE: PRT
<213> ORGANISM: Homo sapiens

<400> SEQUENCE: 435

Trp Leu Met Pro Val Ile Pro Ala Leu
1               5

<210> SEQ ID NO 436
<211> LENGTH: 9
<212> TYPE: PRT
<213> ORGANISM: Homo sapiens

<400> SEQUENCE: 436

His Leu Ala Glu Val Ser Ala Glu Val
1               5

<210> SEQ ID NO 437
<211> LENGTH: 11
<212> TYPE: PRT
<213> ORGANISM: Homo sapiens

<400> SEQUENCE: 437

Ser Met Ala Pro Gly Leu Val Ile Gln Ala Val
1               5                   10

<210> SEQ ID NO 438
<211> LENGTH: 10
<212> TYPE: PRT
<213> ORGANISM: Homo sapiens

<400> SEQUENCE: 438

Lys Leu Leu Pro Leu Ala Gly Leu Tyr Leu
1               5                   10

<210> SEQ ID NO 439
<211> LENGTH: 9
<212> TYPE: PRT
```

<213> ORGANISM: Homo sapiens

<400> SEQUENCE: 439

Tyr Leu Leu Gln Glu Ile Tyr Gly Ile
1               5

<210> SEQ ID NO 440
<211> LENGTH: 10
<212> TYPE: PRT
<213> ORGANISM: Homo sapiens

<400> SEQUENCE: 440

Ala Leu Ala Asp Gly Val Thr Met Gln Val
1               5                   10

<210> SEQ ID NO 441
<211> LENGTH: 10
<212> TYPE: PRT
<213> ORGANISM: Homo sapiens

<400> SEQUENCE: 441

Ala Leu Leu Glu Asn Pro Lys Met Glu Leu
1               5                   10

<210> SEQ ID NO 442
<211> LENGTH: 11
<212> TYPE: PRT
<213> ORGANISM: Homo sapiens

<400> SEQUENCE: 442

Gly Leu Leu Gly Gly Gly Gly Val Leu Gly Val
1               5                   10

<210> SEQ ID NO 443
<211> LENGTH: 11
<212> TYPE: PRT
<213> ORGANISM: Homo sapiens

<400> SEQUENCE: 443

Gly Leu Trp Glu Ile Glu Asn Asn Pro Thr Val
1               5                   10

<210> SEQ ID NO 444
<211> LENGTH: 11
<212> TYPE: PRT
<213> ORGANISM: Homo sapiens

<400> SEQUENCE: 444

Gly Leu Leu Arg Asp Glu Ala Leu Ala Glu Val
1               5                   10

<210> SEQ ID NO 445
<211> LENGTH: 9
<212> TYPE: PRT
<213> ORGANISM: Homo sapiens

<400> SEQUENCE: 445

Gly Leu Tyr Gln Asp Pro Val Thr Leu
1               5

<210> SEQ ID NO 446
<211> LENGTH: 9
<212> TYPE: PRT
<213> ORGANISM: Homo sapiens

```
<400> SEQUENCE: 446

Gln Leu Ile Pro Ala Leu Ala Lys Val
1               5

<210> SEQ ID NO 447
<211> LENGTH: 9
<212> TYPE: PRT
<213> ORGANISM: Homo sapiens

<400> SEQUENCE: 447

Gln Leu Val Pro Ala Leu Ala Lys Val
1               5

<210> SEQ ID NO 448
<211> LENGTH: 9
<212> TYPE: PRT
<213> ORGANISM: Homo sapiens

<400> SEQUENCE: 448

Asn Leu Leu Glu Thr Lys Leu Gln Leu
1               5

<210> SEQ ID NO 449
<211> LENGTH: 10
<212> TYPE: PRT
<213> ORGANISM: Homo sapiens

<400> SEQUENCE: 449

Lys Leu Ala Glu Gly Leu Asp Ile Gln Leu
1               5                  10

<210> SEQ ID NO 450
<211> LENGTH: 11
<212> TYPE: PRT
<213> ORGANISM: Homo sapiens

<400> SEQUENCE: 450

Phe Met Ile Asp Ala Ser Val His Pro Thr Leu
1               5                  10

<210> SEQ ID NO 451
<211> LENGTH: 11
<212> TYPE: PRT
<213> ORGANISM: Homo sapiens

<400> SEQUENCE: 451

Leu Leu Leu Leu Asp Thr Val Thr Met Gln Val
1               5                  10

<210> SEQ ID NO 452
<211> LENGTH: 11
<212> TYPE: PRT
<213> ORGANISM: Homo sapiens

<400> SEQUENCE: 452

Ile Leu Leu Glu His Gly Ala Asp Pro Asn Leu
1               5                  10

<210> SEQ ID NO 453
<211> LENGTH: 9
<212> TYPE: PRT
<213> ORGANISM: Homo sapiens

<400> SEQUENCE: 453
```

Lys Leu Leu Glu Ala Thr Ser Ala Val
1               5

<210> SEQ ID NO 454
<211> LENGTH: 9
<212> TYPE: PRT
<213> ORGANISM: Homo sapiens

<400> SEQUENCE: 454

Lys Leu Pro Pro Pro Pro Pro Gln Ala
1               5

<210> SEQ ID NO 455
<211> LENGTH: 11
<212> TYPE: PRT
<213> ORGANISM: Homo sapiens

<400> SEQUENCE: 455

Ser Leu Leu Lys Glu Pro Gln Lys Val Gln Leu
1               5                   10

<210> SEQ ID NO 456
<211> LENGTH: 9
<212> TYPE: PRT
<213> ORGANISM: Homo sapiens

<400> SEQUENCE: 456

Leu Leu Ile Gly His Leu Glu Arg Val
1               5

<210> SEQ ID NO 457
<211> LENGTH: 11
<212> TYPE: PRT
<213> ORGANISM: Homo sapiens

<400> SEQUENCE: 457

Ser Leu Leu Pro Gly Asn Leu Val Glu Lys Val
1               5                   10

<210> SEQ ID NO 458
<211> LENGTH: 9
<212> TYPE: PRT
<213> ORGANISM: Homo sapiens

<400> SEQUENCE: 458

Ser Leu Ile Asp Lys Leu Tyr Asn Ile
1               5

<210> SEQ ID NO 459
<211> LENGTH: 9
<212> TYPE: PRT
<213> ORGANISM: Homo sapiens

<400> SEQUENCE: 459

Ala Leu Ile Thr Glu Val Val Arg Leu
1               5

<210> SEQ ID NO 460
<211> LENGTH: 9
<212> TYPE: PRT
<213> ORGANISM: Homo sapiens

<400> SEQUENCE: 460

Ala Met Leu Glu Lys Asn Tyr Lys Leu
1               5

<210> SEQ ID NO 461
<211> LENGTH: 10
<212> TYPE: PRT
<213> ORGANISM: Homo sapiens

<400> SEQUENCE: 461

Val Met Phe Arg Thr Pro Leu Ala Ser Val
1               5                   10

<210> SEQ ID NO 462
<211> LENGTH: 9
<212> TYPE: PRT
<213> ORGANISM: Homo sapiens

<400> SEQUENCE: 462

Lys Leu Ala Lys Gln Pro Glu Thr Val
1               5

<210> SEQ ID NO 463
<211> LENGTH: 13
<212> TYPE: PRT
<213> ORGANISM: Homo sapiens

<400> SEQUENCE: 463

Ser Leu Val Glu Ser His Leu Ser Asp Gln Leu Thr Leu
1               5                   10

<210> SEQ ID NO 464
<211> LENGTH: 9
<212> TYPE: PRT
<213> ORGANISM: Homo sapiens

<400> SEQUENCE: 464

Ala Leu Asn Asp Cys Ile Tyr Ser Val
1               5

<210> SEQ ID NO 465
<211> LENGTH: 9
<212> TYPE: PRT
<213> ORGANISM: Homo sapiens

<400> SEQUENCE: 465

Gln Leu Cys Asp Leu Asn Ala Glu Leu
1               5

<210> SEQ ID NO 466
<211> LENGTH: 9
<212> TYPE: PRT
<213> ORGANISM: Homo sapiens

<400> SEQUENCE: 466

Val Leu Ile Ala Asn Leu Glu Lys Leu
1               5

<210> SEQ ID NO 467
<211> LENGTH: 9
<212> TYPE: PRT
<213> ORGANISM: Homo sapiens

<400> SEQUENCE: 467

Phe Leu Ala Lys Asp Phe Asn Phe Leu
1               5

```
<210> SEQ ID NO 468
<211> LENGTH: 11
<212> TYPE: PRT
<213> ORGANISM: Homo sapiens

<400> SEQUENCE: 468

Tyr Leu Arg Ser Val Gly Asp Gly Glu Thr Val
1               5                   10

<210> SEQ ID NO 469
<211> LENGTH: 10
<212> TYPE: PRT
<213> ORGANISM: Homo sapiens

<400> SEQUENCE: 469

Tyr Leu Ala Ser Asp Glu Ile Thr Thr Val
1               5                   10

<210> SEQ ID NO 470
<211> LENGTH: 9
<212> TYPE: PRT
<213> ORGANISM: Homo sapiens

<400> SEQUENCE: 470

Met Leu Gln Asp Ser Ile His Val Val
1               5

<210> SEQ ID NO 471
<211> LENGTH: 10
<212> TYPE: PRT
<213> ORGANISM: Homo sapiens

<400> SEQUENCE: 471

Tyr Leu Tyr Asn Asn Met Ile Ala Lys Ile
1               5                   10

<210> SEQ ID NO 472
<211> LENGTH: 11
<212> TYPE: PRT
<213> ORGANISM: Homo sapiens

<400> SEQUENCE: 472

Lys Leu Leu Glu Val Ser Asp Asp Pro Gln Val
1               5                   10

<210> SEQ ID NO 473
<211> LENGTH: 11
<212> TYPE: PRT
<213> ORGANISM: Homo sapiens

<400> SEQUENCE: 473

Ala Met Ala Thr Glu Ser Ile Leu His Phe Ala
1               5                   10

<210> SEQ ID NO 474
<211> LENGTH: 13
<212> TYPE: PRT
<213> ORGANISM: Homo sapiens

<400> SEQUENCE: 474

Tyr Leu Asp Pro Ala Leu Glu Leu Gly Pro Arg Asn Val
1               5                   10

<210> SEQ ID NO 475
<211> LENGTH: 11
```

```
<212> TYPE: PRT
<213> ORGANISM: Homo sapiens

<400> SEQUENCE: 475

Leu Leu Leu Asn Glu Glu Ala Leu Ala Gln Ile
1               5                   10

<210> SEQ ID NO 476
<211> LENGTH: 11
<212> TYPE: PRT
<213> ORGANISM: Homo sapiens

<400> SEQUENCE: 476

Ala Leu Met Glu Arg Thr Gly Tyr Ser Met Val
1               5                   10

<210> SEQ ID NO 477
<211> LENGTH: 11
<212> TYPE: PRT
<213> ORGANISM: Homo sapiens

<400> SEQUENCE: 477

Ala Leu Leu Pro Ala Ser Gly Gln Ile Ala Leu
1               5                   10

<210> SEQ ID NO 478
<211> LENGTH: 9
<212> TYPE: PRT
<213> ORGANISM: Homo sapiens

<400> SEQUENCE: 478

Tyr Leu Leu His Glu Lys Leu Asn Leu
1               5

<210> SEQ ID NO 479
<211> LENGTH: 12
<212> TYPE: PRT
<213> ORGANISM: Homo sapiens

<400> SEQUENCE: 479

Ser Leu Phe Gly Asn Ser Gly Ile Leu Glu Asn Val
1               5                   10

<210> SEQ ID NO 480
<211> LENGTH: 10
<212> TYPE: PRT
<213> ORGANISM: Homo sapiens

<400> SEQUENCE: 480

Ala Leu Leu Glu Asp Ser Cys His Tyr Leu
1               5                   10

<210> SEQ ID NO 481
<211> LENGTH: 10
<212> TYPE: PRT
<213> ORGANISM: Homo sapiens

<400> SEQUENCE: 481

Gly Leu Ile Glu Asp Tyr Glu Ala Leu Leu
1               5                   10

<210> SEQ ID NO 482
<211> LENGTH: 10
<212> TYPE: PRT
<213> ORGANISM: Homo sapiens
```

<400> SEQUENCE: 482

Ser Leu Ala Pro Ala Gly Ile Ala Asp Ala
1               5                   10

<210> SEQ ID NO 483
<211> LENGTH: 9
<212> TYPE: PRT
<213> ORGANISM: Homo sapiens

<400> SEQUENCE: 483

Ala Leu Thr Asp Ile Val Ser Gln Val
1               5

<210> SEQ ID NO 484
<211> LENGTH: 9
<212> TYPE: PRT
<213> ORGANISM: Homo sapiens

<400> SEQUENCE: 484

Ser Leu Ile Glu Lys Val Thr Gln Leu
1               5

<210> SEQ ID NO 485
<211> LENGTH: 9
<212> TYPE: PRT
<213> ORGANISM: Homo sapiens

<400> SEQUENCE: 485

Asn Val Pro Asp Ser Phe Asn Glu Val
1               5

<210> SEQ ID NO 486
<211> LENGTH: 9
<212> TYPE: PRT
<213> ORGANISM: Homo sapiens

<400> SEQUENCE: 486

Ala Val Met Glu Ser Ile Gln Gly Val
1               5

<210> SEQ ID NO 487
<211> LENGTH: 9
<212> TYPE: PRT
<213> ORGANISM: Homo sapiens

<400> SEQUENCE: 487

Leu Leu Ile Asn Ser Val Phe His Val
1               5

<210> SEQ ID NO 488
<211> LENGTH: 10
<212> TYPE: PRT
<213> ORGANISM: Homo sapiens

<400> SEQUENCE: 488

Phe Leu Ala Glu Asp Pro Lys Val Thr Leu
1               5                   10

<210> SEQ ID NO 489
<211> LENGTH: 10
<212> TYPE: PRT
<213> ORGANISM: Homo sapiens

<400> SEQUENCE: 489

Lys Met Trp Glu Glu Leu Pro Glu Val Val
1               5                   10

<210> SEQ ID NO 490
<211> LENGTH: 9
<212> TYPE: PRT
<213> ORGANISM: Homo sapiens

<400> SEQUENCE: 490

Phe Leu Leu Gln His Val Gln Glu Leu
1               5

<210> SEQ ID NO 491
<211> LENGTH: 9
<212> TYPE: PRT
<213> ORGANISM: Homo sapiens

<400> SEQUENCE: 491

Gly Leu Asn Asp Arg Ser Asp Ala Val
1               5

<210> SEQ ID NO 492
<211> LENGTH: 12
<212> TYPE: PRT
<213> ORGANISM: Homo sapiens

<400> SEQUENCE: 492

Ser Leu Phe Asp Gly Phe Ala Asp Gly Leu Gly Val
1               5                   10

<210> SEQ ID NO 493
<211> LENGTH: 13
<212> TYPE: PRT
<213> ORGANISM: Homo sapiens

<400> SEQUENCE: 493

Gly Leu Leu Gly Glu Lys Thr Gln Asp Leu Ile Gly Val
1               5                   10

<210> SEQ ID NO 494
<211> LENGTH: 9
<212> TYPE: PRT
<213> ORGANISM: Homo sapiens

<400> SEQUENCE: 494

Ala Leu Gln Pro Glu Pro Ile Lys Val
1               5

<210> SEQ ID NO 495
<211> LENGTH: 10
<212> TYPE: PRT
<213> ORGANISM: Homo sapiens

<400> SEQUENCE: 495

Phe Ile Phe Ser Glu Lys Pro Val Phe Val
1               5                   10

<210> SEQ ID NO 496
<211> LENGTH: 10
<212> TYPE: PRT
<213> ORGANISM: Homo sapiens

<400> SEQUENCE: 496

Phe Leu Val Glu Lys Gln Pro Pro Gln Val

<210> SEQ ID NO 497
<211> LENGTH: 9
<212> TYPE: PRT
<213> ORGANISM: Homo sapiens

<400> SEQUENCE: 497

Gly Leu Leu Glu Lys Leu Thr Ala Ile
1               5

<210> SEQ ID NO 498
<211> LENGTH: 11
<212> TYPE: PRT
<213> ORGANISM: Homo sapiens

<400> SEQUENCE: 498

Lys Leu Trp Thr Gly Gly Leu Asp Asn Thr Val
1               5                   10

<210> SEQ ID NO 499
<211> LENGTH: 12
<212> TYPE: PRT
<213> ORGANISM: Homo sapiens

<400> SEQUENCE: 499

Lys Ile Phe Asp Ile Asp Glu Ala Glu Glu Gly Val
1               5                   10

<210> SEQ ID NO 500
<211> LENGTH: 10
<212> TYPE: PRT
<213> ORGANISM: Homo sapiens

<400> SEQUENCE: 500

Ser Leu Met Glu Asp Gln Val Leu Gln Leu
1               5                   10

<210> SEQ ID NO 501
<211> LENGTH: 11
<212> TYPE: PRT
<213> ORGANISM: Homo sapiens

<400> SEQUENCE: 501

Leu Leu Asp Pro Asn Val Lys Ser Ile Phe Val
1               5                   10

<210> SEQ ID NO 502
<211> LENGTH: 9
<212> TYPE: PRT
<213> ORGANISM: Homo sapiens

<400> SEQUENCE: 502

Arg Leu Leu Ala Gln Val Pro Gly Leu
1               5

<210> SEQ ID NO 503
<211> LENGTH: 9
<212> TYPE: PRT
<213> ORGANISM: Homo sapiens

<400> SEQUENCE: 503

Ser Leu Asn His Phe Thr His Ser Val
1               5

```
<210> SEQ ID NO 504
<211> LENGTH: 9
<212> TYPE: PRT
<213> ORGANISM: Homo sapiens

<400> SEQUENCE: 504

Gly Leu Ser Asp Gly Asn Pro Ser Leu
1               5

<210> SEQ ID NO 505
<211> LENGTH: 11
<212> TYPE: PRT
<213> ORGANISM: Homo sapiens

<400> SEQUENCE: 505

Ser Leu Ala Pro Gly Asp Val Val Arg Gln Val
1               5                   10

<210> SEQ ID NO 506
<211> LENGTH: 9
<212> TYPE: PRT
<213> ORGANISM: Homo sapiens

<400> SEQUENCE: 506

Lys Leu Leu Gly Lys Val Glu Thr Ala
1               5

<210> SEQ ID NO 507
<211> LENGTH: 12
<212> TYPE: PRT
<213> ORGANISM: Homo sapiens

<400> SEQUENCE: 507

Lys Leu Ile Asp Asp Gln Asp Ile Ser Ile Ser Leu
1               5                   10

<210> SEQ ID NO 508
<211> LENGTH: 11
<212> TYPE: PRT
<213> ORGANISM: Homo sapiens

<400> SEQUENCE: 508

Ile Leu Ala Gln Glu Gln Leu Val Val Gly Val
1               5                   10

<210> SEQ ID NO 509
<211> LENGTH: 10
<212> TYPE: PRT
<213> ORGANISM: Homo sapiens

<400> SEQUENCE: 509

Phe Leu Phe Asp Thr Lys Pro Leu Ile Val
1               5                   10

<210> SEQ ID NO 510
<211> LENGTH: 9
<212> TYPE: PRT
<213> ORGANISM: Homo sapiens

<400> SEQUENCE: 510

Lys Leu Tyr Ser Val Val Ser Gln Leu
1               5

<210> SEQ ID NO 511
```

```
<211> LENGTH: 10
<212> TYPE: PRT
<213> ORGANISM: Homo sapiens

<400> SEQUENCE: 511

Phe Leu Asp Pro Tyr Cys Ser Ala Ser Val
1               5                   10

<210> SEQ ID NO 512
<211> LENGTH: 9
<212> TYPE: PRT
<213> ORGANISM: Homo sapiens

<400> SEQUENCE: 512

Ser Leu Ser Glu Ile Val Pro Cys Leu
1               5

<210> SEQ ID NO 513
<211> LENGTH: 9
<212> TYPE: PRT
<213> ORGANISM: Homo sapiens

<400> SEQUENCE: 513

Ser Leu Trp Pro Ser Pro Glu Gln Leu
1               5

<210> SEQ ID NO 514
<211> LENGTH: 9
<212> TYPE: PRT
<213> ORGANISM: Homo sapiens

<400> SEQUENCE: 514

Ile Leu Val Asp Trp Leu Val Gln Val
1               5

<210> SEQ ID NO 515
<211> LENGTH: 9
<212> TYPE: PRT
<213> ORGANISM: Homo sapiens

<400> SEQUENCE: 515

Leu Leu Gln Glu Leu Val Leu Phe Leu
1               5

<210> SEQ ID NO 516
<211> LENGTH: 11
<212> TYPE: PRT
<213> ORGANISM: Homo sapiens

<400> SEQUENCE: 516

Ala Val Gly Pro Ala Ser Ile Leu Lys Glu Val
1               5                   10

<210> SEQ ID NO 517
<211> LENGTH: 11
<212> TYPE: PRT
<213> ORGANISM: Homo sapiens

<400> SEQUENCE: 517

Leu Leu Met Pro Ile Pro Glu Gly Leu Thr Leu
1               5                   10

<210> SEQ ID NO 518
<211> LENGTH: 9
<212> TYPE: PRT
```

-continued

<213> ORGANISM: Homo sapiens

<400> SEQUENCE: 518

Lys Leu Asn Ala Glu Val Ala Cys Val
1               5

<210> SEQ ID NO 519
<211> LENGTH: 9
<212> TYPE: PRT
<213> ORGANISM: Homo sapiens

<400> SEQUENCE: 519

Gly Leu Leu His Leu Thr Leu Leu Leu
1               5

<210> SEQ ID NO 520
<211> LENGTH: 10
<212> TYPE: PRT
<213> ORGANISM: Homo sapiens

<400> SEQUENCE: 520

Leu Ala Val His Pro Ser Gly Val Ala Leu
1               5                   10

<210> SEQ ID NO 521
<211> LENGTH: 9
<212> TYPE: PRT
<213> ORGANISM: Homo sapiens

<400> SEQUENCE: 521

Met Leu Leu Thr Lys Leu Pro Thr Ile
1               5

<210> SEQ ID NO 522
<211> LENGTH: 9
<212> TYPE: PRT
<213> ORGANISM: Homo sapiens

<400> SEQUENCE: 522

Thr Leu Trp Tyr Arg Ser Pro Glu Val
1               5

<210> SEQ ID NO 523
<211> LENGTH: 9
<212> TYPE: PRT
<213> ORGANISM: Homo sapiens

<400> SEQUENCE: 523

Tyr Gln Ile Pro Arg Thr Phe Thr Leu
1               5

<210> SEQ ID NO 524
<211> LENGTH: 10
<212> TYPE: PRT
<213> ORGANISM: Homo sapiens

<400> SEQUENCE: 524

Ala Leu Ile Glu Asn Leu Thr His Gln Ile
1               5                   10

<210> SEQ ID NO 525
<211> LENGTH: 12
<212> TYPE: PRT
<213> ORGANISM: Homo sapiens

```
<400> SEQUENCE: 525

Val Leu Leu Glu Ala Gly Glu Gly Leu Val Thr Ile
1               5                   10

<210> SEQ ID NO 526
<211> LENGTH: 11
<212> TYPE: PRT
<213> ORGANISM: Homo sapiens

<400> SEQUENCE: 526

Arg Leu Ala Glu Val Gly Gln Tyr Glu Gln Val
1               5                   10

<210> SEQ ID NO 527
<211> LENGTH: 10
<212> TYPE: PRT
<213> ORGANISM: Homo sapiens

<400> SEQUENCE: 527

Phe Leu Leu Glu Pro Gly Asn Leu Glu Val
1               5                   10

<210> SEQ ID NO 528
<211> LENGTH: 11
<212> TYPE: PRT
<213> ORGANISM: Homo sapiens

<400> SEQUENCE: 528

Ser Val Ala Glu Gly Arg Ala Leu Met Ser Val
1               5                   10

<210> SEQ ID NO 529
<211> LENGTH: 9
<212> TYPE: PRT
<213> ORGANISM: Homo sapiens

<400> SEQUENCE: 529

Leu Leu Ala Asp Glu Leu Ile Thr Val
1               5

<210> SEQ ID NO 530
<211> LENGTH: 11
<212> TYPE: PRT
<213> ORGANISM: Homo sapiens

<400> SEQUENCE: 530

Val Met Tyr Ala Asp Ile Gly Gly Met Asp Ile
1               5                   10

<210> SEQ ID NO 531
<211> LENGTH: 11
<212> TYPE: PRT
<213> ORGANISM: Homo sapiens

<400> SEQUENCE: 531

Tyr Thr Leu Pro Ile Ala Ser Ser Ile Arg Leu
1               5                   10

<210> SEQ ID NO 532
<211> LENGTH: 9
<212> TYPE: PRT
<213> ORGANISM: Homo sapiens

<400> SEQUENCE: 532
```

Ala Leu Asn Asn Leu Leu His Ser Leu
1               5

<210> SEQ ID NO 533
<211> LENGTH: 9
<212> TYPE: PRT
<213> ORGANISM: Homo sapiens

<400> SEQUENCE: 533

Arg Met Val Ala Glu Ile Gln Asn Val
1               5

<210> SEQ ID NO 534
<211> LENGTH: 9
<212> TYPE: PRT
<213> ORGANISM: Homo sapiens

<400> SEQUENCE: 534

His Leu Ala Asn Ile Val Glu Arg Leu
1               5

<210> SEQ ID NO 535
<211> LENGTH: 9
<212> TYPE: PRT
<213> ORGANISM: Homo sapiens

<400> SEQUENCE: 535

Lys Leu Ile Ala Gln Asn Leu Glu Leu
1               5

<210> SEQ ID NO 536
<211> LENGTH: 9
<212> TYPE: PRT
<213> ORGANISM: Homo sapiens

<400> SEQUENCE: 536

Tyr Leu Val Glu Gly Arg Phe Ser Val
1               5

<210> SEQ ID NO 537
<211> LENGTH: 11
<212> TYPE: PRT
<213> ORGANISM: Homo sapiens

<400> SEQUENCE: 537

Thr Leu Ala Pro Gly Glu Val Leu Arg Ser Val
1               5                   10

<210> SEQ ID NO 538
<211> LENGTH: 9
<212> TYPE: PRT
<213> ORGANISM: Homo sapiens

<400> SEQUENCE: 538

Leu Leu Leu Ala His Ile Ile Ala Leu
1               5

<210> SEQ ID NO 539
<211> LENGTH: 9
<212> TYPE: PRT
<213> ORGANISM: Homo sapiens

<400> SEQUENCE: 539

Ala Leu Phe Asp Ala Gln Ala Gln Val
1               5

<210> SEQ ID NO 540
<211> LENGTH: 11
<212> TYPE: PRT
<213> ORGANISM: Homo sapiens

<400> SEQUENCE: 540

Ala Leu Ile Pro Glu Thr Thr Thr Leu Thr Val
1               5                   10

<210> SEQ ID NO 541
<211> LENGTH: 9
<212> TYPE: PRT
<213> ORGANISM: Homo sapiens

<400> SEQUENCE: 541

Ser Met Leu Glu Pro Val Pro Glu Leu
1               5

<210> SEQ ID NO 542
<211> LENGTH: 11
<212> TYPE: PRT
<213> ORGANISM: Homo sapiens

<400> SEQUENCE: 542

Arg Val Trp Asp Ile Ser Thr Val Ser Ser Val
1               5                   10

<210> SEQ ID NO 543
<211> LENGTH: 13
<212> TYPE: PRT
<213> ORGANISM: Homo sapiens

<400> SEQUENCE: 543

Gly Leu Leu Pro Thr Pro Ile Thr Gln Gln Ala Ser Leu
1               5                   10

<210> SEQ ID NO 544
<211> LENGTH: 10
<212> TYPE: PRT
<213> ORGANISM: Homo sapiens

<400> SEQUENCE: 544

Leu Leu Trp Asp Val Pro Ala Pro Ser Leu
1               5                   10

<210> SEQ ID NO 545
<211> LENGTH: 9
<212> TYPE: PRT
<213> ORGANISM: Homo sapiens

<400> SEQUENCE: 545

Leu Leu Ala Asp Leu Leu His Asn Val
1               5

<210> SEQ ID NO 546
<211> LENGTH: 10
<212> TYPE: PRT
<213> ORGANISM: Homo sapiens

<400> SEQUENCE: 546

Val Met Ile Ala Gly Lys Val Ala Val Val
1               5                   10

```
<210> SEQ ID NO 547
<211> LENGTH: 9
<212> TYPE: PRT
<213> ORGANISM: Homo sapiens

<400> SEQUENCE: 547

Thr Leu Asp Ile Thr Pro His Thr Val
1               5

<210> SEQ ID NO 548
<211> LENGTH: 11
<212> TYPE: PRT
<213> ORGANISM: Homo sapiens

<400> SEQUENCE: 548

Ala Leu Trp Glu Asn Pro Glu Ser Gly Glu Leu
1               5                   10

<210> SEQ ID NO 549
<211> LENGTH: 11
<212> TYPE: PRT
<213> ORGANISM: Homo sapiens

<400> SEQUENCE: 549

Ala Met Leu Glu Asn Ala Ser Asp Ile Lys Leu
1               5                   10

<210> SEQ ID NO 550
<211> LENGTH: 12
<212> TYPE: PRT
<213> ORGANISM: Homo sapiens

<400> SEQUENCE: 550

Phe Leu Tyr Asp Glu Ile Glu Ala Glu Val Asn Leu
1               5                   10

<210> SEQ ID NO 551
<211> LENGTH: 10
<212> TYPE: PRT
<213> ORGANISM: Homo sapiens

<400> SEQUENCE: 551

Lys Leu Tyr Glu Ser Leu Leu Pro Phe Ala
1               5                   10

<210> SEQ ID NO 552
<211> LENGTH: 11
<212> TYPE: PRT
<213> ORGANISM: Homo sapiens

<400> SEQUENCE: 552

Gly Leu Leu Asp Leu Pro Phe Arg Val Gly Val
1               5                   10

<210> SEQ ID NO 553
<211> LENGTH: 11
<212> TYPE: PRT
<213> ORGANISM: Homo sapiens

<400> SEQUENCE: 553

Ser Leu Leu Asn Gln Asp Leu His Trp Ser Leu
1               5                   10

<210> SEQ ID NO 554
<211> LENGTH: 11
```

```
<212> TYPE: PRT
<213> ORGANISM: Homo sapiens

<400> SEQUENCE: 554

Leu Leu Met Pro Ser Ser Glu Asp Leu Leu
1               5                   10

<210> SEQ ID NO 555
<211> LENGTH: 9
<212> TYPE: PRT
<213> ORGANISM: Homo sapiens

<400> SEQUENCE: 555

Tyr Val Leu Glu Gly Leu Lys Ser Val
1               5

<210> SEQ ID NO 556
<211> LENGTH: 10
<212> TYPE: PRT
<213> ORGANISM: Homo sapiens

<400> SEQUENCE: 556

Phe Leu Thr Asp Leu Glu Asp Leu Thr Leu
1               5                   10

<210> SEQ ID NO 557
<211> LENGTH: 9
<212> TYPE: PRT
<213> ORGANISM: Homo sapiens

<400> SEQUENCE: 557

Lys Leu Tyr Asp Asp Met Ile Arg Leu
1               5

<210> SEQ ID NO 558
<211> LENGTH: 9
<212> TYPE: PRT
<213> ORGANISM: Homo sapiens

<400> SEQUENCE: 558

Gly Leu Leu Glu Asn Ile Pro Arg Val
1               5

<210> SEQ ID NO 559
<211> LENGTH: 9
<212> TYPE: PRT
<213> ORGANISM: Homo sapiens

<400> SEQUENCE: 559

Val Thr Val Pro Pro Gly Pro Ser Leu
1               5

<210> SEQ ID NO 560
<211> LENGTH: 13
<212> TYPE: PRT
<213> ORGANISM: Homo sapiens

<400> SEQUENCE: 560

Ala Leu Trp Asp Ile Glu Thr Gly Gln Gln Thr Thr Thr
1               5                   10

<210> SEQ ID NO 561
<211> LENGTH: 9
<212> TYPE: PRT
<213> ORGANISM: Homo sapiens
```

<400> SEQUENCE: 561

Tyr Leu Gln Leu Thr Gln Ser Glu Leu
1               5

<210> SEQ ID NO 562
<211> LENGTH: 11
<212> TYPE: PRT
<213> ORGANISM: Homo sapiens

<400> SEQUENCE: 562

Tyr Leu Glu Glu Leu Pro Glu Lys Leu Lys Leu
1               5                   10

<210> SEQ ID NO 563
<211> LENGTH: 10
<212> TYPE: PRT
<213> ORGANISM: Homo sapiens

<400> SEQUENCE: 563

Trp Leu Leu Pro Tyr Asn Gly Val Thr Val
1               5                   10

<210> SEQ ID NO 564
<211> LENGTH: 9
<212> TYPE: PRT
<213> ORGANISM: Homo sapiens

<400> SEQUENCE: 564

Thr Val Thr Asn Ala Val Val Thr Val
1               5

<210> SEQ ID NO 565
<211> LENGTH: 9
<212> TYPE: PRT
<213> ORGANISM: Homo sapiens

<400> SEQUENCE: 565

Ala Leu Gln Glu Thr Pro Thr Ser Val
1               5

<210> SEQ ID NO 566
<211> LENGTH: 10
<212> TYPE: PRT
<213> ORGANISM: Homo sapiens

<400> SEQUENCE: 566

Val Ile Ala Asp Gly Gly Ile Gln Asn Val
1               5                   10

<210> SEQ ID NO 567
<211> LENGTH: 11
<212> TYPE: PRT
<213> ORGANISM: Homo sapiens

<400> SEQUENCE: 567

Ser Leu Leu Pro Leu Asp Asp Ile Val Arg Val
1               5                   10

<210> SEQ ID NO 568
<211> LENGTH: 11
<212> TYPE: PRT
<213> ORGANISM: Homo sapiens

<400> SEQUENCE: 568

Thr Leu Tyr Asp Ile Ala His Thr Pro Gly Val
1               5                   10

<210> SEQ ID NO 569
<211> LENGTH: 9
<212> TYPE: PRT
<213> ORGANISM: Homo sapiens

<400> SEQUENCE: 569

Lys Leu Val Asp Arg Thr Trp Thr Leu
1               5

<210> SEQ ID NO 570
<211> LENGTH: 9
<212> TYPE: PRT
<213> ORGANISM: Homo sapiens

<400> SEQUENCE: 570

Ala Leu Ala Asn Gln Ile Pro Thr Val
1               5

<210> SEQ ID NO 571
<211> LENGTH: 9
<212> TYPE: PRT
<213> ORGANISM: Homo sapiens

<400> SEQUENCE: 571

Leu Leu Leu Thr Thr Ile Pro Gln Ile
1               5

<210> SEQ ID NO 572
<211> LENGTH: 12
<212> TYPE: PRT
<213> ORGANISM: Homo sapiens

<400> SEQUENCE: 572

Ala Leu Ala Asp Leu Ile Glu Lys Glu Leu Ser Val
1               5                   10

<210> SEQ ID NO 573
<211> LENGTH: 10
<212> TYPE: PRT
<213> ORGANISM: Homo sapiens

<400> SEQUENCE: 573

Ile Leu Val Ala Asn Ala Ile Val Gly Val
1               5                   10

<210> SEQ ID NO 574
<211> LENGTH: 10
<212> TYPE: PRT
<213> ORGANISM: Homo sapiens

<400> SEQUENCE: 574

Tyr Leu Leu Gln Glu Pro Pro Arg Thr Val
1               5                   10

<210> SEQ ID NO 575
<211> LENGTH: 11
<212> TYPE: PRT
<213> ORGANISM: Homo sapiens

<400> SEQUENCE: 575

Tyr Leu Ile Ser Gln Val Glu Gly His Gln Val

```
1               5                   10
```

<210> SEQ ID NO 576
<211> LENGTH: 11
<212> TYPE: PRT
<213> ORGANISM: Homo sapiens

<400> SEQUENCE: 576

```
Ile Leu Leu Asn Asn Ser Gly Gln Ile Lys Leu
1               5                   10
```

<210> SEQ ID NO 577
<211> LENGTH: 11
<212> TYPE: PRT
<213> ORGANISM: Homo sapiens

<400> SEQUENCE: 577

```
Val Met Phe Glu Asp Gly Val Leu Met Arg Leu
1               5                   10
```

<210> SEQ ID NO 578
<211> LENGTH: 11
<212> TYPE: PRT
<213> ORGANISM: Homo sapiens

<400> SEQUENCE: 578

```
Phe Leu Asp Pro Gly Gly Pro Met Met Lys Leu
1               5                   10
```

<210> SEQ ID NO 579
<211> LENGTH: 9
<212> TYPE: PRT
<213> ORGANISM: Homo sapiens

<400> SEQUENCE: 579

```
Asn Leu Met Glu Met Val Ala Gln Leu
1               5
```

<210> SEQ ID NO 580
<211> LENGTH: 9
<212> TYPE: PRT
<213> ORGANISM: Homo sapiens

<400> SEQUENCE: 580

```
Leu Leu Met Glu Asn Ala Glu Arg Val
1               5
```

<210> SEQ ID NO 581
<211> LENGTH: 9
<212> TYPE: PRT
<213> ORGANISM: Homo sapiens

<400> SEQUENCE: 581

```
Arg Leu Trp Asn Glu Thr Val Glu Leu
1               5
```

<210> SEQ ID NO 582
<211> LENGTH: 9
<212> TYPE: PRT
<213> ORGANISM: Homo sapiens

<400> SEQUENCE: 582

```
Thr Leu Cys Asp Val Ile Leu Met Val
1               5
```

```
<210> SEQ ID NO 583
<211> LENGTH: 11
<212> TYPE: PRT
<213> ORGANISM: Homo sapiens

<400> SEQUENCE: 583

Ile Leu Ala Asn Asp Gly Val Leu Leu Ala Ala
1               5                   10

<210> SEQ ID NO 584
<211> LENGTH: 11
<212> TYPE: PRT
<213> ORGANISM: Homo sapiens

<400> SEQUENCE: 584

Ala Leu Ala Glu Val Ala Ala Met Glu Asn Val
1               5                   10

<210> SEQ ID NO 585
<211> LENGTH: 12
<212> TYPE: PRT
<213> ORGANISM: Homo sapiens

<400> SEQUENCE: 585

Ala Leu Trp Asp Leu Ala Ala Asp Lys Gln Thr Leu
1               5                   10

<210> SEQ ID NO 586
<211> LENGTH: 10
<212> TYPE: PRT
<213> ORGANISM: Homo sapiens

<400> SEQUENCE: 586

Lys Leu Lys Pro Gly Asp Leu Val Gly Val
1               5                   10

<210> SEQ ID NO 587
<211> LENGTH: 9
<212> TYPE: PRT
<213> ORGANISM: Homo sapiens

<400> SEQUENCE: 587

Val Met Asn Asp Arg Leu Tyr Ala Ile
1               5

<210> SEQ ID NO 588
<211> LENGTH: 9
<212> TYPE: PRT
<213> ORGANISM: Homo sapiens

<400> SEQUENCE: 588

Ser Leu Leu Pro Leu Ser His Leu Val
1               5

<210> SEQ ID NO 589
<211> LENGTH: 10
<212> TYPE: PRT
<213> ORGANISM: Homo sapiens

<400> SEQUENCE: 589

Lys Leu Tyr Pro Gln Leu Pro Ala Glu Ile
1               5                   10

<210> SEQ ID NO 590
```

```
<211> LENGTH: 9
<212> TYPE: PRT
<213> ORGANISM: Homo sapiens

<400> SEQUENCE: 590

Ser Leu Ile Glu Lys Leu Trp Gln Thr
1               5

<210> SEQ ID NO 591
<211> LENGTH: 9
<212> TYPE: PRT
<213> ORGANISM: Homo sapiens

<400> SEQUENCE: 591

Ser Met Ala Glu Leu Asp Ile Lys Leu
1               5

<210> SEQ ID NO 592
<211> LENGTH: 10
<212> TYPE: PRT
<213> ORGANISM: Homo sapiens

<400> SEQUENCE: 592

Arg Leu Leu Ser Ala Ala Glu Asn Phe Leu
1               5                   10

<210> SEQ ID NO 593
<211> LENGTH: 10
<212> TYPE: PRT
<213> ORGANISM: Homo sapiens

<400> SEQUENCE: 593

Gly Leu Pro Arg Phe Gly Ile Glu Met Val
1               5                   10

<210> SEQ ID NO 594
<211> LENGTH: 10
<212> TYPE: PRT
<213> ORGANISM: Homo sapiens

<400> SEQUENCE: 594

Ile Met Leu Lys Gly Asp Asn Ile Thr Leu
1               5                   10

<210> SEQ ID NO 595
<211> LENGTH: 9
<212> TYPE: PRT
<213> ORGANISM: Homo sapiens

<400> SEQUENCE: 595

Val Leu Leu Ser Ile Tyr Pro Arg Val
1               5

<210> SEQ ID NO 596
<211> LENGTH: 14
<212> TYPE: PRT
<213> ORGANISM: Homo sapiens

<400> SEQUENCE: 596

Ala Leu Leu Asp Gln Thr Lys Thr Leu Ala Glu Ser Ala Leu
1               5                   10

<210> SEQ ID NO 597
<211> LENGTH: 10
<212> TYPE: PRT
```

<213> ORGANISM: Homo sapiens

<400> SEQUENCE: 597

Lys Leu Leu Glu Gly Gln Val Ile Gln Leu
1               5                   10

<210> SEQ ID NO 598
<211> LENGTH: 9
<212> TYPE: PRT
<213> ORGANISM: Homo sapiens

<400> SEQUENCE: 598

Phe Leu Phe Pro His Ser Val Leu Val
1               5

<210> SEQ ID NO 599
<211> LENGTH: 11
<212> TYPE: PRT
<213> ORGANISM: Homo sapiens

<400> SEQUENCE: 599

Tyr Leu Leu Asn Asp Ala Ser Leu Ile Ser Val
1               5                   10

<210> SEQ ID NO 600
<211> LENGTH: 11
<212> TYPE: PRT
<213> ORGANISM: Homo sapiens

<400> SEQUENCE: 600

Ala Leu Ala Ala Pro Asp Ile Val Pro Ala Leu
1               5                   10

<210> SEQ ID NO 601
<211> LENGTH: 9
<212> TYPE: PRT
<213> ORGANISM: Homo sapiens

<400> SEQUENCE: 601

Ser Ala Phe Pro Phe Pro Val Thr Val
1               5

<210> SEQ ID NO 602
<211> LENGTH: 11
<212> TYPE: PRT
<213> ORGANISM: Homo sapiens

<400> SEQUENCE: 602

Tyr Leu Leu Glu Gln Ile Lys Leu Ile Glu Val
1               5                   10

<210> SEQ ID NO 603
<211> LENGTH: 11
<212> TYPE: PRT
<213> ORGANISM: Homo sapiens

<400> SEQUENCE: 603

Phe Leu Ile Glu Pro Glu His Val Asn Thr Val
1               5                   10

<210> SEQ ID NO 604
<211> LENGTH: 10
<212> TYPE: PRT
<213> ORGANISM: Homo sapiens

```
<400> SEQUENCE: 604

Ser Ile Leu Asp Arg Asp Asp Ile Phe Val
1               5                   10

<210> SEQ ID NO 605
<211> LENGTH: 9
<212> TYPE: PRT
<213> ORGANISM: Homo sapiens

<400> SEQUENCE: 605

Lys Leu Tyr Glu Ala Val Pro Gln Leu
1               5

<210> SEQ ID NO 606
<211> LENGTH: 9
<212> TYPE: PRT
<213> ORGANISM: Homo sapiens

<400> SEQUENCE: 606

Ala Leu Trp Glu Thr Glu Val Tyr Ile
1               5

<210> SEQ ID NO 607
<211> LENGTH: 11
<212> TYPE: PRT
<213> ORGANISM: Homo sapiens

<400> SEQUENCE: 607

Arg Leu Tyr Ser Gly Ile Ser Gly Leu Glu Leu
1               5                   10

<210> SEQ ID NO 608
<211> LENGTH: 9
<212> TYPE: PRT
<213> ORGANISM: Homo sapiens

<400> SEQUENCE: 608

Ser Leu Leu Ser Val Ser His Ala Leu
1               5

<210> SEQ ID NO 609
<211> LENGTH: 9
<212> TYPE: PRT
<213> ORGANISM: Homo sapiens

<400> SEQUENCE: 609

Ala Leu Trp Lys Gln Leu Leu Glu Leu
1               5

<210> SEQ ID NO 610
<211> LENGTH: 11
<212> TYPE: PRT
<213> ORGANISM: Homo sapiens

<400> SEQUENCE: 610

Leu Leu Ala Pro Thr Pro Tyr Ile Ile Gly Val
1               5                   10

<210> SEQ ID NO 611
<211> LENGTH: 10
<212> TYPE: PRT
<213> ORGANISM: Homo sapiens

<400> SEQUENCE: 611
```

-continued

Tyr Leu Leu Asp Asp Gly Thr Leu Val Val
1               5                   10

<210> SEQ ID NO 612
<211> LENGTH: 9
<212> TYPE: PRT
<213> ORGANISM: Homo sapiens

<400> SEQUENCE: 612

Tyr Leu Tyr Asn Glu Gly Leu Ser Val
1               5

<210> SEQ ID NO 613
<211> LENGTH: 11
<212> TYPE: PRT
<213> ORGANISM: Homo sapiens

<400> SEQUENCE: 613

Arg Leu Leu Pro Pro Gly Ala Val Val Ala Val
1               5                   10

<210> SEQ ID NO 614
<211> LENGTH: 11
<212> TYPE: PRT
<213> ORGANISM: Homo sapiens

<400> SEQUENCE: 614

Leu Leu Leu Pro Asp Gln Pro Pro Tyr His Leu
1               5                   10

<210> SEQ ID NO 615
<211> LENGTH: 9
<212> TYPE: PRT
<213> ORGANISM: Homo sapiens

<400> SEQUENCE: 615

Val Leu Pro Pro Asp Thr Asp Pro Ala
1               5

<210> SEQ ID NO 616
<211> LENGTH: 9
<212> TYPE: PRT
<213> ORGANISM: Homo sapiens

<400> SEQUENCE: 616

Val Leu Ile Asp Glu Val Glu Ser Leu
1               5

<210> SEQ ID NO 617
<211> LENGTH: 11
<212> TYPE: PRT
<213> ORGANISM: Homo sapiens

<400> SEQUENCE: 617

Ala Leu Met Tyr Glu Ser Glu Lys Val Gly Val
1               5                   10

<210> SEQ ID NO 618
<211> LENGTH: 12
<212> TYPE: PRT
<213> ORGANISM: Homo sapiens

<400> SEQUENCE: 618

Val Leu Phe Asp Ser Glu Ser Ile Gly Ile Tyr Val
1               5                   10

```
<210> SEQ ID NO 619
<211> LENGTH: 9
<212> TYPE: PRT
<213> ORGANISM: Homo sapiens

<400> SEQUENCE: 619

Ala Leu Gln Asp Arg Val Pro Leu Ala
1               5

<210> SEQ ID NO 620
<211> LENGTH: 9
<212> TYPE: PRT
<213> ORGANISM: Homo sapiens

<400> SEQUENCE: 620

Lys Leu Leu Asn Lys Ile Tyr Glu Ala
1               5

<210> SEQ ID NO 621
<211> LENGTH: 10
<212> TYPE: PRT
<213> ORGANISM: Homo sapiens

<400> SEQUENCE: 621

Val Leu Met Asp Arg Leu Pro Ser Leu Leu
1               5                   10

<210> SEQ ID NO 622
<211> LENGTH: 13
<212> TYPE: PRT
<213> ORGANISM: Homo sapiens

<400> SEQUENCE: 622

Arg Leu Leu Gly Glu Glu Val Val Arg Val Leu Gln Ala
1               5                   10

<210> SEQ ID NO 623
<211> LENGTH: 9
<212> TYPE: PRT
<213> ORGANISM: Homo sapiens

<400> SEQUENCE: 623

Tyr Leu Val Glu Asp Ile Gln His Ile
1               5

<210> SEQ ID NO 624
<211> LENGTH: 10
<212> TYPE: PRT
<213> ORGANISM: Homo sapiens

<400> SEQUENCE: 624

Phe Leu Gln Glu Glu Pro Gly Gln Leu Leu
1               5                   10

<210> SEQ ID NO 625
<211> LENGTH: 11
<212> TYPE: PRT
<213> ORGANISM: Homo sapiens

<400> SEQUENCE: 625

Val Val Leu Glu Gly Ala Ser Leu Glu Thr Val
1               5                   10
```

```
<210> SEQ ID NO 626
<211> LENGTH: 9
<212> TYPE: PRT
<213> ORGANISM: Homo sapiens

<400> SEQUENCE: 626

Leu Leu Met Ala Thr Ile Leu His Leu
1               5

<210> SEQ ID NO 627
<211> LENGTH: 11
<212> TYPE: PRT
<213> ORGANISM: Homo sapiens

<400> SEQUENCE: 627

Lys Leu Leu Glu Thr Glu Leu Leu Gln Glu Ile
1               5                   10

<210> SEQ ID NO 628
<211> LENGTH: 10
<212> TYPE: PRT
<213> ORGANISM: Homo sapiens

<400> SEQUENCE: 628

Lys Leu Trp Glu Phe Phe Gln Val Asp Val
1               5                   10

<210> SEQ ID NO 629
<211> LENGTH: 9
<212> TYPE: PRT
<213> ORGANISM: Homo sapiens

<400> SEQUENCE: 629

His Leu Leu Asn Glu Ser Pro Met Leu
1               5

<210> SEQ ID NO 630
<211> LENGTH: 9
<212> TYPE: PRT
<213> ORGANISM: Homo sapiens

<400> SEQUENCE: 630

Leu Leu Ser His Val Ile Val Ala Leu
1               5

<210> SEQ ID NO 631
<211> LENGTH: 9
<212> TYPE: PRT
<213> ORGANISM: Homo sapiens

<400> SEQUENCE: 631

Phe Leu Asp Val Phe Leu Pro Arg Val
1               5

<210> SEQ ID NO 632
<211> LENGTH: 10
<212> TYPE: PRT
<213> ORGANISM: Homo sapiens

<400> SEQUENCE: 632

Tyr Leu Ile Pro Asp Ile Asp Leu Lys Leu
1               5                   10

<210> SEQ ID NO 633
<211> LENGTH: 9
```

-continued

```
<212> TYPE: PRT
<213> ORGANISM: Homo sapiens

<400> SEQUENCE: 633

Ala Leu Ser Arg Val Ser Val Asn Val
1               5

<210> SEQ ID NO 634
<211> LENGTH: 9
<212> TYPE: PRT
<213> ORGANISM: Homo sapiens

<400> SEQUENCE: 634

Val Val Ala Glu Phe Val Pro Leu Ile
1               5

<210> SEQ ID NO 635
<211> LENGTH: 9
<212> TYPE: PRT
<213> ORGANISM: Homo sapiens

<400> SEQUENCE: 635

Ser Leu Asp Ser Thr Leu His Ala Val
1               5

<210> SEQ ID NO 636
<211> LENGTH: 9
<212> TYPE: PRT
<213> ORGANISM: Homo sapiens

<400> SEQUENCE: 636

Leu Leu Thr Glu Ile Arg Ala Val Val
1               5

<210> SEQ ID NO 637
<211> LENGTH: 10
<212> TYPE: PRT
<213> ORGANISM: Homo sapiens

<400> SEQUENCE: 637

Ser Ile Tyr Gly Gly Phe Leu Leu Gly Val
1               5                   10

<210> SEQ ID NO 638
<211> LENGTH: 9
<212> TYPE: PRT
<213> ORGANISM: Homo sapiens

<400> SEQUENCE: 638

Lys Leu Ile Gln Glu Ser Pro Thr Val
1               5

<210> SEQ ID NO 639
<211> LENGTH: 9
<212> TYPE: PRT
<213> ORGANISM: Homo sapiens

<400> SEQUENCE: 639

Ser Leu Phe Gln Asn Cys Phe Glu Leu
1               5

<210> SEQ ID NO 640
<211> LENGTH: 10
<212> TYPE: PRT
<213> ORGANISM: Homo sapiens
```

```
<400> SEQUENCE: 640

Tyr Leu Phe Ser Glu Ala Leu Asn Ala Ala
1               5                   10

<210> SEQ ID NO 641
<211> LENGTH: 12
<212> TYPE: PRT
<213> ORGANISM: Homo sapiens

<400> SEQUENCE: 641

Val Leu Leu Pro Val Glu Val Ala Thr His Tyr Leu
1               5                   10

<210> SEQ ID NO 642
<211> LENGTH: 10
<212> TYPE: PRT
<213> ORGANISM: Homo sapiens

<400> SEQUENCE: 642

Phe Leu His Asp Ile Ser Asp Val Gln Leu
1               5                   10

<210> SEQ ID NO 643
<211> LENGTH: 10
<212> TYPE: PRT
<213> ORGANISM: Homo sapiens

<400> SEQUENCE: 643

Ala Leu Phe Pro His Leu Leu Gln Pro Val
1               5                   10

<210> SEQ ID NO 644
<211> LENGTH: 9
<212> TYPE: PRT
<213> ORGANISM: Homo sapiens

<400> SEQUENCE: 644

Leu Thr Phe Gly Asp Val Val Ala Val
1               5

<210> SEQ ID NO 645
<211> LENGTH: 9
<212> TYPE: PRT
<213> ORGANISM: Homo sapiens

<400> SEQUENCE: 645

Leu Leu Tyr Asp Ala Val His Ile Val
1               5

<210> SEQ ID NO 646
<211> LENGTH: 9
<212> TYPE: PRT
<213> ORGANISM: Homo sapiens

<400> SEQUENCE: 646

Ile Leu Ser Pro Thr Val Val Ser Ile
1               5

<210> SEQ ID NO 647
<211> LENGTH: 9
<212> TYPE: PRT
<213> ORGANISM: Homo sapiens

<400> SEQUENCE: 647
```

-continued

```
Ser Leu Gly Leu Phe Leu Ala Gln Val
1               5

<210> SEQ ID NO 648
<211> LENGTH: 9
<212> TYPE: PRT
<213> ORGANISM: Homo sapiens

<400> SEQUENCE: 648

Leu Leu Trp Gly Asn Ala Ile Phe Leu
1               5

<210> SEQ ID NO 649
<211> LENGTH: 9
<212> TYPE: PRT
<213> ORGANISM: Homo sapiens

<400> SEQUENCE: 649

Ala Leu Ala Phe Lys Leu Asp Glu Val
1               5

<210> SEQ ID NO 650
<211> LENGTH: 10
<212> TYPE: PRT
<213> ORGANISM: Homo sapiens

<400> SEQUENCE: 650

Ala Ile Met Gly Phe Ile Gly Phe Phe Val
1               5                   10

<210> SEQ ID NO 651
<211> LENGTH: 9
<212> TYPE: PRT
<213> ORGANISM: Homo sapiens

<400> SEQUENCE: 651

Ile Leu Gln Asp Arg Leu Asn Gln Val
1               5

<210> SEQ ID NO 652
<211> LENGTH: 9
<212> TYPE: PRT
<213> ORGANISM: Homo sapiens

<400> SEQUENCE: 652

Thr Leu Trp Tyr Arg Ala Pro Glu Val
1               5

<210> SEQ ID NO 653
<211> LENGTH: 9
<212> TYPE: PRT
<213> ORGANISM: Homo sapiens

<400> SEQUENCE: 653

Thr Leu Ile Ser Arg Leu Pro Ala Val
1               5

<210> SEQ ID NO 654
<211> LENGTH: 9
<212> TYPE: PRT
<213> ORGANISM: Homo sapiens

<400> SEQUENCE: 654

Lys Ile Leu Glu Asp Val Val Gly Val
```

```
1               5
```

```
<210> SEQ ID NO 655
<211> LENGTH: 11
<212> TYPE: PRT
<213> ORGANISM: Homo sapiens

<400> SEQUENCE: 655

Ala Leu Met Asp Lys Glu Gly Leu Thr Ala Leu
1               5                   10

<210> SEQ ID NO 656
<211> LENGTH: 9
<212> TYPE: PRT
<213> ORGANISM: Homo sapiens

<400> SEQUENCE: 656

Lys Leu Leu Glu Tyr Ile Glu Glu Ile
1               5

<210> SEQ ID NO 657
<211> LENGTH: 10
<212> TYPE: PRT
<213> ORGANISM: Homo sapiens

<400> SEQUENCE: 657

Ser Leu Ala Glu Arg Leu Phe Phe Gln Val
1               5                   10

<210> SEQ ID NO 658
<211> LENGTH: 9
<212> TYPE: PRT
<213> ORGANISM: Homo sapiens

<400> SEQUENCE: 658

Leu Leu Gln Asp Arg Leu Val Ser Val
1               5

<210> SEQ ID NO 659
<211> LENGTH: 10
<212> TYPE: PRT
<213> ORGANISM: Homo sapiens

<400> SEQUENCE: 659

Ile Leu Phe Pro Asp Ile Ile Ala Arg Ala
1               5                   10

<210> SEQ ID NO 660
<211> LENGTH: 9
<212> TYPE: PRT
<213> ORGANISM: Homo sapiens

<400> SEQUENCE: 660

Ala Ile Leu Asp Thr Leu Tyr Glu Val
1               5

<210> SEQ ID NO 661
<211> LENGTH: 9
<212> TYPE: PRT
<213> ORGANISM: Homo sapiens

<400> SEQUENCE: 661

Ser Leu Ile Asp Ala Asp Pro Tyr Leu
1               5
```

```
<210> SEQ ID NO 662
<211> LENGTH: 9
<212> TYPE: PRT
<213> ORGANISM: Homo sapiens

<400> SEQUENCE: 662

Lys Ile Gln Glu Ile Leu Thr Gln Val
1               5

<210> SEQ ID NO 663
<211> LENGTH: 9
<212> TYPE: PRT
<213> ORGANISM: Homo sapiens

<400> SEQUENCE: 663

Lys Ile Gln Glu Met Gln His Phe Leu
1               5

<210> SEQ ID NO 664
<211> LENGTH: 10
<212> TYPE: PRT
<213> ORGANISM: Homo sapiens

<400> SEQUENCE: 664

Glu Leu Ala Gly Ile Gly Ile Leu Thr Val
1               5                   10

<210> SEQ ID NO 665
<211> LENGTH: 9
<212> TYPE: PRT
<213> ORGANISM: Homo sapiens

<400> SEQUENCE: 665

Tyr Leu Leu Pro Ala Ile Val His Ile
1               5
```

US 11,384,128 B2

PEPTIDES AND COMBINATION OF PEPTIDES FOR USE IN IMMUNOTHERAPY AGAINST OVARIAN CANCER AND OTHER CANCERS

CROSS REFERENCE TO RELATED APPLICATIONS

This application is a continuation of U.S. patent application Ser. No. 16/713,157, filed 13 Dec. 2019, which is a continuation of U.S. patent application Ser. No. 16/281,790, filed 21 Feb. 2019, now U.S. Pat. No. 10,533,041, issued 14 Jan. 2020, which is a continuation of U.S. patent application Ser. No. 16/101,081, filed 10 Aug. 2018, now U.S. Pat. No. 10,239,925, issued 26 Mar. 2019, which is a continuation of U.S. patent application Ser. No. 15/980,328, filed 15 May 2018, now U.S. Pat. No. 10,174,089, issued 8 Jan. 2019, which is a continuation of U.S. patent application Ser. No. 15/198,471, filed 30 Jun. 2016, now U.S. Pat. No. 10,000,539, issued 19 Jun. 2018, which claims the benefit of U.S. Provisional Application Ser. No. 62/187,507, filed 1 Jul. 2015, and Great Britain Application No. 1511546.2, filed 1 Jul. 2015, the content of each of these applications is herein incorporated by reference in their entirety.

This application is also related to PCT/EP2016/065166 filed 29 Jun. 2016, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2912919-050022_Sequence_Listing_ST25.txt" created on 2 Nov. 2021, and 105,654 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

Ovarian Cancer

With an estimated 239 000 new cases in 2012, ovarian cancer is the seventh most common cancer in women, representing 4% of all cancers in women. The fatality rate of ovarian cancer tends to be rather high relative to other cancers of the female reproductive organs, and case fatality is higher in lower-resource settings. As a consequence, ovarian cancer is the eighth most frequent cause of cancer death among women, with 152 000 deaths. In 2012, almost 55% of all new cases occurred in countries with high or very high levels of human development; 37% of the new cases and 39% of the deaths occurred in Europe and North America. Incidence rates are highest in northern and eastern Europe, North America, and Oceania, and tend to be relatively low in Africa and much of Asia. Incidence rates have been declining in certain countries with very high levels of human development, notably in Europe and North America.

The most common ovarian cancers are ovarian carcinomas, which are also the most lethal gynecological malignancies. Based on histopathology and molecular genetics, ovarian carcinomas are divided into five main types: high-grade serous (70%), endometrioid (10%), clear cell (10%), mucinous (3%), and low-grade serous carcinomas (<5%), which together account for more than 95% of cases. Much less common are malignant germ cell tumours (dysgerminomas, yolk sac tumours, and immature teratomas) (3% of ovarian cancers) and potentially malignant sex cord stromal tumours (1-2%), the most common of which are granulosa cell tumours.

Family history of ovarian cancer accounts for 10% of cases; the risk is increased 3-fold when two or more first-degree relatives have been affected. Women with germline mutations in BRCA1 or BRCA2 have a 30-70% risk of developing ovarian cancer, mainly high-grade serous carcinomas, by age 70 (Risch et al., 2006).

Surgical resection is the primary therapy in early as well as advanced stage ovarian carcinoma. Surgical removal is followed by systemic chemotherapy with platinum analogs, except for very low grade ovarian cancers (stage IA, grade 1), where post-operative chemotherapy is not indicated. In advanced stage ovarian cancer, the first line chemotherapy comprises a combination of carboplatin with paclitaxel, which can be supplemented with bevacizumab. The standard treatment for platinum-resistant ovarian cancers consists of a monotherapy with one of the following chemotherapeutics: pegylated liposomal doxorubicin, topotecane, gemcitabine or paclitaxel (S3-Leitlinie maligne Ovarialtumore, 2013).

Immunotherapy appears to be a promising strategy to ameliorate the treatment of ovarian cancer patients, as the presence of pro-inflammatory tumor infiltrating lymphocytes, especially CD8-positive T cells, correlates with good prognosis and T cells specific for tumor-associated antigens can be isolated from cancer tissue.

Therefore, a lot of scientific effort is put into the investigation of different immunotherapies in ovarian cancer. A considerable number of pre-clinical and clinical studies has already been performed and further studies are currently ongoing. Clinical data are available for cytokine therapy, vaccination, monoclonal antibody treatment, adoptive cell transfer and immunomodulation.

Cytokine therapy with interleukin-2, interferon-alpha, interferon-gamma or granulocyte-macrophage colony stimulating factor aims at boosting the patient's own anti-tumor immune response and these treatments have already shown promising results in small study cohorts.

Phase I and II vaccination studies, using single or multiple peptides, derived from several tumor-associated proteins (Her2/neu, NY-ESO-1, p53, Wilms tumor-1) or whole tumor antigens, derived from autologous tumor cells revealed good safety and tolerability profiles, but only low to moderate clinical effects.

Monoclonal antibodies that specifically recognize tumor-associated proteins are thought to enhance immune cell-mediated killing of tumor cells. The anti-CA-125 antibodies oregovomab and abagovomab as well as the anti-EpCAM antibody catumaxomab achieved promising results in phase II and III studies. In contrast, the anti-MUC1 antibody HMFG1 failed to clearly enhance survival in a phase III study.

An alternative approach uses monoclonal antibodies to target and block growth factor and survival receptors on tumor cells. While administration of trastuzumab (anti-HER2/neu antibody) and MOv18 and MORAb-003 (anti-folate receptor alpha antibodies) only conferred limited clinical benefit to ovarian cancer patients, addition of bevacizumab (anti-VEGF antibody) to the standard chemotherapy in advanced ovarian cancer appears to be advantageous.

Adoptive transfer of immune cells achieved heterogeneous results in clinical trials. Adoptive transfer of autologous, in vitro expanded tumor infiltrating T cells was shown to be a promising approach in a pilot trial. In contrast, transfer of T cells harboring a chimeric antigen receptor specific for folate receptor alpha did not induce a significant clinical response in a phase I trial. Dendritic cells pulsed with tumor cell lysate or tumor-associated proteins in vitro were shown to enhance the anti-tumor T cell response upon transfer, but the extent of T cell activation did not correlate with clinical effects. Transfer of natural killer cells caused significant toxicities in a phase II study.

Intrinsic anti-tumor immunity as well as immunotherapy are hampered by an immunosuppressive tumor microenvironment. To overcome this obstacle immunomodulatory drugs, like cyclophosphamide, anti-CD25 antibodies and pegylated liposomal doxorubicin are tested in combination with immunotherapy. Most reliable data are currently available for ipilimumab, an anti-CTLA4 antibody, which enhances T cell activity. Ipilimumab was shown to exert significant anti-tumor effects in ovarian cancer patients (Mantia-Smaldone et al., 2012).

Considering the severe side-effects and expense associated with treating cancer, there is a need to identify factors that can be used in the treatment of cancer in general and ovarian cancer in particular. There is also a need to identify factors representing biomarkers for cancer in general and ovarian cancer in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes. T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 640 or a variant sequence thereof which is at least 77%, preferably at least 88%, homologous (preferably at least 77% or at least 88% identical) to SEQ ID NO: 1 to SEQ ID NO: 640, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 640 or a variant thereof, which is at least 77%, preferably at least 88%, homologous (preferably at least 77% or at least 88% identical) to SEQ ID NO: 1 to SEQ ID NO: 640, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before. The peptides in Table 3 are additional peptides that may be useful in combination with the other peptides of the invention. The peptides in Table 4 are furthermore useful in the diagnosis and/or treatment of various other malignancies that involve an over-expression or over-presentation of the respective underlying polypeptide.

TABLE 1

Peptides according to the present invention.
J = phospho-serine.

| SEQ ID NO. | Sequence | Gene ID(s) | Official Gene Symbol(s) |
|---|---|---|---|
| 1 | SLMEPPAVLLL | 8900 | CCNA1 |
| 2 | SLLEADPFL | 8900 | CCNA1 |
| 3 | SLASKLTTL | 94025 | MUC16 |
| 4 | GIMEHITKI | 94025 | MUC16 |
| 5 | HLTEVYPEL | 94025 | MUC16 |
| 6 | VLVSDGVHSV | 1952 | CELSR2 |
| 7 | SLVGLLLYL | 100101267, 9883 | POM121C, POM121 |
| 8 | FTLGNVVGMYL | 100287425, 647087 | C7orf73 |
| 9 | GAAKDLPGV | 100534599, 57461 | ISY1-RAB43, ISY1 |
| 10 | FLATFPLAAV | 10076 | PTPRU |
| 11 | KIFEMLEGV | 101060208, 101060210, 101060211, 441519, 441520, 441521, 541465, 541466, 728911 | CT45A3, CT45A4, CT45A5, CT45A6, CT45A1, CT45A2 |

TABLE 1-continued

Peptides according to the present invention.
J = phospho-serine.

| SEQ ID NO. | Sequence | Gene ID(s) | Official Gene Symbol(s) |
|---|---|---|---|
| 12 | SLWPDPMEV | 101060557, 146177 | VWA3A |
| 13 | YLMDESLNL | 101060756, 115948 | CCDC151 |
| 14 | AAYGGLNEKSFV | 10140 | TOB1 |
| 15 | VLLTFKIFL | 10149 | GPR64 |
| 16 | VLFQGQASL | 10154 | PLXNC1 |
| 17 | GLLPGDRLVSV | 10207 | INADL |
| 18 | YLVAKLVEV | 10277 | UBE4B |
| 19 | FMVDNEAIYDI | 10376, 112714, 113457, 51807, 7277, 7278, 7846, 84790 | TUBA1B, TUBA3E, TUBA3D, TUBA8, TUBA4A, TUBA3C, TUBA1A, TUBA1C |
| 20 | RMIEYFIDV | 10396, 153020 | ATP8A1, RASGEF1B |
| 21 | VLDELDMEL | 10437 | IFI30 |
| 22 | IMEENPGIFAV | 10558 | SPTLC1 |
| 23 | VLLDDIFAQL | 10565 | ARFGEF1 |
| 24 | SLSDGLEEV | 10651 | MTX2 |
| 25 | FLPDEPYIKV | 10686 | CLDN16 |
| 26 | ALLELAEEL | 10694, 644131 | CCT8, CCT8P1 |
| 27 | ILADIVISA | 10797 | MTHFD2 |
| 28 | QLLDETSAITL | 10915 | TCERG1 |
| 29 | KMLGIPISNILMV | 10964 | IFI44L |
| 30 | LILDWVPYI | 10975 | UQCR11 |
| 31 | YLAPELFVNV | 11035 | RIPK3 |
| 32 | KLDDLTQDLTV | 11116 | FGFR1OP |
| 33 | VLLSLLEKV | 1130 | LYST |
| 34 | ILVEADSLWVV | 11329 | STK38 |
| 35 | KINDTIYEV | 113510 | HELQ |
| 36 | YVLEDLEVTV | 114960, 22820, 26958 | TSGA13, COPG1, COPG2 |
| 37 | LLWDVVTGQSV | 114987 | WDR31 |
| 38 | FLLEDDIHVS | 116461 | TSEN15 |
| 39 | SVAPNLPAV | 120114 | FAT3 |
| 40 | TLLVKVFSV | 122402 | TDRD9 |
| 41 | SLMPHIPGL | 122402 | TDRD9 |
| 42 | VLLQKIVSA | 122402 | TDRD9 |
| 43 | VLSSLEINI | 1233 | CCR4 |
| 44 | ILDPISSGFLL | 127795 | C1orf87 |
| 45 | SLWQDIPDV | 128272 | ARHGEF19 |
| 46 | ILTEENIHL | 130540 | ALS2CR12 |
| 47 | ILLSVPLLVV | 1314 | COPA |
| 48 | ALAELYEDEV | 137886 | UBXN2B |
| 49 | YLPAVFEEV | 9961 | MVP |
| 50 | SLSELEALM | 143686 | SESN3 |
| 51 | LLPDLEFYV | 143888 | KDELC2 |
| 52 | FLLAHGLGFLL | 144110 | TMEM86A |
| 53 | KMIETDILQKV | 146562 | C16orf71 |
| 54 | SLLEQGKEPWMV | 147949, 163087, 342892, 374899, 84503 | ZNF583, ZNF383, ZNF850, ZNF829, ZNF527 |
| 55 | SLLDLETLSL | 148137 | C19orf55 |
| 56 | KLYEGIPVLL | 152110 | NEK10 |
| 57 | TLAELQPPVQL | 157922 | CAMSAP1 |
| 58 | FLDTLKDLI | 162 | AP1B1 |
| 59 | IMEDIILTL | 1656 | DDX6 |
| 60 | SLTIDGIYYV | 1659 | DHX8 |
| 61 | FLQGYQLHL | 19 | ABCA1 |
| 62 | VLLDVSAGQLLM | 196463 | PLBD2 |
| 63 | YLLPSGGSVTL | 196483, 286042, 348926 | FAM86A, FAM86B3P, FAM86EP, FAM86C1, FAM86DP |

TABLE 1-continued

Peptides according to the present invention.
J = phospho-serine.

| SEQ ID NO. | Sequence | Gene ID(s) | Official Gene Symbol(s) |
|---|---|---|---|
| | | 55199, 692099 | |
| 64 | YAAPGGLIGV | 1968, 255308 | EIF2S3 |
| 65 | LKVNQGLESL | 197358 | NLRC3 |
| 66 | FLDENIGGVAV | 200424 | TET3 |
| 67 | TLLAEALVTV | 200958 | MUC20 |
| 68 | SLMELPRGLFL | 219527 | LRRC55 |
| 69 | FQLDPSSGVLVTV | 2196 | FAT2 |
| 70 | GLLDYPVGV | 219736 | STOX1 |
| 71 | GILARIASV | 221322 | C6orf170 |
| 72 | SLLELDGINL | 221806 | VWDE |
| 73 | NIFDLQIYV | 222256 | CDHR3 |
| 74 | ALLDPEVLSIFV | 22898 | DENND3 |
| 75 | GLLEVMVNL | 23001 | WDFY3 |
| 76 | ILIDSIYKV | 23007 | PLCH1 |
| 77 | ILVEADGAWVV | 23012 | STK38L |
| 78 | SLFSSLEPQIQPV | 23029 | RBM34 |
| 79 | SLFIGEKAVLL | 23029 | RBM34 |
| 80 | FLYDNLVESL | 23132 | RAD54L2 |
| 81 | FLFSQLQYL | 23165 | NUP205 |
| 82 | FLSSVTYNL | 23312 | DMXL2 |
| 83 | ILAPTVMMI | 23312 | DMXL2 |
| 84 | VTFGEKLLGV | 23428 | SLC7A8 |
| 85 | KMSELRVTL | 23499 | MACF1 |
| 86 | NLIGKIENV | 23639 | LRRC6 |
| 87 | ALPEAPAPLLPHIT | 23786 | BCL2L13 |
| 88 | FLLVGDLMAV | 23787 | MTCH1 |
| 89 | YILPTETIYV | 254956 | MORN5 |
| 90 | TLLQIIETV | 256309 | CCDC110 |
| 91 | IMQDFPAEIFL | 25914 | RTTN |
| 92 | YLIPFTGIVGL | 26001 | RNF167 |
| 93 | LLQAIKLYL | 260293 | CYP4X1 |
| 94 | YLIDIKTIAI | 26160 | IFT172 |
| 95 | SVIPQIQKV | 26272 | FBXO4 |
| 96 | YIFTDNPAAV | 26301 | GBGT1 |
| 97 | SLINGSFLV | 27 | ABL2 |
| 98 | LIIDQADIYL | 27042 | DIEXF |
| 99 | ALVSKGLATV | 27044 | SND1 |
| 100 | YLLSTNAQL | 27285 | TEKT2 |
| 101 | ILVGGGALATV | 2820 | GPD2 |
| 102 | YLFESEGLVL | 283431 | GAS2L3 |
| 103 | TLAEEVVAL | 283755, 400322, 8924 | HERC2P3, HERC2P2, HERC2 |
| 104 | STMEQNFLL | 284110 | GSDMA |
| 105 | LLLEHSFEI | 284361 | EMC10 |
| 106 | LLYDAVHIVSV | 2899 | GRIK3 |
| 107 | FLQPVDDTQHL | 2906 | GRIN2D |
| 108 | ALFPGVALLLA | 2923 | PDIA3 |
| 109 | IILSILEQA | 2953, 653689 | GSTT2, GSTT2B |
| 110 | FLSQVDFEL | 2968 | GTF2H4 |
| 111 | YVWGFYPAEV | 3109 | HLA-DMB |
| 112 | FLITSNNQL | 353497, 79441 | POLN, HAUS3 |
| 113 | GLLPTPLFGV | 359710 | BPIFB3 |
| 114 | SLVGEPILQNV | 359710 | BPIFB3 |
| 115 | AIAGAGILYGV | 362 | AQP5 |
| 116 | YHIDEEVGF | 3620 | IDO1 |
| 117 | ILPDGEDFLAV | 3636 | INPPL1 |
| 118 | KLIDNNINV | 3696 | ITGB8 |
| 119 | FLYIGDIVSL | 3709 | ITPR2 |
| 120 | ALLGIPLTLV | 3777, 60598 | KCNK3, KCNK15 |
| 121 | GVVDPRAISVL | 387522, 7335 | TMEM189-UBE2V1, UBE2V1 |
| 122 | FLLAEDDIYL | 389677 | RBM12B |
| 123 | NLWDLTDASVV | 3959 | LGALS3BP |
| 124 | ALYETELADA | 4001 | LMNB1 |
| 125 | VQIHQVAQV | 4053 | LTBP2 |
| 126 | VLAYFLPEA | 4171 | MCM2 |
| 127 | KIGDEPPKV | 4291 | MLF1 |
| 128 | YLFDDPLSAV | 4363 | ABCC1 |
| 129 | GLLDGGVDILL | 4548 | MTR |
| 130 | FLWNGEDSALL | 4586, 727897 | MUC5AC, MUC5B |
| 131 | FVPPVTVFPSL | 4586, 727897 | MUC5AC, MUC5B |
| 132 | LLVEQPPLAGV | 4773 | NFATC2 |
| 133 | KVLSNIHTV | 4867 | NPHP1 |
| 134 | YLQELIFSV | 51000 | SLC35B3 |
| 135 | ALSEVDFQL | 51059 | FAM135B |
| 136 | YLADPSNLFVV | 51072, 728556 | MEMO1, MEMO1P1 |
| 137 | TLVLTLPTV | 51073 | MRPL4 |
| 138 | YQYPRAILSV | 51105 | PHF20L1 |
| 139 | SVMEVNSGIYRV | 51182 | HSPA14 |
| 140 | YMDAPKAAL | 51246 | SHISA5 |
| 141 | YLDFSNNRL | 51284 | TLR7 |
| 142 | FLFATPVFI | 51296 | SLC15A3 |
| 143 | LLLDITPEI | 51430 | SUCO |
| 144 | YIMEPSIFNTL | 51497 | TH1L |
| 145 | FLATSGTLAGI | 51522 | TMEM14C |
| 146 | SLATAGDGLIEL | 5245 | PHB |
| 147 | SLLEAVSFL | 5261 | PHKG2 |
| 148 | ALNPEIVSV | 5277 | PIGA |
| 149 | NLLELFVQL | 5297 | PI4KA |
| 150 | RLWEEGEELEL | 5329 | PLAUR |
| 151 | KILQQLVTL | 541468 | LURAP1 |
| 152 | ILFEDIFDV | 5437 | POLR2H |
| 153 | FLIANVLYL | 5476 | CTSA |
| 154 | ALDDGTPAL | 54798 | DCHS2 |
| 155 | RVANLHFPSV | 54809 | SAMD9 |
| 156 | AISQGITLPSL | 54856 | GON4L |
| 157 | SLNDEVPEV | 54919 | HEATR2 |
| 158 | KLFDVDEDGYI | 54947 | LPCAT2 |
| 159 | GLVGNPLPSV | 55127 | HEATR1 |
| 160 | FLFDEEIEQI | 55132 | LARP1B |
| 161 | ALLEGVNTV | 55211 | DPPA4 |
| 162 | YQQAQVPSV | 55217 | TMLHE |
| 163 | ALDEMGDLLQL | 55304 | SPTLC3 |
| 164 | ALLPQPKNLTV | 5546 | PRCC |
| 165 | SLLDEIRAV | 55567 | DNAH3 |
| 166 | YLNHLEPPV | 55666 | NPLOC4 |
| 167 | KVLEVTEEFGV | 55705 | IPO9 |
| 168 | KILDADIQL | 55779 | WDR52 |
| 169 | NLPEYLPFV | 55832, 91689 | CAND1, C22orf32 |
| 170 | RLQETLSAA | 5591 | PRKDC |
| 171 | LLLPLQILL | 5650 | KLK7 |
| 172 | VLYSYTIITV | 56941 | C3orf37 |
| 173 | LLDSASAGLYL | 56992 | KIF15 |
| 174 | ALAQYLITA | 57060 | PCBP4 |
| 175 | YLFENISQL | 57115 | PGLYRP4 |
| 176 | YLMEGSYNKVFL | 5714 | PSMD8 |
| 177 | YLLPEEYTSTL | 57143 | ADCK1 |
| 178 | ALTEIAFVV | 57148 | RALGAPB |
| 179 | KVLNELYTV | 57522 | SRGAP1 |
| 180 | FQIDPHSGLVTV | 57526 | PCDH19 |
| 181 | LLWAGTAFQV | 57535 | KIAA1324 |
| 182 | MLLEAPGIFL | 57570 | TRMT5 |
| 183 | FGLDLVTEL | 57674 | RNF213 |
| 184 | YLMDINGKMWL | 57674 | RNF213 |
| 185 | FLIDDKGYTL | 57685 | CACHD1 |
| 186 | TLFFQQNAL | 5771 | PTPN2 |
| 187 | RQISIRGIVGV | 5836 | PYGL |
| 188 | GLFPVTPEAV | 59352 | LGR6 |
| 189 | ALQRKLPYV | 60598 | KCNK15 |
| 190 | FLSSLTETI | 629 | CFB |
| 191 | LLQEGQALEYV | 629 | CFB |
| 192 | KMLDGASFTL | 63941 | NECAB3 |
| 193 | QLLDADGFLNV | 63967 | CLSPN |
| 194 | ALPLFVITV | 64078 | SLC28A3 |
| 195 | GLFADLLPRL | 642475 | MROH6 |
| 196 | YLYSVEIKL | 642987 | TMEM232 |
| 197 | ALGPEGGRV | 64321 | SOX17 |
| 198 | KTINKVPTV | 6498 | SKIL |

TABLE 1-continued

Peptides according to the present invention.
J = phospho-serine.

| SEQ ID NO. | Sequence | Gene ID(s) | Official Gene Symbol(s) |
|---|---|---|---|
| 199 | ALQDVPLSSV | 65003 | MRPL11 |
| 200 | LLFGSVQEV | 65250 | C5orf42 |
| 201 | RLVDYLEGI | 65260 | SELRC1 |
| 202 | ALLDQQGSRWTL | 6565 | SLC15A2 |
| 203 | VLLEDAHSHTL | 6614 | SIGLEC1 |
| 204 | KIAENVEEV | 6804 | STX1A |
| 205 | SLYPGTETMGL | 6840 | SVIL |
| 206 | VLQEGKLQKLAQL | 6891 | TAP2 |
| 207 | GLTSTNAEV | 7029 | TFDP2 |
| 208 | KISPVTFSV | 728661, 9906 | SLC35E2B, SLC35E2 |
| 209 | KLIESKHEV | 7328 | UBE2H |
| 210 | LLLNAVLTV | 7374 | UNG |
| 211 | LLWPGAALL | 7462 | LAT2 |
| 212 | ALWDQDNLSV | 7464 | CORO2A |
| 213 | VTAAYMDTVSL | 7498 | XDH |
| 214 | FLLDLDPLLL | 7915 | ALDH5A1 |
| 215 | QLINHLHAV | 79365 | BHLHE41 |
| 216 | NLWEDPYYL | 79659 | DYNC2H1 |
| 217 | ALIHPVSTV | 79690 | GAL3ST4 |
| 218 | SALEELVNV | 79707 | NOL9 |
| 219 | KLSDIGITV | 79725 | THAP9 |
| 220 | LLQKFVPEI | 79832 | QSER1 |
| 221 | ALYEEGLLL | 80311 | KLHL15 |
| 222 | NLIENVQRL | 8195 | MKKS |
| 223 | ALLENIALYL | 833 | CARS |
| 224 | TLIDAQWVL | 84000 | TMPRSS13 |
| 225 | SLLKVLPAL | 84125 | LRRIQ1 |
| 226 | MLYVVPIYL | 84187 | TMEM164 |
| 227 | ALMNTLLYL | 84197 | |
| 228 | AMQEYIAVV | 84320 | ACBD6 |
| 229 | RLPGPLGTV | 84875 | PARP10 |
| 230 | ILVDWLVEV | 85417, 890, 8900 | CCNB3, CCNA2, CCNA1 |
| 231 | FLSPQQPPLLL | 8621 | CDK13 |
| 232 | ALLEAQDVELYL | 8701 | DNAH11 |
| 233 | VLSETLYEL | 8914 | TIMELESS |
| 234 | ALMEDTGRQML | 89782 | LMLN |
| 235 | YLNDLHEVLL | 898 | CCNE1 |
| 236 | GLLEAKVSL | 89845 | ABCC10 |
| 237 | ALLEASGTLLL | 90580 | C19orf52 |
| 238 | YLISFQTHI | 90592 | ZNF700 |
| 239 | AAFAGKLLSV | 91543 | RSAD2 |
| 240 | ILLEQAFYL | 92255 | LMBRD2 |
| 241 | SLVEVNPAYSV | 92305 | TMEM129 |
| 242 | AIAYILQGV | 92335 | STRADA |
| 243 | LLLNELPSV | 92345 | NAF1 |
| 244 | SLFGGTEITI | 93035 | PKHD1L1 |
| 245 | SMIDDLLGV | 93233 | CCDC114 |
| 246 | LLWEVVSQL | 9462 | RASAL2 |
| 247 | VLLPNDLLEKV | 9472 | AKAP6 |
| 248 | FLFPNQYVDV | 9632 | SEC24C |
| 249 | LLDGFLVNV | 9632 | SEC24C |
| 250 | ALSEEGLLVYL | 9690 | UBE3C |
| 251 | ALYTGFSILV | 972 | CD74 |
| 252 | LLIGTDVSL | 9730 | VPRBP |
| 253 | GLDAATATV | 9869 | SETDB1 |
| 254 | TLLAFIMEL | 987 | LRBA |
| 255 | VLASYNLTV | 987 | LRBA |
| 256 | FLPPEHTIVYI | 9896 | FIG4 |
| 257 | SIFSAFLSV | 9918 | NCAPD2 |
| 258 | ELAERVPAI | 9918 | NCAPD2 |
| 259 | TLMRQLQQV | 140680 | C20orf96 |
| 260 | TLLEGPDPAELLL | 100101267, 9883 | POM121C, POM121 |
| 261 | YVLEFLEEI | 10026 | PIGK |
| 262 | LLWGDLIWL | 101060729, 548593, 79008 | SLX1A, SLX1B |
| 263 | LLVSNLDFGV | 10189 | ALYREF |
| 264 | SLQEQLHSV | 133584 | EGFLAM |
| 265 | LLFGGTKTV | 1572 | CYP2F1 |
| 266 | KITDTLIHL | 2099 | ESR1 |
| 267 | ALQDFLLSV | 2189 | FANCG |
| 268 | IAGPGLPDL | 220074 | LRTOMT |
| 269 | RVLEVGALQAV | 25885 | POLR1A |
| 270 | LLLDEEGTFSL | 27013 | CNPPD1 |
| 271 | LVYPLELYPA | 29956 | CERS2 |
| 272 | ALGNTVPAV | 352909 | DNAAF3 |
| 273 | NLFQSVREV | 367 | AR |
| 274 | SLLFSLFEA | 3938 | LCT |
| 275 | YLVYILNEL | 51202 | DDX47 |
| 276 | ALFTFSPLTV | 54665 | RSBN1 |
| 277 | LLPPLESLATV | 5518 | PPP2R1A |
| 278 | QLLDVVLTI | 55295 | KLHL26 |
| 279 | ALWGGTQPLL | 56063 | TMEM234 |
| 280 | VLPDPEVLEAV | 57326 | PBXIP1 |
| 281 | ILRESTEEL | 57639 | CCDC146 |
| 282 | LLADVVPTT | 57661 | PHRF1 |
| 283 | ALYIGDGYVIHLA | 5920 | RARRES3 |
| 284 | ILLSQTTGV | 7175 | TPR |
| 285 | QLLHVGVTV | 79598 | CEP97 |
| 286 | YLFPGIPEL | 80308 | FLAD1 |
| 287 | FLNEFFLNV | 833 | CARS |
| 288 | NLINEINGV | 8672 | EIF4G3 |
| 289 | VLLEIEDLQV | 8826 | IQGAP1 |
| 290 | GLLDLNNAILQL | 2104 | ESRRG |
| 291 | GLDSNLKYILV | 23269 | MGA |
| 292 | LLWEAGSEA | 26167 | PCDHB5 |
| 293 | GLGELQELYL | 2811 | GP1BA |
| 294 | ILDPFQYQL | 9420 | CYP7B1 |
| 295 | VLDRESPNV | 1000 | CDH2 |
| 296 | FMEGAIIYV | 10006 | ABI1 |
| 297 | VLADIELAQA | 10039 | PARP3 |
| 298 | VMITKLVEV | 10076 | PTPRU |
| 299 | YLLETSGNL | 10135 | NAMPT |
| 300 | ALLGQTFSL | 10147 | SUGP2 |
| 301 | FLVEDLVDSL | 10313, 6253 | RTN3, RTN2 |
| 302 | ALLQEGEVYSA | 10594 | PRPF8 |
| 303 | AILPQLFMV | 10945 | KDELR1 |
| 304 | MTLGQIYYL | 10959 | TMED2 |
| 305 | SIANFSEFYV | 111, 112 | ADCY5, ADCY6 |
| 306 | ALVNVQIPL | 11194 | ABCB8 |
| 307 | ALPVSLPQI | 11218 | DDX20 |
| 308 | SQYSGQLHEV | 114884 | OSBPL10 |
| 309 | GLFDGVPTTA | 122618 | PLD4 |
| 310 | FLVDTPLARA | 124975 | GGT6 |
| 311 | RLYTGMHTV | 130367 | SGPP2 |
| 312 | IISDLTIAL | 144110 | TMEM86A |
| 313 | VLFDDELLMV | 1687 | DFNA5 |
| 314 | ALIAEGIALV | 1778 | DYNC1H1 |
| 315 | YLQDVVEQA | 19 | ABCA1 |
| 316 | ILLERLWYV | 215 | ABCD1 |
| 317 | SLAALVVHV | 2196 | FAT2 |
| 318 | GLINTGVLSV | 221656 | KDM1B |
| 319 | SLEPQIQPV | 23029 | RBM34 |
| 320 | KMFEFVEPLL | 23092 | ARHGAP26 |
| 321 | GLFEDVTQPGILL | 23140 | ZZEF1 |
| 322 | TLMTSLPAL | 23154 | NCDN |
| 323 | IQIGEETVITV | 2316 | FLNA |
| 324 | FLYDEIEAEV | 23191, 26999 | CYFIP1, CYFIP2 |
| 325 | FIMPATVADATAV | 23352 | UBR4 |
| 326 | FLPEALDFV | 23511 | NUP188 |
| 327 | GLAPFTEGISFV | 23780 | APOL2 |
| 328 | ALNDQVFEI | 2475 | MTOR |
| 329 | FLVTLNNVEV | 25839 | COG4 |
| 330 | QLALKVEGV | 25896 | INTS7 |
| 331 | KVDTVWVNV | 25917 | THUMPD3 |
| 332 | YLISELEAA | 25940 | FAM98A |
| 333 | FLPDANSSV | 25942 | SIN3A |
| 334 | TLTKVLVAL | 26292 | MYCBP |
| 335 | YSLSSVVTV | 28396, 3500, 3501, | IGHV4-31, IGHG1, IGHG2, IGHG3, IGHG4, IGHM |

TABLE 1-continued

Peptides according to the present invention.
J = phospho-serine.

| SEQ ID NO. | Sequence | Gene ID(s) | Official Gene Symbol(s) |
|---|---|---|---|
| | | 3502, 3503, 3507 | |
| 336 | ILLTAIVQV | 29100 | TMEM208 |
| 337 | HLLSELEAAPYL | 2976 | GTF3C2 |
| 338 | SVLEDPVHAV | 29927 | SEC61A1 |
| 339 | GLWEIENNPTVKA | 3068 | HDGF |
| 340 | ALLSMTFPL | 3094 | HINT1 |
| 341 | SQIALNEKLVNL | 339799, 8665 | EIF3FP3, EIF3F |
| 342 | HIYDKVMTV | 340706 | VWA2 |
| 343 | SLLEVNEESTV | 3428 | IFI16 |
| 344 | YLQDQHLLLTV | 3636 | INPPL1 |
| 345 | VIWKALIHL | 3689 | ITGB2 |
| 346 | LLDSKVPSV | 3691 | ITGB4 |
| 347 | SLFKHDPAAWEA | 3728 | JUP |
| 348 | ILLDVKTRL | 3728, 3861, 3868, 3872 | JUP, KRT14, KRT16, KRT17 |
| 349 | SLTEYLQNV | 3799 | KIF5B |
| 350 | ALLDVTHSELTV | 3911 | LAMA5 |
| 351 | SLIPNLRNV | 3949 | LDLR |
| 352 | SLLELLHIYV | 401494 | PTPLAD2 |
| 353 | YLFEMDSSL | 4074 | M6PR |
| 354 | LILEGVDTV | 4126 | MANBA |
| 355 | SIQQSIERLLV | 4809 | NHP2L1 |
| 356 | KLLGKLPEL | 4929 | NR4A2 |
| 357 | SMHDLVLQV | 51435 | SCARA3 |
| 358 | ALDEYTSEL | 51477 | ISYNA1 |
| 359 | YLLPESVDL | 51657 | STYXL1 |
| 360 | ALDJGASLLHL | 54101 | RIPK4 |
| 361 | ALYELEGTTV | 54625 | PARP14 |
| 362 | TLYGLSVLL | 54896 | PQLC2 |
| 363 | KVLDVSDLESV | 54961 | SSH3 |
| 364 | LLQNEQFEL | 55329 | MNS1 |
| 365 | YVIDQGETDVYV | 5573 | PRKAR1A |
| 366 | RLLDMGETDLML | 55898 | UNC45A |
| 367 | SLQNHNHQL | 56254, 9810 | RNF20, RNF40 |
| 368 | ILLEEVSPEL | 5660 | PSAP |
| 369 | GLFPEHLIDV | 56997 | ADCK3 |
| 370 | SLLQDLVSV | 57169 | ZNFX1 |
| 371 | FLQAHLHTA | 57674 | RNF213 |
| 372 | TMLLNIPLV | 57674 | RNF213 |
| 373 | SLLEDKGLAEV | 59342 | SCPEP1 |
| 374 | FLLQQHLISA | 5993 | RFX5 |
| 375 | SLTETIEGV | 629 | CFB |
| 376 | AMFESSQNVLL | 64328 | XPO4 |
| 377 | FLLDSSASV | 64856 | VWA1 |
| 378 | ALGYFVPYV | 6567 | SLC16A2 |
| 379 | IMEGTLTRV | 6654 | SOS1 |
| 380 | TLIEDEIATI | 6788 | STK3 |
| 381 | FIDEAYVEV | 6873 | TAF2 |
| 382 | ALQNYIKEA | 7022 | TFAP2C |
| 383 | ALLELENSVTL | 715, 83481 | C1R, EPPK1 |
| 384 | ILFANPNIFV | 728689, 8663 | EIF3CL, EIF3C |
| 385 | SLLEQGLVEA | 7468 | WHSC1 |
| 386 | ILFRYPLTI | 767 | CA8 |
| 387 | ALFQATAEV | 7840 | ALMS1 |
| 388 | SLTIDGIRYV | 79665 | DHX40 |
| 389 | LLADVTHLL | 79699 | ZYG11B |
| 390 | ALFMKQIYL | 79781 | IQCA1 |
| 391 | YVYPQRLNFV | 81704 | DOCK8 |
| 392 | ALLHPQGFEV | 8269 | TMEM187 |
| 393 | GLLDTQTSQVLTA | 83481 | EPPK1 |
| 394 | LLAVIGGLVYL | 84061 | MAGT1 |
| 395 | ALALGGIAVV | 84159 | ARID5B |
| 396 | ALLPDLPAL | 84273 | NOA1 |
| 397 | YLFGERLLEC | 84365 | MKI67IP |
| 398 | KLLEEDGTIITL | 84612 | PARD6B |
| 399 | YLFEPLYHV | 8534 | CHST1 |
| 400 | SLLTEQDLWTV | 90806 | ANGEL2 |
| 401 | ILLDDTGLAYI | 9125 | RQCD1 |
| 402 | VLFSGALLGL | 968 | CD68 |
| 403 | KLYDRILRV | 9746 | CLSTN3 |
| 404 | AIDIJGRDPAV | 100288805, 54768 | HYDIN2, HYDIN |
| 405 | ALYDVFLEV | 1774 | DNASE1L1 |
| 406 | SVQGEDLYLV | 2880 | GPX5 |
| 407 | YLMDLINFL | 54536 | EXOC6 |
| 408 | VLDDSIYLV | 57565 | KLHL14 |
| 409 | LLDAMNYHL | 57565 | KLHL14 |
| 410 | VLSDVIPJI | 139231 | FAM199X |
| 411 | LLAHLSPEL | 57194 | ATP10A |
| 412 | YLDDLNEGVYI | 9897 | KIAA0196 |
| 413 | TLLEKVEGC | 149371 | EXOC8 |
| 414 | YVDDIFLRV | 19 | ABCA1 |
| 415 | LLDKVYSSV | 221960, 51622 | CCZ1B, CCZ1 |
| 416 | VLSDIIQNLSV | 3071 | NCKAP1L |
| 417 | NLQDTEYNL | 472 | ATM |
| 418 | ALAELENIEV | 55561 | CDC42BPG |
| 419 | GQYEGKVSSV | 55705 | IPO9 |
| 420 | FMYDTPQEV | 629 | CFB |
| 421 | RLPETLPSL | 6337 | SCNN1A |
| 422 | FLPKLLLLA | 6614 | SIGLEC1 |
| 423 | GLDGPPPTV | 7127 | TNFAIP2 |
| 424 | TLLDALYEI | 8690 | JRKL |
| 425 | FLYEKSSQV | 89876 | MAATS1 |
| 426 | RLADKSVLV | 9918 | NCAPD2 |

TABLE 2

Additional peptides according to the present invention with no prior known cancer association.
J = phospho-serine.

| SEQ ID NO. | Sequence | Gene ID(s) | Official Gene Symbol(s) |
|---|---|---|---|
| 427 | ALLPLSPYL | 79679 | VTCN1 |
| 428 | KLGHTDILVGV | 23016 | EXOSC7 |
| 429 | GLVNDLARV | 10075 | HUWE1 |
| 430 | HLYSSIEHLTT | 10075 | HUWE1 |
| 431 | SLVNVVPKL | 1020 | CDK5 |
| 432 | TLIEESAKV | 10257 | ABCC4 |
| 433 | AMLNEPWAV | 10379, 55072 | IRF9, RNF31 |
| 434 | KVSNSGITRV | 10575 | CCT4 |
| 435 | WLMPVIPAL | 10809, 134266, 26259, 30820, 54906, 56260, 57461, 57619, 9016, 91133, 91574 | STARD10, GRPEL2, FBXW8, KCNIP1, FAM208B, C8orf44, ISY1, SHROOM3, SLC25A14, L3MBTL4, C12orf65 |
| 436 | HLAEVSAEV | 11130 | ZWINT |
| 437 | SMAPGLVIQAV | 11160 | ERLIN2 |
| 438 | KLLPLAGLYL | 113655 | MFSD3 |
| 439 | YLLQEIYGI | 114804, 23295 | RNF157, MGRN1 |
| 440 | ALADGVTMQV | 114960, 26958 | TSGA13, COPG2 |
| 441 | ALLENPKMEL | 140901, 149420 | STK35, PDIK1L |
| 442 | GLLGGGGVLGV | 149954 | BPIFB4 |
| 443 | GLWEIENNPTV | 154150, 3068 | HDGFL1, HDGF |

TABLE 2-continued

Additional peptides according to the present invention with no prior known cancer association.
J = phospho-serine.

| SEQ ID NO. | Sequence | Gene ID(s) | Official Gene Symbol(s) |
|---|---|---|---|
| 444 | GLLRDEALAEV | 1663, 440081, 642846 | DDX11, DDX12P |
| 445 | GLYQDPVTL | 201292 | TRIM65 |
| 446 | QLIPALAKV | 2070, 2138, 2139 | EYA4, EYA1, EYA2 |
| 447 | QLVPALAKV | 2140 | EYA3 |
| 448 | NLLETKLQL | 219988 | PATL1 |
| 449 | KLAEGLDIQL | 221656 | KDM1B |
| 450 | FMIDASVHPTL | 221960, 51622 | CCZ1B, CCZ1 |
| 451 | LLLLDTVTMQV | 22820 | COPG1 |
| 452 | ILLEHGADPNL | 22852 | ANKRD26 |
| 453 | KLLEATSAV | 100129478, 201725 | C4orf46 |
| 454 | KLPPPPPQA | 23028 | KDM1A |
| 455 | SLLKEPQKVQL | 23154 | NCDN |
| 456 | LLIGHLERV | 23165 | NUP205 |
| 457 | SLLPGNLVEKV | 23341 | DNAJC16 |
| 458 | SLIDKLYNI | 25885 | POLR1A |
| 459 | ALITEVVRL | 26005 | C2CD3 |
| 460 | AMLEKNYKL | 26160 | IFT172 |
| 461 | VMFRTPLASV | 26271 | FBXO5 |
| 462 | KLAKQPETV | 27085 | MTBP |
| 463 | SLVESHLSDQLTL | 284361 | EMC10 |
| 464 | ALNDCIYSV | 3652 | IPP |
| 465 | QLCDLNAEL | 3833 | KIFC1 |
| 466 | VLIANLEKL | 440590 | ZYG11A |
| 467 | FLAKDFNFL | 4600 | MX2 |
| 468 | YLRSVGDGETV | 4904, 8531 | YBX1, CSDA |
| 469 | YLASDEITTV | 4976 | OPA1 |
| 470 | MLQDSIHVV | 4999 | ORC2 |
| 471 | YLYNNMIAKI | 51284 | TLR7 |
| 472 | KLLEVSDDPQV | 51606 | ATP6V1H |
| 473 | AMATESILHFA | 5297 | PI4KA |
| 474 | YLDPALELGPRNV | 537 | ATP6AP1 |
| 475 | LLLNEEALAQI | 54497 | HEATR5B |
| 476 | ALMERTGYSMV | 54502 | RBM47 |
| 477 | ALLPASGQIAL | 54512 | EXOSC4 |
| 478 | YLLHEKLNL | 55010 | PARPBP |
| 479 | SLFGNSGILENV | 55125 | CEP192 |
| 480 | ALLEDSCHYL | 55161 | TMEM33 |
| 481 | GLIEDYEALL | 55755 | CDK5RAP2 |
| 482 | SLAPAGIADA | 55839 | CENPN |
| 483 | ALTDIVSQV | 56924 | PAK6 |
| 484 | SLIEKVTQL | 56992 | KIF15 |
| 485 | NVPDSFNEV | 57508 | INTS2 |
| 486 | AVMESIQGV | 57646 | USP28 |
| 487 | LLINSVFHV | 57655 | GRAMD1A |
| 488 | FLAEDPKVTL | 60489 | APOBEC3G |
| 489 | KMWEELPEVV | 622 | BDH1 |
| 490 | FLLQHVQEL | 64127 | NOD2 |
| 491 | GLNDRSDAV | 64151 | NCAPG |
| 492 | SLFDGFADGLGV | 64219, 9867 | PJA1, PJA2 |
| 493 | GLLGEKTQDLIGV | 6522 | SLC4A2 |
| 494 | ALQPEPIKV | 6653 | SORL1 |
| 495 | FIFSEKPVFV | 6653 | SORL1 |
| 496 | FLVEKQPPQV | 6778 | STAT6 |
| 497 | GLLEKLTAI | 6875 | TAF4B |
| 498 | KLWTGGLDNTV | 7088, 7090, 7091 | TLE1, TLE3, TLE4 |
| 499 | KIFDIDEAEEGV | 728350, 8894 | EIF2S2P4, EIF2S2 |
| 500 | SLMEDQVLQL | 7486 | WRN |
| 501 | LLDPNVKSIFV | 79033 | ERI3 |
| 502 | RLLAQVPGL | 79096 | C11orf49 |
| 503 | SLNHFTHSV | 79670 | ZCCHC6 |
| 504 | GLSDGNPSL | 79684 | MSANTD2 |
| 505 | SLAPGDVVRQV | 79729 | SH3D21 |
| 506 | KLLGKVETA | 80185 | TTI2 |
| 507 | KLIDDQDISISL | 80208 | SPG11 |
| 508 | ILAQEQLVVGV | 80347 | COASY |
| 509 | FLFDTKPLIV | 821 | CANX |
| 510 | KLYSVVSQL | 8239, 8287 | USP9X, USP9Y |
| 511 | FLDPYCSASV | 85415 | RHPN2 |
| 512 | SLSEIVPCL | 8900 | CCNA1 |
| 513 | SLWPSPEQL | 90480 | GADD45GIP1 |
| 514 | ILVDWLVQV | 9133 | CCNB2 |
| 515 | LLQELVLFL | 93589 | CACNA2D4 |
| 516 | AVGPASILKEV | 9406 | ZRANB2 |
| 517 | LLMPIPEGLTL | 9540 | TP53I3 |
| 518 | KLNAEVACV | 9569 | GTF2IRD1 |
| 519 | GLLHLTLLL | 9603 | NFE2L3 |
| 520 | LAVHPSGVAL | 9636 | ISG15 |
| 521 | MLLTKLPTI | 9804 | TOMM20 |
| 522 | TLWYRSPEV | 983 | CDK1 |
| 523 | YQIPRTFTL | 9846 | GAB2 |
| 524 | ALIENLTHQI | 100508782, 9677 | PPIP5K1 |
| 525 | VLLEAGEGLVTI | 10072, 582 | DPP3, BBS1 |
| 526 | RLAEVGQYEQV | 23019 | CNOT1 |
| 527 | FLLEPGNLEV | 23218 | NBEAL2 |
| 528 | SVAEGRALMSV | 51428 | DDX41 |
| 529 | LLADELITV | 56904 | SH3GLB2 |
| 530 | VMYADIGGMDI | 5704 | PSMC4 |
| 531 | YTLPIASSIRL | 7249 | TSC2 |
| 532 | ALNNLLHSL | 101060416, 101060589, 23049, 440345, 440354, 552900, 641298 | SMG1, BOLA2, SMG1P1 |
| 533 | RMVAEIQNV | 11262 | SP140 |
| 534 | HLANIVERL | 117854, 445372, 53840 | TRIM6, TRIM6-TRIM34, TRIM34 |
| 535 | KLIAQNLEL | 3832 | KIF11 |
| 536 | YLVEGRFSV | 55125 | CEP192 |
| 537 | TLAPGEVLRSV | 3996 | LLGL1 |
| 538 | LLLAHIIAL | 9415 | FADS2 |
| 539 | ALFDAQAQV | 7297 | TYK2 |
| 540 | ALIPETTTLTV | 100529251, 51192 | CKLF-CMTM1, CKLF |
| 541 | SMLEPVPEL | 10277 | UBE4B |
| 542 | RVWDISTVSSV | 11137 | PWP1 |
| 543 | GLLPTPITQQASL | 133619 | PRRC1 |
| 544 | LLWDVPAPSL | 1388, 7148 | ATF6B, TNXB |
| 545 | LLADLLHNV | 1677 | DFFB |
| 546 | VMIAGKVAVV | 191 | AHCY |
| 547 | TLDITPHTV | 2177 | FANCD2 |
| 548 | ALWENPESGEL | 22893 | BAHD1 |
| 549 | AMLENASDIKL | 23 | ABCF1 |
| 550 | FLYDEIEAEVNL | 23191, 26999 | CYFIP1, CYFIP2 |
| 551 | KLYESLLPFA | 23310 | NCAPD3 |
| 552 | GLLDLPFRVGV | 23347 | SMCHD1 |
| 553 | SLLNQDLHWSL | 23355 | VPS8 |
| 554 | LLMPSSEDLLL | 26046 | LTN1 |
| 555 | YVLEGLKSV | 26098 | C10orf37 |
| 556 | FLTDLEDLTL | 26151 | NAT9 |
| 557 | KLYDDMIRL | 26160 | IFT172 |
| 558 | GLLENIPRV | 2618 | GART |
| 559 | VTVPPGPSL | 266971, 5710 | PIPSL, PSMD4 |

TABLE 2-continued

Additional peptides according to the present invention with no prior known cancer association.
J = phospho-serine.

| SEQ ID NO. | Sequence | Gene ID(s) | Official Gene Symbol(s) |
|---|---|---|---|
| 560 | ALWDIETGQQTTT | 2782 | GNB1 |
| 561 | YLQLTQSEL | 283237 | TTC9C |
| 562 | YLEELPEKLKL | 2944, 2949 | GSTM1, GSTM5 |
| 563 | WLLPYNGVTV | 2976 | GTF3C2 |
| 564 | TVTNAVVTV | 3312 | HSPA8 |
| 565 | ALQETPTSV | 3434 | IFIT1 |
| 566 | VIADGGIQNV | 3615 | IMPDH2 |
| 567 | SLLPLDDIVRV | 3708, 3709 | ITPR1, ITPR2 |
| 568 | TLYDIAHTPGV | 4191 | MDH2 |
| 569 | KLVDRTWTL | 441733, 5613, 5616 | PRKXP1, PRKX, PRKY |
| 570 | ALANQIPTV | 4436 | MSH2 |
| 571 | LLLTTIPQI | 4507 | MTAP |
| 572 | ALADLIEKELSV | 4850 | CNOT4 |
| 573 | ILVANAIVGV | 488, 489 | ATP2A2, ATP2A3 |
| 574 | YLLQEPPRTV | 5074 | PAWR |
| 575 | YLISQVEGHQV | 51002 | TPRKB |
| 576 | ILLNNSGQIKL | 51755 | CDK12 |
| 577 | VMFEDGVLMRL | 545 | ATR |
| 578 | FLDPGGPMMKL | 55627 | SMPD4 |
| 579 | NLMEMVAQL | 55636 | CHD7 |
| 580 | LLMENAERV | 55726 | ASUN |
| 581 | RLWNETVEL | 55789 | DEPDC1B |
| 582 | TLCDVILMV | 55975 | KLHL7 |
| 583 | ILANDGVLLAA | 5685 | PSMA4 |
| 584 | ALAEVAAMENV | 56987 | BBX |
| 585 | ALWDLAADKQTL | 5701 | PSMC2 |
| 586 | KLKPGDLVGV | 5702 | PSMC3 |
| 587 | VMNDRLYAI | 57565 | KLHL14 |
| 588 | SLLPLSHLV | 57674 | RNF213 |
| 589 | KLYPQLPAEI | 57724 | EPG5 |
| 590 | SLIEKLWQT | 5991 | RFX3 |
| 591 | SMAELDIKL | 60561 | RINT1 |
| 592 | RLLJAAENFL | 64092 | SAMSN1 |
| 593 | GLPRFGIEMV | 64397 | ZFP106 |
| 594 | IMLKGDNITL | 6635 | SNRPE |
| 595 | VLLSIYPRV | 6890 | TAP1 |
| 596 | ALLDQTKTLAESAL | 7094 | TLN1 |
| 597 | KLLEGQVIQL | 7629 | ZNF76 |
| 598 | FLFPHSVLV | 79022 | TMEM106C |
| 599 | YLLNDASLISV | 79145 | CHCHD7 |
| 600 | ALAAPDIVPAL | 79886 | CAAP1 |
| 601 | SAFPFPVTV | 79939 | SLC35E1 |
| 602 | YLLEQIKLIEV | 79956 | ERMP1 |
| 603 | FLIEPEHVNTV | 80124 | VCPIP1 |
| 604 | SILDRDDIFV | 8237 | USP11 |
| 605 | KLYEAVPQL | 8317 | CDC7 |
| 606 | ALWETEVYI | 8398 | PLA2G6 |
| 607 | RLYSGISGLEL | 84172 | POLR1B |
| 608 | SLLSVSHAL | 84219 | WDR24 |
| 609 | ALWKQLLEL | 85441 | HELZ2 |
| 610 | LLAPTPYIIGV | 8567 | MADD |
| 611 | YLLDDGTLVV | 8872 | CDC123 |
| 612 | YLYNEGLSV | 899 | CCNF |
| 613 | RLLPGAVVAV | 90353 | CTU1 |
| 614 | LLLPDQPPYHL | 9246 | UBE2L6 |
| 615 | VLPPDTDPA | 93100 | NAPRT1 |
| 616 | VLIDEVESL | 9319 | TRIP13 |
| 617 | ALMYESEKVGV | 9342 | SNAP29 |
| 618 | VLFDSESIGIYV | 9555 | H2AFY |
| 619 | ALQDRVPLA | 9636 | ISG15 |
| 620 | KLLNKIYEA | 9875 | URB1 |
| 621 | VLMDRLPSLL | 9875 | URB1 |
| 622 | RLLGEEVVRVLQA | 9894 | TELO2 |
| 623 | YLVEDIQHI | 9985 | REC8 |
| 624 | FLQEEPGQLL | 101060729, 548593, 79008 | SLX1A, SLX1B |
| 625 | VVLEGASLETV | 10436 | EMG1 |
| 626 | LLMATILHL | 1315 | COPB1 |
| 627 | KLLETELLQEI | 151636 | DTX3L |
| 628 | KLWEFFQVDV | 178 | AGL |
| 629 | HLLNESPML | 23165 | NUP205 |
| 630 | LLSHVIVAL | 545 | ATR |
| 631 | FLDVFLPRV | 5591 | PRKDC |
| 632 | YLIPDIDLKL | 6599 | SMARCC1 |
| 633 | ALSRVSVNV | 80746 | TSEN2 |
| 634 | VVAEFVPLI | 8295 | TRRAP |
| 635 | SLDSTLHAV | 85444 | LRRCC1 |
| 636 | LLTEIRAVV | 9263 | STK17A |
| 637 | SIYGGFLLGV | 9276 | COPB2 |
| 638 | KLIQESPTV | 9702 | CEP57 |
| 639 | SLFQNCFEL | 9716 | AQR |
| 640 | YLFSEALNAA | 987 | LRBA |

TABLE 3

Peptides useful for cancer therapy, e.g. personalized cancer therapies

| SEQ ID NO. | Sequence | Gene ID(s) | Official Gene Symbol(s) |
|---|---|---|---|
| 641 | VLLPVEVATHYL | 10568 | SLC34A2 |
| 642 | FLHDISDVQL | 10715 | CERS1 |
| 643 | ALFPHLLQPV | 1434 | CSE1L |
| 644 | LTFGDVVAV | 2173 | FABP7 |
| 645 | LLYDAVHIV | 2899 | GRIK3 |
| 646 | ILSPTVVSI | 3832 | KIF11 |
| 647 | SLGLFLAQV | 51435 | SCARA3 |
| 648 | LLWGNAIFL | 547 | KIF1A |
| 649 | ALAFKLDEV | 201780 | SLC10A4 |
| 650 | AIMGFIGFFV | 23480 | SEC61G |
| 651 | ILQDRLNQV | 990 | CDC6 |
| 652 | TLWYRAPEV | 1019, 1021 | CDK4, CDK6 |
| 653 | TLISRLPAV | 1104 | RCC1 |
| 654 | KILEDVVGV | 22974 | TPX2 |
| 655 | ALMDKEGLTAL | 26115 | TANC2 |
| 656 | KLLEYIEEI | 3161 | HMMR |
| 657 | SLAERLFFQV | 339983 | NAT8L |
| 658 | LLQDRLVSV | 57664 | PLEKHA4 |
| 659 | ILFPDIIARA | 64110 | MAGEF1 |
| 660 | AILDTLYEV | 84725 | PLEKHA8 |
| 661 | SLIDADPYL | 890 | CCNA2 |
| 662 | KIQEILTQV | 10643 | IGF2BP3 |
| 663 | KIQEMQHFL | 4321 | MMP12 |

The present invention furthermore generally relates to the peptides according to the present invention for use in the treatment of proliferative diseases, such as, for example non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, bile duct cancer.

Of particular interest and thus preferred is the peptide SEQ ID NO. 466 (VLIANLEKL) and its uses in the immunotherapy of ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, bile duct cancer, and preferably ovarian cancer.

Particularly preferred are the peptide—alone or in combination—according to the present invention selected from the group consisting of SEQ ID NO: 1, 11, 427, 408, 198, 512, 519, and 587 and their uses in the immunotherapy of ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, bile duct cancer, and preferably ovarian cancer.

Particularly preferred are the peptide—alone or in combination—according to the present invention selected from the group consisting of SEQ ID NO: 3, 4, 5, 6, 8, 10, 12, 14, 15, 18, 20, 25, 29, 32, 37, 38, 39, 41, 44, 45, 52, 53, 54, 57, 64, 69, 72, 73, 77, 78, 83, 89, 90, 91, 93, 94, 96, 99, 100, 102, 104, 106, 107, 109, 113, 114, 117, 120, 123, 124, 136, 137, 138, 139, 141, 143, 148, 150, 151, 157, 158, 160, 163, 165, 166, 170, 171, 173, 175, 179, 180, 184, 185, 187, 189, 191, 192, 193, 194, 195, 196, 200, 202, 204, 206, 209, 211, 215, 216, 217, 218, 219, 221, 224, 225, 226, 230, 231, 232, 233, 234, 235, 238, 239, 243, 244, 245, 247, 248, 250, 253, 258, 266, 267, 269, 301, 306, 347, 348, 350, 365, 367, 369, 378, 380, 426, 430, 432, 433, 438, 441, 442, 444, 449, 451, 455, 460, 461, 462, 463, 465, 467, 468, 470, 471, 478, 479, 481, 482, 484, 485, 489, 491, 494, 498, 505, 509, 511, 514, 515, 516, 518, 522, 532, 542, 547, 548, 552, 560, 578, and 620 and their uses in the immunotherapy of ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, bile duct cancer, and preferably ovarian cancer.

Particularly preferred are the peptides—alone or in combination—according to the present invention selected from the group consisting of SEQ ID NO: 1 to SEQ ID NO: 640. More preferred are the peptides—alone or in combination—selected from the group consisting of SEQ ID NO: 1 to SEQ ID NO: 259 (see Table 1), and their uses in the immunotherapy of ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, bile duct cancer, and preferably ovarian cancer.

As shown in the following Table 4A and B, many of the peptides according to the present invention are also found on other tumor types and can, thus, also be used in the immunotherapy of other indications. Also refer to FIGS. 1A-1AE and Example 1.

TABLE 4A

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 1 | SLMEPPAVLLL | NSCLC, SCLC, Esophageal Cancer |
| 2 | SLLEADPFL | Esophageal Cancer |
| 6 | VLVSDGVHSV | SCLC, Brain Cancer, BrCa, MCC, Esophageal Cancer |
| 7 | SLVGLLLYL | RCC, PC, BrCa |
| 9 | GAAKDLPGV | RCC, GC, HCC, Urinary bladder Cancer |
| 10 | FLATFPLAAV | Urinary bladder Cancer |
| 11 | KIFEMLEGV | NSCLC |
| 14 | AAYGGLNEKSFV | HCC, Urinary bladder Cancer |
| 17 | GLLPGDRLVSV | NSCLC, SCLC, BrCa |
| 19 | FMVDNEAIYDI | SCLC, CRC, HCC, Leukemia, Melanoma, Esophageal Cancer, Urinary bladder Cancer |
| 20 | RMIEYFIDV | SCLC, HCC, MCC |
| 22 | IMEENPGIFAV | CRC, Leukemia, Melanoma |
| 24 | SLSDGLEEV | CRC, PC, Urinary bladder Cancer |
| 26 | ALLELAEEL | Leukemia, Esophageal Cancer |
| 27 | ILADIVISA | NSCLC, SCLC, PC, BrCa, Esophageal Cancer |
| 28 | QLLDETSAITL | SCLC, HCC, Leukemia, Urinary bladder Cancer |
| 31 | YLAPELFVNV | SCLC, GC, Leukemia, Melanoma |
| 32 | KLDDLTQDLTV | HCC, |
| 33 | VLLSLLEKV | Leukemia |
| 34 | ILVEADSLWVV | SCLC, PrC, Leukemia, Melanoma |
| 36 | YVLEDLEVTV | SCLC, HCC, Leukemia |
| 38 | FLLEDDIHVS | SCLC, Leukemia, Melanoma |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 45 | SLWQDIPDV | NSCLC, SCLC |
| 47 | ILLSVPLLVV | SCLC, Leukemia, Gallbladder Cancer, Bile Duct Cancer |
| 48 | ALAELYEDEV | SCLC, Brain Cancer, HCC, Leukemia, Melanoma, Uterine Cancer |
| 49 | YLPAVFEEV | Leukemia |
| 51 | LLPDLEFYV | SCLC, PrC, Gallbladder Cancer, Bile Duct Cancer |
| 54 | SLLEQGKEPWMV | SCLC, HCC, Gallbladder Cancer, Bile Duct Cancer |
| 55 | SLLDLETLSL | SCLC |
| 56 | KLYEGIPVLL | BrCa |
| 57 | TLAELQPPVQL | NSCLC, SCLC, HCC, Leukemia, Melanoma, Esophageal Cancer |
| 58 | FLDTLKDLI | NSCLC, SCLC, GC, CRC, HCC, Leukemia, Melanoma, Esophageal Cancer, Gallbladder Cancer, Bile Duct Cancer |
| 59 | IMEDIILTL | SCLC, Leukemia, BrCa |
| 60 | SLTIDGIYYV | SCLC, Prostate, Leukemia |
| 61 | FLQGYQLHL | NSCLC, SCLC, BrCa, Melanoma, Esophageal Cancer |
| 62 | VLLDVSAGQLLM | NSCLC, Melanoma |
| 63 | YLLPSGGSVTL | HCC, Melanoma, Esophageal Cancer |
| 64 | YAAPGGLIGV | HCC, PC, Melanoma, Esophageal Cancer, Gallbladder Cancer, Bile Duct Cancer |
| 65 | LKVNQGLESL | NSCLC, SCLC, PC, Leukemia, BrCa, Esophageal Cancer |
| 66 | FLDENIGGVAV | SCLC, HCC |
| 68 | SLMELPRGLFL | Brain Cancer |
| 69 | FQLDPSSGVLVTV | Esophageal Cancer |
| 72 | SLLELDGINL | NSCLC, SCLC, Prostate |
| 74 | ALLDPEVLSIFV | NSCLC, Leukemia, Melanoma |
| 75 | GLLEVMVNL | SCLC |
| 76 | ILIDSIYKV | SCLC, CRC, BrCa |
| 77 | ILVEADGAWVV | Melanoma, Esophageal Cancer |
| 79 | SLFIGEKAVLL | NSCLC, SCLC, CRC, Leukemia, Esophageal Cancer, Urinary bladder Cancer |
| 80 | FLYDNLVESL | Leukemia |
| 82 | FLSSVTYNL | SCLC, |
| 84 | VTFGEKLLGV | NSCLC, CRC, PC, PrC, Gallbladder Cancer, Bile Duct Cancer |
| 85 | KMSELRVTL | SCLC, Esophageal Cancer |
| 86 | NLIGKIENV | Colon, Rectum |
| 87 | ALPEAPAPLLPHIT | HCC, PC, Urinary bladder Cancer, Gallbladder Cancer, Bile Duct Cancer |
| 88 | FLLVGDLMAV | SCLC |
| 91 | IMQDFPAEIFL | SCLC |
| 92 | YLIPFTGIVGL | SCLC, HCC, Leukemia, Melanoma |
| 93 | LLQAIKLYL | BrCa |
| 94 | YLIDIKTIAI | HCC |
| 95 | SVIPQIQKV | PC, Esophageal Cancer |
| 97 | SLINGSFLV | NSCLC, RCC, CRC, HCC, PC, Melanoma, Esophageal Cancer |
| 98 | LIIDQADIYL | NSCLC, SCLC, RCC, CRC, HCC, Leukemia, Melanoma, Esophageal Cancer |
| 101 | ILVGGGALATV | Melanoma, Urinary bladder Cancer |
| 103 | TLAEEVVAL | SCLC, BrCa, Esophageal Cancer |
| 104 | STMEQNFLL | NSCLC, |
| 105 | LLLEHSFEI | NSCLC, Melanoma |
| 106 | LLYDAVHIVSV | Brain Cancer |
| 107 | FLQPVDDTQHL | Melanoma, Esophageal Cancer |
| 108 | ALFPGVALLLA | SCLC, HCC, Endometrium |
| 110 | FLSQVDFEL | BrCa |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 117 | ILPDGEDFLAV | SCLC |
| 118 | KLIDNNINV | Brain Cancer |
| 119 | FLYIGDIVSL | Leukemia |
| 121 | GVVDPRAISVL | Esophageal Cancer |
| 123 | NLWDLTDASVV | SCLC, Prostate |
| 125 | VQIHQVAQV | NSCLC, SCLC, HCC, PC, Esophageal Cancer, Gallbladder Cancer, Bile Duct Cancer |
| 126 | VLAYFLPEA | NSCLC, SCLC, CRC, PC, Leukemia, Esophageal Cancer, Uterine Cancer |
| 127 | KIGDEPPKV | NSCLC, SCLC, Brain Cancer, PC, Esophageal Cancer, Uterine Cancer |
| 128 | YLFDDPLSAV | Leukemia, Esophageal Cancer |
| 129 | GLLDGGVDILL | HCC, Leukemia, Esophageal Cancer, Uterine Cancer |
| 130 | FLWNGEDSALL | PC |
| 131 | FVPPVTVFPSL | BrCa |
| 132 | LLVEQPPLAGV | Leukemia |
| 134 | YLQELIFSV | Endometrium |
| 135 | ALSEVDFQL | SCLC, Brain Cancer |
| 137 | TLVLTLPTV | PC |
| 139 | SVMEVNSGIYRV | HCC, MCC |
| 141 | YLDFSNNRL | SCLC, BrCa |
| 142 | FLFATPVFI | SCLC |
| 143 | LLLDITPEI | NSCLC, Brain Cancer, HCC, PC, BrCa, Melanoma, Esophageal Cancer |
| 144 | YIMEPSIFNTL | HCC, Leukemia, Melanoma, Urinary bladder Cancer |
| 145 | FLATSGTLAGI | Prostate |
| 146 | SLATAGDGLIEL | Urinary bladder, Endometrium |
| 148 | ALNPEIVSV | Esophageal Cancer, Urinary bladder Cancer |
| 149 | NLLELFVQL | SCLC, Leukemia, BrCa, Urinary bladder Cancer, Uterine Cancer |
| 150 | RLWEEGEELEL | NSCLC, Melanoma, Esophageal Cancer |
| 151 | KILQQLVTL | Endometrium |
| 152 | ILFEDIFDV | SCLC, Endometrium |
| 153 | FLIANVLYL | SCLC, Urinary bladder Cancer, Uterine Cancer |
| 154 | ALDDGTPAL | HCC |
| 155 | RVANLHFPSV | Melanoma, Esophageal Cancer |
| 157 | SLNDEVPEV | NSCLC, Brain Cancer, HCC, Esophageal Cancer, Uterine Cancer |
| 159 | GLVGNPLPSV | HCC, Leukemia |
| 161 | ALLEGVNTV | NSCLC, Leukemia |
| 163 | ALDEMGDLLQL | HCC |
| 166 | YLNHLEPPV | SCLC, HCC, Leukemia, Esophageal Cancer |
| 167 | KVLEVTEEFGV | NSCLC, HCC, Melanoma |
| 169 | NLPEYLPFV | SCLC, BrCa, Urinary bladder Cancer |
| 170 | RLQETLSAA | HCC, Esophageal Cancer |
| 171 | LLLPLQILL | SCLC |
| 174 | ALAQYLITA | Brain Cancer, HCC, PrC, Esophageal Cancer, Urinary bladder Cancer |
| 176 | YLMEGSYNKVFL | NSCLC, SCLC, CRC, HCC, Melanoma |
| 177 | YLLPEEYTSTL | Melanoma, Esophageal Cancer |
| 178 | ALTEIAFVV | CRC, HCC, PrC |
| 179 | KVLNELYTV | NSCLC |
| 183 | FGLDLVTEL | NSCLC, SCLC, RCC, GC, PC, Leukemia, BrCa, Melanoma |
| 184 | YLMDINGKMWL | NSCLC, SCLC, Melanoma |
| 186 | TLFFQQNAL | Prostate, |
| 188 | GLFPVTPEAV | Colon, Rectum, HCC |
| 190 | FLSSLTETI | Urinary bladder Cancer |
| 195 | GLFADLLPRL | NSCLC |
| 197 | ALGPEGGRV | HCC |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 198 | KTINKVPTV | NSCLC, HCC |
| 199 | ALQDVPLSSV | Melanoma |
| 200 | LLFGSVQEV | SCLC, PC, PrC, Esophageal Cancer, Gallbladder Cancer, Bile Duct Cancer |
| 201 | RLVDYLEGI | NSCLC, HCC, Esophageal Cancer |
| 204 | KIAENVEEV | NSCLC, HCC, PC, Leukemia, BrCa, Esophageal Cancer |
| 205 | SLYPGTETMGL | SCLC, Gallbladder, Bile duct |
| 207 | GLTSTNAEV | HCC, PrC, Esophageal Cancer, Uterine Cancer |
| 208 | KISPVTFSV | HCC |
| 209 | KLIESKHEV | Brain Cancer, HCC |
| 210 | LLLNAVLTV | Urinary bladder Cancer |
| 212 | ALWDQDNLSV | HCC, PrC, BrCa, Urinary bladder Cancer |
| 213 | VTAAYMDTVSL | NSCLC, SCLC, HCC, Melanoma, Esophageal Cancer, Gallbladder Cancer, Bile Duct Cancer |
| 214 | FLLDLDPLLL | SCLC, HCC, Leukemia, Uterine Cancer |
| 216 | NLWEDPYYL | SCLC, PrC, BrCa, Urinary bladder Cancer |
| 217 | ALIHPVSTV | NSCLC, RCC, HCC, Melanoma, Esophageal Cancer |
| 218 | SALEELVNV | RCC |
| 222 | NLIENVQRL | NSCLC, RCC, CRC, HCC, Melanoma, Esophageal Cancer, Urinary bladder Cancer |
| 223 | ALLENIALYL | Esophageal Cancer, Urinary bladder Cancer |
| 226 | MLYVVPIYL | BrCa |
| 228 | AMQEYIAVV | NSCLC, SCLC, Uterine Cancer, Gallbladder Cancer, Bile Duct Cancer |
| 229 | RLPGPLGTV | HCC, Esophageal Cancer, Endometrium |
| 230 | ILVDWLVEV | Melanoma, Endometrium |
| 233 | VLSETLYEL | SCLC, Endometrium |
| 234 | ALMEDTGRQML | NSCLC, SCLC, HCC, Esophageal Cancer |
| 235 | YLNDLHEVLL | Esophageal Cancer, Uterine Cancer, Gallbladder Cancer, Bile Duct Cancer |
| 237 | ALLEASGTLLL | SCLC, HCC, PrC, Leukemia, Uterine Cancer, Gallbladder Cancer, Bile Duct Cancer |
| 240 | ILLEQAFYL | SCLC |
| 241 | SLVEVNPAYSV | Prostate, Gallbladder, Bile duct |
| 242 | AIAYILQGV | SCLC, Leukemia, BrCa, Esophageal Cancer, Urinary bladder Cancer |
| 243 | LLLNELPSV | Colon, Rectum, Esophageal Cancer |
| 247 | VLLPNDLLEKV | Brain Cancer |
| 248 | FLFPNQYVDV | NSCLC, SCLC, HCC, Leukemia, Melanoma |
| 249 | LLDGFLVNV | SCLC |
| 251 | ALYTGFSILV | SCLC, Leukemia, Melanoma |
| 252 | LLIGTDVSL | PrC, Leukemia, Esophageal Cancer, Urinary bladder Cancer |
| 253 | GLDAATATV | Prostate, Leukemia |
| 255 | VLASYNLTV | BrCa |
| 256 | FLPPEHTIVYI | SCLC, HCC, Leukemia, Melanoma |
| 257 | SIFSAFLSV | Stomach, Urinary bladder Cancer |
| 258 | ELAERVPAI | Esophageal Cancer |
| 262 | LLWGDLIWL | Leukemia |
| 263 | LLVSNLDFGV | NSCLC, SCLC, RCC, Leukemia |
| 264 | SLQEQLHSV | NSCLC, SCLC, PrC, BrCa, Melanoma, Esophageal Cancer |
| 266 | KITDTLIHL | BrCa |
| 267 | ALQDFLLSV | HCC, Esophageal Cancer, Endometrium |
| 268 | IAGPGLPDL | NSCLC, RCC, BrCa |
| 269 | RVLEVGALQAV | HCC |
| 270 | LLLDEEGTFSL | Leukemia |
| 271 | LVYPLELYPA | RCC, HCC, Leukemia, BrCa, Esophageal Cancer, Urinary bladder Cancer |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 272 | ALGNTVPAV | PC, Leukemia, Endometrium |
| 273 | NLFQSVREV | HCC, BrCa |
| 275 | YLVYILNEL | RCC, GC, HCC, PC, Leukemia, Esophageal Cancer |
| 276 | ALFTFSPLTV | Leukemia |
| 277 | LLPPLESLATV | SCLC, Leukemia, Melanoma |
| 279 | ALWGGTQPLL | SCLC, Brain Cancer, Esophageal Cancer |
| 280 | VLPDPEVLEAV | Prostate, Leukemia |
| 282 | LLADVVPTT | Leukemia, Melanoma |
| 283 | ALYIGDGYVIHLA | SCLC, BrCa, MCC, Melanoma |
| 284 | ILLSQTTGV | Prostate, Leukemia |
| 285 | QLLHVGVTV | NSCLC, RCC, CRC, Leukemia, Esophageal Cancer |
| 286 | YLFPGIPEL | SCLC, HCC |
| 287 | FLNEFFLNV | NSCLC, Leukemia, Melanoma, Esophageal Cancer |
| 288 | NLINEINGV | SCLC, PrC, Esophageal Cancer, Urinary bladder Cancer, Uterine Cancer |
| 289 | VLLEIEDLQV | Leukemia, BrCa |
| 290 | GLLDLNNAILQL | HCC |
| 291 | GLDSNLKYILV | PC, Melanoma |
| 292 | LLWEAGSEA | Brain Cancer, PC |
| 294 | ILDPFQYQL | HCC, Esophageal Cancer |
| 296 | FMEGAIIYV | SCLC, Leukemia |
| 298 | VMITKLVEV | Urinary bladder Cancer |
| 299 | YLLETSGNL | Leukemia, Urinary bladder Cancer |
| 300 | ALLGQTFSL | SCLC, Brain Cancer, CRC |
| 301 | FLVEDLVDSL | SCLC, HCC, Leukemia |
| 303 | AILPQLFMV | NSCLC, RCC, CRC, BrCa, Esophageal Cancer, Urinary bladder Cancer |
| 306 | ALVNVQIPL | HCC, Esophageal Cancer |
| 308 | SQYSGQLHEV | Leukemia, Gallbladder, Bile duct |
| 309 | GLFDGVPTTA | HCC, Leukemia, BrCa, Melanoma |
| 310 | FLVDTPLARA | Urinary bladder Cancer |
| 311 | RLYTGMHTV | RCC, CRC, PC, Esophageal Cancer, Urinary bladder Cancer |
| 312 | IISDLTIAL | SCLC, PC |
| 313 | VLFDDELLMV | NSCLC, RCC, Brain Cancer, HCC, Esophageal Cancer |
| 314 | ALIAEGIALV | SCLC, Melanoma |
| 315 | YLQDVVEQA | SCLC, Endometrium |
| 316 | ILLERLWYV | Melanoma |
| 317 | SLAALVVHV | Esophageal Cancer, Urinary bladder Cancer |
| 318 | GLINTGVLSV | Colon, Rectum |
| 319 | SLEPQIQPV | NSCLC, CRC, Leukemia, Esophageal Cancer |
| 320 | KMFEFVEPLL | Colon, Rectum |
| 321 | GLFEDVTQPGILL | Leukemia, Melanoma |
| 322 | TLMTSLPAL | SCLC, |
| 323 | IQIGEETVITV | NSCLC, SCLC, PrC, Leukemia, Melanoma, Esophageal Cancer, Uterine Cancer, Gallbladder Cancer, Bile Duct Cancer |
| 324 | FLYDEIEAEV | Leukemia |
| 325 | FIMPATVADATAV | Leukemia |
| 327 | GLAPFTEGISFV | HCC |
| 328 | ALNDQVFEI | SCLC, Brain Cancer, HCC, Esophageal Cancer, Uterine Cancer |
| 329 | FLVTLNNVEV | Melanoma |
| 330 | QLALKVEGV | Esophageal Cancer |
| 331 | KVDTVWVNV | SCLC, Leukemia, BrCa, Melanoma, Urinary bladder Cancer |
| 332 | YLISELEAA | Brain Cancer, HCC, PC, PrC, Esophageal Cancer, Uterine Cancer |
| 333 | FLPDANSSV | NSCLC, Brain Cancer, PrC, Leukemia, BrCa, Esophageal Cancer, Urinary bladder Cancer |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 334 | TLTKVLVAL | Urinary bladder Cancer |
| 335 | YSLSSVVTV | NSCLC, GC, PC, BrCa, Gallbladder Cancer, Bile Duct Cancer |
| 336 | ILLTAIVQV | BrCa, Esophageal Cancer |
| 338 | SVLEDPVHAV | NSCLC, SCLC, HCC, Melanoma |
| 339 | GLWEIENNPTVKA | HCC, Melanoma, Endometrium |
| 340 | ALLSMTFPL | Brain Cancer, HCC, BrCa |
| 341 | SQIALNEKLVNL | SCLC, HCC |
| 342 | HIYDKVMTV | Colon, Rectum |
| 343 | SLLEVNEESTV | NSCLC, Leukemia, Melanoma |
| 344 | YLQDQHLLLTV | SCLC, Melanoma |
| 345 | VIWKALIHL | SCLC |
| 346 | LLDSKVPSV | SCLC, HCC, PC, Esophageal Cancer, Urinary bladder Cancer, Gallbladder Cancer, Bile Duct Cancer |
| 347 | SLFKHDPAAWEA | NSCLC, HCC, Esophageal Cancer, Urinary bladder Cancer |
| 348 | ILLDVKTRL | NSCLC, CRC, Esophageal Cancer, Urinary bladder Cancer |
| 349 | SLTEYLQNV | Colon, Rectum, HCC |
| 351 | SLIPNLRNV | PC |
| 354 | LILEGVDTV | Esophageal Cancer |
| 355 | SIQQSIERLLV | NSCLC, CRC, HCC, Leukemia, Melanoma, Esophageal Cancer |
| 356 | KLLGKLPEL | NSCLC, CRC, Esophageal Cancer |
| 357 | SMHDLVLQV | Brain Cancer, PC, Endometrium |
| 358 | ALDEYTSEL | Brain Cancer, PC, Leukemia, BrCa, Uterine Cancer |
| 359 | YLLPESVDL | NSCLC, CRC, HCC, Esophageal Cancer |
| 360 | ALDJGASLLHL | RCC, HCC, Esophageal Cancer, Urinary bladder Cancer, Uterine Cancer |
| 361 | ALYELEGTTV | Esophageal Cancer |
| 362 | TLYGLSVLL | BrCa |
| 363 | KVLDVSDLESV | Urinary bladder, Endometrium |
| 364 | LLQNEQFEL | RCC |
| 365 | YVIDQGETDVYV | Leukemia, Melanoma |
| 366 | RLLDMGETDLML | SCLC, Leukemia, Melanoma |
| 367 | SLQNHNHQL | HCC, Urinary bladder Cancer |
| 369 | GLFPEHLIDV | HCC |
| 370 | SLLQDLVSV | HCC |
| 371 | FLQAHLHTA | BrCa |
| 372 | TMLLNIPLV | SCLC, HCC, PC, PrC, BrCa |
| 373 | SLLEDKGLAEV | NSCLC, SCLC, Leukemia, BrCa, MCC, Melanoma |
| 374 | FLLQQHLISA | Leukemia |
| 375 | SLTETIEGV | BrCa, Esophageal Cancer |
| 376 | AMFESSQNVLL | Colon, Rectum |
| 378 | ALGYFVPYV | HCC |
| 379 | IMEGTLTRV | Leukemia |
| 381 | FIDEAYVEV | Leukemia |
| 382 | ALQNYIKEA | Esophageal Cancer |
| 383 | ALLELENSVTL | HCC |
| 384 | ILFANPNIFV | CRC, Leukemia, Melanoma |
| 385 | SLLEQGLVEA | NSCLC, SCLC, Brain Cancer, HCC, Esophageal Cancer, Uterine Cancer, Gallbladder Cancer, Bile Duct Cancer |
| 386 | ILFRYPLTI | Urinary bladder Cancer |
| 387 | ALFQATAEV | HCC, Esophageal Cancer |
| 388 | SLTIDGIRYV | SCLC, Melanoma |
| 389 | LLADVTHLL | Brain Cancer, Endometrium |
| 390 | ALFMKQIYL | Urinary bladder Cancer |
| 391 | YVYPQRLNFV | Leukemia, Melanoma |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 393 | GLLDTQTSQVLTA | HCC, BrCa, Esophageal Cancer, Urinary bladder Cancer |
| 394 | LLAVIGGLVYL | NSCLC, SCLC, RCC, HCC, PrC, Leukemia, Melanoma, Urinary bladder Cancer |
| 395 | ALALGGIAVV | NSCLC, CRC, HCC, PrC, Leukemia, BrCa, Melanoma, Esophageal Cancer, Urinary bladder Cancer, Uterine Cancer |
| 396 | ALLPDLPAL | HCC, BrCa |
| 397 | YLFGERLLEC | Colon, Rectum, Leukemia |
| 398 | KLLEEDGTIITL | Colon, Rectum, PC |
| 399 | YLFEPLYHV | SCLC |
| 400 | SLLTEQDLWTV | Leukemia |
| 401 | ILLDDTGLAYI | SCLC, HCC, Leukemia, BrCa, Melanoma |
| 403 | KLYDRILRV | NSCLC, RCC |
| 404 | AIDIJGRDPAV | SCLC, Leukemia |
| 405 | ALYDVFLEV | PC, Esophageal Cancer |
| 406 | SVQGEDLYLV | HCC, Endometrium |
| 407 | YLMDLINFL | PC, Prostate |
| 408 | VLDDSIYLV | Leukemia |
| 409 | LLDAMNYHL | HCC, Leukemia |
| 410 | VLSDVIPJI | SCLC, RCC, Brain Cancer, GC, HCC, PC, PrC, Leukemia, Melanoma, Esophageal Cancer |
| 411 | LLAHLSPEL | HCC |
| 412 | YLDDLNEGVYI | Leukemia, Melanoma |
| 415 | LLDKVYSSV | NSCLC, HCC, Leukemia, Esophageal Cancer |
| 418 | ALAELENIEV | SCLC, MCC |
| 419 | GQYEGKVSSV | HCC |
| 420 | FMYDTPQEV | SCLC, HCC, BrCa |
| 421 | RLPETLPSL | NSCLC, SCLC, GC, CRC, PC |
| 422 | FLPKLLLLA | BrCa |
| 423 | GLDGPPPTV | HCC, PC, BrCa, Urinary bladder Cancer, Uterine Cancer, Gallbladder Cancer, Bile Duct Cancer |
| 424 | TLLDALYEI | RCC, Esophageal Cancer, Endometrium |
| 425 | FLYEKSSQV | Brain Cancer, Endometrium |
| 426 | RLADKSVLV | Colon, Rectum |
| 427 | ALLPLSPYL | NSCLC, SCLC, HCC, PC, BrCa, Uterine Cancer |
| 428 | KLGHTDILVGV | NSCLC, SCLC, CRC, HCC, Leukemia |
| 429 | GLVNDLARV | NSCLC, HCC |
| 430 | HLYSSIEHLTT | NSCLC, CRC, HCC, MCC, Esophageal Cancer |
| 431 | SLVNVVPKL | NSCLC, SCLC, RCC, Brain Cancer, Melanoma, Esophageal Cancer |
| 432 | TLIEESAKV | Prostate |
| 433 | AMLNEPWAV | SCLC |
| 434 | KVSNSGITRV | NSCLC |
| 435 | WLMPVIPAL | SCLC |
| 437 | SMAPGLVIQAV | SCLC, Prostate |
| 439 | YLLQEIYGI | SCLC, BrCa |
| 440 | ALADGVTMQV | Gallbladder, Bile duct |
| 441 | ALLENPKMEL | NSCLC, SCLC, CRC, HCC, MCC, Esophageal Cancer |
| 443 | GLWEIENNPTV | NSCLC, SCLC, HCC, PC, PrC, Melanoma |
| 444 | GLLRDEALAEV | NSCLC, SCLC, CRC, Melanoma, Esophageal Cancer |
| 446 | QLIPALAKV | NSCLC, SCLC, PrC, BrCa, MCC, Uterine Cancer |
| 447 | QLVPALAKV | NSCLC, SCLC, HCC, PrC, Esophageal Cancer, Urinary bladder Cancer |
| 448 | NLLETKLQL | Colon, Rectum, Leukemia |
| 449 | KLAEGLDIQL | SCLC, Colon, Rectum |
| 450 | FMIDASVHPTL | NSCLC, SCLC, RCC, Brain Cancer, CRC, HCC, Leukemia, Melanoma, Esophageal Cancer |
| 451 | LLLLDTVTMQV | SCLC, HCC |
| 452 | ILLEHGADPNL | HCC, Leukemia, Melanoma |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 454 | KLPPPPPQA | NSCLC, SCLC |
| 455 | SLLKEPQKVQL | RCC |
| 456 | LLIGHLERV | NSCLC, Brain Cancer, CRC, |
| 457 | SLLPGNLVEKV | NSCLC, HCC, Leukemia, Melanoma |
| 458 | SLIDKLYNI | NSCLC, Colon, Rectum, |
| 459 | ALITEVVRL | NSCLC, CRC, PC, Leukemia, BrCa, Esophageal Cancer |
| 461 | VMFRTPLASV | SCLC, Melanoma, Esophageal Cancer |
| 463 | SLVESHLSDQLTL | NSCLC, SCLC, HCC, Melanoma |
| 464 | ALNDCIYSV | Brain Cancer, HCC, PC |
| 465 | QLCDLNAEL | HCC, Esophageal Cancer |
| 466 | VLIANLEKL | BrCa, Esophageal Cancer |
| 468 | YLRSVGDGETV | Leukemia, Melanoma |
| 469 | YLASDEITTV | SCLC, |
| 472 | KLLEVSDDPQV | HCC, MCC, Melanoma, Esophageal Cancer |
| 473 | AMATESILHFA | SCLC, Brain Cancer, CRC, HCC, MCC, Gallbladder Cancer, Bile Duct Cancer |
| 474 | YLDPALELGPRNV | NSCLC, SCLC, Brain Cancer, HCC, MCC, Melanoma |
| 475 | LLLNEEALAQI | SCLC, Leukemia |
| 476 | ALMERTGYSMV | HCC |
| 477 | ALLPASGQIAL | NSCLC, HCC, Esophageal Cancer, Urinary bladder Cancer |
| 478 | YLLHEKLNL | Colon, Rectum, |
| 479 | SLFGNSGILENV | NSCLC, SCLC, HCC, MCC, Urinary bladder Cancer |
| 480 | ALLEDSCHYL | NSCLC, CRC, HCC, Leukemia, Esophageal Cancer |
| 481 | GLIEDYEALL | SCLC |
| 483 | ALTDIVSQV | Urinary bladder Cancer |
| 484 | SLIEKVTQL | HCC |
| 485 | NVPDSFNEV | Stomach |
| 486 | AVMESIQGV | NSCLC, HCC, PrC, Leukemia, Esophageal Cancer, Urinary bladder Cancer, Uterine Cancer |
| 487 | LLINSVFHV | Melanoma |
| 488 | FLAEDPKVTL | Leukemia |
| 489 | KMWEELPEVV | NSCLC, HCC, Leukemia |
| 490 | FLLQHVQEL | Leukemia |
| 491 | GLNDRSDAV | Esophageal Cancer, Endometrium |
| 492 | SLFDGFADGLGV | NSCLC, SCLC, Brain Cancer, HCC, PrC, Esophageal Cancer |
| 493 | GLLGEKTQDLIGV | NSCLC, SCLC |
| 494 | ALQPEPIKV | Urinary bladder, Gallbladder, Bile duct |
| 495 | FIFSEKPVFV | Urinary bladder Cancer |
| 496 | FLVEKQPPQV | Leukemia, Melanoma |
| 497 | GLLEKLTAI | NSCLC, RCC, Esophageal Cancer, Uterine Cancer |
| 498 | KLWTGGLDNTV | HCC, Esophageal Cancer |
| 499 | KIFDIDEAEEGV | PC, Melanoma, Esophageal Cancer |
| 500 | SLMEDQVLQL | SCLC, Colon, Rectum |
| 501 | LLDPNVKSIFV | NSCLC, SCLC, Brain Cancer, HCC, PrC, MCC, Melanoma, Esophageal Cancer, Gallbladder Cancer, Bile Duct Cancer |
| 502 | RLLAQVPGL | RCC, Urinary bladder Cancer |
| 503 | SLNHFTHSV | NSCLC, Leukemia |
| 504 | GLSDGNPSL | Leukemia, BrCa |
| 505 | SLAPGDVVRQV | Esophageal Cancer |
| 506 | KLLGKVETA | NSCLC, Brain Cancer, Leukemia, Esophageal Cancer |
| 507 | KLIDDQDISISL | Leukemia |
| 508 | ILAQEQLVVGV | Leukemia, Esophageal Cancer |
| 510 | KLYSVVSQL | Colon, Rectum, Leukemia |
| 513 | SLWPSPEQL | HCC, Esophageal Cancer |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 514 | ILVDWLVQV | NSCLC, SCLC, RCC, Brain Cancer, GC, CRC, HCC, Melanoma, Esophageal Cancer, Urinary bladder Cancer, Uterine Cancer |
| 517 | LLMPIPEGLTL | NSCLC, SCLC, HCC, Melanoma |
| 518 | KLNAEVACV | CRC, PrC, Esophageal Cancer |
| 520 | LAVHPSGVAL | Leukemia |
| 521 | MLLTKLPTI | NSCLC, SCLC, CRC, HCC, BrCa, Melanoma, Urinary bladder Cancer |
| 522 | TLWYRSPEV | SCLC |
| 523 | YQIPRTFTL | SCLC, Brain Cancer, HCC, Leukemia, Melanoma |
| 525 | VLLEAGEGLVTI | Melanoma |
| 526 | RLAEVGQYEQV | NSCLC, HCC, MCC, Gallbladder Cancer, Bile Duct Cancer |
| 527 | FLLEPGNLEV | Urinary bladder Cancer |
| 528 | SVAEGRALMSV | Brain Cancer, CRC, HCC, Esophageal Cancer |
| 529 | LLADELITV | Prostate, Leukemia, Urinary bladder Cancer |
| 530 | VMYADIGGMDI | SCLC, Melanoma |
| 531 | YTLPIASSIRL | SCLC, CRC, HCC |
| 533 | RMVAEIQNV | Leukemia, Esophageal Cancer |
| 535 | KLIAQNLEL | Colon, Rectum |
| 536 | YLVEGRFSV | Leukemia |
| 538 | LLLAHIIAL | NSCLC, Brain Cancer, HCC |
| 539 | ALFDAQAQV | NSCLC, SCLC, Brain Cancer, HCC, PC, PrC, BrCa, Esophageal Cancer, Urinary bladder Cancer, Uterine Cancer, Gallbladder Cancer, Bile Duct Cancer |
| 540 | ALIPETTTLTV | HCC, PC, Melanoma |
| 541 | SMLEPVPEL | NSCLC, SCLC, Brain Cancer, CRC, HCC, Esophageal Cancer |
| 542 | RVWDISTVSSV | SCLC, Leukemia, Melanoma, Esophageal Cancer |
| 543 | GLLPTPITQQASL | Esophageal Cancer |
| 544 | LLWDVPAPSL | Leukemia, Melanoma |
| 545 | LLADLLHNV | NSCLC, SCLC, Colon, Rectum |
| 546 | VMIAGKVAVV | Colon, Rectum, HCC |
| 549 | AMLENASDIKL | Melanoma |
| 550 | FLYDEIEAEVNL | Leukemia, Melanoma |
| 551 | KLYESLLPFA | SCLC, HCC, PrC, Melanoma |
| 552 | GLLDLPFRVGV | SCLC, Brain Cancer, Leukemia, Melanoma |
| 554 | LLMPSSEDLLL | NSCLC, SCLC, CRC, HCC, PrC, BrCa, Esophageal Cancer, Urinary bladder Cancer, Gallbladder Cancer, Bile Duct Cancer |
| 555 | YVLEGLKSV | SCLC, Melanoma |
| 556 | FLTDLEDLTL | SCLC, Leukemia |
| 557 | KLYDDMIRL | Colon, Rectum, |
| 558 | GLLENIPRV | NSCLC, SCLC, RCC, Brain Cancer, HCC, Leukemia, Uterine Cancer, Gallbladder Cancer, Bile Duct Cancer |
| 559 | VTVPPGPSL | Leukemia |
| 560 | ALWDIETGQQTTT | SCLC, HCC, Melanoma, Esophageal Cancer |
| 561 | YLQLTQSEL | SCLC, Leukemia, Esophageal Cancer, Gallbladder Cancer, Bile Duct Cancer |
| 563 | WLLPYNGVTV | SCLC, Melanoma |
| 564 | TVTNAVVTV | RCC, GC, HCC, Melanoma |
| 565 | ALQETPTSV | SCLC, Melanoma, Esophageal Cancer, Uterine Cancer |
| 566 | VIADGGIQNV | Leukemia, Melanoma, Endometrium |
| 567 | SLLPLDDIVRV | Leukemia |
| 568 | TLYDIAHTPGV | NSCLC, SCLC, CRC, Melanoma, Esophageal Cancer |
| 571 | LLLTTIPQI | Prostate, Leukemia |
| 572 | ALADLIEKELSV | Leukemia |
| 573 | ILVANAIVGV | NSCLC, HCC, Leukemia, Melanoma |
| 574 | YLLQEPPRTV | SCLC |
| 575 | YLISQVEGHQV | CRC, HCC, MCC, Melanoma, Esophageal Cancer |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 576 | ILLNNSGQIKL | NSCLC, CRC, HCC, Leukemia, BrCa, Melanoma, Esophageal Cancer |
| 577 | VMFEDGVLMRL | Colon, Rectum, Leukemia |
| 578 | FLDPGGPMMKL | NSCLC, CRC, MCC, Melanoma |
| 579 | NLMEMVAQL | NSCLC, CRC, HCC, Leukemia |
| 580 | LLMENAERV | CRC, Leukemia, BrCa, Melanoma |
| 581 | RLWNETVEL | SCLC, Colon, Rectum |
| 583 | ILANDGVLLAA | HCC, Esophageal Cancer |
| 584 | ALAEVAAMENV | Melanoma |
| 585 | ALWDLAADKQTL | Urinary bladder Cancer |
| 586 | KLKPGDLVGV | Brain Cancer, HCC |
| 587 | VMNDRLYAI | Leukemia |
| 588 | SLLPLSHLV | Melanoma, Esophageal Cancer |
| 589 | KLYPQLPAEI | NSCLC, SCLC, Brain Cancer, HCC, Leukemia, MCC, Melanoma, Esophageal Cancer |
| 590 | SLIEKLWQT | SCLC, Brain Cancer |
| 591 | SMAELDIKL | Leukemia, Esophageal Cancer, Endometrium |
| 592 | RLLJAAENFL | SCLC, Brain Cancer, BrCa, Esophageal Cancer |
| 593 | GLPRFGIEMV | Brain Cancer |
| 594 | IMLKGDNITL | Esophageal Cancer |
| 595 | VLLSIYPRV | NSCLC, SCLC, RCC, Leukemia, BrCa |
| 596 | ALLDQTKTLAESAL | Leukemia, Melanoma |
| 597 | KLLEGQVIQL | NSCLC, SCLC, CRC, HCC, BrCa |
| 599 | YLLNDASLISV | NSCLC, CRC, HCC, Melanoma, Uterine Cancer |
| 600 | ALAAPDIVPAL | Leukemia |
| 601 | SAFPFPVTV | Stomach, Leukemia, Esophageal Cancer |
| 602 | YLLEQIKLIEV | NSCLC, SCLC |
| 603 | FLIEPEHVNTV | HCC, PC, Leukemia, Melanoma |
| 604 | SILDRDDIFV | Leukemia |
| 606 | ALWETEVYI | SCLC, Brain Cancer, HCC, PrC |
| 607 | RLYSGISGLEL | NSCLC |
| 608 | SLLSVSHAL | RCC |
| 609 | ALWKQLLEL | PC |
| 610 | LLAPTPYIIGV | NSCLC, SCLC, RCC, Brain Cancer, CRC, HCC, PrC, Leukemia, BrCa, MCC, Melanoma, Esophageal Cancer, Urinary bladder Cancer, Gallbladder Cancer, Bile Duct Cancer |
| 611 | YLLDDGTLVV | HCC, Melanoma |
| 613 | RLLPPGAVVAV | NSCLC, SCLC, HCC |
| 614 | LLLPDQPPYHL | Melanoma |
| 616 | VLIDEVESL | NSCLC, SCLC, RCC, GC, BrCa, Melanoma, Esophageal Cancer, Urinary bladder Cancer |
| 617 | ALMYESEKVGV | HCC, Gallbladder, Bile duct |
| 618 | VLFDSESIGIYV | SCLC, Melanoma |
| 619 | ALQDRVPLA | Brain Cancer, CRC, Esophageal Cancer, Uterine Cancer |
| 620 | KLLNKIYEA | Brain Cancer |
| 621 | VLMDRLPSLL | Melanoma |
| 622 | RLLGEEVVRVLQA | NSCLC, SCLC, CRC, Melanoma |
| 624 | FLQEEPGQLL | Leukemia, Melanoma, Esophageal Cancer |
| 625 | VVLEGASLETV | SCLC, Melanoma |
| 626 | LLMATILHL | SCLC, Melanoma, Urinary bladder Cancer, Gallbladder Cancer, Bile Duct Cancer |
| 627 | KLLETELLQEI | NSCLC, SCLC, CRC, HCC, MCC, Melanoma |
| 628 | KLWEFFQVDV | SCLC, Brain Cancer, HCC |
| 629 | HLLNESPML | SCLC, Esophageal Cancer |
| 630 | LLSHVIVAL | PC, Leukemia |
| 631 | FLDVFLPRV | PC, Leukemia, Melanoma, Esophageal Cancer |
| 632 | YLIPDIDLKL | NSCLC, SCLC, CRC, HCC, PC, Leukemia, Melanoma, Urinary bladder Cancer, Uterine Cancer |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, gallbladder, heart, kidney, liver, lung, lymph node, mononuclear white blood cells, pancreas, peripheral nerve, peritoneum, pituitary, pleura, rectum, salivary gland, skeletal muscle, skin, small intestine, spleen, stomach, thymus, thyroid gland, trachea, ureter, urinary bladder, vein. J = phospho-serine

| SEQ ID No | Sequence | Other relevant organs/cancerous diseases |
|---|---|---|
| 633 | ALSRVSVNV | Melanoma, Esophageal Cancer |
| 634 | VVAEFVPLI | Brain Cancer, Leukemia |
| 635 | SLDSTLHAV | NSCLC, Brain Cancer, CRC, HCC, BrCa, Esophageal Cancer |
| 637 | SIYGGFLLGV | NSCLC, SCLC, HCC, PrC, BrCa, Uterine Cancer |
| 638 | KLIQESPTV | SCLC, HCC, Prostate |
| 639 | SLFQNCFEL | Leukemia |
| 640 | YLFSEALNAA | SCLC, GC, CRC, HCC, PrC, BrCa, MCC, Esophageal Cancer, Urinary bladder Cancer, Uterine Cancer, Gallbladder Cancer, Bile Duct Cancer |

NSCLC = non-small cell lung cancer,
SCLC = small cell lung cancer,
RCC = kidney cancer,
CRC = colorectal cancer,
GC = gastric cancer,
HCC = liver cancer,
PC = pancreatic cancer,
PrC = prostate cancer,
BrCa = breast cancer,
MCC = Merkel cell carcinoma

TABLE 5B

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 1 | SLMEPPAVLLL | BRCA, Urinary Bladder Cancer, Uterine Cancer, AML, HNSCC |
| 2 | SLLEADPFL | CLL, Uterine Cancer, Gallbladder Cancer and Bile Duct Cancer |
| 3 | SLASKLTTL | Uterine Cancer |
| 5 | HLTEVYPEL | Urinary Bladder Cancer, Uterine Cancer |
| 6 | VLVSDGVHSV | Melanoma, Urinary Bladder Cancer, Uterine Cancer, HNSCC |
| 7 | SLVGLLLYL | Gallbladder Cancer and Bile Duct Cancer, AML |
| 8 | FTLGNVVGMYL | Melanoma, Urinary Bladder Cancer, Uterine Cancer |
| 9 | GAAKDLPGV | Esophageal Cancer |
| 11 | KIFEMLEGV | Gallbladder Cancer and Bile Duct Cancer |
| 13 | YLMDESLNL | NSCLC, Brain Cancer, BRCA, Melanoma |
| 14 | AAYGGLNEKSFV | CLL, Esophageal Cancer |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 15 | VLLTFKIFL | Uterine Cancer, NHL |
| 16 | VLFQGQASL | Melanoma, Uterine Cancer, AML, NHL |
| 18 | YLVAKLVEV | NSCLC, BRCA, Urinary Bladder Cancer, HNSCC |
| 21 | VLDELDMEL | Melanoma |
| 22 | IMEENPGIFAV | CLL, Urinary Bladder Cancer, Gallbladder Cancer and Bile Duct Cancer |
| 23 | VLLDDIFAQL | CLL, Uterine Cancer, AML |
| 24 | SLSDGLEEV | NSCLC, BRCA, Melanoma, Uterine Cancer, HNSCC |
| 26 | ALLELAEEL | BRCA, Melanoma, Urinary Bladder Cancer, Uterine Cancer, Gallbladder Cancer and Bile Duct Cancer, AML, NHL, HNSCC |
| 27 | ILADIVISA | Melanoma, Uterine Cancer, Gallbladder Cancer and Bile Duct Cancer |
| 28 | QLLDETSAITL | CLL |
| 29 | KMLGIPISNILMV | Urinary Bladder Cancer, Gallbladder Cancer and Bile Duct Cancer |
| 30 | LILDWVPYI | Melanoma, Uterine Cancer, HNSCC |
| 31 | YLAPELFVNV | BRCA, Uterine Cancer |
| 32 | KLDDLTQDLTV | SCLC, Esophageal Cancer, Urinary Bladder Cancer, Gallbladder Cancer and Bile Duct Cancer, HNSCC |
| 33 | VLLSLLEKV | CLL, Melanoma |
| 34 | ILVEADSLWVV | AML |
| 36 | YVLEDLEVTV | NSCLC, CLL, BRCA, Melanoma, Urinary Bladder Cancer, Uterine Cancer, Gallbladder Cancer and Bile Duct Cancer, NHL, HNSCC |
| 38 | FLLEDDIHVS | CLL, Urinary Bladder Cancer, NHL |
| 40 | TLLVKVFSV | Melanoma |
| 42 | VLLQKIVSA | Esophageal Cancer, AML |
| 43 | VLSSLEINI | NHL |
| 45 | SLWQDIPDV | BRCA, Urinary Bladder Cancer, HNSCC |
| 47 | ILLSVPLLVV | CLL, Uterine Cancer |
| 49 | YLPAVFEEV | CLL |
| 51 | LLPDLEFYV | Melanoma, Urinary Bladder Cancer |
| 54 | SLLEQGKEPWMV | NSCLC, CLL |
| 57 | TLAELQPPVQL | CLL, Urinary Bladder Cancer, Uterine Cancer, Gallbladder Cancer and Bile Duct Cancer, NHL, HNSCC |
| 58 | FLDTLKDLI | Urinary Bladder Cancer, Uterine Cancer, AML, NHL |
| 60 | SLTIDGIYYV | BRCA, Uterine Cancer |
| 61 | FLQGYQLHL | Urinary Bladder Cancer, Uterine Cancer, Gallbladder Cancer and Bile Duct Cancer, NHL, HNSCC |
| 63 | YLLPSGGSVTL | Gallbladder Cancer and Bile Duct Cancer, HNSCC |
| 64 | YAAPGGLIGV | NSCLC, SCLC, CLL, BRCA, Urinary Bladder Cancer, Uterine Cancer, AML, NHL, HNSCC |
| 65 | LKVNQGLESL | Melanoma, Gallbladder Cancer and Bile Duct Cancer, AML, NHL |
| 66 | FLDENIGGVAV | Melanoma, Urinary Bladder Cancer, Uterine Cancer, Gallbladder Cancer and Bile Duct Cancer, AML, NHL, HNSCC |
| 67 | TLLAEALVTV | SCLC |
| 69 | FQLDPSSGVLVTV | HNSCC |
| 71 | GILARIASV | AML, NHL |
| 72 | SLLELDGINL | BRCA, Uterine Cancer |
| 73 | NIFDLQIYV | BRCA |
| 75 | GLLEVMVNL | Gallbladder Cancer and Bile Duct Cancer |
| 76 | ILIDSIYKV | Uterine Cancer |
| 77 | ILVEADGAWVV | BRCA, Uterine Cancer, AML, NHL |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 78 | SLFSSLEPQIQPV | CLL, Melanoma, Urinary Bladder Cancer, AML, HNSCC |
| 79 | SLFIGEKAVLL | CLL, BRCA, Melanoma, Gallbladder Cancer and Bile Duct Cancer, AML, NHL, HNSCC |
| 80 | FLYDNLVESL | CLL, NHL |
| 81 | FLFSQLQYL | Gallbladder Cancer and Bile Duct Cancer, AML |
| 82 | FLSSVTYNL | Melanoma |
| 83 | ILAPTVMMI | Melanoma |
| 84 | VTFGEKLLGV | Melanoma |
| 88 | FLLVGDLMAV | Melanoma |
| 91 | IMQDFPAEIFL | CLL, BRCA, Melanoma, Gallbladder Cancer and Bile Duct Cancer, AML, NHL, HNSCC |
| 92 | YLIPFTGIVGL | CLL, AML, NHL, HNSCC |
| 93 | LLQAIKLYL | Urinary Bladder Cancer, Gallbladder Cancer and Bile Duct Cancer |
| 94 | YLIDIKTIAI | SCLC, Melanoma, Urinary Bladder Cancer |
| 97 | SLINGSFLV | CLL, BRCA, Urinary Bladder Cancer, Uterine Cancer, Gallbladder Cancer and Bile Duct Cancer |
| 98 | LIIDQADIYL | CLL, Urinary Bladder Cancer, Gallbladder Cancer and Bile Duct Cancer, AML, NHL |
| 100 | YLLSTNAQL | Urinary Bladder Cancer |
| 102 | YLFESEGLVL | CLL, Melanoma |
| 103 | TLAEEVVAL | Melanoma, HNSCC |
| 104 | STMEQNFLL | SCLC, BRCA, Melanoma, Gallbladder Cancer and Bile Duct Cancer, HNSCC |
| 105 | LLLEHSFEI | Urinary Bladder Cancer, Gallbladder Cancer and Bile Duct Cancer, NHL, HNSCC |
| 107 | FLQPVDDTQHL | Uterine Cancer, Gallbladder Cancer and Bile Duct Cancer |
| 108 | ALFPGVALLLA | Melanoma |
| 111 | YVWGFYPAEV | CLL, Uterine Cancer, NHL |
| 117 | ILPDGEDFLAV | CLL, BRCA, Uterine Cancer, NHL |
| 119 | FLYIGDIVSL | CLL, Melanoma |
| 120 | ALLGIPLTLV | Uterine Cancer |
| 123 | NLWDLTDASVV | NSCLC, BRCA, Melanoma, Esophageal Cancer, Uterine Cancer, Gallbladder Cancer and Bile Duct Cancer, HNSCC |
| 124 | ALYETELADA | CLL, Uterine Cancer, AML, NHL |
| 126 | VLAYFLPEA | CLL, BRCA, Urinary Bladder Cancer, Gallbladder Cancer and Bile Duct Cancer, AML, NHL, HNSCC |
| 127 | KIGDEPPKV | BRCA, Melanoma, Urinary Bladder Cancer, Gallbladder Cancer and Bile Duct Cancer, HNSCC |
| 128 | YLFDDPLSAV | CLL, BRCA, Uterine Cancer, Gallbladder Cancer and Bile Duct Cancer, AML, NHL, HNSCC |
| 129 | GLLDGGVDILL | HNSCC |
| 131 | FVPPVTVFPSL | Uterine Cancer |
| 132 | LLVEQPPLAGV | CLL, Melanoma |
| 134 | YLQELIFSV | CLL, HNSCC |
| 137 | TLVLTLPTV | SCLC, CLL, Urinary Bladder Cancer, Uterine Cancer, Gallbladder Cancer and Bile Duct Cancer, AML, NHL, HNSCC |
| 138 | YQYPRAILSV | NSCLC, AML |
| 139 | SVMEVNSGIYRV | SCLC, CLL, Urinary Bladder Cancer, Uterine Cancer, Gallbladder Cancer and Bile Duct Cancer, NHL, HNSCC |
| 140 | YMDAPKAAL | Melanoma, AML |
| 141 | YLDFSNNRL | CLL |
| 144 | YIMEPSIFNTL | CLL, BRCA |
| 146 | SLATAGDGLIEL | BRCA |
| 147 | SLLEAVSFL | Gallbladder Cancer and Bile Duct Cancer, AML, HNSCC |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 148 | ALNPEIVSV | SCLC, CLL, Melanoma, NHL, HNSCC |
| 150 | RLWEEGEELEL | Uterine Cancer, Gallbladder Cancer and Bile Duct Cancer, HNSCC |
| 151 | KILQQLVTL | BRCA, Melanoma, Gallbladder Cancer and Bile Duct Cancer |
| 152 | ILFEDIFDV | BRCA, Gallbladder Cancer and Bile Duct Cancer |
| 153 | FLIANVLYL | HNSCC |
| 154 | ALDDGTPAL | Uterine Cancer |
| 155 | RVANLHFPSV | CLL, HNSCC |
| 157 | SLNDEVPEV | BRCA, Melanoma, Urinary Bladder Cancer, Gallbladder Cancer and Bile Duct Cancer, NHL, HNSCC |
| 159 | GLVGNPLPSV | BRCA |
| 160 | FLFDEEIEQI | BRCA |
| 161 | ALLEGVNTV | AML |
| 163 | ALDEMGDLLQL | BRCA, Gallbladder Cancer and Bile Duct Cancer, HNSCC |
| 164 | ALLPQPKNLTV | Melanoma |
| 166 | YLNHLEPPV | Brain Cancer, CLL, BRCA, AML, NHL |
| 167 | KVLEVTEEFGV | BRCA, Urinary Bladder Cancer |
| 170 | RLQETLSAA | Urinary Bladder Cancer, AML |
| 171 | LLLPLQILL | HNSCC |
| 172 | VLYSYTIITV | SCLC, CLL, Uterine Cancer, NHL |
| 173 | LLDSASAGLYL | SCLC, Uterine Cancer, AML, NHL |
| 174 | ALAQYLITA | SCLC, BRCA, Melanoma, Gallbladder Cancer and Bile Duct Cancer |
| 175 | YLFENISQL | Esophageal Cancer, Urinary Bladder Cancer, HNSCC |
| 176 | YLMEGSYNKVFL | Urinary Bladder Cancer, Gallbladder Cancer and Bile Duct Cancer |
| 177 | YLLPEEYTSTL | NHL, HNSCC |
| 178 | ALTEIAFVV | SCLC, CLL, BRCA, Melanoma, Uterine Cancer |
| 179 | KVLNELYTV | CRC, BRCA, Melanoma, Uterine Cancer |
| 180 | FQIDPHSGLVTV | SCLC |
| 182 | MLLEAPGIFL | CLL |
| 183 | FGLDLVTEL | CLL, Urinary Bladder Cancer, Uterine Cancer, AML, NHL, HNSCC |
| 184 | YLMDINGKMWL | CLL, Uterine Cancer, Gallbladder Cancer and Bile Duct Cancer, NHL |
| 185 | FLIDDKGYTL | HNSCC |
| 186 | TLFFQQNAL | PC, NHL, HNSCC |
| 187 | RQISIRGIVGV | NSCLC, Urinary Bladder Cancer, Uterine Cancer, AML, HNSCC |
| 188 | GLFPVTPEAV | Uterine Cancer |
| 190 | FLSSLTETI | BRCA, Uterine Cancer, Gallbladder Cancer and Bile Duct Cancer |
| 191 | LLQEGQALEYV | Uterine Cancer, Gallbladder Cancer and Bile Duct Cancer |
| 192 | KMLDGASFTL | BRCA |
| 193 | QLLDADGFLNV | SCLC, NHL |
| 194 | ALPLFVITV | AML, HNSCC |
| 195 | GLFADLLPRL | PC, Uterine Cancer, AML, HNSCC |
| 197 | ALGPEGGRV | Uterine Cancer |
| 198 | KTINKVPTV | SCLC, Brain Cancer, CRC, Urinary Bladder Cancer, Uterine Cancer, HNSCC |
| 199 | ALQDVPLSSV | SCLC, Urinary Bladder Cancer |
| 201 | RLVDYLEGI | SCLC, Uterine Cancer, Gallbladder Cancer and Bile Duct Cancer, AML |
| 205 | SLYPGTETMGL | AML |
| 206 | VLQEGKLQKLAQL | NSCLC, SCLC, BRCA, Uterine Cancer, HNSCC |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
| --- | --- | --- |
| 207 | GLTSTNAEV | AML |
| 209 | KLIESKHEV | Melanoma, Uterine Cancer |
| 210 | LLLNAVLTV | SCLC, AML, NHL |
| 211 | LLWPGAALL | CLL, AML, NHL |
| 214 | FLLDLDPLLL | Brain Cancer, CRC, CLL, Urinary Bladder Cancer |
| 217 | ALIHPVSTV | BRCA, Urinary Bladder Cancer, Uterine Cancer, Gallbladder Cancer and Bile Duct Cancer |
| 218 | SALEELVNV | GC |
| 224 | TLIDAQWVL | HNSCC |
| 226 | MLYVVPIYL | SCLC, Melanoma, AML, NHL |
| 227 | ALMNTLLYL | Uterine Cancer, AML, HNSCC |
| 228 | AMQEYIAVV | PC, Melanoma, HNSCC |
| 229 | RLPGPLGTV | BRCA, Melanoma, Gallbladder Cancer and Bile Duct Cancer |
| 230 | ILVDWLVEV | Esophageal Cancer, Gallbladder Cancer and Bile Duct Cancer, AML, NHL, HNSCC |
| 233 | VLSETLYEL | BRCA, HNSCC |
| 234 | ALMEDTGRQML | Brain Cancer, Urinary Bladder Cancer, Gallbladder Cancer and Bile Duct Cancer, HNSCC |
| 235 | YLNDLHEVLL | NSCLC, Urinary Bladder Cancer |
| 236 | GLLEAKVSL | Gallbladder Cancer and Bile Duct Cancer |
| 237 | ALLEASGTLLL | BRCA, AML |
| 238 | YLISFQTHI | CLL |
| 242 | AIAYILQGV | RCC, CRC, CLL, Melanoma, Uterine Cancer, AML, NHL, HNSCC |
| 243 | LLLNELPSV | SCLC, BRCA, Melanoma, Urinary Bladder Cancer, Gallbladder Cancer and Bile Duct Cancer, AML, HNSCC |
| 244 | SLFGGTEITI | Uterine Cancer |
| 246 | LLWEVVSQL | BRCA |
| 247 | VLLPNDLLEKV | Melanoma |
| 248 | FLFPNQYVDV | CLL, BRCA |
| 249 | LLDGFLVNV | CLL, Melanoma, NHL |
| 250 | ALSEEGLLVYL | BRCA, Melanoma |
| 252 | LLIGTDVSL | CLL, NHL |
| 256 | FLPPEHTIVYI | CLL, Uterine Cancer |
| 257 | SIFSAFLSV | Melanoma, Gallbladder Cancer and Bile Duct Cancer, AML, NHL |
| 258 | ELAERVPAI | CLL, Urinary Bladder Cancer, Gallbladder Cancer and Bile Duct Cancer, AML, NHL, HNSCC |
| 259 | TLMRQLQQV | Uterine Cancer |
| 260 | TLLEGPDPAELLL | AML |
| 261 | YVLEFLEEI | RCC, CLL, BRCA |
| 262 | LLWGDLIWL | CRC, PrC, CLL, Melanoma, AML |
| 263 | LLVSNLDFGV | CRC, CLL, Urinary Bladder Cancer, AML, NHL |
| 264 | SLQEQLHSV | Uterine Cancer |
| 266 | KITDTLIHL | Uterine Cancer |
| 267 | ALQDFLLSV | NSCLC, SCLC, CRC, BRCA, Melanoma, Urinary Bladder Cancer, AML, NHL, HNSCC |
| 268 | IAGPGLPDL | HCC, Uterine Cancer, NHL |
| 269 | RVLEVGALQAV | CLL |
| 270 | LLLDEEGTFSL | CLL, BRCA, Melanoma, NHL |
| 271 | LVYPLELYPA | Gallbladder Cancer and Bile Duct Cancer |
| 274 | SLLFSLFEA | Urinary Bladder Cancer, AML, NHL |
| 275 | YLVYILNEL | CLL, Melanoma, NHL |
| 276 | ALFTFSPLTV | Uterine Cancer |
| 277 | LLPPLESLATV | CLL, BRCA, Urinary Bladder Cancer, HNSCC |
| 278 | QLLDVVLTI | HNSCC |
| 280 | VLPDPEVLEAV | Gallbladder Cancer and Bile Duct Cancer, NHL, SCLC |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
| --- | --- | --- |
| 281 | ILRESTEEL | Melanoma |
| 282 | LLADVVPTT | CLL, Uterine Cancer, AML, NHL, HNSCC |
| 283 | ALYIGDGYVIHLA | Esophageal Cancer, Urinary Bladder Cancer, Uterine Cancer, NHL |
| 284 | ILLSQTTGV | CLL, Urinary Bladder Cancer, AML, HNSCC |
| 285 | QLLHVGVTV | CLL, Melanoma, Urinary Bladder Cancer, AML, NHL |
| 286 | YLFPGIPEL | NSCLC, CLL, Melanoma, AML, NHL, HNSCC |
| 289 | VLLEIEDLQV | CLL, NHL |
| 290 | GLLDLNNAILQL | Uterine Cancer |
| 292 | LLWEAGSEA | Melanoma |
| 293 | GLGELQELYL | AML, NHL |
| 294 | ILDPFQYQL | Melanoma, Gallbladder Cancer and Bile Duct Cancer, NHL, HNSCC |
| 297 | VLADIELAQA | CLL |
| 298 | VMITKLVEV | Gallbladder Cancer and Bile Duct Cancer |
| 300 | ALLGQTFSL | AML, HNSCC |
| 301 | FLVEDLVDSL | CLL, BRCA, Melanoma, Uterine Cancer, AML |
| 302 | ALLQEGEVYSA | Melanoma, Urinary Bladder Cancer |
| 303 | AILPQLFMV | Melanoma |
| 304 | MTLGQIYYL | NSCLC, SCLC, CRC, HCC, BRCA, Melanoma, Urinary Bladder Cancer, Uterine Cancer, Gallbladder Cancer and Bile Duct Cancer, AML, HNSCC |
| 306 | ALVNVQIPL | Melanoma, Uterine Cancer |
| 307 | ALPVSLPQI | CLL, BRCA, Melanoma, AML, NHL, HNSCC |
| 308 | SQYSGQLHEV | CLL |
| 309 | GLFDGVPTTA | SCLC, Urinary Bladder Cancer, Gallbladder Cancer and Bile Duct Cancer, HNSCC |
| 310 | FLVDTPLARA | Gallbladder Cancer and Bile Duct Cancer, HNSCC |
| 311 | RLYTGMHTV | SCLC, BRCA, NHL, HNSCC |
| 312 | IISDLTIAL | NSCLC, CRC, BRCA, Melanoma, Esophageal Cancer, Uterine Cancer, Gallbladder Cancer and Bile Duct Cancer, NHL, HNSCC |
| 314 | ALIAEGIALV | Uterine Cancer |
| 317 | SLAALVVHV | NSCLC, Gallbladder Cancer and Bile Duct Cancer, HNSCC |
| 318 | GLINTGVLSV | SCLC, CLL, NHL, HNSCC |
| 319 | SLEPQIQPV | HCC, CLL, BRCA, Melanoma, Gallbladder Cancer and Bile Duct Cancer, AML, HNSCC |
| 320 | KMFEFVEPLL | SCLC, Brain Cancer, BRCA, Melanoma, Urinary Bladder Cancer, Uterine Cancer, Gallbladder Cancer and Bile Duct Cancer, AML, HNSCC |
| 321 | GLFEDVTQPGILL | CLL |
| 322 | TLMTSLPAL | CLL, BRCA, Melanoma, Uterine Cancer, Gallbladder Cancer and Bile Duct Cancer, AML, NHL |
| 323 | IQIGEETVITV | CRC, CLL, BRCA |
| 324 | FLYDEIEAEV | CLL |
| 325 | FIMPATVADATAV | CLL, BRCA, Melanoma, Uterine Cancer, NHL |
| 326 | FLPEALDFV | CLL, AML, NHL |
| 327 | GLAPFTEGISFV | NSCLC, Gallbladder Cancer and Bile Duct Cancer |
| 328 | ALNDQVFEI | AML |
| 330 | QLALKVEGV | CLL, Urinary Bladder Cancer, AML, NHL, HNSCC |
| 331 | KVDTVWVNV | CLL, Gallbladder Cancer and Bile Duct Cancer, HNSCC |
| 332 | YLISELEAA | RCC, GC, BRCA, Melanoma |
| 333 | FLPDANSSV | HCC, Melanoma |
| 334 | TLTKVLVAL | CLL |
| 335 | YSLSSVVTV | HNSCC |
| 336 | ILLTAIVQV | Melanoma |
| 337 | HLLSELEAAPYL | CLL |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 338 | SVLEDPVHAV | BRCA, Esophageal Cancer, Uterine Cancer, Gallbladder Cancer and Bile Duct Cancer, NHL |
| 339 | GLWEIENNPTVKA | Gallbladder Cancer and Bile Duct Cancer |
| 340 | ALLSMTFPL | SCLC, AML |
| 341 | SQIALNEKLVNL | Urinary Bladder Cancer |
| 342 | HIYDKVMTV | Esophageal Cancer, Gallbladder Cancer and Bile Duct Cancer |
| 343 | SLLEVNEESTV | CLL |
| 345 | VIWKALIHL | NSCLC, Melanoma, NHL |
| 346 | LLDSKVPSV | HNSCC |
| 347 | SLFKHDPAAWEA | Uterine Cancer, HNSCC |
| 348 | ILLDVKTRL | Melanoma, Gallbladder Cancer and Bile Duct Cancer, HNSCC |
| 350 | ALLDVTHSELTV | BRCA, HNSCC |
| 351 | SLIPNLRNV | CRC, Esophageal Cancer |
| 352 | SLLELLHIYV | CLL, AML |
| 354 | LILEGVDTV | BRCA, Urinary Bladder Cancer, Uterine Cancer, NHL |
| 356 | KLLGKLPEL | Melanoma, Urinary Bladder Cancer |
| 358 | ALDEYTSEL | Urinary Bladder Cancer |
| 359 | YLLPESVDL | CLL, Uterine Cancer, NHL, HNSCC |
| 360 | ALDJGASLLHL | HNSCC |
| 361 | ALYELEGTTV | NSCLC, SCLC, CLL, BRCA, Urinary Bladder Cancer, Uterine Cancer, Gallbladder Cancer and Bile Duct Cancer, HNSCC |
| 362 | TLYGLSVLL | AML |
| 363 | KVLDVSDLESV | NSCLC, Esophageal Cancer, Urinary Bladder Cancer, Gallbladder Cancer and Bile Duct Cancer, HNSCC |
| 364 | LLQNEQFEL | Urinary Bladder Cancer, Uterine Cancer, Gallbladder Cancer and Bile Duct Cancer |
| 365 | YVIDQGETDVYV | CLL, Urinary Bladder Cancer, NHL |
| 366 | RLLDMGETDLML | CLL, Urinary Bladder Cancer, AML, NHL |
| 367 | SLQNHNHQL | NSCLC, CRC, Melanoma, Esophageal Cancer, AML, NHL, HNSCC |
| 370 | SLLQDLVSV | BRCA, Melanoma, Gallbladder Cancer and Bile Duct Cancer, HNSCC |
| 372 | TMLLNIPLV | CLL, Gallbladder Cancer and Bile Duct Cancer, AML, NHL |
| 374 | FLLQQHLISA | CLL |
| 375 | SLTETIEGV | Gallbladder Cancer and Bile Duct Cancer |
| 376 | AMFESSQNVLL | CLL |
| 379 | IMEGTLTRV | RCC, CLL, Melanoma, Urinary Bladder Cancer, NHL |
| 380 | TLIEDEIATI | SCLC, Melanoma, Uterine Cancer, Gallbladder Cancer and Bile Duct Cancer, AML, HNSCC |
| 381 | FIDEAYVEV | GC, CLL, Melanoma, NHL |
| 382 | ALQNYIKEA | BRCA |
| 384 | ILFANPNIFV | CLL, Urinary Bladder Cancer, Uterine Cancer, NHL |
| 385 | SLLEQGLVEA | BRCA, AML, HNSCC |
| 386 | ILFRYPLTI | Melanoma, Uterine Cancer, AML |
| 387 | ALFQATAEV | SCLC, Melanoma, Urinary Bladder Cancer, Uterine Cancer, Gallbladder Cancer and Bile Duct Cancer, AML, NHL, HNSCC |
| 388 | SLTIDGIRYV | Brain Cancer |
| 389 | LLADVTHLL | Melanoma, AML |
| 393 | GLLDTQTSQVLTA | CRC, Gallbladder Cancer and Bile Duct Cancer, HNSCC |
| 394 | LLAVIGGLVYL | BRCA |
| 395 | ALALGGIAVV | CLL, NHL, HNSCC |
| 396 | ALLPDLPAL | SCLC, Gallbladder Cancer and Bile Duct Cancer, AML, NHL, HNSCC |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 397 | YLFGERLLEC | CLL, Uterine Cancer |
| 398 | KLLEEDGTIITL | BRCA, Esophageal Cancer, Gallbladder Cancer and Bile Duct Cancer |
| 400 | SLLTEQDLWTV | CLL |
| 401 | ILLDDTGLAYI | CLL, Urinary Bladder Cancer, Gallbladder Cancer and Bile Duct Cancer, NHL |
| 403 | KLYDRILRV | BRCA |
| 407 | YLMDLINFL | AML |
| 408 | VLDDSIYLV | CLL, Uterine Cancer, NHL |
| 409 | LLDAMNYHL | CLL, NHL |
| 411 | LLAHLSPEL | Melanoma |
| 412 | YLDDLNEGVYI | BRCA |
| 413 | TLLEKVEGC | Melanoma |
| 414 | YVDDIFLRV | GC, Melanoma |
| 415 | LLDKVYSSV | Brain Cancer, CLL, BRCA, Urinary Bladder Cancer, Uterine Cancer, Gallbladder Cancer and Bile Duct Cancer, AML, NHL, HNSCC |
| 416 | VLSDIIQNLSV | CLL, NHL |
| 417 | NLQDTEYNL | CLL, AML, NHL |
| 418 | ALAELENIEV | CLL, BRCA, Urinary Bladder Cancer, Gallbladder Cancer and Bile Duct Cancer, HNSCC |
| 419 | GQYEGKVSSV | BRCA |
| 420 | FMYDTPQEV | Gallbladder Cancer and Bile Duct Cancer |
| 422 | FLPKLLLA | Melanoma |
| 423 | GLDGPPPTV | NHL |
| 424 | TLLDALYEI | Melanoma, Gallbladder Cancer and Bile Duct Cancer, AML, HNSCC |
| 425 | FLYEKSSQV | SCLC |
| 426 | RLADKSVLV | BRCA, AML |
| 427 | ALLPLSPYL | Gallbladder Cancer and Bile Duct Cancer |
| 428 | KLGHTDILVGV | CLL, Uterine Cancer, HNSCC |
| 429 | GLVNDLARV | SCLC, BRCA, Melanoma, Gallbladder Cancer and Bile Duct Cancer, NHL |
| 430 | HLYSSIEHLTT | SCLC, BRCA, Urinary Bladder Cancer, NHL |
| 431 | SLVNVVPKL | CLL, BRCA, Urinary Bladder Cancer, Gallbladder Cancer and Bile Duct Cancer, AML, NHL |
| 433 | AMLNEPWAV | BRCA, Melanoma, Urinary Bladder Cancer, HNSCC |
| 434 | KVSNSGITRV | Esophageal Cancer, HNSCC |
| 435 | WLMPVIPAL | Melanoma, Gallbladder Cancer and Bile Duct Cancer, AML |
| 436 | HLAEVSAEV | NSCLC, SCLC, CLL, BRCA, Melanoma, Urinary Bladder Cancer, Gallbladder Cancer and Bile Duct Cancer, AML, NHL, HNSCC |
| 438 | KLLPLAGLYL | CLL, BRCA, Melanoma, Uterine Cancer, Gallbladder Cancer and Bile Duct Cancer, AML, HNSCC |
| 439 | YLLQEIYGI | AML |
| 440 | ALADGVTMQV | SCLC, BRCA, Melanoma, Uterine Cancer |
| 441 | ALLENPKMEL | Urinary Bladder Cancer |
| 443 | GLWEIENNPTV | Gallbladder Cancer and Bile Duct Cancer |
| 444 | GLLRDEALAEV | CLL, BRCA, Urinary Bladder Cancer, Uterine Cancer, AML, NHL, HNSCC |
| 445 | GLYQDPVTL | Uterine Cancer, AML |
| 446 | QLIPALAKV | Brain Cancer |
| 447 | QLVPALAKV | BRCA, Melanoma, HNSCC |
| 448 | NLLETKLQL | CLL, Melanoma, NHL, HNSCC |
| 450 | FMIDASVHPTL | CLL, Urinary Bladder Cancer, HNSCC |
| 451 | LLLLDTVTMQV | Melanoma, HNSCC |
| 452 | ILLEHGADPNL | CLL, Urinary Bladder Cancer, NHL |
| 453 | KLLEATSAV | SCLC, BRCA, Uterine Cancer, Gallbladder Cancer and Bile Duct Cancer, AML, NHL, HNSCC |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 454 | KLPPPPPQA | BRCA, AML, HNSCC |
| 455 | SLLKEPQKVQL | CLL, Melanoma, HNSCC |
| 456 | LLIGHLERV | BRCA, AML, NHL, HNSCC |
| 458 | SLIDKLYNI | SCLC, Brain Cancer, Melanoma, Urinary Bladder Cancer, AML, HNSCC |
| 459 | ALITEVVRL | SCLC, CLL, AML, NHL |
| 461 | VMFRTPLASV | BRCA, Urinary Bladder Cancer, Uterine Cancer, NHL |
| 462 | KLAKQPETV | NHL |
| 463 | SLVESHLSDQLTL | CLL, BRCA, Urinary Bladder Cancer, Uterine Cancer, Gallbladder Cancer and Bile Duct Cancer, NHL, HNSCC |
| 464 | ALNDCIYSV | HNSCC |
| 465 | QLCDLNAEL | SCLC, Melanoma, AML, HNSCC |
| 466 | VLIANLEKL | Urinary Bladder Cancer, NHL |
| 467 | FLAKDFNFL | NSCLC, Melanoma, Urinary Bladder Cancer, Gallbladder Cancer and Bile Duct Cancer, NHL, HNSCC |
| 468 | YLRSVGDGETV | Uterine Cancer |
| 469 | YLASDEITTV | CLL |
| 470 | MLQDSIHVV | BRCA |
| 472 | KLLEVSDDPQV | HNSCC |
| 473 | AMATESILHFA | AML |
| 474 | YLDPALELGPRNV | BRCA |
| 476 | ALMERTGYSMV | Uterine Cancer |
| 477 | ALLPASGQIAL | CLL, BRCA, Melanoma, Gallbladder Cancer and Bile Duct Cancer, HNSCC |
| 478 | YLLHEKLNL | NHL |
| 479 | SLFGNSGILENV | Melanoma, Uterine Cancer, AML, HNSCC |
| 480 | ALLEDSCHYL | HNSCC |
| 481 | GLIEDYEALL | Melanoma, AML |
| 482 | SLAPAGIADA | Melanoma, Uterine Cancer, HNSCC |
| 483 | ALTDIVSQV | NSCLC, SCLC, BRCA, Uterine Cancer, Gallbladder Cancer and Bile Duct Cancer, HNSCC |
| 484 | SLIEKVTQL | SCLC, CRC, CLL, BRCA, Melanoma, Esophageal Cancer, Urinary Bladder Cancer, Uterine Cancer, AML, NHL |
| 486 | AVMESIQGV | CLL |
| 487 | LLINSVFHV | Urinary Bladder Cancer, NHL |
| 488 | FLAEDPKVTL | CLL, BRCA, Melanoma, Urinary Bladder Cancer, NHL |
| 489 | KMWEELPEVV | CLL, Esophageal Cancer, Urinary Bladder Cancer, AML, NHL, HNSCC |
| 490 | FLLQHVQEL | CLL, NHL |
| 491 | GLNDRSDAV | BRCA, AML, HNSCC |
| 492 | SLFDGFADGLGV | BRCA |
| 493 | GLLGEKTQDLIGV | CLL, Melanoma, Urinary Bladder Cancer, Uterine Cancer, Gallbladder Cancer and Bile Duct Cancer, HNSCC |
| 495 | FIFSEKPVFV | Melanoma, AML, NHL |
| 496 | FLVEKQPPQV | CLL, NHL |
| 497 | GLLEKLTAI | SCLC, CLL, BRCA, Melanoma, Urinary Bladder Cancer, AML, NHL |
| 498 | KLWTGGLDNTV | NSCLC, Brain Cancer, CLL, Urinary Bladder Cancer, Uterine Cancer, NHL |
| 500 | SLMEDQVLQL | CLL, AML |
| 501 | LLDPNVKSIFV | BRCA, Urinary Bladder Cancer, HNSCC |
| 502 | RLLAQVPGL | Melanoma, Uterine Cancer, Gallbladder Cancer and Bile Duct Cancer, AML, NHL |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 503 | SLNHFTHSV | HCC, CLL, Urinary Bladder Cancer, AML, NHL, HNSCC |
| 504 | GLSDGNPSL | CLL, Uterine Cancer |
| 505 | SLAPGDVVRQV | BRCA, Urinary Bladder Cancer, HNSCC |
| 506 | KLLGKVETA | CLL, NHL |
| 507 | KLIDDQDISISL | CLL, Urinary Bladder Cancer, NHL |
| 508 | ILAQEQLVVGV | SCLC, Gallbladder Cancer and Bile Duct Cancer |
| 509 | FLFDTKPLIV | CLL |
| 510 | KLYSVVSQL | NHL |
| 511 | FLDPYCSASV | SCLC, Uterine Cancer |
| 512 | SLSEIVPCL | Uterine Cancer, AML, HNSCC |
| 513 | SLWPSPEQL | Melanoma, AML, NHL, HNSCC |
| 514 | ILVDWLVQV | BRCA, Gallbladder Cancer and Bile Duct Cancer, AML, NHL, HNSCC |
| 517 | LLMPIPEGLTL | Urinary Bladder Cancer, Uterine Cancer, HNSCC |
| 518 | KLNAEVACV | BRCA, Melanoma, Urinary Bladder Cancer, Uterine Cancer, HNSCC |
| 519 | GLLHLTLLL | SCLC, Gallbladder Cancer and Bile Duct Cancer, AML, HNSCC |
| 520 | LAVHPSGVAL | SCLC, CLL, BRCA, Gallbladder Cancer and Bile Duct Cancer |
| 521 | MLLTKLPTI | Brain Cancer, CLL, Uterine Cancer, AML, NHL, HNSCC |
| 522 | TLWYRSPEV | Melanoma |
| 523 | YQIPRTFTL | CLL, AML |
| 524 | ALIENLTHQI | CLL, Melanoma, NHL |
| 525 | VLLEAGEGLVTI | NSCLC, SCLC, CLL, Urinary Bladder Cancer, Uterine Cancer, NHL, HNSCC |
| 526 | RLAEVGQYEQV | Uterine Cancer, NHL |
| 528 | SVAEGRALMSV | NSCLC, CLL, BRCA, Urinary Bladder Cancer, Gallbladder Cancer and Bile Duct Cancer, HNSCC |
| 529 | LLADELITV | SCLC, CLL, HNSCC |
| 530 | VMYADIGGMDI | CLL, Urinary Bladder Cancer, Uterine Cancer, Gallbladder Cancer and Bile Duct Cancer, HNSCC |
| 531 | YTLPIASSIRL | BRCA |
| 532 | ALNNLLHSL | Melanoma, Esophageal Cancer, Urinary Bladder Cancer, Uterine Cancer, Gallbladder Cancer and Bile Duct Cancer, AML, NHL |
| 533 | RMVAEIQNV | CLL, NHL |
| 534 | HLANIVERL | CLL |
| 535 | KLIAQNLEL | AML, NHL, HNSCC |
| 536 | YLVEGRFSV | CLL, Urinary Bladder Cancer |
| 538 | LLLAHIIAL | BRCA, Urinary Bladder Cancer, Uterine Cancer |
| 539 | ALFDAQAQV | Melanoma, AML |
| 540 | ALIPETTTLTV | NHL |
| 541 | SMLEPVPEL | Gallbladder Cancer and Bile Duct Cancer |
| 542 | RVWDISTVSSV | NSCLC, CLL, BRCA |
| 543 | GLLPTPITQQASL | BRCA |
| 544 | LLWDVPAPSL | CLL, Uterine Cancer, HNSCC |
| 545 | LLADLLHNV | BRCA |
| 546 | VMIAGKVAVV | SCLC, Urinary Bladder Cancer, HNSCC |
| 547 | TLDITPHTV | Esophageal Cancer |
| 548 | ALWENPESGEL | BRCA |
| 549 | AMLENASDIKL | SCLC, CLL, Urinary Bladder Cancer |
| 550 | FLYDEIEAEVNL | CLL |
| 551 | KLYESLLPFA | CLL, BRCA, Urinary Bladder Cancer, Gallbladder Cancer and Bile Duct Cancer, AML, NHL, HNSCC |
| 552 | GLLDLPFRVGV | CLL, AML, NHL |
| 553 | SLLNQDLHWSL | CLL |
| 554 | LLMPSSEDLLL | CLL, Melanoma, HNSCC |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 555 | YVLEGLKSV | CRC, CLL, Esophageal Cancer, Urinary Bladder Cancer, Uterine Cancer, NHL, HNSCC |
| 556 | FLTDLEDLTL | CLL, Uterine Cancer, NHL |
| 557 | KLYDDMIRL | Brain Cancer, NHL |
| 558 | GLLENIPRV | CLL, BRCA, Melanoma, AML, NHL |
| 559 | VTVPPGPSL | CLL, AML |
| 560 | ALWDIETGQQTTT | CLL, Urinary Bladder Cancer, Uterine Cancer, Gallbladder Cancer and Bile Duct Cancer, NHL, HNSCC |
| 561 | YLQLTQSEL | CLL, NHL, HNSCC |
| 563 | WLLPYNGVTV | CLL, Uterine Cancer, NHL |
| 565 | ALQETPTSV | BRCA, Gallbladder Cancer and Bile Duct Cancer |
| 566 | VIADGGIQNV | CRC, CLL, BRCA, Urinary Bladder Cancer, Gallbladder Cancer and Bile Duct Cancer, NHL |
| 567 | SLLPLDDIVRV | CLL, BRCA |
| 568 | TLYDIAHTPGV | CLL, Urinary Bladder Cancer, NHL, HNSCC |
| 570 | ALANQIPTV | HCC |
| 571 | LLLTTIPQI | Melanoma |
| 572 | ALADLIEKELSV | CLL, NHL |
| 573 | ILVANAIVGV | CLL, SCLC, Urinary Bladder Cancer |
| 575 | YLISQVEGHQV | NSCLC, SCLC, BRCA, Urinary Bladder Cancer, HNSCC |
| 577 | VMFEDGVLMRL | SCLC, CLL, Urinary Bladder Cancer, AML, NHL, HNSCC |
| 578 | FLDPGGPMMKL | SCLC, CLL, BRCA, Urinary Bladder Cancer, HNSCC |
| 579 | NLMEMVAQL | SCLC, CLL, Melanoma, Urinary Bladder Cancer, NHL |
| 580 | LLMENAERV | CLL, Esophageal Cancer, Urinary Bladder Cancer, Uterine Cancer, NHL, HNSCC |
| 581 | RLWNETVEL | AML, NHL |
| 582 | TLCDVILMV | Melanoma |
| 583 | ILANDGVLLAA | CLL, BRCA, Urinary Bladder Cancer, Uterine Cancer, Gallbladder Cancer and Bile Duct Cancer, NHL, HNSCC |
| 585 | ALWDLAADKQTL | Melanoma |
| 586 | KLKPGDLVGV | Uterine Cancer |
| 587 | VMNDRLYAI | CLL, NHL |
| 588 | SLLPLSHLV | CLL, Gallbladder Cancer and Bile Duct Cancer, AML, NHL, HNSCC |
| 589 | KLYPQLPAEI | CLL, BRCA, Urinary Bladder Cancer |
| 590 | SLIEKLWQT | Uterine Cancer, AML |
| 591 | SMAELDIKL | AML, HNSCC |
| 594 | IMLKGDNITL | Uterine Cancer |
| 595 | VLLSIYPRV | CLL, Urinary Bladder Cancer, Gallbladder Cancer and Bile Duct Cancer |
| 596 | ALLDQTKTLAESAL | CLL, NHL |
| 597 | KLLEGQVIQL | CLL, Melanoma, Gallbladder Cancer and Bile Duct Cancer, AML |
| 598 | FLFPHSVLV | CRC |
| 599 | YLLNDASLISV | SCLC |
| 600 | ALAAPDIVPAL | CLL, Uterine Cancer, AML |
| 601 | SAFPFPVTV | CLL, Gallbladder Cancer and Bile Duct Cancer, AML |
| 603 | FLIEPEHVNTV | CLL |
| 604 | SILDRDDIFV | CLL, Melanoma, NHL |
| 605 | KLYEAVPQL | Gallbladder Cancer and Bile Duct Cancer, HNSCC |
| 607 | RLYSGISGLEL | CLL, Melanoma, AML, NHL |
| 609 | ALWKQLLEL | CRC, Esophageal Cancer, Uterine Cancer |
| 611 | YLLDDGTLVV | Uterine Cancer |
| 612 | YLYNEGLSV | BRCA, Urinary Bladder Cancer, AML, NHL, HNSCC |
| 613 | RLLPPGAVVAV | CLL, BRCA, Urinary Bladder Cancer, Gallbladder Cancer and Bile Duct Cancer, HNSCC |

TABLE 5B-continued

Peptides according to the present invention and their specific uses in other proliferative diseases, especially in other cancerous diseases (amendment of Table 4). The table shows, like Table 4A, for selected peptides on which additional tumor types they were found showing over-presentation (including specific presentation) on more than 5% of the measured tumor samples, or presentation on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon, duodenum, esophagus, eye, gallbladder, heart, kidney, liver, lung, lymph node, mononuclear white blood cells, pancreas, parathyroid gland, peripheral nerve, peritoneum, pituitary, pleura, rectum, salivary gland, skeletal muscle, skin, small intestine, spleen, stomach, thyroid gland, trachea, ureter, urinary bladder, vein.

| SEQ ID NO. | Sequence | Additional organs/cancerous diseases |
|---|---|---|
| 614 | LLLPDQPPYHL | CLL |
| 615 | VLPPDTDPA | Melanoma, Esophageal Cancer |
| 616 | VLIDEVESL | CRC, Uterine Cancer, Gallbladder Cancer and Bile Duct Cancer, AML, NHL, HNSCC |
| 619 | ALQDRVPLA | BRCA, Gallbladder Cancer and Bile Duct Cancer |
| 620 | KLLNKIYEA | BRCA, AML |
| 621 | VLMDRLPSLL | CLL |
| 622 | RLLGEEVVRVLQA | Urinary Bladder Cancer, AML, NHL |
| 623 | YLVEDIQHI | NSCLC, PC |
| 624 | FLQEEPGQLL | CLL, Urinary Bladder Cancer, Uterine Cancer, Gallbladder Cancer and Bile Duct Cancer, NHL |
| 625 | VVLEGASLETV | CLL, Urinary Bladder Cancer |
| 626 | LLMATILHL | CLL, AML, NHL, HNSCC |
| 627 | KLLETELLQEI | CLL, Urinary Bladder Cancer |
| 628 | KLWEFFQVDV | Melanoma |
| 629 | HLLNESPML | RCC, PC, BRCA, Melanoma, Uterine Cancer, Gallbladder Cancer and Bile Duct Cancer, AML |
| 630 | LLSHVIVAL | CLL, Gallbladder Cancer and Bile Duct Cancer, NHL |
| 631 | FLDVFLPRV | SCLC, CLL, NHL |
| 632 | YLIPDIDLKL | CLL, AML, NHL, HNSCC |
| 633 | ALSRVSVNV | CLL |
| 634 | VVAEFVPLI | CLL, AML, NHL |
| 635 | SLDSTLHAV | SCLC, Melanoma, Urinary Bladder Cancer, Uterine Cancer, Gallbladder Cancer and Bile Duct Cancer |
| 636 | LLTEIRAVV | CLL, NHL |
| 637 | SIYGGFLLGV | Urinary Bladder Cancer, Gallbladder Cancer and Bile Duct Cancer, HNSCC |
| 638 | KLIQESPTV | Gallbladder Cancer and Bile Duct Cancer, AML |
| 639 | SLFQNCFEL | CLL, Melanoma, Uterine Cancer, NHL, HNSCC |

NSCLC = non-small cell lung cancer,
SCLC = small cell lung cancer,
RCC = kidney cancer,
CRC = colon or rectum cancer,
GC = stomach cancer,
HCC = liver cancer,
PC = pancreatic cancer,
PrC = prostate cancer,
BRCA = breast cancer,
NHL = non-Hodgkin lymphoma,
AML = acute myeloid leukemia,
CLL = chronic lymphocytic leukemia,
HNSCC = head and neck squamous cell carcinoma.

Thus, another aspect of the present invention relates to the use of at least one peptide according to the present invention according to any one of SEQ ID No. 1, 11, 17, 27, 45, 57, 58, 61, 62, 65, 72, 74, 79, 84, 97, 98, 104, 105, 125, 126, 143, 150, 157, 161, 167, 176, 179, 183, 184, 195, 198, 201, 204, 213, 217, 222, 228, 234, 248, 263, 264, 268, 285, 287, 303, 313, 319, 323, 333, 335, 338, 343, 347, 348, 355, 356, 359, 373, 385, 394, 395, 403, 415, 421, 427, 428, 429, 430, 431, 434, 441, 443, 444, 446, 447, 450, 454, 456, 457, 458, 459, 463, 474, 477, 479, 480, 486, 489, 492, 493, 497, 501, 503, 506, 514, 517, 521, 526, 538, 539, 540, 541, 545, 554, 558, 568, 573, 576, 578, 579, 589, 595, 597, 599, 602, 607, 610, 613, 616, 627, 632, 635, and 637 for the—in one preferred embodiment combined—treatment of NSCLC.

Thus, another aspect of the present invention relates to the use of at least one peptide according to the present invention according to any one of SEQ ID No 1, 6, 17, 19, 20, 27, 28, 31, 34, 36, 38, 45, 47, 48, 51, 54, 55, 56, 57, 58, 59, 60, 61, 65, 66, 72, 75, 76, 79, 82, 85, 88, 91, 92, 98, 103, 108, 117, 123, 125, 126, 127, 135, 141, 142, 149, 152, 153, 166, 167, 169, 171, 176, 183, 184, 200, 205, 213, 214, 216, 228, 233, 234, 237, 240, 242, 248, 249, 251, 256, 263, 264, 277, 279, 283, 286, 288, 296, 300, 301, 312, 314, 315, 322, 323, 328, 331, 338, 341, 344, 345, 346, 366, 372, 373, 385, 388, 394, 399, 401, 404, 410, 418, 420, 421, 427, 428, 431, 433, 435, 437, 439, 441, 443, 444, 446, 449, 450, 451, 454, 461, 463, 469, 473, 474, 475, 479, 481, 492, 493, 500, 501, 514, 517, 521, 522, 523, 530, 531, 539, 541, 542, 545, 551, 552, 554, 555, 556, 558, 560, 561, 563, 565, 568, 574, 575, 581, 589, 590, 592, 595, 597, 602, 606, 610, 613, 616, 618, 622, 625, 626, 627, 628, 629, 632, 637, 638, and 640 for the—in one preferred embodiment combined—treatment of SCLC.

Thus, another aspect of the present invention relates to the use of at least one peptide according to the present invention according to any one of SEQ ID No 1, 2, 6, 19, 26, 27, 57, 58, 61, 63, 64, 65, 69, 77, 79, 85, 95, 97, 98, 103, 107, 121, 125, 126, 127, 128, 129, 143, 148, 150, 155, 157, 166, 170, 174, 177, 200, 201, 204, 207, 213, 217, 222, 223, 229, 234, 235, 242, 243, 252, 258, 264, 267, 271, 275, 279, 285, 287, 294, 303, 306, 311, 313, 317, 319, 323, 328, 330, 332, 333, 336, 346, 347, 348, 354, 355, 356, 359, 360, 361, 375, 382, 385, 387, 393, 395, 405, 410, 415, 424, 430, 431, 441, 444, 447, 450, 459, 461, 465, 466, 472, 477, 480, 486, 491, 492, 497, 498, 499, 501, 505, 506, 508, 513, 514, 518, 528, 533, 539, 541, 542, 543, 554, 560, 561, 565, 568, 575, 576, 583, 588, 589, 591, 592, 594, 601, 610, 616, 619, 624, 629, 631, 633, 635, and 640 for the—in one preferred embodiment combined—treatment of esophageal cancer.

Thus, another aspect of the present invention relates to the use of at least one peptide according to the present invention according to any one of SEQ ID No. 6, 48, 68, 106, 118, 127, 135, 143, 157, 174, 209, 247, 279, 292, 300, 313, 28, 332, 333, 340, 357, 358, 385, 389, 410, 425, 431, 450, 456, 464, 473, 474, 492, 501, 506, 514, 523, 528, 538, 539, 541, 558, 586, 589, 590, 592, 593, 606, 610, 619, 620, 628, and 635 for the—in one preferred embodiment combined—treatment of brain cancer.

Thus, another aspect of the present invention relates to the use of at least one peptide according to the present invention according to any one of SEQ ID No 6, 7, 17, 27, 56, 59, 61, 65, 76, 93, 103, 110, 131, 141, 143, 149, 169, 204, 212, 216, 226, 228, 229, 230, 242, 255, 264, 266, 268, 271, 273, 283, 284, 285, 286, 287, 288, 289, 303, 309, 331, 333, 335, 336, 340, 358, 362, 371, 372, 373, 375, 393, 395, 396, 401, 420, 422, 423, 427, 439, 446, 459, 466, 504, 521, 539, 554, 576, 580, 592, 595, 597, 610, 616, 635, 637, and 640 for the—in one preferred embodiment combined—treatment of breast cancer (BrCa).

Thus, another aspect of the present invention relates to the use of at least one peptide according to the present invention according to any one of SEQ ID No. 6, 20, 139, 283, 373, 396, 418, 430, 441, 446, 472, 473, 474, 479, 501, 575, 578, 589, 627, and 640 for the—in one preferred embodiment combined—treatment of MCC.

Thus, another aspect of the present invention relates to the use of at least one peptide according to the present invention according to any one of SEQ ID No. 7, 9, 97, 98, 183, 217, 218, 222, 234, 235, 237, 240, 241, 242, 263, 268, 271, 275, 285, 303, 311, 313, 360, 364, 394, 403, 410, 424, 431, 450, 455, 497, 502, 514, 558, 564, 595, 608, 610, and 616 for the—in one preferred embodiment combined—treatment of RCC.

Thus, another aspect of the present invention relates to the use of at least one peptide according to the present invention according to any one of SEQ ID No. 7, 24, 27, 64, 65, 84, 87, 95, 97, 125, 126, 127, 130, 137, 143, 183, 200, 272, 275, 291, 292, 311, 312, 332, 335, 346, 351, 357, 358, 364, 372, 398, 405, 407, 410, 421, 423, 427, 443, 459, 464, 499, 539, 540, 603, 609, 630, 631, and 632 for the—in one preferred embodiment combined—treatment of pancreatic cancer (PC).

Thus, another aspect of the present invention relates to the use of at least one peptide according to the present invention according to any one of SEQ ID No. 9, 31, 58, 183, 275, 335, 410, 421, 499, 514, 564, 616, and 640 for the—in one preferred embodiment combined—treatment of gastric cancer (GC).

Thus, another aspect of the present invention relates to the use of at least one peptide according to the present invention according to any one of SEQ ID No. 9, 14, 19, 20, 28, 32, 36, 48, 54, 57, 58, 63, 64, 66, 87, 92, 94, 97, 98, 108, 125, 129, 139, 143, 144, 154, 157, 159, 163, 166, 167, 170, 174, 176, 178, 188, 197, 198, 201, 204, 207, 208, 209, 212, 213, 214, 217, 222, 229, 234, 237, 248, 256, 267, 269, 271, 273, 275, 286, 290, 294, 301, 306, 309, 313, 327, 328, 332, 338, 339, 340, 341, 346, 347, 349, 355, 359, 360, 367, 369, 370, 371, 372, 378, 383, 385, 387, 393, 394, 395, 396, 401, 406, 409, 410, 411, 415, 419, 420, 423, 427, 428, 429, 430, 432, 441, 443, 447, 450, 451, 452, 457, 463, 464, 465, 472, 473, 474, 476, 477, 479, 480, 484, 486, 489, 492, 498, 501, 513, 514, 517, 521, 523, 526, 528, 531, 538, 539, 540, 541, 546, 551, 554, 558, 560, 564, 573, 575, 576, 579, 583, 586, 589, 597, 599, 603, 606, 610, 611, 613, 617, 627, 628, 632, 635, 637, 638, and 640 for the—in one preferred embodiment combined—treatment of hepatocellular carcinoma (HCC).

Thus, another aspect of the present invention relates to the use of at least one peptide according to the present invention according to any one of SEQ ID No. 9, 10, 14, 19, 24, 28, 79, 87, 101, 144, 148, 149, 153, 169, 174, 190, 210, 212, 216, 222, 223, 242, 252, 257, 271, 288, 298, 299, 303, 310, 311, 317, 331, 333, 334, 346, 347, 348, 360, 367, 386, 390, 393, 394, 395, 423, 477, 479, 483, 486, 494, 495, 502, 514, 521, 527, 529, 539, 554, 585, 610, 616, 626, 632, and 640 for the—in one preferred embodiment combined—treatment of urinary bladder cancer.

Thus, another aspect of the present invention relates to the use of at least one peptide according to the present invention according to any one of SEQ ID No. 19, 22, 26, 28, 31, 33, 34, 36, 38, 47, 48, 49, 57, 58, 59, 60, 65, 74, 79, 80, 92, 98, 119, 126, 128, 129, 132, 144, 149, 159, 161, 166, 183, 204, 214, 237, 242, 248, 251, 252, 253, 256, 262, 263, 270, 271, 272, 275, 276, 277, 280, 282, 284, 285, 287, 289, 296, 299, 301, 308, 309, 319, 321, 323, 324, 325, 331, 333, 343, 355, 358, 365, 366, 373, 374, 379, 381, 384, 391, 394, 395, 397, 400, 401, 404, 408, 409, 410, 412, 415, 428, 448, 450, 451, 452, 457, 459, 468, 475, 480, 486, 488, 489, 490, 496, 503, 504, 506, 507, 508, 510, 520, 523, 529, 533, 536, 542, 544, 550, 552, 556, 558, 559, 561, 566, 567, 571, 572, 573, 576, 577, 579, 580, 587, 589, 591, 595, 596, 600, 601, 603, 604, 610, 624, 630, 631, 632, 634, and 639 for the—in one preferred embodiment combined—treatment of leukemia.

Thus, another aspect of the present invention relates to the use of at least one peptide according to the present invention according to any one of SEQ ID No. 19, 22, 31, 34, 38, 48, 57, 58, 61, 62, 63, 64, 74, 77, 92, 97, 98, 101, 105, 107, 143, 144, 150, 155, 167, 176, 177, 183, 184, 199, 213, 217, 222, 230, 248, 251, 256, 264, 277, 282, 283, 287, 291, 309, 314, 316, 321, 323, 329, 331, 338, 339, 343, 344, 355, 365, 366, 373, 384, 388, 391, 394, 395, 401, 410, 412, 431, 443, 444, 450, 452, 457, 461, 463, 468, 472, 474, 487, 496, 499, 501, 514, 517, 521, 523, 525, 530, 540, 542, 544, 549, 550, 551, 552, 555, 560, 563, 564, 565, 566, 568, 572, 573, 575, 576, 578, 580, 584, 588, 589, 596, 599, 603, 611, 614, 616, 618, 621, 622, 624, 625, 626, 627, 631, 632, and 633 for the—in one preferred embodiment combined—treatment of melanoma.

Thus, another aspect of the present invention relates to the use of at least one peptide according to the present invention according to any one of SEQ ID No. 19, 22, 24, 58, 76, 79, 84, 86, 97, 98, 126, 176, 178, 188, 222, 243, 285, 300, 301, 303, 311, 318, 319, 320, 342, 348, 349, 355, 356, 359, 376, 384, 395, 397, 398, 421, 426, 428, 430, 441, 444, 448, 449, 450, 456, 458, 459, 473, 478, 480, 510, 514, 518, 521, 528, 531, 535, 541, 545, 546, 554, 557, 568, 575, 576, 577, 578, 579, 580, 581, 597, 599, 610, 619, 622, 627, 632, 635, and 640 for the—in one preferred embodiment combined—treatment of colorectal cancer (CRC).

Thus, another aspect of the present invention relates to the use of at least one peptide according to the present invention according to any one of SEQ ID No. 34, 51, 84, 174, 178, 200, 207, 212, 216, 237, 252, 264, 288, 323, 332, 333, 372, 394, 395, 410, 443, 446, 447, 486, 492, 501, 518, 539, 551, 554, 606, 610, 637, and 640 for the—in one preferred embodiment combined—treatment of prostate cancer (PrC)

Thus, another aspect of the present invention relates to the use of at least one peptide according to the present invention according to any one of SEQ ID No. 47, 51, 54, 58, 64, 84, 87, 125, 200, 213, 228, 235, 237, 323, 335, 346, 385, 423, 473, 501, 526, 539, 554, 558, 561, 610, 626, and 640 for the—in one preferred embodiment combined—treatment of gallbladder cancer.

Thus, another aspect of the present invention relates to the use of at least one peptide according to the present invention according to any one of SEQ ID No. 47, 51, 54, 58, 64, 84, 87, 125, 200, 213, 228, 235, 237, 323, 335, 346, 385, 423, 473, 501, 526, 539, 554, 558, 561, 610, 626, and 640 for the—in one preferred embodiment combined—treatment of bile duct cancer.

Thus, another aspect of the present invention relates to the use of at least one peptide according to the present invention according to any one of SEQ ID No. 48, 126, 127, 129, 149, 153, 157, 207, 214, 228, 235, 237, 288, 323, 328, 332, 358, 360, 385, 395, 423, 427, 446, 497, 514, 539, 558, 565, 599, 619, 632, 637, and 640 for the—in one preferred embodiment combined—treatment of uterine cancer.

Then, another aspect of the present invention relates to the use of the peptides according to the present invention for the—preferably combined—treatment of a proliferative disease selected from the group of ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, bile duct cancer.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 640.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 640, preferably containing SEQ ID No. 1 to SEQ ID No. 259, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are ovarian cancer, non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, bile duct cancer, and preferably ovarian cancer cells.

The present invention further relates to biomarkers based on the peptides according to the present invention, herein called "targets", that can be used in the diagnosis of cancer, preferably ovarian cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

ABCA1 has been shown to be hyper-methylated in ovarian and prostate cancer cell lines. ABCA1 methylation was linked with poor prognosis in ovarian cancer patients (Lee et al., 2013a; Chou et al., 2015). In colon cancer, over-expression of ABCA1 resulted in a decrease of cellular cholesterol and inhibition of tumor growth. This growth inhibition could be due to apoptosis since over-expression of ABCA1 enhanced cytochrome c release from mitochondria (Smith and Land, 2012).

ABCB8 is associated with drug resistance in human melanomas (Chen et al., 2009b).

ABCC1 is up-regulated in primary breast cancer, lung and esophageal cancers, leukemia and childhood neuroblastoma (Cole et al., 1992; Burger et al., 1994; Norris et al., 1996; Nooter et al., 1997). Scientists have identified ABCC1 as a direct transcriptional target of Notch1 signaling in an etoposide-resistant variant of the MCF7 breast cancer cell line (Cho et al., 2011). Several publications have demonstrated that increased ABCC1 expression in cancers was linked with loss of functional p53 (Fukushima et al., 1999; Sullivan et al., 2000).

ABCC10 was shown to be associated with paclitaxel and gemcitabine resistance in breast cancer, gemcitabine resistance in the non-small cell lung cancer cell line A549 and vinorelbine resistance in the non-small cell lung cancer cell lines SK-LC6 and NCI-H23 (Ikeda et al., 2011; Bessho et al., 2009; Dorman et al., 2015). ABCC10 was shown to be associated with breast cancer pathogenesis (Domanitskaya et al., 2014). ABCC10 was shown to be up-regulated in pancreatic ductal adenocarcinoma, hepatocellular carcinoma, non-small cell lung cancer, chronic lymphocytic leukemia and pediatric acute myeloid leukemia (Mohelnikova-Duchonova et al., 2013b; Borel et al., 2012; Steinbach et al., 2006; Wang et al., 2009c; Hoellein et al., 2010). ABCC10 expression was shown to be correlated with tumor grade in colorectal cancer and pathological grades and TNM stages in adenocarcinoma of the lung (Hlavata et al., 2012; Wang et al., 2009c).

Elevated levels of ABCC4 were present in human NK/T-cell lymphoma cells, lung cancer cells and gastric cancer cells. Moreover, copy number variation in the ABCC4 gene has been associated with the risk of esophageal squamous cell carcinoma (Sun et al., 2014b; Zhao et al., 2014b; Zhang et al., 2015d; Zhang et al., 2015n). Furthermore, silencing of ABCC4 expression in drug-resistant gastric cancer cells resulted in an increase in apoptosis and cell cycle arrest in the G1 phase. Another group has shown that knockdown of ABCC4 inhibited gastric cancer cell growth and blocked cell cycle progression (Chen et al., 2014d; Zhang et al., 2015d).

Down-regulation of ABCD1 expression was observed in renal cell carcinoma, colorectal cancers and melanoma tumorigenesis (Heimerl et al., 2007; Galamb et al., 2009; Hour et al., 2009).

ABCF1 was up-regulated in post-treatment tumors compared with non-neoplastic tissues (Hlavac et al., 2013). Moreover, repressing ABCF1 expression by miR-23a over-expression or siABCF1 resulted in recovery of 5-fluorouracil sensitivity in microsatellite unstable colorectal cancer cells (Li et al., 2015c).

Several publications have shown elevated levels of ABI1 in various types of cancer such as epithelial ovarian cancer, colorectal carcinoma, breast cancer and hepatocellular carcinoma (Wang et al., 2007a; Liu et al., 2009a; Steinestel et al., 2013; Steinestel et al., 2014; Zhang et al., 2015f). In epithelial ovarian cancer, over-expression of ABI1 was significantly associated with advanced stage, high grade and elevated Ca-125 level (Zhang et al., 2015f). Knockdown of ABI1 resulted in decreased invasiveness and migration ability in breast cancer cell lines. Similarly, silencing of ABI1 gene in leukemic cells led to impaired cell migration and abnormal actin remodeling (Wang et al., 2007a; Yu et al., 2008).

ABL2 was over-expressed in non-small cell lung cancers, anaplastic thyroid cancers, melanoma, colorectal, pancreatic cancers, hepatocellular carcinomas, ovarian serous cystadenocarcinoma, lung adenocarcinoma and lung squamous cell carcinoma (Gil-Henn et al., 2013; Greuber et al., 2013; Xing et al., 2014). In highly invasive breast cancer cell lines, ABL2 regulates proliferation, survival, and invasion downstream of de-regulated EGFR, Her2, IGFR and Src kinases (Srinivasan and Plattner, 2006; Srinivasan et al., 2008).

ADCK3 expression was shown to be altered in colorectal cancer (Hennig et al., 2012).

ADCY5 encodes adenylate cyclase 5, a membrane-bound adenylyl cyclase enzyme that mediates G protein-coupled receptor signaling through the synthesis of the second messenger cAMP (RefSeq, 2002). ADCY5 gene hyper-methylation and reduced mRNA expression occurs in acute lymphoblastic leukemia, chronic lymphocytic leukemia and lung adenocarcinoma (Kuang et al., 2008; Tong et al., 2010; Sato et al., 2013).

The expression of ADCY6 was shown to be differentially regulated in laryngeal squamous cell carcinoma (Colombo et al., 2009).

AGL has been shown to be a tumor suppressor in bladder cancer. Loss of AGL in cancer cells induces tumor growth both in vitro and in vivo through increased glycine synthesis via induction of the glycine synthesizing enzyme serine hydroxymethyltransferase 2 (Guin et al., 2014; Ritterson et al., 2015).

AHCY down-regulation contributes to tumorigenesis (Leal et al., 2008). AHCY can promote apoptosis. It inhibits migration and adhesion of esophageal squamous cell carcinoma cells suggesting a role in carcinogenesis of the esophagus (Li et al., 2014c). AHCY protein expression is upregulated in colon cancer (Kim et al., 2009a; Watanabe et al., 2008; Fan et al., 2011). AHCY might be a potential biomarker in ovarian cancer (Peters et al., 2005).

Recent work has identified a mutation in the AKAP6 gene in gastric cancer (Li et al., 2016).

ALDH5A1 has been reported to be over-expressed in breast ductal carcinoma in situ. In addition, inhibitors of ALDH5A1 such as disulfiram and valproic acid were able to inhibit net proliferation of a breast ductal carcinoma models (Kaur et al., 2012).

It has been observed that a patient suffering from Alström syndrome due to mutations in the ALMS1 gene developed also papillary thyroid carcinoma. Another study identified ALMS1 as a tumor neo-antigen in chronic lymphocytic leukemia (Rajasagi et al., 2014; Papadakis et al., 2015).

ALS2CR12 was shown to be associated with cutaneous basal cell carcinoma susceptibility (Stacey et al., 2015). An intronic single nucleotide polymorphism in ALS2CR12 was shown to be associated with breast cancer risk (Lin et al., 2015b).

In oral squamous cell carcinomas (OSCC) up-regulation of ALYREF mRNA and protein level is linked to regional lymph node metastasis caused by cellular invasiveness and migration (Saito et al., 2013). ALYREF mRNA is over-expressed in a wide variety of tumor tissues, whereas the protein level is poorly detected in high-grade cancers (Dominguez-Sanchez et al., 2011). ALYREF is a target of nuclear PI3K signaling, which regulates its sub-nuclear residency, cell proliferation and mRNA export activities through nuclear Akt phosphorylation and phosphoinositide association (Okada et al., 2008).

ANKRD26 belongs to a gene family that was shown to be highly expressed in cancer patients with poor outcome (Sahab et al., 2010). ANKRD26 was shown to be associated with the putative tumor suppressor RARRES1 (Sahab et al., 2010).

Homozygous deletion of the AP1B1 gene was found to be inactive in sporadic meningioma. These findings imply that AP1B1 gene could play an important role in meningioma development (Peyrard et al., 1994; Sayagues et al., 2007).

APOBEC3G is associated with liver metastasis of colorectal cancer, hepatocellular carcinoma and lymphomas (Nowarski et al., 2012; Chang et al., 2014b; Weidle et al., 2015). APOBEC3G is associated with poor prognosis in colon carcinoma with hepatic metastasis and with reduced overall survival in diffuse large B-cell lymphoma (Lan et al., 2014; Jais et al., 2008).

APOL2 was shown to be over-expressed in ovarian/peritoneal carcinoma (Davidson et al., 2011).

Over-expression of AQP5 has been linked to many kinds of cancers such as colorectal, cervical, lung, breast and epithelial ovarian cancer (Shan et al., 2014; Yan et al., 2014a). In non-small cell lung cancer elevated AQP5 expression levels were associated with lymph node metastasis. Furthermore, the expression levels of AQP5 in stage III and IV tumors were significantly higher compared with stage I and II tumors (Song et al., 2015a). Previous studies have revealed that AQP5 can activate the RAS/ERK/RB pathway in rectal cancer cells and enhance the incidence and progression of cancer (Woo et al., 2008; Kang et al., 2008b).

AR has been implicated in the development of various cancers such as prostate, castrate-resistant prostate, breast, glioblastoma multiforme, colon and gastric (Wang et al., 2009d; Yu et al., 2015b; Mehta et al., 2015; Wang et al., 2015a; Sukocheva et al., 2015). In addition to promoting prostate cancer proliferation, androgen signaling through AR leads to apoptosis via inducing the expression of p21 (WAF1/CIP1), a cyclin-dependent kinase inhibitor (Yeh et al., 2000).

A study has shown down-regulation of ARFGEF1 in breast cancer cell lines. Another group reported ARFGEF1 to be a tumor suppressor in breast cancer patients (Pongor et al., 2015; Kim et al., 2011a). It is postulated that microRNA-27b mediated up-regulation of ARFGEF1 promotes tumor growth by activating the ARFGEF1/Akt pathway (Matsuyama et al., 2016).

ARHGAP26 was shown to be down-regulated in acute myeloid leukemia and during the progression of CML (Qian et al., 2010; Aly and Ghazy, 2014). ARHGAP26 is associated with metastatic brain tumors from primary lung adenocarcinoma (Zohrabian et al., 2007). ARHGAP26 is associated with risk and tumor size of uterine leiomyoma, increased CML risk and is a favorable prognostic marker for AML (Dzikiewicz-Krawczyk et al., 2014; Aissani et al., 2015).

ARHGEF19 was shown to be associated with metastasis of hepatocellular carcinoma (Zhou et al., 2014a). ARHGEF19 was described as a part of the planar cell polarity/non-canonical Wnt pathway, a pathway associated with cancer (Miller et al., 2011).

ARID5B was shown to be dysregulated in prostate cancer (Davalieva et al., 2015). ARID5B was shown to be associated with susceptibility, relapse hazard and poorer treatment outcome in childhood acute lymphoblastic leukemia (Xu et al., 2012; Evans et al., 2014). ARID5B was shown to be a potential target regulated by SALL4, a transcription factor which is associated with acute myeloid leukemia (Milanovich et al., 2015). ARID5B was shown to be a target of the oncogenic TEAD4 protein in gastric cancer (Lim et al., 2014). ARID5B was shown to be frequently mutated in endometrioid tumors (Kandoth et al., 2013). ARID5B might play a role in cervical cancer development through its function as a human papillomavirus 16 integration site (Matovina et al., 2009). ARID5B was shown to be up-regulated in the highly metastatic adenoid cystic carcinoma cell line ACC-M of human salivary glands, may be involved in adenoid cystic carcinoma lung metastasis and might serve as a diagnostic marker and therapeutic target (Sun et al., 2004a).

ARL6IP1 is associated with cervical cancer cell growth and invasion (Guo et al., 2010).

ASUN was shown to be up-regulated in testicular seminomas and an ovarian carcinoma cell line (Bourdon et al., 2002). A study has shown that ATF6B was essential for lysophosphatidic acid-induced YAP dephosphorylation in human epithelial ovarian cancer cell lines (Cai and Xu, 2013).

ATM is a tumor suppressor which is frequently mutated in a broad range of human cancers including lung, colorectal, breast and hematopoietic cancers (Weber and Ryan, 2014). Loss of ATM has been associated with the increased risk of various cancers including, breast, colorectal, prostate, lung and pancreatic ductal adenocarcinoma (Swift et al., 1987; Geoffroy-Perez et al., 2001; Angele et al., 2004; Roberts et al., 2012; Grant et al., 2013; Russell et al., 2015). Studies have shown that IL-8 was able to rescue cell migration and invasion defects in ATM-depleted cells (Chen et al., 2015d). Low level of ATM protein was correlated with poor metastasis-free survival in breast cancer patients. In addition, miR-203 and miR-421 over-expression may be involved in ATM de-regulation in these patients (Bueno et al., 2014; Rondeau et al., 2015).

ATP10A is associated with relapse and decrease of event-free survival in B-cell precursor acute lymphatic leukemia (Olsson et al., 2014).

ATP2A2 is associated with skin cancer, colon cancer and lung cancer (Korosec et al., 2006; Hovnanian, 2007).

The expression of ATP2A3 is markedly decreased in colon, stomach, lung and breast cancer and ATP2A3 expression is induced when these cells undergo differentiation in vitro (Gelebart et al., 2002; Arbabian et al., 2013; Papp et al., 2012). In colon cancer, the expression of ATP2A3 has been shown to be negatively regulated by the APC/beta-catenin/TCF4 oncogenic pathway (Brouland et al., 2005). In addition, ATP2A3 expression was found to be negatively related with lymphatic invasion (Gou et al., 2014).

Researchers have shown that patients with a variety of malignancies such as melanoma, non-small cell lung carcinoma and chronic myelogenous leukemia develop high-titer IgG antibodies against ATP6AP1 following vaccination with irradiated, autologous GM-CSF secreting tumor cells or allogeneic bone marrow transplantation. Another report has detected elevated levels of ATP6AP1 in invasive ductal and lobular carcinoma as well as breast cancer. Furthermore, mutations in the ATP6AP1 gene were found in follicular lymphoma (Hodi et al., 2002; Anderson et al., 2011; Okosun et al., 2016).

ATP6V1H was shown to interact with the tumor associated gene TM9SF4 in the colon cancer cell lines HCT116 and SW480 (Lozupone et al., 2015). ATP6V1H, as part of the V-ATPase V1 sector, was shown to be associated with invasive behavior of colon cancer cells and tumor pH gradient (Lozupone et al., 2015).

Elevated levels of intracellular ATP8A1 protein diminished the inhibitory role of miR-140-3p in the growth and mobility of non-small-cell lung cancer cells (Dong et al., 2015).

ATR encodes ATR serine/threonine kinase, which belongs to the PI3/PI4-kinase family. This kinase has been shown to phosphorylate checkpoint kinase CHK1, checkpoint proteins RAD17, and RAD9, as well as tumor suppressor protein BRCA1 (RefSeq, 2002). Copy number gain, amplification, or translocations of the ATR gene were observed in oral squamous cell carcinoma cell lines (Parikh et al., 2014). It has been demonstrated that truncating ATR mutations in endometrial cancers are associated with reduced disease-free and overall survival (Zighelboim et al., 2009). VE-822, an ATR inhibitor was shown to radiosensitize and chemosensitize pancreatic cancer cells in vitro and pancreatic tumor xenografts in vivo (Fokas et al., 2012; Benada and Macurek, 2015).

AURKA is over-expressed in many tumors arising from breast, colon, ovary, skin and other tissues, and it has been shown to function as an oncogene when exogenously expressed in numerous cell line models (Nikonova et al., 2013).

AURKB expression is up-regulated in different cancer types, including lung, colorectal and breast cancer as well as leukemia and thereby associated with poor prognosis. So development of AURKB inhibitors for clinical therapy is an interesting field (Hayama et al., 2007; Pohl et al., 2011; Hegyi et al., 2012; Goldenson and Crispino, 2015). AURKB over-expression leads to phosphorylation of histone H3 and to chromosome instability, a crucial factor for carcinogenesis (Ota et al., 2002; Tatsuka et al., 1998). AURKB activity augments the oncogenic Ras-mediated cell transformation (Kanda et al., 2005).

Over-expression and gene amplification of AURKC was detected in prostate and breast cancer cell lines as well as in colorectal cancers, thyroid carcinoma and cervical cancer. Others have observed an increase of AURKC protein in seminomas, implying that it might play a role in the progression of testicular cancers. In addition, AURKC has been shown to be oncogenic since its over-expression transforms NIH 3T3 cells into tumors (Baldini et al., 2010; Tsou et al., 2011; Khan et al., 2011; Zekri et al., 2012). In colorectal cancer, the expression of AURKC was correlated with the grade of disease and tumor size (Hosseini et al., 2015). Furthermore, over-expression of AURKC induces an increase in the proliferation, transformation and migration of cancer cells (Tsou et al., 2011).

Heterozygous carriers of BBS1 gene seem to be at increased risk of developing clear cell renal cell carcinoma (Beales et al., 2000). Furthermore, BBS1 was recognized by serum antibodies of melanoma patients but not by healthy controls (Hartmann et al., 2005). It was reported that malignant pleural mesothelioma patients with high BBS1 expression had an increased median overall survival of 16.5 versus 8.7 months compared to those that showed low BBS1 expression (Vavougios et al., 2015).

BBX expression was shown to be associated with the NF-kB/Snail/YY1/RKIP circuitry gene expression, which is associated with metastatic prostate cancer and non-Hodgkin's lymphoma (Zaravinos et al., 2014).

BCL2L13 was shown to be over-expressed in solid and blood cancers, including glioblastoma and acute lymphoblastic leukemia (Jensen et al., 2014; Yang et al., 2010). BCL2L13 is associated with an unfavorable clinical outcome in childhood acute lymphoblastic leukemia (Holleman et al., 2006).

Quantitative PCR and immunohistochemistry analysis revealed that BDH1 was up-regulated in high-grade prostate cancer. Moreover, the BDH1 gene was frequently amplified in metastatic conjunctival melanomas (Lake et al., 2011; Saraon et al., 2013).

BHLHE41 is associated with breast cancer metastasis, endometrial cancer metastasis, triple-negative breast cancer metastasis, pancreatic cancer, human squamous carcinoma and lung cancer (Sato et al., 2012a; Piccolo et al., 2013; Liao et al., 2014a; Takeda et al., 2014; Falvella et al., 2008; Adam et al., 2009). BHLHE41 is associated with CDDP resistance in human oral cancer (Wu et al., 2012e).

BOLA2 was described as a novel candidate target gene of the c-Myc oncogene which may be associated with malignant hepatocyte transformation by altering cell cycle control (Hunecke et al., 2012).

BOP1 is associated with ovarian cancer and colorectal cancer (Wrzeszczynski et al., 2011; Killian et al., 2006). BOP1 was shown to be a target gene of Wnt-catenin which induced EMT, cell migration and experimental metastasis of colorectal cancer cells in mice. Thus, BOP1 may serve as a therapeutic target in the treatment of colorectal cancer metastasis (Qi et al., 2015). BOP1 is associated with hepatocellular carcinoma invasiveness and metastasis (Chung et al., 2011). BOP1 was described as a member of a molecular pathway associated with cell cycle arrest in a gastric cancer cell line upon treatment with mycophenolic acid, indicating a potential association of BOP1 with the anticancer activity of the drug (Dun et al., 2013a; Dun et al., 2013b). BOP1 may be a possible marker for rectal cancer (Lips et al., 2008). BOP1 was described as a potential oncogene in ovarian cancer (Wrzeszczynski et al., 2011). BOP1 was shown to be up-regulated in hepatocellular carcinoma (Chung et al., 2011). BOP1 was shown to be associated with microvascular invasion, shorter disease-free survival and metastasis in hepatocellular carcinoma (Chung et al., 2011). BOP1 was described as a subunit of the PeBoW complex, which is essential for cell proliferation and maturation of the large ribosomal subunit. Over-expression of BOP1 was shown to inhibit cell proliferation (Rohrmoser et al., 2007). Expression of an amino-terminally truncated form of BOP1 resulted in down-regulation of G(1)-specific Cdk2 and Cdk4 kinase complexes, retinoblastoma and cyclin A while Cdk inhibitors p21 and p27 were up-regulated. This led to an arrest in the G(1) phase (Pestov et al., 2001).

BUB1B is a tumor inhibitory protein. BUB1B regulates the spindle assembly checkpoint. BUB1B is inactivated or down-regulated in tumors. Mutations in BUB1B are also linked to tumor development (Ayton and Oren, 2011; Fagin, 2002; Malumbres and Barbacid, 2007; Rao et al., 2009). BUB1B is associated with gastric carcinogenesis through oncogenic activation (Resende et al., 2010). BUB1B mutation is one of the causes for colorectal cancer (Karess et al., 2013; Grady, 2004).

C10orf137 is associated with squamous cell lung cancer and colorectal cancer (Gylfe et al., 2010; Zheng et al., 2013).

Over-expression of Cl R has been found in the saliva of oral squamous cell carcinoma patients. On the other hand, inactivation of C1R was observed in paclitaxel-based treatment in hypopharynx cancer patients (Xu et al., 2013a; Kawahara et al., 2016).

C2CD3 was shown to be associated with oropharyngeal squamous cell carcinomas (Wang et al., 2013g).

C4orf46 was shown to be down-regulated in renal cell carcinoma and C4orf46 expression was shown to be negatively correlated with the Fuhrman grade in clear cell renal cell carcinoma (Yu et al., 2014).

Increased expression of CA8 has previously been shown in squamous cell carcinomas, adenocarcinomas, adenosquamous cell carcinomas and colorectal carcinoma (Akisawa et al., 2003). Over-expression of CA8 has been shown to induce apoptosis in lung carcinoma A549 and human embryonic kidney HEK293 cells. Furthermore, it inhibits cell proliferation in melanoma, prostate, liver and bladder cancer cells (Liu et al., 2002a). siRNA-mediated knockdown of CA8 revealed significant inhibition in cell proliferation and colony formation of a colon cancer cell line HCT116 (Nishikata et al., 2007).

CAAP1 was shown to be associated with drug resistance in cancers (Wijdeven et al., 2015).

CAMSAP1 was shown to be associated with outcome in pediatric acute lymphoblastic leukemia and prognosis of laryngeal squamous cell carcinoma (Sun et al., 2014a; Wang et al., 2015c). CAMSAP1 was shown to be up-regulated in laryngeal squamous cell carcinoma (Sun et al., 2014a).

CAND1 is associated with prostate cancer and lung cancer (Zhai et al., 2014; Salon et al., 2007).

Recent studies have shown that CANX was over-expressed in lung cancer patients compared to healthy controls. These findings imply that CANX could be used as a diagnostic marker for lung cancer (Kobayashi et al., 2015b). CANX was down-regulated in HT-29 cells and MCF-7 human breast adenocarcinoma cells growing as colonies compared to monolayers (Yeates and Powis, 1997).

Polymorphisms in the CARS gene have been linked to the development of breast cancer in the Chinese population. Moreover, CARS showed significantly higher association with different molecular networks in glioblastoma multiforme (He et al., 2014; Kim et al., 2012c).

CCAR1 is associated with medulloblastoma, small cell prostate carcinoma, colon carcinoma and non-Hodgkin's Lymphoma (Bish and Vogel, 2014; Levi et al., 2011; Scott et al., 2014; Ou et al., 2009). CCAR1 was shown to be down-regulated in breast cancer (Zhang et al., 2007).

CCDC110 was shown to interact with the high-risk human papillomavirus 18 E6 oncogene in a yeast two-hybrid system and thus may be a potential oncogenic target for cancer biotherapy (Li et al., 2008b). CCDC110 was described as a cancer-testis antigen associated with multiple myeloma which could potentially be used to vaccinate patients (Condomines et al., 2007). CCDC110 was shown to be a novel cancer-testis antigen which elicited humoral immune responses in patients with various types of cancer. Thus, CCDC110 might be a target for cancer immunotherapy (Monji et al., 2004).

CCNA1 encodes cyclin A1, which belongs to the highly conserved cyclin family involved in the regulation of CDK kinases (RefSeq, 2002). Elevated levels of CCNA1 were detected in epithelial ovarian cancer, lymphoblastic leukemic cell lines as well as in childhood acute lymphoblastic leukemia patients. Others have observed over-expression of CCNA1 protein and mRNA in prostate cancer and in tumor tissues of anaplastic thyroid carcinoma patients (Holm et al., 2006; Wegiel et al., 2008; Marlow et al., 2012; Arsenic et al., 2015). Recent studies have shown that silencing of CCNA1 in highly cyclin Al expressing ML1 leukemic cells slowed S phase entry, decreased proliferation and inhibited colony formation (Ji et al., 2005).

Over-expression of CCNA2 inhibits the proliferation of hepatocellular carcinoma cells. Over-expression of CCNA2 in endometrial adenocarcinoma cells decreases cell growth and increases apoptosis. CCNA2 expression in melanoma cells reduces tumor growth and metastasis and concomitantly increases apoptosis in tumors (Lau, 2011). CCNA2 can promote cancer cell proliferation, invasion, adhesion, differentiation, survival and metastasis. It plays an important role in angiogenesis and extracellular matrix production. CCNA2 promotes tumor growth and increases tumor vascularization when over-expressed in gastric adenocarcinoma cells. Silencing of CCNA2 expression decreases tumor growth in pancreatic cancer cells. CCNA2 can promote the proliferation of prostate cancer cells (Lau, 2011; Chen and Du, 2007). CCNA2 over-expression induces epithelial-mesenchymal transition, leading to laryngeal tumor invasion and metastasis (Liu et al., 2015e). CCNA2 is dysregulated in colorectal cancer (Chang et al., 2014a). CCNA2 is over-expressed in prostate cancer, gliomas, pancreatic cancer, and breast cancer. CCNA2 is associated with increased aggressiveness, vascularization, and estrogen independence in breast cancer, suggesting a major role of CCNA2 in breast cancer progression (Zuo et al., 2010).

CCNB2 is up-regulated in colorectal adenocarcinoma (Park et al., 2007). CCNB2 is over-expressed in various human tumors. Strong CCNB2 expression in tumor cells is associated with a poor prognosis in patients with adenocarcinoma of lung and invasive breast carcinoma (Takashima et al., 2014; Albulescu, 2013).

A CCNB3-BCOR gene fusion was shown to be associated with the cancer entity of undifferentiated small round cell sarcomas (Haidar et al., 2015). CCNB3-BCOR (Ewing-like) sarcomas located in the axial skeleton and soft tissues were shown to be associated with shorter survival compared to Ewing sarcomas (Puls et al., 2014). CCNB3 was shown to interact with cdk2, a protein involved in cell cycle transition (Nguyen et al., 2002).

Over-expression and amplification of CCNE1 was observed in various types of cancer, including breast, colon, gastric, lung, endometrial intraepithelial carcinoma, uterine serous carcinoma and high grade serous ovarian cancer (Donnellan and Chetty, 1999; Kuhn et al., 2014; Noske et al., 2015). In addition, increased expression of CCNE1 is a useful marker of poor prognosis in lung cancer (Huang et al., 2012). A study has shown that CCNE1 is down-regulated by both miR-497 and miR-34a, which synergistically retard the growth of human lung cancer cells (Han et al., 2015b).

Studies have shown that acute myeloid leukemia patients with long-term in vitro proliferation of AML cells showed altered expression in CCNF (Hatfield et al., 2014). Furthermore, low CCNF expression was related to poor overall survival and recurrence-free survival in hepatocellular carcinoma patients (Fu et al., 2013a).

CCR4 has been described as a prognostic marker in various tumors such as renal cell carcinoma, head and neck squamous cell carcinoma, gastric cancer, breast cancer, colon cancer and Hodgkin lymphoma (Ishida et al., 2006; Olkhanud et al., 2009; Yang et al., 2011; Tsujikawa et al., 2013; Al-haidari et al., 2013; Liu et al., 2014d). Studies have revealed that gastric cancer patients with CCR4-positive tumors had significantly poorer prognosis compared to those with CCR4-negative tumors (Lee et al., 2009).

CCT4 deregulation causes esophageal squamous cell carcinoma and lung adenocarcinoma (Wang et al., 2015i; Tano et al., 2010). CCT4 is upregulated in gastric cancers (Malta-Vacas et al., 2009).

CCT5 is associated with breast cancer (Campone et al., 2008). CCT5 was shown to be up-regulated in sinonasal adenocarcinoma (Tripodi et al., 2009). CCT5 is associated with overall survival in small cell lung cancer, drug resistance in gastric carcinoma and breast cancer and lymph node metastasis in esophageal squamous cell carcinoma (Niu et al., 2012; Ooe et al., 2007; Uchikado et al., 2006; Ludwig et al., 2002).

CCT8 was shown to be up-regulated in hepatocellular carcinoma (Huang et al., 2014b). CCT8 is associated with histologic grades, tumor size and poor prognosis of hepatocellular carcinoma (Huang et al., 2014b).

Strong CD68 expression was found in basal cell carcinoma, fibrolamellar carcinomas, Hodgkin lymphoma, human glioma, squamous cell carcinoma, adenocarcinoma, adenosquamous cell carcinoma, small cell carcinoma, papillary adenocarcinoma, metastatic adenocarcinoma, bronchioloalveolar carcinoma as well as in induced rat tumors (Strojnik et al., 2006; Strojnik et al., 2009; Ross et al., 2011; Glaser et al., 2011; Yoon et al., 2012; Banat et al., 2015). In breast cancer, increased CD68 expression was correlated with larger tumor size, higher TNM stages and Her-2 positivity. Moreover, the number of CD68 cells was positively correlated with the expression of Ras (Li et al., 2015b).

CD74 expression has been observed in various cancers, including gastrointestinal, renal, non-small cell lung, glioblastoma cell lines, thymic epithelial neoplasms and head and neck squamous cell carcinomas (Ioachim et al., 1996; Datta et al., 2000; Young et al., 2001; Ishigami et al., 2001; Kitange et al., 2010; Gold et al., 2010; Kindt et al., 2014). Preclinical studies in B-cell lymphoma and multiple myeloma revealed that CD74 could be used as a therapeutic target for these disorders (Burton et al., 2004).

Over-expression of CDC123 was observed in a choriocarcinoma cell line. Other studies have detected CDC123 protein in basal breast cancer (Adelaide et al., 2007; Kobayashi et al., 2013).

CDC6 expression is de-regulated in different cancer types including gallbladder, cervical and prostate cancer (Wu et al., 2009; Wang et al., 2009e; Robles et al., 2002; Shu et al., 2012). CDC6 co-operates with c-Myc to promote genetic instability, tumor-like transformation and apoptosis attenuation (Chen et al., 2014a). Hypoxia-induced ATR promotes the degradation of CDC6. Initiation of DNA replication is regulated by p53 through Cdc6 protein stability (Duursma and Agami, 2005; Martin et al., 2012).

Several publications have reported over-expression of CDCl7 in many human tumors, including ovarian cancer, colorectal cancer, melanoma, diffuse large B-cell lymphoma, oral squamous cell carcinoma and breast cancer (Clarke et al., 2009; Kulkarni et al., 2009; Choschzick et al., 2010; Hou et al., 2012; Cheng et al., 2013a; Chen et al., 2013b). Elevated levels of CDCl7 protein predicts disease-free survival in patients suffering from ovarian cancer (Kulkarni et al., 2009).

Elevated levels of CDH2 have been reported in patients suffering from gastric, breast, prostate, bladder, malignant bone and soft tissue tumors (Rieger-Christ et al., 2001; Chan et al., 2001; Jaggi et al., 2006; Nagi et al., 2005; Niimi et al., 2013). In colorectal cancer, over-expression of CDH2 correlated with local infiltration depth, tumor staging, vascular invasion and tumor differentiation level (Ye et al., 2015).

CDK1 is over-expressed in different cancer types including breast, gastric, liver and colorectal cancer and is associated with tumor progression and poor prognosis (Kim et al., 1999; Sung et al., 2014; Masuda et al., 2003; Kim, 2007; Ito et al., 2000; Chae et al., 2011). CDK1 regulates via phosphorylation HIF-1alpha, Bcl-2 proteins, Sp1 and p53 and thereby influences tumor growth, apoptosis and DNA damage response (Nantajit et al., 2010; Zhang et al., 2011; Chuang et al., 2012; Sakurikar et al., 2012; Warfel et al., 2013).

CDK12 mutations were identified in a variety of tumors, including ovarian, breast, prostate, and intestinal tumors (Vrabel et al., 2014).

CDK13 is associated with pancreatic cancer and skin cancer (Ansari et al., 2015; Nelson et al., 1999; Chandramouli et al., 2007). CDK13 is amplified in hepatocellular carcinoma (Kim et al., 2012a).

Over-expression of CDK4 has been observed in many tumor types, such as oral squamous cell carcinoma, pancreatic endocrine tumors, lung cancer and nasopharyngeal carcinoma (Dobashi et al., 2004; Wikman et al., 2005; Lindberg et al., 2007; Poomsawat et al., 2010; Jiang et al., 2014c). Researchers have noted that patients suffering from nasopharyngeal carcinoma with higher levels of CDK4 expression had poorer survival rates compared to those with lower levels of CDK4 expression (Liu et al., 2014j).

CDK5 is over-expressed in many tumors including prostate cancer, pancreatic cancer, lung cancer, glioblastoma and breast cancer (Strock et al., 2006; Liu et al., 2008b; Feldmann et al., 2010; Demelash et al., 2012; Liang et al., 2013). Inhibition of CDK5 kinase activity using a CDK5 dominant-negative mutant or the drug roscovitine significantly decreased the migration and invasion of pancreatic cancer cells in vitro (Eggers et al., 2011; Pozo et al., 2013).

CDK6 has been shown to regulate the activity of tumor suppressor protein Rb. CDK6 can exert its tumor-promoting function by enhancing proliferation and stimulating angiogenesis (Kollmann et al., 2013). The pharmacological inhibition of CDK6 was shown to inhibit the growth differentiation of abnormal leukemic cells (Placke et al., 2014).

Over-expression of CELSR2 was found in head and neck squamous cell carcinoma samples, whereas in breast cancer CELSR2 was down-regulated (Lin et al., 2004; Huang et al., 2005a).

CENPN may be a prognostic marker for early breast cancer (Li et al., 2013d).

CEP55 is strongly up-regulated in human gastric cancer (Tao et al., 2014b). Fibulin-5 increases the activity of CEP55 resulting in a promotion of cell metastasis in nasopharyngeal carcinoma (Hwang et al., 2013). CEP55 may regulate nasopharyngeal carcinoma via the osteopontin/CD44 pathway (Chen et al., 2012a). CEP55 is over-expressed in oropharyngeal squamous cell carcinoma (Janus et al., 2011). CEP55 was identified as novel target in lung cancer (Lai et al., 2010). CEP55 can be detected in colon cancer and breast cancer (Colak et al., 2013; Inoda et al., 2009; Inoda et al., 2011b; Inoda et al., 2011a; Castle et al., 2014). Down-regulation of CEP55 inhibits cell motility and invasion in ovarian cancer (Zhang et al., 2015m). CEP55 is significantly up-regulated in ovarian cancer cell lines and lesions compared to normal cells and adjacent non-cancerous ovarian tissue (Zhang et al., 2015m). CEP55 is classified as an oncogene and its dys-regulation affects the cell cycle pathway. This may play a role in laryngeal squamous cell carcinoma progression (Hui et al., 2015). CEP55 over-expression significantly correlates with tumor stage, aggressiveness, metastasis and poor prognosis across multiple tumor types (Jeffery et al., 2015b; Chen et al., 2009a; Janus et al., 2011). The complex of CEP55 with Aurora-A may enhance the progression and metastasis of head and neck cancer (Chen et al., 2015a; Waseem et al., 2010). An extract of *Graptopetalum paraguayense* can down-regulate the expression level of CEP55 in hepatocellular carcinoma (Hsu et al., 2015). CEP55 is over-expressed in bladder cancer and prostate cancer (Singh et al., 2015; Shiraishi et al., 2011). CEP55 mRNA is significantly higher expressed in muscle-invasive bladder cancer compared to non-muscle-invasive bladder cancer. However, there is no difference in protein expression (Singh et al., 2015).

It was reported that CEP57 is up-regulated in a subset of primary prostate adenocarcinomas, whereas deletion in CEP57 gene was detected in breast carcinoma (Gentile et al., 2001; Sinha et al., 2011; Cuevas et al., 2013). Moreover, alterations of CEP57 were linked with poor prognosis in patients suffering from breast cancer with early age of onset. On the other hand, in prostate cancer elevated levels of CEP57 were not correlated with poor patient survival but instead with a moderate yet significant BCR-free survival advantage (Sinha et al., 2011; Mang et al., 2015). It has been postulated that CEP57 may contribute to apoptosis by modulating the activity or function of Bcl-2 in breast cancer (Zhao et al., 2005).

CEP97 is associated with breast cancer (Rappa et al., 2014).

CERS1 is down-regulated in in nilotinib-resistant chronic myeloid leukemia cells (Camgoz et al., 2013). CERS1 generated C(18)-ceramide levels are significantly decreased in head and neck squamous cell carcinoma (HNSCC) tumors. Decreased C(18)-ceramide levels in HNSCC tumor tissues are significantly associated with the higher incidences of lymphovascular invasion, and pathologic nodal metastasis (Karahatay et al., 2007). CERS1 generated C(18)-ceramide mediates cell death in cancer cells (Saddoughi and Ogretmen, 2013).

CERS2 was shown to be down-regulated in meningioma (Ke et al., 2014b). CERS2 was shown to be up-regulated in colorectal cancer, lung squamous cell cancer and breast cancer (Moriya et al., 2012; Chen et al., 2015c; Schiffmann et al., 2009). CERS2 is associated with metastasis and drug-resistance of breast cancer, growth, invasion and metastasis of prostate cancer, diverse proliferation, metastasis and invasion of bladder cancer and hepatocellular carcinoma (Tang et al., 2010; Zhao et al., 2013a; Perez et al., 2014; Xu et al., 2014a; Zi et al., 2015). CERS2 may be a potential biomarker for colorectal cancer, meningioma and bladder cancer (Zhao et al., 2013a; Ke et al., 2014b; Chen et al., 2015c).

Studies have shown that the expression of CFB was reduced in sera of patients suffering from nasopharyngeal carcinoma. On the other hand, the expression of CFB was more than two times higher in plasma samples from pancreatic ductal adenocarcinoma patients compared with plasma from healthy individuals. Others have observed an association of the CFB locus with melanoma (Budowle et al., 1982; Seriramalu et al., 2010; Lee et al., 2014a).

CHCHD7 is associated with pleomorphic adenoma (Matsuyama et al., 2011).

CHD7 is associated with cutaneous T-cell lymphoma, CpG island methylator phenotype 1 colorectal carcinoma, gastric cancer with microsatellite instability and small-cell lung cancer (Kim et al., 2011b; Tahara et al., 2014; Litvinov et al., 2014b; Pleasance et al., 2010). CHD7 was shown to be up-regulated in colon cancer (Scanlan et al., 2002). CHD7 is associated with survival outcomes of pancreatic cancer (Colbert et al., 2014).

A report has postulated that polymorphisms in the CHST1 gene could account for 5-fluorouracil-induced toxicity in colorectal cancer patients. Another study found that LN229 glioblastoma cells express elevated levels of CHST1 (Hayatsu et al., 2008; Rumiato et al., 2013; Arbitrio et al., 2016).

CKLF was shown to be up-regulated in high-grade glioma (Yang et al., 2013).

CLDN16 was shown to be up-regulated in papillary thyroid carcinomas and ovarian cancer (Rangel et al., 2003; Fluge et al., 2006). CLDN16 expression was shown to be associated aggressiveness, high mortality and poor prognosis in breast cancer (Martin et al., 2008; Martin and Jiang, 2011). CLDN16 was shown to be associated with kidney cancer (Men et al., 2015). CLDN16 was described as a potential biomarker for breast cancer (Kuo et al., 2010).

CLSPN is up-regulated in non-small cell lung carcinoma (NSCLC). Over-expression of CLSPN is associated with a bad prognosis in NSCLC (Allera-Moreau et al., 2012).

Over-expression of CLSTN3 has been found in testicular cancer as well as human embryonal carcinoma (Dormeyer et al., 2008).

Single-nucleotide polymorphisms (SNPs) in the CNOT1 gene were detected in osteosarcoma and acute lymphoblastic leukemia (ALL) (Gutierrez-Camino et al., 2014; Bilbao-Aldaiturriaga et al., 2015). CNOT1 depletion induces stabilization of mRNAs and activation of ER stress-mediated apoptosis (Ito et al., 2011).

Single nucleotide polymorphism in the CNOT4 gene was correlated with the risk of osteosarcoma (Bilbao-Aldaiturriaga et al., 2015).

Changes in COPA gene expression and RNA editing were shown to be associated with hepatocellular carcinoma and an experimental study revealed anti-apoptotic effects of COPA in mesothelioma cells (Qi et al., 2014; Sudo et al., 2010; Wong et al., 2003).

shRNA library screening identified COPB1 as determinants of sensitivity to 2-deoxyglucose, a glycolytic inhibitor in cancer cells. Moreover, silencing of COPB1 expression sensitized cells to 2-deoxyglucose toxicity (Kobayashi et al., 2015a).

COPB2 is expressed in various types of cancer such as breast, colon, prostate, pancreas carcinomas, glioblastoma and lung adenocarcinoma (Erdogan et al., 2009). Others have implicated COPB2 to be involved in anti-apoptotic function in mesothelioma (Sudo et al., 2010).

COPG1 correlates with the age of the patients as well as a higher grade of malignancy and the grade of gliosarcomas (Coppola et al., 2014). COPG1 was found abundantly expressed in lung cancer and lung cancer-related endothelial cells (Park et al., 2008).

Function-based genomic screening identified COPZ1 as an essential gene for different tumor cells. Knock-down of COPZ1 was shown to cause Golgi apparatus collapse, block autophagy, and induce apoptosis in both proliferating and non-dividing tumor cells. Thus, COPZ1 could be a novel therapeutic target, which offers an opportunity for proliferation-independent selective killing of tumor cells (Shtutman et al., 2011).

Over-expression of CORO2A has been found in breast cancer and colon carcinoma (Bubnov et al., 2012; Rastetter et al., 2015). Researchers have revealed that both MAPK14 and PRMT5 signaling pathways play a crucial role in tumor progression (Rastetter et al., 2015). Down-regulation of CORO2A in colorectal cancer cells was correlated with reduced early apoptosis (Kim et al., 2013a).

Single nucleotide polymorphisms as well as mutations in the CSDA gene were associated with hepatocellular carcinoma. Another group found higher mRNA expression levels of CSDA in hepatocellular carcinoma compared to corresponding non-tumor tissues. In addition, elevated levels of CSDA were observed in gastric cancer tissues and cell lines compared to adjacent normal tissues (Hayashi et al., 2002; Wang et al., 2009a; Yasen et al., 2012). Recent work has shown a correlation between elevated levels of CSDA in hepatocarcinomas and poorer prognosis (Yasen et al., 2005). In chronic myeloid leukemia, both Akt and MEK/p90 ribosomal S6 kinase can phosphorylate the serine 134 residue of CSDA (Sears et al., 2010).

CSE1L was shown to be highly expressed in hepatocellular carcinoma, bladder urothelial carcinoma, serous ovarian cancer, breast cancer and metastatic cancer (Behrens et al., 2001; Tung et al., 2009; Stawerski et al., 2010; Tai et al., 2012; Zang et al., 2012). Researchers have demonstrated that CSE1L regulates translocation and secretion of MMP-2 from colorectal cancer cells (Liao et al., 2008; Tsao et al., 2009). Furthermore, inhibition of MEK1 mediated phosphorylation resulted in enhanced paclitaxel (Taxol) induced apoptosis in breast, ovarian, and lung tumor cell lines. Since CSE1L is also activated by MEK1 altering the activity/phosphorylation status of CSE1L via MEK1 inhibition may present a potential strategy in experimental cancer therapy (Behrens et al., 2003).

CT45 genes were shown to be potential prognostic biomarkers and therapeutic targets in epithelial ovarian cancer (Zhang et al., 2015I). The CT45A1 protein which is usually only expressed in testicular germ cells was shown to be also expressed in lung cancer, breast cancer and ovarian cancer (Chen et al., 2009d). CT45A1 was also shown to be associated with poor prognosis and poor outcomes in multiple myeloma (Andrade et al., 2009). CT45A1 was described as gene up-regulating epithelial-mesenchymal transition (EMT) and metastatic genes, promoting EMT and tumor dissemination. Furthermore, CT45A1 was described as being implicated in the initiation or maintenance of cancer stem-like cells, promoting tumorigenesis and malignant progression (Yang et al., 2015a). CT45A1 over-expression in a breast cancer model was shown to result in the up-regulation of various oncogenic and metastatic genes, constitutively activated ERK and CREB signaling pathways and increased tumorigenesis, invasion and metastasis. Silencing of CT45A1 was shown to reduce cancer cell migration and invasion. Thus, CT45A1 may function as a novel proto-oncogene and may be a target for anticancer drug discovery and therapy (Shang et al., 2014).

CT45A2 was shown to be a novel spliced MLL fusion partner in a pediatric patient with de novo bi-phenotypic acute leukemia and thus might be relevant for leukemogenesis (Cerveira et al., 2010). The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015I).

The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015I).

The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015I).

The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015I).

The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015I).

Elevated levels of CTSA were found in squamous cell carcinoma compared to normal mucosa. Others have detected higher levels of CTSA activity in lysates of metastatic lesions of malignant melanoma than in primary focus lysates. Another report has demonstrated that the CTSA activity was twice as high in the vitreous body of patients suffering from absolute glaucoma compared to patients with intraocular tumors (Obuchowska et al., 1999; Kozlowski et al., 2000; Marques Filho et al., 2006).

CYFIP1 was shown to be down-regulated during invasion of epithelial tumors (Silva et al., 2009). CYFIP1 down-regulation is associated with poor prognosis in epithelial tumors (Silva et al., 2009).

CYFIP2 expression is increased in newly formed lymph nodes in breast cancer (Gantsev et al., 2013). CYFIP2 expression is reduced in human gastric tumor samples, compared with control tissues (Cheng et al., 2013b). CYFIP2 is one of several apoptosis-related genes methylated in chronic lymphocytic leukemia (Halldorsdottir et al., 2012).

The expression of CYP2F1 was found in primary ovarian cancer and non-cancerous nasopharynx tissues. However, it was absent in breast tumors as well as in control tissues (Downie et al., 2005; (scan et al., 2001; Jiang et al., 2004). In colorectal cancer, the expression of CYP2F1 in the lymph node metastasis strongly correlated with its presence in corresponding primary tumors (Kumarakulasingham et al., 2005).

CYP4X1 was shown to be present as an off-frame fusion transcript with CYP4Z2P in breast cancer (Kim et al., 2015a). CYP4X1 was shown to be associated with tumor grade in breast cancer and may be a potential biomarker to aid decisions regarding optimal adjuvant hormonal therapy (Murray et al., 2010). CYP4X1 was shown to be a potential primary target of estrogen receptor beta (ERbeta) in the ERbeta over-expressing HEK293 cell line (Zhao et al., 2009).

A single polymorphism in the CYP7B1 gene has been associated with the risk of prostate cancer. In addition, elevated levels of CYP7B1 have been found in high-grade prostatic intraepithelial neoplasia, adenocarcinomas and breast carcinoma (Jakobsson et al., 2004; Olsson et al., 2007; Pu et al., 2015).

DCBLD2 is up-regulated in glioblastomas and head and neck cancers (HNCs) and is required for EGFR-stimulated tumorigenesis (Feng et al., 2014a). Furthermore, DCBLD2 is up-regulated in highly metastatic lung cancer sublines and tissue samples (Koshikawa et al., 2002). In contrast, the expression of DCBLD2 is silenced by hypermethylation of its promoter in gastric cancer (Kim et al., 2008b).

DCHS2 is associated with gastric cancers and colorectal cancers with high microsatellite instability (An et al., 2015).

DDX11, belonging to the DEAH family of DNA helicases, is highly expressed in advanced melanoma and is essential for the survival of melanoma cells (Bhattacharya et al., 2012).

DDX20 was shown to be down-regulated in hepatocellular carcinoma (Takata et al., 2013a). DDX20 is associated with increased risk of colorectal cancer and bladder cancer as well as reduced overall survival in breast cancer and increased metastatic potential (Yang et al., 2008a; Zhao et al., 2015b; Shin et al., 2014). DDX20 may be a prognostic biomarker for breast cancer (Shin et al., 2014).

DDX41 is associated with acute myeloid leukemia (Antony-Debre and Steidl, 2015).

DDX47 may be a potential marker to discriminate different disease phases of chronic myeloid leukemia (Oehler et al., 2009).

DDX6 was found to be over-expressed in colorectal adenocarcinomas, gastric cancer, hepatocellular carcinoma, nodal marginal zone lymphoma, neuroblastoma, rhabdomyosarcoma and lung cancer cell lines (Akao et al., 1995; Nakagawa et al., 1999; Miyaji et al., 2003; Lin et al., 2008a; Stary et al., 2013; Iio et al., 2013). In nodal marginal zone lymphoma, DDX6 seems to interfere with the expression of BCL6 and BCL2 in an NF-ÎºB independent manner (Stary et al., 2013). Recent studies have shown that DDX6 post-transcriptionally down-regulated miR-143/145 expression by prompting the degradation of its host gene product, NCR143/145 RNA (Iio et al., 2013).

DEPDC1B was shown to be up-regulated in oral cancer and non-small cell lung cancer (Yang et al., 2014e; Su et al., 2014). DEPDC1B expression is associated with patient survival, migration and metastasis of non-small cell lung cancer and radiation sensitivity of lymphoblastoid tumor cell lines (Niu et al., 2010; Yang et al., 2014e).

High levels of the DFFB gene were detected in cisplatin resistance in bladder cancer, whereas the levels of DFFB were decreased in oligodendrogliomas with 1p-allelic loss. Another group found no mutation in the DFFB gene in neuroblastomas (Judson et al., 2000; McDonald et al., 2005; Kim et al., 2016). Over-expression of DFFB resulted in a decrease in the viability of breast cancer cells incubated with acetazolamide and sulfabenzamide. In addition, there was enhanced apoptosis in these groups, especially with acetazolamide. Similarly, DFFB fused with GM-CSF was found to facilitate targeted killing of acute myeloid leukemia cells by inducing apoptosis (Mathew et al., 2013; Bagheri et al., 2014).

DFNA5 expression was found to be lower in hepatocellular carcinoma cells, estrogen receptor (ER)-positive breast carcinoma and gastric cancer cell lines (Thompson and Weigel, 1998; Akino et al., 2007; Wang et al., 2013c). Moreover, etoposide resistance in melanoma cells was linked to reduced DFNA5 expression (Lage et al., 2001). DFNA5 knock-down resulted in an increase in cell invasion, colony numbers, colony size and cell growth in colorectal carcinoma cell lines (Kim et al., 2008c).

DHX40 is associated with epithelial ovarian cancer (Zheng et al., 2004).

PrognoScan database revealed that DHX8 is expressed in bladder cancer, blood cancer, brain cancer, breast cancer, colorectal cancer, eye cancer, head and neck cancer, lung cancer, ovarian cancer, skin cancer and soft tissue cancer tissues (Wang et al., 2014f). Researchers have observed that DHX8 was present both in the normal adrenal cortex as well as in the malignant adrenocortical cancer (Szabo et al., 2009).

DEF was shown to mediate the non-proteasomal degradation of the tumor-suppressor p53 (Tao et al., 2013).

Studies have revealed that DLG5 is down-regulated in prostate cancer as well as bladder cancer. On the other hand, over-expression of DLG5 was observed in pancreatic ductal adenocarcinoma. Moreover, single nucleotide polymorphisms in the DLG5 gene were not correlated with risk of colorectal cancer (Taniuchi et al., 2005; Suchy et al., 2008; Tomiyama et al., 2015; Zhou et al., 2015b). Knockdown of endogenous DLG5 resulted in an increase in prostate cancer cell migration and invasion, while it suppressed the growth of pancreatic ductal adenocarcinoma (Taniuchi et al., 2005; Tomiyama et al., 2015).

DMXL2 was shown to be up-regulated in ER-alpha positive breast cancer (Faronato et al., 2015). DMXL2 is a functional biomarker for ER-alpha positive breast cancer (Faronato et al., 2015).

DNAH3 is associated with colon cancer (Tanaka et al., 2008a).

Studies have detected DNASE1L1 in patients suffering from oral squamous cell carcinoma. Furthermore, DNASE1L1 expression was linked with poor disease-free survival rate in these patients (Grimm et al., 2013).

DOCK8 was shown to be down-regulated in squamous cell carcinoma of the lung (Kang et al., 2010). DOCK8 was shown to be associated with neuroblastomas, pediatric pilocytic astrocytomas, hepatocellular carcinomas, gliomas and lung cancer (Schramm et al., 2015; Saelee et al., 2009; Takahashi et al., 2006; Zhao et al., 2014a; Idbaih et al., 2008). DOCK8 was shown to be associated with radiosensitivity in the esophageal cancer cell line TE-11 (Ogawa et al., 2008).

A report has revealed over-expression of DPP3 in glioblastoma cells as well as in squamous cell lung carcinoma. Similarly, higher DPP3 activity was observed in endometrial and ovarian malignant tumors compared to the activity in normal tissues (Simaga et al., 1998; Simaga et al., 2003; Hast et al., 2013; Singh et al., 2014).

DPPA4 was shown to be up-regulated in colon cancer (Zhang et al., 2015j). DPPA4 is associated with bladder cancer, prostate cancer, embryonal carcinomas, pluripotent germ cell tumors and sarcoma (Tung et al., 2013; Amini et al., 2014). DPPA4 is associated with stage, invasion depth, distant metastasis and differentiation of colon cancer (Zhang et al., 2015j). DPPA4 is an independent prognostic indicator of disease-free survival and overall survival of colon cancer (Zhang et al., 2015j).

DTX3L was shown to be up-regulated in melanomas, squamous cell carcinomas of the cervix and diffuse large B-cell lymphomas with a prominent inflammatory infiltrate (Thang et al., 2015; Wilting et al., 2008; Juszczynski et al., 2006). DTX3L was shown to mediate regulation of invasion and metastasis in melanoma through FAK/PI3K/AKT signaling. Thus, DTX3L may serve as a potential therapeutic target as well as a potential biomarker for melanomas (Thang et al., 2015). DTX3L was described as a chemotherapy resistance factor which is up-regulated in EZH2 gain-of-function mutant diffuse large B-cell lymphomas (Johnson et al., 2015). DTX3L was shown to be a novel oncogenic factor in metastatic prostate cancer cells which mediates proliferation, chemo-resistance and survival of metastatic prostate cancer in interaction with oncogenic proteins ARTD8 and ARTD9 (Bachmann et al., 2014). DTX3L was shown to be associated with transcription factors STAT1 and STAT3 as well as the tumor suppressor IRF1 in metastatic prostate cancer cells (Bachmann et al., 2014). DTX3L was described as a bona fide member of a DNA damage response pathway, which is directly associated with PARP1 activation and recruitment of the tumor suppressor BRCA1 (Yan et al., 2013b).

A whole exome sequencing study uncovered somatic mutations within the DYNC1H1 gene in patients with intra-ductal papillary mucinous neoplasm of the pancreas (Furukawa et al., 2011).

DYNC2H1 was shown to be up-regulated in glioblastoma multiforme (Yokota et al., 2006).

EGFLAM promoter CGI methylation ratio was decreased in epithelial ovarian cancer compared to benign ovarian diseases (Gu et al., 2009). The promoter CGI of EGFLAM may be a novel candidate for ovarian cancer-specific hypomethylated tumor markers (Gu et al., 2009).

EIF2S2 has been shown to be amplified in patients suffering from highly proliferative luminal breast tumors (Gatza et al., 2014).

EIF2S3 is one of 5 molecular markers that were differentially expressed between peripheral blood samples of colorectal cancer patients and healthy controls (Chang et al., 2014c). EIF2S3 interacts with N-myc down-stream regulated gene 1 (NDRG1), which plays a role in cell differentiation and inhibition of prostate cancer metastasis (Tu et al., 2007).

EIF3C is highly expressed in colon cancer (Song et al., 2013c). EIF3C mRNA is over-expressed in testicular seminomas (Rothe et al., 2000).

Down-regulation of EIF3F expression was reported in pancreatic cancer and in melanoma. Furthermore, loss of EIF3F and a statistically significant reduced gene copy number was demonstrated in both melanoma and pancreatic tumors as compared to normal tissues (Shi et al., 2006; Doldan et al., 2008a; Doldan et al., 2008b). Recent work showed that decreased expression of EIF3F could be used as a prognostic marker for poor outcome in patients affected by gastric cancer (Cheng et al., 2015a). High levels of EIF3F inhibited cell proliferation and induced apoptosis in melanoma and pancreatic cancer cells (Shi et al., 2006; Doldan et al., 2008a).

EIF4G3 is up-regulated in diffuse large B-cell lymphoma. Moreover, down-regulation of EIF4G3 by siRNA resulted in a reduction of translation, cell proliferation and the ability to form colonies as well as induction of cellular senescence (Mazan-Mamczarz et al., 2014).

EMC10 up-regulation was shown to be associated with high-grade gliomas and modulation of signaling pathways involved in tumorigenesis (Junes-Gill et al., 2011; Junes-Gill et al., 2014). EMC10 was shown to inhibit glioma-induced cell cycle progression, cell migration, invasion and angiogenesis and thus may be a potential therapeutic for malignant glioblastoma (Junes-Gill et al., 2014).

Down-regulation of EMG1 was noted in hepatocellular carcinoma cell lines after treatment with platycodin D (Lu et al., 2015).

EPG5 is associated with breast cancer (Halama et al., 2007).

EPPK1 was shown to be associated with intrahepatic cholangiocarcinoma and cervical squamous cell carcinoma (Zou et al., 2014b; Guo et al., 2015).

ERLIN2 is associated with breast cancer and hepatocellular carcinoma (Wang et al., 2012a).

ERMP1 was shown to be associated with breast cancer (Wu et al., 2012c).

Mutations and single nucleotide polymorphisms of ESR1 are associated with risk for different cancer types including liver, prostate, gallbladder and breast cancer. The up-regulation of ESR1 expression is connected with cell proliferation and tumor growth but the overall survival of patients with ESR1 positive tumors is better due to the successfully therapy with selective estrogen receptor modulators (Sun et al., 2015c; Hayashi et al., 2003; Bogush et al., 2009; Miyoshi et al., 2010; Xu et al., 2011; Yakimchuk et al., 2013; Fuqua et al., 2014). ESR1 signaling interferes with different pathways responsible for cell transformation, growth and survival like the EGFR/IGFR, PI3K/Akt/mTOR, p53, HER2, NFkappaB and TGF-beta pathways (Frasor et al., 2015; Band and Laiho, 2011; Berger et al., 2013; Skandalis et al., 2014; Mehta and Tripathy, 2014; Ciruelos Gil, 2014).

ESRRG signaling has been correlated with reduced distant metastasis-free survival in ER+ breast cancer treated with tamoxifen (Madhavan et al., 2015). Recent work demonstrated that ESRRG mediated the effects of estrogen on the proliferation of endometrial cancer cells via the activation of AKT and ERK1/2 signaling pathways (Sun et al., 2014c). High levels of ESRRG induced proliferation in ER+ breast cancer cells in the presence or absence of estrogen. In contrast, silencing of ESRRG inhibited hepatocellular carcinoma cell lines growth and induced cell apoptosis (Ijichi et al., 2011; Yuan et al., 2015).

EXOC8 was shown to interact with the cancer-associated Ras-like small GTPase RalA in the brain (Das et al., 2014). EXOC8 interaction with RalA was described as necessary for migration and invasion of prostate cancer tumor cells (Hazelett and Yeaman, 2012). EXOC8 was shown to be involved in the tumor-promoting function of dermal fibroblasts, which is executed by RalA. The RalA signaling cascade in dermal fibroblasts involves EXOC8 and was described as a potential anti-cancer target upon progression of squamous cell carcinoma of the skin (Sowalsky et al., 2011). EXOC8 was described as a protein fostering oncogenic ras-mediated tumorigenesis (Issaq et al., 2010).

EXOSC4 promotor activity is increased in hepatocellular carcinoma, due to DNA hypomethylation. EXOSC4 effectively and specifically inhibits cancer cell growth and cell invasive capacities (Stefanska et al., 2014; Drazkowska et al., 2013).

EXOSC7 is associated with cervical cancer (Choi et al., 2007).

In gastric tumor tissues, the expression of EYA1 is significantly decreased compared with adjacent normal tissues. Moreover, EYA1 was significantly over-expressed in Wilms tumors (Li et al., 2002; Nikpour et al., 2014). It is reported that genetic silencing of EYA1 significantly sensitizes breast cancer cells to pharmacological inhibition of PI3K/Akt signaling. These findings imply that they may function together to regulate cancer cell behavior (Sun et al., 2015g).

EYA2 over-expression has been observed in several tumor types, such as epithelial ovarian tumor, prostate, breast cancer, urinary tract cancers, glioblastoma, lung adenocarcinoma, cervical cancer, colon and hematopoietic cancers (Bierkens et al., 2013; Zhang et al., 2005a; Guo et al., 2009; Patrick et al., 2013; Kohrt et al., 2014). Studies have revealed that EYA2 influences transcription of TGF beta pathway members as well as phosphorylation of TGFBR2, implying a dual role of EYA2 in the pancreas (Vincent et al., 2014).

EYA3 is highly expressed in Ewing sarcoma tumor samples and cell lines compared with mesenchymal stem cells. On the other hand, deletion of the EYA3 gene has been linked to certain pancreatic ductal adenocarcinomas (Gutierrez et al., 2011; Robin et al., 2012). Recent work has shown that over-expression of EYA3 results in increased proliferation, migration, invasion and transformation of breast cancer cells (Pandey et al., 2010).

It has been reported that EYA4 is frequently and concomitantly deleted, hyper-methylated and under-expressed in non-small-cell lung cancer subtypes as well as in the earliest stages of lung cancer and in adenocarcinoma in situ, colorectal cancer and hepatocellular carcinoma (Selamat et al., 2011; Wilson et al., 2014; Hou et al., 2014; Kim et al., 2015c). In colorectal cancer, EYA4 is a tumor suppressor gene that acts by inducing up-regulation of DKK1 and inhibiting the Wnt signaling pathway (Kim et al., 2015c).

Expression analyses have shown FABP7 transcripts in tumors or urine of patients with renal cell carcinoma, as well as in tissues of glioblastoma and melanoma (Liang et al., 2005; Seliger et al., 2005; Goto et al., 2010; Takaoka et al., 2011). In addition, FABP7 over-expression in glioblastoma and melanoma correlates with shorter survival (Liang et al., 2006; Slipicevic et al., 2008). In glioma cell lines, NFI de-phosphorylation is correlated with FABP7 expression (Bisgrove et al., 2000).

FADS2 is up-regulated in hepatocellular carcinoma (Muir et al., 2013). FADS2 activity is increased in breast cancer tissue (Pender-Cudlip et al., 2013). FADS2 expression is associated with aggressiveness of breast cancer (Lane et al., 2003). FADS2 inhibition impedes intestinal tumorigenesis (Hansen-Petrik et al., 2002).

FAM135B is associated with esophageal squamous cell carcinoma (Song et al., 2014b).

FAM86A was shown to interact with the tumor-associated eukaryotic elongation factor 2 (Davydova et al., 2014).

Down-regulation or dysfunction of FANCD2 due to genetic mutations has been reported in different cancer types including breast cancer, acute lymphatic leukemia and testicular seminomas and is associated with cancer development. Otherwise also re-expression and up-regulation of FANCD2 was shown to be associated with tumor progression and metastasis in gliomas and colorectal cancer (Patil et al., 2014; Shen et al., 2015a; Shen et al., 2015b; Ozawa et al., 2010; Rudland et al., 2010; Zhang et al., 2010a; Smetsers et al., 2012). PI3K/mTOR/Akt pathway promotes FANCD2 inducing the ATM/Chk2 checkpoint as DNA damage response and mono-ubiquitinilated FANCD2 activates the transcription of the tumor suppressor TAp63 (Shen et al., 2013; Park et al., 2013).

The expression level of FANCG mRNA in newly diagnosed acute myeloid leukemia patients is significantly lower than that in control and acute myeloid leukemia complete remission groups. Moreover, germline mutations of FANCG might contribute to the progression of pancreatic cancer. In contrast, mutations in FANCG could not be detected in bladder carcinoma cell lines (Couch et al., 2005; Neveling et al., 2007; Duan et al., 2013). Endogenous disruption of FANCG in a human adenocarcinoma cell line resulted in increased clastogenic damage, G2/M arrest and decreased proliferation (Gallmeier et al., 2006).

Mutations in the FAT2 gene have been found in esophageal squamous cell carcinoma as well as head and neck squamous cell carcinoma. In addition, FAT2 mRNA was expressed in gastric cancer, pancreatic cancer and ovarian cancer (Katoh and Katoh, 2006; Lin et al., 2014; Gao et al., 2014).

FAT3 was shown to be down-regulated in taxol resistant ovarian carcinoma cell lines upon silencing of androgen receptor, resulting in increased sensitization to taxol in these cell lines. Thus, FAT3 may be a candidate gene associated with taxol resistance (Sun et al., 2015e). FAT3 was shown to be mutated in esophageal squamous cell carcinoma, resulting in dysregulation of the Hippo signaling pathway (Gao et al., 2014). FAT3 was shown to be mutated recurrently in early T-cell precursor acute lymphoblastic leukemia (Neumann et al., 2013). FAT3 was described as a gene with signatures specific for meningothelial meningiomas, therefore being associated with tumorigenesis in this subtype of benign meningiomas (Fevre-Montange et al., 2009). FAT3 was described as a tumor suppressor which is repressed upon lung cancer development from dysplastic cells (Rohrbeck and Borlak, 2009).

FBXO4 was shown to be down-regulated in hepatocellular carcinoma (Chu et al., 2014). FBXO4 is associated with esophageal squamous cell carcinoma, melanoma, lymphomas and histiocytic sarcomas (Vaites et al., 2011; Lee et al., 2013b; Lian et al., 2015).

FBXO5 was shown to be up-regulated in breast cancer and hepatocellular carcinoma (Zhao et al., 2013c; Liu et al., 2014h). FBXO5 was shown to be down-regulated in primary gastric cancer (Zhang et al., 2014e). FBXO5 is associated with invasion and metastatic potential in breast cancer, tumor size, infiltration, clinical grade and prognosis in gastric cancer, histologic grade in breast cancer, histologic grade and poor overall survival in ovarian clear cell carcinoma, stage and prognosis in hepatocellular carcinoma and poor prognosis in esophageal squamous cell carcinoma (Kogo et al., 2011; Zhao et al., 2013c; Min et al., 2013; Liu et al., 2013d; Zhang et al., 2014e; Liu et al., 2014h). FBXO5 is associated with breast cancer, ovarian cancer, hepatocellular cancer, prostate cancer and mantle cell lymphoma (Johansson et al., 2014; Schraders et al., 2008). FBXO5 is a prognostic predictor of breast cancer and esophageal squamous cell carcinoma (Kogo et al., 2011; Liu et al., 2014h).

FBXW8 was shown to be up-regulated in choriocarcinoma (Shi et al., 2014a). FBXW8 is associated with pancreatic cancer and choriocarcinoma (Wang et al., 2014b; Lin et al., 2011).

FGFR1OP is associated with chronic myelomonocytic leukemia, acute myeloid leukemia and myeloproliferative neoplasms (Hu et al., 2011; Bossi et al., 2014). FGFR1OP was shown to be up-regulated in lung cancer (Mano et al., 2007). FGFR1OP expression is associated with shorter tumor-specific survival times (Mano et al., 2007). FGFR1OP is a prognostic biomarker for lung cancer (Mano et al., 2007).

Over-expression of FIG. 4 was found in the triple negative breast cancer compared to non-tumorigenic cells (Ikonomov et al., 2013).

FLAD1 was shown to be associated with non-small cell lung cancer (Mitra et al., 2011).

Depending on its subcellular localization, filamin A plays a dual role in cancer: In the cytoplasm, filamin A functions in various growth signaling pathways, in addition to being involved in cell migration and adhesion pathways. Thus, its over-expression has a tumor-promoting effect. In contrast to full-length filamin A, the C-terminal fragment, which is released upon proteolysis of the protein, localizes to the nucleus, where it interacts with transcription factors and thereby suppresses tumor growth and metastasis (Savoy and Ghosh, 2013).

Over-expression of FOXM1 has been found in a variety of aggressive human carcinomas including lung cancer, glioblastomas, prostate cancer, basal cell carcinomas, hepatocellular carcinoma, primary breast cancer and pancreatic cancer (Teh et al., 2002; Kalinichenko et al., 2004; Kalin et al., 2006; Kim et al., 2006; Liu et al., 2006; Wang et al., 2007b). Recent study suggest that the FOXM1 gene is up-regulated in pancreatic cancer due to transcriptional regulation by the Sonic Hedgehog pathway (Katoh and Katoh, 2004).

Several lines of evidence have implicated GAB2 in cancer, for instance elevated levels of GAB2 were found in breast cancer, ovarian cancer as well as some metastatic melanomas. Others have revealed that GAB2 is required for BCR/ABL-mediated transformation in chronic myeloid leukemia (Sattler et al., 2002; Daly et al., 2002; Horst et al., 2009; Wang et al., 2012c). In ovarian cancer, over-expression of GAB2 resulted in the activation of the phosphatidylinositol 3-kinase pathway (Dunn et al., 2014).

GADD45GIP1 was shown to interact with leukemia-associated Lck (Vahedi et al., 2015). GADD45GIP1 was shown to be down-regulated in acute myeloid leukemia (Ran et al., 2014). GADD45GIP1 was shown to have a tumor suppressor effect in the cervical and ovarian cancer cell lines HeLa and SKOV3 (Nakayama et al., 2007). GADD45GIP1 was shown to interact with the tumor suppressor STAT3 in prostate cancer and with CDK2 as a cyclin-dependent kinase inhibitor (Ran et al., 2014; Tan et al., 2014). GADD45GIP1 was shown to be negatively regulated by NAC1, which is considered to have adverse effects on prognosis in ovarian and cervical carcinomas (Nishi et al., 2012). GADD45GIP1 was shown to be associated with paclitaxel resistance in ovarian cancer (Jinawath et al., 2009). GADD45GIP1 may play an important role in the regulation of androgen receptor (AR)-positive growth of prostate cancer through its function as an AR corepressor (Suh et al., 2008). GADD45GIP1 was shown to be up-regulated in lymph node (+) breast carcinomas (Abba et al., 2007).

The expression of GART is significantly up-regulated in human glioma and hepatocellular carcinoma. Single nucleotide polymorphisms in GART are significantly associated with hepatocellular carcinoma risk in the Chinese population (Liu et al., 2014g; Cong et al., 2014; Zhang et al., 2015e). In hepatocellular carcinoma, over-expression of GART correlated positively with the histologic grade, tumor size, number of tumorous nodes and intrahepatic metastases (Cong et al., 2014). GART is able to act as a regulator of tumor progression and survival in renal cell carcinoma by targeting tumor associated macrophages (Ohba et al., 2005).

GAS2L3 was shown to be down-regulated in the gastric cancer cell line HSC45-M2 upon incubation in lethal doses of (213) Bi-d9Mab. Thus, GAS2L3 might be a new target for selective elimination of tumor cells (Seidl et al., 2010).

GBGT1 is associated with ovarian cancer and oral squamous cell carcinoma (Viswanathan et al., 2003; Jacob et al., 2014).

GGT6 was shown to be amplified in a patient with choroid plexus papilloma (de Leon et al., 2015).

Researchers have observed higher mRNA transcript levels of GNB1 in breast cancer specimens compared to normal glandular tissue. In endometrial cancer, the expression of GNB1 was significantly changed in comparison to the control group (Orchel et al., 2012; Wazir et al., 2013). Furthermore, the mRNA expression of GNB1 increased with TNM stage, tumor grade and was linked with adverse patient outcomes (Wazir et al., 2013).

GON4L is associated with hepatocellular carcinoma and salivary gland cancer (Simons et al., 2013; Kim et al., 2009b).

The variable number of tandem repeats polymorphism of the GP1BA gene has been associated with the risk of oral and breast cancer. On the contrary, others did not detect any association between the variable number of tandem repeats polymorphism of the GP1BA gene and breast cancer aggressiveness (Oleksowicz et al., 1998; Ayala et al., 2003; Vairaktaris et al., 2007). In breast cancer, GP1BA expression correlated significantly with tumor stage, tumor size and estrogen receptor negativity (Oleksowicz et al., 1998).

GPD2 abundance and activity is significantly up-regulated in prostate cancer cells and is associated with the high reactive oxygen species (ROS) production in cancer cells (Chowdhury et al., 2005; Chowdhury et al., 2007).

In breast cancer cell lines, knockdown of GPR64 resulted in a strong reduction in cell adhesion as well as in cell migration (Peeters et al., 2015).

GPX5 rs451774 was found to be associated with overall survival in patients suffering from non-small cell lung cancer receiving platinum plus gemcitabine treatment (Li et al., 2011c).

GRAMD1A was shown to be expressed in cancer cell lines (Song et al., 2014a).

GRHL2 was shown to be up-regulated in colorectal cancer and oral squamous cell carcinoma (Quan et al., 2015b; Kang et al., 2009). GRHL2 was shown to be down-regulated in cervical cancer and diverse breast cancer subclasses (Cieply et al., 2012; Torres-Reyes et al., 2014). GRHL2 was shown to be associated with poor prognosis in colorectal cancer, lower disease-free survival in clear cell renal cell carcinoma and poor relapse free survival in breast cancer (Butz et al., 2014; Quan et al., 2015b; Xiang et al., 2012). GRHL2 was shown to be associated with metastasis in breast cancer and hepatocellular carcinoma (Tanaka et al., 2008b; Werner et al., 2013). GRHL2 may be a prognostic biomarker for colorectal cancer, clear cell renal cell carcinoma and hepatocellular carcinoma (Butz et al., 2014; Quan et al., 2015b; Tanaka et al., 2008b).

GRIK3 is associated with lung adenocarcinoma (methylation, functional modifications), pediatric central nervous system tumors, lymphocytic leukemia, and neuroblastoma (Pradhan et al., 2013). GRIK3 is differentially expressed in several pediatric tumors of the central nervous system (Brocke et al., 2010).

Over-expression or somatic mutations of GRIN2D was found in pediatric central nervous system tumors, human breast cancers as well as prostate cancer cell lines. In addition, knockdown of GRIN2D did not influence cancer phenotype in TE671 and RPMI8226 cancer cell lines (Brocke et al., 2010; Pissimissis et al., 2009; Luksch et al., 2011; Jiao et al., 2012).

GSDMA was described as frequently silenced in gastric cancer cell lines and to be associated with apoptosis (Lin et al., 2015a). GSDMA was shown to be mutated in the 3'-UTR in different cancers, resulting in the creation or disruption of putative microRNA target sites, thus, potentially resulting in dysregulation of gene expression (Ziebarth et al., 2012). Expression analysis of GSDMA in esophageal and gastric cancer suggests that GSDMA is a tumor suppressor (Saeki et al., 2009).

Breast cancer patients exhibited higher frequency of homozygous deletion of the GSTM1 gene compared with the control group. Genetic polymorphism of the GSTM1 gene has been also associated with bladder cancer susceptibility in the Iranian population, lung cancer risk in the Chinese population, prostate, esophageal and cervical cancer in the Indian population (Mittal et al., 2004; Singh et al., 2008; Safarinejad et al., 2013; Sharma et al., 2013; Possuelo et al., 2013; Chen et al., 2014g).

Studies have shown frequent down-regulation and promoter DNA hyper-methylation of GSTM5 in Barrett's adenocarcinoma compared to normal samples. On the other hand, GSTM5 transcript was not detected in acute lymphoblastic leukemia patients (Kearns et al., 2003; Peng et al., 2009). Researchers have observed that single-nucleotide polymorphisms in GSTM5 gene may affect overall survival in stages I to II or low-stage non-small cell lung cancer (Pankratz et al., 2011).

GSTT2 promoter polymorphisms and their haplotypes are associated with colorectal cancer risk in the Korean population. Others have reported that deletion in the GSTT2 gene may have a protective effect on the initiation and development of esophageal squamous cell carcinoma in the Mixed Ancestry South African population. In addition, low frequency of DNA methylation of GSTT2 gene was found in Barrett's adenocarcinoma (Peng et al., 2009; Jang et al., 2007; Matejcic et al., 2011).

GSTT2B was shown to be associated with esophageal squamous cell carcinoma since a GSTT2B deletion had a potential protective effect on the risk of esophageal squamous cell carcinoma in the Mixed Ancestry South African population (Matejcic et al., 2011).

Single nucleotide polymorphisms in the GTF2H4 gene were reported to increase the risk to develop smoking-related lung cancer and papilloma virus-induced cervical cancer (Buch et al., 2012; Mydlikova et al., 2010; Wang et al., 2010).

Researchers have observed GTF2IRD1-ALK fusion in thyroid cancer (Stransky et al., 2014).

Researchers have identified GTF3C2 as a novel ALK fusion in a cohort of Spitz tumors (Yeh et al., 2015).

Several publications have reported down-regulation of H2AFY in variety of human cancers including colorectal, lung, testicular, bladder, cervical, breast, colon, ovarian and endometrial (Novikov et al., 2011; Sporn and Jung, 2012). Additionally, knockdown of H2AFY in melanoma cells resulted in significantly increased proliferation and migration in vitro and growth and metastasis in vivo (Kapoor et al., 2010). In bladder cancer, depletion of H2AFY expression was significantly associated with elevated levels of Lin28B expression (Park et al., 2016).

HAUS3 is associated with breast cancer (Shah et al., 2009).

High level of HDGF expression has been linked with poor prognosis in breast cancer and pancreatic ductal carcinoma (Uyama et al., 2006; Chen et al., 2012b). Studies have revealed that HDGF plays an important role in inducing cancer cell proliferation, angiogenesis, invasion and migration in various malignancies such as oral squamous cell carcinoma, gastric, colonic, lung and esophageal cancers (Yamamoto et al., 2007; Mao et al., 2008; Liao et al., 2010; Meng et al., 2010; Lin et al., 2012; Tao et al., 2014a).

HEATR1 was shown to be up-regulated in glioblastoma (Wu et al., 2014c).

HELQ was described to interact with the RAD51 paralog complex BCDX2. Different components of this complex are associated with increased risk of ovarian cancer and breast cancer, respectively (Pelttari et al., 2015). HELQ was shown to be a candidate ovarian cancer gene due to its association with RAD51 paralogs (Takata et al., 2013b). HELQ, as part of the polymerase pathway, was shown to be associated with oral cavity/pharynx cancers due to a missense mutation in the second exon (Babron et al., 2014). HELQ was shown to play a role in DNA repair and tumor suppression (Adelman et al., 2013). HELQ was shown to be associated with esophageal squamous cell carcinoma using a genome-wide association study in a Han Chinese population (Li et al., 2013b).

HELZ2 was shown to be one biomarker in gene panel allowing earlier diagnosis of epithelial ovarian cancer (Pils et al., 2013).

The HERC2/OCA2 region on chromosome 15q13.1 is one of several loci that predispose to cutaneous melanoma (Amos et al., 2011; Xiao et al., 2014). HERC2 regulates the stability of different DNA repair factors including CHK1, p53 and BRCA1 (Bekker-Jensen et al., 2010; Cubillos-Rojas et al., 2014; Zhu et al., 2014a; Peng et al., 2015c).

HINT1 is transcriptionally silenced or down-regulated in various cancers including hepatocellular carcinoma, some human non-small cell lung cancer cell lines and gastric cancer. In contrast, HINT1 is over-expressed in prostate cancer (Zhang et al., 2009; Huang et al., 2011; Symes et al., 2013). It has been observed that in a hepatoma cell line, HINT1 inhibits activity of Wnt/beta-catenin signaling and gene transcription via TCF4 (Wang et al., 2009b).

It has been demonstrated that variants in the HLA-DMB gene could be associated with the risk of HIV-related Kaposi's sarcoma. In addition, deregulation of HLA-DMB gene was noted in ERG-positive and ETV1-positive prostate carcinomas (Paulo et al., 2012; Aissani et al., 2014). Furthermore, elevated levels of HLA-DMB expression in the tumor epithelium was correlated with improved survival in advanced serous ovarian cancer (Callahan et al., 2008).

HLTF is a member of the SWI/SNF family of transcriptional regulators with helicase and E3 ubiquitin ligase activity and was found to be inactivated by hyper-methylation in colon, gastric, uterine, bladder and lung tumors (Castro et al., 2010; Debauve et al., 2008; Garcia-Baquero et al., 2014).

HMMR expression is up-regulated in different cancer entities including breast, colon, gastric, pancreatic and prostate cancer and correlates with cell motility, invasion and metastasis (Yamada et al., 1999; Wang et al., 1998; Abetamann et al., 1996; Gust et al., 2009; Ishigami et al., 2011; Sankaran et al., 2012). HMMR interacts with BRCA1 leading to tumor progression by promoting genomic instability. Furthermore, HMMR associates with Src, which elevates cell motility and HMMR-CD44 partnering stimulates ERK signaling resulting in tumor promotion. Additionally, HMMR is a target of several tumor associated proteins including E2F1, p53 and Ras (Blanco et al., 2015; Hall et al., 1995; Hall and Turley, 1995; Maxwell et al., 2008; Sohr and Engeland, 2008; Meier et al., 2014).

HSPA14 was shown to be up-regulated in hepatocellular carcinoma (Yang et al., 2015c). HSPA14 is associated with non-small cell lung cancer (Wu et al., 2011a).

HSPA8 was shown to be over-expressed in esophageal squamous cell carcinoma and high expression levels of HSPA8 in esophageal cancer cells in vitro counter-acted oxidative stress-induced apoptosis of these cells. Furthermore, HSPA8 is over-expressed in multiple myeloma and colonic carcinoma and BCR-ABL1-induced expression of HSPA8 promotes cell survival in chronic myeloid leukemia (Chatterjee et al., 2013; Dadkhah et al., 2013; Jose-Eneriz et al., 2008; Kubota et al., 2010; Wang et al., 2013b).

Over-expression of HUWE1 has been found in various types of tumors such as lung carcinoma, breast carcinoma, prostate carcinoma, glioblastoma and colon carcinoma. Another report has revealed that HUWE1 is implicated in the pathogenesis of hepatocellular carcinoma (Yoon et al., 2005; Adhikary et al., 2005; Liu et al., 2012). In addition, depletion of HUWE1 prevented the proliferation of a subset of human tumor cells while elevated levels of HUWE1 correlated with detectable p53 (Adhikary et al., 2005; Confalonieri et al., 2009).

IDO1 was found to be expressed in a variety of tumors, such as colorectal cancer, melanoma, serous ovarian cancer and papillary thyroid micro-carcinoma (Brandacher et al., 2006; Takao et al., 2007; Brody et al., 2009; Ryu et al., 2014). Over-expression of IDO1 in endometrial cancer tissues as well as in childhood acute myeloid leukemia positively correlated with disease progression and impaired patient survival (Ino et al., 2008; Folgiero et al., 2014).

IFI16 protein was relatively low or was not detectable in certain human prostate and breast cancer cell lines (Xin et al., 2003; Alimirah et al., 2007). Researchers have noted that IFI16 is expressed in the human-papillomavirus-positive head and neck squamous cell carcinomas and correlates with a better prognosis (Azzimonti et al., 2004). Furthermore, treatment of breast cancer cell lines with 5-aza-dC resulted in up-regulation of IFI16 expression (Fujiuchi et al., 2004).

IFI30 expression was shown to be associated with diminished cellular activation, including decrease of phosphorylated ERK1/2, decreased cellular proliferation and cancer patient survival (Rausch and Hastings, 2015). IFI30 was shown to be down-regulated in primary and metastatic breast cancer (Xiang et al., 2014). Reduced IFI30 expression in breast cancer was shown to be associated with poorer disease-free survival while absence of IFI30 was positively correlated with adverse characteristics of breast cancers such as tumor size and lymph node status (Xiang et al., 2014). Thus, IFI30 may act as a potential tumor suppressor and novel independent prognostic factor in breast cancer (Xiang et al., 2014). Reduced IFI30 expression in diffuse large B-cell lymphoma was shown to be associated with poor overall survival (Phipps-Yonas et al., 2013). A single nucleotide polymorphism in IFI30 was shown to be a significant predictor for disease progression in advanced prostate cancer patients treated with androgen-deprivation therapy (Bao et al., 2011). IFI30 was shown to be one of several genes up-regulated in squamous cell carcinoma and basal cell carcinoma of the skin (Wenzel et al., 2008). IFI30 was shown to be associated with disparities in the profile of antigenic epitopes displayed by melanomas and bystander antigen-presenting cells, and thus may contribute to tumor cell survival in the face of immunological defenses (Hague et al., 2002).

IFI44L was shown to be associated with CDKN2A, a gene associated with cutaneous melanoma and non-melanoma skin cancer and miR-9, which is associated with nasopharyngeal carcinoma (Gao et al., 2013; Puig-Butille et al., 2014).

The IFIT1 gene is down-regulated in MCF7 breast cancer cells. Others reported that the IFIT1 gene was inactivated in hypopharynx cancer (Xu et al., 2013a; Motaghed et al., 2014). Furthermore, miR-9 can modulate the expression of IFIT1 gene in human cancer cells (Gao et al., 2013).

IFT172 is associated with chemoresistance in gastric cancer (Huang et al., 2014a).

IGHG1 was over-expressed in human pancreatic cancer tissues compared to adjacent non-cancerous tissues. On the contrary, the IGHG1 protein was down-regulated in infiltrating ductal carcinomas tissues (Kabbage et al., 2008; Li et al., 2011b). siRNA targeted silencing of IGHG1 was able to inhibit cell viability and promote apoptosis (Pan et al., 2013).

Researchers have observed expression of IGHG3 in Saudi females affected by breast cancer. Similarly, gains in copy number as well as elevated levels of IGHG3 were detected in African American men suffering from prostate cancer. Another report showed that IGHG3 expression is found in squamous non-small cell lung cancers, malignant mesothelioma as well as on tumor cells that are sporadically seen in MALT lymphomas and that show a propensity for differentiation into plasma cells (Remmelink et al., 2005; Bin Amer et al., 2008; Ledet et al., 2013; Zhang et al., 2013c; Sugimoto et al., 2014).

Recent work has detected rearrangements involving IGHG4 in primary testicular diffuse large B cell lymphoma (Twa et al., 2015).

Studies have observed down-regulation of IGHM in Chinese patients affected by rhabdomyosarcoma. Others have detected expression of IGHM in diffuse large B-cell lymphoma. Another group has found that in diffuse large B-cell lymphoma the IGHM gene is conserved only on the productive IGH allele in most IgM+ tumors. In addition, epithelioid angiomyolipoma samples did not show any reactivity for transcription factor binding to IGHM enhancer 3 or transcription factor EB (Kato et al., 2009; Blenk et al., 2007; Ruminy et al., 2011; Liu et al., 2014a).

IMPDH2 over-expression was found in osteosarcoma and human prostate cancer tissues as well as in leukemic cells (Nagai et al., 1991; Zhou et al., 2014b). Inhibitors of IMPDH2 such as tiazofurin and benzamide riboside exhibited a good clinical response in patients with acute myeloid leukemia and chronic myeloid leukemia in blast crisis (Wright et al., 1996; Jayaram et al., 1999).

INADL is down-regulated in non-small cell lung cancer in response to cisplatin-gemcitabine combination chemotherapy (Ma et al., 2015).

Over-expression of INPPL1 has been observed in breast cancer, non-small cell lung cancer, hepatocellular carcinoma and laryngeal squamous cell carcinoma (Prasad et al., 2008b; Zhou et al., 2011; Fu et al., 2013b; Fu et al., 2013c). It has been reported that INPPL1 silencing in breast cancer cells reduces cell proliferation in vitro and cancer growth in vivo and inhibits tumor metastases (Prasad et al., 2008a).

The expression of IPP was elevated in human breast tumor samples compared to non-cancer tissues (Govindaraj et al., 2012).

Several lines of evidence have shown that IQGAP1 is over-expressed in various tumor types, including colorectal carcinoma, gastric cancer, hepatocellular carcinoma, pancreatic cancer, ovarian cancer and esophageal squamous cell carcinoma (Takemoto et al., 2001; Dong et al., 2006; Hayashi et al., 2010; White et al., 2010; Wang et al., 2013i; Wang et al., 2014i). In addition, high levels of IQGAP1 were correlated with poor prognosis in ovarian carcinomas and colorectal carcinoma (Dong et al., 2006; Hayashi et al., 2010).

A recent study suggested a genetic association of IRAK2 rs35060588 with colorectal cancer survival. On the other hand, no mutations were found in IRAK2 in patients suffering from chronic lymphocytic leukemia (Martinez-Trillos et al., 2014; Wang et al., 2014c). Researchers have observed that over-expression of IRAK2 correlated with decreased disease-free survival of patients with non-adenocarcinoma (Seol et al., 2014).

IL6 up-regulates IRF9 in prostate cancer cell lines both at the mRNA and protein levels (Erb et al., 2013). Another study has shown that that up-regulated IRF9 confers resistance to the anti-microtubule agent paclitaxel in drug-resistant breast cancer cells (Luker et al., 2001).

Many studies have reported over-expression of ISG15 in several tumors, such as bladder cancer, breast cancer, oral squamous cell carcinoma, cervical cancer and prostate cancer (Andersen et al., 2006; Chi et al., 2009; Kiessling et al., 2009; Rajkumar et al., 2011; Wood et al., 2012; Vincent-Chong et al., 2012). In breast cancer, high ISG15 expression was associated with an unfavorable prognosis (Wood et al., 2012).

ISYNA1 is associated with chemotherapy response in cutaneous malignant melanoma (Azimi et al., 2014). ISYNA1 was shown to be up-regulated in the human liver carcinoma cell line HepG2 under various conditions (Guan et al., 2003). ISYNA1 inhibition is associated with decreased proliferation in the SK-N-SH neuroblastoma cell line (Ye and Greenberg, 2015).

ITGB2 gene polymorphisms have been associated with colorectal neoplasia and sporadic infiltrative duct breast carcinoma. Moreover, over-expression of ITGB2 was observed in peripheral blood neutrophils in patients with advanced epithelial ovarian cancer as well as in leukemia. On the contrary, ITGB2 was absent or only dimly expressed in promyelocytic leukemia (Phongpradist et al., 2010; Fu et al., 2011; Zhou et al., 2012b; Chang et al., 2013; Bednarska et al., 2016). cIBR-coupled PLGA nanoparticles targeting ITGB2 hold promise as a selective drug delivery system for leukemia treatment (Chittasupho et al., 2010).

ITGB4 is associated with prostate cancer, gastric cancer, breast cancer, oral squamous cell carcinoma and ovarian cancer and was shown to be up-regulated in pancreatic ductal adenocarcinoma (Chen et al., 2014e; Xin et al., 2014; Zubor et al., 2015; Masugi et al., 2015; Gao et al., 2015; Kawakami et al., 2015). ITGB4 (also called CD104) tends to associate with the alpha 6 subunit and is likely to play a pivotal role in the biology of several invasive carcinomas such as esophageal squamous cell carcinoma, bladder and ovarian carcinoma (Kwon et al., 2013; Pereira et al., 2014; Chen et al., 2014e). A single nucleotide polymorphism in ITGB4 seems to influence tumor aggressiveness and survival and may have prognostic value for breast cancer patients (Brendle et al., 2008).

Over-expression of ITGB8 has been observed in several cancers including hepatocellular carcinoma, head and neck cancer, some ovarian cancer and melanoma cell lines as well as primary non-small lung cancer samples and brain metastases from several epithelial cancers (Liu et al., 2002b; Goodman et al., 2012; Vogetseder et al., 2013). Furthermore, silencing of ITGB8 caused Snail and NF-1° B transcriptional activation and MEK and Akt phosphorylation level changes in lung cancer cell lines (Xu and Wu, 2012). Knockdown of ITGB8 in PC-3 and 22Rv1 prostate cancer cells in vitro resulted in significant reduction of cell migration and invasion (Mertens-Walker et al., 2015). Researchers have found that over-expression of ITGB8 could be an inducer of gefitinib resistance of hepatic cancer. ITGB8 might interact with TGF-beta pathway to achieve its anti-gefitinib effects (Wang et al., 2015f).

It has been reported that the expression of ITPR1 is altered in tamoxifen resistance breast cancer cell lines (Elias et al., 2015). Researchers have postulated a role for the HIF2alpha/ITPR1 axis in regulating clear cell renal cell carcinomas cell survival. In addition, ITPR1 was significantly correlated with overall survival in breast cancer (Messai et al., 2014; Gu et al., 2016).

Single nucleotide polymorphism in the ITPR2 gene was correlated with risk of renal cell carcinoma in a Chinese population. Likewise, two common variants in linkage disequilibrium, rs718314 and rs1049380 in the ITPR2 gene were identified as novel susceptibility loci for renal cell carcinoma. Moreover, over-expression of ITPR2 was observed in normal acute myeloid leukemia patients compared to healthy persons (Wu et al., 2012d; Shi et al., 2015; Zhang et al., 2016a). In normal acute myeloid leukemia, elevated levels of ITPR2 expression were associated with shorter overall survival and event-free survival (Shi et al., 2015).

Studies have detected expression of JUP in colorectal cancer and lung adenocarcinoma, while a high ITGB4/JUP ratio was found in oral squamous cell carcinoma (Wang and Zheng, 2014; Yang et al., 2012a; Schuetz et al., 2012; Sheng and Zhu, 2014; Nagata et al., 2013).

Over-expression of KARS was found in gastric carcinoma as well as tumor-associated inflammatory cells. Moreover, mutations in the KARS gene were identified in patients suffering from colorectal cancer. Others have observed that whole-arm loss of chromosome 16q in breast cancer was related with decreased expression of KARS (Yen et al., 2009; Hungermann et al., 2011; Kim et al., 2014a). It is reported that KARS is involved in cell-cell and cell-ECM adhesion during KARS-mediated metastasis (Nam et al., 2015).

KCNK15 gene hyper-methylation was found in several cell lines, including colon cancer, leukemia, and bladder cancer (Shu et al., 2006).

KDELR1 has a role in tumorigenesis (Yi et al., 2009). Decreased KDELR1 levels are found in hepatoma cells (Hou et al., 2015). Down-regulation of KDELR1 is seen in acute myeloid leukemia (Caldarelli et al., 2013).

Over-expression of KDM1A promotes tumor cell proliferation, migration and invasion and was associated with poor prognosis in NSCLC and HCC (Lv et al., 2012; Zhao et al., 2013d). Elevated expression of KDM1A correlates with prostate cancer recurrence and with increased VEGF-A expression (Kashyap et al., 2013). Inhibition of KDM1A with a combination of trichostatin A (TSA) and 5-aza-2'-deoxycytidine (decitabine) suppresses the tumorigenicity of the ovarian cancer ascites cell line SKOV3 (Meng et al., 2013).

KDM1B was shown to inhibit cell growth in the lung cancer cell line A549 due to its E3 ubiquitin ligase activity (Yang et al., 2015b). KDM1B was shown to be involved in the regulation of the presumed tumor suppressor tissue factor pathway inhibitor-2 (Mino et al., 2014). KDM1B was shown to be up-regulated in breast cancer and amplified and up-regulated in high grade urothelial carcinomas (Heidenblad et al., 2008; Katz et al., 2014). KDM1B was shown to play a role in DNA methylation and gene silencing in breast cancer. Inhibition of both KDM1B and DNA methyltransferase was described as a novel approach for epigenetic therapy of breast cancer (Katz et al., 2014). KDM1B was shown to be associated with the acquisition of cancer stem cell properties, including self-renewal, clonal formation, and chemotherapy resistance in hyaluronan-CD44v3 activated head and neck cancer (Bourguignon et al., 2012).

Over-expression of KIAA0196 was observed in clinical prostate carcinomas and was also amplified in 30-40% of xenografts and hormone-refractory tumors (Porkka et al., 2004). Amplification of KIAA0196 gene was correlated with worse prognosis in high-grade estrogen receptor-negative breast cancer (Chin et al., 2007). In prostate cancer, KIAA0196 did not seem to have any significant role in growth, anchorage-independent growth or invasion in vitro (Jalava et al., 2009).

KIAA1324 is over-expressed in different cancer types including breast, lung, pancreatic and ovarian cancer (Schlumbrecht et al., 2011; Estrella et al., 2014; Bauer et al., 2004). KIAA1324 shows a tumor suppressor behavior in gastric cancer where KIAA1324 is down-regulated and this is associated with poor prognosis (Kang et al., 2015b).

Inhibition of KIF11 was shown to stop growth of the more treatment-resistant glioblastoma tumor-initiating cells (TICs) as well as non-TICs and impeded tumor initiation and self-renewal of the TIC population (Venere et al., 2015). Targeting KIF11 was also shown to reduce glioma cell invasion and to prolong survival of mice bearing ortho-topic glioblastoma (Venere et al., 2015). Thus, KIF11 plays a role as a driver of invasion, proliferation, and self-renewal in glioblastoma (Venere et al., 2015). Higher expression of mitosis-associated genes such as KIF11 was shown to be associated with complete response of hepatocellular carcinomas to trans-arterial chemoembolization treatment (Gaba et al., 2015). Interfering with KIF11 function was described to cause potent inhibition of tumor angiogenesis in experimental tumor models (Exertier et al., 2013). KIF11 was shown to be down-regulated in bone marrow samples from patients with multiple myeloma and acute myeloid leukemia (Cohen et al., 2014). Nuclear KIF11 expression was described as a potential predictive biomarker for docetaxel response in metastatic castrate-resistant aggressive prostate cancer and as a prognostic biomarker for prostate cancer aggressiveness (Wissing et al., 2014). KIF11 was shown to be essential for tumor cell survival in non-small cell lung cancer and head and neck squamous cell carcinoma and thus may be a potential anti-cancer target (Martens-de Kemp et al., 2013). Up-regulation of KIF11 was shown to be associated with ependymoma recurrence in children (Peyre et al., 2010).

In breast cancer, KIF15 was shown to be over-expressed and to be immunogenic, as anti-KIF15 antibodies could be isolated from breast cancer patients (Scanlan et al., 2001). Furthermore, KIF15 appears to be implicated in lung adenocarcinoma (Bidkhori et al., 2013).

Methylation of KIF1A is known to be frequent and higher levels were shown in thyroid cancer, breast cancer, head and neck squamous cell carcinoma (Aviles et al., 1991; Hogue et al., 2008; Demokan et al., 2010; Guerrero-Preston et al., 2014). Moreover, KIF1A was found in plasma and saliva of lung cancer and head and neck squamous cell carcinoma patients compared to controls. These findings suggest that it could be used as a biomarker for early detection in these disorders (Ostrow et al., 2010). In breast cancer, overexpression of KIF1A was found to correlate with chemotherapy resistance in cell lines (De et al., 2009).

Over-expression of KIF20A was detected in pancreatic ductal adenocarcinoma, melanoma, bladder cancer, non-small cell lung cancer and cholangiocellular carcinoma (Imai et al., 2011; Yamashita et al., 2012; Stange) et al., 2015). Recently, it was reported that patients with pancreatic ductal adenocarcinoma vaccinated with a KIF20A-derived peptide exhibited better prognosis compared to the control group (Asahara et al., 2013). In addition, silencing of KIF20A resulted in an inhibition of proliferation, motility, and invasion of pancreatic cancer cell lines (Stange) et al., 2015).

Fusions of the KIF8 gene and the ret proto-oncogene (RET) have been observed in patients suffering from lung cancers, adenocarcinoma and non-small cell lung cancer (Kohno et al., 2012; Cai et al., 2013b; Qian et al., 2014). KIF5B-RET expression in Ba/F3 cells resulted in oncogenic transformation as determined by interleukin-3 (IL-3)-independent growth (Lipson et al., 2012).

KIFC1 plays a crucial role by the cell division of meiotic cells by focusing acentrisomal microtubule organizing centers into two spindle poles. In cancer cells, KIFC1 was shown to be essential for proper spindle assembly, stable pole-focusing and survival of cancer cells independently from number of formed centrosomes (normal or supernumerary centrisomes). A constitutive activation of the DNA damage response in cancer was shown partially to mediate acentrisomal spindle formation. The dependency of acentrisomal spindle formation from KIFC1 makes KIFC1 to the attractive target for cancer therapy. A number of potential KIFC1 inhibitors are under current investigation (Li et al., 2015e; Kleylein-Sohn et al., 2012; Wu et al., 2013a; Watts et al., 2013; Zhang et al., 2016b). Furthermore, KIFC1 shows centrosome clustering-independent pro-proliferative effects which is based on the protection of survivin from proteasome-mediated degradation (Pannu et al., 2015). KIFC1 expression was shown to be up-regulated in breast cancer, particularly in estrogen receptor negative, progesterone receptor negative and triple negative breast cancer, and 8 human breast cancer cell lines. In estrogen receptor-positive breast cancer cells, KIFC1 was one of 19 other kinesins whose expression was strongly induced by estrogen. In breast cancer, the overexpression of KIFC1 and its nuclear accumulation was shown to correlate with histological grade and predict poor progression-free and overall survival. In breast cancer cell lines, the overexpression of KIFC1 was shown to mediate the resistance to docetaxel. The KIFC1 silencing negatively affected the breast cancer cell viability (Zou et al., 2014a; Pannu et al., 2015; De et al., 2009; Li et al., 2015e). KIFC1 was shown to be overexpressed in ovarian cancer which was associated with tumor aggressiveness, advanced tumor grade and stage. Thus, KIFC1 may serve as a potential biomarker that predicts worse prognosis, poor overall survival and onset of metastatic dissemination (Pawar et al., 2014). KIFC1 was identified as one of three genes, whose higher expression in primary NSCLC tumors indicated the higher risk for development of brain metastasis (Grinberg-Rashi et al., 2009).

KLHL14 is associated with primary central nervous system lymphoma (Vater et al., 2015).

KLHL15 was shown to interact as an E3 ubiquitin ligase adaptor with the protein phosphatase 2A, a tumor suppressor that was shown to be genetically altered or functionally inactivated in many solid cancers (Oberg et al., 2012; Perrotti and Neviani, 2013).

KLHL7 was shown to be up-regulated in thyroid tumors (Jacques et al., 2005). KLHL7 is associated with lymphocyte-rich classical Hodgkin's lymphoma, follicular lymphoma and diffuse large B-cell lymphoma (Weigert et al., 2012; Trifonov et al., 2013; Nam-Cha et al., 2009).

Several publications have detected over-expression of KLK7 mRNA and protein in early-stage ovarian tumors, colon cancer, cervical cancer and breast cancer. Others have observed low levels of KLK7 expression in prostate cancer (Talieri et al., 2004; Walker et al., 2014; Li et al., 2014e; Zhang et al., 2015c; Tamir et al., 2014). In addition, KLK7 expression was correlated with poor outcome of patients suffering from unresectable pancreatic ductal adenocarcinomas and breast cancer (Talieri et al., 2004; Iakovlev et al., 2012). It seems that KLK7 induces cancer cell migration, invasiveness and induces epithelial-mesenchymal transition-like changes in prostate tumor cells (Mo et al., 2010).

KRT14 is highly expressed in various squamous cell carcinomas such as esophageal, lung, larynx, uterine cervical as well as in adenomatoid odontogenic tumor. However, it was absent in small cell carcinoma of the urinary bladder and weak in lung adenocarcinoma, gastric adenocarcinoma, colorectal adenocarcinoma, hepatocellular carcinoma, pancreatic ductal adenocarcinoma, breast infiltrating ductal adenocarcinoma, thyroid papillary carcinoma and uterine endometrioid adenocarcinoma (Xue et al., 2010; Terada, 2012; Vasca et al., 2014; Hammam et al., 2014; Shruthi et al., 2014). In bladder cancer, KRT14 expression was strongly associated with poor survival (Volkmer et al., 2012).

Over-expression of KRT16 was found in basal-like breast cancer cell lines as well as in carcinoma in situ. Others did not find significant difference in immunohistochemical expression of KRT16 between non-recurrent ameloblastomas and recurrent ameloblastomas (Joosse et al., 2012; Ida-Yonemochi et al., 2012; Safadi et al., 2016). In addition, in silico analyses showed correlation between KRT16 expression and shorter relapse-free survival in metastatic breast cancer (Joosse et al., 2012).

Over-expression of KRT17 was found in various cancers such as carcinoma in situ, squamous cell carcinoma, Ewing sarcoma and epithelial ovarian cancer (Mikami et al., 2011; Wang et al., 2013j; Sankar et al., 2013). Furthermore, high levels of KRT17 expression were significantly associated with poor survival of squamous cell carcinoma, epithelial ovarian cancer, breast cancer and pancreatic cancer (van de Rijn et al., 2002; Sarbia et al., 2007; Wang et al., 2013j; Escobar-Hoyos et al., 2014). Researchers have demonstrated that KRT17 expression promotes squamous cell carcinoma cell growth and cell size but does not affect cell migration (Mikami et al., 2015).

L3MBTL4 was shown to be targeted by deletion, breakage and mutations in breast cancer. It was also shown to be down-regulated in breast cancer and thus may be a potential tumor suppressor gene (Addou-Klouche et al., 2010). L3MBTL4 resides in a chromosome region that was shown to be frequently deleted in a rare subtype with poor prognosis of acute myeloid leukemia (Veigaard et al., 2011).

Studies have shown that the level of LAMA5 was elevated in basal cell carcinoma, cervical cancer and breast carcinoma (Simonova et al., 2015; Scotto et al., 2008; Mostafa et al., 2010; Georgiou et al., 2013).

LAT2 expression is able to separate T lineage leukemias into two subgroups, while others have reported that LAT2 acts as a tumor suppressor able to enhance the proximal signaling of leukemic blasts (Svojgr et al., 2009; Svojgr et al., 2012). In addition, loss of LAT2 suppressed AKT activation, decreased cell proliferation and increased cell sensitivity to drugs such as ODPC, perifosine and arsenic trioxide (Thome et al., 2012).

The C/C(-13910) genotype of the LCT gene is significantly associated with increased risk of colorectal cancer in the Finnish population but not in the British or Spanish subjects (Fairfield et al., 2004; Rasinpera et al., 2005; Travis et al., 2013). A decreased survival rate was observed in patients suffering from colorectal cancer with LCT C/C(-13910) genotype (Bacsi et al., 2008).

Several studies have observed high levels or ineffectively regulated LDLR expression in various types of cancer, for instance over-expression of LDLR was reported in lung adenocarcinoma cell line, prostate cancer cells as well as human colorectal cancer biopsies. In contrast, decreased feedback regulation of LDLR has been reported in leukemic cells from acute myelogenous patients (Gueddari et al., 1993; Tatidis et al., 1997; Lum et al., 1999; Chen and Hughes-Fulford, 2001).

Studies have detected up-regulation of mRNA and protein level of LGALS3BP in colorectal carcinoma tissues as well as in lung cancer (Ozaki et al., 2004; Iacovazzi et al., 2010; Wu et al., 2008). Elevated levels of LGALS3BP were correlated with poor prognosis in diffuse large B-cell lymphomas (Kim et al., 2008d). Moreover, in lung cancer LGALS3BP is involved in cancer metastasis by increasing adhesiveness of cancer cells (Ozaki et al., 2004).

LGR6 is associated with triple-negative breast cancer, gastric cancer and colon cancer (Gong et al., 2012; Rocken, 2013; Purrington et al., 2014). LGR6 was shown to be up-regulated in gastric cancer (Steffen et al., 2012). LGR6 is associated with local tumor growth and patient survival in gastric cancer (Steffen et al., 2012).

LLGL1 expression is reduced or absent in breast cancers, lung cancers, prostate cancers, ovarian cancers, colorectal cancers, melanomas, endometrial cancers and hepatocellular carcinomas (Schimanski et al., 2005; Kuphal et al., 2006; Tsuruga et al., 2007; Lu et al., 2009; Song et al., 2013b). It seems that LLGL1 inhibits proliferation and promotes apoptosis in the esophageal carcinoma cell line through a mitochondria-related pathway. Furthermore, reduced LLGL1 transcription has been linked with lymph node metastases, whereas over-expression of LLGL1 resulted in increased cell adhesion and decreased cell migration (Schimanski et al., 2005; Kuphal et al., 2006; Tsuruga et al., 2007; Song et al., 2013b).

Expression of LMNB1 is reduced in colon cancer and gastric cancer, whereas it is over-expressed in prostate cancer, hepatocellular carcinoma and pancreatic cancer (Moss et al., 1999; Lim et al., 2002; Coradeghini et al., 2006; Li et al., 2013a). In hepatocellular carcinoma, the expression level of LMNB1 correlated positively with tumor stage, tumor sizes and number of nodules. These findings suggest that LMNB1 could be used to detect early stages of hepatocellular carcinoma (Sun et al., 2010).

The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015l).

LPCAT2 is associated with prostate cancer (Williams et al., 2014). LPCAT2 was shown to be up-regulated in breast cancer, cervical cancer and colorectal cancer (Agarwal and Garg, 2010). LPCAT2 expression is associated with patient outcome in prostate cancer (Williams et al., 2014).

Inhibition of LRBA expression by RNA interference, or by a dominant-negative mutant, resulted in the growth inhibition of cancer cells. These findings imply that deregulated expression of LRBA contributes to the altered growth properties of a cancer cell (Wang et al., 2004).

LTBP2 has been shown to be up-regulated in hepatocellular carcinoma, pancreatic ductal adenocarcinoma, whereas in esophageal squamous cell carcinoma cell lines and tumor tissues the expression of LTBP2 was down-regulated (Chan et al., 2011; Turtoi et al., 2011; Cho et al., 2016). In hepatocellular carcinoma, high levels of LTBP2 were significantly correlated with shorter time to tumor recurrence. Similarly, elevated levels of LTBP2 were associated with poor outcome for ER(−)/PR(−) breast cancer patients (Naba et al., 2014; Cho et al., 2016).

LTN1, also known as ZNF294, encodes the listerin E3 ubiquitin protein ligase 1 and is located on chromosome 21q22.11 (RefSeq, 2002). LTN1 is associated with high level microsatellite instability in colorectal cancer (Reuschenbach et al., 2010).

LURAP1 was shown to be a NF-kB activator which may be a candidate gene for regulating the function of dendritic cells to resist tumor-associated factor-mediated dysfunction (Jing et al., 2010).

It has been reported that the LYST gene is localized within the copy number aberration regions in multiple myeloma (Ivyna Bong et al., 2014).

Researchers have reported expression of M6PR in colon carcinoma cell lines as well as in choriocarcinoma cells (Braulke et al., 1992; O'Gorman et al., 2002). In breast cancer, low-level expression of M6PR was associated with poor patient prognosis (Esseghir et al., 2006). Furthermore, over-expression of M6PR resulted in a decreased cellular growth rate in vitro and decreased tumor growth in nude mice (O'Gorman et al., 2002).

MACF1 is associated with colorectal cancer, renal cell carcinoma and lung adenocarcinoma (Bidkhori et al., 2013; Arai et al., 2014; Kim et al., 2015b). MACF1 was shown to be associated with neuroblastoma in the CLB-Bar cell line (Schleiermacher et al., 2005).

Over-expression of MADD has been found in many types of human tumors, including non-small cell lung cancer, lung adenocarcinoma, squamous cell carcinoma, thyroid cancer, breast cancer and ovarian cancer (Subramanian et al., 2009; Li et al., 2011a; Wei et al., 2012; Bi et al., 2013; Turner et al., 2013). Researchers have demonstrated that elevated levels of MADD in the A549 cells inhibited apoptosis and increased survival, while knock-down of MADD promoted apoptosis and reduced cell proliferation (Wei et al., 2012; Bi et al., 2013). Additionally, MADD function is regulated by PTEN-PI3K-Akt signaling pathway (Jayarama et al., 2014).

MAGEA4 was described as a cancer testis antigen which was found to be expressed in a small fraction of classic seminomas but not in non-seminomatous testicular germ cell tumors, in breast carcinoma, Epstein-Barr Virus-negative cases of Hodgkin's lymphoma, esophageal carcinoma, lung carcinoma, bladder carcinoma, head and neck carcinoma, and colorectal cancer, oral squamous cell carcinoma, and hepatocellular carcinoma (Ries et al., 2005; Bode et al., 2014; Li et al., 2005; Ottaviani et al., 2006; Hennard et al., 2006; Chen et al., 2003). MAGEA4 was shown to be frequently expressed in primary mucosal melanomas of the head and neck and thus may be a potential target for cancer testis antigen-based immunotherapy (Prasad et al., 2004). MAGEA4 was shown to be preferentially expressed in cancer stem-like cells derived from LHK2 lung adenocarcinoma cells, SW480 colon adenocarcinoma cells and MCF7 breast adenocarcinoma cells (Yamada et al., 2013). Over-expression of MAGEA4 in spontaneously transformed normal oral keratinocytes was shown to promote growth by preventing cell cycle arrest and by inhibiting apoptosis mediated by the p53 transcriptional targets BAX and CDKN1A (Bhan et al., 2012). MAGEA4 was shown to be more frequently expressed in hepatitis C virus-infected patients with cirrhosis and late-stage hepatocellular carcinoma compared to patients with early stage hepatocellular carcinoma, thus making the detection of MAGEA4 transcripts potentially helpful to predict prognosis (Hussein et al., 2012). MAGEA4 was shown to be one of several cancer/testis antigens that are expressed in lung cancer and which may function as potential candidates in lung cancer patients for polyvalent immunotherapy (Kim et al., 2012b). MAGEA4 was described as being up-regulated in esophageal carcinoma and hepatocellular carcinoma (Zhao et al., 2002; Wu et al., 2011c). A MAGEA4-derived native peptide analogue called p286-1Y2L9L was described as a novel candidate epitope suitable to develop peptide vaccines against esophageal cancer (Wu et al., 2011c). Several members of the MAGE gene family, including MAGEA4, were shown to be frequently mutated in melanoma (Caballero et al., 2010).

The expression of MAGEA8 was detected in various tumors such as hepatocellular carcinoma, colorectal carcinoma and ovarian cancer (Hasegawa et al., 1998; Tahara et al., 1999; Eng et al., 2015). Furthermore, over-expression of MAGEA8 was associated with poor progression free survival in patients with high CD3 tumors (Eng et al., 2015).

MAGEC3 was described as being expressed only in testis and in tumors of different histological origins. Thus, MAGEC3 could be a target for cancer immunotherapy (Lucas et al., 2000).

Flavopiridol induces an inhibition of human tumor cell proliferation and the down-regulation of MAGEF1 in different human tumor cell lines (Lu et al., 2004). MAGEF1 is significantly over-expressed in colorectal cancer tissues (Chung et al., 2010).

MAGT1 was shown to be associated with a predisposition to lymphoma (Chaigne-Delalande et al., 2013).

A polymorphism in the MANBA gene was associated with the risk of colorectal cancer in the Swedish population, but not in the Chinese population. Others have observed elevated levels of MANBA in esophageal cancer (Sud et al., 2004; Gao et al., 2008).

MCM10 was show to be up-regulated in esophageal squamous cell carcinoma and cervical cancer (Das et al., 2013a; Lu et al., 2014b). MCM10 expression is associated with tumor grade in glioma and cervical cancer (Das et al., 2013a; Hua et al., 2014). MCM10 is associated with early gastric cancer, breast cancer and lung cancer (Wu et al., 2012a; Kang et al., 2013). MCM10 may be used as a biomarker for esophageal squamous cell carcinoma (Lu et al., 2014b).

MCM2 has been shown to be the most sensitive marker of proliferation and prognosis in early breast cancer, renal cell carcinomas, esophageal and laryngeal squamous cell carcinoma and oligodendroglioma of the brain (Wharton et al., 2001; Going et al., 2002; Rodins et al., 2002; Gonzalez et al., 2003; Cai et al., 2012; Joshi et al., 2015).

Researchers have observed lower levels of MDH2 expression in paragangliomas. On the other hand, others reported over-expression of MDH2 in gastric cancer as well as in prostate cancer cell lines and in patient specimens (Liu et al., 2013b; Yao et al., 2015; Cascon et al., 2015). In gastric cancer, elevated levels of MDH2 were associated with depth of invasion, lymph node metastasis, distant metastasis and TNM staging (Yao et al., 2015). MDH2 has been shown to be involved in the development of doxorubicin-resistant uterine cancer, while others have revealed that MDH2 induces prostate cancer resistance to docetaxel-chemotherapy via JNK pathway (Liu et al., 2013b; Lo et al., 2015).

MEMO1 is associated with buccal mucosa squamous cell carcinoma (Shah et al., 2013). MEMO1 is associated with migration, invasion and lung metastasis of breast cancer (MacDonald et al., 2014). MEMO1 was shown to be up-regulated in the pancreatic cancer cell line PaCa (Kalinina et al., 2010). MEMO1 is a prognostic factor of early distant metastasis of primary breast cancer (MacDonald et al., 2014).

Over-expression of MFGE8 has been found in various tumors including breast cancer, malignant melanoma, bladder tumors, ovarian cancer and squamous cell carcinoma (Jinushi et al., 2008; Sugano et al., 2011; Carrascosa et al., 2012; Tibaldi et al., 2013; Yamazaki et al., 2014). It seems that MFGE8 is able to enhance tumorigenicity and metastatic capacity via Akt-dependent and Twist-dependent pathways (Jinushi et al., 2008).

MGA was shown to be mutated in lung adenocarcinoma (2014). MGA was shown to be inactivated in non-small cell lung cancer, small cell lung cancer and chronic lymphocytic leukemia (De et al., 2013; Romero et al., 2014).

MGRN1 is associated with osteosarcoma (Man et al., 2004).

MKI67IP was shown to be trans-activated by c-Myc and silencing of MKI67IP resulted in inhibition of cell proliferation. Thus, MKI67IP may play a role in cancer (Pan et al., 2015).

A study has shown that MKKS is up-regulated in tumors with synchronous adenoma (Kim et al., 2008a).

Methylation and over-expression of MLF1 has been linked with lung squamous cell carcinoma, myeloid leukemia and gastric cancer. Genomic profiling studies have identified MLF1 gene in human esophageal cancer (Shi et al., 2012; Matsumoto et al., 2000; Sun et al., 2004b; Chen et al., 2008). In gastric cancer, methylation of MLF1 gene was positively associated with the number of lymph node metastasis. However, it did not have any prognostic value for gastric cancer patients (Shi et al., 2012). It is reported that MLF1 promotes prostate cancer cell proliferation, colony formation and significantly inhibits apoptosis (Zhang et al., 2015h).

MMP7 is frequently over-expressed in human cancer tissue, including colorectal cancer, metastatic lung carcinoma and gastric cancer and is associated with cancer progression and metastasis formation (li et al., 2006; Sun et al., 2015b; Han et al., 2015a; Long et al., 2014). MMP7 has been shown to play important tumor promoting roles, like degradation of extracellular matrix proteins, activation of tumor cell proliferation by increasing the bioavailability of insulin-like growth factor and heparin-binding epidermal growth factor and induction of apoptosis in tumor-adjacent cells by cleaving membrane bound Fas ligand (li et al., 2006).

MRPL11 was shown to be differently expressed in squamous cell carcinoma compared to normal tissue (Sugimoto et al., 2009). MRPL11 expression is associated with progression free survival and metastatic phenotypes of cervical cancer (Lyng et al., 2006).

Several studies have reported associations between MSH2 gene methylation and various malignancies such as hepatocellular carcinoma, acute lymphoblastic leukemia, clear cell renal cell carcinoma and esophageal squamous cell carcinoma. On the contrary, promoter hyper-methylation of MSH2 in sporadic colorectal cancer was a rare event (Vlaykova et al., 2011; Ling et al., 2012; Hinrichsen et al., 2014; Wang et al., 2014a; Yoo et al., 2014). Recent work has demonstrated that cisplatin could up-regulate the expression of MSH2 by down-regulating miR-21 to inhibit A549 cell proliferation (Zhang et al., 2013e).

In mesothelioma, it has been shown that MSLN induces tumor cell invasion by increasing MMP-9 secretion (Servais et al., 2012). Several publications have shown over-expression of MSLN in various types of cancer such as mesothelioma, triple negative breast carcinomas, pancreatic, ovarian and lung adenocarcinomas (Chang and Pastan, 1996; Argani et al., 2001; Ho et al., 2007; Tozbikian et al., 2014).

Loss of MTAP activity was observed in many tumors such as breast cancer, leukemia, glioblastoma, non-small cell lung cancer and bladder cancer. In addition, promoter hyper-methylation is thought to be the preponderant inactivating mechanism in MTAP-deficient hepatocellular carcinomas (Nobori et al., 1991; Smaaland et al., 1987; Kamatani and Carson, 1980; Stadler et al., 1994; Nobori et al., 1993; Hellerbrand et al., 2006). MTAP re-expression in MTAP-deficient myxofibrosarcoma cell lines inhibited cell migration, invasion, proliferation, anchorage-independent colony formation and down-regulated cyclin D1 (Li et al., 2014a).

MTBP was shown to be down-regulated in hepatocellular carcinoma (Bi et al., 2015). MTBP was shown to be up-regulated in breast cancer and lymphomas (Grieb et al., 2014; Odvody et al., 2010). MTBP was shown to be negatively correlated with capsular/vascular invasion and lymph node metastasis in hepatocellular carcinoma (Bi et al., 2015). MTBP is associated with patient survival in breast cancer and head and neck squamous cell carcinoma (Iwakuma and Agarwal, 2012; Grieb et al., 2014). MTBP may be a potential biomarker for cancer progression in osteosarcoma (Agarwal et al., 2013).

MTCH1 is associated with 5-fluorouracil resistance in ContinB and ContinD colon cancer cell lines (De Angelis et al., 2006).

MTHFD2 was shown to be up-regulated in Burkitt's lymphoma, diffuse large cell lymphoma, breast cancer and in the saPC-3 prostate cancer cell line (Liu et al., 2014b; Patrikainen et al., 2007; Tedeschi et al., 2015). MTHFD2 expression is correlated with tumor size, histological grade, lymph node metastasis and distant metastases in breast cancer (Liu et al., 2014b). MTHFD2 is associated with poor survival in breast cancer and greater cancer susceptibility and survival in bladder cancer (Nilsson et al., 2014; Andrew et al., 2009). MTHFD2 is a prognostic factor in breast cancer (Liu et al., 2014b).

Over-expression of MTOR signaling has been linked with poor clinical outcome in various types of cancers such as renal, lung, breast, laryngeal squamous cell carcinoma, neuroendocrine tumors, biliary tract adenocarcinoma, colorectal, cervical, ovarian, esophageal cancers, malignant melanoma and head and neck squamous cell carcinoma (Faried et al., 2006; Hou et al., 2007; Liu et al., 2007; Molinolo et al., 2007; Karbowniczek et al., 2008; Faried et al., 2008; Shao et al., 2014). Researchers have revealed that MTOR gene knockdown via lentivirus mediated MTOR specific shRNA resulted in a significant decrease in the viability and growth of prostate cancer cells (Du et al., 2014b).

Researchers found a significant association of polymorphisms in the MTR gene with breast cancer, multiple myeloma and squamous cell carcinoma of the head and neck (Zhang et al., 2005b; Kim et al., 2007; Cui et al., 2012; Lopez-Cortes et al., 2013; Hosseini, 2013; Yang et al., 2014a).

MTX2 is associated with discrimination of patient prognosis among acute myelogenous leukemia subgroups (Vey et al., 2004).

MUC1 was up-regulated in several tumors such as colorectal cancer, breast cancer, lung cancer and esophageal adenocarcinoma (Khodarev et al., 2009; Gronnier et al., 2014; Kesari et al., 2015). In pancreatic cancer, MUC1 affects cell proliferation, migration and invasion by targeting certain signaling pathways such as p42-44 MAPK, Akt, Bcl-2 and MMP13. Others have observed that elevated levels of MUC1 in B16 and B16BL6 murine melanoma cells mediates up-regulation of Akt phosphorylation (Trehoux et al., 2015; Wang et al., 2015h). Over-expression of MUC1 has been shown to decrease translocation of î²-catenin into the nucleus, reduce the activity of T cell factor and inhibit the expression of cyclin D1 and c-Myc (Wang et al., 2013e).

MUC16 was initially recognized to be over-expressed in ovarian cancer. It can be detected in the serum of ovarian cancer patients and is an established biomarker for this cancer type. Furthermore, MUC16 over-expression has been reported in pancreatic and breast cancer. Cancer patients carrying elevated levels of MUC16 exhibit higher likelihood of tumor recurrence (Haridas et al., 2014).

MUC20 was described as a prognostic molecular biomarker which is up-regulated in some epithelial tumors (Wang et al., 2015b). MUC20 expression in combination with MUC13 expression was shown to be a potential prognostic marker for patients with esophageal squamous cell carcinoma, who received neoadjuvant chemotherapy followed by surgery (Wang et al., 2015b). MUC20 was shown to be up-regulated in colorectal cancer and endometrial cancer (Chen et al., 2013a; Xiao et al., 2013). MUC20 expression was shown to be associated with recurrence and poor outcome in colorectal cancer. Disease-free survival and overall survival were significantly worse upon up-regulation of MUC20 (Xiao et al., 2013). MUC20 was shown to be a prognostic factor for poor survival which is also associated with cell growth, migration, and invasion in endometrial cancer (Chen et al., 2013a). MUC20 might play a role in tumorigenesis of carcinosarcomas (Vekony et al., 2009).

MUC5AC is de-regulated in a variety of cancer types including colorectal, gastric, lung and pancreatic cancer. Depletion or low expression in colorectal and gastric tumors is associated with a more aggressive behavior and poor prognosis. Over-expression in lung cancer results in an increased likelihood of recurrence and metastases (Yonezawa et al., 1999; Kocer et al., 2002; Kim et al., 2014b; Yu et al., 1996). MUC5AC expression is regulated by different pathways and transcription factors including Sp1, PKC/ERK/AP-1, PKC/JNK/AP-1, CREB, NF-kappaB and Il-1beta/EGFR/Akt/GK-3beta/beta-catenin (Kato et al., 2006; Raja et al., 2012; Chen et al., 2014h).

MUC5B is over-expressed in different cancer entities including colorectal, lung and breast cancer and is associated with tumor progression (Sonora et al., 2006; Valque et al., 2012; Walsh et al., 2013; Nagashio et al., 2015). MUC5B can be repressed under the influence of methylation and can be up-regulated by ATF-1, c-Myc, NFkappaB, Sp1, CREB, TTF-11 and GCR (Perrais et al., 2001; Van, I et al., 2000).

MVP is highly expressed in several central nervous system tumors (Yang et al., 2012b). MVP is highly expressed in cancer, and in several chemoresistant cancer cell lines (Szaflarski et al., 2011; Mossink et al., 2003). MVP expression level increases with age and facilitates apoptosis resistance (Ryu and Park, 2009).

Allelic gene expression of MX2 following lipopolysaccharide stimulation has been shown in hepatocellular carcinoma cells. Furthermore, single nucleotide polymorphism in the MX2 gene was significantly associated with multiple primary melanoma (Park et al., 2014; Gibbs et al., 2015).

MYCBP was shown to be up-regulated in colon carcinoma cells and the oral cancer cell lines Hep-2, SSC-9 and Tu-177 (Rey et al., 1999; Jung and Kim, 2005). MYCBP is associated with chemosensitivity in oligodendroglial tumors (Shaw et al., 2011). MYCBP was shown to be associated with cancer cell survival during limited glucose and oxygen availability in the breast cancer cell line MCF-7 (Sedoris et al., 2010). MYCBP was shown to be differentially expressed in chronic myeloid leukemia (Pizzatti et al., 2006).

MYO1G was shown to be important for cell survival and lysosomal stability in the breast cancer cell line MCF7 (Groth-Pedersen et al., 2012).

NAF1 was shown to interact with GRIM-1, a potential co-tumor suppressor in the prostate (Nallar et al., 2011).

Polymorphisms of NAMPT gene were linked with the risk of developing esophageal squamous cell carcinoma as well as bladder cancer. Moreover, elevated levels of NAMPT were reported in colorectal, breast, prostatic, gastric, thyroid, ovarian and pancreatic cancers (Shackelford et al., 2010; Dalamaga, 2012; Zhang et al., 2014c; Zhang et al., 2015b; Sawicka-Gutaj et al., 2015). Furthermore, single nucleotide polymorphisms of NAMPT gene were significantly correlated with recurrence-free survival for total bladder cancer patients and non-muscle-invasive bladder cancer patients (Zhang et al., 2014c).

NAPRT1 was shown to be associated with cancer. It was also shown that mutations that decrease NAPRT1 expression can predict usefulness of nicotinic acid in tumor treatments with NAMPT inhibitors (Duarte-Pereira et al., 2014). NAPRT1 expression was shown to be lost in many cancer types due to promoter hyper-methylation, resulting in inactivation of one of two NAD salvage pathways. Co-administration of a NAMPT inhibitor blocking the second NAD salvage pathway resulted in synthetic lethality. Thus, NAPRT1 provides a novel predictive biomarker for NAMPT inhibitors (Shames et al., 2013). NAPRT1 was described to be lost in a high frequency of glioblastomas, neuroblastomas, and sarcomas and may be associated with tumor apoptosis (Cerna et al., 2012). NARPT1 was shown to be down-regulated in Hodgkin's lymphoma (Olesen et al., 2011).

NAT8L expression is elevated in approximately 40% of adenocarcinoma and squamous cell carcinoma cases. The over-expression leads to elevated N-acetylaspartate levels in the blood of NSCLC patients presenting a potential biomarker for early lung-cancer detection (Lou et al., 2016).

NBEAL2 deficiency is associated with protection against cancer metastasis in mice (Guerrero et al., 2014). NBEAL2 is part of a set of biomarkers for stage discrimination in ovarian cancer (Kashuba et al., 2012).

NCAPD2 over-expression was found in the development of ovarian cancer together with its amplification and mutation during tumor progression (Emmanuel et al., 2011).

NCAPD3 is a potential biomarker for subtype-1 prostate cancer and for postoperative biochemical recurrence in prostate cancer (Jung et al., 2014; Lapointe et al., 2008).

NCAPG is down-regulated in patients with multiple myeloma, acute myeloid leukemia, and leukemic cells from blood or myeloma cells (Cohen et al., 2014). NCAPG may be a multi-drug resistant gene in colorectal cancer (Li et al., 2012a). NCAPG is highly up-regulated in the chromophobe subtype of human cell carcinoma but not in conventional human renal cell carcinoma (Kim et al., 2010). Up-regulation of NCAPG is associated with melanoma progression (Ryu et al., 2007). NCAPG is associated with uveal melanoma (Van Ginkel et al., 1998). NCAPG shows variable expression in different tumor cells (Jager et al., 2000).

NCKAP1L over-expression was linked with poor outcome in chronic lymphocytic leukemia. On the other hand, down-regulation of NCKAP1L in patient chronic lymphocytic leukemia cells resulted in a significant increase in their susceptibility to fludarabine-mediated killing (Joshi et al., 2007).

The non-synonymous single-nucleotide polymorphism NEK10-L513S at 3p24 was shown to be associated with breast cancer risk (Milne et al., 2014). Single-nucleotide polymorphisms in SLC4A7/NEK10 in BRCA2 carriers were shown to be associated with ER-positive breast cancer (Mulligan et al., 2011). NEK10 was described as being implicated in DNA damage response (Fry et al., 2012). NEK10 was described as a mediator of G2/M cell cycle arrest which is associated with the MAPK/ERK signaling pathway members ERK1/2, Raf-1 and MEK1 (Moniz and Stambolic, 2011).

NFATC2 has been shown to be expressed in human cancers, such as breast cancer and lung cancer. In addition, chromosomal translocation of NFATC2 and in-frame fusion with the EWSR1 oncogene have been found in Ewing sarcomas. Moreover, the NFATC2 gene was highly amplified in pancreatic cancer (Holzmann et al., 2004; Yiu and Toker, 2006; Szuhai et al., 2009; Liu et al., 2013a). In breast cancer, NFATC2 is able to induce invasion through the induction of COX-2. Others have reported that NFATC2 increases invasion of breast cancer cells via a LCN2/TWEAKR/TWEAK axis (Yiu and Toker, 2006; Gaudineau et al., 2012).

Loss of NFE2L3 predisposes mice to lymphoma development. Others have observed high levels of NFE2L3 in colorectal cancer cells, whereas aberrant expression of NFE2L3 was found in Hodgkin lymphoma. Furthermore, NFE2L3 exhibited hyper-methylation in ER positive tumors (Kuppers et al., 2003; Chevillard et al., 2011; Palma et al., 2012; Rauscher et al., 2015).

Elevated levels of NHP2L1 were found in lung tumors containing neuroendocrine elements as well as in small cell lung cancer (Jensen et al., 1994; Harken et al., 1999).

NLRC3 was shown to be down-regulated in colorectal cancer, and down-regulation was correlated with cancer progression (Liu et al., 2015d). NLRC3 was described as a potential negative regulator of inflammatory responses which interacts with different inflammasome components, such as caspases 1 and 5 (Gultekin et al., 2015).

NOA1 over-expression was shown to induce apoptosis in the human mammary adenocarcinoma cell line MCF-7 by increasing mitochondrial protein tyrosine nitration and cytochrome c release (Parihar et al., 2008a). NOA1 was shown to regulate apoptosis of human neuroblastoma cells (Parihar et al., 2008b).

NOD2 is associated with colorectal cancer, risk of gastric cancer, MALT lymphoma, breast cancer, lung cancer, laryngeal cancer and prostate cancer (Kang et al., 2012; Liu et al., 2014c; Castano-Rodriguez et al., 2014; Ahangari et al., 2014). NOD2 is associated with lymph node metastasis in urothelial bladder cancer (Guirado et al., 2012). NOD2 gene polymorphisms may be associated with altered risk of testicular, liver, gallbladder, biliary tract, pancreatic, small bowel, kidney and skin cancer, non-thyroid endocrine tumors, lymphoma and leukemia (Kutikhin, 2011).

NPLOC4 was shown to be associated with p97 and Ufd1 in a complex mediating the alternative NF-kB pathway, which has been implicated in cancer (Zhang et al., 2015o).

NR4A2 is highly expressed in several cancers such as bladder, colorectal cancer and gastric cancer. In contrast, down-regulation of NR4A2 expression was observed in breast cancer compared to normal breast tissues (Holla et al., 2006; Inamoto et al., 2008; Llopis et al., 2013; Han et al., 2013). In nasopharyngeal carcinoma, high cytoplasmic expression of NR4A2 was significantly correlated with tumor size, lymph node metastasis and clinical stage. In addition, patients with higher cytoplasmic NR4A2 expression exhibited a significantly lower survival rate compared to those with lower cytoplasmic NR4A2 expression (Wang et al., 2013f).

siRNAs targeting MAPK inhibit cervical cancer cell line growth and lead to a down-regulation of NUP188 (Huang et al., 2008; Yuan et al., 2010). NUP188 seems to be a target of the tumor suppressor gene BRCA1 in breast cancer (Bennett et al., 2008). NUP188 is required for the chromosome alignment in mitosis through K-fiber formation and recruitment of NUMA to the spindle poles (Itoh et al., 2013).

NUP205 is stabilized by TMEM209. This interaction is a critical driver for lung cancer proliferation (Fujitomo et al., 2012).

NUP62 is associated with drug resistance in cultured high-grade ovarian carcinoma cells (Kinoshita et al., 2012).

Over-expression of OPA1 was detected in oncocytic thyroid tumors as well as lung adenocarcinoma (Fang et al., 2012; Ferreira-da-Silva et al., 2015). Others reported that hepatocellular carcinoma cells can be sensitized to sorafenib-induced apoptosis by OPA1 siRNA knockdown. Furthermore, silencing of OPA1 expression resulted in reduced cisplatin resistance, increased release of cytochrome c and activation of caspase-dependent apoptotic pathway (Fang et al., 2012; Zhao et al., 2013b).

Elevated levels of ORC2 have been observed in metastatic clear-cell renal-cell carcinoma specimens (Tan et al., 2008). Researchers have demonstrated that pancreatic cancer cells expressing the Plk1 non-phosphorylatable mutant of ORC2 are more sensitive to gemcitabine treatment (Song et al., 2013a).

OSBPL10 was shown to be an oncogene mutated in breast cancer (Pongor et al., 2015). OSBPL10 was shown to be a target of aberrant somatic hyper-mutation associated with primary central nervous system lymphoma (Vater et al., 2015).

PAK6 was shown to be up-regulated in colon cancer tissues and cell lines and hepatocellular carcinoma (Chen et al., 2014b; Tian et al., 2015). PAK6 was shown to be down-regulated in clear cell renal cell carcinoma (Liu et al., 2014e). PAK6 was shown to promote chemoresistance and progression in colon cancer and motility and invasion of prostate cancer cells in the cell line LNCap (Liu et al., 2013c; Chen et al., 2015b). PAK6 is associated with prostate cancer (Zapatero et al., 2014). PAK6 is associated with unfavorable overall survival and recurrence-free survival in clear cell renal cell carcinoma, poor prognosis in hepatocellular carcinoma and drug (gefitinib) resistance in head and neck cancer cell lines (Chen et al., 2014b; Liu et al., 2014e; Hickinson et al., 2009). PAK6 is a prognostic biomarker for adjuvant 5-FU chemotherapy in stage II and III colon cancer, overall and disease-free survival in colon cancer and overall survival as well as recurrence-free survival in clear cell renal cell carcinoma after nephrectomy (Liu et al., 2014e; Chen et al., 2015b). PAK6 may be a useful marker to distinguish uterine cervical adenocarcinoma from uterine cervical squamous cell carcinoma (Lee et al., 2010).

PARD6B was shown to be a novel candidate target gene of p53 (Garritano et al., 2013). PARD6B was shown to be up-regulated in breast cancer cell lines (Cunliffe et al., 2012). PARD6B was shown to play a role in morphogenesis of the human epithelial colorectal adenocarcinoma cell line Caco-2 (Durgan et al., 2011). PARD6B was shown to be regulated by the oncogene steroid receptor coactivator-3 in the breast cancer cell line MCF-7 (Labhart et al., 2005).

PARP10 was shown to be associated with apoptosis, NF-kB signaling, and DNA damage repair and might have a function in cancer biology (Kaufmann et al., 2015). PARP10 was shown to be a regulator of NF-kB signaling (Verheugd et al., 2013). PARP10 was shown to interact with the proto-oncogene c-Myc (Yu et al., 2005).

PARP14 is one factor that mediates proliferation, chemo-resistance and survival of metastatic prostate cancer cells (Bachmann et al., 2014). PARP14 is highly expressed in myeloma plasma cells and associated with disease progression and poor survival. PARP14 is critically involved in JNK2-dependent survival. PARP14 was found to promote the survival of myeloma cells by binding and inhibiting JNK1 (Barbarulo et al., 2013).

Researchers have detected elevated levels of mRNA and protein of PARP3 in primary glioblastoma tissues. Another group found down-regulation of PARP3 in breast cancer as well as in non-small cell lung cancer (Frias et al., 2008; Bieche et al., 2013; Quan et al., 2015a). Silencing of PARP3 gene resulted in decreased cell proliferation and inhibition of tumor growth in vivo in a glioblastoma xenograft mouse model. In lung cancer cell lines, miR-630 reduced apoptosis by downregulating several apoptotic modulators such as PARP3 (Cao et al., 2014; Quan et al., 2015a).

PARPBP was shown to be up-regulated in pancreatic cancer (O'Connor et al., 2013). PARPBP was shown to be potentially associated with cervical cancer in the HeLa cell line (van et al., 2012).

PAWR has been shown to be down-regulated in many cancers including, breast cancer, lymphoma and renal cell carcinoma (Cook et al., 1999; Boehrer et al., 2001; Nagai et al., 2010). In addition, reduced expression of PAWR was correlated with poor prognosis in breast cancer patients (Nagai et al., 2010; Alvarez et al., 2013). Phosphorylation of PAWR by Akt results in its binding and sequestration in the cytoplasm hence preventing apoptosis in prostate cancer cells (Goswami et al., 2005).

PBXIP1 was shown to be up-regulated in colorectal cancer, oral squamous cell carcinoma, high-grade glioma, ependymoma and liver cancer (Xu et al., 2013b; van Vuurden et al., 2014; Okada et al., 2015; Feng et al., 2015b). PBXIP1 is associated with breast cancer and hepatocellular carcinoma (Okada et al., 2015; Bugide et al., 2015; Wang et al., 2008). PBXIP1 promotes cell migration and invasion in colorectal cancer (Feng et al., 2015b). PBXIP1 is associated with poor clinical outcome in colorectal cancer and overall survival in leiomyosarcoma (Silveira et al., 2013; Feng et al., 2015b).

PCBP4 was shown to be down-regulated in lung cancer (Pio et al., 2004).

PDIA3 may be used as a biomarker and in the diagnosis of tumors (Shishkin et al., 2013). PDIA3 is differentially expressed in gliomas (Deighton et al., 2010). PDIA3 is implicated in human pathology including cancer and Alzheimer's disease (Coe and Michalak, 2010). PDIA3 is an auxiliary factor of TAP which loads viral and self-peptides on MHC class I (Coe and Michalak, 2010; Abele and Tampe, 2011).

PHB activates the Raf/MEK/ERK pathway which is involved in cell growth and malignant transformation (Rajalingam and Rudel, 2005). PHB is a potential biomarker in nasopharyngeal carcinoma that predicts the treatment response to radiotherapy (Chen et al., 2015e). PHB was identified in the proteomic analysis of drug-resistant cancer cells, drug action, and disease state tissues (Guo et al., 2013). PHB is over-expressed in many cancer entities (Zhou and Qin, 2013). The core protein of hepatitis C virus, which is a major risk factor for hepatocellular carcinoma, induces over-production of oxidative stress by impairing prohibitin (Theiss and Sitaraman, 2011; Schrier and Falk, 2011; Koike, 2014). PHB is differentially expressed in gliomas (Deighton et al., 2010).

PHF20L1 was shown to be associated with breast cancer in the cell line ZR-75-30 (Schulte et al., 2012). PHF20L1 is associated with ovarian cancer (Wrzeszczynski et al., 2011).

PHKG2 is frequently methylated in papillary thyroid cancer (Kikuchi et al., 2013). PHKG2 is de-regulated in endometrial carcinomas and may function as a molecular biomarker (Colas et al., 2011).

PHRF1 is associated with acute promyelocytic leukemia (Prunier et al., 2015). PHRF1 was shown to be deleted or silenced in breast cancer (Ettahar et al., 2013).

Elevated levels of PI4KA were observed in hepatocellular carcinoma versus normal liver tissue. In addition, the PI4KA gene was detected in pancreatic cancer cell line (Ishikawa et al., 2003; Ilboudo et al., 2014). Patients suffering from hepatocellular carcinoma with higher PI4KA mRNA concentrations had a higher risk of tumor recurrence as well as shorter disease-specific survival (Ilboudo et al., 2014). Recently, PI4KA has been identified to be involved in cell proliferation and resistance to cisplatin treatment in a medulloblastoma cell line. Others have revealed that PI4KA plays a crucial role in invasion and metastasis in pancreatic cancer (Ishikawa et al., 2003; Guerreiro et al., 2011).

Researchers have demonstrated the use of loss of GPI-anchored protein expression resulting from PIGA mutation as a new technique for finding mutator (Mut) phenotypes in cancer (Chen et al., 2001). Recent work has revealed that PIGA causes apoptosis in rat C6 glioma cells. In addition, cytosolic accumulation of cytochrome c, caspase-3 activation and DNA fragmentation were observed in PIGA-treated cells. Others have reported that leukemic cells with PIGA mutations were less susceptible than their control counterparts to be killed by natural killer cells in vitro (Nagakura et al., 2002; Chelli et al., 2005).

Single nucleotide polymorphism in the PIGK gene was detected in patients affected by colorectal cancer. Another report observed down-regulation of PIGK mRNA level in bladder carcinoma, hepatocellular carcinoma and colon carcinoma (Nagpal et al., 2008; Dasgupta et al., 2012).

PJA1 was shown to be up-regulated in gastric cancer (Mishra et al., 2005a).

Over-expression of PJA2 was found in lysates from papillary thyroid cancer and glioblastoma samples compared to anaplastic thyroid cancers (Cantara et al., 2012; Lignitto et al., 2013). In addition, PJA2-FER tyrosine kinase mRNA chimeras were found to be associated with poor postoperative prognosis in non-small cell lung cancer (Kawakami et al., 2013). Recent work has demonstrated that PJA2 is a key element in controlling cAMP dependent PKA activity and pro-survival signaling (Hedrick et al., 2013).

PKHD1L1 was shown to be expressed as a fusion transcript in T-cell large granular lymphocyte leukemia (lzykowska et al., 2014).

In gastric cancer, elevated levels of PLA2G6 were correlated to tumor size, tumor differentiation, TNM stage and it was an independent predictor of survival for patients with gastric cancer (Wang et al., 2013h). Over-expression of PLA2G6 was detected in a variety of human cancers, including cholangiocarcinomas, gastric cancer, colorectal cancer, lung cancer, pancreatic cancer, bladder cancer and Barrett's adenocarcinoma (Wu et al., 2002; Lagorce-Pages et al., 2004; Cai et al., 2013a; Wang et al., 2013h). Bromoenol lactone, an inhibitor of PLA2G6 caused an increase in apoptosis in ovarian cancer cells as well as inducing cell cycle arrest in S- and G2/M-phases (Song et al., 2007).

Several publications have shown up-regulation of PLAUR in various tumors such as urothelial neoplasia of the bladder, colorectal cancer and breast cancer (Bianchi et al., 1994; Illemann et al., 2014; Dohn et al., 2015). Overexpression of PLAUR was correlated with overall survival of colorectal and gastric cancer patients (Yang et al., 2000; Seetoo et al., 2003; Alpizar-Alpizar et al., 2012).

PLCH1 is associated with squamous cell carcinoma of the lungs (Zhang et al., 2013d).

PLEKHA8 was shown to be associated with colorectal cancer (Eldai et al., 2013). PLEKHA8 was shown to be associated with responsiveness to 5-fluorouracil in primary breast cancer culture cells (Tsao et al., 2010).

Recent work identified somatic missense mutations of PLXNC1 and copy number loss in pancreatic ductal adenocarcinomas and melanoma. Another group showed a significant loss of PLXNC1 in metastatic melanoma compared with primary melanoma. Others have reported down-regulation of PLXNC1 in acute myeloid leukemia (Stirewalt et al., 2008; Lazova et al., 2009; Balakrishnan et al., 2009). It appears that PLXNC1 significantly inhibits migration and proliferation in melanoma (Chen et al., 2013c).

POLN was shown to be borderline significant in lung cancer in a gene-based association analysis (Kazma et al., 2012). POLN was shown to be associated with increased melanoma risk in melanoma families with and without CDKN2A mutations (Liang et al., 2012b). POLN was shown to be involved in DNA repair and is associated with homologous recombination and cross-link repair (Moldovan et al., 2010). POLN was shown to be disrupted by translocation breakpoints in neuroblastoma and therefore might play a role in neuroblastoma development (Schleiermacher et al., 2005).

RNA polymerase I (Pol I) activity is commonly deregulated in human cancers. POLR1A functions as the Pol I large catalytic subunit protein and may therefore represent a therapeutic target in cancer (Colis et al., 2014). Furthermore, drug induced POLR1A destruction was shown to be associated with cancer cell killing across NCI60 cancer cell lines (Peltonen et al., 2014). Interference of POLR1A was shown to inhibit rRNA synthesis and to hinder cell cycle progression in cells with inactivated p53. Thus, POLR1A may be a novel selective target to hinder proliferation of p53-deficient cancer cells (Donati et al., 2011).

POLR1B was shown to be regulated by the proto-oncogene c-Myc (Poortinga et al., 2011). POLR1B was shown to be associated with the pathogenesis of therapy-related acute myeloid leukemia (Cahan and Graubert, 2010).

A recent study has identified POM121 as a PAX5 fusion protein in leukemia and childhood acute lymphoblastic leukemia (Nebral et al., 2009; Fortschegger et al., 2014).

Low levels of PPIP5K1 were found in the MCF7DAP3kd and MDA-MB-231 DAP1kd breast cancer cell lines (Wazir et al., 2015a; Wazir et al., 2015b). High levels of PPIP5K1 have been shown to promote the induction of the pro-apoptotic gene TRAIL, whereas anti-apoptotic genes like BCL2, BIRC3 and PRKCE were suppressed. Moreover, PPIP5K1 is able to induce caspase activation. A recent work has revealed that PPIP5K1 induces cancer cell migration, invasion and tumor metastasis via LKB1 inactivation (Rao et al., 2015; Kumar et al., 2015).

Mutations in the PPP2R1A gene have been attributed to various cancers such as breast cancer, prostate cancer and uterine serous carcinomas. Others observed that mutations in PPP2R1A were infrequent in ovarian carcinoma, endometrioid cancer and absent in clear cell and carcinosarcoma subtypes (Calin et al., 2000; Shih et al., 2011; Cheng et al., 2011; Nagendra et al., 2012; Rahman et al., 2013). Researchers have demonstrated that the PRAME was shown to be up-regulated in multiple myeloma, clear cell renal cell carcinoma, breast cancer, acute myeloid leukemia, melanoma, chronic myeloid leukemia, head and neck squamous cell carcinoma and osteosarcoma cell lines (Dannenmann et al., 2013; Yao et al., 2014a; Zou et al., 2012; Szczepanski and Whiteside, 2013; Zhang et al., 2013b; Beard et al., 2013; Abdelmalak et al., 2014; Qin et al., 2014). PRAME is associated with myxoid and round-cell liposarcoma (Hemminger et al., 2014). PRAME is associated with shorter progression-free survival and chemotherapeutic response in diffuse large B-cell lymphoma treated with R-CHOP, markers of poor prognosis in head and neck squamous cell carcinoma, poor response to chemotherapy in urothelial carcinoma and poor prognosis and lung metastasis in osteosarcoma (Tan et al., 2012; Dyrskjot et al., 2012; Szczepanski et al., 2013; Mitsuhashi et al., 2014). PRAME is associated with lower relapse, lower mortality and overall survival in acute lymphoblastic leukemia (Abdelmalak et al., 2014). PRAME may be a prognostic marker for diffuse large B-cell lymphoma treated with R-CHOP therapy (Mitsuhashi et al., 2014).

Several publications have shown that translocation found in papillary renal cell carcinoma leads to the fusion of a PRCC gene to the TFE3 transcription factor (Sidhar et al., 1996; Weterman et al., 1996; Weterman et al., 2001).

Some researchers have observed a significant increase in PRKAR1A expression in undifferentiated thyroid carcinomas compared to normal thyroid tissue and differentiated thyroid tumors. On the contrary, down-regulation of PRKAR1A expression was reported in a subset of odontogenic tumors. Another group revealed that PRKAR1A could be involved in the pathogenesis of odontogenic myxomas as well as in sporadic adrenocortical adenomas (Bertherat et al., 2003; Perdigao et al., 2005; Ferrero et al., 2015; Sousa et al., 2015).

PRKDC is a frequently mutated gene in endometriosis-associated ovarian cancer and breast cancer (Er et al., 2016; Wheler et al., 2015). PRKDC is up-regulated in cancerous tissues compared with normal tissues in colorectal carcinoma. Patients with high PRKDC expression show poorer overall survival (Sun et al., 2016).

Over-expression of PRKX was detected in keratocystic odontogenic tumor of the jaw bones (Kong et al., 2015). It was reported that down-regulation of PRKX sensitized kidney carcinoma and melanoma-cell lines against Sunitinib. Similarly, decreased levels of PRKX were detected in the three FOLR1 siRNA-treated taxol-resistant nasopharyngeal carcinoma cells (Bender and Ullrich, 2012; Song et al., 2015b).

Studies have detected expression of PRKY in prostate cancer tissues, whereas in gonadoblastoma PRKY expression was undetectable (Dasari et al., 2001; Lau and Zhang, 2000; Su et al., 2006).

PRPF8 is associated with poor prognosis in acute myeloid leukemia and drug resistance in Mcl1-dependent neuroblastoma (Laetsch et al., 2014; Kurtovic-Kozaric et al., 2015).

PRRC1 was shown to be fused with MLL in secondary acute lymphoblastic leukemia (Douet-Guilbert et al., 2014).

It has been reported that PSAP is amplified and over-expressed in a number of androgen independent human prostate cancer cell lines, breast cancer cell lines and esophageal squamous cell carcinoma (Koochekpour et al., 2005b; Pawar et al., 2011; Wu et al., 2012f). Furthermore, high mRNA levels of PSAP were significantly linked with shorter progression-free survival in patients suffering from breast cancer with recurrent disease treated with first-line tamoxifen therapy (Meijer et al., 2009). Recent studies showed that PSAP induces cell proliferation, migration and invasion in prostate cancer cell lines (Lee et al., 2004; Koochekpour et al., 2005a).

Single nucleotide polymorphisms in the PSMA4 gene have been associated with the risk of lung cancer in Chinese Han population. Others reported that single nucleotide polymorphisms in the PSMA4 gene are no major contributors to non-small cell lung cancer susceptibility. In addition, over-expression of PSMA4 was observed in lung tumors compared to normal lung tissues (Liu et al., 2008a; Liu et al., 2009b; Yongjun Zhang et al., 2013; Wang et al., 2015e).

Up-regulation of PSMC2 has been reported in tumors of transgenic mice as well as in human hepatocellular carcinoma (Cui et al., 2006). It has been postulated that PSMC2 could play an important role in the apoptosis and partial differentiation of acute promyelocytic leukemia cell line (Wang et al., 2003).

PSMC3 was identified as human gastric carcinoma-associated antigen. In addition, PSMC3 was able to react with sera from patients suffering from hepatocellular carcinoma (Zeng et al., 2007; Uemura et al., 2003).

PSMC4 is significantly and coherently up-regulated in prostate carcinoma cells compared with the corresponding adjacent normal prostate tissue (Hellwinkel et al., 2011).

Increased PSMD4 levels were detected in colon cancer, myeloma and hepatocellular carcinoma (Arlt et al., 2009; Midorikawa et al., 2002; Shaughnessy, Jr. et al., 2011).

Increased expression of PSMD8 in the peripheral lung may be potentially informative as to what critical cell populations are involved in the development of invasive cancers (Zhou et al., 1996).

PTPLAD2 was shown to be down-regulated in esophageal squamous cell carcinoma, which is correlated with poor prognosis (Zhu et al., 2014b). PTPLAD2 was shown to interact with STAT3 and to inhibit tumor proliferation upon up-regulation. Thus, PTPLAD2 is a potential tumor suppressor and prognostic indicator as well as a possible target for esophageal squamous cell carcinoma treatment (Zhu et al., 2014b). PTPLAD2 was described as a novel candidate tumor suppressor gene encompassed within homozygously deleted loci in glioblastoma (Nord et al., 2009).

Down-regulation of PTPN2 protein levels were observed in a subset of human breast cancer cell lines. In addition, PTPN2 was deleted in all human T-cell acute lymphoblastic leukemias. Furthermore, a bi-allelic inactivation of the PTPN2 gene was identified in the Hodgkin's lymphoma cell line SUP-HD1 (Kleppe et al., 2010; Kleppe et al., 2011a; Kleppe et al., 2011 b; Shields et al., 2013). Recent work has revealed that PTPN2 gene loss and lower mRNA levels were correlated with poor prognosis in breast cancer (Karlsson et al., 2015). It seems that PTPN2 acts as classical tumor suppressor via inhibition of JAK/STAT signaling pathways (Kleppe et al., 2011 b).

Elevated levels of PTPRU expression were found in gastric cancer tissues as well as in glioma. Others have reported PTPRU to act as a tumor suppressor in colon cancer (Yan et al., 2006; Zhu et al., 2014c; Liu et al., 2014i). Furthermore, knockdown of PTPRU repressed growth and motility in gastric cancer, whereas in glioma it suppressed proliferation, survival, invasion, migration and adhesion. In breast cancer, PTPRU prevents tumor growth and the formation of metastases (Zhu et al., 2014c; Liu et al., 2014i; Liu et al., 2015f).

PWP1 was shown to be up-regulated in pancreatic cancer (Honore et al., 2002).

Over-expression of PYGL was observed in a multidrug-resistant cancer cell line. In addition, polymorphisms in the PYGL gene were correlated with higher risk of relapse in childhood acute lymphoblastic leukemia (Heim and Lage, 2005; Yang et al., 2012c).

RAD54L2 is associated with shorter overall survival in gastrointestinal stromal tumors (Schoppmann et al., 2013).

RALGAPB depletion was shown to cause chromosome misalignment and decrease of mitotic cyclin B1, whereas over-expression interfered with cell division. Deregulation of RALGAPB might cause genomic instability, leading to carcinogenesis (Personnic et al., 2014). Suppression of the Ral GTPase activating protein was shown to cause mTORC1-dependent pancreatic tumor cell invasion, indicating a crosstalk between the Ral and mTOR signaling networks. MTOR signaling is associated with cancer (Martin et al., 2014).

Several publications have observed diminished RARRES3 expression in basal cell carcinomas and in advanced squamous cell carcinomas (DiSepio et al., 1998; Duvic et al., 2000; Duvic et al., 2003). In addition, RARRES3 was shown to inhibit RAS signaling pathways in cervical cancer cells (Tsai et al., 2006). In skin cancer, RARRES3 has been shown to induce pericentrosomal organelle accumulation, which in turn resulted in reduced cyclin D1, cyclin E and cyclin A levels and increased p21 level. Moreover, in testicular cancer cells RARRES3 significantly inhibited cell migration and invasion (Scharadin et al., 2011; Wu et al., 2012b).

RASAL2 is a RAS-GTPase-activating protein with tumor suppressor functions in estrogen receptor-positive breast cancer, ovarian cancer and lung cancer (Huang et al., 2014d; Li and Li, 2014). In contrast, RASAL2 is oncogenic in triple-negative breast cancer and drives mesenchymal invasion and metastasis (Feng et al., 2014b).

RASGEF1B was described as a promoter of Ras activation which is regulated by the cell cycle-associated transcription factor E2F1 (Korotayev et al., 2008).

RBM47 is associated with breast cancer progression and metastasis (Vanharanta et al., 2014).

Recent work revealed down-regulation of RCC1 in poorly differentiated gastric cell lines and gastric carcinoma tissues. Others have reported elevated levels of RCC1 in response to PTEN expression in a PTEN-null T-cell leukemia line (Huang et al., 2005b; Lin et al., 2015c). In gastric cancer, loss of RCC1 expression was associated with tumor differentiation and depth of invasion (Lin et al., 2015c).

REC8 encodes REC8 meiotic recombination protein a member of the kleisin family of structural maintenance of chromosome protein partners (RefSeq, 2002). A recent study has revealed that the REC8 gene is heterogeneously expressed in patients with cutaneous T-cell lymphoma as well as in patient-derived cell lines. Others have shown that REC8 was hypermethylated in melanoma. In addition, REC8 was constitutively expressed in endopolyploid tumor cells (Litvinov et al., 2014a; Furuta et al., 2006; Erenpreisa et al., 2009). Hyper-methylation of REC8 has been correlated with poor clinicopathological outcomes of patients affected by thyroid cancer, including advanced tumor, disease stages and patient mortality (Liu et al., 2015a).

Genomic rearrangement or over-expression of RFX3 has been detected in papillary tumors of the pineal region and primary testicular diffuse large B cell lymphoma. Others have reported low levels of RFX3 expression in gastric cancer cells (Twa et al., 2015; Fevre-Montange et al., 2006; Seidl et al., 2010).

Mutations in the RFX5 gene have been found in microsatellite instability colorectal cancer lesions. These findings suggest that mutations of the RFX5 gene represent a new mechanism of loss of HLA class II antigen expression in tumor cells. Recent work has shown that RFX5 is related to gastrointestinal cancer (Satoh et al., 2004; Michel et al., 2010; Surmann et al., 2015).

RHPN2 was shown to be associated with colorectal cancer (He et al., 2015). A RHPN2 polymorphism may be a prognostic biomarker for patients with surgically resected colorectal cancer (He et al., 2015). RHPN2 was shown to be associated with survival outcome, worse prognosis for disease-free survival and overall survival in colorectal cancer and decreased survival of patients with glioblastoma (Danussi et al., 2013; Kang et al., 2015a). RHPN2 was shown to play a role in the formation of human pituitary nonfunctional adenoma (Zhan and Desiderio, 2006).

RINT1 is described as an oncogene in glioblastoma multiforme and as a moderately penetrant cancer susceptibility gene seen in breast cancer as well as in Lynch syndrome-related cancers (Ngeow and Eng, 2014; Quayle et al., 2012).

RIPK3 was shown to be down-regulated in colorectal cancer, breast cancer and serous ovarian cancer (McCabe et al., 2014; Koo et al., 2015a; Feng et al., 2015a). RIPK3 expression is associated with the clinical outcome of PolyIC-based immunotherapeutic approaches in cervical cancer and better survival in the osteosarcoma cell line U2OS after 5-aminolevulic acid-mediated photodynamic therapy (Coupienne et al., 2011; Schmidt et al., 2015). RIPK3 is associated with non-Hodgkin lymphoma and lung cancer (Yang et al., 2005; Fukasawa et al., 2006; Cerhan et al., 2007). RIPK3 is an independent prognostic factor for overall survival and disease-free survival in colorectal cancer (Feng et al., 2015a). RIPK3 is a potential marker for predicting cisplatin sensitivity in apoptosis-resistant and advanced esophageal cancer (Xu et al., 2014b).

RIPK4 was shown to be down-regulated in squamous cell carcinoma of the skin (Poligone et al., 2015). RIPK4 is associated with migration and invasion in the tongue squamous cell carcinoma cell line Tca-8113, survival of diffuse large B-cell lymphoma and overall as well as disease-free survival, progression and poor prognosis in cervical squamous cell carcinoma (Wang et al., 2014h; Liu et al., 2015b; Kim et al., 2008e). RIPK4 is associated with familial pancreatic cancer (Lucito et al., 2007). RIPK4 may be a potential diagnostic and independent prognostic biomarker for cervical squamous cell carcinoma and a biomarker for tongue cancer prognosis and treatment (Wang et al., 2014h; Liu et al., 2015b).

Point mutations of the RING domain of RNF167 have been identified in human tumor samples, which abrogate ubiquitin ligase activity and function (van Dijk et al., 2014). RNF167 functions in concert with UbcH6 as an ubiquitin ligase for the putative tumor suppressor TSSC5, a gene found to be mutated in certain tumors. Together with UbcH6, RNF167 may define a novel ubiquitin-proteasome pathway that targets TSSC5 (Yamada and Gorbsky, 2006).

RNF20 was shown to be down-regulated in testicular seminoma and metastatic prostate cancer (Jaaskelainen et al., 2012; Chernikova et al., 2012).

RNF213 is associated with chronic myeloid leukemia (Zhou et al., 2013b). RNF213 is associated with poor prognosis in anaplastic lymphoma kinase positive anaplastic large cell lymphoma (Moritake et al., 2011).

RNF31 was shown to be up-regulated in breast cancer and in lung metastasis of the osteosarcoma LM8 cell line (Tomonaga et al., 2012; Zhu et al., 2015). RNF31 is associated with the activated B cell-like subtype of diffuse large B-cell lymphoma (Yang et al., 2014f; Grumati and Dikic, 2014). RNF31 is associated with cisplatin-resistance in ovarian cancer (Mackay et al., 2014).

Down-regulation of RNF40 has been reported in testicular germ cell cancer seminoma compared to normal testis. Others have also observed low levels of RNF40 in colorectal cancer (Chernikova et al., 2012; Tarcic et al., 2016). Moreover, loss of RNF40 strongly retarded the growth of prostate cancer cells (Jaaskelainen et al., 2012).

Recently, a mutation in the RQCD1 gene was identified in melanoma. In addition, over-expression of RQCD1 was found in breast cancer specimens as well as breast cancer cell lines (Ajiro et al., 2009; Wong et al., 2015). In breast cancer cell lines, RQCD1 protein was shown to interact with GIGYF1 and GIGYF2 proteins, which are involved in regulation of Akt activation. Furthermore, knockdown of RQCD1 resulted in a reduction in the Akt phosphorylation level that was induced by epidermal growth factor stimulation (Ajiro et al., 2009; Ajiro et al., 2010).

Recent work has demonstrated that over-expression of RTN2 induces anti-estrogen resistance in human breast cancer cell lines (Near et al., 2007; Makkinje et al., 2009).

Over-expression of RTN3 was detected in the saliva of patients suffering from oral squamous cell cancer. Similarly, elevated levels of RTN3 were detected in the sera of epithelial ovarian carcinoma patients in all stages, but in particular it was highest in stage III. Others have observed high levels RTN3 in leukemia and urogenital cancer (Mitchell et al., 1988; Dunzendorfer et al., 1980; Chen et al., 2009c; Jessie et al., 2013). Furthermore, it was shown that circulating RTN3 was significantly associated with the stage of tumor and survival of epithelial ovarian carcinoma patients (Zhao et al., 2007).

SAMD9 was shown to be down-regulated in breast cancer, colon cancer, non-small cell lung cancer and fibromatosis (Ma et al., 2014; Li et al., 2007). SAMD9 is associated with invasion, migration and proliferation in the non-small cell lung cancer cell line H1299, lymphatic invasion and metastasis in esophageal squamous cell carcinoma and myeloid leukemias (Nagamachi et al., 2013; Tang et al., 2014b; Ma et al., 2014).

SAMSN1 was shown to be up-regulated in glioblastoma multiforme (Yan et al., 2013c). SAMSN1 was shown to be down-regulated in hepatocellular carcinoma, multiple myeloma and in the large cell lung carcinoma cell line Calu-6 (Noll et al., 2014; Sueoka et al., 2015; Yamada et al., 2008). SAMSN1 is associated with ulcerative colitis-associated cancer and acute myeloid leukemias (Watanabe et al., 2011; Claudio et al., 2001). SAMSN1 is associated with shorter overall and recurrence-free survival in hepatocellular carcinoma and poor overall survival of glioblastoma multiforme (Yan et al., 2013c; Sueoka et al., 2015). SAMSN1 is an independent prognostic factor of hepatocellular carcinoma progression and a potential prognostic marker of multiple myeloma (Ni et al., 2012; Sueoka et al., 2015).

SCARA3 was shown to be up-regulated in ovarian/primary peritoneal carcinoma (Bock et al., 2012). SCARA3 is a predictor of multiple myeloma progression and therapeutic response (Brown et al., 2013).

Methylation of SCNN1A was detected in breast cancer cell lines as well as in neuroblastoma. A recent study suggested that SCNN1A could be implicated in the aetiology of testicular germ cell tumors, since retinoic acid suppresses the tumorigenicity of embryonal carcinoma cells (Giuliano et al., 2005; Roll et al., 2008; Caren et al., 2011). Researchers have used a cox proportional hazards model and showed that SCNN1A could predict patients' prognosis in adenocarcinoma (Endoh et al., 2004).

SEC61A1 is associated with prostate cancer (Bull et al., 2001).

SEC61G was shown to be up-regulated in gastric cancer (Tsukamoto et al., 2008). SEC61G is associated with gliomas (Neidert et al., 2013).

SESN3 was described as a unique cellular inhibitor of mTOR complex 1 (Vakana et al., 2013). SESN3 was described to be induced through the tumor suppressor FOXO3 in the context of reactive oxygen species detoxification (Hagenbuchner and Ausserlechner, 2013). SESN3 repression was shown to be induced through oncogenic Ras in the context of regulation of reactive oxygen species upon cell proliferation (Zamkova et al., 2013). SESN3 was shown to be regulated by the tumor suppressor p53 upon nerve growth factor-mediated differentiation of the PC12 cell line (Brynczka et al., 2007). SESN3 5' CpG island methylation was shown to be a novel endometrial cancer-specific marker (Zighelboim et al., 2007).

Researchers have identified SETDB1 as a novel oncogene in a zebrafish melanoma model as well as in human lung cancers. Furthermore, over-expression of SETDB1 has been found in non-small cell lung cancer, prostate cancer and glioma (Ceol et al., 2011; Rodriguez-Paredes et al., 2014; Spyropoulou et al., 2014; Sun et al., 2014d; Sun et al., 2015f). It appears that SETDB1 is able to positively stimulate the activity of the WNT-beta-catenin pathway (Sun et al., 2015f). In addition, knockdown of SETDB1 by siRNA inhibited prostate cancer cell growth, invasion, migration, reduced colony formation and induced cell cycle arrest (Sun et al., 2014d).

SGPP2 was shown to be down-regulated in sphingosine-1-phosphate enriched glioblastomas (Abuhusain et al., 2013). SGPP2 was shown to be a NF-kB dependent gene which thus might be a potential novel player in pro-inflammatory signaling (Mechtcheriakova et al., 2007).

SH3GLB2 was shown to be up-regulated in prostate cancer metastasis (Fasso et al., 2008).

SHISA5 is associated with squamous cell carcinoma of the head and neck (Ghosh et al., 2008).

Increased SIGLEC1 expression has been observed in splenic marginal cell lymphoma as well as in AIDS-related Kaposi's sarcoma. Others have found mutations in the SIGLEC1 gene to be linked to the development of pancreatic ductal adenocarcinoma (Zhou et al., 2012a; Cornelissen et al., 2003; Marmey et al., 2006). Elevated levels of SIGLEC1 expression correlated with a better prognosis in patients suffering from colorectal carcinoma and malignant melanoma (Ohnishi et al., 2013; Saito et al., 2015).

SIN3A was shown to be associated with invasion in the lung adenocarcinoma cell line A549 (Das et al., 2013b). SIN3A is associated with breast cancer (Ellison-Zelski and Alarid, 2010). SIN3A was shown to be down-regulated in non-small cell lung cancer (Suzuki et al., 2008).

Over-expression of SKIL has been observed in human breast cancer cell lines, lung adenocarcinoma cell lines, melanoma and osteosarcoma. Others reported that SKIL was amplified in primary esophageal squamous cell carcinomas (Imoto et al., 2001; Zhang et al., 2003; Zhu et al., 2007). In breast cancer, reduced expression of SKIL was associated with longer distant disease-free survival in estrogen receptor-positive patients (Zhang et al., 2003).

A study has revealed that the highest SLC15A2 mRNA levels were found on prostate cancer cell line LNCaP compared to PC-3 and DU145 cells. Others reported that genomic variants in the SLC15A2 gene could be associated with sorafenib response in patients suffering from hepatocellular carcinoma (Tai et al., 2013; Lee et al., 2015).

SLC15A3 is associated with colorectal cancer (Zhou et al., 2013a). SLC15A3 was shown to be associated with prostate cancer in the prostate cancer cell lines LNCaP, DU-145, PC-3 and MDA2b (Ibragimova et al., 2010).

Down-regulation of SLC16A2 was reported in medullary thyroid carcinomas compared to non-tumor thyroid tissue (Hudson et al., 2013).

A report has shown that the expression of SLC25A14 was significantly and negatively associated with postmenopausal human breast tumors with a low ERalpha/ERbeta ratio. Others have observed elevated levels of SLC25A14 in breast cancer cell lines with low ERalpha/ERbeta ratio. In addition, high levels of SLC25A14 were found in colonic cancer cells, which were correlated with mitochondrial dysfunction (Santandreu et al., 2009; Nadal-Serrano et al., 2012; Sastre-Serra et al., 2013).

SLC28A3 was shown to be down-regulated in pancreatic ductal adenocarcinoma (Mohelnikova-Duchonova et al., 2013a). SLC28A3 is associated with clinical outcome in metastatic breast cancer treated with paclitaxel and gemcitabine chemotherapy, overall survival in gemcitabine treated non-small cell lung cancer and overall survival in gemcitabine-based chemoradiation treated pancreatic adenocarcinoma (Li et al., 2012c; Lee et al., 2014b; Marechal et al., 2009). SLC28A3 is associated with fludarabine resistance in chronic lymphocytic leukemia and drug resistance in T-cell leukemia (Karim et al., 2011; Fernandez-Calotti et al., 2012).

SLC29A3 is associated with overall survival in non-small cell lung cancer patients treated with gemcitabine-based chemotherapy and overall survival in pancreatic cancer patients treated with nucleoside analogs (Mohelnikova-Duchonova et al., 2013a; Chen et al., 2014f). SLC29A3 is a potential prognostic biomarker for patients with advanced non-small cell lung cancer who receive gemcitabine (Chen et al., 2014f).

The expression of SLC34A2 was significantly different between surgical samples of non-small cell lung cancer and normal tissues. Furthermore, low levels of SLC34A2 expression were found in lung adenocarcinoma cell lines. Others have demonstrated that SLC34A2 could be the target of MX35, an antibody developed to treat ovarian cancer (Yin et al., 2008; Yang et al., 2014c; Wang et al., 2015k). Moreover, up-regulation of SLC34A2 in lung adenocarcinoma cell lines was able to significantly inhibit cell viability and invasion in vitro (Wang et al., 2015k). On the other hand, decreased SLC34A2 expression sensitized breast cancer stem cells to doxorubicin via SLC34A2-Bmi1-ABCC5 signaling (Ge et al., 2015).

SLC35B3 is associated with colorectal carcinoma (Kamiyama et al., 2011). SLC35B3 was shown to be associated with chemotherapy resistance in ovarian cancer (Cheng et al., 2010).

SLC35E1 was shown to be associated with rectal carcinoma response to neoadjuvant radiochemotherapy (Rimkus et al., 2008).

Down-regulation of SLC35E2 has been reported in neuroblastoma (Thorell et al., 2009).

The SLC35E2B transcripts showed significantly lower expression in unfavorable neuroblastoma tumors (Thorell et al., 2009).

Over-expression of SLC4A2 has been observed in colon cancer and hepatocellular carcinoma. On the other hand, SLC4A2 expression was down-regulated in gastric cancer (Wu et al., 2006; Yang et al., 2008b; Song et al., 2012). In colon cancer, elevated levels of SLC4A2 were correlated with poor prognosis (Song et al., 2012). In addition, inhibition of SLC4A2 expression reduced cell viability, arrested cell cycle at sub-G1 phase, and induced cell apoptosis in poorly differentiated hepatocellular carcinoma cells (Hwang et al., 2009).

SLC7A8 is associated with leiomyoma (Xia et al., 2010; Luo et al., 2009). SLC7A8 was shown to be associated with drug resistance in ovarian cancer cell line W1 variants (Januchowski et al., 2013). SLC7A8 was shown to be up-regulated in the estrogen receptor alpha positive breast cancer cell line T-47D (Thakkar et al., 2010).

Several publications have reported increased expression of SMARCC1 mRNA and protein in prostate cancer, colorectal cancer and cervical intraepithelial neoplasia. In contrast, SMARCC1 protein expression was not detected in ovarian cancer cell lines (Shadeo et al., 2008; Heeboll et al., 2008; Andersen et al., 2009; DelBove et al., 2011). Furthermore, over-expression of SMARCC1 was associated with poor prognosis and recurrence in colorectal cancer (Andersen et al., 2009). Researchers have shown that methylation of SMARCC1 at arginine residue R1064 affects the colony-formation capacity of MCF7 breast cancer cells. Moreover, it seems that this modification is entirely dependent on CARM1 (Wang et al., 2014e).

SMCHD1 is associated with hematopoietic cancers (Leong et al., 2013).

SMG1 was shown to be up-regulated in pancreatic cancer (Wang et al., 2015d). SMG1 was shown to be down-regulated in hepatocellular carcinoma (Han et al., 2014). SMG1 was shown to be associated with gemcitabine and cisplatin chemosensitivity in pancreatic cancer cell lines and in the lung cancer cell line H1299 and sorafenib resistance in hepatocellular carcinoma cell lines (Xia et al., 2011; Nam et al., 2014; Wang et al., 2015d). SMG1 is associated with acute myeloid leukemia (Du et al., 2014a). SMG1 is associated with poor overall survival in hepatocellular carcinoma (Han et al., 2014).

SMPD4 was shown to be associated with cellular stress response, DNA damage and p53 activation and expression was shown to be deregulated in several types of primary tumors (Corcoran et al., 2008).

SND1 was shown to be up-regulated in non-small cell lung cancer, breast cancer, colon cancer, hepatocellular carcinoma, glioma and prostate cancer (Cappellari et al., 2014; Emdad et al., 2015; Yu et al., 2015a; Zagryazhskaya et al., 2015). SND1 is associated with chemoresistance in non-small cell lung cancer (Zagryazhskaya et al., 2015). SND1 is associated with prostate cancer, primary cutaneous malignant melanoma and cutaneous malignant melanoma metastases (Sowalsky et al., 2015; Sand et al., 2012). SND1 is associated with migration and invasion in hepatocellular carcinoma (Santhekadur et al., 2014). SND1 is associated with shorter overall survival and poor prognosis in colon cancer (Wang et al., 2012b). SND1 is a promising prostate cancer biomarker (Kuruma et al., 2009).

SNRPE was over-expressed in hepatocellular carcinoma as well as in high-grade prostate cancer (Jia et al., 2011; Anchi et al., 2012; Xu et al., 2015c). Furthermore, elevated levels of SNRPE were correlated with worse prognosis in patients with lung cancer (Valles et al., 2012). siRNA-mediated depletion of SNRPE resulted in reduction of cell viability in breast, lung and melanoma cancer cell lines (Quidville et al., 2013).

Studies have detected high levels of serum SORL1 in follicular lymphoma, diffuse large B-cell lymphoma and peripheral T-cell lymphoma patients compared to healthy controls. Another report also observed elevated levels of SORL1 in acute leukemia patients, whereas patients with acute myeloid leukemia and acute lymphoblastic leukemia in remission exhibited significantly decreased SORL1 levels. Additionally, down-regulation of SORL1 was also seen in high-grade astrocytomas (MacDonald et al., 2007; Sakai et al., 2012; Bujo, 2012; Fujimura et al., 2014).

Over-expression of SOS1 was found in Egyptian patients suffering from bladder cancer as well as prostate cancer epithelial cells. Another report has identified missense SOS1 mutations in a single pancreatic tumor, one lung adenocarcinoma and a T-cell acute lymphoblastic leukemia cell line (Zekri et al., 2015; Swanson et al., 2008; Timofeeva et al., 2009). In prostate cancer cells, depletion of SOS1 resulted in decreased cell proliferation, migration and invasion (Timofeeva et al., 2009).

SOX17 was shown to be down-regulated in breast cancer, penile carcinoma, hepatocellular carcinoma, acute myeloid leukemia and esophageal squamous cell carcinoma (Kuo et al., 2014; Tang et al., 2014a; Yang et al., 2014b; Kuasne et al., 2015; Fu et al., 2015). SOX17 is associated with ovarian cancer, oligodendroglioma, melanoma, papillary thyroid carcinoma and gastric cancer (Oishi et al., 2012; Li et al., 2012b; Lu et al., 2014a; Li et al., 2014b; Du et al., 2015b). SOX17 is associated with poor disease-free survival and overall survival in breast cancer, progression and unfavorable survival of melanoma patients, shorter overall survival in acute myeloid leukemia and overall survival in gastric cancer (Balgkouranidou et al., 2013; Tang et al., 2014a; Lu et al., 2014a; Fu et al., 2015). SOX17 is a useful prognostic biomarker for breast cancer, melanoma, germ cell cancer and esophageal squamous cell carcinoma (Kuo et al., 2014; van der Zwan et al., 2015; Lu et al., 2014a; Fu et al., 2015).

SP140 was shown to be up-regulated in laryngeal squamous cell carcinoma (Zhou et al., 2007). SP140 is associated with chronic lymphocytic leukemia, multiple myeloma and acute promyelocytic leukemia (Bloch et al., 1996; Lan et al., 2010; Kortum et al., 2015).

SPG11 was shown to be down-regulated in the gastric cancer cell line HSC45-M2 in response to treatment with alpha-emitter (213)Bi conjugated antibodies and may be a potential new target for selective elimination of tumor cells (Seidl et al., 2010).

Elevated expression and activity of SPLTC1 was detected in malignant tissues and in endometrial cancer tissue (Carton et al., 2003; Knapp et al., 2010). Moreover, SPTLC1 could be used as a potential therapeutic target to alleviate imatinib resistance in BCR-ABL-positive leukemia cells (Taouji et al., 2013).

SPTLC3 is associated with invasive micropapillary carcinoma of the breast (Gruel et al., 2014).

SRGAP1 was shown to be associated with glioblastoma multiforme in the cell lines U87-IM3 and U251-IM3, familial forms of non-medullary thyroid carcinoma, papillary thyroid carcinoma and epithelial ovarian cancer (He et al., 2013; Chen et al., 2014c; Pereira et al., 2015; Koo et al., 2015b).

STARD10 was shown to be up-regulated in breast cancer (Olayioye et al., 2005). STARD10 is associated with poor prognosis in breast cancer (Murphy et al., 2010).

Researchers have identified single nucleotide polymorphisms as well as mutations in the STAT6 gene to be involved in the development of cervical cancer and follicular lymphoma. Moreover, over-expression of STAT6 was noted in solitary fibrous tumor, prostate and colon cancer (Ni et al., 2002; Li et al., 2008a; Yoshida et al., 2014; Zhang et al., 2014g; Yildiz et al., 2015). Others have reported that STAT6 knockdown induces the inhibition of cell proliferation, G1/S phase arrest and apoptosis in HT-29 colon cancer cells. On the contrary, un-phosphorylated STAT6 increases the expression of COX-2, thereby protecting non-small cell lung cancer against apoptosis (Zhang et al., 2006; Cui et al., 2007).

De-regulated expression of STK17A is associated with different cancer types. Decreased expression in cervical and colorectal cancer is related to the pro-apoptotic character of STK17A connected with tumor progression. STK17A in glioblastoma and head and neck cancer is over-expressed in a grade-dependent manner, maybe caused through the influence on other tumor relevant pathways like TGF-beta (Mao et al., 2013a; Thomas et al., 2013; Park et al., 2015; Bandres et al., 2004). STK17A is a direct target of the tumor suppressor gene p53 and a modulator of reactive oxygen species (ROS) (Kerley-Hamilton et al., 2005; Mao et al., 2011).

Hypermethylation of STK3 was found in soft tissue sarcoma, whereas in squamous cell carcinomas of head and neck it was less frequent. Others reported that loss of STK3 resulted in the development of hepatocellular carcinoma (Seidel et al., 2007; Zhou et al., 2009; Steinmann et al., 2009).

STK35 was shown to regulate CDKN2A and to inhibit G1- to S-phase transition in endothelial cells, thus, playing a role in the linkage of the cell cycle and migration of endothelial cells (Goya) et al., 2011).

STK38 is associated with B-cell lymphoma (Bisikirska et al., 2013). STK38 was shown to be associated with radiosensitivity in the cervical cancer cell line HeLa (Enomoto et al., 2013). STK38 was shown to be down-regulated in gastric cancer (Cui et al., 2005).

STK38L was shown to be down-regulated in human skin tumors (Hummerich et al., 2006). STK38L is associated with glioma (Deng et al., 2005).

STRADA is a regulatory partner of the tumor suppressor LKB1 (Sun et al., 2015a). STRADA was shown to play a role in cell proliferation and viability of the prostate cancer cell line LNCaP and thus may be a novel prostate cancer drug target (Dahlman et al., 2012). STRADA was shown to be involved in cell proliferation and cisplatin resistance in medulloblastoma cell lines (Guerreiro et al., 2011). STRADA was shown to be up-regulated in medulloblastoma (Guerreiro et al., 2011). STRADA was shown to be a breast cancer antigen (Scanlan et al., 2001).

Over-expression of STX1A was found in breast cancer as well as in small cell lung carcinoma. Recent work has identified STX1A as a target for the treatment of metastatic osteosarcoma (Graff et al., 2001; Diao et al., 2014; Fernandez-Nogueira et al., 2016). Studies have revealed that the expression of STX1A was significantly associated with a shorter overall survival and distant metastasis-free survival in breast cancer subtypes (Fernandez-Nogueira et al., 2016).

Inhibition of STX1A reduced the proliferation and migratory capacity of glioblastoma cells (Ulloa et al., 2015).

STYXL1 is associated with Ewing's sarcoma family tumors (Siligan et al., 2005).

SVIL is significantly down-regulated in prostate cancer tissue mainly through promoter methylation (Vanaja et al., 2006). SVIL regulates cell survival through control of p53 levels. SVIL expression is necessary for the cross-talk between survival signaling and cell motility pathways (Fang and Luna, 2013).

Researchers have observed amplifications, copy number gains and mRNA over-expression of TAF2 in high-grade serous ovarian cancers (Ribeiro et al., 2014).

Amplifications, copy number gains, or mRNA up-regulation of TAF4B has been reported in high-grade serous ovarian cancers (Ribeiro et al., 2014). In addition, TAF4B is able together with AP-1 to regulate the target gene integrin alpha 6 involved in epithelial-to-mesenchymal transition, hence changing the cancer related migration properties (Kalogeropoulou et al., 2010).

TANC2 was shown to be up-regulated in breast cancer (Mahmood et al., 2014).

Single nucleotide polymorphisms as well as loss of the TAP1 gene seem to be implicated in certain cancer types such as melanoma, cervical carcinoma, colorectal cancer and head and neck squamous cell carcinoma. On the other hand, up-regulation of TAP1 has been observed in lung cancer and ovarian serous carcinoma (Yang et al., 2003; Meissner et al., 2005; Vermeulen et al., 2007; Yamauchi et al., 2014; Zhang et al., 2015g; Nymoen et al., 2015). In addition, expression of TAP1 was significantly associated with tumor grade, clinical stage, overall survival and progression-free survival in patients affected by prostate cancer (Tahara et al., 2015). In lung cancer, loss of TAP1 inhibited cell proliferation and caused cell cycle arrest in a p53-independent manner (Zhang et al., 2015g).

Some studies did not find an association between TAP2 gene polymorphism with renal cell carcinoma and cervical cancer. In contrast, others observed a correlation between the TAP2 gene polymorphism and susceptibility to chronic lymphoid leukemia. In addition, the expression of TAP2 was reduced in breast carcinoma, gastric cancer, small cell lung carcinoma and head and neck squamous cell carcinoma (Restifo et al., 1993; Vitale et al., 1998; Kang et al., 2000; Hodson et al., 2003; Kordi Tamandani et al., 2009; Bandoh et al., 2010; Ozbas-Gerceker et al., 2013).

TCERG1 was shown to function as a transcriptional co-regulator of DACH1, a transcription factor which was shown to be associated with various types of cancer (Zhou et al., 2010).

TELO2 is de-regulated in different cancer types including leukemias, breast cancer and nasopharyngeal carcinoma (He et al., 2007; Sang et al., 2015; Kawagoe et al., 2004). Over-expression of TELO2 decreases cell cycle length, hyper-sensitizes the cell to apoptosis and increases telomere length. Inhibition of TELO2 expression arrests the cell cycle reversibly (Jiang et al., 2003). Activated TELO2 is essential for the stability of PIKK family proteins like mTOR, ATM, ATR and SMG-1. TELO2 plays an important role in the regulation of translation, cell growth and DNA damage signaling (Kaizuka et al., 2010; Horejsi et al., 2010).

TET3 was shown to be down-regulated in hepatocellular carcinoma, colorectal cancer and gastric cancer (Rawluszko-Wieczorek et al., 2015; Sajadian et al., 2015; Du et al., 2015a). TET3 was shown to be up-regulated in diffuse intrinsic pontine glioma (Ahsan et al., 2014). TET3 was shown to be associated with tumor hypoxia, tumor malignancy, and poor prognosis in breast cancer (Wu et al., 2015). TET3 was shown to be associated with TNFalpha-p38-MAPK signaling (Wu et al., 2015). TET3 was described as a regulator of 5-hydroxymethylation, an epigenetic modification associated with malignant tumors. In leiomyoma, epigenetic imbalance in the 5-hydroxymethylation content was described as a result of TET3 up-regulation which might lead to the discovery of new therapeutic targets in leiomyoma (Navarro et al., 2014). TET3 was shown to be recurrently mutated in colon cancer and may provide a potential therapeutic intervention opportunity (Seshagiri et al., 2012). TET3 was described as a potential regulator of histone modification and WNT pathways in myelodysplastic syndromes and acute myeloid leukemia (Gelsi-Boyer et al., 2009).

Over-expression of TFAP2C has been found in breast carcinomas as well as in germ cell tumors (Turner et al., 1998; Hoei-Hansen et al., 2004). It is reported that TFAP2C induces p21 expression, arrests cell cycle and suppresses the tumor growth of breast carcinoma cells (Li et al., 2006).

Down-regulation of TFDP2 was observed in human papillary carcinoma tissues, while others reported over-expression of TFDP2 in hepatocellular carcinoma compared to normal liver tissues. In addition, TFDP2 variants have been linked to ovarian cancer (Liu et al., 2003; Lapouge et al., 2005; Cunningham et al., 2009).

TH1L might play an important role in regulation of proliferation and invasion in human breast cancer, and could be a potential target for human breast cancer treatment (Zou et al., 2010).

Some researchers have reported over-expression of TIMELESS protein and mRNA in hepatocellular carcinoma as well as in colorectal cancer, cervical cancer, lung cancer and prostate cancer. On the other hand, another study reported down-regulation of TIMELESS in hepatocellular carcinomas. In addition, single nucleotide polymorphism in the TIMELESS gene were not associated with risk of prostate cancer but correlated with breast cancer risk (Lin et al., 2008b; Fu et al., 2012; Mazzoccoli et al., 2011; Yoshida et al., 2013; Mao et al., 2013b; Markt et al., 2015; Elgohary et al., 2015). In lung cancer, elevated levels of TIMELESS were associated with poor overall survival (Yoshida et al., 2013).

Over-expression and epigenetic inactivation of TLE1 have been found in various cancers including lung tumors, synovial sarcoma, malignant mesothelioma, leukemia and lymphoma (Allen et al., 2006; Fraga et al., 2008; Matsuyama et al., 2010; Seo et al., 2011; Rekhi et al., 2012). Additionally, TLE1 suppresses apoptosis induced by doxorubicin in synovial sarcoma cells. In lung cancer cell lines TLE1 was able to potentiate epithelial-to-mesenchymal transition by suppressing the tumor suppressor gene E-cadherin (Seo et al., 2011; Yao et al., 2014b). Furthermore, it was observed that trichostatin A significantly inhibited lung tumorigenesis in TLE1 transgenic mice (Liu et al., 2015c).

Over-expression of TLE3 has been observed in some malignant meningiomas compared to benign and atypical meningiomas. Others have reported elevated levels of spliced isoform of TLE3 in prostate tumors as well as in prostate tumor cell lines (Cuevas et al., 2005; Nakaya et al., 2007). Studies have revealed that TLE3 mRNA levels were predictive for progression-free survival in breast cancer patients receiving tamoxifen. In contrast, others reported that TLE3 expression does not represent a viable biomarker for taxane benefit in breast cancer. Another report demonstrated that TLE3 expression predicts a favorable response to taxane containing chemotherapy regimens in ovarian carcinoma (van et al., 2009; Samimi et al., 2012; Bartlett et al., 2015).

Recent work has identified a missense mutation in the TLE4 gene in acute myeloid leukemia. Other studies have shown over-expression of TLE4 in colorectal cancer as well as in adenomas (Greif et al., 2011; Ruebel et al., 2006; Wang et al., 2016a). In colorectal cancer, elevated levels of TLE4 were correlated with advanced Dukes stage, lymph node metastasis and poor prognosis of colorectal cancer (Wang et al., 2016a). It seems that over-expression of miR-93 negatively regulates mRNA and protein expression of TLE4 (Yu et al., 2011).

Previous studies have found over-expression of TLN1 in several tumors, including prostate cancer, oral squamous cell carcinoma, ovarian serous carcinoma and nasopharyngeal carcinoma (Sakamoto et al., 2010; Lai et al., 2011; Tang et al., 2013; Xu et al., 2015d). Over-expression of TLN1 was associated with reduced overall survival in patients suffering from oral squamous cell carcinoma (Lai et al., 2011). It appears that TLN1 S425 phosphorylation plays a crucial role in betal integrin activation, cell adhesion, migration, invasion and metastasis of prostate cancer cells. In addition, elevated levels of TLN1 are correlated with reduced invasion, migration as well as decreased malignancy in hepatocellular carcinoma cell lines (Fang et al., 2014; Jin et al., 2015).

TLR7 was shown to be up-regulated in pancreatic cancer, oral squamous cell carcinoma and hepatocellular carcinoma (Mohamed et al., 2015; Ni et al., 2015; Grimmig et al., 2015). TLR7 is associated with tumor cell proliferation and chemoresistance in pancreatic cancer (Grimmig et al., 2015). TLR7 over-expression is associated with poor clinical outcome and chemotherapy resistance in lung cancer and poor prognosis in oral squamous cell carcinoma (Ni et al., 2015; Dajon et al., 2015). TLR7 is associated with bladder cancer (Cheng et al., 2014).

TMEM14C is associated with breast cancer survival (Burleigh et al., 2015). TMEM14C is associated with tamoxifen resistance in the breast cancer cell line ZR-75-1 (Zarubin et al., 2005).

TMEM189-UBE2V1 isoform 2 (Uev1B) was shown to be associated with ubiquitin and Hrs and over-expression of the protein abrogated the ability of Hrs to colocalize with the cancer-associated protein EGFR (Duex et al., 2010).

TMPRSS13 encodes a member of the type II transmembrane serine protease family, which is known to function in development, homeostasis, infection, and tumorigenesis (RefSeq, 2002). TMPRSS13 was shown to function as a hepatocyte growth factor (HGF)-converting protease, converting pro-HGF to biologically active HGF. HGF was shown to interact with the oncogene c-Met and is associated with a variety of cancers (Hashimoto et al., 2010).

TNFAIP2 encodes TNF alpha induced protein 2 and it has been suggested to be a retinoic acid target gene in acute promyelocytic leukemia (RefSeq, 2002). TNFAIP2 rs8126 polymorphism has been significantly associated with susceptibility of head and neck squamous cell carcinoma, gastric cancer and esophageal squamous cell carcinoma. Moreover, the TNFAIP2 mRNA and protein were found to be elevated in nasopharyngeal carcinoma tumor cells compared with adjacent normal tissues. Others have observed over-expression of TNFAIP2 in glioma samples (Chen et al., 2011; Liu et al., 2011; Xu et al., 2013c; Zhang et al., 2014b; Cheng et al., 2015b). Furthermore, over-expression of TNFAIP2 was correlated with shorter distant metastasis-free survival in nasopharyngeal carcinoma patients (Chen et al., 2011).

Up-regulation of TNXB has been observed in ovarian cancer and malignant mesothelioma, whereas in peripheral nerve sheath tumors TNXB was significantly down-regulated. Recent work has identified TNXB in glioblastoma multiforme cell lines (Levy et al., 2007; Yuan et al., 2009; Polisetty et al., 2011; Kramer et al., 2015). Studies have shown that deficiency in TNXB led to tumor invasion and metastasis through the activation of the MMP2 and MMP9 genes (Matsumoto et al., 2001).

Low levels of TOB1 have been observed in gastric, lung and breast cancers. Others have shown that mice lacking TOB1 are predisposed to spontaneous formation of tumors in various tissues (Yoshida et al., 2003; Iwanaga et al., 2003; O'Malley et al., 2009; Zhang et al., 2015k). In gastric cancer, cytoplasmic expression levels of TOB1 were correlated with the depth of invasion, differentiation grade and tumor-node-metastasis stage (Zhang et al., 2015k). Down-regulation of TOB1 increased the metastasis, invasion and proliferation of gastric cancer cells (Li et al., 2015a).

Some reports have shown high staining of TOMM20 in papillary thyroid cancer compared to noncancerous thyroid tissue. Others have observed that epithelial cancer cells exhibited high levels of the mitochondrial membrane marker TOMM20. On the contrary, no significant difference in the mRNA expression of the TOMM20 gene was found in prostate cancer tissue (Whitaker-Menezes et al., 2011; Asmarinah et al., 2014; Curry et al., 2015). In gastric cancer, over-expression of TOMM20 was correlated with reduced overall survival and disease-free survival (Zhao et al., 2014c).

Over-expression of TP53I3 was found in papillary thyroid carcinoma, gemcitabine resistant non-small cell lung cancer, whereas it was down-regulated in esophageal squamous cell carcinoma and diffuse large B cell lymphoma. In addition, variant genotypes of (TGYCC)n repeats in the TP53I3 promoter were correlated with risk of squamous cell carcinoma of the head and neck. Others have reported an association of TP53I3 promoter VNTRs with generation of invasive bladder cancer (Dadkhah et al., 2013; Ito et al., 2006; Guan et al., 2013; Zhu et al., 2013a; Zhang et al., 2013a; Xu et al., 2015b). Researchers have observed that TP53I3 silencing in papillary thyroid carcinoma cell lines resulted in a reduction in the activity of the PI3K/AKT/PTEN pathway (Xu et al., 2015b).

The TPR-MET rearrangement has been detected in several cell lines derived from human tumors of non-hematopoietic origin as well as in gastric carcinoma. One study has detected a TPR-NTRK1 fusion in colorectal cancer, while TPR-ALK fusion has been seen in lung adenocarcinoma. In addition, loss or deletion of TPR gene has been reported in gastric cancer (Soman et al., 1991; Soman et al., 1990; Cunningham et al., 1997; Yu et al., 2000; Choi et al., 2014; Creancier et al., 2015). Recent work has revealed that TPR depletion leads to G0/G1 phase arrest, which in turn induces a senescent-like phenotype in tumor cell lines (David-Watine, 2011).

TPX2 was shown to be up-regulated in hepatocellular carcinoma, pancreatic cancer, cervical cancer, medullary thyroid cancer, colon cancer and prostate cancer (Vainio et al., 2012; Wei et al., 2013; Yang et al., 2014d; Jiang et al., 2014b; Miwa et al., 2015; Liang et al., 2015b). TPX2 is associated with poor prognosis in hepatocellular carcinoma, poor overall survival and lower disease free survival in high-grade serous epithelial ovarian cancer, patient outcome and poor prognosis of esophageal squamous cell carcinoma, development and progression of bladder carcinoma and poor 5-year survival in lung adenocarcinoma (Li et al., 2013c; Yan et al., 2013a; Hsu et al., 2014; Caceres-Gorriti et al., 2014; Liang et al., 2015b). TPX2 is associated with colorectal cancer, non-small cell lung cancer, head and neck squamous cell carcinoma, metastasis of ER positive breast cancer, metastasis of hepatocellular carcinoma, metastasis and disease stage of medullary thyroid cancer and metastasis of colon cancer (Martens-de Kemp et al., 2013; Wei et al., 2013; Yang et al., 2014d; Huang et al., 2014c; Geiger et al., 2014; Takahashi et al., 2015). TPX2 is a potential biomarker for early diagnosis and prognosis of hepatocellular carcinoma and for prognosis of high-grade serous epithelial ovarian cancer and colon cancer (Wei et al., 2013; Caceres-Gorriti et al., 2014; Liang et al., 2015a).

TRIM6 was shown to regulate the transcriptional activity of the proto-oncogene Myc (Sato et al., 2012b).

TRIP13 was shown to promote Mad2 localization to unattached kinetochores in the spindle checkpoint response (Nelson et al., 2015). TRIP13 over-expression was described as a hallmark of cancer cells showing chromosomal instability (Wang et al., 2014d). Premature mitotic checkpoint silencing triggered by TRIP13 over-expression was suggested to promote cancer development (Wang et al., 2014d). TRIP13 was shown to be involved in modulating tumor cell motility in breast cancer (Maurizio et al., 2016). High expression of TRIP13 in squamous cell carcinoma of the head and neck was shown to lead to aggressive, treatment-resistant tumors and enhanced repair of DNA damage and promoted error-prone non-homologous end joining (Banerjee et al., 2014). TRIP13 was described as a putative marker of prostate cancer progression which can be used to predict recurrence in prostate cancer when combined with pre-operative PSA level and Gleason score (Larkin et al., 2012). TRIP13 was described as one of several genes evidencing high genomic copy number changes in early-stage non-small cell lung cancer (Kang et al., 2008a).

Recent studies have implicated TRPS1 in several human cancers such as breast cancer, colon cancer, osteosarcoma, leukemia, endometrial cancer and prostate cancer (Chang et al., 2004; Asou et al., 2007; Chen et al., 2010; Liang et al., 2012a; Hong et al., 2013; Li et al., 2015f). In addition, TRPS1 expression was correlated significantly with improved survival in patients with breast cancer (Chen et al., 2010). Furthermore, over-expression of TRPS1 induced angiogenesis by affecting the expression of vascular endothelial growth factor in breast cancer (Hu et al., 2014).

Mutations in the TRRAP gene were found in colorectal cancer and in melanoma, whereas in thyroid and ovarian cancers mutations in the TRRAP gene were absent (Wei et al., 2011; Murugan et al., 2013; Mouradov et al., 2014; Zou et al., 2015). Furthermore, knockdown of TRRAP resulted in a decreased self-renewal of cultured brain tumor-initiating cells and sensitized the cells to temozolomide-induced apoptosis (Wurdak et al., 2010).

A single nucleotide polymorphism of the TSC2 gene was significantly associated with colon cancer. Furthermore, down-regulation of TSC2 was observed in patients suffering from hepatocellular carcinoma and acute myeloid leukemia. In one case, a mutation in the TSC2 gene seemed to be responsible for pancreatic neuroendocrine tumors. Others have noted elevated levels of phosphorylated TSC2 in non-small cell lung carcinoma (Xu et al., 2009; Yoshizawa et al., 2010; Slattery et al., 2010; Bombardieri et al., 2013; Huynh et al., 2015). Recent work has demonstrated that expression of TSC2 in ERC-18 cells increases susceptibility to apoptosis induced by OKA and the phosphatidylinositol-3' kinase inhibitor LY294002 (Kolb et al., 2005).

TSEN15 is a target of miRNA-449a, which functions as a tumor suppressor in neuroblastoma. TSEN15 plays an important role in mediating the differentiation-inducing function of miRNA-449a (Zhao et al., 2015c). TSEN15 is associated with cell differentiation potential in human fetal femur-derived cells (Mirmalek-Sani et al., 2009).

TSGA13 was shown to be down-regulated in most types of human carcinoma tissues compared to adjacent normal tissues except glioblastoma and lung cancer. Hence, an association between TSGA13 and tumor malignancy is likely (Zhao et al., 2015a).

De-regulated expression of TUBA1A and some other genes, caused by chromosomal rearrangements in radiation-transformed and tumorigenic breast cell lines, might reflect early molecular events in breast carcinogenesis (Unger et al., 2010). Using comparative proteomic analysis of advanced serous epithelial ovarian carcinoma, TUBA1A was identified as one potential predictor for chemoresistance (Kim et al., 2011c).

The differential expression of TUBA1B in combination with the expression of some other genes was associated with prognosis in mantle cell lymphoma, prediction of relapse among patients with stage II colorectal cancer and differentiation between uveal melanomas that subsequently metastasized and those that did not (Blenk et al., 2008; Agesen et al., 2012; Linge et al., 2012). TUBA1B expression was up-regulated in hepatocellular cancer tissues and proliferating hepatocellular cancer cells. An increased TUBA1B expression was associated with poor overall survival and resistance to paclitaxel of hepatocellular cancer patients (Lu et al., 2013). In ovarian cancer cells, the reduced expression of TUBA1B was associated with oxaliplatin resistance (Tummala et al., 2009).

The expression of TUBA1C was shown to be up-regulated in osteosarcoma and HCV-associated hepatocellular cancer and may be a potential biomarker for osteosarcoma tumorigenesis or well-differentiated HCV-associated hepatocellular cancer (Li et al., 2010; Kuramitsu et al., 2011).

The comparative proteomic analysis of esophageal squamous cell carcinoma (ESCC) showed an increased expression of TUBA4A (Qi et al., 2005).

In mouse liver, TUBA8 was induced after treatment with phenobarbital, a non-genotoxic carcinogen. In hepatocellular carcinoma cell lines, the over-expression of TUBA8 was shown to affect cell growth, proliferation and migration (Kamino et al., 2011).

Several publications have observed over-expression of TYK2 in human breast cancer cell lines, as well as in prostate cancers and squamous cervical carcinomas. In contrast, lack of TYK2 in mice has been linked to the development of Abelson-induced B lymphoid leukemia and lymphoma. In addition, single nucleotide polymorphism in the TYK2 gene has been associated with rectal cancer (Stoiber et al., 2004; Ide et al., 2008; Song et al., 2008; Zhu et al., 2009; Slattery et al., 2013). In prostate cancer cell lines, suppression of Tyk2 with siRNA inhibited the ability of these cells to migrate (Ide et al., 2008).

Recent work has identified a gain in copy number of the UBE2H gene in hepatocellular carcinoma. Others have observed an increase in the levels of UBE2H in breast cancer, whereas this was not the case in colon cancer (Chen and Madura, 2005; Keng et al., 2009).

Down-regulation of UBE2L6 has been observed in nasopharyngeal carcinoma, whereas in esophageal squamous cell carcinoma UBE2L6 was over-expressed (Dadkhah et al., 2013; Zhou et al., 2015a). In addition, low levels of UBE2L6 have been linked with poor outcome in patients suffering from nasopharyngeal carcinoma (Zhou et al., 2015a). Moreover, UBE2L6 has been shown to disrupt F-actin architecture and formation of focal adhesions in breast cancer cell lines as well as promoting cell migration. Furthermore, restored expression of UBE2L6 suppressed proliferation and colony formation in nasopharyngeal carcinoma cells, while at the same time inducing apoptosis (Desai et al., 2012; Zhou et al., 2015a). Researchers have postulated that UBE2L6 could be used as a biomarker of treatment response to bortezomib in patients with acute promyelocytic leukemia (Takenokuchi et al., 2015).

Elevated levels of UBE2V1 expression were detected in breast cancer samples as well as in cultured tumor cell lines. Moreover, UBE2V1 gene has been identified to be associated with the development of prostate cancer (Stubbs et al., 1999; Xiao et al., 1998; Tanner et al., 1995). Researchers have shown that UBE2V1 induced cell migration and invasion in breast cancer. Similarly, high levels of UBE2V1 promoted tumor growth and metastasis in a xenograft mouse model. NSC697923, an inhibitor of UBE2V1 was able to inhibit proliferation and survival of diffuse large B-cell lymphoma cells (Pulvino et al., 2012; Wu et al., 2014b).

Some researchers have observed over-expression of UBE3C in clear-cell renal cell carcinoma tissues compared with adjacent normal tissues. Others have also found elevated levels of UBE3C in hepatocellular carcinoma. In addition, up-regulation of UBE3C gene was reported in myeloma side-population cells (Jiang et al., 2014a; Tagawa, 2014; Wen et al., 2015). Furthermore, over-expression of UBE3C in hepatocellular carcinoma tissues was associated with decreased survival and early tumor recurrence in post-operative hepatocellular carcinoma patients (Jiang et al., 2014a).

Researchers have identified a mutation in the UBE4B gene in a patient suffering from neuroblastoma. Genome-wide association study revealed that the UBE4B gene might be involved in hepatitis B virus-related hepatocellular carcinoma. Others reported over-expression of UBE4B in breast cancer and in brain tumors (Krona et al., 2003; Zhang et al., 2010b; Wu et al., 2011 b; Zhang et al., 2014f). Moreover, down-regulation of UBE4B was correlated with poor outcome in patients with neuroblastoma (Zage et al., 2013).

UBR4 was shown to be associated with invasive micropapillary carcinoma of the breast (Gruel et al., 2014).

UNC45A was shown to be up-regulated in breast carcinoma and ovarian carcinoma (Guo et al., 2011; Bazzaro et al., 2007). UNC45A is associated with metastasis in breast cancer (Guo et al., 2011). UNC45A is associated with drug resistance in neuroblastoma (Epping et al., 2009).

Novel germline sequence variations in UNG were detected in patients affected by colorectal cancer with familial aggregation, emphasizing that these variants could be involved in disease susceptibility. In addition, UNG activity in colorectal tissue appeared to be higher in tumor tissue compared to normal bowel (Dusseau et al., 2001; Broderick et al., 2006; Marian et al., 2011; Yin et al., 2014). Furthermore, knockdown of UNG induced apoptosis in prostate cancer cell lines, reduced cell proliferation and increased cellular sensitivity to genotoxic stress. Others have observed that colon cancer cells lacking UNG are hypersensitive to pemetrexed-induced uracil accumulation, which leads to cell cycle arrest, DNA double strand break formation and apoptosis (Pulukuri et al., 2009; Weeks et al., 2013).

UQCR11 is associated with renal cell carcinoma (Sarto et al., 1997).

USP11 plays a major role in promyelocytic leukemia and pancreatic cancer (Burkhart et al., 2013; Wu et al., 2014a).

USP28 was shown to be up-regulated in intestinal cancer, bladder cancer, colon carcinoma and breast carcinoma (Guo et al., 2014; Diefenbacher et al., 2014; Popov et al., 2007). USP28 is associated with colorectal cancer and breast cancer (Wu et al., 2013b; Diefenbacher et al., 2014). USP28 over-expression is associated with low survival and poor prognosis in non-small cell lung cancer patients (Zhang et al., 2015i). USP28 is a potential prognostic marker for bladder cancer (Guo et al., 2014).

Several publications have found an association between USP9X and various types of cancer including, breast cancer, lung cancer, colon cancer, non-small cell lung cancer and low grade serous ovarian tumors (Deng et al., 2007; Peddaboina et al., 2012; Peng et al., 2015b; Hunter et al., 2015). Furthermore, elevated levels of USP9X were correlated with positive lymph node metastasis, clinical stage and a reduced overall survival rate in patients affected by non-small cell lung cancer (Wang et al., 2015j). Silencing of USP9X expression by siRNA resulted in cell apoptosis, inhibited cell growth and cell migration in hepatocellular carcinoma cell lines (Hu et al., 2015).

Over-expression of USP9Y has been observed in breast cancer and prostate cancer. Recently, a USP9Y-TTTY15 fusion was identified in a Chinese population suffering from prostate cancer. However, others have demonstrated that the USP9Y-TTTY15 fusion is not specific to prostate cancer, but it was also found in non-malignant prostate tissues as well as non-malignant tissue from other organs (Deng et al., 2007; Dasari et al., 2001; Ren et al., 2012; Ren et al., 2014).

VCPIP1 was shown to be associated with breast cancer (Kuznetsova et al., 2007). VCPIP1 is down-regulated in breast cancer (Kuznetsova et al., 2007). VCPIP1 is one of the de-ubiquitinating enzymes, being part of the ovarian tumor family (OTU) (Enesa and Evans, 2014).

In lung adenocarcinoma patients, VPRBP was correlated with poor prognosis (Wang et al., 2013a). Others have revealed that down-regulation of VPRBP-mediated phosphorylation of Histone 2A (H2AT120p) impeded cancer cell proliferation and xenograft tumor progression (Kim et al., 2013b).

VPS13D was shown to be a phosphopeptide relevant for the oncogenic phosphatidylinositol 3-kinase (PI3K) pathway which can be regulated by PI3K pathway inhibiting drugs (Andersen et al., 2010).

VTCN1 was shown to be up-regulated in lung cancer, colorectal cancer, hepatocellular carcinoma, osteosarcoma, breast cancer, cervical cancer, urothelial cell carcinoma, gastric cancer, endometrial cancer, thyroid cancer and laryngeal carcinoma (Klatka et al., 2013; Zhu et al., 2013b; Vanderstraeten et al., 2014; Shi et al., 2014b; Fan et al., 2014; Wang et al., 2014g; Leong et al., 2015; Dong and Ma, 2015; Zhang et al., 2015a; Peng et al., 2015a; Xu et al., 2015a). VTCN1 is associated with poor overall survival and higher recurrence probability in hepatocellular carcinoma and poor overall survival in osteosarcoma, urothelial cell carcinoma, pancreatic cancer, gastric cancer, cervical cancer, melanoma and thyroid cancer (Zhu et al., 2013b; Seliger, 2014; Liu et al., 2014f; Chen et al., 2014i; Fan et al., 2014; Dong and Ma, 2015; Zhang et al., 2015a). VTCN1 is associated with clear cell renal cell carcinoma (Xu et al., 2014c). VTCN1 expression levels were shown to be inversely correlated with patient survival in ovarian cancer (Smith et al., 2014). VTCN1 may be a potential prognostic indicator of urothelial cell carcinoma and gastric cancer (Shi et al., 2014b; Fan et al., 2014).

VWA1 is associated with clear-cell ovarian cancer (Cicek et al., 2013).

VWA2 was shown to be associated with colorectal cancer (Hoff et al., 2015). VWA2 was shown to be highly induced in stage II, III and IV colon cancers, colon adenomas and colon cancer cell lines. Thus, VWA2 is a novel candidate for development as a diagnostic serum marker of early stage colon cancer (Xin et al., 2005).

VWA3A was shown to be associated with survival in ovarian cancer (Madden et al., 2014).

VWDE is mutated and shows an oncogenic character in breast cancer patients (Pongor et al., 2015).

WDFY3 was shown to be down-regulated in colorectal cancer (Piepoli et al., 2012).

Recent studies have observed elevated levels of WHSC1 protein in several types of human cancers such as carcinomas of the gastrointestinal tract (esophagus, stomach, colon, anal canal), small cell lung carcinoma, prostate cancer and tumors of the urinary bladder, female genitals and skin. Others have reported that WHSC1 over-expression resulting from chromosomal translocation significantly affected the tumorigenicity of multiple myeloma cells in a xenograft model (Lauring et al., 2008; Hudlebusch et al., 2011; Yang et al., 2012d). Knock-down of WHSC1 in prostate cancer cell lines resulted in a reduction of cell proliferation, colony formation in soft agar as well as decreased cell migration and invasion. Similarly, in squamous cell carcinoma of the head and neck cell knock-down of WHSC1 resulted in significant growth suppression, induction of apoptosis, and delay of the cell-cycle progression. Furthermore, WHSC1 expression has been shown to induce cellular adhesion, clonogenic growth and tumorigenicity in multiple myeloma (Kassambara et al., 2009; Ezponda et al., 2013; Saloura et al., 2015).

Single nucleotide polymorphisms of the WRN gene have been associated with the risk of breast cancer both in a German and Australian population. Others have found a correlation between single nucleotide polymorphisms of the WRN gene and susceptibility for colorectal, prostate and esophageal cancers. In addition, aberrant methylation of WRN was observed in specimens of cervical cancer (Wirtenberger et al., 2006; Wang et al., 2011; Li et al., 2012d; Masuda et al., 2012; Sun et al., 2015d; Zins et al., 2015). Furthermore, siRNA-mediated silencing of WRN gene suppressed carcinoma cell growth in vitro (Arai et al., 2011).

Accumulating evidence reveals that the WT1 gene is highly expressed in different forms of tumors including acute myeloid leukemias, acute lymphoid leukemias, hepatocellular carcinoma and squamous cell carcinoma of the head and neck (Miwa et al., 1992; Perugorria et al., 2009; Li et al., 2015d). Additionally, over-expression of WT1 is a significant positive prognostic factor in primary high-grade serous ovarian carcinoma regarding overall survival and progression free survival. Similarly, overall survival and disease-free survival was significantly lower in acute myeloblastic leukemia patients with WT1 gene mutation. Others have also reported a correlation between the WT1 variant rs2234593 and relapse as well as overall survival in acute myeloid leukemia (Niavarani et al., 2015; Taube et al., 2016; Toogeh et al., 2016).

Some researchers have observed low XDH expression in hepatocellular carcinomas, serous ovarian cancer and breast cancer. However, others reported a significant increase in XDH activity in bilharzial bladder cancer and non-bilharzial bladder cancer, brain tumors and small-cell and non-small cell lung cancer (Kokoglu et al., 1990; Stirpe et al., 2002; Linder et al., 2005; Kaynar et al., 2005; Metwally et al., 2011; Linder et al., 2012). Moreover, down-regulation of XDH was reported to be associated with poorer prognosis in patients with serous ovarian cancer and breast cancer (Linder et al., 2005; Linder et al., 2012).

XPO4 expression is down-regulated by promoter methylation in hepatocellular cancer and associated with tumor size, histopathological classification and a significantly poor prognosis of patient's survival (Liang et al., 2011; Zhang et al., 2014a). Mutation of the catalytic subunit of the PI3K leads to a highly activated Akt/mTOR pathway and down-regulation of the tumor suppressor genes Pten, Xpo4 and Dlc1 (Kudo et al., 2011).

YBX1 has been shown to be up-regulated in various types of cancer, including colorectal, gastric, multiple myeloma and breast cancer (Bargou et al., 1997; Chatterjee et al., 2008; Wu et al., 2012g; Yan et al., 2014b). In breast cancer, over-expression of YBX1 was neither associated with lymph node status nor high histological grade, but with ER negativity, HE R2 positivity and it had an adverse impact on 5-year overall survival (Wang et al., 2015g). Researchers have shown that YBX1 may promote the proliferation, apoptosis resistance, invasion and migration of colorectal cancer cells by regulating epithelial-mesenchymal transition (Yan et al., 2014c).

The TUTase ZCCHC6 was shown to be recruited by the tumorigenesis associated RNA-binding protein Lin28 to block let-7 biogenesis. Restoring let-7 expression in cancer through TUTase inhibitors could be exploited in future drug discovery (Lin and Gregory, 2015).

ZNF583 was described as a potential biomarker for colorectal cancer (Mori et al., 2011). ZNF700 was shown to be a capture antigen for the detection of autoantibodies in colorectal cancer. In a panel with other zinc finger proteins, ZNF-specific autoantibody detection allowed the detection of colorectal cancer (O'Reilly et al., 2015).

ZNFX1 could function as a novel prostate cancer antigen (Dunphy and McNeel, 2005).

ZRANB2 has been shown to be over-expressed in grade III ovarian serous papillary carcinoma (Schaner et al., 2003; Mangs and Morris, 2008).

ZWINT was shown to be associated with the arrest of prostate cancer cell cycle progression upon inhibition of COX-2 (Bieniek et al., 2014). ZWINT expression in chronic lymphocytic leukemia cells in lymph nodes was shown to be correlated with clinical outcome (Gilling et al., 2012). ZWINT was described as an androgen receptor target gene which was shown to be up-regulated in castration-resistant prostate cancer (Urbanucci et al., 2012). ZWINT was described as a gene of particular predictive value in a prognostic model of pulmonary adenocarcinoma (Endoh et al., 2004).

ZYG11A serves as an oncogene in non-small cell lung cancer and influences CCNE1 expression (Wang et al., 2016b).

ZZEF1 was described to be potentially linked to cancer and is located in a chromosome region associated with medulloblastomas (Cvekl, Jr. et al., 2004).

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

As used herein and except as noted otherwise all terms are defined as given below.

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13, or 14 or longer, and in case of MHC class II peptides (elongated variants of the peptides of the invention) they can be as long as 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 6

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |

TABLE 6-continued

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1 - (C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity, then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 640 or a variant thereof which is 88% homologous to SEQ ID NO: 1 to SEQ ID NO: 640, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 640. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 640, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or -II is substantially changed, or is negatively affected, when compared to the non-modified peptide.

The amino acid residues that do not substantially contribute to interactions with the T-cell receptor can be modified by replacement with other amino acids whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 7

Variants and motif of the peptides according to SEQ ID NO: 20, 40, and 217

| Position | 1 | 2 | 3 | 4 | 5 | 6 | 7 | 8 | 9 |
|---|---|---|---|---|---|---|---|---|---|
| SEQ ID NO. 20 | R | M | I | E | Y | F | I | D | V |
| Variants | | | | | | | | | I |
| | | | | | | | | | L |
| | | | | | | | | | A |
| | | L | | | | | | | I |
| | | L | | | | | | | L |
| | | L | | | | | | | |
| | | L | | | | | | | A |
| | | A | | | | | | | I |
| | | A | | | | | | | L |
| | | A | | | | | | | |
| | | A | | | | | | | A |
| | | V | | | | | | | I |
| | | V | | | | | | | L |
| | | V | | | | | | | |
| | | V | | | | | | | A |
| | | T | | | | | | | I |
| | | T | | | | | | | L |
| | | T | | | | | | | |
| | | T | | | | | | | A |
| | | Q | | | | | | | I |
| | | Q | | | | | | | L |
| | | Q | | | | | | | |
| | | Q | | | | | | | A |
| SEQ ID NO. 40 | T | L | L | V | K | V | F | S | V |
| Variants | | I | | | | | | | L |
| | | I | | | | | | | I |
| | | I | | | | | | | |
| | | I | | | | | | | A |
| | | M | | | | | | | L |
| | | M | | | | | | | I |
| | | M | | | | | | | |
| | | M | | | | | | | A |
| | | A | | | | | | | L |
| | | A | | | | | | | I |
| | | A | | | | | | | |
| | | A | | | | | | | A |
| | | V | | | | | | | L |
| | | V | | | | | | | I |
| | | V | | | | | | | |
| | | V | | | | | | | A |
| | | T | | | | | | | L |
| | | T | | | | | | | I |
| | | T | | | | | | | |
| | | T | | | | | | | A |
| | | Q | | | | | | | L |
| | | Q | | | | | | | I |
| | | Q | | | | | | | |
| | | Q | | | | | | | A |
| SEQ ID NO. 217 | A | L | I | H | P | V | S | T | V |
| Variants | | | | | | | | | L |
| | | | | | | | | | I |
| | | | | | | | | | A |
| | | M | | | | | | | L |
| | | M | | | | | | | I |
| | | M | | | | | | | |
| | | M | | | | | | | A |
| | | A | | | | | | | L |
| | | A | | | | | | | I |
| | | A | | | | | | | |
| | | A | | | | | | | A |
| | | V | | | | | | | L |
| | | V | | | | | | | I |
| | | V | | | | | | | |
| | | V | | | | | | | A |
| | | T | | | | | | | L |
| | | T | | | | | | | I |
| | | T | | | | | | | |
| | | T | | | | | | | A |
| | | Q | | | | | | | L |
| | | Q | | | | | | | I |
| | | Q | | | | | | | |
| | | Q | | | | | | | A |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 8.

TABLE 8

Combinations of the elongations of the peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |
| N-terminus | C-terminus |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 640.

"Consisting essentially of" shall mean that a peptide according to the present invention, in addition to the sequence according to any of SEQ ID NO: 1 to SEQ ID NO 640 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897, 445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine, threonine, and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs) recorded from ovarian cancer samples (N=20 A*02-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 20 ovarian cancer patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from ovarian cancer tissue samples were purified and HLA-associated peptides were isolated and analyzed by LC-MS (see examples). All TUMAPs contained in the present application were identified with this approach on primary ovarian cancer samples confirming their presentation on primary ovarian cancer.

TUMAPs identified on multiple ovarian cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization. Furthermore, the discovery pipeline XPRESIDENT® v2.x allows the direct absolute quantitation of MHC-, preferably HLA-restricted, peptide levels on cancer or other infected tissues. Briefly, the total cell count was calculated from the total DNA content of the analyzed tissue sample. The total peptide amount for a TUMAP in a tissue sample was measured by nanoLC-MS/MS as the ratio of the natural TUMAP and a known amount of an isotope-labelled version of the TUMAP, the so-called internal standard. The efficiency of TUMAP isolation was determined by spiking peptide:MHC complexes of all selected TUMAPs into the tissue lysate at the earliest possible point of the TUMAP isolation procedure and their detection by nanoLC-MS/MS following completion of the peptide isolation procedure. The total cell count and the amount of total peptide were calculated from triplicate measurements per tissue sample. The peptide-specific isolation efficiencies were calculated as an average from 10 spike experiments each measured as a triplicate (see Example 6 and Table 12).

In addition to an over-presentation of the peptide, the mRNA expression of the underlying gene was analyzed as well. mRNA data were obtained via RNASeq analyses of normal tissues and cancer tissues (see Example 2). An additional source of normal tissue data was a database of publicly available RNA expression data from around 3000 normal tissue samples (Lonsdale, 2013). Peptides which are derived from proteins that show a highly expressed coding mRNA in cancer tissue, but a very low or absent one in vital healthy (normal) tissues, were included as preferred into the present invention.

The present invention provides peptides that are useful in treating cancers/tumors, preferably ovarian cancer that over- or exclusively present the peptides of the invention. These peptides were shown by mass spectrometry to be naturally presented by HLA molecules on primary human ovarian cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy ovaries or other normal tissues, demonstrating a high degree of tumor association of the source genes (see Example 2). Moreover, the peptides themselves are strongly over-presented on tumor tissue—"tumor tissue" in relation to this invention shall mean a sample from a patient suffering from ovarian cancer, but not on normal tissues (see Example 1).

HLA-bound peptides can be recognized by the immune system, specifically T lymphocytes. T cells can destroy the cells presenting the recognized HLA/peptide complex, e.g. ovarian cancer cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are HAVCR1-001 peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain"

refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to an HAVCR1-001 peptide-HLA molecule complex with a binding affinity (KD) of about 100 µM or less, about 50 µM or less, about 25 µM or less, or about 10 µM or less. More preferred are high affinity TCRs having binding affinities of about 1 µM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for an HAVCR1-001 peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta hetero-dimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, a HAVCR1-001 peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to HAVCR1-001 can be enhanced by methods well known in the art.

The present description further relates to a method of identifying and isolating a TCR according to the present description, said method comprising incubating PBMCs from HLA-A*02-negative healthy donors with A2/HAVCR1-001 monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with HAVCR1-001, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutics such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 640, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988).This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example E. coli and Bacillus subtilis), yeasts (for example Saccharomyces cerevisiae), filamentous fungi (for example Aspergillus spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343).

Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen, Hiltonal®, poly-(ICLC), poly(IC-R), poly (I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonal®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore, different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one Ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example, a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed, aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 640, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 640, or a variant thereof which is at least 88% homologous (preferably identical) to SEQ ID NO: 1 to SEQ ID NO: 640 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 640 or a variant thereof which is at least 88% homologous (preferably identical) to SEQ ID NO: 1 to SEQ ID NO: 640, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 640.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of ovarian cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 640 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are ovarian cancer cells or other solid or hematological tumor cells such as non-small cell lung cancer, small cell lung cancer, kidney cancer, brain cancer, colon or rectum cancer, stomach cancer, liver cancer, pancreatic cancer, prostate cancer, leukemia, breast cancer, Merkel cell carcinoma, melanoma, esophageal cancer, urinary bladder cancer, uterine cancer, gallbladder cancer, bile duct cancer.

The present invention further relates to particular marker proteins and biomarkers based on the peptides according to the present invention, herein called "targets" that can be used in the diagnosis and/or prognosis of ovarian cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a ovarian cancer marker (poly)peptide, delivery of a toxin to a ovarian cancer cell expressing a cancer marker gene at an increased level, and/or inhibiting the activity of a ovarian cancer marker polypeptide) according to the invention.

Whenever possible, the antibodies of the invention may be purchased from commercial sources. The antibodies of the invention may also be generated using well-known methods. The skilled artisan will understand that either full length ovarian cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 640 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the ovarian cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating ovarian cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occur in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than $1 \times 10$ μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 640, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin: streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore, such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, vaccinia-infected target cells. In addition, plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 640.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in normal (healthy) tissues. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore, any molecule of the present invention may be used as medicament or in the manufacture of a medicament. The molecule may be used by itself or combined with other molecule(s) of the invention or (a) known molecule(s).

The present invention further provides a medicament that is useful in treating cancer, in particular ovarian cancer and other malignancies.

The present invention is further directed at a kit comprising:

(a) a container containing a pharmaceutical composition as described above, in solution or in lyophilized form;

(b) optionally a second container containing a diluent or reconstituting solution for the lyophilized formulation; and (c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from ovarian cancer, the medicament of the invention is preferably used to treat ovarian cancer.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of ovarian cancer patients with various HLA-A HLA-B and HLA-C alleles. It may contain MHC class I and MHC class II peptides or elongated MHC class I peptides. In addition to the tumor associated peptides collected from several ovarian cancer tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, ovarian cancer samples from patients and blood from healthy donors were analyzed in a stepwise approach:

1. HLA ligands from the malignant material were identified by mass spectrometry

2. Genome-wide messenger ribonucleic acid (mRNA) expression analysis was used to identify genes over-expressed in the malignant tissue (ovarian cancer) compared with a range of normal organs and tissues 3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.

4. Literature research was performed in order to identify additional evidence supporting the relevance of the identified peptides as TUMAPs 5. The relevance of over-expression at the mRNA level was confirmed by redetection of selected TUMAPs from step 3 on tumor tissue and lack of (or infrequent) detection on healthy tissues.

6. In order to assess, whether an induction of in vivo T-cell responses by the selected peptides may be feasible, in vitro immunogenicity assays were performed using human T cells from healthy donors as well as from ovarian cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g.

5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients' tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 µg per peptide) will be applied for intradermal injection.

In addition to being useful for treating cancer, the peptides of the present invention are also useful as diagnostics. Since the peptides were generated from ovarian cancer samples and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for ovarian cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance.

Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

BRIEF DESCRIPTION OF THE DRAWINGS

FIG. 1A) Gene symbol: CLSR2, Peptide: VLVSDGVHSV (SEQ ID NO.: 6); Tissues from left to right: 1 adipose tissues, 3 adrenal glands, 6 arteries, 5 bone marrows, 7 brains, 3 breasts, 1 central nerve, 13 colons, 1 duodenum, 8 esophagi, 2 gallbladders, 5 hearts, 16 kidneys, 2 lymph nodes, 21 livers, 46 lungs, 1 lymph node metastasis, 4 leukocyte samples, 7 pancreas, 4 peripheral nerves, 1 peritoneum, 3 pituitary glands, 2 placentas, 3 pleuras, 3 prostates, 6 recti, 7 salivary glands, 3 skeletal muscles, 5 skins, 2 small intestines, 4 spleens, 7 stomachs, 4 testis, 3 thymi, 4 thyroid glands, 7 tracheas, 3 ureters, 6 urinary bladders, 2 uteri, 2 veins, 3 ovaries, 20° C. The peptide has additionally been detected on 1/6 breast cancers, 1/2 Merkel cell carcinomas, 3/17 esophageal cancers, 3/91 lung cancers, 10/29 brain cancers, 1/22 renal cancers and 1/15 small cell lung cancers (not shown). FIG. 1D) Gene symbol: AP1B1, Peptide: FLDTLKDLI SEQ ID NO.: 514); Tissues from left to right: 6 cell lines (1 lyphocytic, 1 kidney, 1 pancreatic, 2 PBMCs, K562-A2), 4 normal tissues (2 bone marrows, 2 spleens), 49 cancer tissues (1 breast cancer, 3 colon cancers, 2 esophageal cancers, 1 gallbladder cancer, 2 leukemias, 3 liver cancers, 21 lung cancers, 7 ovarian cancers, 23 rectum cancers, 1 skin cancer, 4 stomach cancers, 1 testis cancer, 1 urinary bladder cancer). The normal tissue panel and the cancer cell lines and xenografts tested were the same as in FIG. 1A-1C, consisting of 1 adipose tissue, 3 adrenal glands, 6 arteries, 5 bone marrows, 7 brains, 3 breasts, 1 central nerve, 13 colons, 1 duodenum, 8 esophagi, 2 gallbladders, 5 hearts, 16 kidneys, 2 lymph nodes, 21 livers, 46 lungs, 1 lymph node metastasis, 4 leukocyte samples, 7 pancreas, 4 peripheral nerves, 1 peritoneum, 3 pituitary glands, 2 placentas, 3 pleuras, 3 prostates, 6 recti, 7 salivary glands, 3 skeletal muscles, 5 skins, 2 small intestines, 4 spleens, 7 stomachs, 4 testes, 3 thymi, 4 thyroid glands, 7 tracheas, 3 ureters, 6 urinary bladders, 2 uteri, 2 veins, 3 ovaries, 20° C. The peptide has additionally been detected on 2/12 chronic lymphocytic leukemias, 5/28 colorectal cancers, 2/16 liver cancers, 1/2 melanomas, 2/17 esophageal cancers, 17/91 lung cancers, 4/46 stomach cancers, 4/15 small cell lung cancers and 1/4 urinary bladder cancers. Discrepancies regarding the list of tumor types between FIG. 1D and table 4 might be due to the more stringent selection criteria applied in table 4 (for details please refer to table 4). FIG. 1D shows all samples with detectable presentation of the peptide Y, regardless of over-presentation parameters and technical sample quality check. FIG. 1I) Gene symbol(s): VTCN1, Peptide: ALLPLSPYL (SEQ ID NO.: 427). Tissues from left to right: 6 adipose tissues, 8 adrenal glands, 24 blood cells, 15 blood vessels, 10 bone marrows, 13 brains, 7 breasts, 9 esophagi, 2 eyes, 3 gallbladders, 16 hearts, 17 kidneys, 25 large intestines, 24 livers, 49 lungs, 7 lymph nodes, 12 nerves, 3 ovaries, 13 pancreases, 6 parathyroid glands, 1 peritoneum, 6 pituitary glands, 7 placentas, 1 pleura, 4 prostates, 7 salivary glands, 9 skeletal muscles, 11 skins, 9 small intestines, 12 spleens, 8 stomachs, 5 testes, 3 thymi, 5 thyroid glands, 16 tracheas, 7 ureters, 8 urinary bladders, 6 uteri, 20 ovarian cancer samples. The peptide has additionally been found on 7/17 gallbladder and bile duct cancers, 9/18 breast cancers, 2/18 esophageal cancers, 1/12 head and neck cancers, 7/21 liver cancers, 22/107 lung cancers, 4/19 pancreas cancers, 4/87 prostate cancers, 2/15 urinary bladder cancers, 11/16 uterus cancers. FIG. 1L) Gene symbol(s): CCNA1, Peptide: SLMEPPAVLLL (SEQ ID NO.: 1). Tissues from left to right: 1 cancer cell line, 1 normal tissue (1 lymph node), 45 cancer tissues (3 bone marrow cancers, 1 brain cancer, 1 breast cancer, 2 esophageal cancers, 1 head and neck cancer, 1 kidney cancer, 3 leukocytic leukemia cancers, 12 lung cancers, 1 myeloid cell cancer, 11 ovarian cancers, 2 urinary bladder cancers, 7 uterus cancers. The normal tissue panel tested was the same as in FIGS. 1E-1K. FIG. 1O) Gene symbol(s): TSEN15, Peptide: FLLEDDIHVS (SEQ ID NO.: 38). Tissues from left to right: 1 primary culture, 1 normal tissue (1 trachea), 28 cancer tissues (2 breast cancers, 1 head and neck cancer, 4 leukocytic leukemia cancers, 5 lung cancers, 6 lymph node cancers, 1 myeloid cell cancer, 2 ovarian cancers, 1 rectum cancer, 3 skin cancers, 2 urinary bladder cancers, 1 uterus cancer). The normal tissue panel tested was the same as in FIGS. 1E-1K. FIG. 1P) Gene symbol(s): ZNF527, ZNF829, ZNF383, ZNF850, ZNF583, Peptide: SLLEQGKEPWMV (SEQ ID NO.: 54). Tissues from left to right: 1 cell line, 18 cancer tissues (2 brain cancers, 1 breast cancer, 1 gallbladder cancer, 1 leukocytic leukemia cancer, 2 liver cancers, 7 lung cancers, 1 lymph node cancer, 2 ovarian cancers, 1 urinary bladder cancer). The normal tissue panel tested was the same as in FIGS. 1E-1K. FIG. 1T) Gene symbol(s): NPLOC4, Peptide: YLNHLEPPV (SEQ ID NO.: 166). Tissues from left to right: 2 cell lines, 20 cancer tissues (3 brain cancers, 1 breast cancer, 1 esophageal cancer, 3 leukocytic leukemia cancers, 2 liver cancers, 4 lung cancers, 2 lymph node cancers, 1 myeloid cells cancer, 3 ovarian cancers). The normal tissue panel tested was the same as in FIGS. 1E-1K. FIG. 1V) Gene symbol(s): SKIL, Peptide: KTINKVPTV (SEQ ID NO.: 198). Tissues from left to right: 2 cell lines and primary cultures, 1 normal tissue (1 lung), 36 cancer tissues (3 brain cancers, 2 breast cancers, 2 colon cancers, 1 head and neck cancer, 1 liver cancer, 14 lung cancers, 1 lymph node cancer, 8 ovarian cancers, 1 rectum cancer, 2 urinary bladder cancers, 1 uterus cancer). The normal tissue panel tested was the same as in FIGS. 1E-1K. FIG. 1W) Gene symbol(s): SEC24C, Peptide: FLFPNQYVDV (SEQ ID NO.: 248). Tissues from left to right: 3 cell lines and primary cultures, 1 normal tissue (1 spleen), 24 cancer tissues (1 bile duct cancer, 2 breast cancers, 2 leukocytic leukemia cancers, 1 liver cancer, 9 lung cancers, 2 lymph node cancers, 3 ovarian cancers, 1 prostate cancer, 2 skin cancers, 1 uterus cancer). The normal tissue panel tested was the same as in FIGS. 1E-1K. FIG. 1X) Gene symbol(s): PDIK1L, STK35, Peptide: ALLENPKMEL (SEQ ID NO.: 441). Tissues from left to right: 5 cell lines and primary cultures, 1 normal tissue (1 adrenal gland), 26 cancer tissues (1 breast cancer, 1 colon cancer, 1 esophageal cancer, 1 head and neck cancer, 2 liver cancers, 10 lung cancers, 5 ovarian cancers, 1 prostate cancer, 1 rectum cancer, 2 urinary bladder cancers, 1 uterus cancer). The normal tissue panel tested was the same as in FIGS. 1E-1K. FIG. 1Z) Gene symbol(s): ZYG11A, Peptide: VLIANLEKL (SEQ ID NO.: 466). Tissues from left to right: 5 cell lines, 17 cancer tissues (3 breast cancers, 2 esophageal cancers, 1 liver cancer, 2 lung cancers, 5 lymph node cancers, 3 ovarian cancers, 1 urinary bladder cancer). The normal tissue panel tested was the same as in FIGS. 1E-1K. FIG. 1Z) Gene symbol(s): CEP192, Peptide: SLFGNSGILENV (SEQ ID NO.: 479). Tissues from left to right: 7 cell lines, 1 normal tissue (1 spleen), 33 cancer tissues (1 breast cancer, 1 colon cancer, 1 esophageal cancer, 1 head and neck cancer, 1 leukocytic leukemia cancer, 3 liver cancers, 10 lung cancers, 1 lymph node cancer, 1 myeloid cell cancer, 7 ovarian cancers, 2 skin cancers, 3 urinary bladder cancers, 1 uterus cancer). The normal tissue panel tested was the same as in FIGS. 1E-1K. FIG. 1AB) Gene symbol(s): CCNA1, Peptide: SLSEIVPCL (SEQ ID NO.: 512). Tissues from left to right: 9 cancer tissues (1 head and neck cancer, 2 lung cancers, 1 myeloid cell cancer, 3 ovarian cancers, 2 uterus cancers). The normal tissue panel tested was the same as in FIGS. 1E-1K. FIG. 1AC) Gene symbol(s): GNB1, Peptide: ALWDIETGQQTTT (SEQ ID NO.: 560), Tissues from left to right: 5 cell lines and primary cultures, 26 cancer tissues (1 brain cancer, 1 esophageal cancer, 1 esophageal and stomach cancer, 1 gallbladder cancer, 2 head and neck cancers, 1 leukocytic leukemia cancer, 1 liver cancer, 5 lung cancers, 6 lymph node cancers, 3 ovarian cancers, 1 prostate cancer, 1 skin cancer, 1 urinary bladder cancer, 1 uterus cancer). The normal tissue panel tested was the same as in FIGS. 1E-1K. FIG. 1AD) Gene symbol(s): KLHL14, Peptide: VMNDRLYAI (SEQ ID NO.: 587), Tissues from left to right: 5 normal tissues (1 pancreas, 3 spleens, 1 thyroid gland), 38 cancer tissues (14 leukocytic leukemia cancers, 10 lymph node cancers, 9 ovarian cancers, 1 prostate cancer, 4 uterus cancers). The normal tissue panel tested was the same as in FIGS. 1E-1K. FIG. 1AE) Gene symbol(s): URB1, Peptide: KLLNKIYEA (SEQ ID NO.: 620), Tissues from left to right: 3 cell lines and primary cultures, 2 normal tissues (1 lung, 1 uterus), 27 cancer tissues (5 brain cancers, 2 breast cancers, 2 esophageal cancers, 5 lung cancers, 1 lymph node cancer, 1 myeloid cell cancer, 5 ovarian cancers, 3 prostate cancers, 1 rectum cancer, 1 urinary bladder cancer, 1 uterus cancer). The normal tissue panel tested was the same as in FIGS. 1E-1K.

FIGS. 2A to 2D show exemplary expression profiles of source genes of the present invention that are highly overexpressed or exclusively expressed in ovarian cancer in a panel of normal tissues (white bars) and 20 ovarian cancer samples (black bars). Tissues from left to right: 7 arteries, 1 brain, 1 heart, 2 livers, 2 lungs, 2 veins, 1 adipose tissue, 1 adrenal gland, 4 bone marrows, 1 colon, 2 esophagi, 2 gallbladders, 1 kidney, 6 lymph nodes, 1 pancreas, 1 pituitary gland, 1 rectum, 1 skeletal muscle, 1 skin, 1 small intestine, 1 spleen, 1 stomach, 1 thymus, 1 thyroid gland, 5 tracheae, 1 urinary bladder, 1 breast, 3 ovaries, 3 placentae, 1 prostate, 1 testis, 1 uterus. FIG. 2A) CT45A1, CT45A3, CT45A5, CT45A6, CT45A2, RP11-342L5.1, FIG. 2B) CLDN16; FIG. 2C) ESR1; FIG. 2D) IDO1.

EXAMPLES

Example 1

Identification and Quantitation of Tumor Associated Peptides Presented on the Cell Surface Tissue Samples Patients' tumor tissues were obtained from Asterand (Detroit, USA and Royston, Herts, UK); Val d'Hebron University Hospital (Barcelona); ProteoGenex Inc., (Culver City, Calif., USA); Stanford Cancer Center (Stanford, Calif., USA); University Hospital of Tübingen. Normal (healthy) tissues were obtained from Asterand (Detroit, USA and Royston, Herts, UK); Bio-Options Inc., CA, USA; BioServe, Beltsville, Md., USA; Capital BioScience Inc., Rockville, Md., USA; Geneticist Inc., Glendale, Calif., USA; University Hospital of Geneva; University Hospital of Heidelberg; University Hospital Munich; ProteoGenex Inc., Culver City, Calif., USA; University Hospital of Tübingen, Kyoto Precatural University if Medicine (KPUM). Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, —B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOPS strategy. In brief, a scan cycle was initiated with a full scan of high mass accuracy in the Orbitrap (R=30 000), which was followed by MS/MS scans also in the Orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Figure 1A:
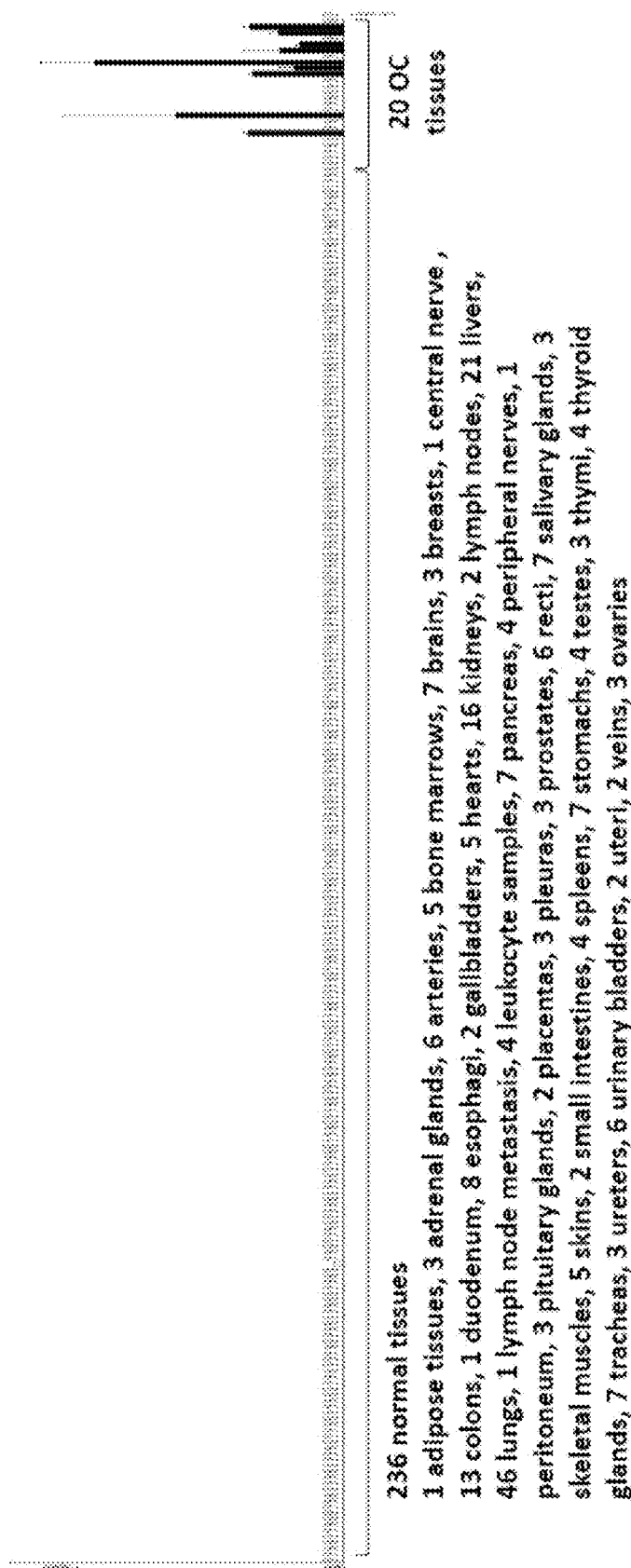
FIGS. 1A to 1AE show the over-presentation of various peptides in normal tissues (white bars) and ovarian cancer (black bars).
Figure 1B:
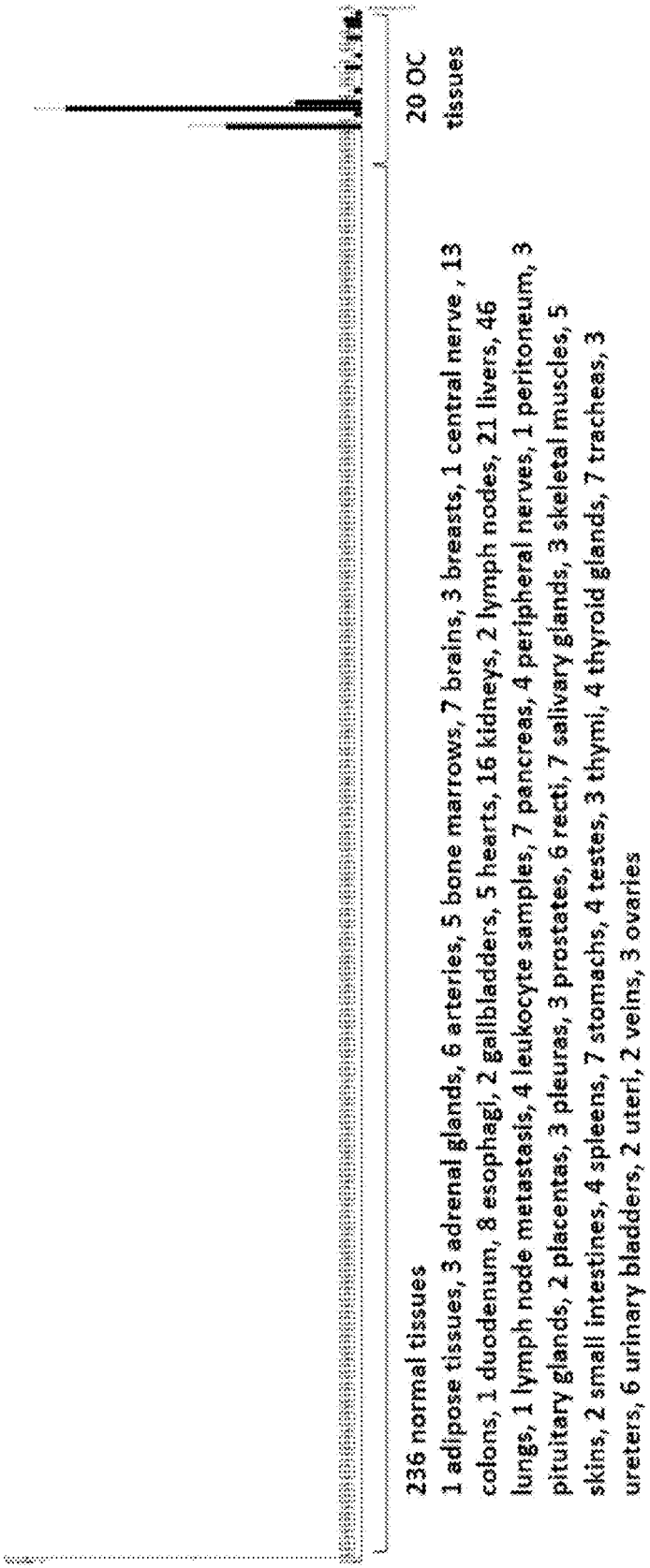
FIG. 1B) Gene symbol: CCNA1, Peptide: SLMEPPAVLLL (SEQ ID NO.: 1); Tissues from left to right: 1 adipose tissues, 3 adrenal glands, 6 arteries, 5 bone marrows, 7 brains, 3 breasts, 1 central nerve, 13 colons, 1 duodenum, 8 esophagi, 2 gallbladders, 5 hearts, 16 kidneys, 2 lymph nodes, 21 livers, 46 lungs, 1 lymph node metastasis, 4 leukocyte samples, 7 pancreas, 4 peripheral nerves, 1 peritoneum, 3 pituitary glands, 2 placentas, 3 pleuras, 3 prostates, 6 recti, 7 salivary glands, 3 skeletal muscles, 5 skins, 2 small intestines, 4 spleens, 7 stomachs, 4 testis, 3 thymi, 4 thyroid glands, 7 tracheas, 3 ureters, 6 urinary bladders, 2 uteri, 2 veins, 3 ovaries, 20° C. The peptide has additionally been detected on 1/2 AMLs, 1/28 colorectal cancers, 2/17 esophageal cancers, 7/91 lung cancers, 1/29 brain cancers, 1/22 renal cancers and 2/15 small cell lung cancers (not shown).
Figure 1C:
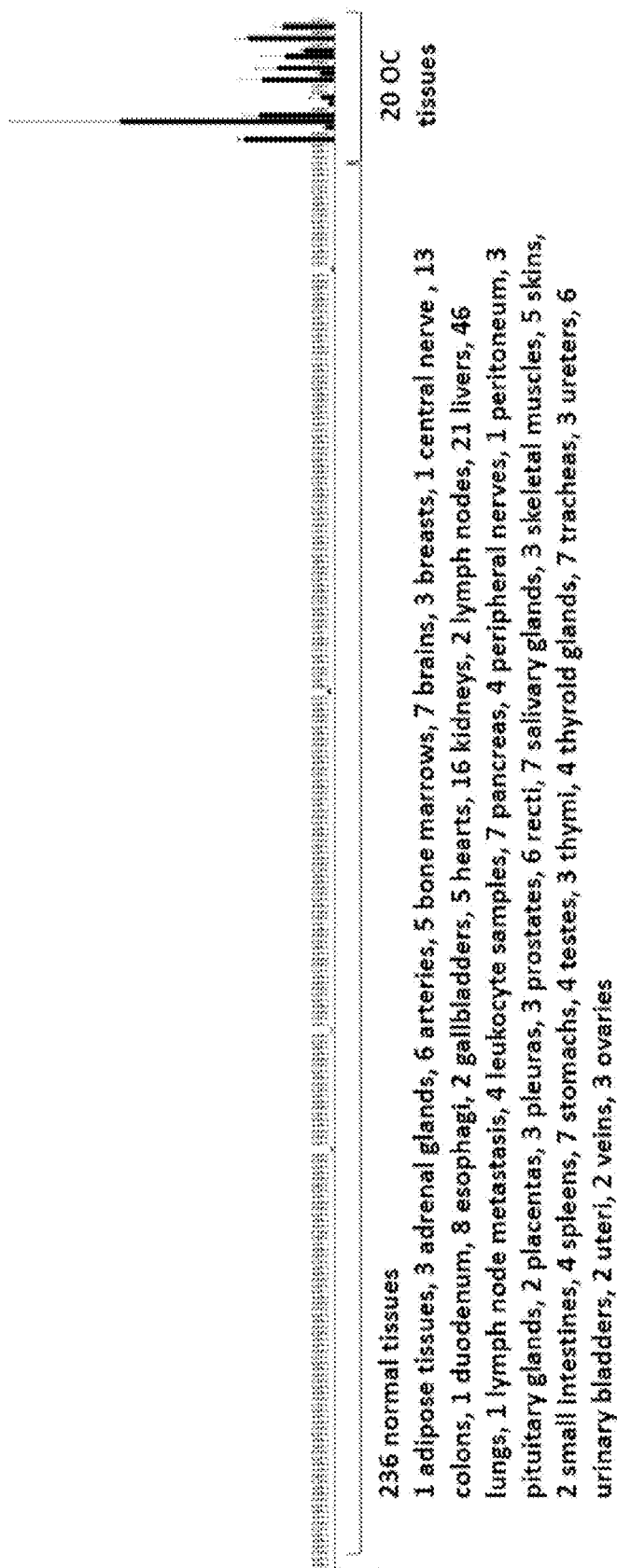
FIG. 1C) Gene symbol: VTCN1, Peptide: ALLPLSPYL (SEQ ID NO.: 427); Tissues from left to right: 1 adipose tissues, 3 adrenal glands, 6 arteries, 5 bone marrows, 7 brains, 3 breasts, 1 central nerve, 13 colons, 1 duodenum, 8 esophagi, 2 gallbladders, 5 hearts, 16 kidneys, 2 lymph nodes, 21 livers, 46 lungs, 1 lymph node metastasis, 4 leukocyte samples, 7 pancreas, 4 peripheral nerves, 1 peritoneum, 3 pituitary glands, 2 placentas, 3 pleuras, 3 prostates, 6 recti, 7 salivary glands, 3 skeletal muscles, 5 skins, 2 small intestines, 4 spleens, 7 stomachs, 4 testis, 3 thymi, 4 thyroid glands, 7 tracheas, 3 ureters, 6 urinary bladders, 2 uteri, 2 veins, 3 ovaries, 20° C. The peptide has additionally been detected on 4/43 prostate cancers, 3/6 breast cancers, 4/16 liver cancers, 1/17 esophageal cancers, 4/19 pancreatic cancers, 19/91 lung cancers, 1/15 small cell lung cancers, 1/4 urinary bladder cancers and 3/4 uterine cancers (not shown).
Figure 1E:
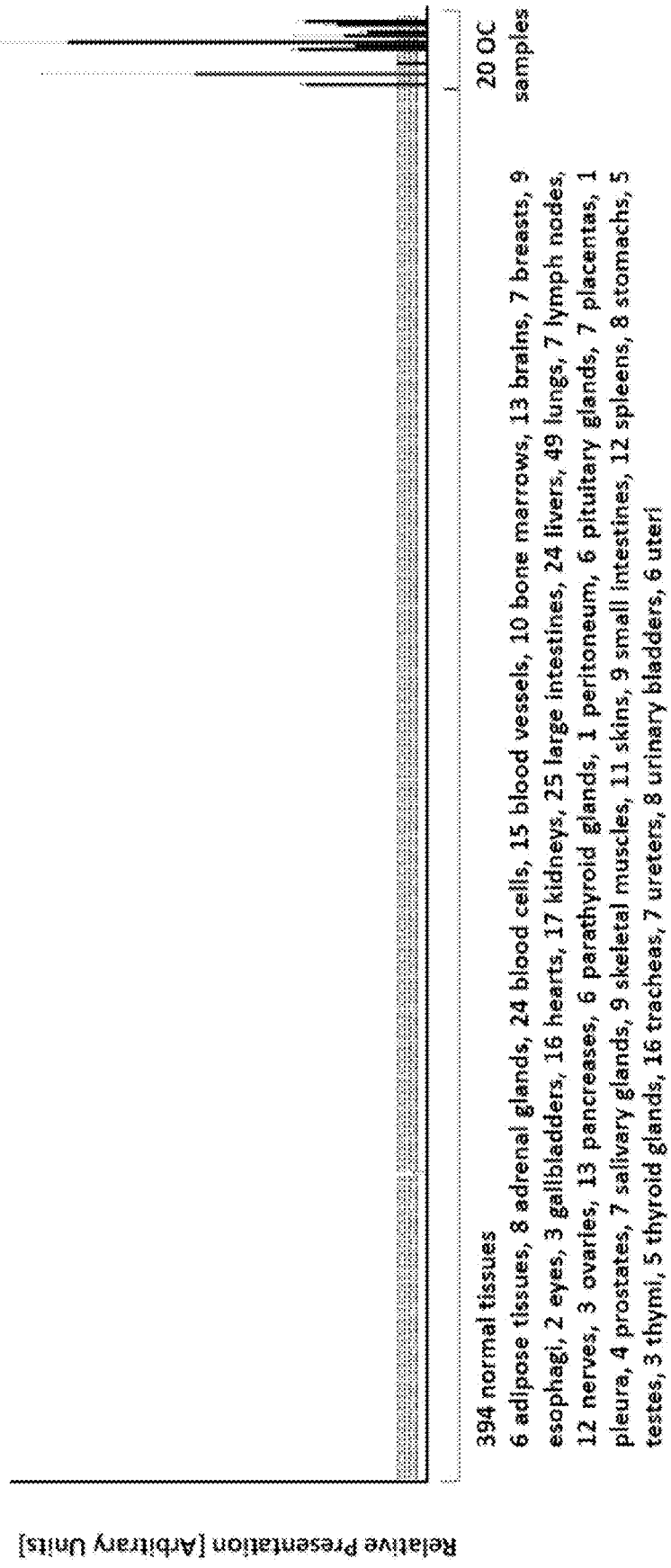
FIG. 1E) Gene symbol(s): CELSR2, Peptide: VLVSDGVHSV (SEQ ID NO.: 6). Tissues from left to right: 6 adipose tissues, 8 adrenal glands, 24 blood cells, 15 blood vessels, 10 bone marrows, 13 brains, 7 breasts, 9 esophagi, 2 eyes, 3 gallbladders, 16 hearts, 17 kidneys, 25 large intestines, 24 livers, 49 lungs, 7 lymph nodes, 12 nerves, 3 ovaries, 13 pancreases, 6 parathyroid glands, 1 peritoneum, 6 pituitary glands, 7 placentas, 1 pleura, 4 prostates, 7 salivary glands, 9 skeletal muscles, 11 skins, 9 small intestines, 12 spleens, 8 stomachs, 5 testes, 3 thymi, 5 thyroid glands, 16 tracheas, 7 ureters, 8 urinary bladders, 6 uteri, 20 ovarian cancer samples. The peptide has additionally been found on 15/34 brain cancers, 3/18 breast cancers, 3/18 esophageal cancers, 4/12 head and neck cancers, 1/23 kidney cancers, 6/107 lung cancers, 5/18 skin cancers, 5/15 urinary bladder cancers, 3/16 uterus cancers.
Figure 1F:
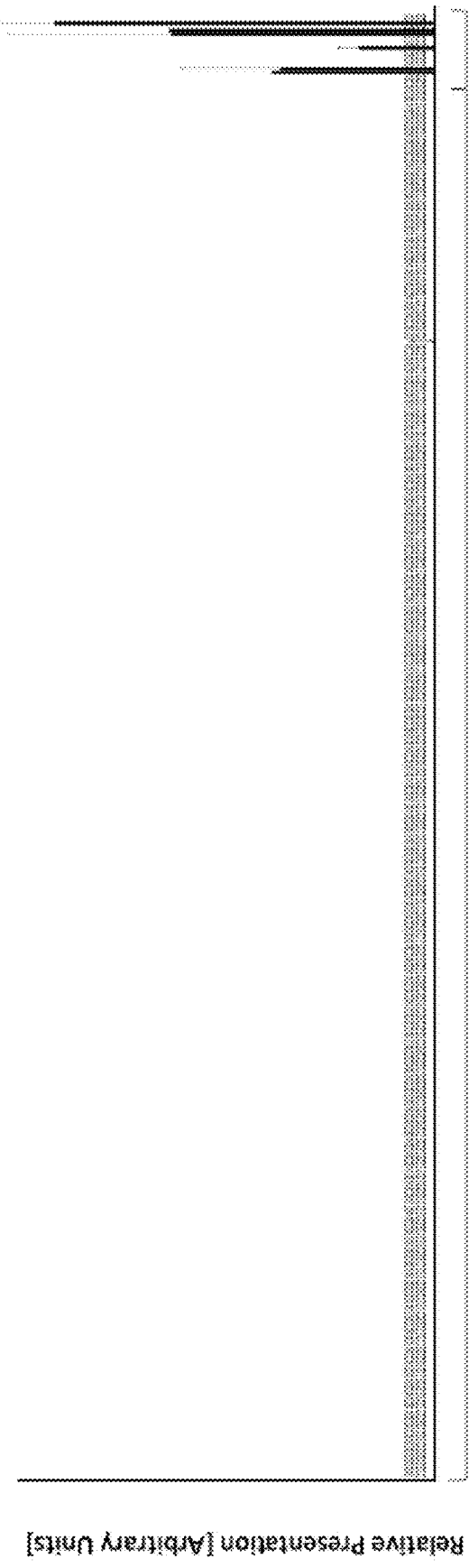
FIG. 1F) Gene symbol(s): SUCO, Peptide: LLLDITPEI (SEQ ID NO.: 143). Tissues from left to right: 6 adipose tissues, 8 adrenal glands, 24 blood cells, 15 blood vessels, 10 bone marrows, 13 brains, 7 breasts, 9 esophagi, 2 eyes, 3 gallbladders, 16 hearts, 17 kidneys, 25 large intestines, 24 livers, 49 lungs, 7 lymph nodes, 12 nerves, 3 ovaries, 13 pancreases, 6 parathyroid glands, 1 peritoneum, 6 pituitary glands, 7 placentas, 1 pleura, 4 prostates, 7 salivary glands, 9 skeletal muscles, 11 skins, 9 small intestines, 12 spleens, 8 stomachs, 5 testes, 3 thymi, 5 thyroid glands, 16 tracheas, 7 ureters, 8 urinary bladders, 6 uteri, 20 ovarian cancer samples. The peptide has additionally been found on 2/34 brain cancers, 4/18 breast cancers, 2/18 esophageal cancers, 1/12 head and neck cancers, 2/21 liver cancers, 6/107 lung cancers, 2/18 skin cancers, 1/45 stomach cancers, 2/15 urinary bladder cancers.
Figure 1G:
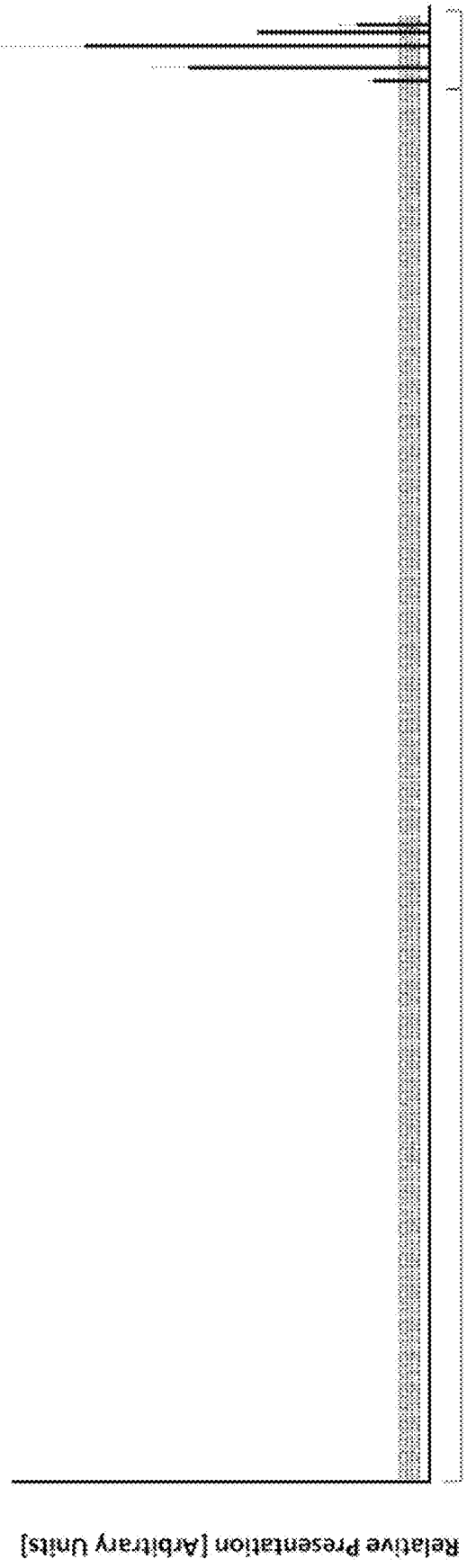
FIG. 1G) Gene symbol(s): PLAUR, Peptide: RLWEEGEELEL (SEQ ID NO.: 150). Tissues from left to right: 6 adipose tissues, 8 adrenal glands, 24 blood cells, 15 blood vessels, 10 bone marrows, 13 brains, 7 breasts, 9 esophagi, 2 eyes, 3 gallbladders, 16 hearts, 17 kidneys, 25 large intestines, 24 livers, 49 lungs, 7 lymph nodes, 12 nerves, 3 ovaries, 13 pancreases, 6 parathyroid glands, 1 peritoneum, 6 pituitary glands, 7 placentas, 1 pleura, 4 prostates, 7 salivary glands, 9 skeletal muscles, 11 skins, 9 small intestines, 12 spleens, 8 stomachs, 5 testes, 3 thymi, 5 thyroid glands, 16 tracheas, 7 ureters, 8 urinary bladders, 6 uteri, 20 ovarian cancer samples. The peptide has additionally been found on 4/17 gallbladder and bile duct cancers, 1/18 breast cancers, 1/29 colon cancers, 2/18 esophageal cancers, 1/12 head and neck cancers, 10/107 lung cancers, 2/18 skin cancers, 1/16 uterus cancers.
Figure 1H:
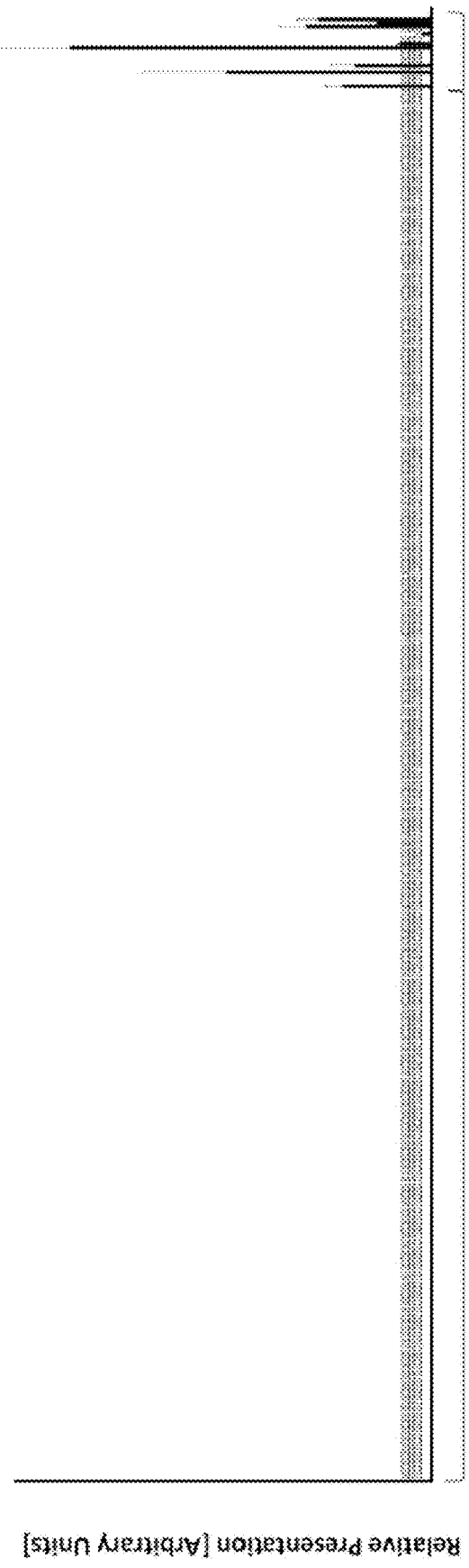
FIG. 1H) Gene symbol(s): HEATR2, Peptide: SLNDEVPEV (SEQ ID NO.: 157). Tissues from left to right: 6 adipose tissues, 8 adrenal glands, 24 blood cells, 15 blood vessels, 10 bone marrows, 13 brains, 7 breasts, 9 esophagi, 2 eyes, 3 gallbladders, 16 hearts, 17 kidneys, 25 large intestines, 24 livers, 49 lungs, 7 lymph nodes, 12 nerves, 3 ovaries, 13 pancreases, 6 parathyroid glands, 1 peritoneum, 6 pituitary glands, 7 placentas, 1 pleura, 4 prostates, 7 salivary glands, 9 skeletal muscles, 11 skins, 9 small intestines, 12 spleens, 8 stomachs, 5 testes, 3 thymi, 5 thyroid glands, 16 tracheas, 7 ureters, 8 urinary bladders, 6 uteri, 20 ovarian cancer samples. The peptide has additionally been found on 1/17 bile duct cancers, 5/34 brain cancers, 1/18 breast cancers, 1/29 colon cancers, 2/18 esophageal cancers, 1/12 head and neck cancers, 2/23 kidney cancers, 1/21 liver cancers, 4/107 lung cancers, 2/20 lymph node cancers, 1/18 skin cancers, 1/15 urinary bladder cancers, 1/16 uterus cancers.
Figure 11:
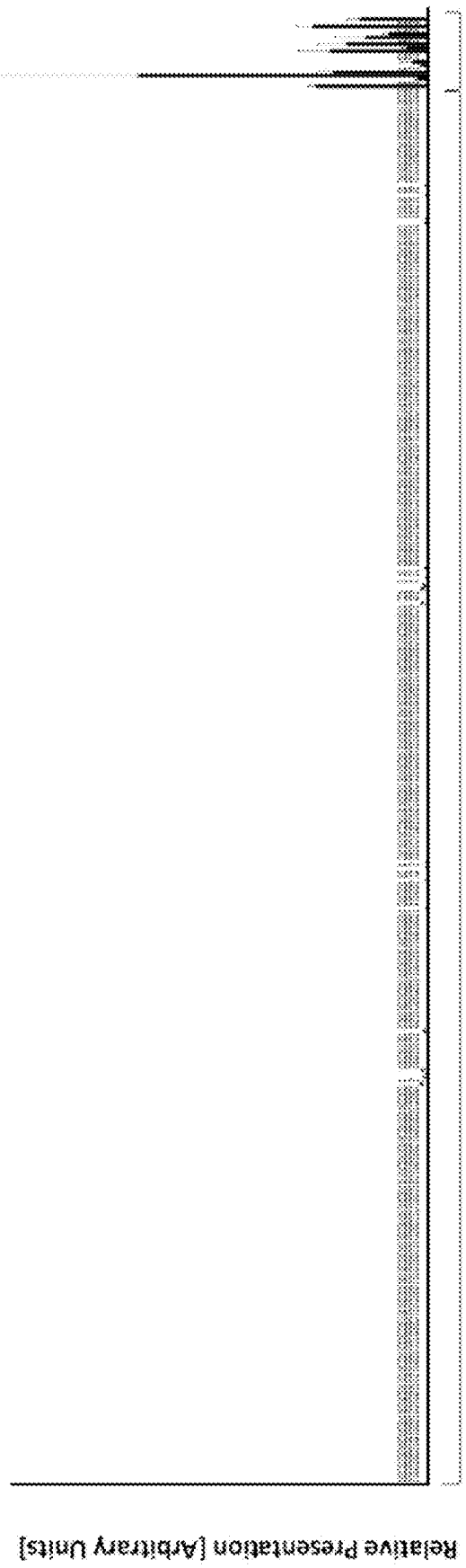
Figure 1J:
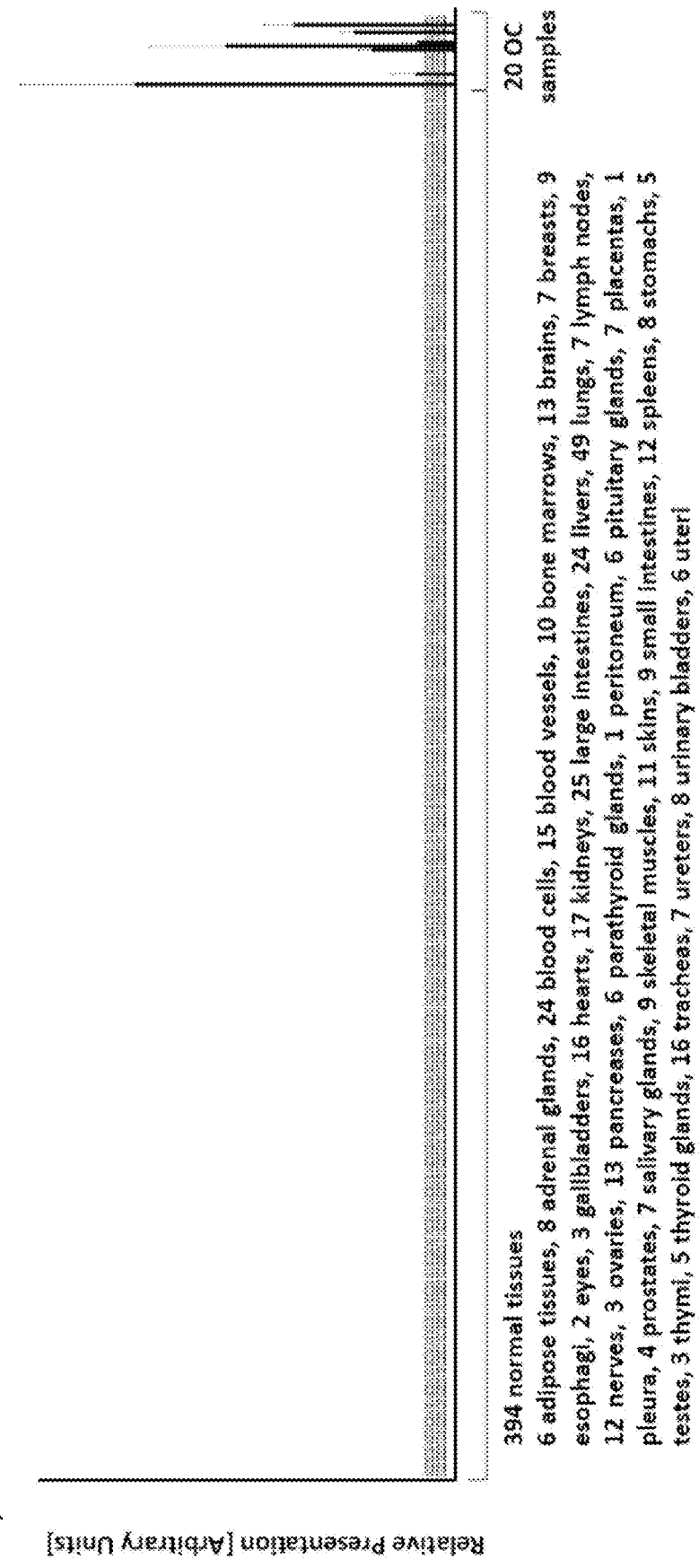
FIG. 1J) Gene symbol(s): DDX11, DDX12P, LOC642846, Peptide: GLLRDEALAEV (SEQ ID NO.: 444). Tissues from left to right: 6 adipose tissues, 8 adrenal glands, 24 blood cells, 15 blood vessels, 10 bone marrows, 13 brains, 7 breasts, 9 esophagi, 2 eyes, 3 gallbladders, 16 hearts, 17 kidneys, 25 large intestines, 24 livers, 49 lungs, 7 lymph nodes, 12 nerves, 3 ovaries, 13 pancreases, 6 parathyroid glands, 1 peritoneum, 6 pituitary glands, 7 placentas, 1 pleura, 4 prostates, 7 salivary glands, 9 skeletal muscles, 11 skins, 9 small intestines, 12 spleens, 8 stomachs, 5 testes, 3 thymi, 5 thyroid glands, 16 tracheas, 7 ureters, 8 urinary bladders, 6 uteri, 20 ovarian cancer samples. The peptide has additionally been found on 2/18 breast cancers, 3/29 colon or rectum cancers, 1/18 esophageal cancers, 1/12 head and neck cancers, 1/23 kidney cancers, 2/17 leukocytic leukemia cancers, 9/107 lung cancers, 6/20 lymph node cancers, 1/18 myeloid cells cancer, 2/18 skin cancers, 2/15 urinary bladder cancers, 1/16 uterus cancers.
Figure 1K:
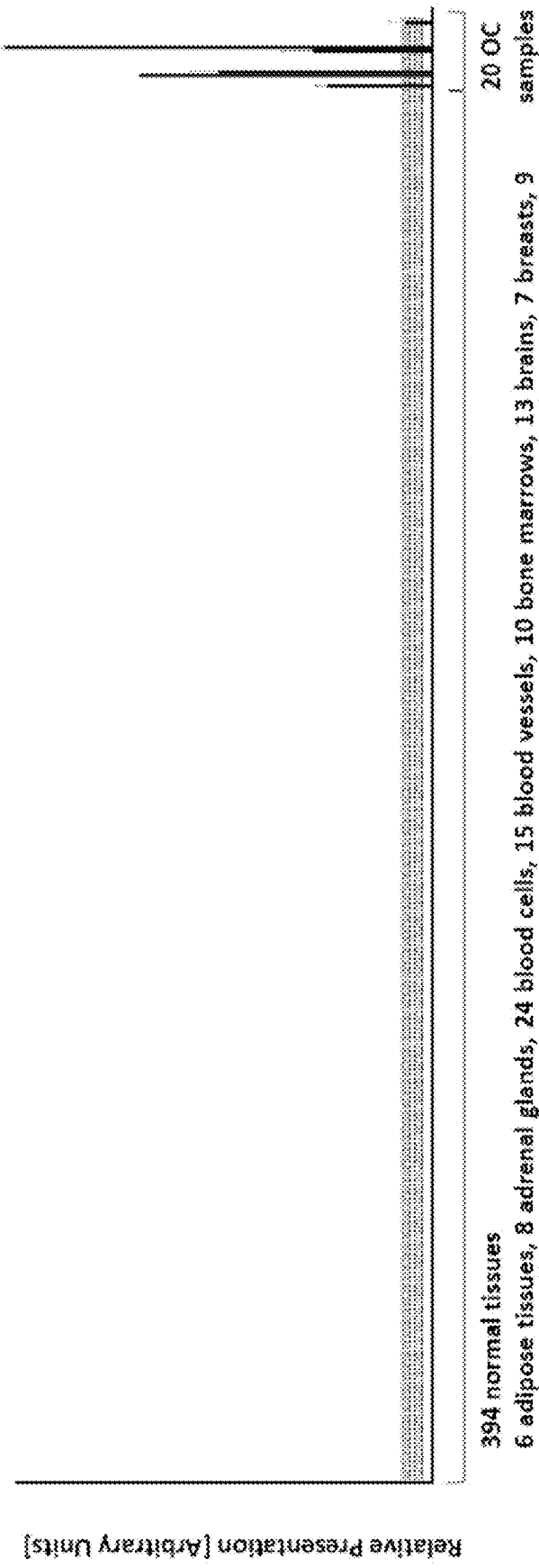
FIG. 1K) Gene symbol(s): KDM1B, Peptide: KLAEGLDIQL (SEQ ID NO.: 449). Tissues from left to right: 6 adipose tissues, 8 adrenal glands, 24 blood cells, 15 blood vessels, 10 bone marrows, 13 brains, 7 breasts, 9 esophagi, 2 eyes, 3 gallbladders, 16 hearts, 17 kidneys, 25 large intestines, 24 livers, 49 lungs, 7 lymph nodes, 12 nerves, 3 ovaries, 13 pancreases, 6 parathyroid glands, 1 peritoneum, 6 pituitary glands, 7 placentas, 1 pleura, 4 prostates, 7 salivary glands, 9 skeletal muscles, 11 skins, 9 small intestines, 12 spleens, 8 stomachs, 5 testes, 3 thymi, 5 thyroid glands, 16 tracheas, 7 ureters, 8 urinary bladders, 6 uteri, 20 ovarian cancer samples. The peptide has additionally been found on 3/29 colon or rectum cancers, 6/107 lung cancers, 1/20 lymph node cancers.
Figure 1M:
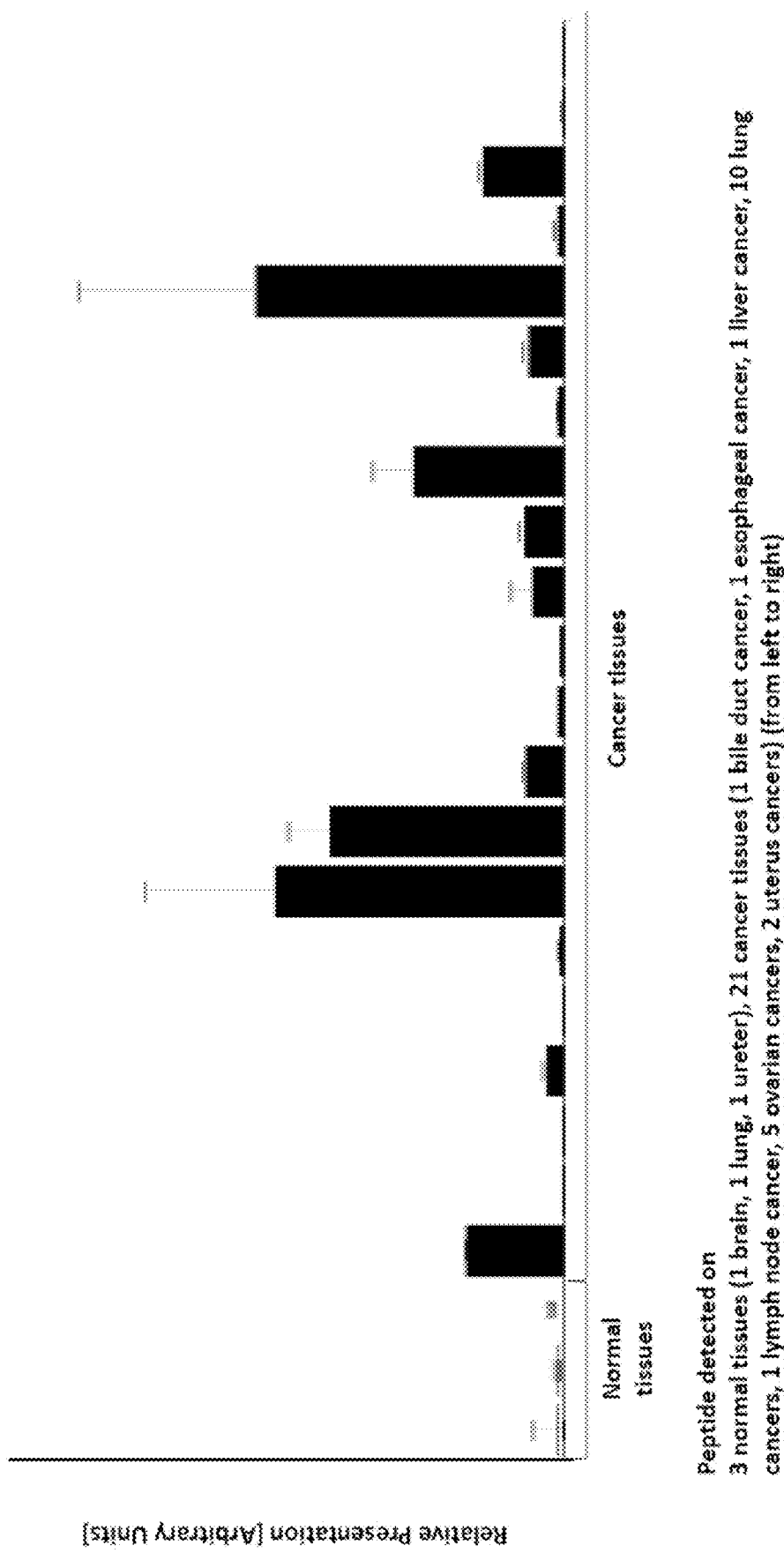
FIG. 1M) Gene symbol(s): CT45A5, LOC101060208, CT45A3, CT45A1, LOC101060211, CT45A6, CT45A4, LOC101060210, CT45A2, Peptide: KIFEMLEGV (SEQ ID NO.: 11). Tissues from left to right: 3 normal tissues (1 brain, 1 lung, 1 ureter), 21 cancer tissues (1 bile duct cancer, 1 esophageal cancer, 1 liver cancer, 10 lung cancers, 1 lymph node cancer, 5 ovarian cancers, 2 uterus cancers). The normal tissue panel tested was the same as in FIGS. 1E-1K.
Figure 1N:
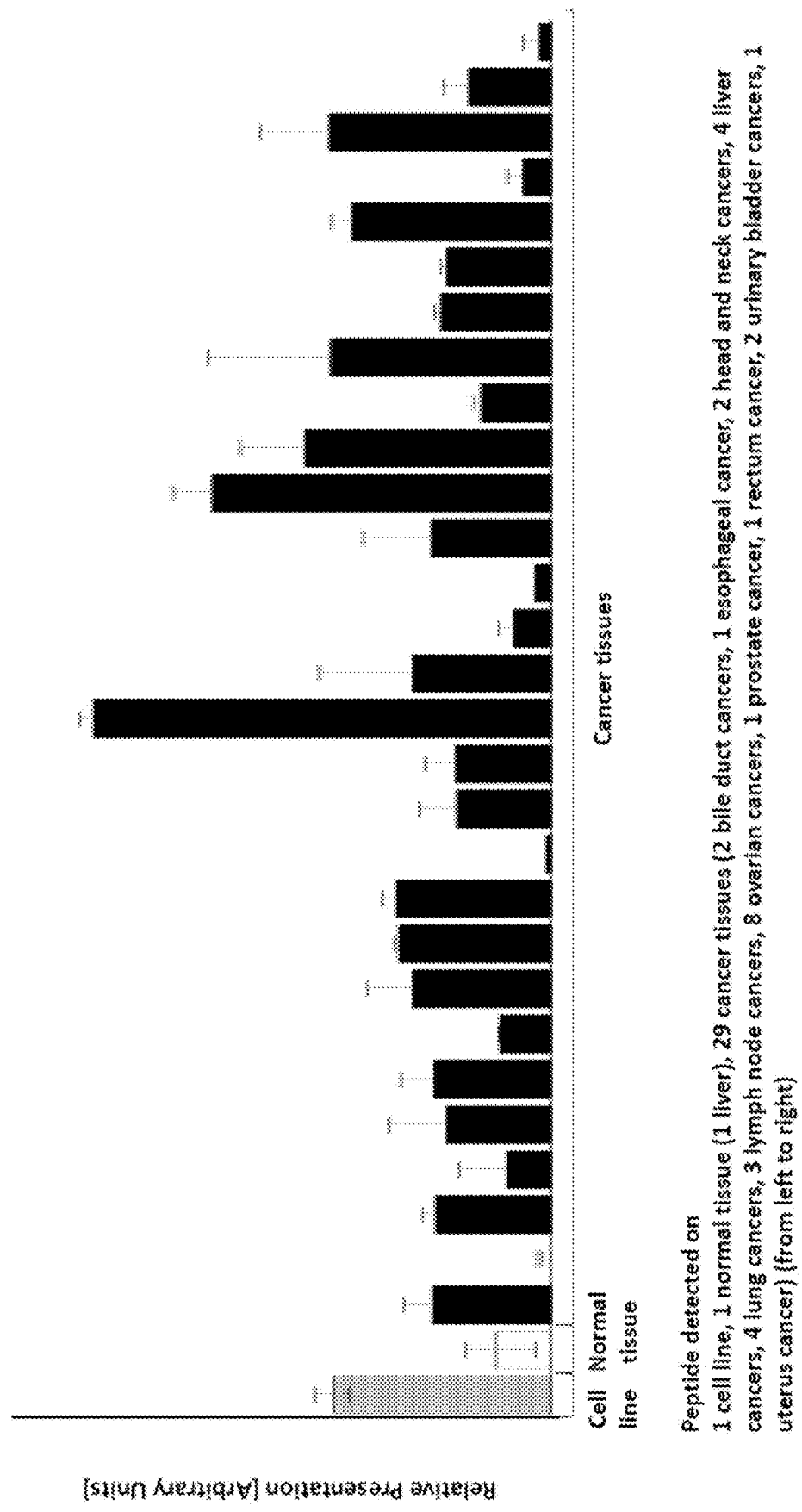
FIG. 1N) Gene symbol(s): FGFR1OP, Peptide: KLDDLTQDLTV (SEQ ID NO.: 32). Tissues from left to right: 1 cell line, 1 normal tissue (1 liver), 29 cancer tissues (2 bile duct cancers, 1 esophageal cancer, 2 head and neck cancers, 4 liver cancers, 4 lung cancers, 3 lymph node cancers, 8 ovarian cancers, 1 prostate cancer, 1 rectum cancer, 2 urinary bladder cancers, 1 uterus cancer). The normal tissue panel tested was the same as in FIGS. 1E-1K.
Figure 10:
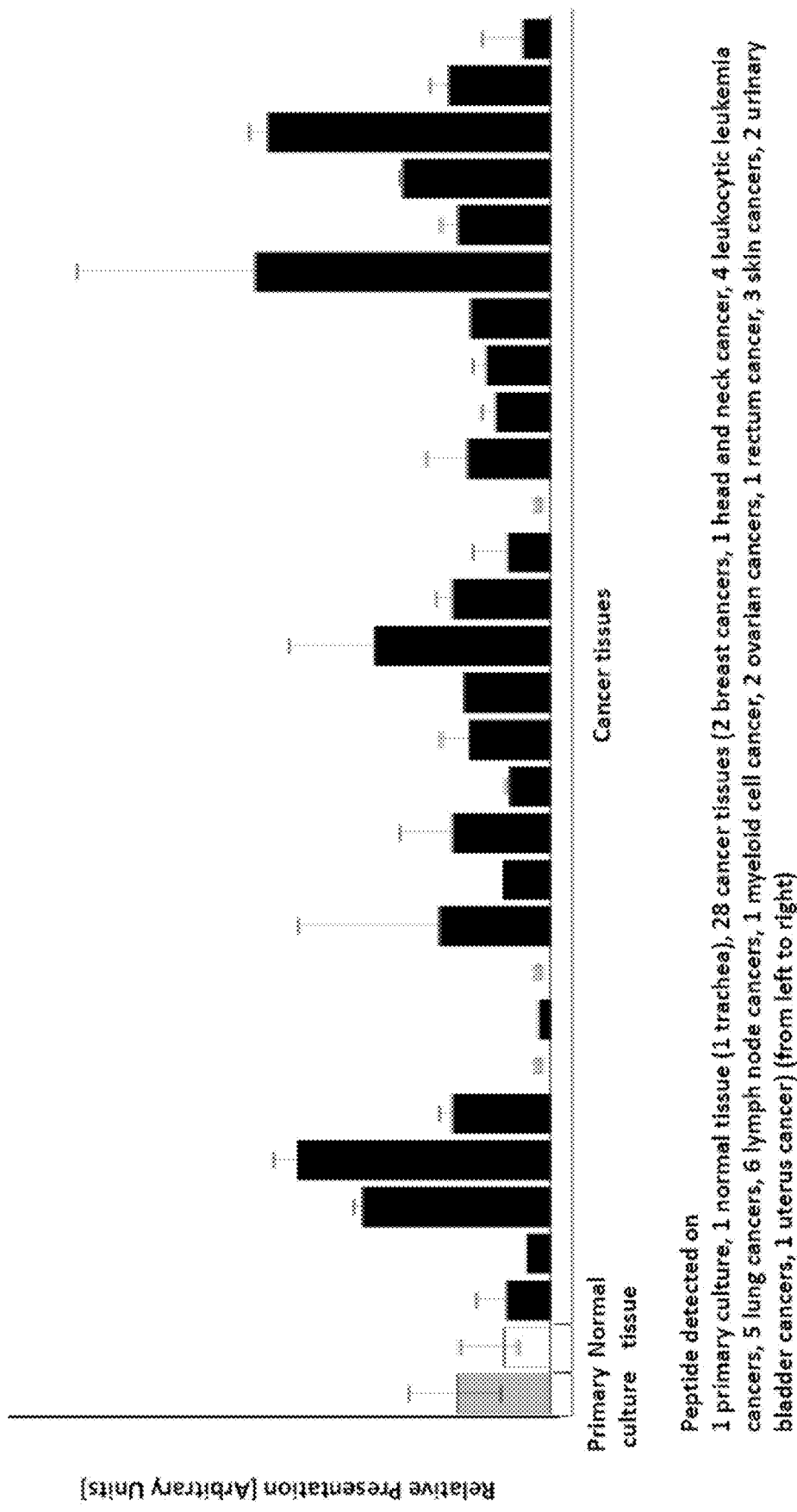
Figure 1Q:
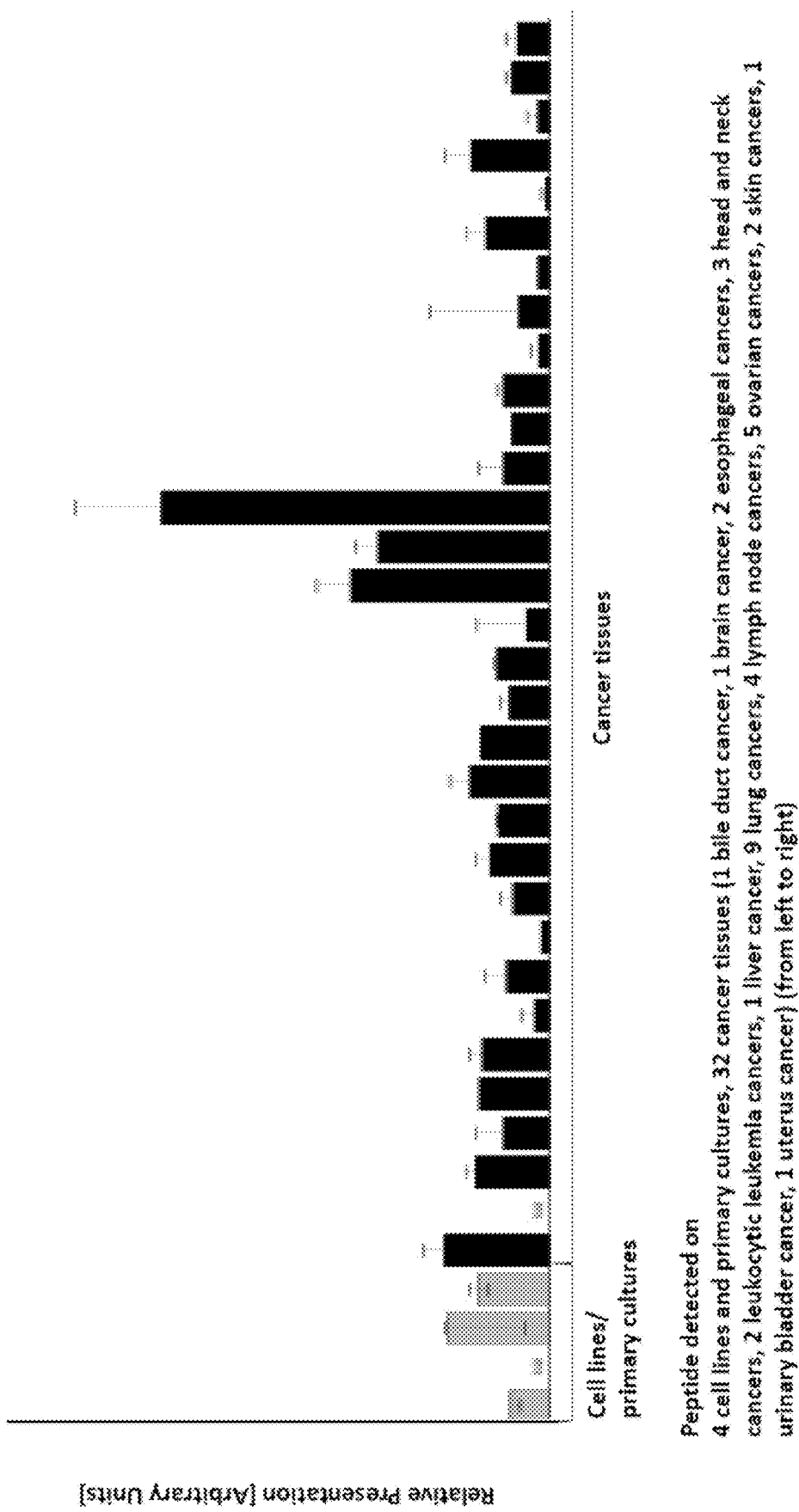
FIG. 1Q) Gene symbol(s): CAMSAP1, Peptide: TLAELQPPVQL (SEQ ID NO.: 57). Tissues from left to right: 4 cell lines and primary cultures, 32 cancer tissues (1 bile duct cancer, 1 brain cancer, 2 esophageal cancers, 3 head and neck cancers, 2 leukocytic leukemia cancers, 1 liver cancer, 9 lung cancers, 4 lymph node cancers, 5 ovarian cancers, 2 skin cancers, 1 urinary bladder cancer, 1 uterus cancer). The normal tissue panel tested was the same as in FIGS. 1E-1K.
Figure 1R:
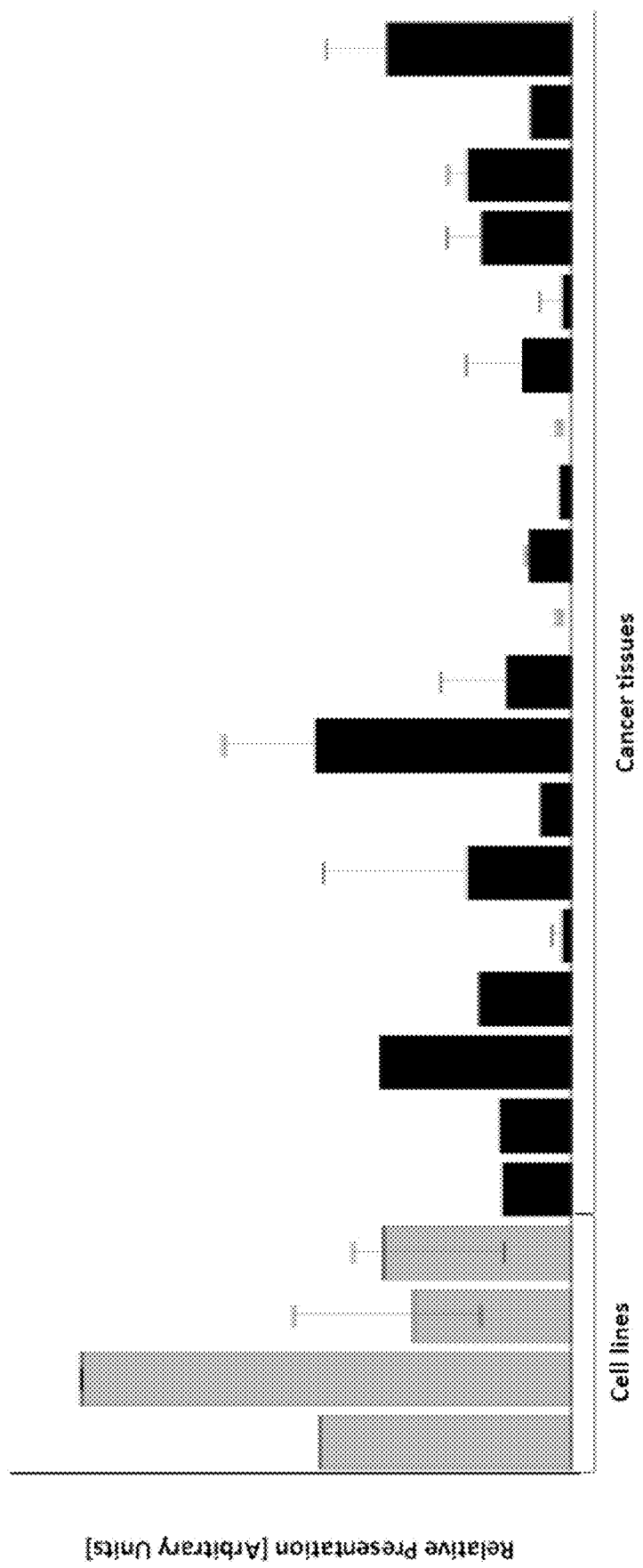
FIG. 1R) Gene symbol(s): STK38L, Peptide: ILVEADGAWVV (SEQ ID NO.: 77). Tissues from left to right: 4 cell lines, 19 cancer tissues (1 brain cancer, 2 breast cancers, 1 colon cancer, 1 leukocytic leukemia cancer, 4 lung cancers, 3 lymph node cancers, 3 ovarian cancers, 1 prostate cancer, 1 skin cancer, 1 urinary bladder cancer, 1 uterus cancer). The normal tissue panel tested was the same as in FIGS. 1E-1K.
Figure 1S:
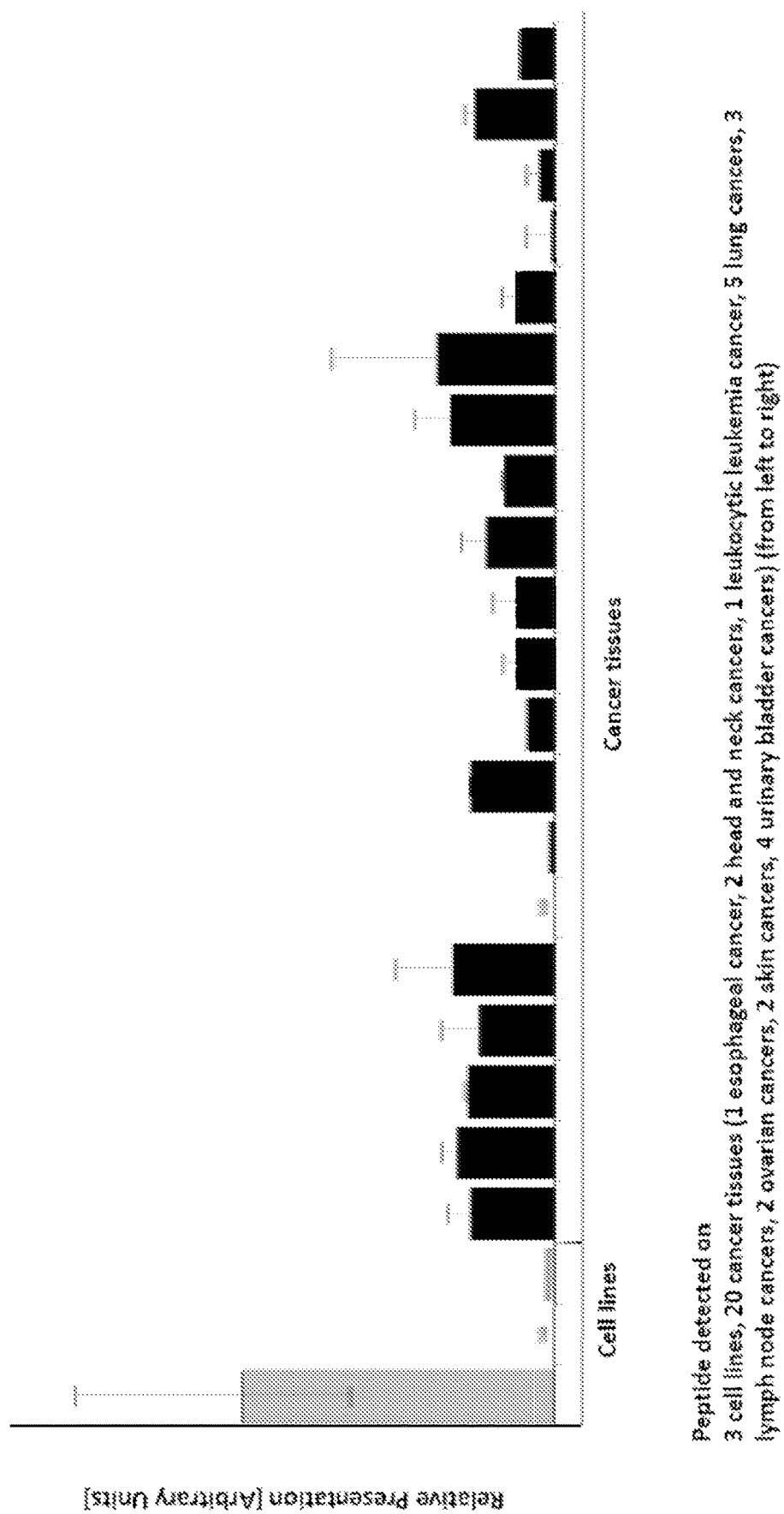
FIG. 1S) Gene symbol(s): PIGA, Peptide: ALNPEIVSV (SEQ ID NO.: 148). Tissues from left to right: 3 cell lines, 20 cancer tissues (1 esophageal cancer, 2 head and neck cancers, 1 leukocytic leukemia cancer, 5 lung cancers, 3 lymph node cancers, 2 ovarian cancers, 2 skin cancers, 4 urinary bladder cancers). The normal tissue panel tested was the same as in FIGS. 1E-1K.
Figure 1U:
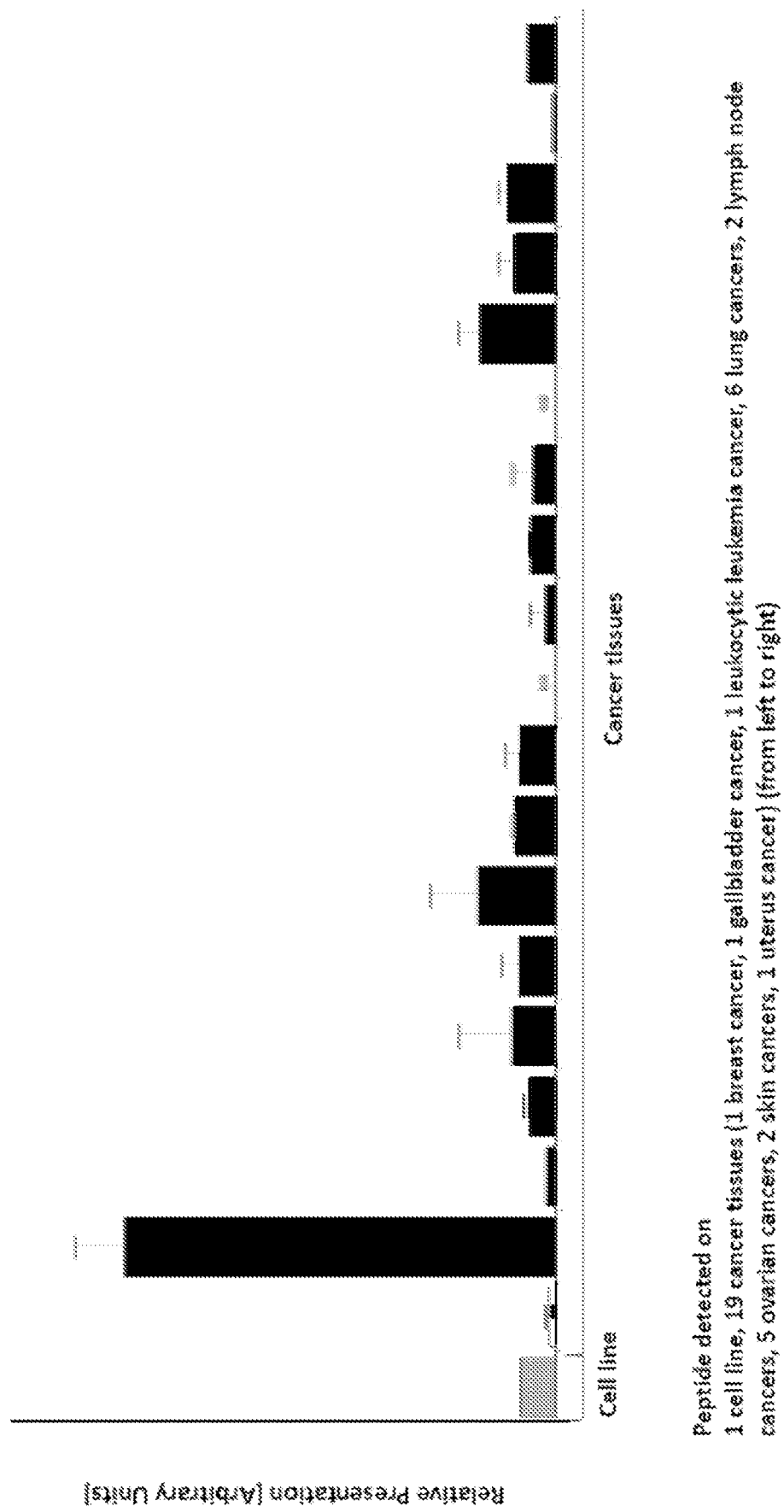
FIG. 1U) Gene symbol(s): RNF213, Peptide: YLMDINGKMWL (SEQ ID NO.: 184). Tissues from left to right: 1 cell line, 19 cancer tissues (1 breast cancer, 1 gallbladder cancer, 1 leukocytic leukemia cancer, 6 lung cancers, 2 lymph node cancers, 5 ovarian cancers, 2 skin cancers, 1 uterus cancer). The normal tissue panel tested was the same as in FIGS. 1E-1K.
Figure 1Y:
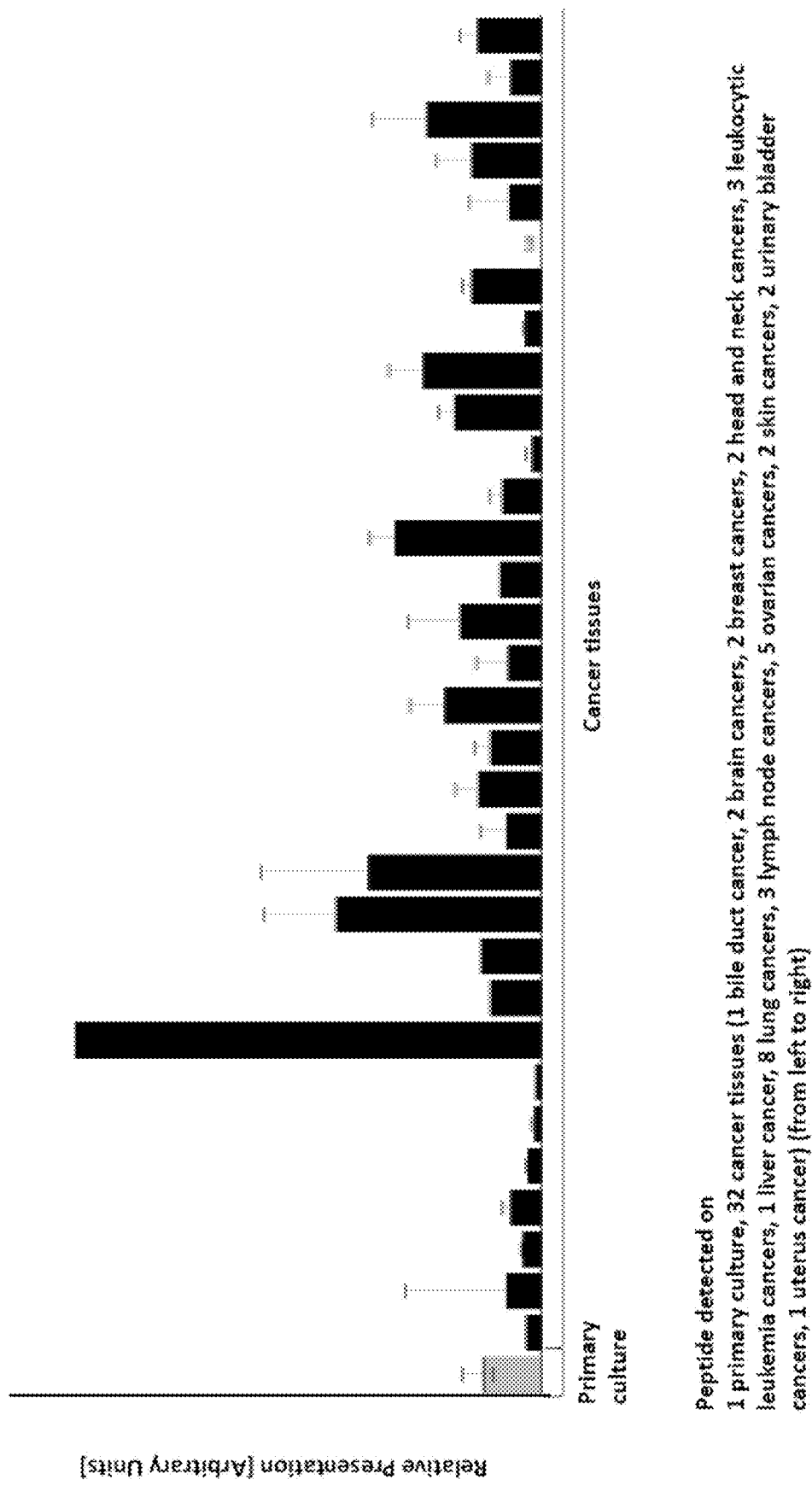
FIG. 1Y) Gene symbol(s): EMC10, Peptide: SLVESHLSDQLTL (SEQ ID NO.: 463). Tissues from left to right: 1 primary culture, 32 cancer tissues (1 bile duct cancer, 2 brain cancers, 2 breast cancers, 2 head and neck cancers, 3 leukocytic leukemia cancers, 1 liver cancer, 8 lung cancers, 3 lymph node cancers, 5 ovarian cancers, 2 skin cancers, 2 urinary bladder cancers, 1 uterus cancer). The normal tissue panel tested was the same as in FIGS. 1E-1K.
Figure 1A:
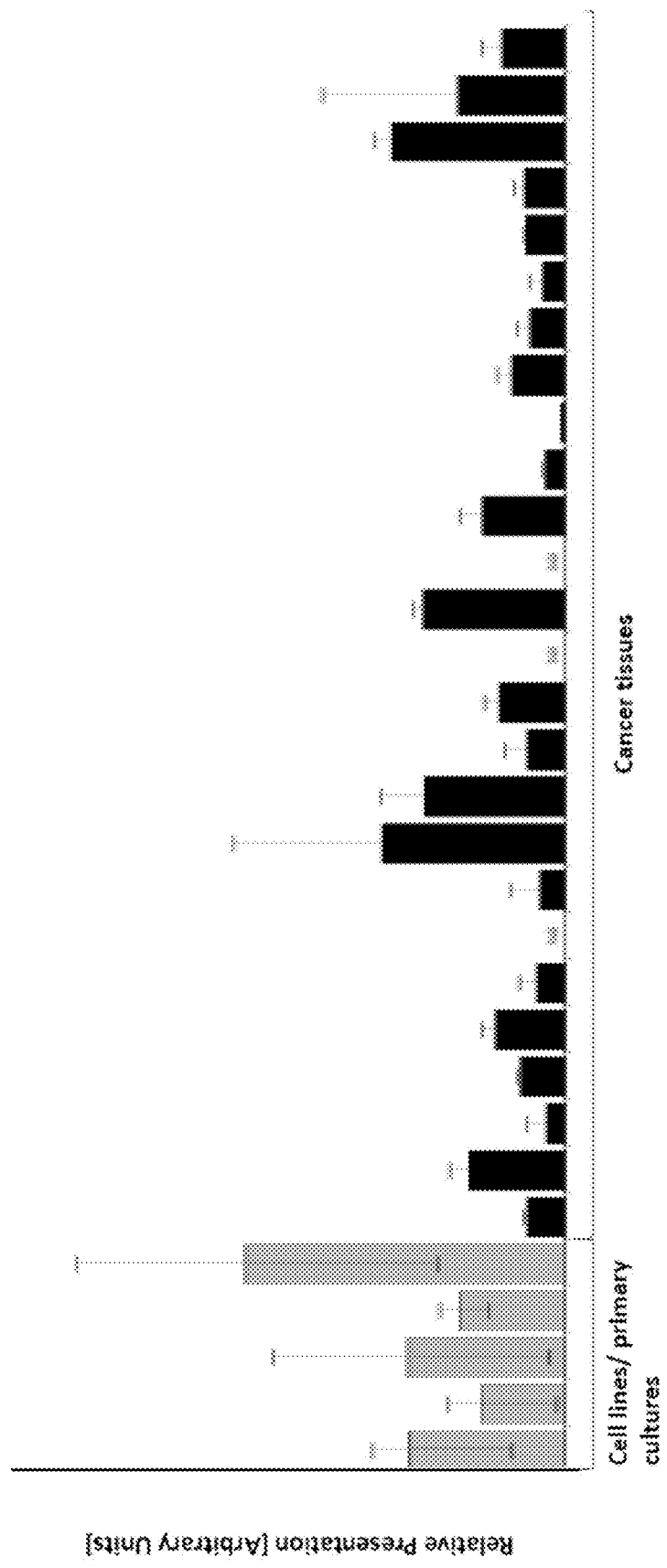
Figure 1A:
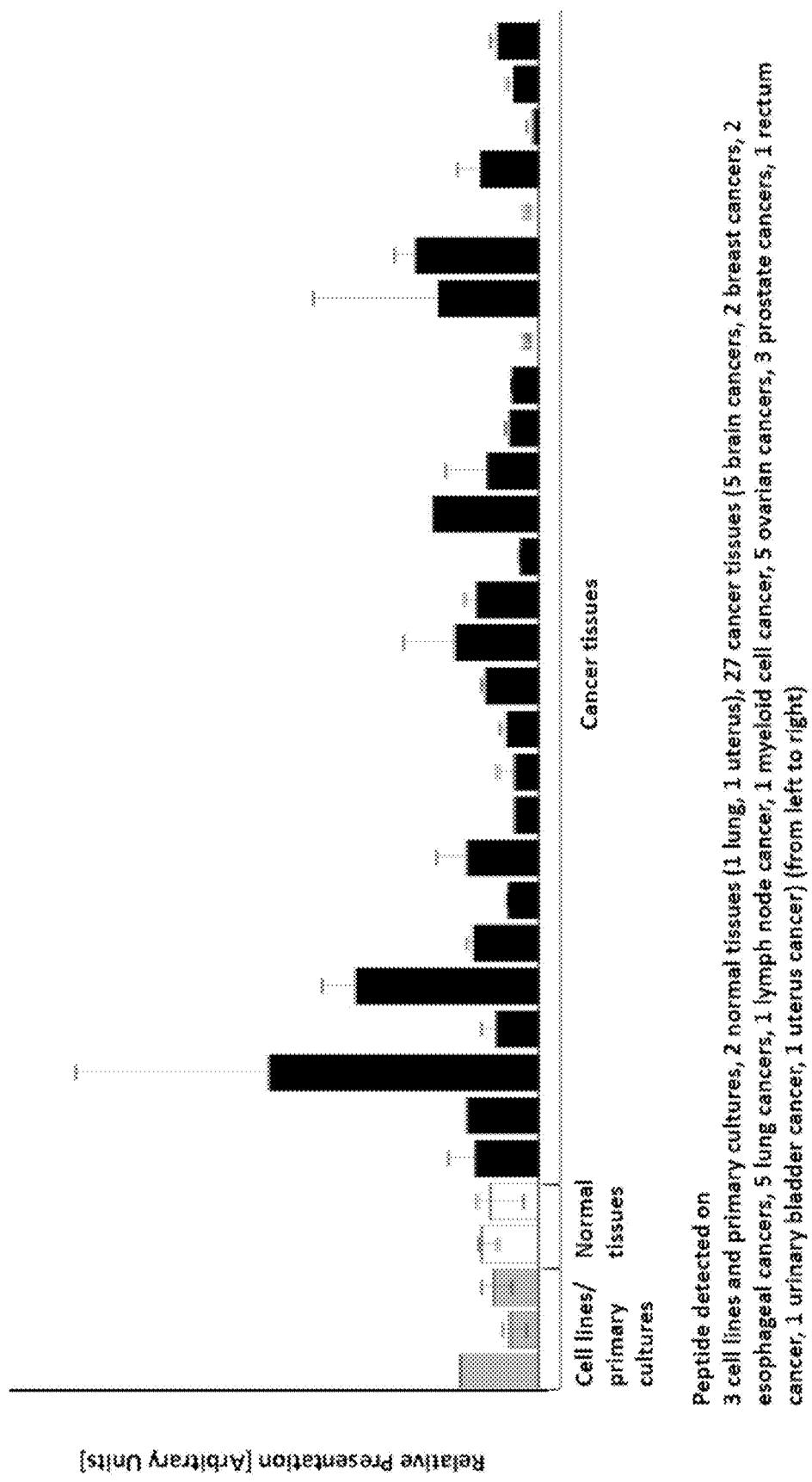
Figure 2D:
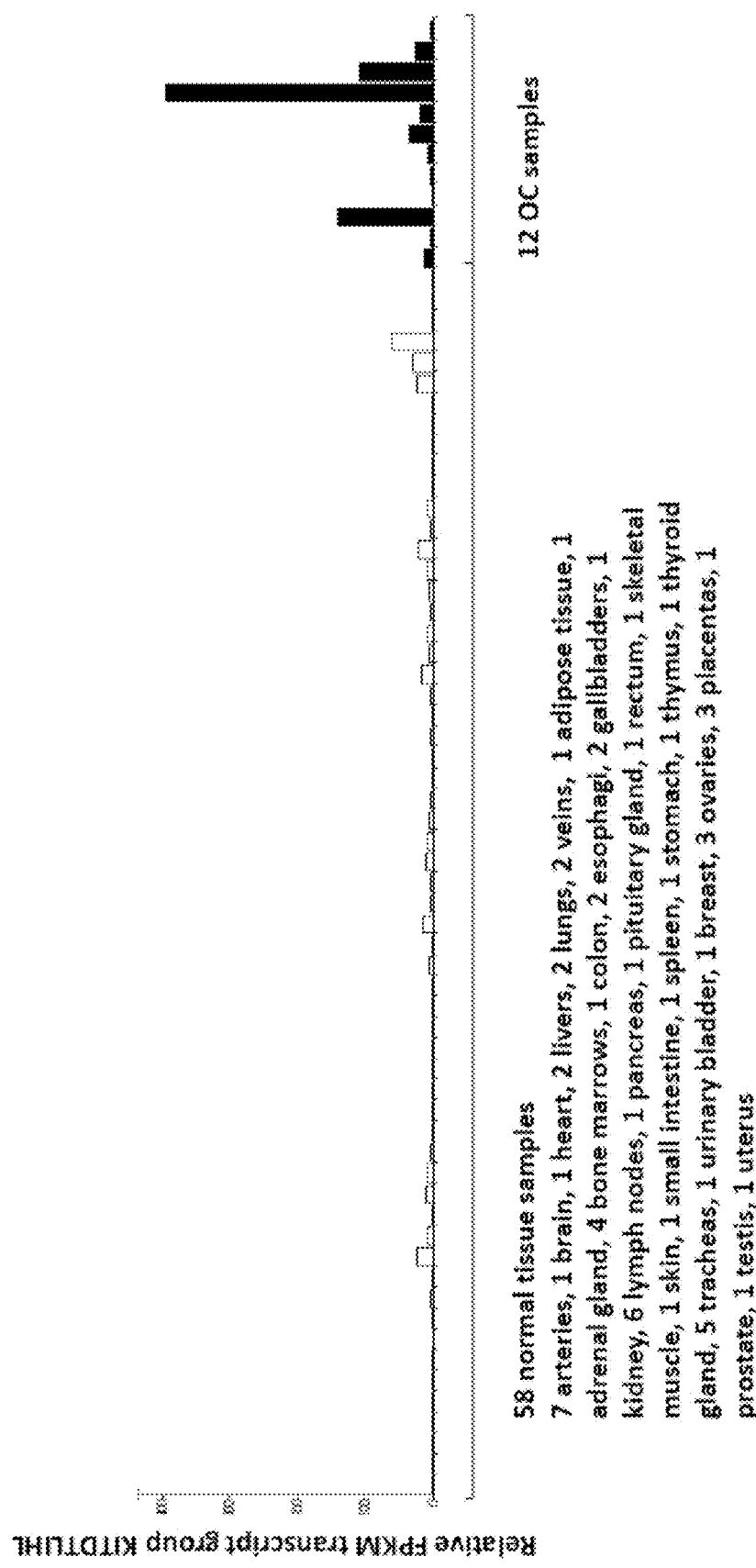
Figure 3A:
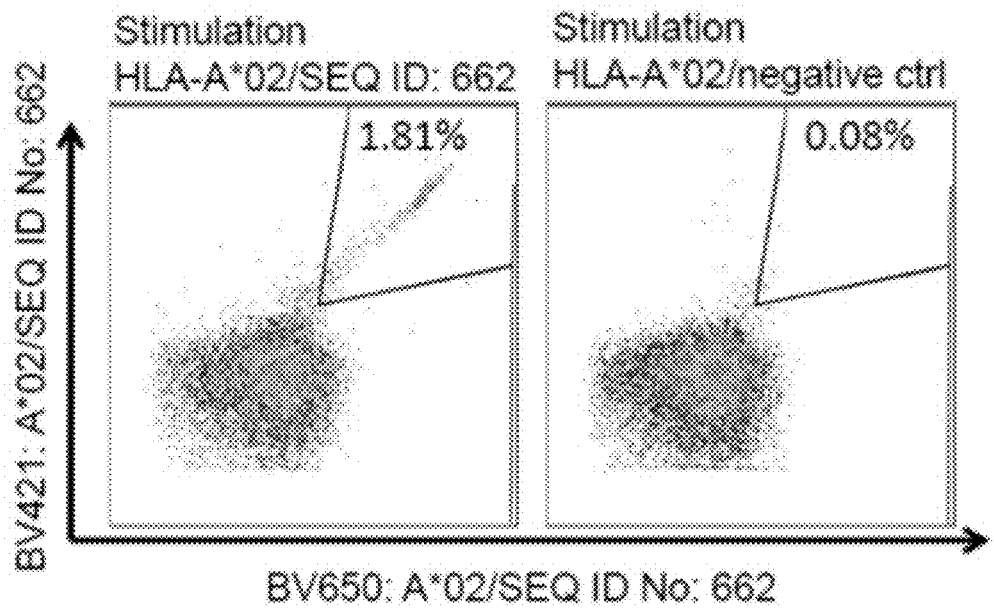
FIGS. 3A to 3F show exemplary immunogenicity data: flow cytometry results after peptide-specific multimer staining. CD8+ T cells were primed using artificial APCs coated with anti-CD28 mAb and HLA-A*02 in complex with SeqID No 662 (FIG. 3A, left panel), SeqID No 663 (FIG. 3B, left panel), SeqID No 11 peptide (FIG. 3C, left panel), SeqID No 198 peptide (FIG. 3D, left panel), SeqID No 587 peptide (FIG. 3E, left panel) and SeqID No 427 peptide (FIG. 3F, left panel), respectively. After three cycles of stimulation, the detection of peptide-reactive cells was performed by 2D multimer staining with A*02/SeqID No 662 (FIG. 3A), A*02/SeqID No 663 (FIG. 3B), A*02/SeqID No 11 (FIG. 3C), A*02/SeqID No 198 (FIG. 3D), A*02/SeqID No 587 (FIG. 3E) or A*02/SeqID No 427 (FIG. 3F). Right panels (FIGS. 3A, 3B, 3C, 3D, 3E, and 3F) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.
Figure 3B:
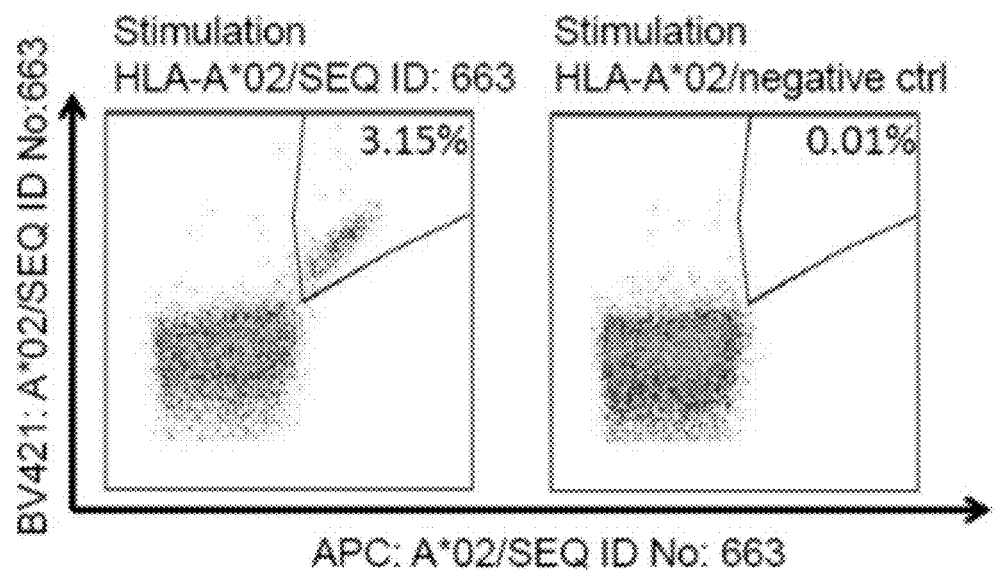
Figure 3C:
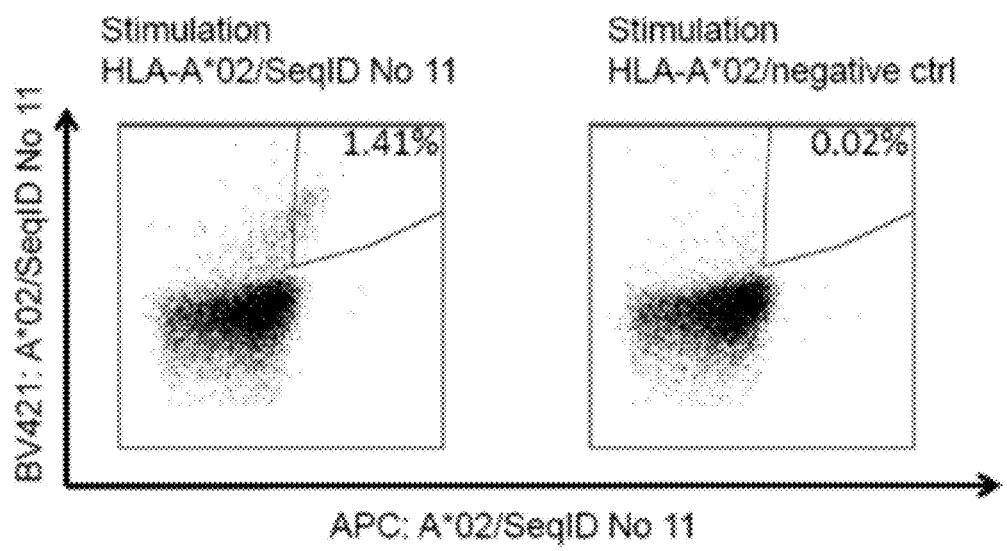
Figure 3D:
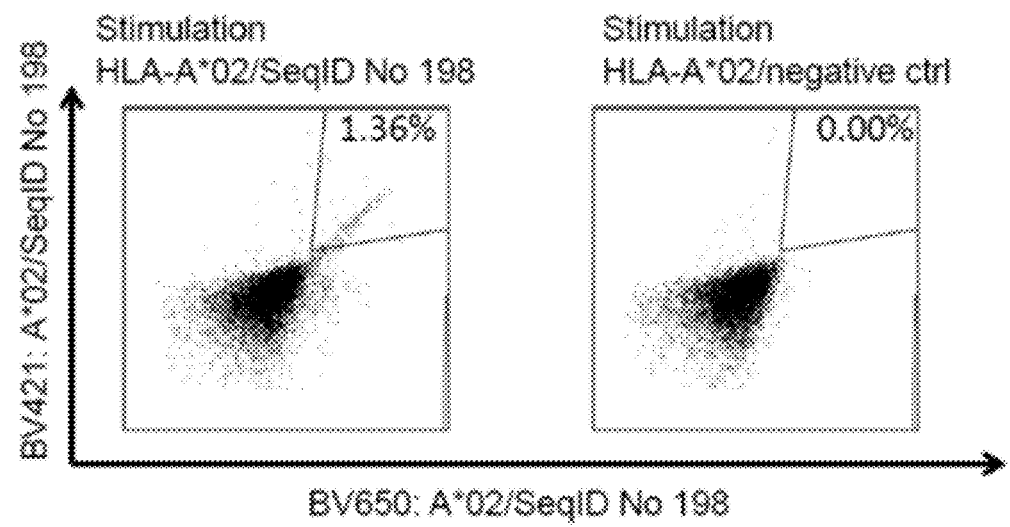
Figure 3E:
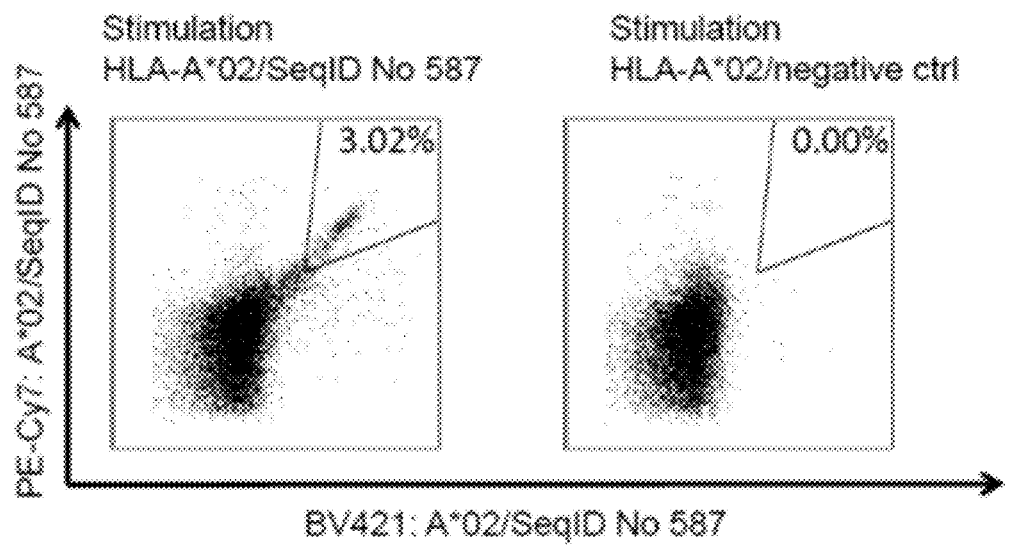
Figure 3F:
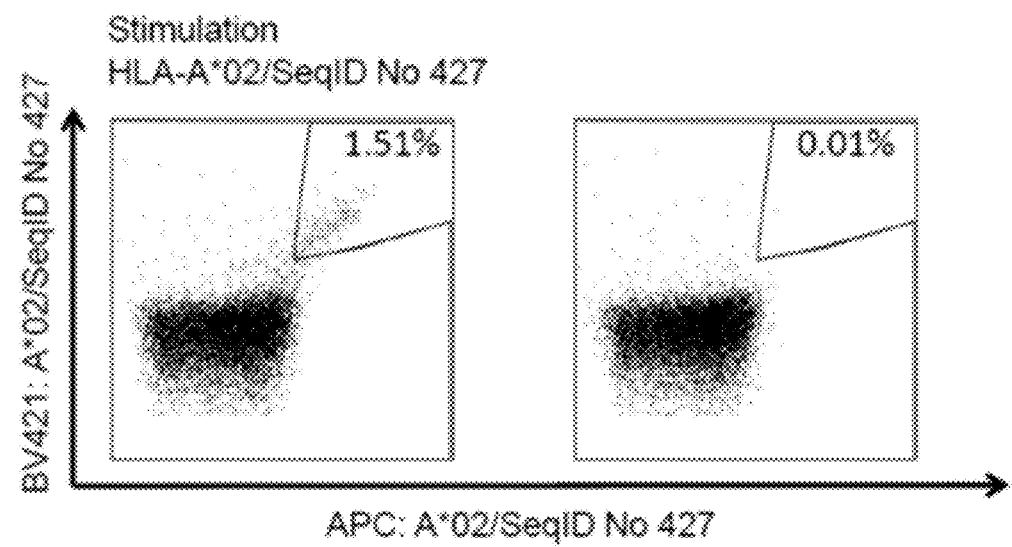

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose ovarian cancer samples to a baseline of normal tissue samples. Presentation profiles of exemplary over-presented peptides are shown in FIGS. 1A-1AE. Presentation scores for exemplary peptides are shown in Table 9.

TABLE 9

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues consisted of: adipose tissue, adrenal gland, artery, vein, bone marrow, brain, central and peripheral nerve, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID No. | Sequence | Peptide Presentation |
|---|---|---|
| 1 | SLMEPPAVLLL | +++ |
| 2 | SLLEADPFL | +++ |
| 3 | SLASKLTTL | +++ |
| 4 | GIMEHITKI | +++ |
| 5 | HLTEVYPEL | +++ |
| 6 | VLVSDGVHSV | +++ |
| 7 | SLVGLLLYL | +++ |
| 8 | FTLGNVVGMYL | +++ |
| 9 | GAAKDLPGV | ++ |
| 10 | FLATFPLAAV | +++ |
| 11 | KIFEMLEGV | +++ |
| 12 | SLWPDPMEV | +++ |
| 13 | YLMDESLNL | +++ |
| 14 | AAYGGLNEKSFV | +++ |
| 15 | VLLTFKIFL | +++ |
| 16 | VLFQGQASL | ++ |
| 17 | GLLPGDRLVSV | +++ |
| 18 | YLVAKLVEV | +++ |
| 20 | RMIEYFIDV | +++ |
| 21 | VLDELDMEL | +++ |
| 23 | VLLDDIFAQL | +++ |
| 24 | SLSDGLEEV | ++ |
| 25 | FLPDEPYIKV | +++ |
| 26 | ALLELAEEL | +++ |
| 27 | ILADIVISA | + |
| 28 | QLLDETSAITL | +++ |
| 29 | KMLGIPISNILMV | ++ |
| 30 | LILDWVPYI | ++ |
| 31 | YLAPELFVNV | +++ |
| 32 | KLDDLTQDLTV | +++ |
| 33 | VLLSLLEKV | ++ |
| 34 | ILVEADSLWVV | +++ |
| 35 | KINDTIYEV | +++ |
| 36 | YVLEDLEVTV | +++ |
| 37 | LLWDVVTGQSV | +++ |
| 38 | FLLEDDIHVS | +++ |
| 39 | SVAPNLPAV | +++ |

TABLE 9-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues consisted of: adipose tissue, adrenal gland, artery, vein, bone marrow, brain, central and peripheral nerve, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID No. | Sequence | Peptide Presentation |
|---|---|---|
| 40 | TLLVKVFSV | +++ |
| 41 | SLMPHIPGL | +++ |
| 42 | VLLQKIVSA | +++ |
| 43 | VLSSLEINI | + |
| 44 | ILDPISSGFLL | +++ |
| 45 | SLWQDIPDV | +++ |
| 46 | ILTEENIHL | +++ |
| 47 | ILLSVPLLVV | +++ |
| 48 | ALAELYEDEV | +++ |
| 50 | SLSELEALM | +++ |
| 51 | LLPDLEFYV | +++ |
| 52 | FLLAHGLGFLL | +++ |
| 53 | KMIETDILQKV | +++ |
| 54 | SLLEQGKEPWMV | +++ |
| 55 | SLLDLETLSL | +++ |
| 56 | KLYEGIPVLL | +++ |
| 57 | TLAELQPPVQL | +++ |
| 58 | FLDTLKDLI | ++ |
| 59 | IMEDIILTL | +++ |
| 60 | SLTIDGIYYV | +++ |
| 61 | FLQGYQLHL | +++ |
| 62 | VLLDVSAGQLLM | +++ |
| 63 | YLLPSGGSVTL | +++ |
| 64 | YAAPGGLIGV | + |
| 65 | LKVNQGLESL | +++ |
| 67 | TLLAEALVTV | +++ |
| 68 | SLMELPRGLFL | +++ |
| 69 | FQLDPSSGVLVTV | +++ |
| 70 | GLLDYPVGV | +++ |
| 71 | GILARIASV | +++ |
| 72 | SLLELDGINL | +++ |
| 73 | NIFDLQIYV | +++ |
| 74 | ALLDPEVLSIFV | +++ |
| 75 | GLLEVMVNL | +++ |
| 76 | ILIDSIYKV | +++ |
| 77 | ILVEADGAWVV | +++ |
| 78 | SLFSSLEPQIQPV | +++ |
| 79 | SLFIGEKAVLL | ++ |
| 81 | SLFSQLQYL | +++ |
| 82 | FLSSVTYNL | +++ |
| 83 | ILAPTVMMI | +++ |
| 84 | VTFGEKLLGV | +++ |
| 86 | NLIGKIENV | + |
| 87 | ALPEAPAPLLPHIT | +++ |
| 88 | FLLVGDLMAV | +++ |
| 89 | YILPTETIYV | +++ |
| 90 | TLLQIIETV | +++ |
| 91 | IMQDFPAEIFL | +++ |
| 92 | YLIPFTGIVGL | +++ |
| 93 | LLQAIKLYL | +++ |
| 94 | YLIDIKTIAI | +++ |
| 96 | YIFTDNPAAV | +++ |
| 97 | SLINGSFLV | +++ |
| 98 | LIIDQADIYL | +++ |
| 99 | ALVSKGLATV | +++ |
| 100 | YLLSTNAQL | +++ |
| 101 | ILVGGGALATV | +++ |
| 102 | YLFESEGLVL | +++ |
| 103 | TLAEVVVAL | +++ |
| 105 | LLLEHSFEI | ++ |
| 106 | LLYDAVHIVSV | +++ |
| 107 | FLQPVDDTQHL | +++ |
| 108 | ALFPGVALLLA | +++ |
| 109 | IILSILEQA | +++ |
| 110 | FLSQVDFEL | +++ |
| 111 | YVWGFYPAEV | +++ |
| 112 | FLITSNNQL | +++ |
| 113 | GLLPTPLFGV | +++ |
| 114 | SLVGEPILQNV | +++ |
| 116 | YHIDEEVGF | +++ |
| 117 | ILPDGEDFLAV | +++ |
| 118 | KLIDNNINV | +++ |
| 119 | FLYIGDIVSL | ++ |
| 120 | ALLGIPLTLV | +++ |
| 122 | FLLAEDDIYL | +++ |
| 123 | NLWDLTDASVV | +++ |
| 124 | ALYETELADA | +++ |
| 125 | VQIHQVAQV | +++ |
| 126 | VLAYFLPEA | + |
| 127 | KIGDEPPKV | ++ |
| 129 | GLLDGGVDILL | ++ |
| 130 | FLWNGEDSALL | +++ |
| 131 | FVPPVTVFPSL | +++ |
| 132 | LLVEQPPLAGV | +++ |
| 134 | YLQELIFSV | +++ |
| 135 | ALSEVDFQL | +++ |
| 136 | YLADPSNLFVV | +++ |
| 137 | TLVLTLPTV | +++ |
| 138 | YQYPRAILSV | +++ |
| 139 | SVMEVNSGIYRV | +++ |
| 141 | YLDFSNNRL | +++ |
| 142 | FLFATPVFI | +++ |
| 143 | LLLDITPEI | +++ |
| 144 | YIMEPSIFNTL | ++ |
| 145 | FLATSGTLAGI | +++ |
| 146 | SLATAGDGLIEL | +++ |
| 147 | SLLEAVSFL | + |
| 148 | ALNPEIVSV | +++ |
| 149 | NLLELFVQL | +++ |
| 150 | RLWEEGEELEL | +++ |
| 151 | KILQQLVTL | +++ |
| 152 | ILFEDIFDV | +++ |
| 153 | FLIANVLYL | +++ |
| 155 | RVANLHFPSV | + |
| 156 | AISQGITLPSL | +++ |
| 157 | SLNDEVPEV | +++ |
| 158 | KLFDVDEDGYI | +++ |
| 159 | GLVGNPLPSV | +++ |
| 160 | FLFDEEIEQI | ++ |
| 161 | ALLEGVNTV | +++ |
| 162 | YQQAQVPSV | +++ |
| 163 | ALDEMGDLLQL | +++ |
| 164 | ALLPQPKNLTV | +++ |
| 165 | SLLDEIRAV | +++ |
| 166 | YLNHLEPPV | +++ |
| 167 | KVLEVTEEFGV | ++ |
| 168 | KILDADIQL | +++ |
| 169 | NLPEYLPFV | +++ |
| 170 | RLQETLSAA | +++ |
| 171 | LLLPLQILL | +++ |

TABLE 9-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues consisted of: adipose tissue, adrenal gland, artery, vein, bone marrow, brain, central and peripheral nerve, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID No. | Sequence | Peptide Presentation |
|---|---|---|
| 172 | VLYSYTIITV | +++ |
| 173 | LLDSASAGLYL | +++ |
| 174 | ALAQYLITA | ++ |
| 175 | YLFENISQL | +++ |
| 176 | YLMEGSYNKVFL | +++ |
| 177 | YLLPEEYTSTL | +++ |
| 178 | ALTEIAFVV | + |
| 179 | KVLNELYTV | +++ |
| 180 | FQIDPHSGLVTV | +++ |
| 181 | LLWAGTAFQV | +++ |
| 182 | MLLEAPGIFL | +++ |
| 183 | FGLDLVTEL | ++ |
| 184 | YLMDINGKMWL | +++ |
| 185 | FLIDDKGYTL | +++ |
| 186 | TLFFQQNAL | + |
| 187 | RQISIRGIVGV | +++ |
| 188 | GLFPVTPEAV | + |
| 189 | ALQRKLPYV | +++ |
| 190 | FLSSLTETI | +++ |
| 191 | LLQEGQALEYV | +++ |
| 192 | KMLDGASFTL | +++ |
| 193 | QLLDADGFLNV | +++ |
| 194 | ALPLFVITV | +++ |
| 196 | YLYSVEIKL | +++ |
| 197 | ALGPEGGRV | ++ |
| 198 | KTINKVPTV | +++ |
| 199 | ALQDVPLSSV | +++ |
| 200 | LLFGSVQEV | +++ |
| 201 | RLVDYLEGI | +++ |
| 202 | ALLDQQGSRWTL | +++ |
| 203 | VLLEDAHSHTL | +++ |
| 204 | KIAENVEEV | +++ |
| 205 | SLYPGTETMGL | +++ |
| 206 | VLQEGKLQKLAQL | +++ |
| 208 | KISPVTFSV | +++ |
| 209 | KLIESKHEV | +++ |
| 210 | LLLNAVLTV | ++ |
| 211 | LLWPGAALL | +++ |
| 212 | ALWDQDNLSV | +++ |
| 213 | VTAAYMDTVSL | ++ |
| 215 | QLINHLHAV | +++ |
| 216 | NLWEDPYYL | +++ |
| 217 | ALIHPVSTV | +++ |
| 218 | SALEELVNV | +++ |
| 219 | KLSDIGITV | +++ |
| 220 | LLQKFVPEI | +++ |
| 221 | ALYEEGLLL | +++ |
| 222 | NLIENVQRL | ++ |
| 223 | ALLENIALYL | +++ |
| 224 | TLIDAQWVL | +++ |
| 225 | SLLKVLPAL | +++ |
| 226 | MLYVVPIYL | +++ |
| 227 | ALMNTLLYL | +++ |
| 228 | AMQEYIAVV | + |
| 229 | RLPGPLGTV | ++ |
| 230 | ILVDWLVEV | +++ |
| 231 | FLSPQQPPLLL | +++ |
| 232 | ALLEAQDVELYL | +++ |
| 233 | VLSETLYEL | ++ |
| 234 | ALMEDTGRQML | +++ |
| 235 | YLNDLHEVLL | +++ |
| 236 | GLLEAKVSL | +++ |
| 237 | ALLEASGTLLL | +++ |
| 238 | YLISFQTHI | +++ |
| 239 | AAFAGKLLSV | +++ |
| 240 | ILLEQAFYL | +++ |
| 241 | SLVEVNPAYSV | +++ |
| 242 | AIAYILQGV | +++ |
| 243 | LLLNELPSV | ++ |
| 244 | SLFGGTEITI | +++ |
| 245 | SMIDDLLGV | +++ |
| 246 | LLWEVVSQL | +++ |
| 247 | VLLPNDLLEKV | +++ |
| 248 | FLFPNQYVDV | + |
| 249 | LLDGFLVNV | +++ |
| 251 | ALYTGFSILV | +++ |
| 252 | LLIGTDVSL | +++ |
| 253 | GLDAATATV | +++ |
| 254 | TLLAFIMEL | +++ |
| 255 | VLASYNLTV | +++ |
| 256 | FLPPEHTIVYI | +++ |
| 257 | SIFSAFLSV | +++ |
| 259 | TLMRQLQQV | ++ |
| 261 | YVLEFLEEI | + |
| 263 | LLVSNLDFGV | +++ |
| 267 | ALQDFLLSV | +++ |
| 271 | LVYPLELYPA | ++ |
| 274 | SLLFSLFEA | + |
| 275 | YLVYILNEL | + |
| 277 | LLPPLESLATV | + |
| 278 | QLLDVVLTI | + |
| 279 | ALWGGTQPLL | ++ |
| 280 | VLPDPEVLEAV | + |
| 281 | ILRESTEEL | + |
| 282 | LLADVVPTT | + |
| 285 | QLLHVGVTV | + |
| 288 | NLINEINGV | +++ |
| 289 | VLLEIEDLQV | + |
| 292 | LLWEAGSEA | + |
| 296 | FMEGAIIYV | ++ |
| 298 | VMITKLVEV | ++ |
| 303 | AILPQLFMV | + |
| 307 | ALPVSLPQI | + |
| 308 | SQYSGQLHEV | + |
| 311 | RLYTGMHTV | + |
| 315 | YLQDVVEQA | ++ |
| 318 | GLINTGVLSV | + |
| 319 | SLEPQIQPV | + |
| 320 | KMFEFVEPLL | + |
| 321 | GLFEDVTQPGILL | ++ |
| 322 | TLMTSLPAL | ++ |
| 323 | IQIGEETVITV | + |
| 325 | FIMPATVADATAV | +++ |
| 327 | GLAPFTEGISFV | ++ |
| 328 | ALNDQVFEI | + |
| 331 | KVDTVWVNV | + |
| 332 | YLISELEAA | + |
| 333 | FLPDANSSV | ++ |
| 334 | TLTKVLVAL | + |
| 338 | SVLEDPVHAV | + |

TABLE 9-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues consisted of: adipose tissue, adrenal gland, artery, vein, bone marrow, brain, central and peripheral nerve, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID No. | Sequence | Peptide Presentation |
|---|---|---|
| 341 | SQIALNEKLVNL | + |
| 342 | HIYDKVMTV | + |
| 343 | SLLEVNEESTV | + |
| 345 | VIWKALIHL | ++ |
| 346 | LLDSKVPSV | ++ |
| 348 | ILLDVKTRL | +++ |
| 351 | SLIPNLRNV | +++ |
| 352 | SLLELLHIYV | + |
| 356 | KLLGKLPEL | ++ |
| 357 | SMHDLVLQV | ++ |
| 358 | ALDEYTSEL | + |
| 359 | YLLPESVDL | + |
| 360 | ALDJGASLLHL | + |
| 363 | KVLDVSDLESV | ++ |
| 368 | ILLEEVSPEL | + |
| 370 | SLLQDLVSV | + |
| 372 | TMLLNIPLV | +++ |
| 373 | SLLEDKGLAEV | + |
| 375 | SLTETIEGV | +++ |
| 379 | IMEGTLTRV | + |
| 382 | ALQNYIKEA | + |
| 384 | ILFANPNIFV | + |
| 385 | SLLEQGLVEA | + |
| 386 | ILFRYPLTI | ++ |
| 390 | ALFMKQIYL | ++ |
| 394 | LLAVIGGLVYL | + |
| 395 | ALALGGIAVV | ++ |
| 396 | ALLPDLPAL | ++ |
| 397 | YLFGERLLEC | + |
| 398 | KLLEEDGTIITL | + |
| 399 | YLFEPLYHV | +++ |
| 401 | ILLDDTGLAYI | + |
| 403 | KLYDRILRV | ++ |
| 404 | AIDIJGRDPAV | + |
| 406 | SVQGEDLYLV | ++ |
| 410 | VLSDVIPJI | ++ |
| 411 | LLAHLSPEL | + |
| 413 | TLLEKVEGC | ++ |
| 414 | YVDDIFLRV | + |
| 415 | LLDKVYSSV | + |
| 418 | ALAELENIEV | + |
| 419 | GQYEGKVSSV | + |
| 420 | FMYDTPQEV | ++ |
| 421 | RLPETLPSL | ++ |
| 423 | GLDGPPPTV | +++ |
| 424 | TLLDALYEI | + |
| 425 | FLYEKSSQV | + |
| 427 | ALLPLSPYL | +++ |
| 428 | KLGHTDILVGV | ++ |
| 429 | GLVNDLARV | + |
| 430 | HLYSSIEHLTT | + |
| 431 | SLVNVVPKL | + |
| 432 | TLIEESAKV | +++ |
| 433 | AMLNEPWAV | +++ |
| 434 | KVSNSGITRV | +++ |
| 435 | WLMPVIPAL | +++ |
| 436 | HLAEVSAEV | +++ |
| 437 | SMAPGLVIQAV | +++ |
| 438 | KLLPLAGLYL | +++ |
| 439 | YLLQEIYGI | +++ |
| 440 | ALADGVTMQV | +++ |
| 441 | ALLENPKMEL | +++ |
| 442 | GLLGGGGVLGV | +++ |
| 443 | GLWEIENNPTV | ++ |
| 444 | GLLRDEALAEV | +++ |
| 446 | QLIPALAKV | +++ |
| 447 | QLVPALAKV | +++ |
| 448 | NLLETKLQL | ++ |
| 450 | FMIDASVHPTL | +++ |
| 451 | LLLLDTVTMQV | +++ |
| 454 | KLPPPPPQA | +++ |
| 455 | SLLKEPQKVQL | + |
| 456 | LLIGHLERV | ++ |
| 457 | SLLPGNLVEKV | +++ |
| 458 | SLIDKLYNI | +++ |
| 459 | ALITEVVRL | +++ |
| 460 | AMLEKNYKL | +++ |
| 461 | VMFRTPLASV | +++ |
| 462 | KLAKQPETV | +++ |
| 463 | SLVESHLSDQLTL | +++ |
| 464 | ALNDCIYSV | +++ |
| 465 | QLCDLNAEL | +++ |
| 466 | VLIANLEKL | +++ |
| 468 | YLRSVGDGETV | + |
| 470 | MLQDSIHVV | +++ |
| 471 | YLYNNMIAKI | +++ |
| 472 | KLLEVSDDPQV | ++ |
| 473 | AMATESILHFA | +++ |
| 474 | YLDPALELGPRNV | + |
| 475 | LLLNEEALAQI | +++ |
| 476 | ALMERTGYSMV | +++ |
| 477 | ALLPASGQIAL | +++ |
| 478 | YLLHEKLNL | +++ |
| 479 | SLFGNSGILENV | + |
| 480 | ALLEDSCHYL | + |
| 481 | GLIEDYEALL | +++ |
| 482 | SLAPAGIADA | +++ |
| 483 | ALTDIVSQV | + |
| 486 | AVMESIQGV | ++ |
| 487 | LLINSVFHV | + |
| 488 | FLAEDPKVTL | + |
| 489 | KMWEELPEVV | +++ |
| 490 | FLLQHVQEL | +++ |
| 491 | GLNDRSDAV | +++ |
| 492 | SLFDGFADGLGV | +++ |
| 494 | ALQPEPIKV | +++ |
| 495 | FIFSEKPVFV | + |
| 496 | FLVEKQPPQV | +++ |
| 497 | GLLEKLTAI | + |
| 498 | KLWTGGLDNTV | + |
| 499 | KIFDIDEAEEGV | +++ |
| 500 | SLMEDQVLQL | + |
| 501 | LLDPNVKSIFV | ++ |
| 502 | RLLAQVPGL | +++ |
| 503 | SLNHFTHSV | + |
| 504 | GLSDGNPSL | +++ |
| 505 | SLAPGDVVRQV | +++ |
| 506 | KLLGKVETA | +++ |
| 507 | KLIDDQDISISL | + |
| 508 | ILAQEQLVVGV | +++ |

TABLE 9-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues consisted of: adipose tissue, adrenal gland, artery, vein, bone marrow, brain, central and peripheral nerve, colon, rectum, small intestine incl. duodenum, esophagus, gallbladder, heart, kidney, liver, lung, lymph node, mononuclear white blood cells, pancreas, peritoneum, pituitary, pleura, salivary gland, skeletal muscle, skin, spleen, stomach, thymus, thyroid gland, trachea, ureter, urinary bladder.

| SEQ ID No. | Sequence | Peptide Presentation |
|---|---|---|
| 509 | FLFDTKPLIV | +++ |
| 510 | KLYSVVSQL | +++ |
| 511 | FLDPYCSASV | +++ |
| 512 | SLSEIVPCL | +++ |
| 513 | SLWPSPEQL | +++ |
| 514 | ILVDWLVQV | +++ |
| 515 | LLQELVLFL | +++ |
| 516 | AVGPASILKEV | +++ |
| 517 | LLMPIPEGLTL | + |
| 518 | KLNAEVACV | +++ |
| 519 | GLLHLTLLL | +++ |
| 520 | LAVHPSGVAL | ++ |
| 521 | MLLTKLPTI | ++ |
| 522 | TLWYRSPEV | +++ |
| 523 | YQIPRTFTL | + |
| 525 | VLLEAGEGLVTI | + |
| 526 | RLAEVGQYEQV | + |
| 527 | FLLEPGNLEV | +++ |
| 528 | SVAEGRALMSV | + |
| 529 | LLADELITV | ++ |
| 530 | VMYADIGGMDI | + |
| 531 | YTLPIASSIRL | + |
| 538 | LLLAHIIAL | ++ |
| 539 | ALFDAQAQV | ++ |
| 540 | ALIPETTTLTV | ++ |
| 541 | SMLEPVPEL | + |
| 543 | GLLPTPITQQASL | + |
| 545 | LLADLLHNV | + |
| 546 | VMIAGKVAVV | + |
| 550 | FLYDEIEAEVNL | + |
| 551 | KLYESLLPFA | ++ |
| 554 | LLMPSSEDLLL | ++ |
| 557 | KLYDDMIRL | + |
| 558 | GLLENIPRV | ++ |
| 560 | ALWDIETGQQTTT | + |
| 561 | YLQLTQSEL | +++ |
| 563 | WLLPYNGVTV | + |
| 564 | TVTNAVVTV | ++ |
| 565 | ALQETPTSV | ++ |
| 566 | VIADGGIQNV | ++ |
| 568 | TLYDIAHTPGV | ++ |
| 570 | ALANQIPTV | + |
| 574 | YLLQEPPRTV | + |
| 575 | YLISQVEGHQV | + |
| 576 | ILLNNSGQIKL | ++ |
| 579 | NLMEMVAQL | ++ |
| 586 | KLKPGDLVGV | + |
| 588 | SLLPLSHLV | + |
| 589 | KLYPQLPAEI | + |
| 590 | SLIEKLWQT | + |
| 591 | SMAELDIKL | ++ |
| 593 | GLPRFGIEMV | + |
| 595 | VLLSIYPRV | + |
| 597 | KLLEGQVIQL | + |
| 599 | YLLNDASLISV | ++ |
| 601 | SAFPFPVTV | + |
| 603 | FLIEPEHVNTV | + |
| 606 | ALWETEVYI | ++ |
| 610 | LLAPTPYIIGV | + |
| 613 | RLLPPGAVVAV | ++ |
| 618 | VLFDSESIGIYV | + |
| 619 | ALQDRVPLA | + |
| 625 | VVLEGASLETV | + |
| 626 | LLMATILHL | ++ |
| 627 | KLLETELLQEI | + |
| 629 | HLLNESPML | ++ |
| 630 | LLSHVIVAL | + |
| 631 | FLDVFLPRV | + |
| 632 | YLIPDIDLKL | ++ |
| 634 | VVAEFVPLI | + |
| 637 | SIYGGFLLGV | ++ |
| 638 | KLIQESPTV | + |
| 639 | SLFQNCFEL | + |
| 640 | YLFSEALNAA | + |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues for RNASeq experiments was obtained from: Asterand, Detroit, USA and Royston, Herts, UK; ProteoGenex Inc. Culver City, Calif., USA, Geneticist Inc., Glendale, Calif., USA, Istituto Nazionale Tumori "Pascale", Molecular Biology and Viral Oncology Unit (IRCCS), Naples, Italy, University Hospital of Heidelberg, Germany, BioCat GmbH, Heidelberg, Germany.

Quality and quantity of all RNA samples were assessed on an Agilent 2100 Bioanalyzer (Agilent, Waldbronn, Germany) using the RNA 6000 Pico LabChip Kit (Agilent).

RNAseq Experiments

Gene expression analysis of—tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc., San Diego, Calif., USA), which includes RNA fragmentation, cDNA conversion and addition of sequencing adaptors. Libraries derived from multiple samples are mixed equimolar and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Exemplary expression profiles of source genes of the present invention that are highly over-expressed or exclusively expressed in ovarian cancer are shown in FIGS. 2A to 2D. Expression scores for further exemplary genes are shown in Table 10.

TABLE 10

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following normal tissues: adipose tissue, adrenal gland, artery, bone marrow, brain, colon, esophagus, gallbladders, heart, kidney, liver, lung, lymph node, pancreas, pituitary, rectum, skeletal muscle, skin, small intestine, spleen, stomach, thymus, thyroid gland, trachea, urinary bladder, vein.

| SEQ ID No. | Gene Name | Sequence | Gene Expression |
|---|---|---|---|
| 1 | CCNA1 | SLMEPPAVLLL | +++ |
| 2 | CCNA1 | SLLEADPFL | +++ |
| 3 | MUC16 | SLASKLTTL | +++ |
| 4 | MUC16 | GIMEHITKI | +++ |
| 5 | MUC16 | HLTEVYPEL | +++ |
| 11 | CT45A1, CT45A3, CT45A5, CT45A6, CT45A2, RP11-342L5.1 | KIFEMLEGV | +++ |
| 15 | GPR64 | VLLTFKIFL | +++ |
| 21 | IFI30 | VLDELDMEL | + |
| 25 | CLDN16 | FLPDEPYIKV | +++ |
| 41 | TDRD9 | SLMPHIPGL | + |
| 42 | TDRD9 | VLLQKIVSA | + |
| 45 | ARHGEF19 | SLWQDIPDV | ++ |
| 67 | MUC20 | TLLAEALVTV | + |
| 69 | FAT2 | FQLDPSSGVLVTV | +++ |
| 72 | VWDE | SLLELDGINL | +++ |
| 81 | NUP205 | FLFSQLQYL | + |
| 101 | GPD2 | ILVGGGALATV | + |
| 102 | GAS2L3 | YLFESEGLVL | ++ |
| 113 | BPIFB3 | GLLPTPLFGV | +++ |
| 114 | BPIFB3 | SLVGEPILQNV | +++ |
| 115 | AQP5 | AIAGAGILYGV | ++ |
| 116 | IDO1 | YHIDEEVGF | +++ |
| 118 | ITGB8 | KLIDNNINV | ++ |
| 126 | MCM2 | VLAYFLPEA | + |
| 171 | KLK7 | LLLPLQILL | +++ |
| 173 | KIF15 | LLDSASAGLYL | +++ |
| 181 | KIAA1324 | LLWAGTAFQV | + |
| 183 | RNF213 | FGLDLVTEL | ++ |
| 184 | RNF213 | YLMDINGKMWL | ++ |
| 193 | CLSPN | QLLDADGFLNV | +++ |
| 194 | SLC28A3 | ALPLFVITV | ++ |

TABLE 10-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following normal tissues: adipose tissue, adrenal gland, artery, bone marrow, brain, colon, esophagus, gallbladders, heart, kidney, liver, lung, lymph node, pancreas, pituitary, rectum, skeletal muscle, skin, small intestine, spleen, stomach, thymus, thyroid gland, trachea, urinary bladder, vein.

| SEQ ID No. | Gene Name | Sequence | Gene Expression |
|---|---|---|---|
| 195 | MROH6 | GLFADLLPRL | + |
| 197 | SOX17 | ALGPEGGRV | ++ |
| 210 | UNG | LLLNAVLTV | + |
| 215 | BHLHE41 | QLINHLHAV | ++ |
| 230 | CCNA2, CCNA1, CCNB3 | ILVDWLVEV | +++ |
| 233 | TIMELESS | VLSETLYEL | ++ |
| 235 | CCNE1 | YLNDLHEVLL | ++ |
| 239 | RSAD2 | AAFAGKLLSV | + |
| 244 | PKHD1L1 | SLFGGTEITI | +++ |
| 258 | NCAPD2 | ELAERVPAI | ++ |
| 259 | C20orf96 | TLMRQLQQV | + |
| 266 | ESR1 | KITDTLIHL | +++ |
| 310 | GGT6 | FLVDTPLARA | + |
| 311 | SGPP2 | RLYTGMHTV | + |
| 317 | FAT2 | SLAALVVHV | ++ |
| 327 | APOL2 | GLAPFTEGISFV | ++ |
| 335 | IGHG1, IGHG4, IGHG3, IGHG2 | YSLSSVVTV | +++ |
| 339 | HDGF | GLWEIENNPTVKA | + |
| 342 | VWA2 | HIYDKVMTV | ++ |
| 350 | LAMA5 | ALLDVTHSELTV | ++ |
| 371 | RNF213 | FLQAHLHTA | ++ |
| 372 | RNF213 | TMLLNIPLV | ++ |
| 387 | ALMS1 | ALFQATAEV | + |
| 393 | EPPK1 | GLLDTQTSQVLTA | ++ |
| 395 | ARID5B | ALALGGIAVV | + |
| 408 | KLHL14 | VLDDSIYLV | +++ |
| 409 | KLHL14 | LLDAMNYHL | +++ |
| 421 | SCNN1A | RLPETLPSL | +++ |
| 423 | TNFAIP2 | GLDGPPPTV | ++ |
| 426 | NCAPD2 | RLADKSVLV | + |
| 427 | VTCN1 | ALLPLSPYL | +++ |
| 432 | ABCC4 | TLIEESAKV | + |
| 442 | BPIFB4 | GLLGGGGVLGV | ++ |
| 443 | HDGF, HDGFL1 | GLWEIENNPTV | + |
| 446 | EYA4, EYA1, EYA2 | QLIPALAKV | +++ |
| 456 | NUP205 | LLIGHLERV | + |
| 465 | KIFC1 | QLCDLNAEL | ++ |
| 466 | ZYG11A | VLIANLEKL | ++ |
| 467 | MX2 | FLAKDFNFL | ++ |
| 484 | KIF15 | SLIEKVTQL | +++ |
| 494 | SORL1 | ALQPEPIKV | ++ |
| 495 | SORL1 | FIFSEKPVFV | + |
| 509 | CANX | FLFDTKPLIV | + |
| 512 | CCNA1 | SLSEIVPCL | +++ |
| 519 | NFE2L3 | GLLHLTLLL | +++ |
| 523 | GAB2 | YQIPRTFTL | +++ |
| 551 | NCAPD3 | KLYESLLPFA | + |
| 579 | CHD7 | NLMEMVAQL | ++ |
| 580 | ASUN | LLMENAERV | + |
| 587 | KLHL14 | VMNDRLYAI | +++ |
| 588 | RNF213 | SLLPLSHLV | + |
| 595 | TAP1 | VLLSIYPRV | ++ |
| 602 | ERMP1 | YLLEQIKLIEV | ++ |
| 609 | HELZ2 | ALWKQLLEL | + |
| 614 | UBE2L6 | LLLPDQPPYHL | ++ |
| 616 | TRIP13 | VLIDEVESL | ++ |
| 629 | NUP205 | HLLNESPML | + |
| 631 | PRKDC | FLDVFLPRV | + |
| 632 | SMARCC1 | YLIPDIDLKL | + |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for 22 HLA-A*0201 restricted TUMAPs of the invention so far, demonstrating that these peptides are T-cell epitopes against which CD8+ precursor T cells exist in humans (Table 11).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 664) from modified Melan-A/MART-1) and A*0201/DDX5-001 (YLLPAIVHI from DDX5, SEQ ID NO. 665), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+ CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Ovarian Cancer Peptides

For tested HLA class I peptides, in vitro immunogenicity could be demonstrated by generation of peptide specific T-cell lines. Exemplary flow cytometry results after TUMAP-specific multimer staining for two peptides of the invention are shown in FIGS. 3A to 3F together with corresponding negative controls. Results for six peptides from the invention are summarized in Table 11A and B.

TABLE 11A in vitro immunogenicity of HLA class I peptides of the invention. Exemplary results of in vitro immunogenicity experiments conducted by the applicant for the peptides of the invention.
<20% = +; 20%-49% = ++; 50%-69% = +++; >=70% = ++++

| SEQ ID NO: | Sequence | wells | donors |
|---|---|---|---|
| 283 | ALYIGDGYVIHLA | + | +++ |
| 648 | LLWGNAIFL | ++ | +++ |
| 652 | TLWYRAPEV | +++ | ++++ |
| 659 | ILFPDIIARA | + | +++ |
| 662 | KIQEILTQV | + | +++ |
| 663 | KIQEMQHFL | + | +++ |

TABLE 12B in vitro immunogenicity of additional HLA class I peptides of the invention. Exemplary results of in vitro immunogenicity experiments conducted by the applicant for HLA-A*02 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID NO: | Sequence | Wells positive [%] |
|---|---|---|
| 2 | SLLEADPFL | "+" |
| 3 | SLASKLTTL | "+" |
| 5 | HLTEVYPEL | "+++" |
| 7 | SLVGLLLYL | "++" |
| 8 | FTLGNVVGMYL | "+" |
| 11 | KIFEMLEGV | "+" |
| 17 | GLLPGDRLVSV | "++" |
| 19 | FMVDNEAIYDI | "++" |
| 36 | YVLEDLEVTV | "+" |
| 38 | FLLEDDIHVS | "+" |
| 40 | TLLVKVFSV | "++" |
| 48 | ALAELYEDEV | "+" |
| 49 | YLPAVFEEV | "++" |
| 56 | KLYEGIPVLL | "+" |
| 60 | SLTIDGIYYV | "++++" |
| 61 | FLQGYQLHL | "++" |
| 79 | SLFIGEKAVLL | "+" |
| 108 | ALFPGVALLLA | "++" |
| 113 | GLLPTPLFGV | "+" |
| 118 | KLIDNNINV | "+" |
| 141 | YLDFSNNRL | "+" |
| 143 | LLLDITPEI | "+" |

TABLE 12B-continued in vitro immunogenicity of additional HLA class I peptides of the invention. Exemplary results of in vitro immunogenicity experiments conducted by the applicant for HLA-A*02 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID NO: | Sequence | Wells positive [%] |
|---|---|---|
| 150 | RLWEEGEELEL | "+" |
| 152 | ILFEDIFDV | "++" |
| 157 | SLNDEVPEV | "+++" |
| 166 | YLNHLEPPV | "++++" |
| 191 | LLQEGQALEYV | "+++" |
| 198 | KTINKVPTV | "++" |
| 199 | ALQDVPLSSV | "+" |
| 215 | QLINHLHAV | "++" |
| 242 | AIAYILQGV | "+++" |
| 247 | VLLPNDLLEKV | "+" |
| 319 | SLEPQIQPV | "+" |
| 384 | ILFANPNIFV | "+" |
| 395 | ALALGGIAVV | "+++" |
| 443 | GLWEIENNPTV | "+" |
| 446 | QLIPALAKV | "++" |
| 454 | KLPPPPPQA | "++" |
| 460 | AMLEKNYKL | "+" |
| 463 | SLVESHLSDQLTL | "++" |
| 489 | KMWEELPEVV | "+" |
| 499 | KIFDIDEAEEGV | "+" |
| 511 | FLDPYCSASV | "+" |
| 518 | KLNAEVACV | "++" |
| 603 | FLIEPEHVNTV | "+" |

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizates (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1h at 37° C., washed again and detected with TMB solution that is stopped with NH2SO4. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 11

MHC class I binding scores. Binding of HLA-class I restricted peptides to HLA-A*02:01 was ranged by peptide exchange yield: ≥10% = +; ≥20% = ++; ≥50 = +++; ≥75% = ++++

| SEQID | Sequence | Peptide exchange |
|---|---|---|
| 1 | SLMEPPAVLLL | "+++" |
| 2 | SLLEADPFL | "+++" |
| 3 | SLASKLTTL | "++++" |
| 4 | GIMEHITKI | "++++" |
| 5 | HLTEVYPEL | "+++" |
| 6 | VLVSDGVHSV | "+++" |
| 7 | SLVGLLLYL | "++++" |
| 8 | FTLGNVVGMYL | "++++" |
| 9 | GAAKDLPGV | "++" |
| 10 | FLATFPLAAV | "++++" |
| 11 | KIFEMLEGV | "+++" |
| 12 | SLWPDPMEV | "+++" |
| 13 | YLMDESLNL | "+++" |
| 14 | AAYGGLNEKSFV | "+++" |
| 15 | VLLTFKIFL | "++" |
| 16 | VLFQGQASL | "+++" |
| 17 | GLLPGDRLVSV | "+++" |
| 18 | YLVAKLVEV | "++" |
| 19 | FMVDNEAIYDI | "++++" |
| 20 | RMIEYFIDV | "+++" |
| 21 | VLDELDMEL | "++" |
| 22 | IMEENPGIFAV | "+++" |
| 23 | VLLDDIFAQL | "+++" |
| 24 | SLSDGLEEV | "++" |
| 25 | FLPDEPYIKV | "+++" |
| 26 | ALLELAEEL | "+++" |
| 27 | ILADIVISA | "+++" |
| 28 | QLLDETSAITL | "+++" |
| 29 | KMLGIPISNILMV | "+++" |
| 30 | LILDWVPYI | "+++" |
| 31 | YLAPELFVNV | "++" |
| 32 | KLDDLTQDLTV | "++" |
| 33 | VLLSLLEKV | "++" |
| 34 | ILVEADSLWVV | "+++" |
| 35 | KINDTIYEV | "+++" |
| 36 | YVLEDLEVTV | "++" |
| 38 | FLLEDDIHVS | "+++" |
| 39 | SVAPNLPAV | "+++" |
| 40 | TLLVKVFSV | "+++" |
| 41 | SLMPHIPGL | "+++" |
| 42 | VLLQKIVSA | "+++" |
| 43 | VLSSLEINI | "++" |
| 44 | ILDPISSGFLL | "++" |
| 45 | SLWQDIPDV | "+++" |
| 46 | ILTEENIHL | "+++" |
| 47 | ILLSVPLLVV | "++" |
| 48 | ALAELYEDEV | "+++" |
| 49 | YLPAVFEEV | "+++" |
| 50 | SLSELEALM | "+++" |
| 51 | LLPDLEFYV | "++++" |
| 52 | FLLAHGLGFLL | "++++" |
| 53 | KMIETDILQKV | "++++" |
| 54 | SLLEQGKEPWMV | "+++" |
| 55 | SLLDLETLSL | "++++" |
| 56 | KLYEGIPVLL | "++++" |
| 57 | TLAELQPPVQL | "+++" |
| 58 | FLDTLKDLI | "+++" |
| 59 | IMEDIILTL | "+++" |
| 60 | SLTIDGIYYV | "++++" |
| 61 | FLQGYQLHL | "++++" |

TABLE 11-continued

MHC class I binding scores. Binding of HLA-class I restricted peptides to HLA-A*02:01 was ranged by peptide exchange yield: ≥10% = +; ≥20% = ++; ≥50 = +++; ≥75% = ++++

| SEQID | Sequence | Peptide exchange |
|---|---|---|
| 62 | VLLDVSAGQLLM | "++++" |
| 63 | YLLPSGGSVTL | "++" |
| 64 | YAAPGGLIGV | "++" |
| 66 | FLDENIGGVAV | "+++" |
| 67 | TLLAEALVTV | "+++" |
| 68 | SLMELPRGLFL | "++++" |
| 69 | FQLDPSSGVLVTV | "+++" |
| 70 | GLLDYPVGV | "+++" |
| 71 | GILARIASV | "+++" |
| 72 | SLLELDGINL | "+++" |
| 73 | NIFDLQIYV | "+++" |
| 74 | ALLDPEVLSIFV | "+++" |
| 75 | GLLEVMVNL | "+++" |
| 76 | ILIDSIYKV | "+++" |
| 77 | ILVEADGAWVV | "++++" |
| 78 | SLFSSLEPQIQPV | "+++" |
| 79 | SLFIGEKAVLL | "+++" |
| 80 | FLYDNLVESL | "++" |
| 81 | FLFSQLQYL | "++" |
| 82 | FLSSVTYNL | "+++" |
| 83 | ILAPTVMMI | "+++" |
| 84 | VTFGEKLLGV | "++" |
| 85 | KMSELRVTL | "+++" |
| 86 | NLIGKIENV | "+++" |
| 87 | ALPEAPAPLLPHIT | "++" |
| 88 | FLLVGDLMAV | "+++" |
| 89 | YILPTETIYV | "++++" |
| 90 | TLLQIIETV | "+++" |
| 91 | IMQDFPAEIFL | "++++" |
| 92 | YLIPFTGIVGL | "++" |
| 93 | LLQAIKLYL | "++" |
| 94 | YLIDIKTIAI | "++" |
| 95 | SVIPQIQKV | "+++" |
| 96 | YIFTDNPAAV | "+++" |
| 97 | SLINGSFLV | "+++" |
| 98 | LIIDQADIYL | "+++" |
| 99 | ALVSKGLATV | "++" |
| 100 | YLLSTNAQL | "++++" |
| 101 | ILVGGGALATV | "+++" |
| 102 | YLFESEGLVL | "+++" |
| 103 | TLAEEVVAL | "+++" |
| 104 | STMEQNFLL | "++++" |
| 106 | LLYDAVHIVSV | "+++" |
| 107 | FLQPVDDTQHL | "+++" |
| 108 | ALFPGVALLLA | "++++" |
| 109 | IILSILEQA | "++++" |
| 110 | FLSQVDFEL | "+++" |
| 111 | YVWGFYPAEV | "+++" |
| 113 | GLLPTPLFGV | "+++" |
| 114 | SLVGEPILQNV | "++" |
| 115 | AIAGAGILYGV | "++" |
| 116 | YHIDEEVGF | "+" |
| 117 | ILPDGEDFLAV | "+++" |
| 118 | KLIDNNINV | "+++" |
| 119 | FLYIGDIVSL | "++++" |
| 120 | ALLGIPLTLV | "+++" |
| 121 | GVVDPRAISVL | "++" |
| 122 | FLLAEDDIYL | "+++" |
| 123 | NLWDLTDASVV | "+++" |
| 124 | ALYETELADA | "++" |
| 125 | VQIHQVAQV | "+++" |
| 126 | VLAYFLPEA | "++++" |
| 127 | KIGDEPPKV | "++" |
| 128 | YLFDDPLSAV | "++" |
| 129 | GLLDGGVDILL | "+++" |
| 130 | FLWNGEDSALL | "+++" |
| 131 | FVPPVTVFPSL | "++" |
| 132 | LLVEQPPLAGV | "+++" |
| 133 | KVLSNIHTV | "++" |
| 134 | YLQELIFSV | "+++" |
| 135 | ALSEVDFQL | "+++" |
| 136 | YLADPSNLFVV | "+++" |
| 137 | TLVLTLPTV | "++++" |
| 138 | YQYPRAILSV | "+++" |
| 139 | SVMEVNSGIYRV | "+++" |
| 140 | YMDAPKAAL | "++" |
| 141 | YLDFSNNRL | "++" |
| 142 | FLFATPVFI | "+++" |
| 143 | LLLDITPEI | "++++" |
| 144 | YIMEPSIFNTL | "++++" |
| 145 | FLATSGTLAGI | "++" |
| 146 | SLATAGDGLIEL | "++" |
| 147 | SLLEAVSFL | "+++" |
| 148 | ALNPEIVSV | "++" |
| 149 | NLLELFVQL | "+++" |
| 150 | RLWEEGEELEL | "+++" |
| 151 | KILQQLVTL | "+++" |
| 152 | ILFEDIFDV | "+++" |
| 153 | FLIANVLYL | "+" |
| 154 | ALDDGTPAL | "++" |
| 155 | RVANLHFPSV | "+++" |
| 157 | SLNDEVPEV | "++" |
| 158 | KLFDVDEDGYI | "++++" |
| 159 | GLVGNPLPSV | "++++" |
| 160 | FLFDEEIEQI | "+++" |
| 161 | ALLEGVNTV | "+++" |
| 162 | YQQAQVPSV | "+++" |
| 163 | ALDEMGDLLQL | "+++" |
| 164 | ALLPQPKNLTV | "+++" |
| 165 | SLLDEIRAV | "+++" |
| 166 | YLNHLEPPV | "+++" |
| 167 | KVLEVTEEFGV | "+++" |
| 168 | KILDADIQL | "++++" |
| 169 | NLPEYLPFV | "+++" |
| 170 | RLQETLSAA | "+++" |
| 171 | LLLPLQILL | "+++" |
| 172 | VLYSYTIITV | "++" |
| 173 | LLDSASAGLYL | "+++" |
| 174 | ALAQYLITA | "+++" |
| 175 | YLFENISQL | "+++" |
| 176 | YLMEGSYNKVFL | "++" |
| 177 | YLLPEEYTSTL | "++++" |
| 178 | ALTEIAFVV | "++++" |
| 179 | KVLNELYTV | "+++" |
| 180 | FQIDPHSGLVTV | "++" |
| 181 | LLWAGTAFQV | "+++" |
| 182 | MLLEAPGIFL | "+++" |
| 183 | FGLDLVTEL | "+++" |
| 184 | YLMDINGKMWL | "+++" |
| 185 | FLIDDKGYTL | "++" |
| 186 | TLFFQQNAL | "++" |
| 187 | RQISIRGIVGV | "+++" |
| 188 | GLFPVTPEAV | "+++" |
| 189 | ALQRKLPYV | "+++" |
| 190 | FLSSLTETI | "+++" |
| 191 | LLQEGQALEYV | "++" |
| 192 | KMLDGASFTL | "+++" |
| 193 | QLLDADGFLNV | "+++" |
| 194 | ALPLFVITV | "+++" |
| 195 | GLFADLLPRL | "+++" |
| 196 | YLYSVEIKL | "++++" |
| 197 | ALGPEGGRV | "++" |
| 198 | KTINKVPTV | "+++" |
| 199 | ALQDVPLSSV | "+++" |
| 200 | LLFGSVQEV | "+++" |
| 201 | RLVDYLEGI | "+++" |
| 202 | ALLDQQGSRWTL | "+++" |
| 204 | KIAENVEEV | "++" |
| 205 | SLYPGTETMGL | "+++" |
| 206 | VLQEGKLQKLAQL | "+++" |
| 207 | GLTSTNAEV | "++" |
| 208 | KISPVTFSV | "+++" |
| 209 | KLIESKHEV | "++" |
| 210 | LLLNAVLTV | "++" |
| 211 | LLWPGAALL | "++" |
| 212 | ALWDQDNLSV | "++" |
| 214 | FLLDLDPLLL | "+++" |
| 215 | QLINHLHAV | "+++" |

TABLE 11-continued

MHC class I binding scores. Binding of HLA-class I restricted peptides to HLA-A*02:01 was ranged by peptide exchange yield: ≥10% = +; ≥20% = ++; ≥50 = +++; ≥75% = ++++

| SEQID | Sequence | Peptide exchange |
|---|---|---|
| 216 | NLWEDPYYL | "+++" |
| 217 | ALIHPVSTV | "++" |
| 218 | SALEELVNV | "++" |
| 219 | KLSDIGITV | "+++" |
| 220 | LLQKFVPEI | "++" |
| 221 | ALYEEGLLL | "++" |
| 222 | NLIENVQRL | "++" |
| 223 | ALLENIALYL | "+++" |
| 224 | TLIDAQWVL | "+++" |
| 225 | SLLKVLPAL | "+++" |
| 226 | MLYVVPIYL | "++" |
| 227 | ALMNTLLYL | "++" |
| 228 | AMQEYIAVV | "++" |
| 229 | RLPGPLGTV | "++" |
| 230 | ILVDWLVEV | "+" |
| 231 | FLSPQQPPLLL | "++" |
| 232 | ALLEAQDVELYL | "++" |
| 233 | VLSETLYEL | "++" |
| 234 | ALMEDTGRQML | "++" |
| 235 | YLNDLHEVLL | "++++" |
| 236 | GLLEAKVSL | "+++" |
| 237 | ALLEASGTLLL | "++++" |
| 238 | YLISFQTHI | "++++" |
| 239 | AAFAGKLLSV | "+++" |
| 240 | ILLEQAFYL | "+++" |
| 241 | SLVEVNPAYSV | "+++" |
| 242 | AIAYILQGV | "++" |
| 243 | LLLNELPSV | "+++" |
| 244 | SLFGGTEITI | "+++" |
| 245 | SMIDDLLGV | "+++" |
| 246 | LLWEVVSQL | "+++" |
| 247 | VLLPNDLLEKV | "+++" |
| 248 | FLFPNQYVDV | "+++" |
| 249 | LLDGFLVNV | "+++" |
| 250 | ALSEEGLLVYL | "+++" |
| 251 | ALYTGFSILV | "++" |
| 252 | LLIGTDVSL | "+++" |
| 253 | GLDAATATV | "++" |
| 254 | TLLAFIMEL | "+++" |
| 255 | VLASYNLTV | "++++" |
| 256 | FLPPEHTIVYI | "+++" |
| 257 | SIFSAFLSV | "+++" |
| 258 | ELAERVPAI | "++" |
| 261 | YVLEFLEEI | "++" |
| 262 | LLWGDLIWL | "+++" |
| 263 | LLVSNLDFGV | "+++" |
| 264 | SLQEQLHSV | "+++" |
| 265 | LLFGGTKTV | "++" |
| 266 | KITDTLIHL | "+++" |
| 267 | ALQDFLLSV | "+++" |
| 269 | RVLEVGALQAV | "++" |
| 270 | LLLDEEGTFSL | "++" |
| 271 | LVYPLELYPA | "+++" |
| 272 | ALGNTVPAV | "+++" |
| 273 | NLFQSVREV | "++" |
| 274 | SLLFSLFEA | "++" |
| 275 | YLVYILNEL | "++" |
| 276 | ALFTFSPLTV | "+++" |
| 277 | LLPPLESLATV | "++" |
| 278 | QLLDVVLTI | "++" |
| 279 | ALWGGTQPLL | "++" |
| 280 | VLPDPEVLEAV | "+++" |
| 281 | ILRESTEEL | "+++" |
| 282 | LLADVVPTT | "+++" |
| 283 | ALYIGDYVIHLA | "+++" |
| 284 | ILLSQTTGV | "+++" |
| 285 | QLLHVGVTV | "+++" |
| 286 | YLFPGIPEL | "+++" |
| 287 | FLNEFFLNV | "+++" |
| 288 | NLINEINGV | "+++" |
| 289 | VLLEIEDLQV | "++++" |
| 295 | VLDRESPNV | "+++" |
| 296 | FMEGAIIYV | "+++" |
| 297 | VLADIELAQA | "+++" |
| 298 | VMITKLVEV | "+++" |
| 299 | YLLETSGNL | "+++" |
| 300 | ALLGQTFSL | "+++" |
| 301 | FLVEDLVDSL | "+++" |
| 302 | ALLQEGEVYSA | "+++" |
| 303 | AILPQLFMV | "++++" |
| 304 | MTLGQIYYL | "+++" |
| 305 | SIANFSEFYV | "++++" |
| 306 | ALVNVQIPL | "+++" |
| 307 | ALPVSLPQI | "+++" |
| 308 | SQYSGQLHEV | "+++" |
| 309 | GLFDGVPTTA | "+++" |
| 310 | FLVDTPLARA | "++++" |
| 311 | RLYTGMHTV | "+++" |
| 312 | IISDLTIAL | "+++" |
| 313 | VLFDDELLMV | "+++" |
| 314 | ALIAEGIALV | "+++" |
| 315 | YLQDVVEQA | "+++" |
| 316 | ILLERLWYV | "+++" |
| 317 | SLAALVVHV | "+++" |
| 318 | GLINTGVLSV | "++" |
| 319 | SLEPQIQPV | "++" |
| 320 | KMFEFVEPLL | "++++" |
| 321 | GLFEDVTQPGILL | "++++" |
| 322 | TLMTSLPAL | "+++" |
| 324 | FLYDEIEAEV | "+++" |
| 325 | FIMPATVADATAV | "+++" |
| 326 | FLPEALDFV | "+++" |
| 327 | GLAPFTEGISFV | "+++" |
| 328 | ALNDQVFEI | "+++" |
| 329 | FLVTLNNVEV | "++++" |
| 330 | QLALKVEGV | "+++" |
| 331 | KVDTVWVNV | "+++" |
| 332 | YLISELEAA | "+++" |
| 333 | FLPDANSSV | "++" |
| 334 | TLTKVLVAL | "+++" |
| 335 | YSLSSVVTV | "+++" |
| 336 | ILLTAIVQV | "+++" |
| 337 | HLLSELEAAPYL | "++++" |
| 339 | GLWEIENNPTVKA | "++++" |
| 340 | ALLSMTFPL | "++++" |
| 341 | SQIALNEKLVNL | "+++" |
| 342 | HIYDKVMTV | "+++" |
| 343 | SLLEVNEESTV | "+++" |
| 344 | YLQDQHLLLTV | "+++" |
| 345 | VIWKALIHL | "+++" |
| 346 | LLDSKVPSV | "+++" |
| 347 | SLFKHDPAAWEA | "++++" |
| 348 | ILLDVKTRL | "++++" |
| 349 | SLTEYLQNV | "++++" |
| 350 | ALLDVTHSELTV | "+++" |
| 351 | SLIPNLRNV | "+++" |
| 352 | SLLELLHIYV | "+++" |
| 353 | YLFEMDSSL | "++" |
| 354 | LILEGVDTV | "++" |
| 355 | SIQQSIERLLV | "++" |
| 356 | KLLGKLPEL | "+++" |
| 357 | SMHDLVLQV | "+++" |
| 358 | ALDEYTSEL | "++++" |
| 359 | YLLPESVDL | "+++" |
| 361 | ALYELEGTTV | "+++" |
| 362 | TLYGLSVLL | "+++" |
| 363 | KVLDVSDLESV | "++" |
| 364 | LLQNEQFEL | "+++" |
| 365 | YVIDQGETDVYV | "+++" |
| 366 | RLLDMGETDLML | "+++" |
| 367 | SLQNHHQL | "+++" |
| 369 | GLFPEHLIDV | "+++" |
| 370 | SLLQDLVSV | "+++" |
| 371 | FLQAHLHTA | "++++" |
| 372 | TMLLNIPLV | "++" |
| 373 | SLLEDKGLAEV | "++" |
| 374 | FLLQQHLISA | "++" |
| 375 | SLTETIEGV | "++" |

TABLE 11-continued

MHC class I binding scores. Binding of HLA-class I restricted peptides to HLA-A*02:01 was ranged by peptide exchange yield: ≥10% = +; ≥20% = ++; ≥50 = +++; ≥75% = ++++

| SEQID | Sequence | Peptide exchange |
|---|---|---|
| 376 | AMFESSQNVLL | "++" |
| 377 | FLLDSSASV | "++" |
| 378 | ALGYFVPYV | "+++" |
| 379 | IMEGTLTRV | "++" |
| 380 | TLIEDEIATI | "++" |
| 381 | FIDEAYVEV | "++" |
| 382 | ALQNYIKEA | "++" |
| 383 | ALLELENSVTL | "+++" |
| 384 | ILFANPNIFV | "+++" |
| 385 | SLLEQGLVEA | "++" |
| 386 | ILFRYPLTI | "+++" |
| 387 | ALFQATAEV | "++++" |
| 388 | SLTIDGIRYV | "+++" |
| 389 | LLADVTHLL | "++" |
| 390 | ALFMKQIYL | "+++" |
| 391 | YVYPQRLNFV | "+++" |
| 392 | ALLHPQGFEV | "++" |
| 393 | GLLDTQTSQVLTA | "++" |
| 394 | LLAVIGGLVYL | "+++" |
| 395 | ALALGGIAVV | "++++" |
| 396 | ALLPDLPAL | "+++" |
| 397 | YLFGERLLEC | "+++" |
| 398 | KLLEEDGTIITL | "++" |
| 399 | YLFEPLYHV | "+++" |
| 400 | SLLTEQDLWTV | "++" |
| 401 | ILLDDTGLAYI | "+++" |
| 402 | VLFSGALLGL | "++" |
| 403 | KLYDRILRV | "++" |
| 405 | ALYDVFLEV | "++" |
| 407 | YLMDLINFL | "+++" |
| 408 | VLDDSIYLV | "++" |
| 409 | LLDAMNYHL | "++" |
| 412 | YLDDLNEGVYI | "++" |
| 426 | RLADKSVLV | "+++" |
| 427 | ALLPLSPYL | "+++" |
| 428 | KLGHTDILVGV | "++" |
| 429 | GLVNDLARV | "++" |
| 430 | HLYSSIEHLTT | "+++" |
| 431 | SLVNVVPKL | "++" |
| 432 | TLIEESAKV | "++" |
| 433 | AMLNEPWAV | "+++" |
| 434 | KVSNSGITRV | "++" |
| 436 | HLAEVSAEV | "+++" |
| 437 | SMAPGLVIQAV | "+++" |
| 438 | KLLPLAGLYL | "++++" |
| 439 | YLLQEIYGI | "+++" |
| 440 | ALADGVTMQV | "++" |
| 441 | ALLENPKMEL | "+++" |
| 442 | GLLGGGGVLGV | "+++" |
| 443 | GLWEIENNPTV | "+++" |
| 444 | GLLRDEALAEV | "+++" |
| 446 | QLIPALAKV | "+++" |
| 447 | QLVPALAKV | "++" |
| 448 | NLLETKLQL | "+++" |
| 449 | KLAEGLDIQL | "+++" |
| 450 | FMIDASVHPTL | "+++" |
| 451 | LLLLDTVTMQV | "++" |
| 452 | ILLEHGADPNL | "+++" |
| 453 | KLLEATSAV | "++" |
| 454 | KLPPPPPQA | "+++" |
| 455 | SLLKEPQKVQL | "++" |
| 456 | LLIGHLERV | "+++" |
| 457 | SLLPGNLVEKV | "+++" |
| 458 | SLIDKLYNI | "++" |
| 459 | ALITEVVRL | "++" |
| 460 | AMLEKNYKL | "++++" |
| 461 | VMFRTPLASV | "++" |
| 462 | KLAKQPETV | "+++" |
| 463 | SLVESHLSDQLTL | "+++" |
| 464 | ALNDCIYSV | "+++" |
| 465 | QLCDLNAEL | "+++" |
| 466 | VLIANLEKL | "++++" |
| 467 | FLAKDFNFL | "+++" |
| 468 | YLRSVGDGETV | "+++" |
| 469 | YLASDEITTV | "+++" |
| 471 | YLYNNMIAKI | "+++" |
| 472 | KLLEVSDDPQV | "+++" |
| 473 | AMATESILHFA | "+++" |
| 474 | YLDPALELGPRNV | "+++" |
| 475 | LLLNEEALAQI | "+++" |
| 476 | ALMERTGYSMV | "+++" |
| 477 | ALLPASGQIAL | "+++" |
| 478 | YLLHEKLNL | "+++" |
| 479 | SLFGNSGILENV | "+++" |
| 480 | ALLEDSCHYL | "+++" |
| 481 | GLIEDYEALL | "+++" |
| 484 | SLIEKVTQL | "+++" |
| 485 | NVPDSFNEV | "+++" |
| 486 | AVMESIQGV | "+++" |
| 487 | LLINSVFHV | "+++" |
| 488 | FLAEDPKVTL | "+++" |
| 489 | KMWEELPEVV | "+++" |
| 490 | FLLQHVQEL | "+++" |
| 491 | GLNDRSDAV | "++" |
| 492 | SLFDGFADGLGV | "+++" |
| 493 | GLLGEKTQDLIGV | "+++" |
| 494 | ALQPEPIKV | "++" |
| 495 | FIFSEKPVFV | "+++" |
| 496 | FLVEKQPPQV | "+++" |
| 497 | GLLEKLTAI | "+++" |
| 498 | KLWTGGLDNTV | "+++" |
| 499 | KIFDIDEAEEGV | "++" |
| 500 | SLMEDQVLQL | "+++" |
| 501 | LLDPNVKSIFV | "+++" |
| 502 | RLLAQVPGL | "+++" |
| 503 | SLNHFTHSV | "+++" |
| 504 | GLSDGNPSL | "++" |
| 505 | SLAPGDVVRQV | "++" |
| 506 | KLLGKVETA | "+++" |
| 507 | KLIDDQDISISL | "+++" |
| 508 | ILAQEQLVVGV | "+++" |
| 509 | FLFDTKPLIV | "+++" |
| 510 | KLYSVVSQL | "++" |
| 511 | FLDPYCSASV | "++" |
| 512 | SLSEIVPCL | "+++" |
| 513 | SLWPSPEQL | "++" |
| 514 | ILVDWLVQV | "+++" |
| 515 | LLQELVLFL | "+++" |
| 516 | AVGPASILKEV | "++" |
| 517 | LLMPIPEGLTL | "+++" |
| 518 | KLNAEVACV | "+++" |
| 519 | GLLHLTLLL | "+++" |
| 520 | LAVHPSGVAL | "+" |
| 521 | MLLTKLPTI | "+++" |
| 522 | TLWYRSPEV | "++" |
| 523 | YQIPRTFTL | "++" |
| 524 | ALIENLTHQI | "++" |
| 525 | VLLEAGEGLVTI | "+++" |
| 526 | RLAEVGQYEQV | "++" |
| 527 | FLLEPGNLEV | "++++" |
| 528 | SVAEGRALMSV | "+++" |
| 529 | LLADELITV | "+++" |
| 530 | VMYADIGGMDI | "+++" |
| 531 | YTLPIASSIRL | "+++" |
| 537 | TLAPGEVLRSV | "+++" |
| 538 | LLLAHIIAL | "++" |
| 539 | ALFDAQAQV | "+++" |
| 541 | SMLEPVPEL | "+++" |
| 542 | RVWDISTVSSV | "+++" |
| 543 | GLLPTPITQQASL | "+++" |
| 544 | LLWDVPAPSL | "+++" |
| 545 | LLADLLHNV | "+++" |
| 546 | VMIAGKVAVV | "+++" |
| 547 | TLDITPHTV | "+++" |
| 548 | ALWENPESGEL | "++" |
| 549 | AMLENASDIKL | "+++" |
| 550 | FLYDEIEAEVNL | "+++" |
| 551 | KLYESLLPFA | "+++" |

TABLE 11-continued

MHC class I binding scores. Binding of HLA-class I restricted peptides to HLA-A*02:01 was ranged by peptide exchange yield: ≥10% = +; ≥20% = ++; ≥50 = +++; ≥75% = ++++

| SEQID | Sequence | Peptide exchange |
|---|---|---|
| 552 | GLLDLPFRVGV | "++++" |
| 553 | SLLNQDLHWSL | "++++" |
| 554 | LLMPSSEDLLL | "+++" |
| 555 | YVLEGLKSV | "+++" |
| 556 | FLTDLEDLTL | "+++" |
| 557 | KLYDDMIRL | "+++" |
| 558 | GLLENIPRV | "+++" |
| 559 | VTVPPGPSL | "++" |
| 560 | ALWDIETGQQTTT | "+++" |
| 561 | YLQLTQSEL | "+++" |
| 562 | YLEELPEKLKL | "+++" |
| 563 | WLLPYNGVTV | "+++" |
| 564 | TVTNAVVTV | "+++" |
| 565 | ALQETPTSV | "++" |
| 566 | VIADGGIQNV | "++" |
| 567 | SLLPLDDIVRV | "+++" |
| 568 | TLYDIAHTPGV | "++++" |
| 569 | KLVDRTWTL | "+++" |
| 570 | ALANQIPTV | "++" |
| 571 | LLLTTIPQI | "+++" |
| 572 | ALADLIEKELSV | "+++" |
| 573 | ILVANAIVGV | "+++" |
| 574 | YLLQEPPRTV | "++" |
| 575 | YLISQVEGHQV | "+++" |
| 576 | ILLNNSGQIKL | "++++" |
| 577 | VMFEDGVLMRL | "+++" |
| 578 | FLDPGGPMMKL | "+++" |
| 579 | NLMEMVAQL | "++" |
| 580 | LLMENAERV | "++" |
| 582 | TLCDVILMV | "+++" |
| 583 | ILANDGVLLAA | "+++" |
| 584 | ALAEVAAMENV | "+++" |
| 585 | ALWDLAADKQTL | "++++" |
| 586 | KLKPGDLVGV | "+++" |
| 587 | VMNDRLYAI | "+++" |
| 588 | SLLPLSHLV | "+++" |
| 589 | KLYPQLPAEI | "+++" |
| 590 | SLIEKLWQT | "++" |
| 591 | SMAELDIKL | "+++" |
| 592 | RLLJAAENFL | "+++" |
| 593 | GLPRFGIEMV | "+++" |
| 594 | IMLKGDNITL | "+++" |
| 595 | VLLSIYPRV | "+++" |
| 596 | ALLDQTKTLAESAL | "+++" |
| 597 | KLLEGQVIQL | "+++" |
| 598 | FLFPHSVLV | "+++" |
| 599 | YLLNDASLISV | "+++" |
| 600 | ALAAPDIVPAL | "+++" |
| 601 | SAFPFPVTV | "+++" |
| 602 | YLLEQIKLIEV | "++++" |
| 603 | FLIEPEHVNTV | "++" |
| 604 | SILDRDDIFV | "+++" |
| 605 | KLYEAVPQL | "+++" |
| 606 | ALWETEVYI | "+++" |
| 607 | RLYSGISGLEL | "+++" |
| 608 | SLLSVSHAL | "+++" |
| 609 | ALWKQLLEL | "+++" |
| 610 | LLAPTPYIIGV | "+++" |
| 611 | YLLDDGTLVV | "++++" |
| 612 | YLYNEGLSV | "+++" |
| 613 | RLLPPGAVVAV | "+++" |
| 614 | LLLPDQPPYHL | "+++" |
| 615 | VLPPDTDPA | "++" |
| 616 | VLIDEVESL | "+++" |
| 617 | ALMYESEKVGV | "+++" |
| 618 | VLFDSESIGIYV | "+++" |
| 619 | ALQDRVPLA | "+++" |
| 620 | KLLNKIYEA | "++++" |
| 621 | VLMDRLPSLL | "++++" |
| 622 | RLLGEEVVRVLQA | "+++" |
| 623 | YLVEDIQHI | "+++" |
| 635 | SLDSTLHAV | "+++" |

Example 6

Absolute Quantitation of Tumor Associated Peptides Presented on the Cell Surface The generation of binders, such as antibodies and/or TCRs, is a laborious process, which may be conducted only for a number of selected targets. In the case of tumor-associated and -specific peptides, selection criteria include but are not restricted to exclusiveness of presentation and the density of peptide presented on the cell surface. In addition to the isolation and relative quantitation of peptides as described in EXAMPLE 1, the inventors did analyze absolute peptide copies per cell as described in patent application PCT/EP2015/79873. The quantitation of TUMAP copies per cell in solid tumor samples requires the absolute quantitation of the isolated TUMAP, the efficiency of TUMAP isolation, and the cell count of the tissue sample analyzed. Experimental steps are described below.

Peptide Quantitation by nanoLC-MS/MS

For an accurate quantitation of peptides by mass spectrometry, a calibration curve was generated for each peptide using the internal standard method. The internal standard is a double-isotope-labelled variant of each peptide, i.e. two isotope-labelled amino acids were included in TUMAP synthesis. It differs from the tumor-associated peptide only in its mass but shows no difference in other physicochemical properties (Anderson et al., 2012). The internal standard was spiked to each MS sample and all MS signals were normalized to the MS signal of the internal standard to level out potential technical variances between MS experiments.

The calibration curves were prepared in at least three different matrices, i.e. HLA peptide eluates from natural samples similar to the routine MS samples, and each preparation was measured in duplicate MS runs. For evaluation, MS signals were normalized to the signal of the internal standard and a calibration curve was calculated by logistic regression.

For the quantitation of tumor-associated peptides from tissue samples, the respective samples were also spiked with the internal standard; the MS signals were normalized to the internal standard and quantified using the peptide calibration curve.

Efficiency of Peptide/MHC Isolation

As for any protein purification process, the isolation of proteins from tissue samples is associated with a certain loss of the protein of interest. To determine the efficiency of TUMAP isolation, peptide/MHC complexes were generated for all TUMAPs selected for absolute quantitation. To be able to discriminate the spiked from the natural peptide/MHC complexes, single-isotope-labelled versions of the TUMAPs were used, i.e. one isotope-labelled amino acid was included in TUMAP synthesis. These complexes were spiked into the freshly prepared tissue lysates, i.e. at the earliest possible point of the TUMAP isolation procedure, and then captured like the natural peptide/MHC complexes in the following affinity purification. Measuring the recovery of the single-labelled TUMAPs therefore allows conclusions regarding the efficiency of isolation of individual natural TUMAPs.

The efficiency of isolation was analyzed in a low number of samples and was comparable among these tissue samples. In contrast, the isolation efficiency differs between individual peptides. This suggests that the isolation efficiency, although determined in only a limited number of tissue samples, may be extrapolated to any other tissue preparation. However, it is necessary to analyze each TUMAP individually as the isolation efficiency may not be extrapolated from one peptide to others.

Determination of the Cell Count in Solid, Frozen Tissue

In order to determine the cell count of the tissue samples subjected to absolute peptide quantitation, the inventors applied DNA content analysis. This method is applicable to a wide range of samples of different origin and, most importantly, frozen samples (Alcoser et al., 2011; Forsey and Chaudhuri, 2009; Silva et al., 2013). During the peptide isolation protocol, a tissue sample is processed to a homogenous lysate, from which a small lysate aliquot is taken. The aliquot is divided in three parts, from which DNA is isolated (QiaAmp DNA Mini Kit, Qiagen, Hilden, Germany). The total DNA content from each DNA isolation is quantified using a fluorescence-based DNA quantitation assay (Qubit dsDNA HS Assay Kit, Life Technologies, Darmstadt, Germany) in at least two replicates.

In order to calculate the cell number, a DNA standard curve from aliquots of single healthy blood cells, with a range of defined cell numbers, has been generated. The standard curve is used to calculate the total cell content from the total DNA content from each DNA isolation. The mean total cell count of the tissue sample used for peptide isolation is extrapolated considering the known volume of the lysate aliquots and the total lysate volume.

Peptide Copies Per Cell

With data of the aforementioned experiments, the inventors calculated the number of TUMAP copies per cell by dividing the total peptide amount by the total cell count of the sample, followed by division through isolation efficiency. Copy cell number for selected peptides are shown in Table 12

TABLE 12

Absolute copy numbers. The table lists the results of absolute peptide quantitation in NSCLC tumor samples. The median number of copies per cell are indicated for each peptide: <100 = +; >=100 = ++; >=1,000 +++; >=10,000 = ++++. The number of samples, in which evaluable, high quality MS data are available, is indicated.

| Seq ID | Sequence | Copy Number Category | Number of quantifiable samples |
|---|---|---|---|
| 11 | KIFEMLEGV | ++ | 32 |
| 198 | KTINKVPTV | ++ | 14 |
| 408 | VLDDSIYLV | ++ | 17 |
| 427 | ALLPLSPYL | +++ | 13 |
| 587 | VMNDRLYAI | ++ | 18 |

REFERENCE LIST

Nature 511 (2014): 543-550
Abba, M. C. et al., Mol. Cancer Res 5 (2007): 881-890
Abdelmalak, C. A. et al., Clin Lab 60 (2014): 55-61
Abele, R. et al., Essays Biochem. 50 (2011): 249-264
Abetamann, V. et al., Clin Cancer Res 2 (1996): 1607-1618
Abuhusain, H. J. et al., J Biol Chem 288 (2013): 37355-37364
Adam, A. P. et al., Cancer Res 69 (2009): 5664-5672
Addou-Klouche, L. et al., Mol. Cancer 9 (2010): 213
Adelaide, J. et al., Cancer Res 67 (2007): 11565-11575
Adelman, C. A. et al., Nature 502 (2013): 381-384
Adhikary, S. et al., Cell 123 (2005): 409-421
Agarwal, A. K. et al., J Lipid Res 51 (2010): 2143-2152
Agarwal, N. et al., Oncogene 32 (2013): 462-470
Agesen, T. H. et al., Gut 61 (2012): 1560-1567
Ahangari, F. et al., Med. Oncol 31 (2014): 173
Ahsan, S. et al., Acta Neuropathol. Commun. 2 (2014): 59
Aissani, B. et al., Genes Immun. 15 (2014): 424-429
Aissani, B. et al., Fertil. Steril. 103 (2015): 528-534
Ajiro, M. et al., Int. J Oncol 35 (2009): 673-681
Ajiro, M. et al., Int. J Oncol 37 (2010): 1085-1093
Akao, Y. et al., Cancer Res 55 (1995): 3444-3449
Akino, K. et al., Cancer Sci. 98 (2007): 88-95
Akisawa, Y. et al., Virchows Arch. 442 (2003): 66-70
Al-haidari, A. A. et al., Int. J Colorectal Dis. 28 (2013): 1479-1487
Albulescu, R., Biomark. Med. 7 (2013): 203
Alimirah, F. et al., Mol. Cancer Res 5 (2007): 251-259
Allen, T. et al., Cancer Res 66 (2006): 1294-1301
Allera-Moreau, C. et al., Oncogenesis. 1 (2012): e30
Allison, J. P. et al., Science 270 (1995): 932-933
Alpizar-Alpizar, W. et al., Int. J Cancer 131 (2012): E329-E336
Alvarez, J. V. et al., Cancer Cell 24 (2013): 30-44
Aly, R. M. et al., Blood Cells Mol. Dis. 53 (2014): 185-188
Amini, S. et al., Anat. Cell Biol 47 (2014): 1-11
Amos, C. I. et al., Hum. Mol. Genet. 20 (2011): 5012-5023
An, C. H. et al., Pathol. Oncol Res 21 (2015): 181-185
Anchi, T. et al., Oncol Lett. 3 (2012): 264-268
Andersen, C. L. et al., Br. J Cancer 100 (2009): 511-523
Andersen, J. B. et al., Br. J Cancer 94 (2006): 1465-1471
Andersen, J. N. et al., Sci. Transl. Med. 2 (2010): 43ra55
Andersen, R. S. et al., Nat. Protoc. 7 (2012): 891-902
Anderson, K. S. et al., J Proteome. Res 10 (2011): 85-96
Andrade, V. C. et al., Exp. Hematol. 37 (2009): 446-449
Andrew, A. S. et al., Hum. Genet. 125 (2009): 527-539
Angele, S. et al., Br. J Cancer 91 (2004): 783-787
Ansari, D. et al., J Cancer Res Clin Oncol 141 (2015): 369-380
Antony-Debre, I. et al., Cancer Cell 27 (2015): 609-611
Appay, V. et al., Eur. J Immunol. 36 (2006): 1805-1814
Arai, A. et al., Cancer Res 71 (2011): 4598-4607
Arai, E. et al., Int. J Cancer 135 (2014): 1330-1342
Arbabian, A. et al., FEBS J 280 (2013): 5408-5418
Arbitrio, M. et al., Cancer Chemother. Pharmacol. 77 (2016): 205-209
Argani, P. et al., Clin Cancer Res 7 (2001): 3862-3868
Arlt, A. et al., Oncogene 28 (2009): 3983-3996
Arsenic, R. et al., BMC. Cancer 15 (2015): 784
Asahara, S. et al., J Transl. Med. 11 (2013): 291
Asmarinah, A. et al., Int. J Oncol 45 (2014): 1489-1496
Asou, N. et al., Blood 109 (2007): 4023-4027
Aviles, Velastegui J. et al., Minerva Chir 46 (1991): 533-537
Ayala, F. et al., Breast Cancer Res Treat. 80 (2003): 145-154
Aylon, Y. et al., Mol. Oncol 5 (2011): 315-323
Azimi, A. et al., Br. J Cancer 110 (2014): 2489-2495
Azzimonti, B. et al., Histopathology 45 (2004): 560-572
Babron, M. C. et al., Carcinogenesis 35 (2014): 1523-1527
Bachmann, S. B. et al., Mol Cancer 13 (2014): 125
Bacsi, K. et al., BMC. Cancer 8 (2008): 317
Bagheri, F. et al., Mol. Biol Rep. 41 (2014): 7387-7394
Balakrishnan, A. et al., Hum. Mutat. 30 (2009): 1167-1174
Baldini, E. et al., Andrologia 42 (2010): 260-267
Balgkouranidou, I. et al., Clin Chem Lab Med. 51 (2013): 1505-1510
Ball, A. R., Jr. et al., Mol. Cell Biol 22 (2002): 5769-5781
Banat, G. A. et al., PLoS. One. 10 (2015): e0139073
Banchereau, J. et al., Cell 106 (2001): 271-274
Band, A. M. et al., J Mammary. Gland. Biol Neoplasia. 16 (2011): 109-115
Bandoh, N. et al., Oncol Rep. 23 (2010): 933-939
Bandres, E. et al., Oncol Rep. 12 (2004): 287-292
Banerjee, R. et al., Nat Commun. 5 (2014): 4527

Bao, B. Y. et al., Clin Cancer Res. 17 (2011): 928-936
Bar-Peled, L. et al., Science 340 (2013): 1100-1106
Barbarulo, A. et al., Oncogene 32 (2013): 4231-4242
Bargou, R. C. et al., Nat Med. 3 (1997): 447-450
Bartlett, J. M. et al., Br. J Cancer 113 (2015): 722-728
Bauer, M. et al., Oncol Rep. 11 (2004): 677-680
Bazzaro, M. et al., Am. J Pathol. 171 (2007): 1640-1649
Beales, P. L. et al., Nephrol. Dial. Transplant. 15 (2000): 1977-1985
Beard, R. E. et al., Clin Cancer Res 19 (2013): 4941-4950
Beatty, G. et al., J Immunol 166 (2001): 2276-2282
Bednarska, K. et al., Immunobiology 221 (2016): 323-332
Beggs, J. D., Nature 275 (1978): 104-109
Behrens, P. et al., Anticancer Res 21 (2001): 2413-2417
Behrens, P. et al., Apoptosis. 8 (2003): 39-44
Bekker-Jensen, S. et al., Nat Cell Biol 12 (2010): 80-86
Benada, J. et al., Biomolecules. 5 (2015): 1912-1937
Bender, C. et al., Int. J Cancer 131 (2012): E45-E55
Benjamini, Y. et al., Journal of the Royal Statistical Society. Series B (Methodological), Vol. 57 (1995): 289-300
Bennett, C. B. et al., PLoS. One. 3 (2008): e1448
Berger, C. et al., Curr. Mol. Med. 13 (2013): 1229-1240
Bertherat, J. et al., Cancer Res 63 (2003): 5308-5319
Bessho, Y. et al., Oncol Rep. 21 (2009): 263-268
Bhan, S. et al., Oncol Rep. 28 (2012): 1498-1502
Bhattacharya, C. et al., Mol Cancer 11 (2012): 82
Bi, Q. et al., Clin Exp. Metastasis 32 (2015): 301-311
Bi, W. et al., Oncol Rep. 29 (2013): 1533-1539
Bianchi, E. et al., Cancer Res 54 (1994): 861-866
Bidkhori, G. et al., PLoS. One. 8 (2013): e67552
Bieche, I. et al., Int. J Cancer 133 (2013): 2791-2800
Bieniek, J. et al., Prostate 74 (2014): 999-1011
Bierkens, M. et al., Genes Chromosomes. Cancer 52 (2013): 56-68
Bilbao-Aldaiturriaga, N. et al., Pediatr. Blood Cancer 62 (2015): 766-769
Bin Amer, S. M. et al., Saudi. Med. J 29 (2008): 507-513
Bisgrove, D. A. et al., J Biol Chem 275 (2000): 30668-30676
Bish, R. et al., Mol. Cells 37 (2014): 357-364
Bisikirska, B. C. et al., Oncogene 32 (2013): 5283-5291
Blanco, I. et al., PLoS. One. 10 (2015): e0120020
Blenk, S. et al., Cancer Inform. 3 (2007): 399-420
Blenk, S. et al., BMC. Cancer 8 (2008): 106
Bloch, D. B. et al., J Biol Chem 271 (1996): 29198-29204
Bock, A. J. et al., Hum. Pathol. 43 (2012): 669-674
Bode, P. K. et al., Mod. Pathol. 27 (2014): 899-905
Boehrer, S. et al., Hematol. J 2 (2001): 103-107
Boehringer, J. et al., Biochem. J 448 (2012): 55-65
Bogush, T. A. et al., Antibiot. Khimioter. 54 (2009): 41-49
Boland, A. et al., Nat Struct. Mol. Biol 20 (2013): 1289-1297
Bombardieri, R. et al., Endocr. Pract. 19 (2013): e124-e128
Borel, F. et al., Hepatology 55 (2012): 821-832
Bossi, D. et al., Mol. Oncol 8 (2014): 221-231
Boulter, J. M. et al., Protein Eng 16 (2003): 707-711
Bourdon, V. et al., Cancer Res 62 (2002): 6218-6223
Bourguignon, L. Y. et al., J Biol Chem 287 (2012): 32800-32824
Brandacher, G. et al., Clin Cancer Res 12 (2006): 1144-1151
Brandenberger, R. et al., Nat Biotechnol. 22 (2004): 707-716
Braulke, T. et al., Arch. Biochem. Biophys. 298 (1992): 176-181
Braumuller, H. et al., Nature (2013)
Brendle, A. et al., Carcinogenesis 29 (2008): 1394-1399
Brocke, K. S. et al., Cancer Biol Ther. 9 (2010): 455-468
Broderick, P. et al., BMC. Cancer 6 (2006): 243
Brody, J. R. et al., Cell Cycle 8 (2009): 1930-1934
Brossart, P. et al., Blood 90 (1997): 1594-1599
Brouland, J. P. et al., Am. J Pathol. 167 (2005): 233-242
Brown, C. O. et al., Leuk. Res 37 (2013): 963-969
Bruckdorfer, T. et al., Curr. Pharm. Biotechnol. 5 (2004): 29-43
Brule, H. et al., Biochemistry 43 (2004): 9243-9255
Brynczka, C. et al., BMC. Genomics 8 (2007): 139
Bubnov, V. et al., Exp. Oncol 34 (2012): 370-372
Buch, S. C. et al., Mol Carcinog. 51 Suppl 1 (2012): E11-E20
Budowle, B. et al., Cancer Genet. Cytogenet. 5 (1982): 247-251
Bueno, R. C. et al., Ann. Oncol 25 (2014): 69-75
Bugide, S. et al., Oncogene 34 (2015): 4601-4612
Bujo, H., Rinsho Byori 60 (2012): 469-476
Bull, J. H. et al., Br. J Cancer 84 (2001): 1512-1519
Burger, H. et al., Leukemia 8 (1994): 990-997
Burkhart, R. A. et al., Mol. Cancer Res 11 (2013): 901-911
Burleigh, A. et al., Breast Cancer Res 17 (2015): 4
Burton, J. D. et al., Clin Cancer Res 10 (2004): 6606-6611
Butz, H. et al., Clin Chem 60 (2014): 1314-1326
Caballero, O. L. et al., PLoS. One. 5 (2010)
Caceres-Gorriti, K. Y. et al., PLoS. One. 9 (2014): e91000
Cahan, P. et al., BMC. Genomics 11 (2010): 638
Cai, H. et al., PLoS. One. 8 (2013a): e57081
Cai, H. et al., Cell Commun. Signal. 11 (2013): 31
Cai, K. et al., Lin. Chung Er. Bi Yan. Hou Tou. Jing. Wai Ke. Za Zhi. 26 (2012): 425-428
Cai, W. et al., Cancer 119 (2013b): 1486-1494
Caldarelli, A. et al., Leukemia 27 (2013): 2301-2310
Calin, G. A. et al., Oncogene 19 (2000): 1191-1195
Callahan, M. J. et al., Clin Cancer Res 14 (2008): 7667-7673
Camgoz, A. et al., Leuk. Lymphoma 54 (2013): 1279-1287
Campone, M. et al., Breast Cancer Res Treat. 109 (2008): 491-501
Cantara, S. et al., J Clin Endocrinol. Metab 97 (2012): 4253-4259
Cao, J. X. et al., Cell Death. Dis. 5 (2014): e1426
Cao, L. et al., Biochem. Biophys. Res Commun. 333 (2005): 1050-1059
Cappellari, M. et al., Oncogene 33 (2014): 3794-3802
Card, K. F. et al., Cancer Immunol Immunother. 53 (2004): 345-357
Caren, H. et al., BMC. Cancer 11 (2011): 66 Carrascosa, C. et al., Oncogene 31 (2012): 1521-1532
Carton, J. M. et al., J Histochem. Cytochem. 51 (2003): 715-726
Cascon, A. et al., J Natl. Cancer Inst. 107 (2015)
Castano-Rodriguez, N. et al., Front Immunol. 5 (2014): 336
Castle, J. C. et al., BMC. Genomics 15 (2014): 190
Castro, M. et al., J Transl. Med. 8 (2010): 86
Ceol, C. J. et al., Nature 471 (2011): 513-517
Cerhan, J. R. et al., Blood 110 (2007): 4455-4463
Cerna, D. et al., J Biol Chem 287 (2012): 22408-22417
Cerveira, N. et al., BMC. Cancer 10 (2010): 518
Chae, S. W. et al., Yonsei Med. J 52 (2011): 445-453
Chaigne-Delalande, B. et al., Science 341 (2013): 186-191
Chan, A. O. et al., Gut 48 (2001): 808-811
Chan, S. H. et al., Int. J Cancer 129 (2011): 565-573
Chandramouli, A. et al., Carcinogenesis 28 (2007): 2028-2035
Chang, C. C. et al., World J Gastroenterol. 20 (2014a): 6826-6831
Chang, C. M. et al., Carcinogenesis 34 (2013): 2512-2520
Chang, G. T. et al., Endocr. Relat Cancer 11 (2004): 815-822
Chang, H. et al., Breast Cancer Res Treat. 125 (2011): 55-63
Chang, K. et al., Proc. Natl. Acad. Sci. U.S.A 93 (1996): 136-140

Chang, L. C. et al., Anticancer Drugs 25 (2014b): 456-461
Chang, Y. C. et al., J Biol Chem 287 (2012): 4376-4385
Chang, Y. T. et al., World J Gastroenterol. 20 (2014c): 14463-14471
Chanock, S. J. et al., Hum. Immunol. 65 (2004): 1211-1223
Chatterjee, M. et al., Haematologica 98 (2013): 1132-1141
Chatterjee, M. et al., Blood 111 (2008): 3714-3722
Chelli, B. et al., Chembiochem. 6 (2005): 1082-1088
Chen, C. H. et al., Mol. Cancer 14 (2015a): 83
Chen, C. H. et al., Oncogene 28 (2009a): 2723-2737
Chen, C. H. et al., Oncotarget. 5 (2014a): 6300-6311
Chen, C. H. et al., J Transl. Med. 10 (2012a): 93
Chen, C. H. et al., Gynecol. Oncol 128 (2013a): 560-567
Chen, H. et al., J Surg. Res 189 (2014b): 81-88
Chen, H. J. et al., World J Gastroenterol. 19 (2013b): 3130-3133
Chen, H. S. et al., Zhonghua Gan Zang. Bing. Za Zhi. 11 (2003): 145-148
Chen, J. et al., Int. J Cancer 122 (2008): 2249-2254
Chen, J. et al., Oncotarget. 6 (2015b): 355-367
Chen, J. Q. et al., Horm. Cancer 1 (2010): 21-33
Chen, K. et al., Nat Commun. 5 (2014c): 4682
Chen, K. G. et al., Pigment Cell Melanoma Res 22 (2009b): 740-749
Chen, L. et al., Oncol Rep. 34 (2015c): 447-454
Chen, L. et al., Cell Mol. Biol (Noisy.-le-grand) 60 (2014d): 1-5
Chen, L. et al., Cancer Res 65 (2005): 5599-5606
Chen, L. C. et al., Mod. Pathol. 24 (2011): 175-184
Chen, Q. et al., PLoS. One. 9 (2014e): e88386
Chen, R. et al., Cancer Res 61 (2001): 654-658
Chen, W. T. et al., Elife. 4 (2015d)
Chen, X. et al., Pathol. Res Pract. 208 (2012b): 437-443
Chen, X. et al., Med. Oncol 31 (2014f): 865
Chen, X. P. et al., Asian Pac. J Cancer Prev. 15 (2014g): 7741-7746
Chen, Y. et al., J Cell Biochem. 100 (2007): 1337-1345
Chen, Y. et al., Am. J Physiol Lung Cell Mol. Physiol 306 (2014h): L797-L807
Chen, Y. et al., Int. J Cancer 91 (2001): 41-45
Chen, Y. et al., J Hematol. Oncol 2 (2009c): 37
Chen, Y. et al., Oncogene 32 (2013c): 4941-4949
Chen, Y. et al., Onco. Targets. Ther. 7 (2014i): 1465-1472
Chen, Y. T. et al., Int. J Cancer 124 (2009d): 2893-2898
Chen, Y. T. et al., Proc. Natl. Acad. Sci. U.S.A 102 (2005): 7940-7945
Chen, Z. T. et al., Int. J Mol. Sci. 16 (2015e): 15497-15530
Cheng, A. N. et al., Cancer Lett. 337 (2013a): 218-225
Cheng, A. S. et al., Gastroenterology 144 (2013b): 122-133
Cheng, L. et al., Gynecol. Oncol 117 (2010): 159-169
Cheng, S. et al., Int. J Clin Exp. Pathol. 7 (2014): 8118-8126
Cheng, Y. et al., Cancer Genet. 204 (2011): 375-381
Cheng, Y. et al., Clin Transl. Sci. 8 (2015a): 320-325
Cheng, Z. et al., J Exp. Clin Cancer Res 34 (2015b): 27
Chernikova, S. B. et al., Cancer Res 72 (2012): 2111-2119
Chevillard, G. et al., Blood 117 (2011): 2005-2008
Chi, L. M. et al., Mol. Cell Proteomics. 8 (2009): 1453-1474
Chin, S. F. et al., Genome Biol 8 (2007): R215
Chittasupho, C. et al., Mol. Pharm. 7 (2010): 146-155
Cho, H. J. et al., DNA Cell Biol 35 (2016): 71-80
Cho, S. et al., Proc. Natl. Acad. Sci. U.S.A 108 (2011): 20778-20783
Choi, Y. L. et al., J Thorac. Oncol 9 (2014): 563-566
Choi, Y. W. et al., Int. J Gynecol. Cancer 17 (2007): 687-696
Choschzick, M. et al., Hum. Pathol. 41 (2010): 358-365
Chou, J. L. et al., Clin Epigenetics. 7 (2015): 1
Chowdhury, S. K. et al., Biochem. Biophys. Res Commun. 333 (2005): 1139-1145
Chowdhury, S. K. et al., Free Radic. Res 41 (2007): 1116-1124
Chu, X. et al., Biochem. Biophys. Res Commun. 447 (2014): 158-164
Chuang, J. Y. et al., Oncogene 31 (2012): 4946-4959
Chung, F. Y. et al., J Surg. Oncol 102 (2010): 148-153
Chung, K. Y. et al., Hepatology 54 (2011): 307-318
Cicek, M. S. et al., Hum. Mol. Genet. 22 (2013): 3038-3047
Cieply, B. et al., Cancer Res 72 (2012): 2440-2453
Ciruelos Gil, E. M., Cancer Treat. Rev 40 (2014): 862-871
Clarke, L. E. et al., J Cutan. Pathol. 36 (2009): 433-438
Claudio, J. O. et al., Oncogene 20 (2001): 5373-5377
Coe, H. et al., Int. J Biochem. Cell Biol 42 (2010): 796-799
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A 69 (1972): 2110-2114
Cohen, Y. et al., Hematology. 19 (2014): 286-292
Colak, D. et al., PLoS. One. 8 (2013): e63204 Colas, E. et al., Int. J Cancer 129 (2011): 2435-2444
Colbert, L. E. et al., Cancer Res 74 (2014): 2677-2687
Cole, S. P. et al., Science 258 (1992): 1650-1654
Coligan, J. E. et al., Current Protocols in Protein Science (1995)
Colis, L. et al., J Med. Chem 57 (2014): 4950-4961
Colombetti, S. et al., J Immunol. 176 (2006): 2730-2738
Colombo, J. et al., Oncol Rep. 21 (2009): 649-663
Condomines, M. et al., J Immunol. 178 (2007): 3307-3315
Confalonieri, S. et al., Oncogene 28 (2009): 2959-2968
Cong, X. et al., Hum. Pathol. 45 (2014): 1370-1378
Cook, J. et al., Oncogene 18 (1999): 1205-1208
Coppola, D. et al., J Geriatr. Oncol 5 (2014): 389-399
Coradeghini, R. et al., Oncol Rep. 15 (2006): 609-613
Corcoran, C. A. et al., Mol. Cancer Res 6 (2008): 795-807
Cornelissen, M. et al., BMC. Cancer 3 (2003): 7
Couch, F. J. et al., Cancer Res 65 (2005): 383-386
Coupienne, I. et al., Lasers Surg. Med. 43 (2011): 557-564
Creancier, L. et al., Cancer Lett. 365 (2015): 107-111
Cubillos-Rojas, M. et al., J Biol Chem 289 (2014): 14782-14795
Cuevas, I. C. et al., Cancer Res 65 (2005): 5070-5075
Cuevas, R. et al., Cancer Res 73 (2013): 1400-1410
Cui, D. X. et al., World J Gastroenterol. 11 (2005): 1273-1282
Cui, F. et al., Proteomics. 6 (2006): 498-504
Cui, L. H. et al., Med. Oncol 29 (2012): 1837-1842
Cui, X. et al., Oncogene 26 (2007): 4253-4260
Cunliffe, H. E. et al., Am. J Cancer Res 2 (2012): 478-491
Cunningham, J. D. et al., Am. J Surg. 173 (1997): 521-522
Cunningham, J. M. et al., Br. J Cancer 101 (2009): 1461-1468
Curry, J. M. et al., Laryngoscope (2015)
Cvekl, A., Jr. et al., Eur. J Cancer 40 (2004): 2525-2532
Dadkhah, E. et al., Arch. Iran Med. 16 (2013): 463-470
Dahlman, K. B. et al., PLoS. One. 7 (2012): e34414
Dajon, M. et al., Oncoimmunology 4 (2015): e991615
Dalamaga, M., Med. Hypotheses 79 (2012): 617-621
Daly, R. J. et al., Oncogene 21 (2002): 5175-5181
Dannenmann, S. R. et al., Cancer Immunol. Res. 1 (2013): 288-295
Danussi, C. et al., Cancer Res 73 (2013): 5140-5150
Das, A. et al., J Cell Sci. 127 (2014): 686-699
Das, M. et al., PLoS. One. 8 (2013a): e69607
Das, T. K. et al., Oncogene 32 (2013b): 3184-3197
Dasari, V. K. et al., J Urol. 165 (2001): 1335-1341

Dasgupta, S. et al., Int. J Oncol 41 (2012): 1405-1410
Datta, M. W. et al., Appl. Immunohistochem. Mol. Morphol. 8 (2000): 210-215
Davalieva, K. et al., Prostate 75 (2015): 1586-1600
David-Watine, B., PLoS. One. 6 (2011): e22423
Davidson, B. et al., J Cell Mol. Med. 15 (2011): 535-544
Davydova, E. et al., J Biol Chem 289 (2014): 30499-30510
De Angelis, P. M. et al., Mol. Cancer 5 (2006): 20
de Leon, F. C. et al., Childs Nerv. Syst. 31 (2015): 141-146
De, Paoli L. et al., Leuk. Lymphoma 54 (2013): 1087-1090
De, S. et al., Cancer Res 69 (2009): 8035-8042
Debauve, G. et al., Cell Mol Life Sci. 65 (2008): 591-604
Deighton, R. F. et al., Brain Pathol. 20 (2010): 691-703
DelBove, J. et al., Epigenetics. 6 (2011): 1444-1453
Demelash, A. et al., Mol. Biol Cell 23 (2012): 2856-2866
Demokan, S. et al., Int. J Cancer 127 (2010): 2351-2359
Deng, S. et al., Breast Cancer Res Treat. 104 (2007): 21-30
Deng, Y. C. et al., Ai. Zheng. 24 (2005): 680-684
Dengjel, J. et al., Clin Cancer Res 12 (2006): 4163-4170
Denkberg, G. et al., J Immunol 171 (2003): 2197-2207
Desai, S. D. et al., Exp. Biol Med. (Maywood.) 237 (2012): 38-49
Diao, C. Y. et al., Asian Pac. J Cancer Prev. 15 (2014): 1817-1822
Diefenbacher, M. E. et al., J Clin Invest 124 (2014): 3407-3418
Diggle, C. P. et al., PLoS. Genet. 10 (2014): e1004577
DiSepio, D. et al., Proc. Natl. Acad. Sci. U.S.A 95 (1998): 14811-14815
Dobashi, Y. et al., Int. J Cancer 110 (2004): 532-541
Dohn, L. H. et al., Urol. Oncol 33 (2015): 165-24
Doldan, A. et al., Mol. Carcinog 47 (2008a): 235-244
Doldan, A. et al., Mol. Carcinog 47 (2008b): 806-813
Domanitskaya, N. et al., Br. J Cancer 111 (2014): 696-707
Dominguez-Sanchez, M. S. et al., BMC. Cancer 11 (2011): 77
Donati, G. et al., J Cell Sci. 124 (2011): 3017-3028
Dong, P. et al., Cancer Lett. 243 (2006): 120-127
Dong, Q. et al., Biomed. Res Int. 2015 (2015): 156432
Dong, W. et al., Tumour. Biol (2015)
Donnellan, R. et al., FASEB J 13 (1999): 773-780
Dorman, S. N. et al., Mol. Oncol (2015)
Dormeyer, W. et al., J Proteome. Res 7 (2008): 2936-2951
Douet-Guilbert, N. et al., Leuk. Res 38 (2014): 1316-1319
Downie, D. et al., Clin Cancer Res. 11 (2005): 7369-7375
Drazkowska, K. et al., Nucleic Acids Res 41 (2013): 3845-3858
Du, C. et al., Gastric. Cancer 18 (2015a): 516-525
Du, L. et al., Tumori 101 (2015b): 384-389
Du, Y. et al., Int. J Mol. Sci. 15 (2014a): 17065-17076
Du, Y. F. et al., Int. J Clin Exp. Pathol. 7 (2014b): 923-931
Duan, X. L. et al., Zhongguo Shi Yan. Xue. Ye. Xue. Za Zhi. 21 (2013): 7-11
Duarte-Pereira, S. et al., Sci. Rep. 4 (2014): 6311
Duex, J. E. et al., Exp. Cell Res 316 (2010): 2136-2151
Dun, B. et al., Am. J Transl. Res 6 (2013a): 28-42
Dun, B. et al., Int. J Clin Exp. Pathol. 6 (2013b): 2880-2886
Dunn, G. P. et al., Proc. Natl. Acad. Sci. U.S.A 111 (2014): 1102-1107
Dunphy, E. J. et al., J Immunother. 28 (2005): 268-275
Dunzendorfer, U. et al., Eur. Urol. 6 (1980): 232-236
Durgan, J. et al., J Biol Chem 286 (2011): 12461-1 2474
Dusseau, C. et al., Int. J Oncol 18 (2001): 393-399
Duursma, A. et al., Mol. Cell Biol 25 (2005): 6937-6947
Duvic, M. et al., Clin Cancer Res 6 (2000): 3249-3259
Duvic, M. et al., J Invest Dermatol. 121 (2003): 902-909
Dyrskjot, L. et al., Br. J Cancer 107 (2012): 116-122
Dzikiewicz-Krawczyk, A. et al., J Hematol. Oncol 7 (2014): 43
Eggers, J. P. et al., Clin Cancer Res 17 (2011): 6140-6150
Eldai, H. et al., PLoS. One. 8 (2013): e76251
Elgohary, N. et al., Int. J Oncol 46 (2015): 597-606
Elias, D. et al., Oncogene 34 (2015): 1919-1927
Ellison-Zelski, S. J. et al., Mol. Cancer 9 (2010): 263
Emdad, L. et al., Neuro. Oncol 17 (2015): 419-429
Emmanuel, C. et al., PLoS. One. 6 (2011): e17617
Endoh, H. et al., J Clin Oncol 22 (2004): 811-819
Enesa, K. et al., Adv. Exp. Med. Biol. 809 (2014): 33-48
Eng, K. H. et al., Genes Cancer 6 (2015): 399-407
Enomoto, A. et al., Eur. J Cancer 49 (2013): 3547-3558
Epping, M. T. et al., Mol. Cancer Res 7 (2009): 1861-1870
Er, T. K. et al., J Mol. Med. (Berl) (2016)
Erb, H. H. et al., Endocr. Relat Cancer 20 (2013): 677-689
Erdogan, E. et al., Clin Cancer Res 15 (2009): 1527-1533
Erenpreisa, J. et al., Exp. Cell Res 315 (2009): 2593-2603
Escobar-Hoyos, L. F. et al., Mod. Pathol. 27 (2014): 621-630
Esseghir, S. et al., J Pathol. 210 (2006): 420-430
Estrella, J. S. et al., Pancreas 43 (2014): 996-1002
Ettahar, A. et al., Cell Rep. 4 (2013): 530-541
Evans, T. J. et al., PLoS. One. 9 (2014): e110255
Exertier, P. et al., Oncotarget. 4 (2013): 2302-2316
Ezponda, T. et al., Oncogene 32 (2013): 2882-2890
Fackler, M. et al., FEBS J 281 (2014): 2123-2135
Fagin, J. A., Mol. Endocrinol. 16 (2002): 903-911
Fairfield, K. M. et al., Int. J Cancer 110 (2004): 271-277
Falk, K. et al., Nature 351 (1991): 290-296
Falvella, F. S. et al., Oncogene 27 (2008): 3761-3764
Fan, J. et al., Clin Cancer Res 17 (2011): 2908-2918
Fan, M. et al., Int. J Clin Exp. Pathol. 7 (2014): 6768-6775
Fang, H. Y. et al., Hum. Pathol. 43 (2012): 105-114
Fang, K. P. et al., Asian Pac. J Cancer Prev. 15 (2014): 2655-2661
Fang, Z. et al., J Biol Chem 288 (2013): 7918-7929
Faried, L. S. et al., Mol. Carcinog 47 (2008): 446-457
Faried, L. S. et al., Oncol Rep. 16 (2006): 57-63
Faronato, M. et al., Oncotarget. (2015)
Fasso, M. et al., Proc. Natl. Acad. Sci. U.S.A 105 (2008): 3509-3514
Feldmann, G. et al., Cancer Res 70 (2010): 4460-4469
Feng, H. et al., J Clin Invest 124 (2014a): 3741-3756
Feng, M. et al., J Clin Invest 124 (2014b): 5291-5304
Feng, X. et al., Neoplasma 62 (2015a): 592-601
Feng, Y. et al., Sci. Rep. 5 (2015b): 9429
Fernandez-Calotti, P. X. et al., Haematologica 97 (2012): 943-951
Fernandez-Nogueira, P. et al., Oncotarget. 7 (2016): 5313-5326
Ferreira-da-Silva, A. et al., PLoS. One. 10 (2015): e0122308
Ferrero, S. et al., Histol. Histopathol. 30 (2015): 473-478
Fevre-Montange, M. et al., Int. J Oncol 35 (2009): 1395-1407
Fevre-Montange, M. et al., J Neuropathol. Exp. Neurol. 65 (2006): 675-684
Fitzgerald, J. et al., FEBS Lett. 517 (2002): 61-66
Fluge, O. et al., Thyroid 16 (2006): 161-175
Fokas, E. et al., Cell Death. Dis. 3 (2012): e441
Folgiero, V. et al., Oncotarget. 5 (2014): 2052-2064
Fong, L. et al., Proc. Natl. Acad. Sci. U.S.A 98 (2001): 8809-8814
Fortschegger, K. et al., Mol. Cancer Res 12 (2014): 595-606
Fraga, M. F. et al., Cancer Res 68 (2008): 4116-4122
Frasor, J. et al., Mol. Cell Endocrinol. 418 Pt 3 (2015): 235-239
Frias, C. et al., Lung Cancer 60 (2008): 416-425

Fry, A. M. et al., J Cell Sci. 125 (2012): 4423-4433
Fu, A. et al., Mol. Carcinog 51 (2012): 923-929
Fu, D. Y. et al., Tumour. Biol (2015)
Fu, J. et al., Cancer Sci. 104 (2013a): 508-515
Fu, M. et al., Int. J Clin Exp. Pathol. 6 (2013b): 2185-2191
Fu, M. et al., Int. J Clin Exp. Pathol. 6 (2013c): 2515-2522
Fu, Z. et al., Breast Cancer Res Treat. 127 (2011): 265-271
Fujimura, K. et al., Clin Chim. Acta 430 (2014): 48-54
Fujitomo, T. et al., Cancer Res 72 (2012): 4110-4118
Fujiuchi, N. et al., J Biol Chem 279 (2004): 20339-20344
Fukasawa, M. et al., J Hum. Genet. 51 (2006): 368-374
Fukushima, Y. et al., Eur. J Cancer 35 (1999): 935-938
Fuqua, S. A. et al., Breast Cancer Res Treat. 144 (2014): 11-19
Furukawa, T. et al., Sci. Rep. 1 (2011): 161 Furuta, J. et al., Cancer Res 66 (2006): 6080-6086
Gaba, R. C. et al., J Vasc. Interv. Radiol. 26 (2015): 723-732
Gabrilovich, D. I. et al., Nat Med. 2 (1996): 1096-1103
Galamb, O. et al., Cell Oncol 31 (2009): 19-29
Gallmeier, E. et al., Gastroenterology 130 (2006): 2145-2154
Gantsev, S. K. et al., Biomed. Pharmacother. 67 (2013): 363-366
Gao, F. et al., Biochem. Biophys. Res Commun. 431 (2013): 610-616
Gao, J. et al., Acta Oncol 47 (2008): 372-378
Gao, W. et al., BMC. Cancer 15 (2015): 367
Gao, Y. B. et al., Nat Genet. 46 (2014): 1097-1102
Gao, Z. et al., Biochem. Biophys. Res Commun. 407 (2011): 271-276
Garcia-Baquero, R. et al., Tumour. Biol. 35 (2014): 5777-5786
Garritano, S. et al., Oncogenesis. 2 (2013): e54
Gattinoni, L. et al., Nat Rev. Immunol 6 (2006): 383-393
Gatza, M. L. et al., Nat Genet. 46 (2014): 1051-1059
Gaudineau, B. et al., J Cell Sci. 125 (2012): 4475-4486
Ge, G. et al., Tumour. Biol (2015)
Geiger, T. R. et al., PLoS. One. 9 (2014): e111813
Gelebart, P. et al., J Biol Chem 277 (2002): 26310-26320
Gelsi-Boyer, V. et al., Br. J Haematol. 145 (2009): 788-800
Gentile, M. et al., Oncogene 20 (2001): 7753-7760
Geoffroy-Perez, B. et al., Int. J Cancer 93 (2001): 288-293
Georgiou, G. K. et al., World J Surg. Oncol 11 (2013): 213
Ghosh, S. et al., Int. J Cancer 123 (2008): 2594-2604
Gibbs, D. C. et al., Cancer Epidemiol. Biomarkers Prev. 24 (2015): 992-997
Gil-Henn, H. et al., Oncogene 32 (2013): 2622-2630
Gilling, C. E. et al., Br. J Haematol. 158 (2012): 216-231
Giuliano, C. J. et al., Biochim. Biophys. Acta 1731 (2005): 48-56
Glaser, R. et al., PLoS. One. 6 (2011): e25160
Gnjatic, S. et al., Proc Natl. Acad. Sci. U.S.A 100 (2003): 8862-8867
Godkin, A. et al., Int. Immunol 9 (1997): 905-911
Going, J. J. et al., Gut 50 (2002): 373-377
Gold, D. V. et al., Int. J Clin Exp. Pathol. 4 (2010): 1-12
Goldenson, B. et al., Oncogene 34 (2015): 537-545
Gong, X. et al., PLoS. One. 7 (2012): e37137
Gonzalez, M. A. et al., J Clin Oncol 21 (2003): 4306-4313
Goodman, S. L. et al., Biol Open. 1 (2012): 329-340
Goswami, A. et al., Mol. Cell 20 (2005): 33-44
Goto, Y. et al., J Invest Dermatol. 130 (2010): 221-229
Gou, W. F. et al., Oncol Rep. 31 (2014): 232-240
Govindaraj, V. et al., Horm. Mol. Biol Clin Investig. 9 (2012): 173-178
Goyal, P. et al., PLoS. One. 6 (2011): e16249
Grady, W. M., Cancer Metastasis Rev 23 (2004): 11-27
Graff, L. et al., Cancer Res 61 (2001): 2138-2144
Grant, R. C. et al., Hum. Genomics 7 (2013): 11
Green, M. R. et al., Molecular Cloning, A Laboratory Manual 4th (2012)
Greenfield, E. A., Antibodies: A Laboratory Manual 2nd (2014)
Greif, P. A. et al., Leukemia 25 (2011): 821-827
Greuber, E. K. et al., Nat Rev Cancer 13 (2013): 559-571
Grieb, B. C. et al., Mol. Cancer Res 12 (2014): 1216-1224
Grimm, M. et al., BMC. Cancer 13 (2013): 569
Grimmig, T. et al., Int. J Oncol 47 (2015): 857-866
Grinberg-Rashi, H. et al., Clin Cancer Res 15 (2009): 1755-1761
Gronnier, C. et al., Biochim. Biophys. Acta 1843 (2014): 2432-2437
Groth-Pedersen, L. et al., PLoS. One. 7 (2012): e45381
Gruel, N. et al., Breast Cancer Res 16 (2014): R46
Grumati, P. et al., Cancer Discov 4 (2014): 394-396
Gu, X. H. et al., Zhonghua Fu Chan Ke. Za Zhi. 44 (2009): 754-759
Gu, Y. et al., Mol. Carcinog 55 (2016): 292-299
Guan, G. et al., Arch. Biochem. Biophys. 417 (2003): 251-259
Guan, X. et al., Carcinogenesis 34 (2013): 812-817
Gueddari, N. et al., Biochimie 75 (1993): 811-819
Guerreiro, A. S. et al., Mol. Cancer Res 9 (2011): 925-935
Guerrero, J. A. et al., Blood 124 (2014): 3624-3635
Guerrero-Preston, R. et al., Oncol Rep. 32 (2014): 505-512
Guin, S. et al., J Natl. Cancer Inst. 106 (2014)
Guirado, M. et al., Hum. Immunol. 73 (2012): 668-672
Gultekin, Y. et al., J Innate. Immun. 7 (2015): 25-36
Guo, F. et al., Mol. Biol Rep. 37 (2010): 3819-3825
Guo, G. et al., Tumour. Biol 35 (2014): 4017-4022
Guo, J. T. et al., Zhonghua Zhong. Liu Za Zhi. 31 (2009): 528-531
Guo, S. et al., Drug Des Devel. Ther. 7 (2013): 1259-1271
Guo, W. et al., J Mol. Biol 412 (2011): 365-378
Guo, X. et al., Tumour. Biol 36 (2015): 1711-1720
Gust, K. M. et al., Neoplasia. 11 (2009): 956-963
Gutierrez, M. L. et al., PLoS. One. 6 (2011): e22315
Gutierrez-Camino, A. et al., Pediatr. Res 75 (2014): 767-773
Guyonnet, Duperat, V et al., Biochem. J 305 (Pt 1) (1995): 211-219
Gylfe, A. E. et al., Int. J Cancer 127 (2010): 2974-2980
Hagenbuchner, J. et al., Front Physiol 4 (2013): 147
Haidar, A. et al., Am. J Case. Rep. 16 (2015): 87-94
Halama, N. et al., Int. J Oncol 31 (2007): 205-210
Hall, C. L. et al., J Neurooncol. 26 (1995): 221-229
Hall, C. L. et al., Cell 82 (1995): 19-26
Halldorsdottir, A. M. et al., Am. J Hematol. 87 (2012): 361-367
Hammam, O. et al., J Egypt. Soc. Parasitol. 44 (2014): 733-740
Han, J. C. et al., World J Surg. Oncol 13 (2015a): 5
Han, L. L. et al., Oncol Rep. 31 (2014): 2569-2578
Han, Y. et al., Cancer 119 (2013): 3436-3445
Han, Z. et al., Oncotarget. 6 (2015b): 13149-13163
Hansen-Petrik, M. B. et al., Cancer Lett. 175 (2002): 157-163
Hao, J. et al., Oncol Lett. 9 (2015): 2525-2533
Hague, M. A. et al., J Exp. Med. 195 (2002): 1267-1277
Haridas, D. et al., FASEB J 28 (2014): 4183-4199
Harken, Jensen C. et al., Tumour. Biol 20 (1999): 256-262
Hartmann, T. B. et al., Int. J Cancer 114 (2005): 88-93
Hasegawa, H. et al., Arch. Pathol. Lab Med. 122 (1998): 551-554
Hashimoto, T. et al., FEBS J 277 (2010): 4888-4900

Hast, B. E. et al., Cancer Res 73 (2013): 2199-2210
Hatfield, K. J. et al., Expert. Opin. Ther. Targets. 18 (2014): 1237-1251
Hayama, S. et al., Cancer Res 67 (2007): 4113-4122
Hayashi, H. et al., Int. J Cancer 126 (2010): 2563-2574
Hayashi, J. et al., Int. J Oncol 21 (2002): 847-850
Hayashi, S. I. et al., Endocr. Relat Cancer 10 (2003): 193-202
Hayatsu, N. et al., Biochem. Biophys. Res Commun. 368 (2008): 217-222
Hazelett, C. C. et al., PLoS. One. 7 (2012): e39602
He, D. et al., Biomed. Pharmacother. 74 (2015): 164-168
He, H. et al., J Clin Endocrinol. Metab 98 (2013): E973-E980
He, J. et al., Cancer Biol Ther. 6 (2007): 76-82
He, Y. et al., Mol Carcinog. (2014)
Hedrick, E. D. et al., J Mol. Signal. 8 (2013): 10
Heeboll, S. et al., Histol. Histopathol. 23 (2008): 1069-1076
Hegyi, K. et al., Pathobiology 79 (2012): 314-322
Heidenblad, M. et al., BMC. Med. Genomics 1 (2008): 3
Heim, S. et al., In Vivo 19 (2005): 583-590
Heimerl, S. et al., Melanoma Res 17 (2007): 265-273
Hellerbrand, C. et al., Carcinogenesis 27 (2006): 64-72
Hellwinkel, 0. J. et al., Prostate Cancer Prostatic. Dis. 14 (2011): 38-45
Hemminger, J. A. et al., Mod. Pathol. 27 (2014): 1238-1245
Hennard, C. et al., J Pathol. 209 (2006): 430-435
Hennig, E. E. et al., J Mol. Med. (Berl) 90 (2012): 447-456
Hickinson, D. M. et al., Clin Transl. Sci. 2 (2009): 183-192
Hider, J. L. et al., BMC. Evol. Biol. 13 (2013): 150
Hinrichsen, I. et al., PLoS. One. 9 (2014): e84453
Hirota, Y. et al., Nucleic Acids Res 28 (2000): 917-924
Hlavac, V. et al., Pharmacogenomics. 14 (2013): 515-529
Hlavata, I. et al., Mutagenesis 27 (2012): 187-196
Ho, M. et al., Clin Cancer Res 13 (2007): 1571-1575
Hodi, F. S. et al., Proc. Natl. Acad. Sci. U.S.A 99 (2002): 6919-6924
Hodson, I. et al., Int. J Oncol 23 (2003): 991-999
Hoei-Hansen, C. E. et al., Clin Cancer Res 10 (2004): 8521-8530
Hoellein, A. et al., J Cancer Res Clin Oncol 136 (2010): 403-410
Hoff, A. M. et al., Oncotarget. (2015)
Holla, V. R. et al., J Biol Chem 281 (2006): 2676-2682
Holleman, A. et al., Blood 107 (2006): 769-776
Holm, C. et al., Leuk. Res 30 (2006): 254-261
Holzmann, K. et al., Cancer Res 64 (2004): 4428-4433
Hong, J. et al., Biomed. Res Int. 2013 (2013): 454085
Honore, B. et al., Oncogene 21 (2002): 1123-1129
Hogue, M. O. et al., Cancer Res 68 (2008): 2661-2670
Horani, A. et al., Am J Hum. Genet. 91 (2012): 685-693
Horejsi, Z. et al., Mol. Cell 39 (2010): 839-850
Horst, B. et al., Am. J Pathol. 174 (2009): 1524-1533
Hosseini, M., Pol. J Pathol. 64 (2013): 191-195
Hosseini, S. et al., Clin Lab 61 (2015): 475-480
Hou, G. et al., Cancer Lett. 253 (2007): 236-248
Hou, J. et al., Mol. Oncol 9 (2015): 1312-1323
Hou, X. et al., Ann. Surg. Oncol 21 (2014): 3891-3899
Hou, Y. et al., Med. Oncol 29 (2012): 3498-3503
Hour, T. C. et al., Int. J Biol Markers 24 (2009): 171-178
Hovnanian, A., Subcell. Biochem. 45 (2007): 337-363
Hsu, P. K. et al., J Gastroenterol. 49 (2014): 1231-1240
Hsu, W. H. et al., PLoS. One. 10 (2015): e0121298
Hu, H. et al., Oncol Lett. 10 (2015): 268-272
Hu, J. et al., Exp. Biol Med. (Maywood.) 239 (2014): 423-429
Hu, S. et al., Pediatr. Hematol. Oncol 28 (2011): 140-146
Hua, C. et al., BMC. Cancer 14 (2014): 526
Huang, C. et al., Cell Biol Int. 32 (2008): 1081-1090
Huang, H. et al., Clin Cancer Res 11 (2005a): 4357-4364
Huang, H. et al., Beijing Da. Xue. Xue. Bao. 46 (2014a): 183-189
Huang, H. et al., Int. J Oncol 38 (2011): 1557-1564
Huang, L. N. et al., Clin Chim. Acta 413 (2012): 663-668
Huang, X. et al., APMIS 122 (2014b): 1070-1079
Huang, Y. et al., Int. J Mol. Sci. 15 (2014c): 18148-18161
Huang, Y. et al., Oncogene 24 (2005b): 3819-3829
Huang, Y. et al., Oncotarget. 5 (2014d): 6734-6745
Hudlebusch, H. R. et al., Clin Cancer Res 17 (2011): 2919-2933
Hudson, J. et al., Exp. Mol. Pathol. 95 (2013): 62-67
Hui, L. et al., Oncol Rep. 34 (2015): 2627-2635
Hummerich, L. et al., Oncogene 25 (2006): 111-121
Hunecke, D. et al., J Pathol. 228 (2012): 520-533
Hungermann, D. et al., J Pathol. 224 (2011): 517-528
Hunter, S. M. et al., Oncotarget. 6 (2015): 37663-37677
Hussein, Y. M. et al., Med. Oncol 29 (2012): 3055-3062
Huynh, H. et al., Mol. Cancer Ther. 14 (2015): 1224-1235
Hwang, C. F. et al., PLoS. One. 8 (2013): e84218
Hwang, J. M. et al., Mol. Cell Biochem. 327 (2009): 135-144
Hwang, M. L. et al., J Immunol. 179 (2007): 5829-5838
Iacovazzi, P. A. et al., Immunopharmacol. Immunotoxicol. 32 (2010): 160-164
Iakovlev, V. et al., Cancer Epidemiol. Biomarkers Prev. 21 (2012): 1135-1142
Ibragimova, I. et al., Cancer Prev. Res (Phila) 3 (2010): 1084-1092
Ida-Yonemochi, H. et al., Mod. Pathol. 25 (2012): 784-794
Idbaih, A. et al., J Neurooncol. 90 (2008): 133-140
Ide, H. et al., Biochem. Biophys. Res Commun. 369 (2008): 292-296
Ii, M. et al., Exp. Biol. Med. (Maywood.) 231 (2006): 20-27
Iio, A. et al., Biochim. Biophys. Acta 1829 (2013): 1102-1110
Ijichi, N. et al., J Steroid Biochem. Mol. Biol 123 (2011): 1-7
Ikeda, R. et al., Int. J Oncol 38 (2011): 513-519
Ikonomov, 0. C. et al., Biochem. Biophys. Res Commun. 440 (2013): 342-347
Ilboudo, A. et al., BMC. Cancer 14 (2014): 7
Illemann, M. et al., Cancer Med. 3 (2014): 855-864
Imai, K. et al., Br. J Cancer 104 (2011): 300-307
Imoto, I. et al., Biochem. Biophys. Res Commun. 286 (2001): 559-565
Inamoto, T. et al., Mol. Cancer Ther. 7 (2008): 3825-3833
Ina, K. et al., Clin Cancer Res 14 (2008): 2310-2317
Inoda, S. et al., Am. J Pathol. 178 (2011a): 1805-1813
Inoda, S. et al., J Immunother. 32 (2009): 474-485
Inoda, S. et al., Exp. Mol. Pathol. 90 (2011b): 55-60
Ioachim, H. L. et al., Am. J Surg. Pathol. 20 (1996): 64-71
Iscan, M. et al., Breast Cancer Res Treat. 70 (2001): 47-54
Ishida, T. et al., Leukemia 20 (2006): 2162-2168
Ishigami, S. et al., Cancer Lett. 168 (2001): 87-91
Ishigami, S. et al., BMC. Cancer 11 (2011): 106
Ishikawa, S. et al., J Exp. Clin Cancer Res 22 (2003): 299-306
Issaq, S. H. et al., Mol. Cancer Res 8 (2010): 223-231
Ito, K. et al., Protein Cell 2 (2011): 755-763
Ito, M. et al., Jpn. J Clin Oncol 36 (2006): 116-120
Ito, Y. et al., Oncology 59 (2000): 68-74
Itoh, G. et al., Cancer Sci. 104 (2013): 871-879
Ivyna Bong, P. N. et al., Mol. Cytogenet. 7 (2014): 24
Iwakuma, T. et al., Cancer Metastasis Rev 31 (2012): 633-640

Iwanaga, K. et al., Cancer Lett. 202 (2003): 71-79
Izykowska, K. et al., Eur. J Haematol. 93 (2014): 143-149
Jaaskelainen, T. et al., Mol. Cell Endocrinol. 350 (2012): 87-98
Jackson, R. S. et al., Cell Cycle 6 (2007): 95-103
Jacob, F. et al., BMC. Mol. Biol 15 (2014): 24
Jacques, C. et al., J Clin Endocrinol. Metab 90 (2005): 2314-2320
Jager, D. et al., Cancer Res 60 (2000): 3584-3591
Jaggi, M. et al., Prostate 66 (2006): 193-199
Jais, J. P. et al., Leukemia 22 (2008): 1917-1924
Jakobsson, J. et al., Pharmacogenomics. J 4 (2004): 245-250
Jalava, S. E. et al., Int. J Cancer 124 (2009): 95-102
Jang, S. G. et al., BMC. Cancer 7 (2007): 16
Januchowski, R. et al., Biomed. Pharmacother. 67 (2013): 240-245
Janus, J. R. et al., Laryngoscope 121 (2011): 2598-2603
Jayaram, H. N. et al., Curr. Med. Chem 6 (1999): 561-574
Jayarama, S. et al., J Cell Biochem. 115 (2014): 261-270
Jeffery, J. et al., FASEB J 29 (2015a): 1999-2009
Jeffery, J. et al., Oncogene (2015b)
Jensen, C. H. et al., Eur. J Biochem. 225 (1994): 83-92
Jensen, S. A. et al., Proc. Natl. Acad. Sci. U.S.A 111 (2014): 5682-5687
Jessie, K. et al., Electrophoresis 34 (2013): 2495-2502
Ji, P. et al., Oncogene 24 (2005): 2739-2744
Jia, D. et al., Hepatology 54 (2011): 1227-1236
Jiang, J. H. et al., Ai. Zheng. 23 (2004): 672-677
Jiang, J. H. et al., Hepatology 59 (2014a): 2216-2227
Jiang, N. et al., J Biol Chem 278 (2003): 21678-21684
Jiang, P. et al., Mol. Med. Rep. 9 (2014b): 2347-2351
Jiang, Q. et al., Histopathology 64 (2014c): 722-730
Jiao, X. et al., Genes Chromosomes. Cancer 51 (2012): 480-489
Jin, J. K. et al., Oncogene 34 (2015): 1811-1821
Jinawath, N. et al., Oncogene 28 (2009): 1941-1948
Jing, Z. et al., J Immunol. 185 (2010): 6719-6727
Jinushi, M. et al., Cancer Res 68 (2008): 8889-8898
Johansson, P. et al., J Biol Chem 289 (2014): 18514-18525
Johnson, D. P. et al., Oncotarget. 6 (2015): 4863-4887
Joosse, S. A. et al., Clin Cancer Res 18 (2012): 993-1003
Jose-Eneriz, E. S. et al., Br. J Haematol. 142 (2008): 571-582
Joshi, A. D. et al., Clin Cancer Res 13 (2007): 5295-5304
Joshi, S. et al., BMC. Cancer 15 (2015): 546
Judson, H. et al., Hum. Genet. 106 (2000): 406-413
Junes-Gill, K. S. et al., J Neurooncol. 102 (2011): 197-211
Junes-Gill, K. S. et al., BMC. Cancer 14 (2014): 920
Jung, G. et al., Proc Natl Acad Sci USA 84 (1987): 4611-4615
Jung, H. C. et al., Life Sci. 77 (2005): 1249-1262
Jung, W. Y. et al., Appl. Immunohistochem. Mol. Morphol. 22 (2014): 652-657
Juszczynski, P. et al., Mol. Cell Biol 26 (2006): 5348-5359
Kabbage, M. et al., J Biomed. Biotechnol. 2008 (2008): 564127
Kaizuka, T. et al., J Biol Chem 285 (2010): 20109-20116
Kalin, T. V. et al., Cancer Res 66 (2006): 1712-1720
Kalinichenko, V. V. et al., Genes Dev. 18 (2004): 830-850
Kalinina, T. et al., BMC. Cancer 10 (2010): 295
Kalogeropoulou, M. et al., Mol. Cancer Res 8 (2010): 554-568
Kamatani, N. et al., Cancer Res 40 (1980): 4178-4182
Kamino, H. et al., Cancer Genet. 204 (2011): 382-391
Kamiyama, S. et al., Glycobiology 21 (2011): 235-246
Kanda, A. et al., Oncogene 24 (2005): 7266-7272
Kandoth, C. et al., Nature 497 (2013): 67-73
Kang, B. W. et al., PLoS. One. 10 (2015a): e0119649
Kang, G. et al., PLoS. One. 8 (2013): e82770
Kang, J. K. et al., Int. J Oncol 16 (2000): 1159-1163
Kang, J. M. et al., Cancer Res 75 (2015b): 3087-3097
Kang, J. U. et al., Int. J Oncol 37 (2010): 327-335
Kang, J. U. et al., Cancer Genet. Cytogenet. 182 (2008a): 1-11
Kang, M. J. et al., Prostate 72 (2012): 1351-1358
Kang, S. K. et al., Am. J Pathol. 173 (2008b): 518-525
Kang, X. et al., Oncogene 28 (2009): 565-574
Kapoor, A. et al., Nature 468 (2010): 1105-1109
Karahatay, S. et al., Cancer Lett. 256 (2007): 101-111
Karbowniczek, M. et al., J Invest Dermatol. 128 (2008): 980-987
Karess, R. E. et al., Int. Rev Cell Mol. Biol 306 (2013): 223-273
Karim, H. et al., Biochem. Biophys. Res Commun. 411 (2011): 156-161
Karlsson, E. et al., Breast Cancer Res Treat. 153 (2015): 31-40
Karytinos, A. et al., J Biol Chem 284 (2009): 17775-17782
Kashuba, V. et al., Int. J Mol. Sci. 13 (2012): 13352-13377
Kashyap, V. et al., Mol Oncol 7 (2013): 555-566
Kassambara, A. et al., Biochem. Biophys. Res Commun. 379 (2009): 840-845
Kato, I. et al., Pathol. Int. 59 (2009): 38-43
Kato, S. et al., Int. J Oncol 29 (2006): 33-40
Katoh, M. et al., Int. J Oncol 25 (2004): 1495-1500
Katoh, Y. et al., Int. J Mol. Med. 18 (2006): 523-528
Katz, T. A. et al., Breast Cancer Res Treat. 146 (2014): 99-108
Kaufmann, M. et al., Curr. Top. Microbiol. Immunol. 384 (2015): 167-188
Kaur, H. et al., PLoS. One. 7 (2012): e50249
Kawagoe, H. et al., Cancer Res 64 (2004): 6091-6100
Kawahara, R. et al., Proteomics. 16 (2016): 159-173
Kawakami, K. et al., Int. J Oncol (2015)
Kawakami, M. et al., Cancer Sci. 104 (2013): 1447-1454
Kaynar, H. et al., Cancer Lett. 227 (2005): 133-139
Kazma, R. et al., Carcinogenesis 33 (2012): 1059-1064
Ke, J. Y. et al., J Zhejiang. Univ Sci. B 15 (2014a): 1032-1038
Ke, R. H. et al., J Neurooncol. 118 (2014b): 369-376
Kearns, P. R. et al., Br. J Haematol. 120 (2003): 80-88
Keng, V. W. et al., Nat Biotechnol. 27 (2009): 264-274
Kerley-Hamilton, J. S. et al., Oncogene 24 (2005): 6090-6100
Kesari, M. V. et al., Indian J Gastroenterol. 34 (2015): 63-67
Khan, J. et al., PLoS. One. 6 (2011): e26512
Khodarev, N. N. et al., Cancer Res 69 (2009): 2833-2837
Kibbe, A. H., Handbook of Pharmaceutical Excipients rd (2000)
Kiessling, A. et al., Oncogene 28 (2009): 2606-2620
Kikuchi, Y. et al., Front Genet. 4 (2013): 271
Killian, A. et al., Genes Chromosomes. Cancer 45 (2006): 874-881
Kim, B. H. et al., Ann. Surg. Oncol 21 (2014a): 2020-2027
Kim, D. H., Yonsei Med. J 48 (2007): 694-700
Kim, D. S. et al., J Proteome. Res 9 (2010): 3710-3719
Kim, H. E. et al., PLoS. One. 7 (2012a): e43223
Kim, H. J. et al., J Proteome. Res 8 (2009a): 1368-1379
Kim, H. N. et al., Am. J Hematol. 82 (2007): 798-801
Kim, I. M. et al., Cancer Res 66 (2006): 2153-2161
Kim, J. et al., Genes Chromosomes. Cancer 54 (2015a): 681-691
Kim, J. C. et al., Int. J Radiat. Oncol Biol Phys. 86 (2013a): 350-357

Kim, J. C. et al., World J Gastroenterol. 14 (2008a): 6662-6672
Kim, J. H. et al., Cancer 85 (1999): 546-553
Kim, J. H. et al., BMB. Rep. 44 (2011a): 523-528
Kim, J. W. et al., Int. J Oncol 35 (2009b): 129-137
Kim, K. et al., Mol. Cell 52 (2013b): 459-467
Kim, M. et al., Mol Cancer Res 6 (2008b): 222-230
Kim, M. S. et al., Oncogene 27 (2008c): 3624-3634
Kim, M. S. et al., Histopathology 58 (2011b): 660-668
Kim, R. et al., PLoS. One. 10 (2015b): e0126670
Kim, S. H. et al., Investig. Clin Urol. 57 (2016): 63-72
Kim, S. J. et al., Acta Haematol. 120 (2008d): 211-216
Kim, S. J. et al., Mol. Carcinog 54 (2015c): 1748-1757
Kim, S. M. et al., Int. J Cancer 134 (2014b): 114-124
Kim, S. W. et al., OMICS. 15 (2011c): 281-292
Kim, S. W. et al., Blood 111 (2008e): 1644-1653
Kim, Y. D. et al., Int. J Mol. Med. 29 (2012b): 656-662
Kim, Y. W. et al., PLoS. One. 7 (2012c): e40960
Kindt, N. et al., J Cancer Res Clin Oncol 140 (2014): 937-947
Kinoshita, Y. et al., Am. J Pathol. 180 (2012): 375-389
Kitange, G. J. et al., J Neurooncol. 100 (2010): 177-186
Klatka, J. et al., Eur. Arch. Otorhinolaryngol. 270 (2013): 2683-2693
Kleppe, M. et al., Nat Genet. 42 (2010): 530-535
Kleppe, M. et al., Blood 117 (2011a): 7090-7098
Kleppe, M. et al., Haematologica 96 (2011b): 1723-1727
Kleylein-Sohn, J. et al., J Cell Sci. 125 (2012): 5391-5402
Knapp, P. et al., Prostaglandins Other Lipid Mediat. 92 (2010): 62-66
Ko, H. W. et al., Dev. Cell 18 (2010): 237-247
Kobayashi, H. et al., Biochem. Biophys. Res Commun. 467 (2015a): 121-127
Kobayashi, M. et al., Lung Cancer 90 (2015b): 342-345
Kobayashi, Y. et al., Placenta 34 (2013): 110-118
Kocer, B. et al., Pathol. Int. 52 (2002): 470-477
Kogo, R. et al., Int. J Oncol 39 (2011): 155-159
Kohno, T. et al., Nat Med. 18 (2012): 375-377
Kohrt, D. et al., Cell Cycle 13 (2014): 62-71
Koike, K., Recent Results Cancer Res 193 (2014): 97-111
Kokoglu, E. et al., Cancer Lett. 50 (1990): 179-181
Kolb, T. M. et al., Toxicol. Sci. 88 (2005): 331-339
Kollmann, K. et al., Cancer Cell 24 (2013): 167-181
Kong, L. et al., Shanghai Kou Qiang. Yi. Xue. 24 (2015): 89-93
Koo, G. B. et al., Cell Res 25 (2015a): 707-725
Koo, S. et al., Anticancer Res 35 (2015b): 3209-3215
Koochekpour, S. et al., Asian J Androl 7 (2005a): 147-158
Koochekpour, S. et al., Genes Chromosomes. Cancer 44 (2005b): 351-364
Kordi Tamandani, D. M. et al., J Assist. Reprod. Genet. 26 (2009): 173-178
Korosec, B. et al., Cancer Genet. Cytogenet. 171 (2006): 105-111
Korotayev, K. et al., Cell Signal. 20 (2008): 1221-1226
Kortum, K. M. et al., Ann. Hematol. 94 (2015): 1205-1211
Koshikawa, K. et al., Oncogene 21 (2002): 2822-2828
Kozlowski, L. et al., Arch. Dermatol. Res 292 (2000): 68-71
Kraemer, N. et al., Cell Mol Life Sci. 68 (2011): 1719-1736
Kramer, M. et al., Biomed. Res Int. 2015 (2015): 208017
Krieg, A. M., Nat Rev. Drug Discov. 5 (2006): 471-484
Krona, C. et al., Oncogene 22 (2003): 2343-2351
Kuang, S. Q. et al., Leukemia 22 (2008): 1529-1538
Kuasne, H. et al., Clin Epigenetics. 7 (2015): 46
Kubota, H. et al., Cell Stress. Chaperones. 15 (2010): 1003-1011
Kudo, Y. et al., J Hepatol. 55 (2011): 1400-1408
Kuhn, E. et al., Mod. Pathol. 27 (2014): 1014-1019
Kulkarni, A. A. et al., Clin Cancer Res 15 (2009): 2417-2425
Kumar, S. et al., Cell Death. Dis. 6 (2015): e1758
Kumarakulasingham, M. et al., Clin Cancer Res 11 (2005): 3758-3765
Kuo, I. Y. et al., Int. J Cancer 135 (2014): 563-573
Kuo, S. J. et al., Oncol Rep. 24 (2010): 759-766
Kuphal, S. et al., Oncogene 25 (2006): 103-110
Kuppers, R. et al., J Clin Invest 111 (2003): 529-537
Kuramitsu, Y. et al., Anticancer Res 31 (2011): 3331-3336
Kurtovic-Kozaric, A. et al., Leukemia 29 (2015): 126-136
Kuruma, H. et al., Am. J Pathol. 174 (2009): 2044-2050
Kutikhin, A. G., Hum. Immunol. 72 (2011): 955-968
Kuznetsova, E. B. et al., Mol. Biol. (Mosk) 41 (2007): 624-633
Kwon, J. et al., Int J Oncol 43 (2013): 1523-1530
La, Vecchia C., Eur. J Cancer Prev. 10 (2001): 125-129
Labhart, P. et al., Proc. Natl. Acad. Sci. U.S.A 102 (2005): 1339-1344
Laetsch, T. W. et al., Cell Death. Dis. 5 (2014): e1072
Lage, H. et al., FEBS Lett. 494 (2001): 54-59
Lagorce-Pages, C. et al., Virchows Arch. 444 (2004): 426-435
Lai, J. M. et al., Methods Mol. Biol 623 (2010): 231-242
Lai, M. T. et al., J Pathol. 224 (2011): 367-376
Lake, S. L. et al., Invest Ophthalmol. Vis. Sci. 52 (2011): 5598-5604
Lan, H. et al., Int. J Clin Exp. Med. 7 (2014): 665-672
Lan, Q. et al., Eur. J Haematol. 85 (2010): 492-495
Lane, J. et al., Int. J Mol. Med. 12 (2003): 253-257
Langemeijer, S. M. et al., Cell Cycle 8 (2009): 4044-4048
Lapointe, J. et al., Am. J Surg. Pathol. 32 (2008): 205-209
Lapouge, G. et al., Cell Mol. Life Sci. 62 (2005): 53-64
Lara, P. C. et al., Radiat. Oncol 6 (2011): 148
Larkin, S. E. et al., Br. J Cancer 106 (2012): 157-165
Laske, K. et al., Cancer Immunol. Res 1 (2013): 190-200
Lau, L. F., Cell Mol. Life Sci. 68 (2011): 3149-3163
Lau, Y. F. et al., Mol. Carcinog 27 (2000): 308-321
Lauring, J. et al., Blood 111 (2008): 856-864
Lazova, R. et al., Am. J Dermatopathol. 31 (2009): 177-181
Leal, J. F. et al., Carcinogenesis 29 (2008): 2089-2095
Ledet, E. M. et al., Prostate 73 (2013): 614-623
Lee, B. H. et al., Cancer Res 73 (2013a): 1211-1218
Lee, E. J. et al., Oncol Res 18 (2010): 401-408
Lee, E. K. et al., Mol. Cell Biol 33 (2013b): 4422-4433
Lee, J. H. et al., Ann. Surg. 249 (2009): 933-941
Lee, M. J. et al., J Proteome. Res 13 (2014a): 4878-4888
Lee, S. Y. et al., Eur. J Cancer 50 (2014b): 698-705
Lee, T. J. et al., Mol. Cancer 3 (2004): 31
Lee, Y. S. et al., Oncotarget. 6 (2015): 16449-16460
Leong, H. S. et al., Cancer Res 73 (2013): 1591-1599
Leong, S. R. et al., Mol. Pharm. 12 (2015): 1717-1729
Levi, E. et al., Cancer Chemother. Pharmacol. 67 (2011): 1401-1413
Levy, P. et al., Clin Cancer Res 13 (2007): 398-407
Li, B. H. et al., Biochem. Biophys. Res Commun. 369 (2008a): 554-560
Li, B. S. et al., Oncogene 34 (2015a): 2556-2565
Li, C. F. et al., Oncotarget. 5 (2014a): 11428-11441
Li, C. F. et al., BMC. Genomics 8 (2007): 92
Li, C. M. et al., Am. J Pathol. 160 (2002): 2181-2190
Li, H. et al., Neoplasia. 8 (2006): 568-577
Li, J. et al., Zhonghua Bing. Li Xue. Za Zhi. 43 (2014b): 546-550
Li, J. F. et al., Zhonghua Wei Chang Wai Ke. Za Zhi. 15 (2012a): 388-391
Li, J. Y. et al., Chin Med. J (Engl.) 125 (2012b): 3526-3531

Li, L. et al., Clin Cancer Res 19 (2013a): 4651-4661
Li, L. et al., Pharmacogenet. Genomics 22 (2012c): 105-116
Li, L. C. et al., Am. J Obstet. Gynecol. 205 (2011a): 362-25
Li, M. et al., Clin Cancer Res 11 (2005): 1809-1814
Li, N. et al., Biochem. Biophys. Res Commun. 455 (2014): 358-362
Li, Q. et al., Mol. Biol Rep. 41 (2014c): 2409-2417
Li, S. et al., J Huazhong. Univ Sci. Technolog. Med. Sci. 28 (2008b): 93-96
Li, S. et al., Proc. Natl. Acad. Sci. U.S.A 111 (2014d): 6970-6975
Li, T. et al., J Thorac. Oncol 7 (2012d): 448-452
Li, W. et al., Cancer Cell Int. 15 (2015b): 17
Li, W. et al., Med. Oncol 31 (2014e): 208
Li, W. Q. et al., Carcinogenesis 34 (2013b): 1536-1542
Li, X. et al., Curr. Protein Pept. Sci. 16 (2015c): 301-309
Li, X. et al., Pancreas 40 (2011b): 753-761
Li, X. et al., BMC. Cancer 15 (2015d): 342
Li, X. et al., Cancer Res (2016)
Li, Y. et al., Cancer Genet. Cytogenet. 198 (2010): 97-106
Li, Y. et al., Cancer Biol Ther. 16 (2015e): 1316-1322
Li, Y. et al., Clin Cancer Res 17 (2011c): 3830-3840
Li, Y. et al., Lung Cancer 80 (2013c): 91-98
Li, Z. et al., Diagn. Pathol. 10 (2015f): 167
Li, Z. et al., Nan. Fang Yi. Ke. Da. Xue. Xue. Bao. 33 (2013d): 1483-1488
Lian, Z. et al., Cancer Biol Ther. 16 (2015): 750-755
Liang, B. et al., Zhonghua Yi. Xue. Za Zhi. 95 (2015a): 408-411
Liang, B. et al., Dig. Dis. Sci. 60 (2015b): 2360-2372
Liang, H. et al., Genome Res 22 (2012a): 2120-2129
Liang, Q. et al., Sci. Rep. 3 (2013): 2932
Liang, X. S. et al., Int. J Cancer 130 (2012b): 2062-2066
Liang, X. T. et al., J Gastroenterol. Hepatol. 26 (2011): 544-549
Liang, Y. et al., BMC. Cancer 6 (2006): 97
Liang, Y. et al., Proc. Natl. Acad. Sci. U.S.A 102 (2005): 5814-5819
Liao, C. F. et al., J Exp. Clin Cancer Res 27 (2008): 15
Liao, F. et al., Med. Oncol 27 (2010): 1219-1226
Liao, Y. et al., BMC. Cancer 14 (2014a): 487
Liao, Y. et al., PLoS. One. 9 (2014b): e99907
Liddy, N. et al., Nat Med. 18 (2012): 980-987
Lignitto, L. et al., Nat Commun. 4 (2013): 1822
Lim, B. et al., Carcinogenesis 35 (2014): 1020-1027
Lim, S. O. et al., Biochem. Biophys. Res Commun. 291 (2002): 1031-1037
Lin, D. C. et al., Nat Genet. 46 (2014): 467-473
Lin, F. et al., Cancer Biol Ther. 7 (2008a): 1669-1676
Lin, H. S. et al., Arch. Otolaryngol. Head Neck Surg. 130 (2004): 311-316
Lin, P. et al., Mol. Biol Rep. 38 (2011): 1741-1747
Lin, P. H. et al., J Biomed. Sci. 22 (2015a): 44
Lin, S. et al., RNA. Biol 12 (2015): 792-800
Lin, W. Y. et al., Hum. Mol. Genet. 24 (2015b): 285-298
Lin, Y. L. et al., Int. J Clin Exp. Pathol. 8 (2015c): 14257-14269
Lin, Y. M. et al., Mol. Carcinog 47 (2008b): 925-933
Lin, Y. W. et al., Oral Oncol 48 (2012): 629-635
Lindberg, D. et al., Neuroendocrinology 86 (2007): 112-118
Linder, N. et al., Gynecol. Oncol 124 (2012): 311-318
Linder, N. et al., Clin Cancer Res 11 (2005): 4372-4381
Ling, Z. Q. et al., Eur. J Surg. Oncol 38 (2012): 326-332
Linge, A. et al., Invest Ophthalmol. Vis. Sci. 53 (2012): 4634-4643
Lips, E. H. et al., BMC. Cancer 8 (2008): 314
Lipson, D. et al., Nat Med. 18 (2012): 382-384
Litvinov, I. V. et al., Clin. Cancer Res. 20 (2014a): 3799-3808
Litvinov, I. V. et al., Oncoimmunology 3 (2014b): e970025
Liu, B. et al., Biochem. Biophys. Res Commun. 293 (2002a): 1396-1404
Liu, C. et al., Int. J Clin Exp. Pathol. 7 (2014a): 690-698
Liu, D. et al., Oncotarget. 6 (2015a): 39211-39224
Liu, D. Q. et al., Sci. Rep. 5 (2015b): 11955
Liu, F. et al., Tumour. Biol 35 (2014b): 8685-8690
Liu, J. et al., PLoS. One. 9 (2014c): e89340
Liu, J. et al., Biochem. Biophys. Res Commun. 463 (2015c): 1230-1236
Liu, J. F. et al., Cancer Cell Int. 13 (2013a): 41
Liu, L. X. et al., World J Gastroenterol. 8 (2002b): 631-637
Liu, L. X. et al., Oncol Rep. 10 (2003): 1771-1775
Liu, L. Z. et al., Cancer Res 67 (2007): 6325-6332
Liu, M. et al., Cancer Res 66 (2006): 3593-3602
Liu, P. et al., J Natl. Cancer Inst. 100 (2008a): 1326-1330
Liu, Q. et al., Prostate 73 (2013b): 1028-1037
Liu, Q. et al., Med. Oncol 31 (2014d): 882
Liu, R. et al., Proc. Natl. Acad. Sci. U.S.A 105 (2008b): 7570-7575
Liu, R. et al., Oncotarget. 6 (2015d): 33456-33469
Liu, S. Y. et al., Zhonghua Wai Ke. Za Zhi. 47 (2009a): 1732-1735
Liu, W. et al., Ann. Surg. Oncol 21 Suppl 4 (2014e): S575-S583
Liu, W. et al., J Biol. Chem. 279 (2004): 10167-10175
Liu, W. et al., Mol. Clin Oncol 2 (2014f): 219-225
Liu, X. et al., PLoS. One. 8 (2013c): e77367
Liu, X. et al., Pathol. Res Pract. 210 (2014g): 256-263
Liu, X. et al., Zhonghua Yi. Xue. Za Zhi. 94 (2014h): 2008-2012
Liu, X. et al., Med. Oncol 30 (2013d): 735
Liu, Y. et al., Cancer Res 69 (2009b): 7844-7850
Liu, Y. et al., Asian Pac. J Cancer Prev. 16 (2015e): 2659-2664
Liu, Y. et al., Int. J Clin Exp. Pathol. 7 (2014i): 5750-5761
Liu, Y. X. et al., Oncol Lett. 4 (2012): 847-851
Liu, Z. et al., Oncol Rep. 33 (2015f): 1908-1914
Liu, Z. et al., BMC. Cancer 14 (2014j): 274
Liu, Z. et al., Carcinogenesis 32 (2011): 1668-1674
Ljunggren, H. G. et al., J Exp. Med. 162 (1985): 1745-1759
Llopis, S. et al., BMC. Cancer 13 (2013): 139
Lo, Y. W. et al., J Cell Mol. Med. 19 (2015): 744-759
Long, Z. W. et al., Tumour. Biol. 35 (2014): 11415-11426
Longenecker, B. M. et al., Ann N.Y. Acad. Sci. 690 (1993): 276-291
Lonsdale, J., Nat. Genet. 45 (2013): 580-585
Lopez-Cortes, A. et al., Am. J Med. Sci. 346 (2013): 447-454
Lou, T. F. et al., Cancer Prev. Res (Phila) 9 (2016): 43-52
Lozupone, F. et al., Oncogene (2015)
Lu, C. et al., Mol. Cell Biochem. 312 (2008): 71-80
Lu, C. et al., Dig. Dis. Sci. 58 (2013): 2713-2720
Lu, J. et al., Oncol Rep. 32 (2014a): 2571-2579
Lu, J. J. et al., Chin J Nat Med. 13 (2015): 673-679
Lu, P. et al., PLoS. One. 9 (2014b): e88918
Lu, X. et al., Mol. Cancer Ther. 3 (2004): 861-872
Lu, X. et al., Clin Cancer Res 15 (2009): 3287-3296
Lucas, S. et al., Int. J Cancer 87 (2000): 55-60
Lucito, R. et al., Cancer Biol Ther. 6 (2007): 1592-1599
Ludwig, A. et al., Anticancer Res 22 (2002): 3213-3221
Lukas, T. J. et al., Proc. Natl. Acad. Sci. U.S.A 78 (1981): 2791-2795
Luker, K. E. et al., Cancer Res 61 (2001): 6540-6547
Luksch, H. et al., Anticancer Res 31 (2011): 3181-3192

Lum, D. F. et al., Int. J Cancer 83 (1999): 162-166
Lundblad, R. L., Chemical Reagents for Protein Modification 3rd (2004)
Luo, X. et al., J Clin Endocrinol. Metab 94 (2009): 4533-4539
Lv, T. et al., PLoS. One. 7 (2012): e35065
Lyng, H. et al., BMC. Genomics 7 (2006): 268
Ma, G. F. et al., Eur. Rev. Med. Pharmacol. Sci. 19 (2015): 578-585
Ma, Q. et al., Biochem. Biophys. Res Commun. 454 (2014): 157-161
MacDonald, G. et al., Sci. Signal. 7 (2014): ra56
MacDonald, T. J. et al., Methods Mol. Biol 377 (2007): 203-222
Mackay, C. et al., Cancer Res 74 (2014): 2246-2257
Madden, S. F. et al., Mol. Cancer 13 (2014): 241
Madhavan, S. et al., J Exp. Clin Cancer Res 34 (2015): 45
Magold, A. I. et al., PLoS. One. 4 (2009): e6952
Mahmood, S. F. et al., Carcinogenesis 35 (2014): 670-682
Makkinje, A. et al., Cell Signal. 21 (2009): 1423-1435
Malta-Vacas, J. et al., Clin Chem Lab Med. 47 (2009): 427-431
Malumbres, M. et al., Curr. Opin. Genet. Dev. 17 (2007): 60-65
Man, T. K. et al., BMC. Cancer 4 (2004): 45
Mang, J. et al., Transl. Oncol 8 (2015): 487-496
Mangs, A. H. et al., Int. J Biochem. Cell Biol 40 (2008): 2353-2357
Mano, Y. et al., Cancer Sci. 98 (2007): 1902-1913
Mantia-Smaldone, G. M. et al., Hum. Vaccin. Immunother. 8 (2012): 1179-1191
Mao, J. et al., Cancer Sci. 99 (2008): 2120-2127
Mao, P. et al., J Biol Chem 286 (2011): 19381-19391
Mao, P. et al., PLoS. One. 8 (2013a): e81803
Mao, Y. et al., BMC. Cancer 13 (2013b): 498
Marechal, R. et al., Clin Cancer Res 15 (2009): 2913-2919
Marian, C. et al., Eur. J Clin Nutr. 65 (2011): 683-689
Marini, F. et al., J Biol Chem 277 (2002): 8716-8723
Markt, S. C. et al., Cancer Causes Control 26 (2015): 25-33
Marlow, L. A. et al., J Cell Sci. 125 (2012): 4253-4263
Marmey, B. et al., Hum. Pathol. 37 (2006): 68-77
Marques Filho, M. F. et al., Braz. J Otorhinolaryngol. 72 (2006): 25-30
Martens-de Kemp, S. R. et al., Clin Cancer Res 19 (2013): 1994-2003
Martin, L. et al., Oncogene 31 (2012): 4076-4084
Martin, T. A. et al., J Cell Biochem. 105 (2008): 41-52
Martin, T. A. et al., Methods Mol. Biol 762 (2011): 383-407
Martin, T. D. et al., Mol. Cell 53 (2014): 209-220
Martinez-Trillos, A. et al., Blood 123 (2014): 3790-3796
Masuda, K. et al., Oncol Rep. 28 (2012): 1146-1152
Masuda, T. A. et al., Clin Cancer Res 9 (2003): 5693-5698
Masugi, Y. et al., Lab Invest 95 (2015): 308-319
Matejcic, M. et al., PLoS. One. 6 (2011): e29366
Mathew, M. et al., Apoptosis. 18 (2013): 882-895
Matovina, M. et al., Gynecol. Oncol 113 (2009): 120-127
Matsumoto, K. et al., Genes Cells 6 (2001): 1101-1111
Matsumoto, N. et al., Leukemia 14 (2000): 1757-1765
Matsuyama, A. et al., Virchows Arch. 459 (2011): 539-545
Matsuyama, A. et al., Virchows Arch. 457 (2010): 577-583
Matsuyama, R. et al., Cancer Sci. 107 (2016): 28-35
Maurizio, E. et al., Mol. Cell Proteomics. 15 (2016): 109-123
Maxwell, C. A. et al., J Cell Sci. 121 (2008): 925-932
Mayne, M. et al., Eur. J Immunol. 34 (2004): 1217-1227
Mazan-Mamczarz, K. et al., PLoS. Genet. 10 (2014): e1004105
Mazzoccoli, G. et al., Chronobiol. Int. 28 (2011): 841-851
McCabe, K. E. et al., Cell Death. Dis. 5 (2014): e1496
McClung, J. K. et al., Exp. Gerontol. 30 (1995): 99-124
McDonald, J. M. et al., Mol. Cancer 4 (2005): 35
Mechtcheriakova, D. et al., Cell Signal. 19 (2007): 748-760
Mehta, A. et al., Breast 23 (2014): 2-9
Mehta, J. et al., PLoS. One. 10 (2015): e0120622
Meier, C. et al., J Pathol. 234 (2014): 351-364
Meijer, D. et al., Breast Cancer Res Treat. 113 (2009): 253-260
Meissner, M. et al., Clin Cancer Res 11 (2005): 2552-2560
Men, W. et al., Cancer Genomics Proteomics. 12 (2015): 1-8
Meng, F. et al., Int J Oncol 43 (2013): 495-502
Meng, J. et al., Acta Biochim. Biophys. Sin. (Shanghai) 42 (2010): 52-57
Mertens-Walker, I. et al., BMC. Cancer 15 (2015): 164
Messai, Y. et al., Cancer Res 74 (2014): 6820-6832
Metwally, N. S. et al., Cancer Cell Int. 11 (2011): 8
Meziere, C. et al., J Immunol 159 (1997): 3230-3237
Michel, S. et al., Int. J Cancer 127 (2010): 889-898
Midorikawa, Y. et al., Jpn. J Cancer Res 93 (2002): 636-643
Mikami, T. et al., Oral Oncol 47 (2011): 497-503
Mikami, T. et al., Virchows Arch. 466 (2015): 559-569
Milanovich, S. et al., Exp. Hematol. 43 (2015): 53-64
Miller, R. K. et al., J Am. Soc. Nephrol. 22 (2011): 1654-1664
Milne, R. L. et al., Hum. Mol. Genet. 23 (2014): 6096-6111
Min, K. W. et al., Int. J Gynecol. Pathol. 32 (2013): 3-14
Mino, K. et al., Biosci. Biotechnol. Biochem. 78 (2014): 1010-1017
Mirmalek-Sani, S. H. et al., J Cell Mol. Med. 13 (2009): 3541-3555
Mishra, L. et al., Cancer Biol Ther. 4 (2005a): 694-699
Mishra, S. et al., FEBS J 277 (2010): 3937-3946
Mishra, S. et al., Trends Mol. Med. 11 (2005b): 192-197
Mitchell, R. J. et al., Hum. Hered. 38 (1988): 144-150
Mitra, R. et al., Clin Cancer Res 17 (2011): 2934-2946
Mitsuhashi, K. et al., Int. J Hematol. 100 (2014): 88-95
Mittal, R. D. et al., Indian J Cancer 41 (2004): 115-119
Miwa, H. et al., Leukemia 6 (1992): 405-409
Miwa, T. et al., Cancer Med. 4 (2015): 1091-1100
Miyaji, K. et al., J Viral Hepat. 10 (2003): 241-248
Miyoshi, Y. et al., Med. Mol. Morphol. 43 (2010): 193-196
Mo, L. et al., Anticancer Res 30 (2010): 3413-3420
Mohamed, F. E. et al., Liver Int. 35 (2015): 1063-1076
Mohelnikova-Duchonova, B. et al., Cancer Chemother. Pharmacol. 72 (2013a): 669-682
Mohelnikova-Duchonova, B. et al., Pancreas 42 (2013b): 707-716
Moldovan, G. L. et al., Mol. Cell Biol 30 (2010): 1088-1096
Molinolo, A. A. et al., Clin Cancer Res 13 (2007): 4964-4973
Moniz, L. S. et al., Mol. Cell Biol 31 (2011): 30-42
Monji, M. et al., Clin Cancer Res 10 (2004): 6047-6057
Morgan, R. A. et al., Science 314 (2006): 126-129
Mori, M. et al., Transplantation 64 (1997): 1017-1027
Mori, Y. et al., Endocr. Relat Cancer 18 (2011): 465-478
Moritake, H. et al., Am. J Hematol. 86 (2011): 75-78
Moriya, Y. et al., J Hum. Genet. 57 (2012): 38-45
Mortara, L. et al., Clin Cancer Res. 12 (2006): 3435-3443
Moss, S. F. et al., Gut 45 (1999): 723-729
Mossink, M. H. et al., Oncogene 22 (2003): 7458-7467
Mostafa, W. Z. et al., J Cutan. Pathol. 37 (2010): 68-74
Motaghed, M. et al., Int. J Mol. Med. 33 (2014): 8-16
Mouradov, D. et al., Cancer Res 74 (2014): 3238-3247
Mueller, L. N. et al., J Proteome. Res 7 (2008): 51-61
Mueller, L. N. et al., Proteomics. 7 (2007): 3470-3480

Muir, K. et al., Cancer Res 73 (2013): 4722-4731
Mulligan, A. M. et al., Breast Cancer Res 13 (2011): R110
Mumberg, D. et al., Proc. Natl. Acad. Sci. U.S.A 96 (1999): 8633-8638
Munoz, I. M. et al., Mol. Cell 35 (2009): 116-127
Murphy, N. C. et al., Int. J Cancer 126 (2010): 1445-1453
Murray, G. I. et al., Histopathology 57 (2010): 202-211
Murrin, L. C. et al., J Neuroimmune. Pharmacol. 2 (2007): 290-295
Murugan, A. K. et al., Oncol Lett. 6 (2013): 437-441
Muto, Y. et al., Cell Cycle 7 (2008): 2738-2748
Mydlikova, Z. et al., Neoplasma 57 (2010): 287-290
Naba, A. et al., Elife. 3 (2014): e01308
Nadal-Serrano, M. et al., J Cell Biochem. 113 (2012): 3178-3185
Nagai, M. et al., Cancer Res 51 (1991): 3886-3890
Nagai, M. A. et al., Int. J Oncol 37 (2010): 41-49
Nagakura, S. et al., Blood 100 (2002): 1031-1037
Nagamachi, A. et al., Cancer Cell 24 (2013): 305-317
Nagashio, R. et al., Sci. Rep. 5 (2015): 8649
Nagata, M. et al., BMC. Cancer 13 (2013): 410
Nagendra, D. C. et al., Mol. Carcinog 51 (2012): 826-831
Nagi, C. et al., Breast Cancer Res Treat. 94 (2005): 225-235
Nagpal, J. K. et al., Mod. Pathol. 21 (2008): 979-991
Nakagawa, Y. et al., Br. J Cancer 80 (1999): 914-917
Nakaya, H. I. et al., Biochem. Biophys. Res Commun. 364 (2007): 918-923
Nakayama, K. et al., Cancer Res 67 (2007): 8058-8064
Nallar, S. C. et al., PLoS. One. 6 (2011): e24082
Nam, S. H. et al., Oncotarget. 6 (2015): 21655-21674
Nam, S. W. et al., Int. J Oncol 45 (2014): 1450-1456
Nam-Cha, S. H. et al., Mod. Pathol. 22 (2009): 1006-1015
Nantajit, D. et al., PLoS. One. 5 (2010): e12341
Narita, T. et al., Mol Cell Biol. 23 (2003): 1863-1873
Navarro, A. et al., J Clin Endocrinol. Metab 99 (2014): E2437-E2445
Naylor, D. J. et al., J Biol Chem 273 (1998): 21169-21177
Near, R. I. et al., J Cell Physiol 212 (2007): 655-665
Nebral, K. et al., Leukemia 23 (2009): 134-143
Neidert, M. C. et al., J Neurooncol. 111 (2013): 285-294
Nelson, C. R. et al., J Cell Biol 211 (2015): 503-516
Nelson, M. A. et al., Cancer Genet. Cytogenet. 108 (1999): 91-99
Neumann, M. et al., Blood 121 (2013): 4749-4752
Neveling, K. et al., Cytogenet. Genome Res 118 (2007): 166-176
Ng, Y. et al., J Biol Chem 279 (2004): 34156-34164
Ngeow, J. et al., Cancer Discov. 4 (2014): 762-763
Nguyen, T. B. et al., J Biol Chem 277 (2002): 41960-41969
Ni, I. B. et al., Hematol. Rep. 4 (2012): e19
Ni, Y. H. et al., Histopathology (2015)
Ni, Z. et al., J Urol. 167 (2002): 1859-1862
Niavarani, A. et al., Ann. Hematol. (2015)
Niimi, R. et al., BMC. Cancer 13 (2013): 309
Nikonova, A. S. et al., Cell Mol. Life Sci. 70 (2013): 661-687
Nikpour, P. et al., Med. Oncol 31 (2014): 955
Nilsson, R. et al., Nat Commun. 5 (2014): 3128
Nishi, T. et al., Pathol. Int. 62 (2012): 802-810
Nishikata, M. et al., Mol. Carcinog 46 (2007): 208-214
Niu, N. et al., Genome Res 20 (2010): 1482-1492
Niu, N. et al., BMC. Cancer 12 (2012): 422
Nobori, T. et al., Cancer Res 51 (1991): 3193-3197
Nobori, T. et al., Cancer Res 53 (1993): 1098-1101
Noll, J. E. et al., Neoplasia. 16 (2014): 572-585
Nooter, K. et al., Br. J Cancer 76 (1997): 486-493
Nord, H. et al., Neuro. Oncol 11 (2009): 803-818
Norris, M. D. et al., N. Engl. J Med. 334 (1996): 231-238
Noske, A. et al., Exp. Mol. Pathol. 98 (2015): 47-54
Novikov, L. et al., Mol. Cell Biol 31 (2011): 4244-4255
Nowarski, R. et al., Blood 120 (2012): 366-375
Nymoen, D. A. et al., Gynecol. Oncol 139 (2015): 30-39
O'Connor, K. W. et al., Cancer Res 73 (2013): 2529-2539
O'Gorman, D. B. et al., Endocrinology 143 (2002): 4287-4294
O'Malley, S. et al., Int. J Cancer 125 (2009): 1805-1813
O'Reilly, J. A. et al., PLoS. One. 10 (2015): e0123469
Oberg, E. A. et al., J Biol Chem 287 (2012): 43378-43389
Obuchowska, I. et al., Klin. Oczna 101 (1999): 167-168
Odvody, J. et al., Oncogene 29 (2010): 3287-3296
Oehler, V. G. et al., Blood 114 (2009): 3292-3298
Ogawa, C. et al., J Biol Chem 278 (2003): 1268-1272
Ogawa, R. et al., Dis. Esophagus. 21 (2008): 288-297
Oguri, T. et al., Mol. Cancer Ther. 7 (2008): 1150-1155
Ohba, K. et al., J Urol. 174 (2005): 461-465
Ohnishi, K. et al., Cancer Sci. 104 (2013): 1237-1244
Ohshima, K. et al., Mol Biol. Evol. 27 (2010): 2522-2533
Oishi, Y. et al., Tumour. Biol 33 (2012): 383-393
Okada, M. et al., Proc. Natl. Acad. Sci. U.S.A 105 (2008): 8649-8654
Okada, S. et al., J Oral Pathol. Med. 44 (2015): 115-125
Okosun, J. et al., Nat Genet. 48 (2016): 183-188
Olayioye, M. A. et al., J Biol Chem 280 (2005): 27436-27442
Oleksowicz, L. et al., Cancer J Sci. Am. 4 (1998): 247-253
Olesen, U. H. et al., APMIS 119 (2011): 296-303
Olkhanud, P. B. et al., Cancer Res 69 (2009): 5996-6004
Olsson, L. et al., Leukemia 28 (2014): 302-310
Olsson, M. et al., Prostate 67 (2007): 1439-1446
Ooe, A. et al., Breast Cancer Res Treat. 101 (2007): 305-315
Orchel, J. et al., Int. J Gynecol. Cancer 22 (2012): 937-944
Ostrow, K. L. et al., Clin Cancer Res 16 (2010): 3463-3472
Ota, T. et al., Cancer Res 62 (2002): 5168-5177
Ottaviani, S. et al., Cancer Immunol. Immunother. 55 (2006): 867-872
Ou, C. Y. et al., J Biol Chem 284 (2009): 20629-20637
Ozaki, Y. et al., Oncol Rep. 12 (2004): 1071-1077
Ozawa, H. et al., Ann. Surg. Oncol 17 (2010): 2341-2348
Ozbas-Gerceker, F. et al., Asian Pac. J Cancer Prev. 14 (2013): 5213-5217
Ozgur, S. et al., RNA. Biol 10 (2013): 528-539
Palma, M. et al., BMC. Clin Pathol. 12 (2012): 2
Pan, B. et al., Mol. Biol Rep. 40 (2013): 27-33
Pan, W. A. et al., RNA. Biol 12 (2015): 255-267
Pandey, R. N. et al., Oncogene 29 (2010): 3715-3722
Pankratz, V. S. et al., J Thorac. Oncol 6 (2011): 1488-1495
Pannu, V. et al., Oncotarget. 6 (2015): 6076-6091
Papadakis, M. et al., Fam. Cancer 14 (2015): 599-602
Papp, B. et al., Biomolecules. 2 (2012): 165-186
Parihar, A. et al., Life Sci. 82 (2008a): 1077-1082
Parihar, M. S. et al., Biochim. Biophys. Acta 1780 (2008b): 921-926
Parikh, R. A. et al., Genes Chromosomes. Cancer 53 (2014): 25-37
Park, E. et al., Mol. Cell 50 (2013): 908-918
Park, H. J. et al., J Proteome. Res 7 (2008): 1138-1150
Park, S. H. et al., Clin Cancer Res. 13 (2007): 858-867
Park, S. J. et al., Oncogene 35 (2016): 1292-1301
Park, Y. et al., Oncogene 34 (2015): 5037-5045
Park, Y. M. et al., Gene 551 (2014): 236-242
Patil, A. A. et al., Oncotarget. 5 (2014): 6414-6424
Patrick, A. N. et al., Nat Struct. Mol. Biol 20 (2013): 447-453
Patrikainen, L. et al., Eur. J Clin Invest 37 (2007): 126-133

Paulo, P. et al., Neoplasia. 14 (2012): 600-611
Pavelec, D. M. et al., Genetics 183 (2009): 1283-1295
Pawar, H. et al., Cancer Biol Ther. 12 (2011): 510-522
Pawar, S. et al., J Ovarian. Res 7 (2014): 53
Peddaboina, C. et al., BMC. Cancer 12 (2012): 541
Peeters, M. C. et al., Cell Signal. 27 (2015): 2579-2588
Peltonen, K. et al., Cancer Cell 25 (2014): 77-90
Pelttari, L. M. et al., Fam. Cancer (2015)
Pender-Cudlip, M. C. et al., Cancer Sci. 104 (2013): 760-764
Peng, D. F. et al., Gut 58 (2009): 5-15
Peng, H. X. et al., Biomed. Res Int. 2015 (2015a): 326981
Peng, J. et al., Sichuan. Da. Xue. Xue. Bao. Yi. Xue. Ban. 46 (2015b): 413-416
Peng, Y. et al., Cancer Res 75 (2015c): 378-386
Perdigao, P. F. et al., Genes Chromosomes. Cancer 44 (2005): 204-211
Pereira, J. S. et al., Endocrine. 49 (2015): 204-214
Pereira, P. M. et al., Org. Biomol. Chem. 12 (2014): 1804-1811
Perez, A. et al., Cancers (Basel) 6 (2014): 179-192
Perez-Tomas, R., Curr. Med. Chem 13 (2006): 1859-1876
Perrais, M. et al., J Biol Chem 276 (2001): 15386-15396
Perrotti, D. et al., Lancet Oncol 14 (2013): e229-e238
Personnic, N. et al., FEBS J 281 (2014): 2977-2989
Perugorria, M. J. et al., Cancer Res 69 (2009): 1358-1367
Pestov, D. G. et al., Mol. Cell Biol 21 (2001): 4246-4255
Peters, D. G. et al., Cancer Epidemiol. Biomarkers Prev. 14 (2005): 1717-1723
Peyrard, M. et al., Hum. Mol. Genet. 3 (1994): 1393-1399
Peyre, M. et al., PLoS. One. 5 (2010): e12932
Phipps-Yonas, H. et al., Front Immunol. 4 (2013): 425
Phongpradist, R. et al., Curr. Pharm. Des 16 (2010): 2321-2330
Piccolo, S. et al., Cancer Res 73 (2013): 4978-4981
Piepoli, A. et al., Exp. Biol Med. (Maywood.) 237 (2012): 1123-1128
Pils, D. et al., BMC. Cancer 13 (2013): 178
Pinheiro, J. et al., nlme: Linear and Nonlinear Mixed Effects Models (http://CRAN.R-project.org/packe=nlme) (2015)
Pio, R. et al., Cancer Res 64 (2004): 4171-4179
Pissimissis, N. et al., Anticancer Res 29 (2009): 371-377
Pizzatti, L. et al., Biochim. Biophys. Acta 1764 (2006): 929-942
Placke, T. et al., Blood 124 (2014): 13-23
Pleasance, E. D. et al., Nature 463 (2010): 184-190
Plebanski, M. et al., Eur. J Immunol 25 (1995): 1783-1787
Pohl, A. et al., Pharmacogenomics. J 11 (2011): 93-99
Poligone, B. et al., J Invest Dermatol. 135 (2015): 869-876
Polisetty, R. V. et al., J Proteomics. 74 (2011): 1918-1925
Pongor, L. et al., Genome Med. 7 (2015): 104
Poomsawat, S. et al., J Oral Pathol. Med. 39 (2010): 793-799
Poortinga, G. et al., Nucleic Acids Res 39 (2011): 3267-3281
Popov, N. et al., Nat Cell Biol 9 (2007): 765-774
Porkka, K. P. et al., Genes Chromosomes. Cancer 39 (2004): 1-10
Porta, C. et al., Virology 202 (1994): 949-955
Possuelo, L. G. et al., Rev Bras. Ginecol. Obstet. 35 (2013): 569-574
Pozo, K. et al., Cancer Cell 24 (2013): 499-511
Pradhan, M. P. et al., BMC. Syst. Biol 7 (2013): 141
Prasad, M. L. et al., Head Neck 26 (2004): 1053-1057
Prasad, N. K. et al., Carcinogenesis 29 (2008a): 25-34
Prasad, N. K. et al., Tumour. Biol 29 (2008b): 330-341
Prunier, C. et al., Cell Rep. (2015)
Pu, H. et al., World J Surg. Oncol 13 (2015): 323
Puig-Butille, J. A. et al., Oncotarget. 5 (2014): 1439-1451
Puls, F. et al., Am. J Surg. Pathol. 38 (2014): 1307-1318
Pulukuri, S. M. et al., Mol. Cancer Res 7 (2009): 1285-1293
Pulvino, M. et al., Blood 120 (2012): 1668-1677
Purrington, K. S. et al., Carcinogenesis 35 (2014): 1012-1019
Qi, J. et al., Gut (2015)
Qi, L. et al., Cancer Res 74 (2014): 1301-1306
Qi, Y. et al., Proteomics. 5 (2005): 2960-2971
Qian, Y. et al., Mol. Cancer 13 (2014): 176
Qian, Z. et al., J Exp. Clin Cancer Res 29 (2010): 111
Qin, Y. et al., Chin Med. J (Engl.) 127 (2014): 1666-1671
Quan, J. J. et al., Tumour. Biol 36 (2015a): 8617-8624
Quan, Y. et al., J Cancer 6 (2015b): 342-350
Quayle, S. N. et al., Neuro Oncol 14 (2012): 1325-1331
Quek, H. H. et al., DNA Cell Biol. 16 (1997): 275-280
Quidville, V. et al., Cancer Res 73 (2013): 2247-2258
Rahman, M. et al., Anticancer Res 33 (2013): 113-118
Raja, S. B. et al., J Cell Sci. 125 (2012): 703-713
Rajalingam, K. et al., Cell Cycle 4 (2005): 1503-1505
Rajasagi, M. et al., Blood 124 (2014): 453-462
Rajkumar, T. et al., BMC. Cancer 11 (2011): 80
Ramachandran, C., Curr. Pharm. Biotechnol. 8 (2007): 99-104
Rammensee, H. G. et al., Immunogenetics 50 (1999): 213-219
Ran, Q. et al., PLoS. One. 9 (2014): e85328
Rangel, L. B. et al., Oncogene 22 (2003): 7225-7232
Rao, C. V. et al., Carcinogenesis 30 (2009): 1469-1474
Rao, F. et al., Proc. Natl. Acad. Sci. U.S.A 112 (2015): 1773-1778
Rappa, G. et al., Mol. Cancer Res 12 (2014): 1840-1850
Rasinpera, H. et al., Gut 54 (2005): 643-647
Rastetter, R. H. et al., BMC. Cancer 15 (2015): 638
Rausch, M. P. et al., Mol. Immunol. 68 (2015): 124-128
Rauscher, G. H. et al., BMC. Cancer 15 (2015): 816
Rawluszko-Wieczorek, A. A. et al., J Cancer Res Clin Oncol 141 (2015): 1379-1392
RefSeq, The NCBI handbook [Internet], Chapter 18, (2002), www.ncbi.nlm.nih.gov/books/NBK21091/Rekhi, B. et al., Indian J Med. Res 136 (2012): 766-775
Remmelink, M. et al., Int. J Oncol 26 (2005): 247-258
Ren, G. et al., OMICS. 18 (2014): 615-624
Ren, S. et al., Cell Res 22 (2012): 806-821
Resende, C. et al., *Helicobacter.* 15 Suppl 1 (2010): 34-39
Restifo, N. P. et al., J Exp. Med. 177 (1993): 265-272
Reuschenbach, M. et al., Fam. Cancer 9 (2010): 173-179
Rey, O. et al., Oncogene 18 (1999): 827-831
Ribeiro, J. R. et al., Front Oncol 4 (2014): 45
Rieger-Christ, K. M. et al., Hum. Pathol. 32 (2001): 18-23
Ries, J. et al., Int. J Oncol 26 (2005): 817-824
Rimkus, C. et al., Clin Gastroenterol. Hepatol. 6 (2008): 53-61
Rini, B. I. et al., Cancer 107 (2006): 67-74
Risch, H. A. et al., J Natl. Cancer Inst. 98 (2006): 1694-1706
Ritterson, Lew C. et al., Nat Rev Urol. 12 (2015): 383-391
Roberts, N. J. et al., Cancer Discov 2 (2012): 41-46
Robin, T. P. et al., Mol. Cancer Res 10 (2012): 1098-1108
Robles, L. D. et al., J Biol Chem 277 (2002): 25431-25438
Rock, K. L. et al., Science 249 (1990): 918-921
Rocken, C., Pathologe 34 (2013): 403-412
Rodins, K. et al., Clin Cancer Res 8 (2002): 1075-1081
Rodriguez-Paredes, M. et al., Oncogene 33 (2014): 2807-2813
Rohrbeck, A. et al., PLoS. One. 4 (2009): e7315
Rohrmoser, M. et al., Mol. Cell Biol 27 (2007): 3682-3694
Roll, J. D. et al., Mol. Cancer 7 (2008): 15
Romero, O. A. et al., Cancer Discov 4 (2014): 292-303
Rondeau, S. et al., Br. J Cancer 112 (2015): 1059-1066

Rosado, I. V. et al., RNA. 10 (2004): 1073-1083
Ross, H. M. et al., Mod. Pathol. 24 (2011): 390-395
Rothe, M. et al., Am. J Pathol. 157 (2000): 1597-1604
Rudland, P. S. et al., Am. J Pathol. 176 (2010): 2935-2947
Ruebel, K. H. et al., Endocrine. 29 (2006): 435-444
Rumiato, E. et al., Cancer Chemother. Pharmacol. 72 (2013): 483-488
Ruminy, P. et al., Leukemia 25 (2011): 681-688
Russell, R. et al., Nat Commun. 6 (2015): 7677
Ryu, B. et al., PLoS. One. 2 (2007): e594
Ryu, H. S. et al., Thyroid 24 (2014): 1232-1240
Ryu, S. J. et al., Expert. Opin. Ther. Targets. 13 (2009): 479-484
S3-Leitlinie maligne Ovarialtumore, 032-035OL, (2013)
Saddoughi, S. A. et al., Adv. Cancer Res. 117 (2013): 37-58
Saeki, N. et al., Genes Chromosomes. Cancer 48 (2009): 261-271
Saelee, P. et al., Asian Pac. J Cancer Prev. 10 (2009): 501-506
Safadi, R. A. et al., Oral Surg. Oral Med. Oral Pathol. Oral Radial. 121 (2016): 402-411
Safarinejad, M. R. et al., Urol. Oncol 31 (2013): 1193-1203
Sahab, Z. J. et al., J Cancer 1 (2010): 14-22
Saiki, R. K. et al., Science 239 (1988): 487-491
Saito, Y. et al., J Cancer Res Clin Oncol 139 (2013): 585-594
Saito, Y. et al., Cancer Immunol. Res 3 (2015): 1356-1363
Sajadian, S. O. et al., Clin Epigenetics. 7 (2015): 98
Sakai, S. et al., Clin Chim. Acta 413 (2012): 1542-1548
Sakamoto, S. et al., Cancer Res 70 (2010): 1885-1895
Sakurikar, N. et al., J Biol Chem 287 (2012): 39193-39204
Salon, C. et al., J Pathol. 213 (2007): 303-310
Saloura, V. et al., Mol. Cancer Res 13 (2015): 293-304
Samimi, G. et al., Cancer Epidemiol. Biomarkers Prev. 21 (2012): 273-279
Sand, M. et al., Cell Tissue Res 350 (2012): 119-126
Sang, Y. et al., Oncotarget. (2015)
Sankar, S. et al., Mol. Cell Biol 33 (2013): 4448-4460
Sankaran, D. et al., J Biol Chem 287 (2012): 5483-5491
Santandreu, F. M. et al., Cell Physiol Biochem. 24 (2009): 379-390
Santhekadur, P. K. et al., FEBS Open. Bio 4 (2014): 353-361
Saraon, P. et al., Mol. Cell Proteomics. 12 (2013): 1589-1601
Sarbia, M. et al., Am. J Clin Pathol. 128 (2007): 255-259
Sarto, C. et al., Electrophoresis 18 (1997): 599-604
Sastre-Serra, J. et al., Free Radic. Biol Med. 61 (2013): 11-17
Sato, F. et al., Int. J Mol. Med. 30 (2012a): 495-501
Sato, T. et al., PLoS. One. 8 (2013): e59444
Sato, T. et al., J Cell Sci. 125 (2012b): 1544-1555
Satoh, A. et al., Oncogene 23 (2004): 8876-8886
Sattler, M. et al., Cancer Cell 1 (2002): 479-492
Savoy, R. M. et al., Endocr. Relat Cancer 20 (2013): R341-R356
Sawicka-Gutaj, N. et al., Tumour. Biol 36 (2015): 7859-7863
Sayagues, J. M. et al., Med. Clin (Barc.) 128 (2007): 226-232
Scagliotti, G. V. et al., Ann. Oncol 10 Suppl 5 (1999): S83-S86
Scanlan, M. J. et al., Cancer Immun. 1 (2001): 4
Scanlan, M. J. et al., Cancer Res 62 (2002): 4041-4047
Schaner, M. E. et al., Mol. Biol Cell 14 (2003): 4376-4386
Scharadin, T. M. et al., PLoS. One. 6 (2011): e23230
Scheffer, G. L. et al., Curr. Opin. Oncol 12 (2000): 550-556
Schiffmann, S. et al., Carcinogenesis 30 (2009): 745-752
Schimanski, C. C. et al., Oncogene 24 (2005): 3100-3109
Schleiermacher, G. et al., Oncogene 24 (2005): 3377-3384
Schlumbrecht, M. P. et al., Mod. Pathol. 24 (2011): 453-462
Schmidt, S. V. et al., Oncotarget. 6 (2015): 8635-8647
Schoppmann, S. F. et al., Clin Cancer Res 19 (2013): 5329-5339
Schraders, M. et al., Br. J Haematol. 143 (2008): 210-221
Schramm, A. et al., Nat Genet. 47 (2015): 872-877
Schrier, S. A. et al., Curr. Opin. Ophthalmol. 22 (2011): 325-331
Schuetz, J. M. et al., Cancer Epidemiol. Biomarkers Prev. 21 (2012): 2272-2274
Schulte, I. et al., BMC. Genomics 13 (2012): 719
Scott, A. F. et al., Genes (Basel) 5 (2014): 366-384
Scotto, L. et al., Genes Chromosomes. Cancer 47 (2008): 755-765
Sears, D. et al., Cell Death. Dis. 1 (2010): e93
Sedoris, K. C. et al., BMC. Cancer 10 (2010): 157
Seeger, F. H. et al., Immunogenetics 49 (1999): 571-576
Seeling, J. M. et al., Science 283 (1999): 2089-2091
Seetoo, D. Q. et al., J Surg. Oncol 82 (2003): 184-193
Seidel, C. et al., Mol. Carcinog 46 (2007): 865-871
Seidl, C. et al., Invest New Drugs 28 (2010): 49-60
Sekine, I. et al., Jpn. J Clin Oncol 37 (2007): 329-336
Selamat, S. A. et al., PLoS. One. 6 (2011): e21443
Seliger, B., Methods Mol. Biol 1102 (2014): 367-380
Seliger, B. et al., Proteomics. 5 (2005): 2631-2640
Seo, S. W. et al., J Orthop. Res 29 (2011): 1131-1136
Seol, H. S. et al., Cancer Lett. 353 (2014): 232-241
Seriramalu, R. et al., Electrophoresis 31 (2010): 2388-2395
Servais, E. L. et al., Clin Cancer Res 18 (2012): 2478-2489
Seshagiri, S. et al., Nature 488 (2012): 660-664
Shackelford, R. E. et al., Int. J Clin Exp. Pathol. 3 (2010): 522-527
Shadeo, A. et al., BMC. Genomics 9 (2008): 64
Shah, S. P. et al., Nature 461 (2009): 809-813
Shah, T. M. et al., Oral Oncol 49 (2013): 604-610
Shames, D. S. et al., Clin Cancer Res 19 (2013): 6912-6923
Shan, T. et al., Oncol Rep. 32 (2014): 1564-1570
Shang, B. et al., Cell Death. Dis. 5 (2014): e1285
Shao, J. et al., PLoS. One. 9 (2014): e97085
Sharma, A. et al., Tumour. Biol 34 (2013): 3249-3257
Shaughnessy, J. D., Jr. et al., Blood 118 (2011): 3512-3524
Shaw, E. J. et al., Cell Oncol (Dordr.) 34 (2011): 355-367
Shen, C. et al., Cancer Res 73 (2013): 3393-3401
Shen, Y. et al., Oncotarget. 6 (2015a): 20396-20403
Shen, Y. et al., Cancer Cell Microenviron. 2 (2015b)
Sheng, S. H. et al., Clin Transl. Oncol 16 (2014): 153-157
Sherman, F. et al., Laboratory Course Manual for Methods in Yeast Genetics (1986)
Shi, D. et al., Biochem. Biophys. Res Commun. 450 (2014a): 1241-1246
Shi, H. et al., World J Surg. Oncol 12 (2014b): 188
Shi, J. et al., Oncogene 25 (2006): 4923-4936
Shi, J. et al., Am. J Cancer Res 2 (2012): 116-129
Shi, J. L. et al., Oncotarget. 6 (2015): 5299-5309
Shields, B. J. et al., Mol. Cell Biol 33 (2013): 557-570
Shih, IeM et al., Am. J Pathol. 178 (2011): 1442-1447
Shin, E. M. et al., J Clin Invest 124 (2014): 3807-3824
Shiraishi, T. et al., J Transl. Med. 9 (2011): 153 Shishkin, S. S. et al., Biochemistry (Mosc.) 78 (2013): 1415-1430
Shruthi, D. K. et al., J Oral Maxillofac. Pathol. 18 (2014): 365-371
Shtutman, M. et al., Proc. Natl. Acad. Sci. U.S.A 108 (2011): 12449-12454
Shu, G. S. et al., Cancer Biomark. 11 (2012): 107-114
Shu, J. et al., Cancer Res. 66 (2006): 5077-5084
Sidhar, S. K. et al., Hum. Mol. Genet. 5 (1996): 1333-1338

Siligan, C. et al., Oncogene 24 (2005): 2512-2524
Silva, J. M. et al., Cell 137 (2009): 1047-1061
Silveira, S. M. et al., PLoS. One. 8 (2013): e67643
Simaga, S. et al., Eur. J Cancer 34 (1998): 399-405
Simaga, S. et al., Gynecol. Oncol 91 (2003): 194-200
Simonova, O. A. et al., Mol. Biol (Mosk) 49 (2015): 667-677
Simons, A. L. et al., Lab Invest 93 (2013): 711-719
Singh, G., Pharmaceuticals. (Basel) 7 (2014): 192-206
Singh, H. et al., Am. J Obstet. Gynecol. 198 (2008): 303-306
Singh, P. K. et al., Immunobiology 220 (2015): 103-108
Singh, R. et al., FEBS J 281 (2014): 1629-1641
Singh-Jasuja, H. et al., Cancer Immunol. Immunother. 53 (2004): 187-195
Sinha, S. et al., Mol. Oncol 5 (2011): 454-464
Skandalis, S. S. et al., Matrix Biol 35 (2014): 182-193
Slattery, M. L. et al., Carcinogenesis 31 (2010): 1604-1611
Slattery, M. L. et al., Mol. Carcinog 52 (2013): 155-166
Slipicevic, A. et al., BMC. Cancer 8 (2008): 276
Smaaland, R. et al., Breast Cancer Res Treat. 9 (1987): 53-59
Small, E. J. et al., J Clin Oncol. 24 (2006): 3089-3094
Smetsers, S. et al., Fam. Cancer 11 (2012): 661-665
Smith, B. et al., Cell Rep. 2 (2012): 580-590
Smith, J. B. et al., Gynecol. Oncol 134 (2014): 181-189
Sohr, S. et al., Cell Cycle 7 (2008): 3448-3460
Soman, N. R. et al., Proc. Natl. Acad. Sci. U.S.A 88 (1991): 4892-4896
Soman, N. R. et al., Proc. Natl. Acad. Sci. U.S.A 87 (1990): 738-742
Song, B. et al., Mol. Cancer Ther. 12 (2013a): 58-68
Song, J. et al., World J Gastroenterol. 19 (2013b): 4127-4136
Song, L. J. et al., J Mol. Med. (Berl) 90 (2012): 707-718
Song, N. et al., J Zhejiang. Univ Sci. B 14 (2013c): 451-459
Song, T. et al., Oncol Lett. 9 (2015a): 2799-2804
Song, X. et al., Monoclon. Antib. Immunodiagn. Immunother. 33 (2014a): 246-253
Song, X. C. et al., Mol. Cell Proteomics. 7 (2008): 163-169
Song, Y. et al., Nature 509 (2014b): 91-95
Song, Y. et al., Int. J Clin Exp. Pathol. 8 (2015b): 11314-11322
Song, Y. et al., Biochem. J 406 (2007): 427-436
Sonora, C. et al., J Histochem. Cytochem. 54 (2006): 289-299
Soupene, E. et al., J Lipid Res. 49 (2008): 1103-1112
Sousa, S. F. et al., Endocr. Relat Cancer 22 (2015): 399-408
Sowalsky, A. G. et al., Cancer Res 71 (2011): 758-767
Sowalsky, A. G. et al., Mol. Cancer Res. 13 (2015): 98-106
Sporn, J. C. et al., Am. J Pathol. 180 (2012): 2516-2526
Spyropoulou, A. et al., Neuromolecular. Med. 16 (2014): 70-82
Srinivasan, D. et al., Cancer Res 66 (2006): 5648-5655
Srinivasan, D. et al., Oncogene 27 (2008): 1095-1105
St-Denis, N. et al., Mol. Cell Proteomics. 14 (2015): 946-960
Stacey, S. N. et al., Nat Commun. 6 (2015): 6825
Stadler, W. M. et al., Cancer Res 54 (1994): 2060-2063
Stangel, D. et al., J Surg. Res 197 (2015): 91-100
Stary, S. et al., Genes Chromosomes. Cancer 52 (2013): 33-43
Stawerski, P. et al., Pol. J Pathol. 61 (2010): 219-223
Stefanska, B. et al., Clin Cancer Res 20 (2014): 3118-3132
Steffen, J. S. et al., Virchows Arch. 461 (2012): 355-365
Steinbach, D. et al., Clin Cancer Res 12 (2006): 4357-4363
Steinestel, K. et al., Mol. Cancer 13 (2014): 145
Steinestel, K. et al., Pathologe 34 Suppl 2 (2013): 189-194
Steinmann, K. et al., Oncol Rep. 22 (2009): 1519-1526
Stirewalt, D. L. et al., Genes Chromosomes. Cancer 47 (2008): 8-20
Stirpe, F. et al., Am. J Gastroenterol. 97 (2002): 2079-2085
Stoiber, D. et al., J Clin Invest 114 (2004): 1650-1658
Stone, B. et al., Gene 267 (2001): 173-182
Stransky, N. et al., Nat Commun. 5 (2014): 4846
Strock, C. J. et al., Cancer Res 66 (2006): 7509-7515
Strojnik, T. et al., Anticancer Res 26 (2006): 2887-2900
Strojnik, T. et al., Anticancer Res 29 (2009): 3269-3279
Stubbs, A. P. et al., Am. J Pathol. 154 (1999): 1335-1343
Sturm, M. et al., BMC. Bioinformatics. 9 (2008): 163
Su, M. T. et al., Gynecol. Oncol 103 (2006): 357-360
Su, Y. F. et al., J Biomed. Sci. 21 (2014): 67
Subramanian, M. et al., J Clin Endocrinol. Metab 94 (2009): 1467-1471
Suchy, J. et al., BMC. Cancer 8 (2008): 112
Sud, N. et al., Int. J Cancer 112 (2004): 905-907
Sudo, H. et al., Genomics 95 (2010): 210-216
Sueoka, S. et al., Ann. Surg. Oncol (2015)
Sugano, G. et al., Oncogene 30 (2011): 642-653
Sugimoto, K. J. et al., Int. J Clin Exp. Pathol. 7 (2014): 8980-8987
Sugimoto, T. et al., Genes Chromosomes. Cancer 48 (2009): 132-142
Suh, J. H. et al., Mol. Endocrinol. 22 (2008): 33-46
Sukocheva, O. A. et al., World J Gastroenterol. 21 (2015): 6146-6156
Sullivan, G. F. et al., J Clin Invest 105 (2000): 1261-1267
Sun, A. et al., Prostate (2015a)
Sun, D. W. et al., Cancer Epidemiol. (2015b)
Sun, H. et al., J BUON. 20 (2015c): 296-308
Sun, J. Y. et al., Zhonghua Kou Qiang. Yi. Xue. Za Zhi. 39 (2004a): 114-117
Sun, K. et al., Tumour. Biol 36 (2015d): 1549-1559
Sun, N. K. et al., Oncotarget. 6 (2015e): 27065-27082
Sun, Q. Y. et al., J Pathol. 235 (2015f): 559-570
Sun, S. et al., Gene 584 (2016): 90-96
Sun, S. et al., J Proteome. Res 9 (2010): 70-78
Sun, W. et al., Cancer Lett. 212 (2004b): 83-93
Sun, X. et al., Int. J Oncol 44 (2014a): 1678-1684
Sun, Y. et al., Oncogene 34 (2015g): 2527-2537
Sun, Y. et al., Carcinogenesis 35 (2014b): 1941-1950
Sun, Y. et al., Eur. J Cancer Prev. 23 (2014c): 418-424
Sun, Y. et al., Asian J Androl 16 (2014d): 319-324
Sung, W. W. et al., BMC. Cancer 14 (2014): 951
Surmann, E. M. et al., Cancer Immunol. Immunother. 64 (2015): 357-366
Suzuki, H. et al., Lung Cancer 59 (2008): 24-31
Svendsen, J. M. et al., Cell 138 (2009): 63-77
Svojgr, K. et al., Immunol. Lett. 122 (2009): 185-192
Svojgr, K. et al., Exp. Hematol. 40 (2012): 379-385
Swanson, K. D. et al., Genes Chromosomes. Cancer 47 (2008): 253-259
Swift, M. et al., N. Engl. J Med. 316 (1987): 1289-1294
Symes, A. J. et al., PLoS. One. 8 (2013): e84295
Szabo, P. M. et al., Virchows Arch. 455 (2009): 133-142
Szaflarski, W. et al., Postepy Biochem. 57 (2011): 266-273
Szczepanski, M. J. et al., Oral Oncol 49 (2013): 144-151
Szczepanski, M. J. et al., Biomark. Med. 7 (2013): 575-578
Szuhai, K. et al., Clin Cancer Res 15 (2009): 2259-2268
Tagawa, H., Nihon Rinsho 72 (2014): 1052-1057
Tahara, H. et al., Prostate Cancer Prostatic. Dis. 18 (2015): 56-62
Tahara, K. et al., Cancer 85 (1999): 1234-1240
Tahara, T. et al., Gastroenterology 146 (2014): 530-538
Tai, C. J. et al., Int. J Biol Markers 27 (2012): e280-e284
Tai, W. et al., Mol. Pharm. 10 (2013): 477-487

Takahashi, K. et al., Int. J Oncol 28 (2006): 321-328
Takahashi, Y. et al., Ann. Oncol 26 (2015): 935-942
Takao, M. et al., Oncol Rep. 17 (2007): 1333-1339
Takaoka, N. et al., BMC. Mol. Biol 12 (2011): 31
Takashima, S. et al., Tumour. Biol. 35 (2014): 4257-4265
Takata, A. et al., Hepatology 57 (2013a): 162-170
Takata, K. et al., Nat Commun. 4 (2013b): 2338
Takayanagi, S. et al., J Exp. Ther. Oncol 4 (2004): 239-246
Takeda, S. et al., J Toxicol. Sci. 39 (2014): 711-716
Takemoto, H. et al., Int. J Cancer 91 (2001): 783-788
Takenokuchi, M. et al., Anticancer Res 35 (2015): 3307-3316
Takeyama, K. et al., J Biol Chem 278 (2003): 21930-21937
Talieri, M. et al., Thromb. Haemost. 91 (2004): 180-186
Tamir, A. et al., J Ovarian. Res 7 (2014): 109
Tan, J. A. et al., Mol. Cell Endocrinol. 382 (2014): 302-313
Tan, P. et al., Biochem. Biophys. Res Commun. 419 (2012): 801-808
Tan, X. et al., Int. J Cancer 123 (2008): 1080-1088
Tanahashi, N. et al., Biochem. Biophys. Res Commun. 243 (1998): 229-232
Tanaka, M. et al., Cancer Sci. 99 (2008a): 979-985
Tanaka, Y. et al., J Hepatol. 49 (2008b): 746-757
Tang, C. Y. et al., Clin Chem Lab Med. 52 (2014a): 1843-1850
Tang, H. et al., Int. J Mol. Med. 32 (2013): 381-388
Tang, N. et al., Sheng Li Xue. Bao. 62 (2010): 196-202
Tang, S. et al., Xi. Bao. Yu Fen. Zi. Mian. Yi. Xue. Za Zhi. 30 (2014b): 411-413
Taniuchi, K. et al., Cancer Res 65 (2005): 105-112
Tanner, M. M. et al., Clin Cancer Res 1 (1995): 1455-1461
Tano, K. et al., FEBS Lett. 584 (2010): 4575-4580
Tao, F. et al., World J Gastroenterol. 20 (2014a): 9564-9569
Tao, J. et al., Tumour. Biol 35 (2014b): 4389-4399
Tao, T. et al., Cell Res 23 (2013): 620-634
Taouji, S. et al., J Biol Chem 288 (2013): 17190-17201
Tarcic, O. et al., Cell Rep. 14 (2016): 1462-1476
Tatidis, L. et al., J Lipid Res 38 (1997): 2436-2445
Tatsuka, M. et al., Cancer Res 58 (1998): 4811-4816
Taube, E. T. et al., Gynecol. Oncol 140 (2016): 494-502
Tedeschi, P. M. et al., Mol. Cancer Res (2015)
Teh, M. T. et al., Cancer Res 62 (2002): 4773-4780
Terada, T., Int. J Clin Exp. Pathol. 5 (2012): 596-600
Teufel, R. et al., Cell Mol Life Sci. 62 (2005): 1755-1762
Thakkar, A. D. et al., Biomark. Cancer 2 (2010): 1-15
Thang, N. D. et al., Oncotarget. 6 (2015): 14290-14299
Theiss, A. L. et al., Biochim. Biophys. Acta 1813 (2011): 1137-1143
Thomas, A. et al., Cancer Med. 2 (2013): 836-848
Thome, C. H. et al., Mol. Cell Proteomics. 11 (2012): 1898-1912
Thompson, D. A. et al., Eur. J Biochem. 252 (1998): 169-177
Thorell, K. et al., BMC. Med. Genomics 2 (2009): 53
Tian, X. et al., Oncol Rep. 34 (2015): 707-714
Tibaldi, L. et al., PLoS. One. 8 (2013): e72708
Timofeeva, O. A. et al., Int. J Oncol 35 (2009): 751-760
Tomiyama, L. et al., Oncogene 34 (2015): 1141-1149
Tomonaga, M. et al., Int. J Oncol 40 (2012): 409-417
Tong, W. G. et al., Epigenetics. 5 (2010): 499-508
Toogeh, G. et al., Clin Lymphoma Myeloma. Leuk. 16 (2016): e21-e26
Torres-Reyes, L. A. et al., Int. J Clin Exp. Pathol. 7 (2014): 7409-7418
Tozbikian, G. et al., PLoS. One. 9 (2014): e114900
Tran, E. et al., Science 344 (2014): 641-645
Travis, R. C. et al., Int. J Cancer 132 (2013): 1901-1910
Trehoux, S. et al., Biochem. Biophys. Res Commun. 456 (2015): 757-762
Trifonov, V. et al., BMC. Syst. Biol 7 (2013): 25
Tripodi, D. et al., BMC. Med. Genomics 2 (2009): 65
Trotta, C. R. et al., Nature 441 (2006): 375-377
Tsai, F. M. et al., Cell Signal. 18 (2006): 349-358
Tsao, D. A. et al., DNA Cell Biol 29 (2010): 285-293
Tsao, T. Y. et al., Mol. Cell Biochem. 327 (2009): 163-170
Tsou, J. H. et al., J Pathol. 225 (2011): 243-254
Tsujikawa, T. et al., Int. J Cancer 132 (2013): 2755-2766
Tsukamoto, Y. et al., J Pathol. 216 (2008): 471-482
Tsuruga, T. et al., Oncol Res 16 (2007): 431-435
Tu, L. C. et al., Mol. Cell Proteomics. 6 (2007): 575-588
Tucci, M. et al., Curr. Top. Med. Chem 9 (2009): 218-224
Tummala, R. et al., Cancer Chemother. Pharmacol. 64 (2009): 1187-1194
Tung, M. C. et al., Cancer Epidemiol. Biomarkers Prev. 18 (2009): 1570-1577
Tung, P. Y. et al., Stem Cells 31 (2013): 2330-2342
Turner, A. et al., PLoS. One. 8 (2013): e56817
Turner, B. C. et al., Cancer Res 58 (1998): 5466-5472
Turtoi, A. et al., J Proteome. Res 10 (2011): 4302-4313
Twa, D. D. et al., J Pathol. 236 (2015): 136-141
Uchikado, Y. et al., Int. J Oncol 29 (2006): 1337-1347
Uchiyama, K. et al., J Cell Biol. 159 (2002): 855-866
Uemura, M. et al., Cancer 97 (2003): 2474-2479
Ulloa, F. et al., PLoS. One. 10 (2015): e0119707
Unger, K. et al., Endocr. Relat Cancer 17 (2010): 87-98
Urbanucci, A. et al., Oncogene 31 (2012): 2153-2163
Uyama, H. et al., Clin Cancer Res 12 (2006): 6043-6048
Vahedi, S. et al., Oncol Rep. 34 (2015): 43-50
Vainio, P. et al., PLoS. One. 7 (2012): e39801
Vairaktaris, E. et al., Anticancer Res 27 (2007): 4121-4125
Vaites, L. P. et al., Mol. Cell Biol 31 (2011): 4513-4523
Vakana, E. et al., PLoS. One. 8 (2013): e78780
Valles, I. et al., PLoS. One. 7 (2012): e42086
Valque, H. et al., PLoS. One. 7 (2012): e46699
van de Rijn, M. et al., Am. J Pathol. 161 (2002): 1991-1996
van den Heuvel-Eibrink M M et al., Int. J Clin Pharmacol. Ther. 38 (2000): 94-110
van der Zwan, Y. G. et al., Eur. Urol. 67 (2015): 692-701
van Dijk, J. R. et al., Biochem. J 459 (2014): 27-36
Van Ginkel, P. R. et al., Biochim. Biophys. Acta 1448 (1998): 290-297
van Vuurden, D. G. et al., Neuro. Oncol 16 (2014): 946-959
van, Agthoven T. et al., J Clin Oncol 27 (2009): 542-549
van, Dam S. et al., BMC. Genomics 13 (2012): 535
Van, Seuningen, I et al., Biochem. J 348 Pt 3 (2000): 675-686
Vanaja, D. K. et al., Clin Cancer Res 12 (2006): 1128-1136
Vanderstraeten, A. et al., Cancer Immunol. Immunother. 63 (2014): 545-557
Vanharanta, S. et al., Elife. 3 (2014)
Vanneste, D. et al., Curr. Biol. 19 (2009): 1712-1717
Vasca, V. et al., Oncol Lett. 8 (2014): 2501-2504
Vater, I. et al., Leukemia 29 (2015): 677-685
Vavougios, G. D. et al., Am. J Physiol Lung Cell Mol. Physiol 309 (2015): L677-L686
Veigaard, C. et al., Cancer Genet. 204 (2011): 516-521
Vekony, H. et al., Oral Oncol 45 (2009): 259-265
Venere, M. et al., Sci. Transl. Med. 7 (2015): 304ra143
Verheugd, P. et al., Nat Commun. 4 (2013): 1683
Vermeulen, C. F. et al., Gynecol. Oncol 105 (2007): 593-599
Vey, N. et al., Oncogene 23 (2004): 9381-9391
Vincent, A. et al., Oncotarget. 5 (2014): 2575-2587
Vincent-Chong, V. K. et al., Oral Dis. 18 (2012): 469-476

Viswanathan, M. et al., Clin Cancer Res 9 (2003): 1057-1062
Vitale, M. et al., Cancer Res 58 (1998): 737-742
Vlaykova, T. et al., J BUON. 16 (2011): 265-273
Vogetseder, A. et al., Int. J Cancer 133 (2013): 2362-2371
Volkmer, J. P. et al., Proc. Natl. Acad. Sci. U.S.A 109 (2012): 2078-2083
Vrabel, D. et al., Klin. Onkol. 27 (2014): 340-346
Walker, F. et al., Biol Chem 395 (2014): 1075-1086
Walsh, M. D. et al., Mod. Pathol. 26 (2013): 1642-1656
Walter, S. et al., J Immunol 171 (2003): 4974-4978
Walter, S. et al., Nat Med. 18 (2012): 1254-1261
Wang, B. S. et al., Clin Sci. (Lond) 124 (2013a): 203-214
Wang, B. S. et al., Cell Stress. Chaperones. 18 (2013b): 359-366
Wang, C. et al., Mol. Cancer Res 5 (2007a): 1031-1039
Wang, C. et al., Nucleic Acids Res 43 (2015a): 4893-4908
Wang, C. et al., Clin Cancer Res 4 (1998): 567-576
Wang, C. J. et al., Mol. Biol Rep. 40 (2013c): 6525-6531
Wang, C. X. et al., Asian Pac. J Cancer Prev. 15 (2014a): 355-362
Wang, D. et al., J Biol. Chem. 277 (2002): 36216-36222
Wang, E. et al., Proc. Natl. Acad. Sci. U.S.A 110 (2013d): 3901-3906
Wang, F. et al., Oncol Rep. 30 (2013e): 260-268
Wang, G. et al., Biochem. J 446 (2012a): 415-425
Wang, G. R. et al., Acta Pharmacol. Sin. 30 (2009a): 1436-1442
Wang, H. et al., J Biol. Chem 289 (2014b): 4009-4017
Wang, H. et al., J Biol Chem 289 (2014c): 23123-23131
Wang, H. et al., Chin Med. J (Engl.) 116 (2003): 1074-1077
Wang, H. et al., J Cancer Res Ther. 11 Suppl 1 (2015b): C74-C79
Wang, J. et al., Oncotarget. 6 (2015c): 16527-16542
Wang, J. et al., Asian Pac. J Cancer Prev. 14 (2013f): 2805-2809
Wang, J. W. et al., Oncogene 23 (2004): 4089-4097
Wang, K. et al., J Biol Chem 289 (2014d): 23928-23937
Wang, L. et al., Acta Med. Okayama 65 (2011): 315-323
Wang, L. et al., Int. J Cancer 124 (2009b): 1526-1534
Wang, L. et al., Cancer Cell 25 (2014e): 21-36
Wang, M. et al., Int. J Mol. Med. 33 (2014f): 1019-1026
Wang, N. et al., Mol. Biol Rep. 39 (2012b): 10497-10504
Wang, P. et al., Zhongguo Fei. Ai. Za Zhi. 12 (2009c): 875-878
Wang, Q. et al., Cell 138 (2009d): 245-256
Wang, Q. et al., Mol. Med. Rep. 12 (2015d): 475-481
Wang, S. S. et al., PLoS. One. 5 (2010): e8667
Wang, S. Y. et al., Oncotarget. 7 (2016a): 2878-2888
Wang, T. et al., Clin Transl. Oncol 17 (2015e): 564-569
Wang, V. W. et al., Head Neck 35 (2013g): 831-835
Wang, W. W. et al., Int. J Clin Exp. Med. 8 (2015f): 3063-3071
Wang, W. X. et al., Sichuan. Da. Xue. Xue. Bao. Yi. Xue. Ban. 40 (2009e): 857-860
Wang, X. et al., Int. J Clin Exp. Med. 8 (2015g): 1780-1791
Wang, X. et al., Hum. Pathol. 44 (2013h): 2020-2027
Wang, X. et al., Am. J Cancer Res 5 (2015h): 2590-2604
Wang, X. et al., J Biol Chem 290 (2015i): 3925-3935
Wang, X. et al., Oncotarget. 7 (2016b): 8029-8042
Wang, X. et al., Hum. Immunol. 75 (2014g): 1203-1209
Wang, X. et al., Biochim. Biophys. Acta 1783 (2008): 1220-1228
Wang, X. et al., Int J Biol Markers 29 (2014h): e150-e159
Wang, X. X. et al., Hepatobiliary. Pancreat. Dis. Int. 12 (2013i): 540-545
Wang, X. X. et al., PLoS. One. 9 (2014i): e96501
Wang, Y. et al., J Thorac. Dis. 7 (2015j): 672-679
Wang, Y. et al., Oncogene 31 (2012c): 2512-2520
Wang, Y. et al., J Biomed. Sci. 22 (2015k): 52
Wang, Y. et al., Pathol. Oncol Res. 20 (2014): 611-618
Wang, Y. F. et al., Tumour. Biol 34 (2013j): 1685-1689
Wang, Z. et al., Cancer Res 67 (2007b): 8293-8300
Warfel, N. A. et al., Cell Cycle 12 (2013): 3689-3701
Waseem, A. et al., Oral Oncol 46 (2010): 536-542
Watanabe, M. et al., Proteomics. Clin Appl. 2 (2008): 925-935
Watanabe, T. et al., Clin Colorectal Cancer 10 (2011): 134-141
Waters, M. G. et al., Nature 349 (1991): 248-251
Watson, P. J. et al., Traffic. 5 (2004): 79-88
Watts, C. A. et al., Chem Biol 20 (2013): 1399-1410
Wazir, U. et al., Cancer Genomics Proteomics. 10 (2013): 69-73
Wazir, U. et al., Oncol Rep. 33 (2015a): 1450-1458
Wazir, U. et al., Oncol Rep. 33 (2015b): 2575-2582
Weber, A. M. et al., Pharmacol. Ther (2014)
Weeks, L. D. et al., Mol. Cancer Ther. 12 (2013): 2248-2260
Wegiel, B. et al., J Natl. Cancer Inst. 100 (2008): 1022-1036
Wei, P. et al., J Transl. Med. 11 (2013): 313
Wei, X. et al., Nat Genet. 43 (2011): 442-446
Wei, Y. P. et al., Xi. Bao. Yu Fen. Zi. Mian. Yi. Xue. Za Zhi. 28 (2012): 354-357
Weidle, U. H. et al., Clin Exp. Metastasis 32 (2015): 623-635
Weigert, O. et al., Cancer Discov 2 (2012): 47-55
Wen, J. L. et al., PLoS. One. 10 (2015): e0115622
Wenzel, J. et al., Int. J Cancer 123 (2008): 2605-2615
Werner, S. et al., J Biol Chem 288 (2013): 22993-23008
Weterman, M. A. et al., Cytogenet. Cell Genet. 92 (2001): 326-332
Weterman, M. A. et al., Proc. Natl. Acad. Sci. U.S.A 93 (1996): 15294-15298
Wharton, S. B. et al., Neuropathol. Appl. Neurobiol. 27 (2001): 305-313
Wheler, J. J. et al., BMC. Cancer 15 (2015): 442
Whitaker-Menezes, D. et al., Cell Cycle 10 (2011): 4047-4064
White, C. D. et al., BMC. Gastroenterol. 10 (2010): 125
Wijdeven, R. H. et al., Cancer Res 75 (2015): 4176-4187
Wikman, H. et al., Genes Chromosomes. Cancer 42 (2005): 193-199
Willcox, B. E. et al., Protein Sci. 8 (1999): 2418-2423
Williams, K. A. et al., PLoS. Genet. 10 (2014): e1004809
Wilson, I. M. et al., Oncogene 33 (2014): 4464-4473
Wilting, S. M. et al., Genes Chromosomes. Cancer 47 (2008): 890-905
Wirtenberger, M. et al., Carcinogenesis 27 (2006): 1655-1660
Wissing, M. D. et al., Oncotarget. 5 (2014): 7357-7367
Wong, N. et al., J Hepatol. 38 (2003): 298-306
Wong, S. Q. et al., Oncotarget. 6 (2015): 1115-1127
Woo, J. et al., Biochem. Biophys. Res Commun. 367 (2008): 291-298
Wood, L. M. et al., Cancer Immunol. Immunother. 61 (2012): 689-700
Wright, D. G. et al., Anticancer Res 16 (1996): 3349-3351
Wrzeszczynski, K. O. et al., PLoS. One. 6 (2011): e28503
Wu, C. et al., BMC. Bioinformatics. 13 (2012a): 182
Wu, C. C. et al., Proteomics. Clin Appl. 2 (2008): 1586-1595
Wu, C. C. et al., Biochim. Biophys. Acta 1823 (2012b): 2227-2236
Wu, C. Y. et al., J Biomed. Sci. 18 (2011a): 1
Wu, H. et al., Nat Med. 17 (2011b): 347-355

Wu, H. C. et al., Nat Commun. 5 (2014a): 3214
Wu, J. et al., Oncogene 31 (2012c): 333-341
Wu, J. et al., ACS Chem Biol 8 (2013a): 2201-2208
Wu, M. Z. et al., Cancer Res 75 (2015): 3912-3924
Wu, T. et al., Hepatology 36 (2002): 363-373
Wu, T. T. et al., Chin J Physiol 49 (2006): 192-198
Wu, W. et al., Cancer Res 67 (2007): 951-958
Wu, X. et al., Hum. Mol. Genet. 21 (2012d): 456-462
Wu, Y. et al., Biomed. Res 33 (2012e): 75-82
Wu, Y. et al., Cancer Sci. 103 (2012f): 1820-1825
Wu, Y. et al., Cell Rep. 5 (2013b): 224-236
Wu, Y. et al., J Surg. Oncol 105 (2012g): 724-730
Wu, Z. et al., Neoplasia. 11 (2009): 66-76
Wu, Z. et al., Breast Cancer Res 16 (2014b): R75
Wu, Z. B. et al., J Immunol. Res 2014 (2014c): 131494
Wu, Z. Y. et al., Scand. J Immunol. 74 (2011c): 561-567
Wurdak, H. et al., Cell Stem Cell 6 (2010): 37-47
Xia, Luo et al., Reprod. Sci. 17 (2010): 791-797
Xia, Q. S. et al., Zhonghua Yi. Xue. Za Zhi. 91 (2011): 554-559
Xiang, X. et al., PLoS. One. 7 (2012): e50781
Xiang, Y. J. et al., PLoS. One. 9 (2014): e109449
Xiao, F. et al., Hum. Genet. 133 (2014): 559-574
Xiao, J. et al., J Biol. Chem. 276 (2001): 6105-6111
Xiao, W. et al., Nucleic Acids Res 26 (1998): 3908-3914
Xiao, X. et al., J Transl. Med. 11 (2013): 151
Xin, B. et al., Oncogene 24 (2005): 724-731
Xin, H. et al., Oncogene 22 (2003): 4831-4840
Xin, Z. et al., Virchows Arch. 465 (2014): 35-47
Xing, Q. T. et al., Onco. Targets. Ther. 7 (2014): 881-885
Xu, C. et al., Biomarkers 20 (2015a): 271-274
Xu, C. Z. et al., Int. J Clin Exp. Pathol. 6 (2013a): 2745-2756
Xu, H. et al., J Clin Oncol 30 (2012): 751-757
Xu, J. et al., Oncol Rep. 34 (2015b): 1424-1430
Xu, L. et al., Zhongguo Fei. Ai. Za Zhi. 14 (2011): 727-732
Xu, W. et al., Med. Oncol 32 (2015c): 96
Xu, X. et al., IUBMB. Life 65 (2013b): 873-882
Xu, X. et al., Zhonghua Bing. Li Xue. Za Zhi. 43 (2014a): 177-183
Xu, Y. et al., PLoS. One. 9 (2014b): e100127
Xu, Y. et al., PLoS. One. 8 (2013c): e64973
Xu, Y. et al., Oncol Lett. 7 (2014c): 1474-1478
Xu, Y. F. et al., BMC. Cancer 15 (2015d): 332
Xu, Z. et al., Leuk. Res 33 (2009): 891-897
Xu, Z. et al., Anat. Rec. (Hoboken.) 295 (2012): 1446-1454
Xue, L. Y. et al., Zhonghua Zhong. Liu Za Zhi. 32 (2010): 838-844
Yakimchuk, K. et al., Mol. Cell Endocrinol. 375 (2013): 121-129
Yamada, H. et al., Genes Chromosomes. Cancer 47 (2008): 810-818
Yamada, H. Y. et al., Oncogene 25 (2006): 1330-1339
Yamada, R. et al., Tissue Antigens 81 (2013): 428-434
Yamada, Y. et al., Jpn. J Cancer Res 90 (1999): 987-992
Yamamoto, S. et al., Ann. Surg. Oncol 14 (2007): 2141-2149
Yamashita, J. et al., Acta Derm. Venereol. 92 (2012): 593-597
Yamauchi, T. et al., Environ. Health Prev. Med. 19 (2014): 265-270
Yamazaki, M. et al., Lab Invest 94 (2014): 1260-1272
Yamazoe, S. et al., J Exp. Clin Cancer Res 29 (2010): 53
Yan, C. et al., J Ovarian. Res 7 (2014a): 78
Yan, H. X. et al., J Biol Chem 281 (2006): 15423-15433
Yan, L. et al., Tumour. Biol 34 (2013a): 4089-4100
Yan, Q. et al., Mol. Cell Biol 33 (2013b): 845-857
Yan, X. et al., Int. J Clin Exp. Pathol. 7 (2014b): 8715-8723
Yan, X. B. et al., Mol. Med. Rep. 10 (2014c): 2720-2728
Yan, Y. et al., PLoS. One. 8 (2013c): e81905
Yang, H. et al., Cancer Res 68 (2008a): 2530-2537
Yang, H. Y. et al., J Proteomics. 75 (2012a): 3639-3653
Yang, J. et al., Neurosurg. Clin N. Am. 23 (2012b): 451-458
Yang, J. et al., Cell Biochem. Biophys. 70 (2014a): 1943-1949
Yang, J. J. et al., Blood 120 (2012c): 4197-4204
Yang, J. L. et al., Int. J Cancer 89 (2000): 431-439
Yang, P. et al., Mol. Cell Biol 32 (2012d): 3121-3131
Yang, P. et al., Curr. Pharm. Des 21 (2015a): 1292-1300
Yang, P. et al., Zhonghua Yi. Xue. Za Zhi. 93 (2013): 5-7
Yang, T. et al., Tumour. Biol 35 (2014b): 11199-11207
Yang, T. et al., J Biol Chem 278 (2003): 15291-15296
Yang, W. et al., Mol. Med. Rep. 10 (2014c): 1205-1214
Yang, X. et al., Pathol. Oncol Res 20 (2014d): 641-648
Yang, Y. et al., Biochem. Biophys. Res Commun. 332 (2005): 181-187
Yang, Y. et al., Biochem. Biophys. Res Commun. 450 (2014e): 899-905
Yang, Y. et al., Cancer Discov 4 (2014f): 480-493
Yang, Y. et al., Exp. Oncol 30 (2008b): 81-87
Yang, Y. et al., Mol. Cell 58 (2015b): 47-59
Yang, Y. L. et al., Leuk. Res 34 (2010): 18-23
Yang, Y. M. et al., Cancer Sci. 102 (2011): 1264-1271
Yang, Z. et al., Int. J Med. Sci. 12 (2015c): 256-263
Yao, J. et al., Cancer Immunol. Res. 2 (2014a): 371-379
Yao, X. et al., Biochem. Biophys. Res Commun. 455 (2014b): 277-284
Yao, Y. S. et al., Clin Transl. Sci. 8 (2015): 137-142
Yasen, M. et al., Clin Cancer Res 11 (2005): 7354-7361
Yasen, M. et al., Int. J Oncol 40 (2012): 789-797
Ye, C. et al., J Neurochem. 133 (2015): 273-283
Ye, Z. et al., Int. J Clin Exp. Med. 8 (2015): 3707-3715
Yeates, L. C. et al., Biochem. Biophys. Res Commun. 238 (1997): 66-70
Yeh, I. et al., Am. J Surg. Pathol. 39 (2015): 581-591
Yeh, S. et al., Proc. Natl. Acad. Sci. U.S.A 97 (2000): 11256-11261
Yen, L. C. et al., Clin Cancer Res 15 (2009): 4508-4513
Yi, C. H. et al., Cancer Lett. 284 (2009): 149-156
Yildiz, M. et al., Blood 125 (2015): 668-679
Yin, B. W. et al., Cancer Immun. 8 (2008): 3
Yin, J. et al., Med. Oncol 31 (2014): 272
Yiu, G. K. et al., J Biol Chem 281 (2006): 12210-12217
Yokota, T. et al., Acta Neuropathol. 111 (2006): 29-38
Yonezawa, S. et al., Pathol. Int. 49 (1999): 45-54
Yongjun Zhang, M. M. et al., J Cancer Res Ther. 9 (2013): 660-663
Yoo, K. H. et al., Oncol Lett. 8 (2014): 2135-2139
Yoon, D. H. et al., Eur. J Haematol. 88 (2012): 292-305
Yoon, S. Y. et al., Biochem. Biophys. Res Commun. 326 (2005): 7-17
Yoshida, A. et al., Am. J Surg. Pathol. 38 (2014): 552-559
Yoshida, K. et al., Cancer Sci. 104 (2013): 171-177
Yoshida, Y. et al., Genes Dev. 17 (2003): 1201-1206
Yoshizawa, A. et al., Clin Cancer Res 16 (2010): 240-248
Young, A. N. et al., Am. J Pathol. 158 (2001): 1639-1651
Yu, C. J. et al., Int. J Cancer 69 (1996): 457-465
Yu, J. et al., Cancer 88 (2000): 1801-1806
Yu, L. et al., Cancer Res 75 (2015a): 1275-1286
Yu, M. et al., Oncogene 24 (2005): 1982-1993
Yu, W. et al., Carcinogenesis 29 (2008): 1717-1724
Yu, X. et al., Tumour. Biol 36 (2015b): 967-972
Yu, X. F. et al., World J Gastroenterol. 17 (2011): 4711-4717
Yu, Z. et al., Mol. Med. Rep. 10 (2014): 1583-1589
Yuan, B. et al., Cancer Sci. 106 (2015): 819-824
Yuan, J. Y. et al., Oncol Lett. 1 (2010): 649-655

Yuan, Y. et al., Am. J Surg. Pathol. 33 (2009): 1673-1682
Zage, P. E. et al., Cancer 119 (2013): 915-923
Zagryazhskaya, A. et al., Oncotarget. 6 (2015): 1 21 56-1 21 73
Zamkova, M. et al., Cell Cycle 12 (2013): 826-836
Zang, H. et al., Zhonghua Shi Yan. He. Lin. Chuang. Bing. Du Xue. Za Zhi. 26 (2012): 285-287
Zapatero, A. et al., Urol. Oncol 32 (2014): 1327-1332
Zaravinos, A. et al., Tumour. Biol 35 (2014): 4987-5005
Zaremba, S. et al., Cancer Res. 57 (1997): 4570-4577
Zarubin, T. et al., Cell Res 15 (2005): 439-446
Zekri, A. et al., Oncol Res 20 (2012): 241-250
Zekri, A. R. et al., Asian Pac. J Cancer Prev. 16 (2015): 3543-3549
Zeng, X. et al., Ai. Zheng. 26 (2007): 1080-1084
Zhai, W. et al., Eur. Rev Med. Pharmacol. Sci. 18 (2014): 1354-1360
Zhan, X. et al., Anal. Biochem. 354 (2006): 279-289
Zhang, B. et al., J Huazhong. Univ Sci. Technolog. Med. Sci. 30 (2010a): 322-325
Zhang, C. et al., J Surg. Res 197 (2015a): 301-306
Zhang, C. et al., BMC. Gastroenterol. 15 (2015b): 49
Zhang, C. Y. et al., Asian J Androl 17 (2015c): 106-110
Zhang, F. et al., J Viral Hepat. 21 (2014a): 241-250
Zhang, F. et al., Cancer Res 63 (2003): 5005-5010
Zhang, G. et al., Oncol Rep. 33 (2015d): 1147-1154
Zhang, H. et al., Tumour. Biol 36 (2015e): 997-1002
Zhang, H. et al., Nat Genet. 42 (2010b): 755-758
Zhang, H. H. et al., Int. J Clin Exp. Pathol. 6 (2013a): 1734-1746
Zhang, J. et al., Hum. Pathol. 46 (2015f): 1331-1340
Zhang, J. et al., Tumour. Biol 36 (2015g): 2163-2168
Zhang, J. et al., PLoS. One. 9 (2014b): e109318
Zhang, K. et al., Tumour. Biol 35 (2014c): 4031-4040
Zhang, L. et al., Med. Oncol 32 (2015h): 454 Zhang, L. et al., Mol. Cancer Ther. 6 (2007): 1661-1672
Zhang, L. et al., J Cell Mol. Med. 19 (2015i): 799-805
Zhang, L. et al., Cancer Res 65 (2005a): 925-932
Zhang, M. et al., J Exp. Clin Cancer Res 34 (2015j): 60
Zhang, M. et al., Cancer Lett. 243 (2006): 38-46
Zhang, N. et al., Oncotarget. (2016a)
Zhang, P. et al., Genome 57 (2014d): 253-257
Zhang, S. Q. et al., Mol. Med. Rep. 12 (2015k): 1177-1182
Zhang, W. et al., Epigenetics. 10 (2015l): 736-748
Zhang, W. et al., Acta Haematol. 130 (2013b): 297-304
Zhang, W. et al., Tumour. Biol (2015m)
Zhang, W. et al., J Biol Chem 286 (2011): 35899-35905
Zhang, W. et al., Biochem. J (2016b)
Zhang, X. et al., Oncotarget. 5 (2014e): 6178-6190
Zhang, X. et al., PLoS. One. 8 (2013c): e72458
Zhang, X. et al., Leuk. Res 39 (2015n): 1448-1454
Zhang, Y. et al., Clin Lung Cancer 14 (2013d): 45-49
Zhang, Y. et al., PLoS. One. 9 (2014f): e90154
Zhang, Y. J. et al., Cancer Lett. 275 (2009): 277-284
Zhang, Y. X. et al., Biomed. Pharmacother. 67 (2013e): 97-102
Zhang, Z. et al., Gynecol. Oncol 135 (2014g): 69-73
Zhang, Z. et al., Cancer Epidemiol. Biomarkers Prev. 14 (2005b): 1188-1193
Zhang, Z. et al., J Biol Chem 290 (20150): 19558-19568
Zhao, C. et al., Neoplasia. 9 (2007): 1-7
Zhao, C. et al., Endocrine. 36 (2009): 224-232
Zhao, H. et al., Cancer Gene Ther. 21 (2014a): 448-455
Zhao, H. et al., Cell Tissue Res (2015a)
Zhao, H. et al., Zhonghua Gan Zang. Bing. Za Zhi. 10 (2002): 100-102
Zhao, Q. et al., Exp. Ther. Med. 5 (2013a): 942-946
Zhao, X. et al., Cancer Res 65 (2005): 2125-2129
Zhao, X. et al., Onco. Targets. Ther. 7 (2014b): 343-351
Zhao, X. et al., Lab Invest 93 (2013b): 8-19
Zhao, Y. et al., Onco. Targets. Ther. 8 (2015b): 421-425
Zhao, Y. et al., Hum. Pathol. 44 (2013c): 365-373
Zhao, Z. et al., Eur. J Surg. Oncol 40 (2014c): 1361-1368
Zhao, Z. et al., RNA. Biol 12 (2015c): 538-554
Zhao, Z. K. et al., Tumour. Biol. 34 (2013d): 173-180
Zheng, C. X. et al., Int. J Oncol 43 (2013): 755-764
Zheng, M. et al., Ai. Zheng. 23 (2004): 771-776
Zhou, B. et al., Cancer Biol. Ther 13 (2012a): 871-879
Zhou, D. et al., Cancer Cell 16 (2009): 425-438
Zhou, D. et al., PLoS. One. 8 (2013a): e53310
Zhou, J. et al., Lung Cancer 14 (1996): 85-97
Zhou, J. et al., J Biol Chem 285 (2010): 40342-40350
Zhou, J. et al., J Surg. Res 188 (2014a): 129-136
Zhou, J. B. et al., Mol. Med. Rep. 7 (2013b): 591-597
Zhou, J. R. et al., Zhonghua Er. Bi Yan. Hou Tou. Jing. Wai Ke. Za Zhi. 42 (2007): 934-938
Zhou, L. et al., Clin Transl. Oncol 16 (2014b): 906-913
Zhou, T. B. et al., J Recept. Signal. Transduct. Res 33 (2013): 28-36
Zhou, X. et al., Arch. Med. Res 42 (2011): 589-595
Zhou, X. et al., Oncotarget. 6 (2015a): 41077-41091
Zhou, Y. et al., Am. J Clin Pathol. 138 (2012b): 744-750
Zhou, Z. et al., Exp. Cell Res 331 (2015b): 399-407
Zhu, F. et al., Zhongguo Shi Yan. Xue. Ye. Xue. Za Zhi. 21 (2013a): 396-398
Zhu, J. et al., Asian Pac. J Cancer Prev. 14 (2013b): 3011-3015
Zhu, J. et al., Oncogene (2015)
Zhu, M. et al., Nucleic Acids Res 42 (2014a): 13074-13081
Zhu, Q. et al., Mol. Cell Biol 27 (2007): 324-339
Zhu, S. et al., FEBS Lett. 588 (2014b): 981-989
Zhu, X. et al., Gynecol. Oncol 112 (2009): 248-256
Zhu, Z. et al., Carcinogenesis 35 (2014c): 1901-1910
Zi, Y. et al., Int. J Clin Exp. Pathol. 8 (2015): 1312-1320
Ziebarth, J. D. et al., PLoS. One. 7 (2012): e47137
Zighelboim, I. et al., Clin Cancer Res 13 (2007): 2882-2889
Zighelboim, I. et al., J Clin Oncol 27 (2009): 3091-3096
Zins, K. et al., Int. J Mol. Sci. 16 (2015): 29643-29653
Zohrabian, V. M. et al., Oncol Rep. 18 (2007): 321-328
Zou, C. et al., Cancer 118 (2012): 1845-1855
Zou, J. X. et al., Mol. Cancer Res 12 (2014a): 539-549
Zou, S. et al., Nat Commun. 5 (2014b): 5696
Zou, T. T. et al., Oncogene 21 (2002): 4855-4862
Zou, W. et al., Cancer Sci. 101 (2010): 2156-2162
Zou, Y. et al., Biomed. Rep. 3 (2015): 33-37
Zubor, P. et al., Mol. Biol. Rep. 42 (2015): 977-988
Zuo, G. W. et al., Histol. Histopathol. 25 (2010): 795-806

The invention claimed is:

1. A method of treating a patient who has cancer, comprising administering to said patient a composition comprising a population of activated T cells that kill cancer cells in the patient that express a peptide, wherein said peptide consists of the amino acid sequence of FQLDPSSGVLVTV (SEQ ID NO: 69), wherein said cancer is ovarian cancer or esophageal cancer.

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the composition further comprises an adjuvant selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

6. The method of claim 1, wherein the activated T cells are cytotoxic T cells produced by contacting T cells with an antigen presenting cell that presents the peptide in a complex with an MHC class I molecule on the surface of the antigen presenting cell, for a period of time sufficient to activate said T cell specifically against the peptide.

7. The method of claim 1, wherein the cancer is ovarian cancer.

8. The method of claim 1, wherein the cancer is esophageal cancer.

9. The method of claim 5, wherein the adjuvant is IL-2.

10. The method of claim 5, wherein the adjuvant is IL-21.

11. A method of eliciting an immune response in a patient who has cancer, comprising administering to said patient a composition comprising a population of activated T cells that kill cancer cells in the patient that express a peptide, wherein said peptide consists of the amino acid sequence of FQLDPSSGVLVTV (SEQ ID NO: 69), wherein said cancer is ovarian cancer or esophageal cancer.

12. The method of claim 11, wherein the T cells are autologous to the patient.

13. The method of claim 11, wherein the T cells are obtained from a healthy donor.

14. The method of claim 11, wherein the T cells are obtained from tumor infiltrating lymphocytes or peripheral blood mononuclear cells.

15. The method of claim 11, wherein the composition further comprises an adjuvant selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

16. The method of claim 11, wherein the activated T cells are cytotoxic T cells produced by contacting T cells with an antigen presenting cell that presents the peptide in a complex with an MHC class I molecule on the surface of the antigen presenting cell, for a period of time sufficient to activate said T cell specifically against the peptide.

17. The method of claim 11, wherein the cancer is ovarian cancer.

18. The method of claim 11, wherein the cancer is esophageal cancer.

19. The method of claim 15, wherein the adjuvant is IL-2.

20. The method of claim 15, wherein the adjuvant is IL-21.

* * * * *